US012545662B2

(12) United States Patent
Trzoss et al.

(10) Patent No.: US 12,545,662 B2
(45) Date of Patent: Feb. 10, 2026

(54) MK2 INHIBITORS AND USES THEREOF

(71) Applicant: XinThera, Inc., Foster City, CA (US)

(72) Inventors: Lynnie Trzoss, San Diego, CA (US); Qing Dong, San Diego, CA (US); Stephen W. Kaldor, San Diego, CA (US); Robert L. Hoffman, San Diego, CA (US)

(73) Assignee: XinThera, Inc., Foster City, CA (US)

( * ) Notice: Subject to any disclaimer, the term of this patent is extended or adjusted under 35 U.S.C. 154(b) by 0 days.

(21) Appl. No.: 18/310,943

(22) Filed: May 2, 2023

(65) Prior Publication Data

US 2023/0265076 A1 Aug. 24, 2023

Related U.S. Application Data

(60) Division of application No. 17/868,567, filed on Jul. 19, 2022, now Pat. No. 11,680,056, which is a continuation of application No. PCT/US2022/022525, filed on Mar. 30, 2022.

(60) Provisional application No. 63/318,118, filed on Mar. 9, 2022, provisional application No. 63/168,407, filed on Mar. 31, 2021.

(51) Int. Cl.

| | |
|---|---|
| ***A61K 31/4427*** | (2006.01) |
| ***C07D 401/14*** | (2006.01) |
| ***C07D 405/14*** | (2006.01) |
| ***C07D 409/14*** | (2006.01) |
| ***C07D 417/14*** | (2006.01) |

(52) U.S. Cl.

CPC ........ *C07D 401/14* (2013.01); *A61K 31/4427* (2013.01); *C07D 405/14* (2013.01); *C07D 409/14* (2013.01); *C07D 417/14* (2013.01)

(58) Field of Classification Search

CPC .................................................. A61K 31/4427

See application file for complete search history.

(56) References Cited

U.S. PATENT DOCUMENTS

| | | | |
|---|---|---|---|
| 9,056,110 | B2 | 6/2015 | Selness et al. |
| 9,115,089 | B2 | 8/2015 | Hockerman et al. |
| 9,359,300 | B2 | 6/2016 | Selness et al. |
| 9,365,546 | B2 | 6/2016 | Selness et al. |
| 9,365,547 | B2 | 6/2016 | Selness et al. |
| 9,636,333 | B2 | 5/2017 | Hockerman et al. |
| 9,771,430 | B2 | 9/2017 | Tabas et al. |
| 11,680,056 | B2 | 6/2023 | Trzoss et al. |
| 11,685,719 | B2 | 6/2023 | Hoffman et al. |
| 11,866,414 | B2 | 1/2024 | Spergel et al. |
| 2007/0167621 | A1 | 7/2007 | Durley et al. |
| 2012/0142709 | A1 | 6/2012 | Selness et al. |
| 2013/0143906 | A1 | 6/2013 | Selness et al. |
| 2022/0235025 | A1 | 7/2022 | Decrescenzo et al. |
| 2022/0402892 | A1 | 12/2022 | Trzoss et al. |
| 2023/0053465 | A1 | 2/2023 | Hoffman et al. |

FOREIGN PATENT DOCUMENTS

| | | | |
|---|---|---|---|
| CN | 115636814 | A | 1/2023 |
| CN | 116178345 | A | 5/2023 |
| WO | WO 2003/068230 | A1 | 8/2003 |
| WO | WO 2004/087677 | A2 | 10/2004 |
| WO | WO 2005/018557 | A2 | 3/2005 |
| WO | WO 2007/091176 | A1 | 8/2007 |
| WO | WO 2008/153942 | A1 | 12/2008 |
| WO | WO 2012/078684 | A1 | 6/2012 |
| WO | WO 2013/086208 | A1 | 6/2013 |
| WO | WO 2013/105676 | A1 | 7/2013 |
| WO | WO 2014/197846 | A1 | 12/2014 |
| WO | WO 2010/141538 | A1 | 12/2020 |
| WO | WO 2021/022186 | A1 | 2/2021 |
| WO | WO 2021/195475 | A1 | 9/2021 |

(Continued)

OTHER PUBLICATIONS

Machado et al. ChemistrySelect 2021, 6, 5729-5742.*

Gordon et al., "Selective Inhibition of the MK2 Pathway: Data From a Phase IIa Randomized Clinical Trial in Rheumatoid Arthritis," ACR Open Rheumatology, 2023, vol. 5, No. 2, pp. 63-70.

Kragstrup, et al. MAPK activated kinase 2 inhibition shifts the chemokine signature in arthritis synovial fluid mononuclear cells from CXCR3 to CXCR2. International Immunopharmacology 112 (2022) 109267. 6 pages.

(Continued)

*Primary Examiner* — Brian E McDowell

(74) *Attorney, Agent, or Firm* — Sheppard Mullin Richter & Hampton LLP

(57) ABSTRACT

Described herein are MK2 inhibitors of Formula (II) and pharmaceutical compositions comprising said inhibitors. The subject compounds and compositions are useful for the treatment of autoimmune disorders, chronic inflammatory disorders, acute inflammatory disorders, auto-inflammatory disorders, fibrotic disorders, metabolic disorders, neoplastic disorders, and cardiovascular or cerebrovascular disorders.

Formula (II)

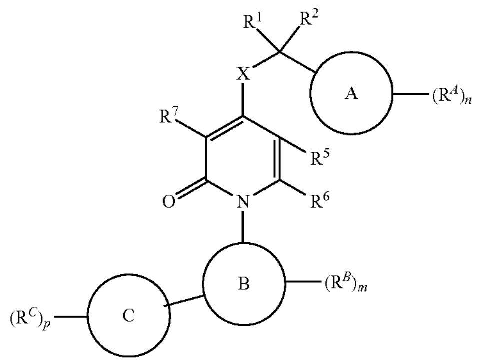

27 Claims, No Drawings

(56) References Cited

FOREIGN PATENT DOCUMENTS

| | | | |
|---|---|---|---|
| WO | WO 2021/195507 | A1 | 9/2021 |
| WO | WO 2021/195562 | A1 | 9/2021 |
| WO | WO 2022/081573 | A1 | 4/2022 |
| WO | WO 2022/109481 | A1 | 5/2022 |
| WO | WO 2022/165148 | A1 | 8/2022 |
| WO | WO 2022/167445 | A1 | 8/2022 |
| WO | WO 2022/207665 | A1 | 10/2022 |
| WO | WO 2022/208356 | A1 | 10/2022 |
| WO | WO 2022/208391 | A1 | 10/2022 |
| WO | WO 2022/212489 | A1 | 10/2022 |
| WO | WO 2023/001282 | A1 | 1/2023 |
| WO | WO 2023/278759 | A1 | 1/2023 |
| WO | WO 2023/283338 | A1 | 1/2023 |
| WO | WO 2023/016535 | A1 | 2/2023 |
| WO | WO 2023/125707 | A1 | 7/2023 |
| WO | WO 2023/125708 | A1 | 7/2023 |

OTHER PUBLICATIONS

Lebish, et al. MK2 Inhibitors as a Potential Crohn's Disease Treatment Approach for Regulating MMP Expression, Cleavage of Checkpoint Molecules and T Cell Activity. Pharmaceuticals 2022, 15, 1508. 13 pages.

Masood et al., Lead Diversification 2: Application to P38, gMTP and lead compounds, Bioorganic & Medicinal Chemistry Letters, 2012, vol. 22, pp. 1255-1262.

International Search Report and Written Opinion, dated Jul. 1, 2022, regarding Application No. PCT/US2022/022525, 24 pages.

International Search Report and Written Opinion, dated Sep. 20, 2022, regarding Application No. PCT/US2022/036362, 16 pages.

Selness et al., "Discovery of PH-797804, a highly selective and potent inhibitor of p38 MAP kinase," Bioorganic & Medicinal Chemistry Letters, 2011, vol. 21, pp. 4066-4071.

U.S. Appl. No. 63/139,553, filed Jan. 20, 2021 as filed with Filing Receipt.

U.S. Appl. No. 17/533,931 Granted Petition to Accept Unitentially Delayed Claim Under 35 U.S.C. 119(e) dated Mar. 20, 2023.

Third Party Submission, dated April 3, 3023, regarding U.S. Appl. No. 17/868,567.

Selness et al., "Design, synthesis and activity of a potent, selective series of N-aryl pyridinone inhibitors of p38 kinase," Bioorganic & Medicinal Chemistry Letters, 2011, vol. 21, Issue 13, pp. 4059-4065.

Funding et al., "Reduced Oxazolone-Induced Skin Inflammation in MAPKAP Kinase 2 Knockout Mice," Journal of Investigative Dermatology, 2009, vol. 129, pp. 891-898.

Lee et al., "p38 MAPK Inhibitor NJK14047 Suppresses CDNB-Induced Atopic Dermatitis-Like Symptoms in BALB/c Mice," Biomolecules & Therapeutics, 2022, vol. 30, No. 6, pp. 501-509.

* cited by examiner

MK2 INHIBITORS AND USES THEREOF

CROSS-REFERENCE

This application is a Divisional Application of U.S, application Ser. No. 17/868,567 filed Jul. 19, 2022, which is a continuation of International Application No. PCT/US2022/022525, filed Mar. 30. 2022, which claims the benefit of U.S. Provisional Application Ser. No. 63/168,407 filed Mar. 31. 2021 and U.S. Provisional Application Ser. No. 63/318,118 filed Mar. 9. 2022 which are hereby incorporated by reference in their entirety.

BACKGROUND OF THE INVENTION

Mitogen-activated protein kinases (MAPK) are a conserved family of enzymes that relay and propagate external stimuli, using phosphorylation cascades to generate a coordinated cellular response to the environment. The MAPK are proline-directed serine/threonine-specific protein kinases that regulate cellular activities, such as gene expression, mitosis, differentiation, and cell survival/apoptosis. To date, four distinct classes of mammalian MAPK have been identified: the extracellular signaling kinases (ERK1 and 2), the c-jun N-terminal kinase-1 (JNK1-3), the p38 MAPK (p38α, β, γ, and 8), and ERK5. The MAPK are activated by the dual phosphorylation of Thr and Tyr residues within a TXY activation motif by coordinated dual-specificity MAPKK, where X is Glu, Pro, and Gly in ERK, JNK, and p38 MAPK, respectively. MAPK are 60-70% identical to each other, yet differ in their activation loop sequences and sizes. The activation loop is adjacent to the enzyme-active site, and its phosphorylation allows the enzyme to reposition active-site residues into the optimal orientation for substrate binding and catalysis. Downstream substrates of MAPK include mitogen-activated protein-kinase-activated protein (MAPKAP) kinases and transcription factors, the phosphorylation of which, either directly or indirectly, regulates gene expression at several points, including transcription, nuclear export, and mRNA stability and translation. The cellular consequences of MAPK activation include inflammation, apoptosis, differentiation, and proliferation.

Distinct genes encode four p38 MAPK in humans: p38α, β, γ, and δ. Significant amino acid sequence homology is observed among the 4 isoforms, with 60-75 overall sequence identity and >90% identity within the kinase domains. Tissue-selective expression is observed, with p38γ found predominantly in skeletal muscle, p388 in the testes, pancreas, and small intestine. In contrast, p38a and B are more ubiquitously expressed.

p38 MAPK is the major isoform involved in the immune and inflammatory response. As such its function is critical for the production and activity of multiple proinflammatory cytokines, including TNFa. IL-1. IL-6, and IL-8, in cells such as macrophages, monocytes, synovial cells, and endothelial cells, p38 MAPK is also responsible for the induction of key inflammatory enzymes such as COX2 and iNOS, the major sources of eicosanoids and nitric oxide at sites of inflammation, respectively. Additionally, the p38 MAPK pathway regulates the expression of matrix metalloproteinases (MMP), including MMP2, MMP9, and MMP13.

The use of selective and potent inhibitors has facilitated the discovery of several families of p38 MAPK substrates, including transcription factors. MAPKAP kinases, and other enzymes, p38 MAPK can directly phosphorylate several transcription factors, such as myocyte-specific enhancer binding factor 2C (MEF2C), CHOP, peroxisome proliferator-activated receptor (PPAR) a. PPAR γ co-activator 1 and p53. These transcription factors are involved in cellular functions such as apoptosis, gluconcogenesis, and synthesis of enzymes involved in fatty acid oxidation, p38 MAPK is also involved in the direct or indirect phosphorylation of enzyme substrates, such as cytosolic phospholipase A2, and the Cdc25 phosphatases, which are involved in the activation of cyclin-dependent protein kinase activity and cell-cycle regulation. Therefore in addition to its role in the inflammatory response, p38 MAPK has other functions associated with normal and abnormal cell growth and survival as well as cellular function and homeostasis. The MAPKAP kinases (MK2, MK-3, and PRAK) are selectively phosphorylated by p38 MAPK, while the phosphorylation of MSK1/2, MNK1/2, and RSKb is catalyzed by both p38 MAPK and ERK.

MK-2. MK-3, and PRAK, once phosphorylated and activated by p38 MAPK, share similar substrate specificities. All of these kinases can phosphorylate the small heat –shock protein Hsp27. Studies have shown that the PRAK-and MK3-deficient mice do not display any resistance to endotoxic shock or a decrease in lipopolysaccharide-(LPS)-induced cytokine production. In contrast. MK-2-deficient mice show a resistance to endotoxic shock and an impaired inflammatory response, as well as a significantly decreased production of cytokines such as TNFa. IFNy and IL-6. Thus, the p38/MK2 axis is important for mediating pro-inflammatory responses.

The p38: MK2 complex is very stable with a Kd of 6 nM. The binding affinity of p38 for MK2 is driven by the C-terminal domain of MK2 containing several positively charged amino acid residues. Crystallographic studies of the p38: MK2 complex demonstrated that the C-terminal region of MK2 wraps around p38a and binds to the negatively charged ED binding site. The tight binding of p38 to MK2 may give rise to conformational changes providing additional binding pockets for inhibitors that would specifically be dependent upon the p38: MK2 interaction. Taken together, these two studies suggests that selective p38/MK2 axis blockade is achievable with small molecule inhibitors. In comparison to traditional p38 MAPK inhibitors these p38/MK2 inhibitors should retain or enhance potency and exhibit improved safety features in animal models of disease or in human clinical settings.

The p38/MK2 role in the regulation of inflammatory cytokines (TNFa, IL-Iβ. IL-6) and enzymes responsible for inflammation (COX-2, iNOS, and MMPs) makes it an attractive drug target. Several classical p38 MAPK inhibitors have progressed to testing in clinical trials. Some of these candidates have failed, for safety or other reasons, but several have reported clinical data in diseases such as rheumatoid arthritis, pain, Crohn's disease, acute coronary syndrome, multiple myeloma and chronic obstructive pulmonary disease. In addition to these diseases several IL-Iβ mediated diseases could be impacted by a p38 inhibitor based upon the key role for the p38 MAPK pathway in the biosynthesis and activity of this cytokine. These diseases include the family of cryopyrin associated periodic disorders (CAPS), chronic gout, diabetes. Still's disease, Familial Mediterranean Fever among others.

SUMMARY OF THE INVENTION

Disclosed herein is a compound of Formula (II), or a pharmaceutically acceptable salt, solvate, N-oxide, or stereoisomer thereof:

Formula (II)

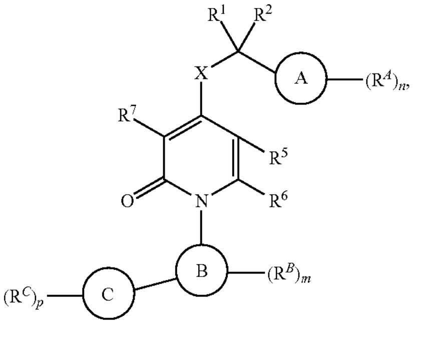

wherein:

Ring A is phenyl or heteroaryl:

each $R^A$ is independently hydrogen, deuterium, halogen, —CN, —$NO_2$, —OH, —$OR^a$, —OC(═O)$R^a$, —OC(—O)$OR^b$, —OC(═O)$NR^cR^d$, —SH, —$SR^a$, —S(═O)$R^a$, —S(═O)$R^a$, —S(═O)$_2NR^cR^d$, —$NR^cR^d$, —$NR^c$C(═O)$NR^cR^d$, —$NR^c$C(═O)$R^a$, —$NR^c$C(═O)$OR^b$, —$NR^c$S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Aa}$;

or two $R^A$ on the same atom are taken together to form an oxo;

each $R^{Aa}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(—O)$_2NR^cR^d$, —$NR^cR^d$, —$NR^c$C(═O)$NR^cR^d$, —$NR^c$C(═O)$R^a$, —$NR^c$C(═O)$OR^b$, —$NR^c$S(═O)$R^a$, —C(═O)$R^a$, —C(═O)C(═O)$R^a$, —C(═O)$OR^b$, —C(—O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl:

or two $R^{Aa}$ on the same atom are taken together to form an oxo:

n is 0-4:

$R^1$ and $R^2$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

X is —C$(R^3)_2$—, —$NR^4$—, —O—, or —S—;

each $R^3$ are independently hydrogen, deuterium, halogen, —CN, —$NO_2$, —OH, —$OR^a$, —$NR^cR^4$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or two $R^3$ are taken together to form an oxo:

$R^4$ is hydrogen, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^5$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^7$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Ring B is heterocycloalkyl or heteroaryl;

each $R^B$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O) $2NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

or two $R^B$ on the same atom are taken together to form an oxo;

each $R^{Ba}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ba}$ on the same atom are taken together to form an oxo:

m is 0-4;

Ring C is 5-membered heteroaryl:

each $R^C$ is independently hydrogen, deuterium, halogen, —CN, —$NO_2$, —OH, —$OR^a$—OC(═O)$R^a$—OC(═O)$OR^b$, —OC(═O)$NR^cR^d$—SH, —$SR^a$, —S(═O)$R^a$—S(═O)$R^a$—S(═O)$NR^cR^d$—S(═O)(═$NR^b$)$R^a$—Si$ROR^dOR^b$—$NR^cR^d$—$NR^c$C(═O)$NR^cR^d$—$NR^c$C(═O)$R^a$—$NR^b$C (═O)$OR^b$—$NR^b$S(═O)$R^a$—C(═O)$R^a$—C(═O)$OR^b$—C(═O)$NR^cR^d$$C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ca}$;

each $R^b$ is independently deuterium, halogen, —CN, —$NO_2$, —OH, —$OR^a$—OC(═O)$R^a$—OC(═O)$OR^b$—OC(═O)$NR^cR^d$—SH, —$SR^a$—S(═O)$R^a$, —S(═O)$R^a$, —S(═O)—$NR^cR^d$—$NR^cR^d$—$NR^c$C(═O)$NR^cR^d$—$NR^c$C(═O)$R^a$, —$NR^c$C(═O)$OR^b$, —$NR^b$S(═O)$R^a$, —C(═O)$R^a$, —C(═O)C(═O)$R^a$—C(═O)$OR^b$, —C(═O)$NR^cR^d$—C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ca}$ on the same atom are taken together to form an oxo:

p is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(—O), $CH_3$, —S(═O), $NH_2$, —S(═O), $NHCH_3$, —S(═O), N($CH_3$), —$NH_2$, —$NHCH_3$, —N$(CH_3)_2$, —C(═O)$CH_3$, —C(═O)OH, —C(—O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH. —$OCH_3$, —S(═O)$CH_3$, —S(═O); $CH_3$, —S$(═O)_2NH_2$, —S$(═O)_2NHCH_3$, —S$(═O)_2N(CH_3)_2$, —$NH_2$, —$NHCH_3$, —N$(CH_2)_2$ , —C(═O)$CH_3$, —C(—O)OH, —C(═O)$OCH_3$$C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl heterocycloalkyl, aryl, and heteroaryl is independently optionally substituted with one or more oxo. deuterium, halogen, —CN, —OH, —$OCH_3$, —S(═O)$CH_3$, —S$(═O)_2CH_3$, —S(═O) $NH_2$, —S(═O)—$NHCH_3$, —S$(═O)_2N(CH_3)_2$, —$NH_2$, —$NHCH_3$, —N$(CH_3)_2$ , —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(═O)$CH_3$, —S$(═O)_2CH_3$, —S(═O)$NH_2$, —S(═O)$NHCH_3$, —S(═O)N$(CH_3)_2$, —$NH_2$, —$NHCH_3$, —N$(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

provided that the compound is not

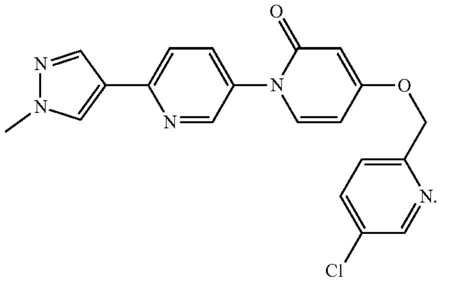 [SMILES: Cn1cc(-c2ccc(-n3ccc(OCc4ccc(Cl)cn4)cc3=O)cn2)cn1]

Disclosed herein is a compound of Formula (I), or a pharmaceutically acceptable salt, solvate, N-oxide, or stereoisomer thereof:

Formula (I)

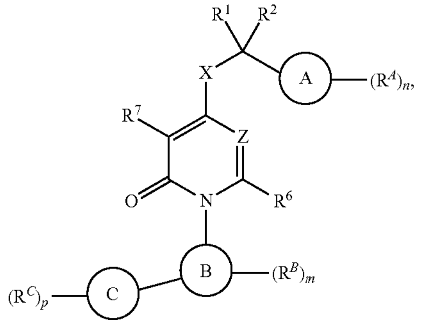

wherein:

Ring A is phenyl or heteroaryl;

each $R^A$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(=O)$R^a$, —S(=O)$R^a$, —S(=O)$NR^cR^d$, —$NR^cR^d$, —$NR^cC$(=O)$NR^cR^d$, —$NR^cC$(=O)$R^a$, —$NR^cC$(=O)$OR^b$, —$NR^cS$(=O)$R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Aa}$;

or two $R^A$ on the same atom are taken together to form an oxo;

each $R^{Aa}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$R^a$, —S(=O)$_2NR^cR^d$, —$NR^cR^d$, —$NR^bC$(=O)$NR^cR^d$, —$NR^cC$(=O)$R^a$, —$NR^cC$(=O)$OR^b$, —NR'S(=O)$R^a$, —C(=O)$R^a$, —C(=O)C(=O)$R^a$, —C(=O)$OR^b$, —C(=O)$NR^cR^d$, —C(=O)C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Aa}$ on the same atom are taken together to form an oxo;

n is 0-4;

$R^1$ and $R^2$ are independently hydrogen, deuterium, halogen, —CN, —$NO_2$, —OH, —$OR^a$, —$NR^cR^d$, —C(—O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

X is —$C(R^3)_2$—, —$NR^4$-, —O—, or —S—;

each $R^3$ are independently hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or two $R^3$ are taken together to form an oxo;

$R^4$ is hydrogen, —C(=O)$R^a$, —C(=O)$OR^b$, —C(=O)$NR^cR^d$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Z is N or $CR^5$;

$R^5$ is hydrogen, deuterium, halogen, —CN, —$NO_2$, —OH, —$OR^a$, —$NR^cR^d$, —C(=O)$R^a$, —C(—O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Ring B is cycloalkyl, heterocycloalkyl, aryl, or heteroaryl;

each $R^B$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$R^a$, —S(=O) $2NR^cR^d$, —$NR^cR^d$, —$NR^cC$(=O)$NR^cR^d$, —$NR^cC$(=O)$R^a$, —$NR^cC$(=O)$OR^b$, —$NR^bS$(=O)$R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

or two $R^B$ on the same atom are taken together to form an oxo;

each $R^{Ba}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_3R^a$, —S(=O)$_2NR^cR^d$, —$NR^cR^d$—$NR^cC$(=O)$NR^cR^d$—$NR^cC$(=O)$R^a$, —$NR^cC$ (=O)$OR^b$, —$NR^bS$(=O)$R^a$, —C(=O)$R^a$, —C(=O)C(=O)$R^a$, —C(=O)$OR^b$, —C(=O)$NR^cR^d$, —C(=O)C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ba}$ on the same atom are taken together to form an oxo;

m is 0-4;

Ring C is heterocycloalkyl or heteroaryl;

each $R^C$ is independently hydrogen, deuterium, halogen, —CN, —$NO_2$, —OH, —$OR^a$, —OC(=O)$R^a$, —OC(=O)$OR^b$. —OC(=O)$NR^cR^d$, —SH, —$SR^a$, —S(=O)$R^a$, —S(=O)$R^a$, —S(=O)$NR^cR^d$, —S(=O) (=$NR^b$)$R^a$, —SiRcRdOR$^b$, —$NR^cR^d$—$NR^cC$(=O)$NR^cR^d$—$NR^cC$(=O)$R^a$, —$NR^cC$(=O)$OR^b$, —$NR^aS$(=O)$R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl) aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ca}$;

or two $R^C$ on the same atom are taken together to form an oxo;

each $R^{Ca}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$R^a$, —S(=O)$NR^cR^d$, —$NR^cR^d$—$NR^cC$(=O)$NR^cR^d$, —$NR^cC$(=O)$R^a$, —$NR^bC$(=O)$OR^b$, —$NR^bS$(=O)$R^a$, —C(=O)$R^a$, —C(=O)C(=O)$R^a$, —C(=O)$OR^b$, —C(=O)$NR^cR^d$, —C(=O)C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ca}$ on the same atom are taken together to form an oxo;

p is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)N$(CH_3)_2$, —$NH_2$, —$NHCH_3$, —N$(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(—O)$_2NH_2$, —S(=O)$_2NHCH_3$, —S(=O)N$(CH_3)_2$, —$NH_2$, —$NHCH_3$, —N$(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O) $2NH_2$, —S(=O),$NHCH_3$, —S(=O)N$(CH_3)_2$, —$NH_2$, —$NHCH_3$, —N$(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(—O)$CH_3$, —S(=O)$_2CH_3$, —S(=O)$_2NH_2$, —S(=O)$_2NHCH_3$, —S(=O)N$(CH_3)_2$, —$NH_2$, —$NHCH_3$, —N$(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

provided that

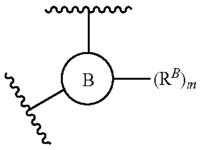

is not

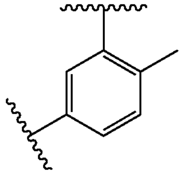
,
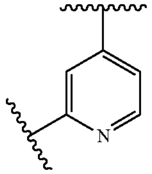
,
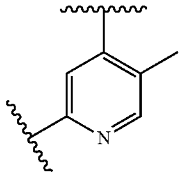
,
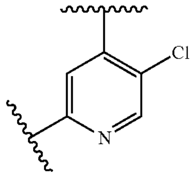
,
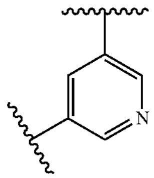
,
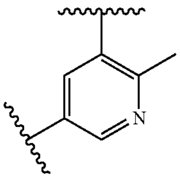
,
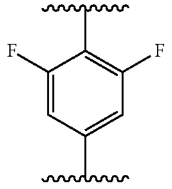
, or
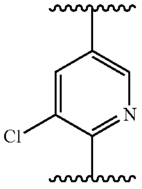
.

Also disclosed herein is a pharmaceutical composition comprising a compound disclosed herein, or a pharmaceutically acceptable salt, solvate, N-oxide, or stereoisomer thereof, and a pharmaceutically acceptable carrier.

Also disclosed herein is a method for treating a condition comprising administering to a subject in need thereof a therapeutically effective amount of a compound disclosed herein, or a pharmaceutically acceptable salt, solvate, N-oxide, or stereoisomer thereof, wherein the condition is selected from the group consisting of an autoimmune disorder, a chronic inflammatory disorder, an acute inflammatory disorder, an auto-inflammatory disorder, a fibrotic disorder, a metabolic disorder, a neoplastic disorder, and a cardiovascular or a cerebrovascular disorder.

Also disclosed herein is a method of treating a p38 MAP kinase-mediated disease in a subject in need thereof comprising administering to the subject a therapeutically effective amount of a compound disclosed herem, or a pharmaceutically acceptable salt, solvate, N-oxide, or stereoisomer thereof.

Also disclosed herein is a method of treating a MK2-mediated disease in a subject in need thereof comprising administering to the subject a therapeutically effective amount of a compound disclosed herein, or a pharmaceutically acceptable salt, solvate, N-oxide, or stereoisomer thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word “comprise” and variations thereof, such as, “comprises” and “comprising” are to be construed in an open, inclusive sense, that is, as “including, but not limited to.” Further, headings provided herein are for convenience only and do not interpret the scope or meaning of the claimed invention.

Reference throughout this specification to “some embodiments” or “an embodiment” means that a particular feature, structure or characteristic described in connection with the embodiment is included in at least one embodiment. Thus, the appearances of the phrases “in one embodiment” or “in an embodiment” in various places throughout this specification are not necessarily all referring to the same embodiment. Furthermore, the particular features, structures, or characteristics may be combined in any suitable manner in one or more embodiments. Also, as used in this specification and the appended claims, the singular forms “a,” “an,” and “the” include plural referents unless the content clearly dictates otherwise. It should also be noted that the term “or” is generally employed in its sense including “and/or” unless the content clearly dictates otherwise.

The terms below, as used herein, have the following meanings, unless indicated otherwise;

“oxo” refers to =O.

“Carboxyl” refers to-COOH.

“Alkyl” refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl. 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as “$C_1$-$C_6$alkyl” or “$C_1$-6alkyl”, means that the alkyl group may consist of 1 carbon atom. 2 carbon atoms. 3 carbon atoms. 4 carbon atoms. 5 carbon atoms or 6 carbon atoms, although the present definition also covers the occurrence of the term “alkyl” where no numerical range is designated. In some embodiments, the alkyl is a $C_1$-poalkyl. In some embodiments, the alkyl is a $C_1$-6alkyl. In some embodiments, the alkyl is a $C_1$-$C_5$alkyl. In some embodiments, the alkyl is a $C_1$-4alkyl. In some embodiments, the alkyl is a $C_1$-3alkyl. Unless stated otherwise specifically in the specification, an alkyl group may be optionally substituted, for example, with oxo, halogen, amino, nitrile, nitro, hydroxyl, haloalkyl, alkoxy, carboxyl. carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —$NH_2$, or —$NO_2$. In some embodiments, the alkyl is optionally substituted with halogen, —CN, —OH, or —OMe. In some embodiments, the alkyl is optionally substituted with halogen.

“Alkenyl” refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—CH—CH=$CH_2$), isopropenyl [—C($CH_3$)=$CH_2$], butenyl, 1,3-butadienyl and the like. Whenever it appears herein, a numerical range such as “$C_2$-$C_6$ alkenyl” or “$C_2$-6alkenyl”, means that the alkenyl group may consist of 2 carbon atoms. 3 carbon atoms. 4 carbon atoms. 5 carbon atoms or 6 carbon atoms, although the present definition also covers the occurrence of the term “alkenyl” where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —$NH_2$, or —$NO_2$. In some embodiments, the alkenyl is optionally substituted with halogen, —CN, —OH, or —OMe. In some embodiments, the alkenyl is optionally substituted with halogen.

“Alkynyl” refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as “$C_2$-$C_6$ alkynyl” or “$C_2$-6alkynyl”, means that the alkynyl group may consist of 2 carbon atoms, 3 carbon atoms, 4 carbon atoms, 5 carbon atoms or 6 carbon atoms, although the present definition also covers the occurrence of the term “alkynyl” where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —$NH_2$, or —$NO_2$. In some embodiments, the alkynyl is optionally substituted with halogen, —CN, —OH, or —OMe. In some embodiments, the alkynyl is optionally substituted with halogen.

“Alkylene” refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —$NH_2$, or —$NO_2$. In some embodiments, the alkylene is optionally substituted with halogen, —CN, —OH, or —OMe. In some embodiments, the alkylene is optionally substituted with halogen.

"Alkoxy" refers to a radical of the formula —$OR^a$ where $R^a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —$NH_2$, or —$NO_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylenc, phenanthrylene, anthracene, azulene, benzene, chrysene, fluoranthene, fluorene, as-indacene, s-indacenc, indanc, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —$CF_3$, —OH, —OMe, —$NH_2$, or —$NO_2$. In some embodiments, the aryl is optionally substituted with halogen, methyl, ethyl, —CN, —CF3, —OH, or —OMe. In some embodiments, the aryl is optionally substituted with halogen.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms ($C_3$-$C_{15}$ cycloalkyl or $C_3$-Cis cycloalkenyl), from three to ten carbon atoms ($C_3$-$C_{10}$ cycloalkyl or $C_3$-$C_{10}$ cycloalkenyl), from three to eight carbon atoms ($C_3$-$C_8$ cycloalkyl or $C_3$-$C_8$ cycloalkenyl), from three to six carbon atoms ($C_3$-$C_6$ cycloalkyl or $C_3$-$C_6$ cycloalkenyl), from three to five carbon atoms ($C_3$-$C_5$ cycloalkyl or $C_3$-$C_8$ cycloalkenyl), or three to four carbon atoms ($C_3$-$C_4$ cycloalkyl or $C_3$-$C_4$ cycloalkenyl). In some embodiments, the cycloalkyl is a 3- to 10-membered cycloalkyl or a 3- to 10-membered cycloalkenyl. In some embodiments, the cycloalkyl is a 3- to 6-membered cycloalkyl or a 3- to 6-membered cycloalkenyl. In some embodiments, the cycloalkyl is a 5- to 6-membered cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl. bicyclo[3.3.0]octane, bicyclo[4.3.0]nonane, cis—decalin, trans-decalin, bicyclo[2.1. 1]hexane, bicyclo [2.2. 1]heptane, bicyclo[2.2.2]octane, bicyclo[3.2.2]nonanc, and bicyclo[3.3.2]decanc, and 7.7-dimethyl-bicyclo[2.2.1] heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —$CF_3$, —OH, —OMe, —$NH_2$, or —$NO_2$. In some embodiments, a cycloalkyl is optionally substituted with oxo, halogen, methyl, ethyl, —CN, —CF3, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl. 2.2.2-trifluoroethyl. 1.2-difluorocthyl. 3-bromo-2-fluoropropyl. 1.2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, $CD_3$, $CH_2D$, $CHD_2$, $CH_2CD_3$, $CD_2CD_3$, $CHDCD_3$, CH—$CH_2D$, or CH—$CHD_2$. In some embodiments, the deuteroalkyl is $CD_3$.

"Heteroalkyl" refers to an alkyl group in which one or more skeletal atoms of the alkyl are selected from an atom other than carbon, e.g., oxygen, nitrogen (e.g., NH—, —N(alkyl)-), sulfur, phosphorus. or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g, —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —$CHOCH_3$, —$CH_2CH_2OCH_3$, —$CH_2CH_2OCH_2CH_2OCH_3$, —$CH(CH_3)OCH_3$, —$CH_2NHCH_3$, —$CH_2N(CH_3)_2$, —CH—$CH_2NHCH_3$, or —CH—$CH_2N(CH_3)_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized: the nitrogen atom may be optionally quaternized. Representative heterocycloalkyls include, but are not limited to, heterocycloalkyls having from two to fifteen carbon atoms ($C_2$-$C_{15}$ heterocycloalkyl or $C_2$-Cis heterocycloalkenyl), from two to ten carbon atoms ($C_2$-$C_{10}$ heterocycloalkyl or $C_2$-$C_{10}$ heterocycloalkenyl), from two to eight carbon atoms ($C_2$-$C_8$ heterocycloalkyl or $C_2$-$C_8$ heterocycloalkenyl), from two to seven carbon atoms ($C_2$-$C_7$ heterocycloalkyl or C, —$C_7$ heterocycloalkenyl), from two to six carbon atoms ($C_2$-$C_6$ heterocycloalkyl or $C_2$-$C_7$ heterocycloalkenyl), from two to five carbon atoms ($C_2$-$C_8$ heterocycloalkyl or $C_2$-$C_8$ heterocycloalkenyl), or two to four carbon atoms ($C_2$-$C_4$ heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e, skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —$CF_3$, —OH, —OMe, —$NH_2$, or —$NO_2$. In some embodiments, the heterocycloalkyl is optionally substituted with halogen, methyl, ethyl, —CN, —$CF_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized: the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl. benzothiazolyl, benzindolyl, benzodioxolyl, benzofuranyl, benzooxazolyl, benzothiazolyl. benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1.2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —$CF_3$, —OH, —OMe, —$NH_2$, or —$NO_2$. In some embodiments, the heteroaryl is optionally substituted with halogen, methyl, ethyl, —CN, —$CF_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example. "optionally substituted alkyl" means either "alkyl" or "substituted alkyl" as defined above. Further, an optionally substituted group may be un-substituted (e.g., CH—$CH_3$), fully substituted (e.g., —$CF_2CF_3$), mono-substituted (e.g., CH—CH—F) or substituted at a level anywhere in-between fully substituted and mono-substituted (e.g., $CH_2CHF_2$, —$CH_2CF_3$, —$CFCH_3$, —$CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1.000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g, a mammal, such as a human) or a cell is any type of intervention used in an attempt to alter the natural course of the individual or cell. In some embodiments, treatment includes administration of a pharmaceutical composition, subsequent to the initiation of a pathologic event or contact with an ctiologic agent and includes stabilization of the condition (e.g., condition does not worsen) or alleviation of the condition.

"Synergy" or "synergize" refers to an effect of a combination that is greater than additive of the effects of each component alone at the same doses.

As used herein, a "disease or disorder associated with MK2" or, alternatively. "an MK2-mediated disease or disorder" means any disease or other deleterious condition in which MK2, or a mutant thereof, is known or suspected to play a role.

As used herein, a "disease or disorder associated with p38 MAP kinase" or, alternatively. "an p38 MAP kinase-mediated discascor disorder" means any disease or other deleterious condition in which p38 MAP kinase, or a mutant thereof, is known or suspected to play a role.

Compounds

Described herein are compounds of Formula (I)-(VIII), or a pharmaceutically acceptable salt, solvate, N-oxide, or stereoisomer thereof useful in the treatment of autoimmune disorders, chronic inflammatory disorders, acute inflammatory disorders, auto-inflammatory disorders, fibrotic disorders, metabolic disorders, neoplastic disorders, or cardiovascular or cerebrovascular disorders.

Disclosed herein is a compound of Formula (I), or a pharmaceutically acceptable salt, solvate, N-oxide, or stereoisomer thereof:

Formula (I)

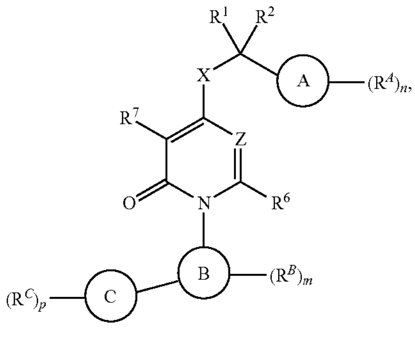

wherein;

Ring A is phenyl or heteroaryl;

each $R^A$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)—$NR^cR^d$, —$NR^cR^d$, —$NR^c$C(═O)$NR^cR^d$, —$NR^c$C(═O)$R^a$, —$NR^c$C(═O)$OR^b$, —$NR^c$S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Aa}$;

or two $R^A$ on the same atom are taken together to form an oxo;

each $R^{Aa}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$_2NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Aa}$ on the same atom are taken together to form an oxo;

n is 0-4;

$R^1$ and $R^2$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —N$(CH_3)_2$, —C(═O)$CH_3$, —C(—O)OH, —C(═O)

$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

X is —C($R^3$)$_2$-, —$NR^4$-, —O—, or —S—;

each $R^3$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or two $R^3$ are taken together to form an oxo;

$R^4$ is hydrogen, —C(═O)$R^a$, —C(═O)$OR^b$, —C(═O) $NR^cR^d$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Z is N or $CR^5$;

$R^3$ is hydrogen, deuterium, halogen, —CN, —$NO_2$, —OH, —$OR^a$, —$NR^cR^d$, —C(═O)$R^a$, —C(═O) $OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —$NR^cR^d$, —C(═O)$R^a$, —C(═O) $OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Ring B is cycloalkyl, heterocycloalkyl, aryl, or heteroaryl;

each $R^B$ is independently hydrogen, deuterium, halogen, —CN, —$NO_2$, —OH, —$OR^a$, —OC(═O)$R^a$, —OC (═O)$OR^b$, —OC(═O)$NR^cR^d$, —SH, —$SR^a$, —S(═O)$R^a$, —S(═O)$R^a$, —S(—O)$_2NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

or two $R^B$ on the same atom are taken together to form an oxo;

each $R^{Ba}$ is independently deuterium, halogen, —CN, —$NO_2$, —OH, —$OR^a$, —OC(═O)$R^a$, —OC(═O) $OR^b$, —OC(═O)$NR^cR^d$, —SH, —$SR^a$, —S(═O)$R^a$, —S(—O)$_3R^a$, —S(═O)$_2NR^cR^d$, —$NR^cR^d$—$NR^c$C (═O)$NR^cR^d$—$NR^c$C(═O)$R^a$, —$NR^c$C(═O)$OR^b$, —$NR^b$S(═O)$R^a$, —C(═O)$R^a$, —C(═O)C(═O)$R^a$, —C(═O)$OR^b$, —C(═O)$NR^cR^d$, —C(═O)C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ba}$ on the same atom are taken together to form an oxo;

m is 0-4;

Ring C is heterocycloalkyl or heteroaryl;

each $R^C$ is independently hydrogen, deuterium, halogen, —CN, —$NO_2$, —OH, —$OR^a$, —OC(═O)$R^a$, —OC (═O)$OR^b$, —OC(═O)$NR^cR^d$, —SH, —$SR^a$, —S(═O)$R^a$, —S(═O)$R^a$, —S(═O)$NR^cR^d$, —S(═O) (═$NR^b$)$R^a$, —SiRcRdOR$^b$, —$NR^cR^d$—$NR^c$C(═O)$NR^cR^d$—$NR^c$C(═O)$R^a$, —$NR^c$C(═O) $OR^b$, —NR'S(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ca}$;

or two $R^C$ on the same atom are taken together to form an oxo;

each $R^{Ca}$ is independently deuterium, halogen, —CN, —$NO_2$, —OH, —$OR^a$, —OC(═O)$R^a$, —OC(═O) $OR^b$, —OC(═O)$NR^cR^d$, —SH, —$SR^a$, —S(═O)$R^a$, —S(═O)$_3R^a$, —S(═O)$_3NR^cR^d$, —$NR^cR^d$—$NR^c$C (═O)$NR^cR^d$, —$NR^c$C(═O)$R^a$, —$NR^b$C(═O)$OR^b$, —$NR^b$S(═O)$R^a$, —C(═O)$R^a$, —C(═O)C(═O)$R^a$, —C(═O)$OR^b$, —C(═O)$NR^cR^d$, —C(═O)C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ca}$ on the same atom are taken together to form an oxo;

p is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)N($CH_3$)$_2$ , —$NH_2$, —$NHCH_3$, —N($CH_3$)$_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(—O): $CH_3$, —S(═O)$NH_2$, —S(═O)$_2NHCH_3$, —S(═O)N($CH_3$)$_2$, —$NH_2$, —$NHCH_3$, —N($CH_3$)$_2$, —C(═O)$CH_3$, —C(═O)OH, —C(—O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O) ¿$NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

provided that

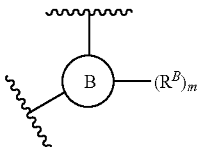

is not

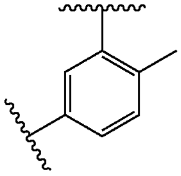
,
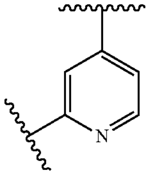
,
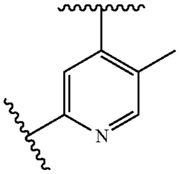
,
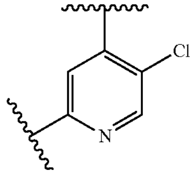
,
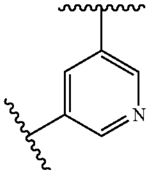
,
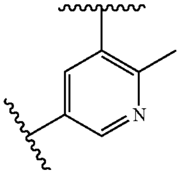
,
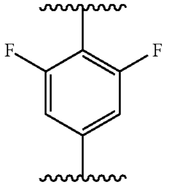
, or
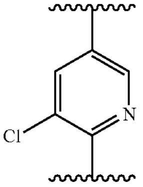
.

In some embodiments of a compound of Formula (I), Ring A is heteroaryl. In some embodiments of a compound of Formula (I), Ring A is pyridyl. In some embodiments of a compound of Formula (I), Ring A is phenyl.

In some embodiments of a compound of Formula (I), each $R^A$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (I), each $R^A$ is independently halogen or $C_1$-$C_6$alkyl. In some embodiments of a compound of Formula (I), each $R^A$ is independently halogen.

In some embodiments of a compound of Formula (I), n is 1 or 2. In some embodiments of a compound of Formula (I), n is 1-3. In some embodiments of a compound of Formula (I), n is 2. In some embodiments of a compound of Formula (I), n is 1.

In some embodiments of a compound of Formula (I), $R^1$ and $R^2$ are independently hydrogen, deuterium, halogen, $C_1$-$C_6$alkyl, $C_1$-$C_6$haloalkyl, or $C_1$-$C_6$deuteroalkyl. In some embodiments of a compound of Formula (I), $R^1$ and $R^2$ are independently hydrogen, deuterium, halogen, or $C_1$-$C_6$alkyl. In some embodiments of a compound of Formula (I), $R^1$ and $R^2$ are hydrogen or deuterium. In some embodiments of a compound of Formula (I), $R^1$ and $R^2$ are hydrogen.

In some embodiments of a compound of Formula (I), X is —O—. In some embodiments of a compound of Formula (I), Z is N. In some embodiments of a compound of Formula (I), Z is $CR^5$.

In some embodiments of a compound of Formula (I), $R^5$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (I), $R^5$ is hydrogen, deuterium, halogen, —CN, or $C_1$-$C_6$alkyl.

In some embodiments of a compound of Formula (I), $R^6$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (I), $R^6$ is hydrogen, deuterium, halogen, —CN, or $C_1$-$C_6$alkyl.

In some embodiments of a compound of Formula (I), Ring B is phenyl. In some embodiments of a compound of Formula (I), Ring B is a 5-membered heteroaryl. In some embodiments of a compound of Formula (I), Ring B is 6-membered heteroaryl. In some embodiments of a compound of Formula (I), Ring B is pyridinyl. In some embodiments of a compound of Formula (I), Ring B is pyridinone.

In some embodiments of a compound of Formula (I), each $R^B$ is independently deuterium, halogen, —CN, —OH, —$OR^a$, $C_1$-$C_6$alkyl, $C_1$-$C_6$haloalkyl, $C_1$-$C_6$deuteroalkyl, $C_2$-$C_6$alkynyl, or cycloalkyl. In some embodiments of a compound of Formula (I), each $R^B$ is independently deuterium, —CN, —OH, —$OR^a$, $C_2$-$C_6$alkyl, $C_1$-$C_6$haloalkyl, $C_1$-$C_6$deuteroalkyl, $C_2$-$C_6$alkynyl, or cycloalkyl. In some embodiments of a compound of Formula (I), each $R^B$ is independently halogen or $C_1$-$C_6$alkyl.

In some embodiments of a compound of Formula (I), m is 1 or 2. In some embodiments of a compound of Formula (I), m is 1-4. In some embodiments of a compound of Formula (I), m is 2-4. In some embodiments of a compound of Formula (I), m is 1. In some embodiments of a compound of Formula (I), m is 2.

In some embodiments of a compound of Formula (I),
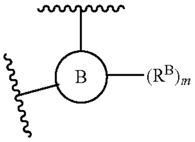 is 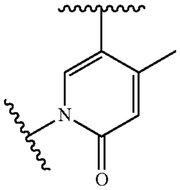, 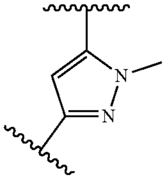, 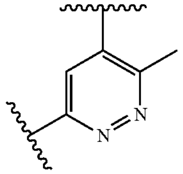, 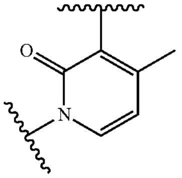, 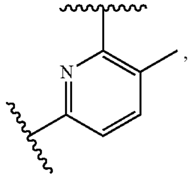, 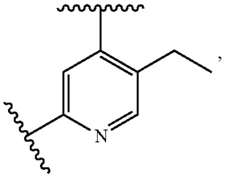 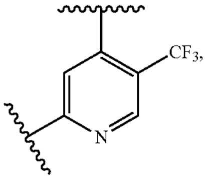 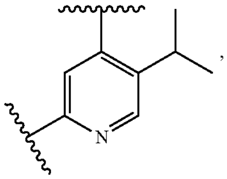, 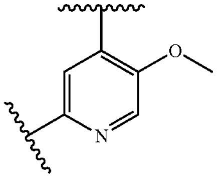, 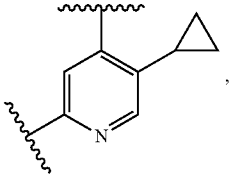, 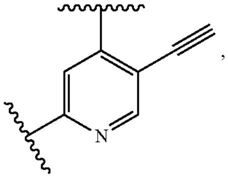 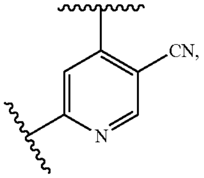 or 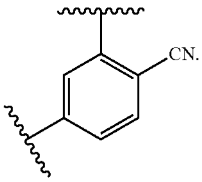
In some embodiments of a compound of Formula (I),
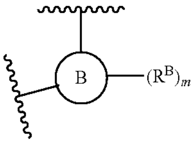 is 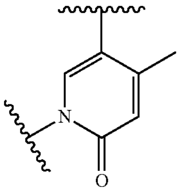,
-continued
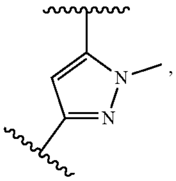, 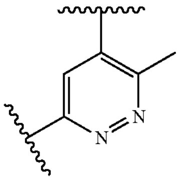, 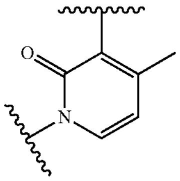, 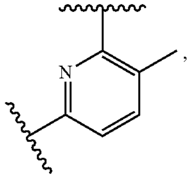, 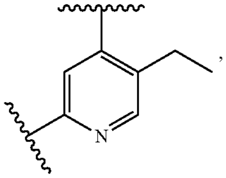 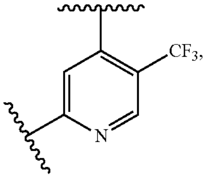 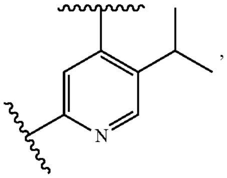, 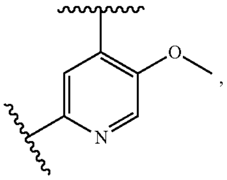, 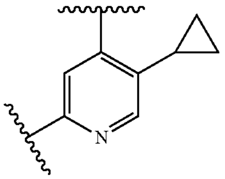, 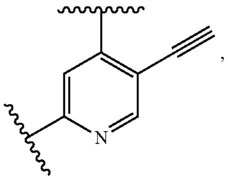, 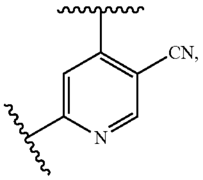 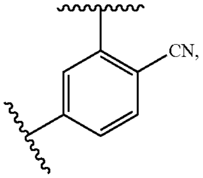 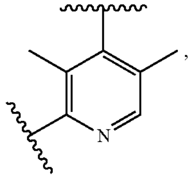, 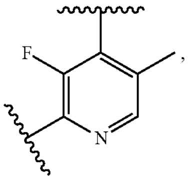, 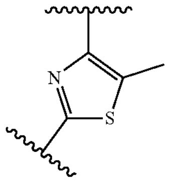, 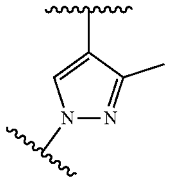, or 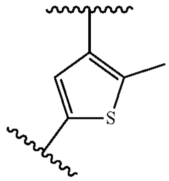.

In some embodiments of a compound of Formula (I),

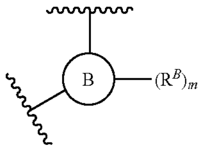

is

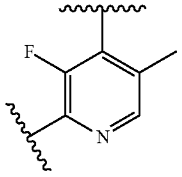

.

In some embodiments of a compound of Formula (I), Ring C is a 5- or 6-membered heteroaryl. In some embodiments of a compound of Formula (I), Ring C is a pyrimidinyl.

In some embodiments of a compound of Formula (I), Ring C is thiazolyl, pyrazolyl, imidazolyl, oxazolyl, thiadiazole, or triazolyl. In some embodiments of a compound of Formula (I), Ring C is thiazolyl. In some embodiments of a compound of Formula (I), Ring C is pyrazolyl. In some embodiments of a compound of Formula (I), Ring C is imidazolyl. In some embodiments of a compound of Formula (I), Ring C is thiadiazole. In some embodiments of a compound of Formula (I), Ring C is triazolyl.

In some embodiments of a compound of Formula (I), each $R^C$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (I), each $R^C$ is independently $C_1$-$C_6$hydroxyalkyl.

In some embodiments of a compound of Formula (I), p is 1 or 2. In some embodiments of a compound of Formula (I), p is 1. In some embodiments of a compound of Formula (I), p 2.

Also disclosed herein is a compound of Formula (II), or a pharmaceutically acceptable salt, solvate, N-oxide, or stereoisomer thereof:

Formula (II)

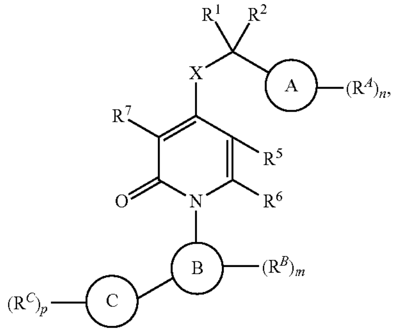

wherein;

Ring A is phenyl or heteroaryl;

each $R^A$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$_2NR^cR^d$, —$NR^cR^d$, —$NR^c$C(═O)$NR^cR^d$, —$NR^c$C(═O)$R^a$, —$NR^c$C(═O)$OR^b$, —NR'S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Aa}$;

or two $R^A$ on the same atom are taken together to form an oxo;

each $R^{Aa}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)—$NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Aa}$ on the same atom are taken together to form an oxo;

n is 0-4;

$R^1$ and $R^2$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

X is —$C(R^3)_2$—, —$NR^4$—, —O—, or —S—;

each $R^3$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or two $R^3$ are taken together to form an oxo;

$R^4$ is hydrogen, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^5$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_1$-$C_6$alkenyl, $C_2$-$C_6$alkynyl, cycloalkyl, or heterocycloalkyl;

$R^7$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Ring B is heterocycloalkyl or heteroaryl;

each $R^B$ is independently hydrogen, deuterium, halogen, —CN, —$NO_2$, —OH, —$OR^a$, —OC(═O)$R^a$, —OC(═O)$OR^b$. —OC(═O)$NR^cR^d$, —SH, —$SR^a$, —S(═O)$R^a$, —S(═O)$R^a$, —S(═O)$_2NR^cR^d$, —$NR^cR^d$, —$NR^c$C(═O)$NR^cR^d$, —$NR^c$C(═O)$R^a$, —$NR^c$C (═O)$OR^b$, —$NR^b$S (═O)$_3R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

or two $R^B$ on the same atom are taken together to form an oxo;

each $R^{Ba}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)—$NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl. C, —$C_6$alkynyl, cycloalkyl, heterocycloalkyl, aryl, or heteroaryl;

or two $R^{Ba}$ on the same atom are taken together to form an oxo;

m is 0-4;

Ring C is 5-membered heteroaryl;

each $R^C$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$_2NR^cR^d$, —S(═O) (═$NR^b$)$R^a$, —SiRCRdOR$^b$, —$NR^cR^d$—$NR^c$C (═O)$NR^cR^d$, —$NR^c$C(═O)$R^a$, —$NR^c$C(═O)$OR^b$, —NR'S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl) aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ca}$;

each $R^{Ca}$ is independently deuterium, halogen, —CN, —$NO_2$, —OH, —$OR^a$-OC(═O)$R^a$, —OC(═O)$OR^b$, —OC(═O)$NR^cR^d$-SH, —$SR^a$, —S(═O)$R^a$, —S(═O)$_3R^a$-S(═O)—$NR^cR^d$—$NR^cR^d$—$NR^c$C(═O)$NR^cR^d$—$NR^c$C(═O)$R^a$, —$NR^c$C(═O)$OR^b$, —$NR^b$S(═O)$R^a$, —C(═O)$R^a$—C(═O)C(═O)$R^a$, —C(═O)$OR^b$, —C(═O)$NR^cR^d$—C(═O)C(═O)$NR^cR^d$. $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ca}$ on the same atom are taken together to form an oxo;

p is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH. —$OCH_3$, —S(═O)$CH_3$, —S(═O)$_2CH_3$, —S(—O)$_2NH_2$, —S(═O)$_2NHCH_3$, —S(═O)—N$(CH_3)_2$, —$NH_2$, —$NHCH_3$, —N$(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH. —$OCH_3$, —S(═O)$CH_3$, —S(—O)$_2CH_3$, —S(═O)$_2NH_2$, —S(═O)$_2NHCH_3$, —S(═O)$_2$N$(CH_3)_2$ , —$NH_2$, —$NHCH_3$, —N$(CH_3)$, —C(═O)$CH_3$, —C(═O)OH, —C(═O)$OCH_3$, $C_1$-$C_6$alkyl, $C_1$-$C_6$ haloalkyl, $C_1$-$C_6$deuteroalkyl. $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl). $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo. deuterium, halogen, —CN, —OH, —$OCH_3$, —S(═O)$CH_3$, —S(═O)$_3CH_3$, —S(═O)$_2NH_2$, —S(═O) ¿$NHCH_3$, —S(═O)$_2$N$(CH_3)_2$ , —$NH_2$, —$NHCH_3$, —N$(CH_3)_2$ , —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)N$(CH_3)_2$ , —$NH_2$, —$NHCH_3$, —N$(CH_3)_2$ , —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

provided that the compound is not

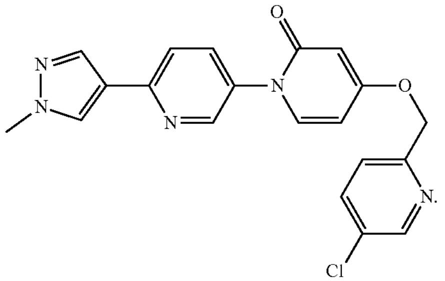 [SMILES: Cn1cc(-c2ccc(-n3ccc(OCc4ccc(Cl)cn4)cc3=O)cn2)cn1]

In some embodiments of a compound of Formula (II), Ring A is heteroaryl. In some embodiments of a compound of Formula (II), Ring A is pyridyl. In some embodiments of a compound of Formula (II), Ring A is phenyl.

In some embodiments of a compound of Formula (II), each $R^A$ is independently deuterium, halogen, —CN, —OH, —$OR^a$, —$NR^cR^d$, $C_1$-$C_6$alkyl, $C_1$-$C_6$ haloalkyl, or $C_1$-$C_6$deuteroalkyl. In some embodiments of a compound of Formula (II), each $R^A$ is independently halogen or $C_1$-$C_6$alkyl. In some embodiments of a compound of Formula (II), each $R^A$ is independently halogen.

In some embodiments of a compound of Formula (II), n is 1 or 2. In some embodiments of a compound of Formula (II), n is 1-3. In some embodiments of a compound of Formula (II), n is 2. In some embodiments of a compound of Formula (II), n is 1.

In some embodiments of a compound of Formula (II), $R^1$ and $R^2$ are independently hydrogen, deuterium, halogen, $C_1$-$C_6$alkyl, $C_1$-$C_6$haloalkyl, or $C_1$-$C_6$deuteroalkyl. In some embodiments of a compound of Formula (II), $R^1$ and $R^2$ are independently hydrogen, deuterium, halogen, or $C_1$-$C_6$alkyl. In some embodiments of a compound of Formula (II), $R^1$ and $R^2$ are independently hydrogen or deuterium. In some embodiments of a compound of Formula (II), $R^1$ and $R^2$ are hydrogen.

In some embodiments of a compound of Formula (II), X is —O—.

In some embodiments of a compound of Formula (II), $R^5$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (II), $R^5$ is hydrogen, deuterium, halogen, —CN, or $C_1$-$C_6$alkyl.

In some embodiments of a compound of Formula (II), $R^6$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (II), $R^6$ is hydrogen, deuterium, halogen, —CN, or $C_1$-$C_6$alkyl.

In some embodiments of a compound of Formula (II), $R^7$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (II), $R^7$ is hydrogen, deuterium, halogen, —CN, or $C_1$-$C_6$alkyl.

In some embodiments of a compound of Formula (II), Ring B is a 6-membered heteroaryl. In some embodiments of a compound of Formula (II), Ring B is pyridinyl.

In some embodiments of a compound of Formula (II), each $R^B$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (II), each $R^B$ is independently halogen or $C_1$-$C_6$alkyl. In some embodiments of a compound of Formula (II), each $R^B$ is independently $C_1$-$C_6$alkyl.

In some embodiments of a compound of Formula (II), m is 1 or 2. In some embodiments of a compound of Formula (II), m is 1-4. In some embodiments of a compound of Formula (II), m is 2-4. In some embodiments of a compound of Formula (II), m is 1. In some embodiments of a compound of Formula (II), m is 2.

In some embodiments of a compound of Formula (II), Ring C is thiazolyl, pyrazolyl, imidazolyl, oxazolyl, thiadiazole, or triazolyl. In some embodiments of a compound of Formula (II), Ring C is thiazolyl. In some embodiments of a compound of Formula (II), Ring C is pyrazolyl. In some embodiments of a compound of Formula (II), Ring C is imidazolyl. In some embodiments of a compound of Formula (II), Ring C is thiadiazole. In some embodiments of a compound of Formula (II), Ring C is triazolyl.

In some embodiments of a compound of Formula (II), each $R^C$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (II), each $R^c$ is independently $C_1$-$C_6$hydroxyalkyl.

In some embodiments of a compound of Formula (II), p is 1 or 2. In some embodiments of a compound of Formula (II), p is 1-3. In some embodiments of a compound of Formula (II), p is 1. In some embodiments of a compound of Formula (II), p is 2.

Also disclosed herein is a compound of Formula (III), or a pharmaceutically acceptable salt, solvate, N-oxide, or stereoisomer thereof:

Formula (III)

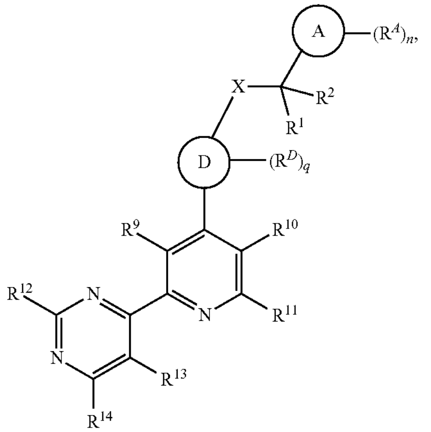

wherein;

Ring A is phenyl or heteroaryl;

each $R^A$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(—O)$NR^cR^d$, —$NR^cR^d$, —$NR^c$C. (—O)$NR^cR^d$, —$NR^c$C(═O)$R^a$, —NR$^c$C(═O)OR$^b$, —NR$^b$S(═O)R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more R$^{4a}$;

or two R$^4$ on the same atom are taken together to form an oxo;

each R$^a$ is independently deuterium, halogen, —CN, —$NO_2$, —OH, —OR$^a$, —OC(═O)R$^a$, —OC(═O)OR$^b$, —OC(═O)NR$^c$R$^4$, —SH, —SR$^a$, —S(═O)R$^a$, —S(═O)R$^a$, —S(═O)NR$^c$R$^d$, —NR$^c$R$^d$, —NR$^c$C(═O)NR$^c$R$^d$, —NR$^c$C(═O)R$^a$, —NR$^c$C(═O)OR$^b$, —NR$^b$S(═O)R$^a$, —C(═O)R$^a$, —C(═O)C(═O)R$^a$, —C(═O)OR$^b$, —C(═O)NR$^c$R$^d$, —C(═O)C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two R$^{4a}$ on the same atom are taken together to form an oxo;

n is 0-4;

R$^1$ and R$^2$ are independently hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or R$^1$ and R$^2$ are taken together to form an oxo;

or R$^1$ and R$^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

X is —C(R$^3$)$_2$-, —NR$^4$—, —O—, or —S—;

each R$^3$ are independently hydrogen, deuterium, halogen, —CN, —$NO_2$, —OH, —OR$^a$, —NR$^c$R$^4$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or two R$^3$ are taken together to form an oxo;

R$^4$ is hydrogen, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Ring D is cycloalkyl, heterocycloalkyl, aryl, or heteroaryl;

each R$^D$ is independently hydrogen, deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)R$^a$, —S(═O)$_2$NR$^c$R$^d$, —NR$^c$R$^d$, —NR$^c$C(═O)NR$^c$R$^d$, —NR$^c$C(═O)R$^a$, —NR$^c$C (═O)OR$^b$, —NR$^b$S (═O)$_3$R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more R$^{Da}$;

or two R$^D$ on the same atom are taken together to form an oxo;

each R$^{Da}$ is independently deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)R$^a$, —S(═O)NR$^c$R$^d$, —NR$^c$R$^d$, —NR$^c$C(═O)NR$^c$R$^d$, —NR$^c$C(═O)R$^a$, —NR$^c$C(═O)OR$^b$, —NR$^b$S (═O)$_3$R$^a$, —C(═O)R$^a$, —C(═O)C(═O)R$^a$, —C(═O)OR$^b$, —C(═O)NR$^c$R$^d$, —C(═O)C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two R$^{Da}$ on the same atom are taken together to form an oxo;

q is 0-6;

R$^9$ is hydrogen, deuterium, halogen, —CN, —$NO_2$, —OH, —OR$^a$, —NR$^c$R$^d$, —C(═O)R$^a$, —C(—O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

R$^{10}$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. $C_2$-$C_6$alkenyl, $C_2$-$C_6$alkynyl, cycloalkyl, or heterocycloalkyl;

R$^{11}$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. $C_2$-$C_6$alkenyl, $C_2$-$C_6$alkynyl, cycloalkyl, or heterocycloalkyl;

R$^{12}$ is hydrogen, deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_3$R$^a$, —S(═O)$_3$NR$^c$R$^d$, —S(═O) (═NR$^b$)R$^a$-SiRCRdOR$^b$, —NR$^c$R$^d$—NR$^c$C(═O)NR$^c$R$^d$—NR$^b$C (═O)R$^a$, —NR$^c$C (═O)OR$^b$, —NR'S(═O)R$^a$, —C(═O)R$^a$, —C(═O) ORh, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl. $C_1$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl) aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more R$^{12a}$;

each R$^{12a}$ is independently deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_3$R$^a$, —S(═O)$_2$NR$^c$R$^d$, —NR$^c$R$^d$—NR$^c$C(═O)NR$^c$R$^d$, —NR$^c$C(═O)R$^a$, —NR$^c$C(═O)OR$^b$, —NR$^b$S(═O)R$^a$, —C(═O)R$^a$, —C(═O)C(═O)R$^a$, —C(═O)OR$^b$, —C(═O)NR$^c$R$^d$, —C(═O)C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{12a}$ on the same atom are taken together to form an oxo;

$R^{13}$ is hydrogen, deuterium, halogen, —CN, —$NO_2$, —OH, —$OR^a$, —$NR^cR^d$-C(=O)$R^a$—C(=O)$OR^b$, —C(—O)$NR^cR^d$. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. $C_2$-$C_6$alkenyl, $C_2$-$C_6$alkynyl, cycloalkyl, or heterocycloalkyl;

$R^1$+ is hydrogen, deuterium, halogen, —CN, —$NO_2$, —OH, —$OR^a$, —$NR^cR^d$-C(=O)$R^a$—C(=O)$OR^b$, —C(=O)$NR^cR^d$. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. $C_1$-$C_6$alkenyl, $C_2$-$C_6$alkynyl, cycloalkyl, or heterocycloalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl. $C_1$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH. —$OCH_3$, —S(=O)$CH_3$, —S(=O)$_2CH_3$, —S(=O)$_2NH_2$, —S(=O)$_2NHCH_3$, —S(=O)$_3$N($CH_3$)$_3$, —$NH_2$, —$NHCH_3$, —N($CH_3$)$_2$, —C(=O)$CH_3$, —C(=O)OH, —C(—O)$OCH_3$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(—O)$_2CH_3$, —S(=O)$_2NH_2$, —S(=O)$_2NHCH_3$, —S(=O)$_2$N($CH_3$)$_2$ , —$NH_2$, —$NHCH_3$, —N($CH_3$)$_2$, —C(=O)$CH_3$, —C(=O)OH, —C(=O)$OCH_3$ $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl). $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo. deuterium, halogen, —CN, —OH, —$OCH_3$, —S(=O)$CH_3$, —S(=O)$_2CH_3$, —S(=O), $NH_2$, —S(=O),$NHCH_3$, —S (=O)$_2$N($CH_3$)$_2$, —$NH_2$, —$NHCH_3$, —N($CH_3$)$_2$, —C(=O)$CH_3$, —C(=O)OH, —C(=O)$OCH_3$, $C_1$-$C_6$alkyl. $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2$N($CH_3$)$_2$ , —$NH_2$, —$NHCH_3$, —N($CH_3$)$_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, or $C_1$-$C_6$heteroalkyl;

provided that

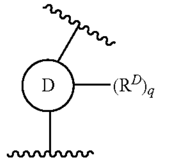

is not

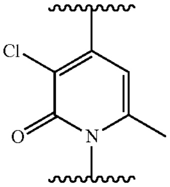
,
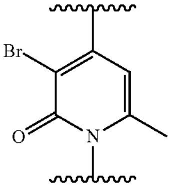
,
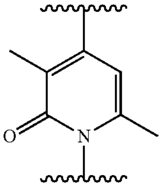
, or
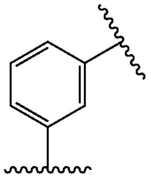
.

In some embodiments of a compound of Formula (III), Ring A is heteroaryl. In some embodiments of a compound of Formula (III), Ring A is pyridyl. In some embodiments of a compound of Formula (III), Ring A is phenyl.

In some embodiments of a compound of Formula (III), each $R^A$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (III), each $R^A$ is independently halogen or $C_1$-$C_6$alkyl. In some embodiments of a compound of Formula (III), each $R^A$ is independently halogen.

In some embodiments of a compound of Formula (III), n is 1 or 2. In some embodiments of a compound of Formula (III), n is 1-3. In some embodiments of a compound of Formula (III), n is 2. In some embodiments of a compound of Formula (III), n is 1.

In some embodiments of a compound of Formula (III), $R^1$ and $R^2$ are independently hydrogen, deuterium, halogen, $C_1$-$C_6$alkyl, $C_1$-$C_6$haloalkyl, or $C_1$-$C_6$deuteroalkyl. In some embodiments of a compound of Formula (III), $R^1$ and $R^2$ are independently hydrogen, deuterium, halogen, or $C_1$-$C_6$alkyl. In some embodiments of a compound of Formula (III), $R^1$ and $R^2$ are hydrogen.

In some embodiments of a compound of Formula (III), X is —O—.

In some embodiments of a compound of Formula (III), Ring D is phenyl. In some embodiments of a compound of Formula (III), Ring D is pyridinyl.

In some embodiments of a compound of Formula (III), each $R^D$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, cycloalkyl, or heterocycloalkyl; or two $R^D$ on the same atom are taken together to form an oxo. In some embodiments of a compound of Formula (III), each $R^D$ is independently hydrogen, deuterium, halogen, —CN, —$OR^a$, $C_1$-$C_6$alkyl, $C_2$-$C_6$alkynyl, cycloalkyl, or heterocycloalkyl; or two $R^D$ on the same atom are taken together to form an oxo.

In some embodiments of a compound of Formula (III), q is 1-4. In some embodiments of a compound of Formula (III), q is 1-3. In some embodiments of a compound of Formula (III), q is 2-4.

In some embodiments of a compound of Formula (III),

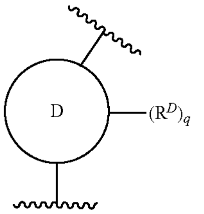

is

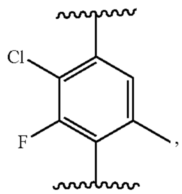,

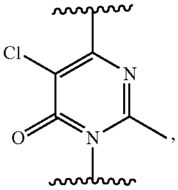,

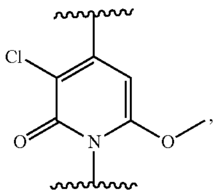,

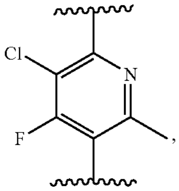,

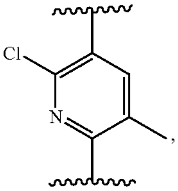,

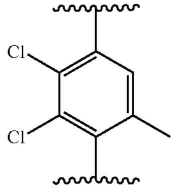,

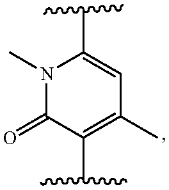,

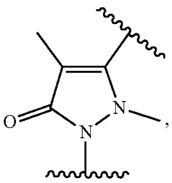,

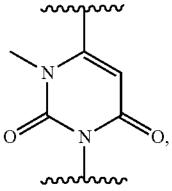,

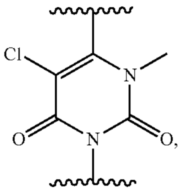,

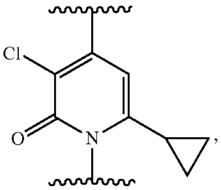,

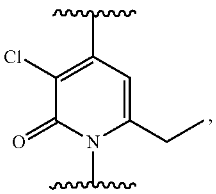,

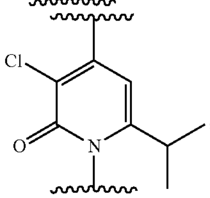,

-continued

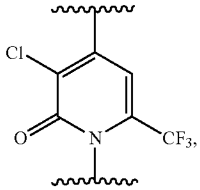,

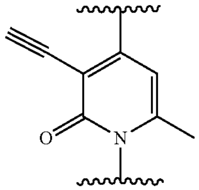,

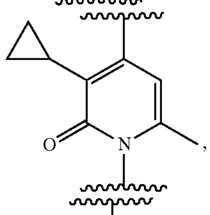,

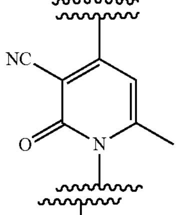,

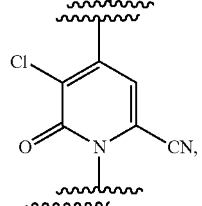,

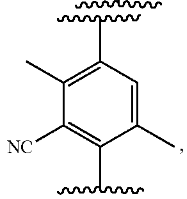,

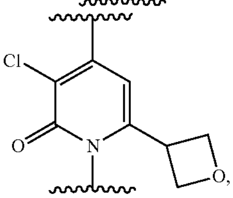,

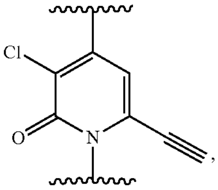,

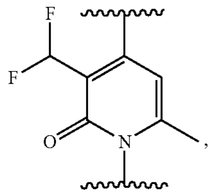,

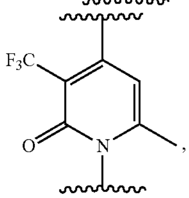, or

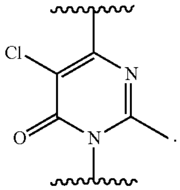.

In some embodiments of a compound of Formula (III), $R^9$ is hydrogen, deuterium, halogen, $C_1$-$C_6$alkyl, or $C_1$-$C_6$haloalkyl.

In some embodiments of a compound of Formula (III), $R^{10}$ is hydrogen, deuterium, halogen, $C_1$-$C_6$alkyl, or $C_1$-$C_6$haloalkyl.

In some embodiments of a compound of Formula (III), $R^{11}$ is hydrogen, deuterium, halogen, $C_1$-$C_6$alkyl, or $C_1$-$C_6$haloalkyl.

In some embodiments of a compound of Formula (III), $R^{12}$ is hydrogen, deuterium, halogen, —CN, —OH, —$OR^a$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (III), $R^{12}$ is $C_1$-$C_6$hydroxyalkyl.

In some embodiments of a compound of Formula (III), $R^{13}$ is hydrogen, deuterium, halogen, or $C_1$-$C_6$alkyl.

In some embodiments of a compound of Formula (III), $R^{14}$ is hydrogen, deuterium, halogen, or $C_1$-$C_6$alkyl.

A compound of Formula (IV), or a pharmaceutically acceptable salt, solvate, N-oxide, or stereoisomer thereof:

Formula (IV)

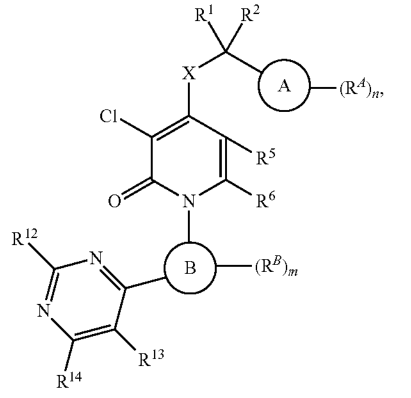

wherein:

Ring A is phenyl or heteroaryl;

each $R^A$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —$S(═O)_2NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Aa}$;

or two $R^A$ on the same atom are taken together to form an oxo;

each $R^{Aa}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Aa}$ on the same atom are taken together to form an oxo;

n is 0-4;

$R^1$ and $R^2$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$ , —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

X is —$C(R^3)_2$-, —$NR^4$—, —O—, or —S—;

each $R^3$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or two $R^3$ are taken together to form an oxo;

$R^4$ is hydrogen, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^5$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Ring B is cycloalkyl, heterocycloalkyl, alkyl, or heteroaryl;

each $R^B$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —$S(═O)_2NR^cR^d$, —$NR^cR^d$, —$NR^c$C(═O)$NR^cR^d$, —$NR^c$C(═O)$R^a$, —$NR^c$C(═O)$OR^b$, —$NR^c$S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

or two $R^B$ on the same atom are taken together to form an oxo;

each $R^{Ba}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ba}$ on the same atom are taken together to form an oxo;

m is 0-4;

$R^{12}$. $R^{13}$, and $R^1$+ are defined in (a), (b), or (c) as follow;

(a)

$R^{12}$ is deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$NR^cR^d$, —S(═O)(═$NR^b$)$R^a$, —SiRÖRdOR$^b$, —$NR^cR^4$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)$OR^b$, —C(═O)

NR$^c$R$^d$, $C_1$-$C_6$haloalkyl, $C_1$-$C_6$dihydroxyalkyl, $C_1$-$C_6$aminoalkyl, $C_1$-$C_6$hydroxyheteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl) aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more R$^{12a}$;

each R$^{12a}$ is independently deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)R$^a$, —S(═O)$_2$NR$^c$R$^d$, —NR$^c$R$^d$, —NR$^c$C(═O)NR$^c$R$^d$, —NR$^c$C(═O)R$^a$, —NR$^c$C(═O)OR$^b$, —NR$^b$S(═O)R$^a$, —C(═O)R$^a$, —C(═O)C(═O)R$^a$, —C(═O)OR$^b$, —C(═O)NR$^c$R$^d$, —C(═O)C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two R$^{12a}$ on the same atom are taken together to form an oxo:

R$^{13}$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

R$^{14}$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or (b)

R$^{12}$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

R$^{13}$ is deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

R$^{14}$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or (c)

R$^{12}$ is hydrogen, deuterium, halogen, —CN, —$NO_2$, —OH, —OR$^a$, —NR$^c$R$^d$, —C(═O)R$^a$, —C(═O)OR$^b$, —C (—O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

R$^{13}$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

R$^{14}$ is deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

each R$^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O) 2N$(CH_3)_2$, —$NH_2$, —$NHCH_3$, —N$(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each R$^b$ is independently hydrogen, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH. —$OCH_3$, —S(═O)$CH_3$, —S(═O)$_2CH_3$, —S(—O)$_3NH_2$, —S(═O)$_2NHCH_3$, —S(═O)$_2$N$(CH_3)_2$, —$NH_2$, —$NHCH_3$, —N$(CH_3)_2$ , —C(═O)$CH_3$, —C(═O)OH, —C(═O)$OCH_3$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, or $C_1$-$C_6$heteroalkyl; and each R$^c$ and R$^d$ are independently hydrogen, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl). $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo. deuterium, halogen, —CN, —OH, —$OCH_3$, —S(═O)$CH_3$, —S(—O)$_3CH_3$, —S(═O),$NH_2$, —S(═O)$NHCH_3$, —S(═O)$_2$N$(CH_3)_2$ , —$NH_2$, —$NHCH_3$, —N$(CH_3)_2$ , —C(═O)$CH_3$, —C(═O)OH, —C(═O)$OCH_3$, $C_1$-$C_6$alkyl. $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or R$^c$ and R$^d$ are taken together with the atom to which they are attached to form a heterocycloalkyl optionally substituted with one or more oxo, deuterium, halogen, —CN, —OH, —$OCH_3$, —S(═O)$CH_3$, —S(═O)$_2CH_3$, —S(═O)$NH_2$, —S(═O)$_2NHCH_3$, —S(═O)N$(CH_3)_2$ , —$NH_2$, —$NHCH_3$, —N$(CH_3)_2$, —C(═O)$CH^3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, or $C_1$-$C_6$heteroalkyl.

In some embodiments of a compound of Formula (IV). Ring A is heteroaryl. In some embodiments of a compound of Formula (IV). Ring A is pyridyl. In some embodiments of a compound of Formula (IV). Ring A is phenyl.

In some embodiments of a compound of Formula (IV), each $R^A$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (IV), each $R^A$ is independently halogen or $C_1$-$C_6$alkyl. In some embodiments of a compound of Formula (IV), each $R^A$ is independently halogen.

In some embodiments of a compound of Formula (IV), n is 1 or 2. In some embodiments of a compound of Formula (IV), n is 1-3. In some embodiments of a compound of Formula (IV), n is 2. In some embodiments of a compound of Formula (IV), n is 1.

In some embodiments of a compound of Formula (IV). $R^1$ and $R^2$ are independently hydrogen. deuterium, halogen, $C_1$-$C_6$alkyl, $C_1$-$C_6$haloalkyl, or $C_1$-$C_6$deuteroalkyl. In some embodiments of a compound of Formula (IV). $R^1$ and $R^2$ are independently hydrogen, deuterium, halogen, or $C_1$-$C_6$alkyl. In some embodiments of a compound of Formula (IV). $R^1$ and $R^2$ are hydrogen.

In some embodiments of a compound of Formula (IV). X is —O—.

In some embodiments of a compound of Formula (IV), $R^5$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (IV), $R^5$ is hydrogen, deuterium, halogen, —CN, or $C_1$-$C_6$alkyl.

In some embodiments of a compound of Formula (IV), $R^6$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl. $C_1$-$C_6$heteroalkyl, $C_2$-$C_6$alkynyl, or cycloalkyl. In some embodiments of a compound of Formula (IV), Ro is hydrogen, deuterium, halogen, —CN, or $C_1$-$C_6$alkyl.

In some embodiments of a compound of Formula (IV), Ring B is a 6-membered heteroaryl. In some embodiments of a compound of Formula (IV), Ring B is pyridinyl.

In some embodiments of a compound of Formula (IV), each $R^B$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (IV), each $R^B$ is independently hydrogen, deuterium, halogen, —CN, —$OR^a$, $C_1$-$C_6$alkyl, $C_2$-$C_6$alkynyl, or cycloalkyl. In some embodiments of a compound of Formula (IV), each $R^B$ is independently $C_1$-$C_6$alkyl.

In some embodiments of a compound of Formula (IV), m is 1 or 2. In some embodiments of a compound of Formula (IV), m is 1-4. In some embodiments of a compound of Formula (IV), m is 2-4. In some embodiments of a compound of Formula (IV), m is 1. In some embodiments of a compound of Formula (IV), m is 2.

In some embodiments of a compound of Formula (IV);

$R^{12}$ is deuterium, halogen, —CN, —OH, —$OR^a$, —$S(=O)_2NR^cR^d$, —S(=O) (=$NR^b$)$R^a$, —SiRCR-dOR$^b$, —NRPS(=O)$R^a$. $C_1$-$C_6$haloalkyl, $C_1$-Codihydroxyalkyl, $C_1$-$C_6$aminoalkyl, $C_1$-$C_6$hydroxyheteroalkyl, $C_2$-$C_6$alkynyl. cycloalkyl, heterocycloalkyl, ($C_1$-$C_6$alkyl)cycloalkyl, or ($C_1$-$C_6$alkyl)heterocycloalkyl; wherein the alkyl, alkynyl, cycloalkyl, and heterocycloalkyl is optionally and independently substituted with one or more $R^{12a}$;

each $R^{12a}$ is independently deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; or two $R^{12a}$ on the same atom are taken together to form an oxo;

$R^{13}$ is hydrogen, deuterium, halogen, or $C_1$-$C_6$alkyl; and $R^{14}$ is hydrogen, deuterium, halogen, or $C_1$-$C_6$alkyl.

In some embodiments of a compound of Formula (IV):

$R^{12}$ is —S(=O) (=$NR^b$)$R^a$, —SiRCRdOR$^b$, —$NR^b$S(=O)$R^a$, $C_1$-$C_6$haloalkyl, $C_1$-$C_6$dihydroxyalkyl, $C_1$-$C_6$aminoalkyl, $C_1$-$C_6$hydroxyheteroalkyl, $C_2$-$C_6$alkynyl, cycloalkyl, heterocycloalkyl, or ($C_1$-$C_6$alkyl)cycloalkyl; wherein the alkyl, alkynyl, cycloalkyl, and heterocycloalkyl is optionally and independently substituted with one or more $R^{12a}$;

each $R^{12a}$ is independently-OH, —$NR^cR^d$, or $C_1$-$C_6$haloalkyl;

$R^{13}$ is hydrogen; and $R^{14}$ is hydrogen.

In some embodiments of a compound of Formula (IV);

$R^{12}$ is $C_1$-$C_6$hydroxyalkyl;

$R^{13}$ is deuterium, halogen, —CN, —OH, —OR3, —$NR^cR^d$, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, cycloalkyl, or heterocycloalkyl; and $R^{14}$ is hydrogen, deuterium, halogen, or $C_1$-$C_6$alkyl.

In some embodiments of a compound of Formula (IV);

$R^{12}$ is $C_1$-$C_6$hydroxyalkyl;

$R^{13}$ is hydrogen, deuterium, halogen, or $C_1$-$C_6$alkyl; and $R^{14}$ is deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, cycloalkyl, or heterocycloalkyl.

Also disclosed herein is a compound of Formula (V), or a pharmaceutically acceptable salt, solvate, N-oxide, or stereoisomer thereof:

Formula (V)

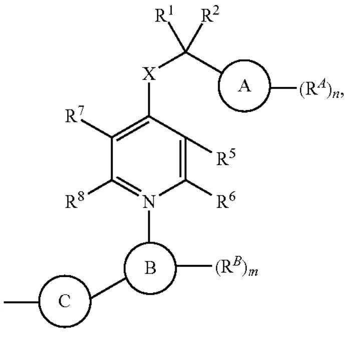

wherein;

Ring A is phenyl or heteroaryl;

each $R^A$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$R^a$, —S(=O)$NR^cR^d$, —$NR^cR^d$, —$NR^c$C(=O)$NR^cR^d$, —$NR^c$C(=O)$R^a$, —$NR^c$C(=O)$OR^b$, —$NR^b$S(=O)$R^a$, —C(=O)$R^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{4a}$.

or two $R^4$ on the same atom are taken together to form an oxo;

each $R^{4a}$ is independently deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)R$^a$, —S(═O)$_2$NR$^c$R$^d$, —NR$^c$R$^d$, —NR$^c$C(═O)NR$^c$R$^d$, —NR$^c$C(═O)R$^a$, —NR$^c$C(═O)OR$^b$, —NR$^b$S(═O)R$^a$, —C(═O)R$^a$, —C(═O)C(═O)R$^a$, —C(═O)OR$^b$, —C(═O)NR$^c$R$^d$, —C(═O)C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{4a}$ on the same atom are taken together to form an oxo;

n is 0-4;

$R^1$ and $R^2$ are independently hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$ , —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

X is —C($R^3$)$_2$-, —NR$^4$—, —O—, or —S—;

each $R^3$ are independently hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or two $R^3$ are taken together to form an oxo;

$R^4$ is hydrogen, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^5$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —OR$^a$, —NR$^c$R$^d$, —C(═O)R$^a$—C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^7$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^8$ is hydrogen, deuterium, halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, CI-Cohydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Ring B is pyridinone, pyrimidinone, pyrazinone, or pyridazinone each $R^B$ is independently hydrogen, deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)R$^a$, —S(═O)$_2$NR$^c$R$^d$, —NR$^c$R$^d$, —NR$^c$C(═O)NR$^c$R$^d$, —NR$^c$C(═O)R$^a$, —NR$^c$C(═O)OR$^b$, —NR'S(═O)R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

or two $R^B$ on the same atom are taken together to form an oxo;

each $R^{Ba}$ is independently deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)R$^a$, —S(═O)—NR$^c$R$^d$, —NR$^c$R$^4$, —NR$^c$C(═O)NR$^c$R$^d$, —NR$^c$C(═O)R$^a$, —NR$^c$C(═O)OR$^b$, —NR'S(═O)R$^a$, —C(═O)R$^a$, —C(═O)C(═O)R$^a$, —C(═O)OR$^b$, —C(═O)NR$^c$R$^d$, —C(═O)C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ba}$ on the same atom are taken together to form an oxo;

m is 0-4;

Ring C is heterocycloalkyl or heteroaryl;

each $R^C$ is independently hydrogen, deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)R$^a$, —S(═O)$_2$NR$^c$R$^d$, —S(═O) (═NR$^b$)R$^a$, —SiRCRdOR$^b$, —NR$^c$R$^d$, —NR$^c$C(═O)NR$^c$R$^d$, —NR$^c$C(═O)R$^a$, —NR$^c$C(═O)OR$^b$, —NR'S(═O)R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl) aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ca}$;

or two $R^C$ on the same atom are taken together to form an oxo;

each $R^{Ca}$ is independently deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)R$^a$, —S(═O)—NR$^c$R$^d$, —NR$^c$R$^d$, —NR$^c$C(═O)NR$^c$R$^d$, —NR$^c$C(═O)R$^a$, —NR$^c$C(═O)OR$^b$, —$NR^bS$(=O)$R^a$, —C(=O)$R^a$, —C(=O)C(=O)$R^a$, —C(=O)$OR^b$, —C(=O)$NR^cR^d$, —C(=O)C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ca}$ on the same atom are taken together to form an oxo;

p is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O) 2N($CH_3$)$_2$, —$NH_2$, —$NHCH_3$, —N($CH_3$)$_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH. —$OCH_3$, —S(=O)$CH_3$, —S(=O)$_2CH_3$, —S(—O)$_3NH_2$, —S(—O)$_3NHCH_3$, —S(=O)$_3$N($CH_3$)$_2$, —$NH_2$, —$NHCH_3$, —N($CH_3$)$_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl). $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo. deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2$N($CH_3$)$_2$ , —$NH_2$, —$NHCH_3$, —N($CH_3$)$_2$ , —C(=O)$CH_3$, —C(=O)OH, —C(=O)$OCH_3$, $C_1$-$C_6$alkyl. $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$NH_2$, —S(=O)$_3NHCH_3$, —S(=O)$_3$N($CH_3$)$_2$ , —$NH_2$, —$NHCH_3$, —N($CH_3$)$_2$ , —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, or $C_1$-$C_6$heteroalkyl.

In some embodiments of a compound of Formula (V). Ring A is heteroaryl.

In some embodiments of a compound of Formula (V). Ring A is pyridyl.

In some embodiments of a compound of Formula (V). Ring A is phenyl.

In some embodiments of a compound of Formula (V), each $R^A$ is independently deuterium, halogen, —CN, —OH, —$OR^a$—$NR^cR^d$, $C_1$-$C_6$alkyl, $C_1$-$C_6$haloalkyl, or $C_1$-$C_6$deuteroalkyl. In some embodiments of a compound of Formula (V), each $R^A$ is independently halogen or $C_1$-$C_6$alkyl. In some embodiments of a compound of Formula (V), each $R^A$ is independently halogen.

In some embodiments of a compound of Formula (V), n is 1 or 2. In some embodiments of a compound of Formula (V), n is 1-3. In some embodiments of a compound of Formula (V), n is 2. In some embodiments of a compound of Formula (V), n is 1.

In some embodiments of a compound of Formula (V). $R^1$ and $R^2$ are independently hydrogen. deuterium, halogen, $C_1$-$C_6$alkyl, $C_1$-$C_6$haloalkyl, or $C_1$-$C_6$deuteroalkyl. In some embodiments of a compound of Formula (V). $R^1$ and $R^2$ are independently hydrogen, deuterium, halogen, or $C_1$-$C_6$alkyl. In some embodiments of a compound of Formula (V). $R^1$ and $R^2$ are hydrogen.

In some embodiments of a compound of Formula (V), X is —O—.

In some embodiments of a compound of Formula (V), $R^5$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (V), $R^5$ is hydrogen, deuterium, halogen, —CN, or $C_1$-$C_6$alkyl.

In some embodiments of a compound of Formula (V), $R^6$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (V), $R^6$ is hydrogen, deuterium, halogen, —CN, or $C_1$-$C_6$alkyl.

In some embodiments of a compound of Formula (V), $R^7$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (V), $R^7$ is hydrogen, deuterium, halogen, —CN, or $C_1$-$C_6$alkyl.

In some embodiments of a compound of Formula (V), $R^8$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (V), is hydrogen, deuterium, halogen, —CN, or $C_1$-$C_6$alkyl.

In some embodiments of a compound of Formula (V), Ring B is pyridinone. In some embodiments of a compound of Formula (V), Ring B is pyrimidinone. In some embodiments of a compound of Formula (V), Ring B is pyrazinone. In some embodiments of a compound of Formula (V), Ring B is pyridazinone.

In some embodiments of a compound of Formula (V), each $R^B$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (V), each $R^B$ is independently $C_1$-$C_6$alkyl.

In some embodiments of a compound of Formula (IV), m is 1 or 2. In some embodiments of a compound of Formula (IV), m is 1-4. In some embodiments of a compound of Formula (IV), m is 2-4. In some embodiments of a compound of Formula (IV), m is 1. In some embodiments of a compound of Formula (IV), m is 2.

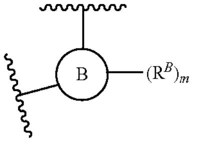

is

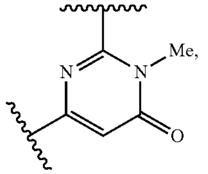

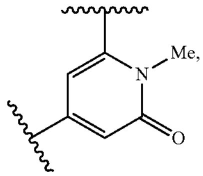

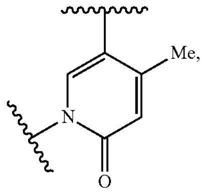

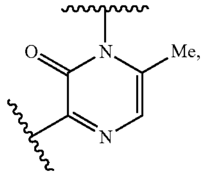

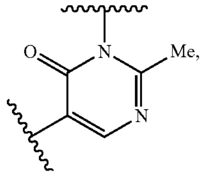

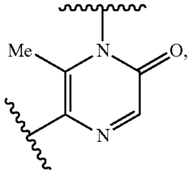

or

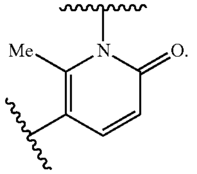

In some embodiments of a compound of Formula (V),

In some embodiments of a compound of Formula (V), Ring C is a 5- or 6-membered heteroaryl. In some embodiments of a compound of Formula (V), Ring C is a pyrimidinyl.

In some embodiments of a compound of Formula (V), each $R^C$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (V), each $R^C$ is independently $C_1$-$C_6$hydroxyalkyl.

In some embodiments of a compound of Formula (V), p is 1 or 2. In some embodiments of a compound of Formula (V), p is 1-3. In some embodiments of a compound of Formula (V), p is 1. In some embodiments of a compound of Formula (V), p is 2.

Also disclosed herein is a compound of Formula (VI), or a pharmaceutically acceptable salt, solvate, N-oxide, or stereoisomer thereof:

Formula (VI)

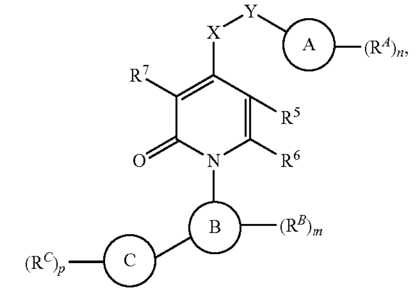

wherein;

Ring A is phenyl or heteroaryl;

each $R^A$ is independently hydrogen, deuterium, halogen, —CN, —$NO_2$, —OH, —$OR^a$, —OC(═O)$R^a$, —OC(═O) OR', —OC(═O)$NR^cR^d$, —SH, —$SR^a$, —S(═O)$R^a$, —S(═O)$R^a$, —S(═O) 2$NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Aa}$.

or two $R^A$ on the same atom are taken together to form an oxo;

each $R^{Aa}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Aa}$ on the same atom are taken together to form an oxo;

n is 0-4;

X and Y are defined in (a) or (b) as follow:

(a)

X is —C$(R^3)_2$—, —$NR^4$—, —O—, or —S—;

Y is —$CR^1R^2$—;

$R^1$ halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^2$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^3$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or two $R^3$ are taken together to form an oxo; and $R^4$ is hydrogen, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or (b)

X is —$C(R^3)_2$—, —$NR^4$—, or —S—;

Y is —$CR^1R^2$—, —$NR^4$—, —O—, or —S—;

$R^1$ and $R^2$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$ , —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^3$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-Calkenyl, $C_2$-$C_6$alkynyl, cycloalkyl, or heterocycloalkyl;

or two $R^3$ are taken together to form an oxo; and $R^4$ is hydrogen, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^5$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^7$ is hydrogen, deuterium, halogen, —CN, —$NO_2$, —OH, —$OR^a$, —$NR^cR^d$, —C(═O)$R^a$, —C(═O)ORh, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_1$-$C_6$alkenyl, $C_2$-$C_6$alkynyl, cycloalkyl, or heterocycloalkyl;

Ring B is heterocycloalkyl or heteroaryl;

each $R^B$ is independently hydrogen, deuterium, halogen, —CN, —$NO_2$, —OH, —$OR^a$, —OC(═O)$R^a$, —OC(═O)$OR^b$. —OC(═O)$NR^cR^d$, —SH, —$SR^a$, —S(═O)$R^a$, —S(═O)$R^a$, —S(═O)$NR^cR^d$, —$NR^cR^d$, —$NR^c$C(═O)$NR^cR^d$, —$NR^c$C(═O)$R^a$, —$NR^c$C (═O)$OR^b$, —NR'S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

or two $R^B$ on the same atom are taken together to form an oxo;

each $R^{Ba}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(—O)$R^a$, —S(═O)$R^a$, —$S(═O)_2NR^cR^d$, —$NR^cR^d$, —$NR^c$C(═O)$NR^cR^d$—$NR^c$C(═O)$R^a$, —$NR^c$C(═O)$OR^b$, —$NR^b$S $(═O)_3R^a$, —C(═O)$R^a$, —C(═O)C(═O)$R^a$, —C(═O)$OR^b$, —C(═O)$NR^cR^d$—C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ba}$ on the same atom are taken together to form an oxo;

m is 0-4;

Ring C is heterocycloalkyl or heteroaryl:

each R' is independently hydrogen, deuterium, halogen, —CN, —$NO_2$, —OH, —$OR^a$, —OC(═O)$R^a$, —OC(═O) ORh. —OC(═O)$NR^cR^d$, —SH, —$SR^a$, —S(═O)$R^a$, —S(═O)$R^a$, —S(—O)$NR^cR^d$, —S(—O) (═$NR^b$)$R^a$, —SiRCRdOR$^b$, —$NR^cR^d$—$NR^c$C(═O)$NR^cR^d$, —$NR^c$C(═O)$R^a$, —$NR^c$C(═O)$OR^b$, —$NR^b$S (—O);$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl) aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ca}$;

or two $R^C$ on the same atom are taken together to form an oxo;

each $R^{Ca}$ is independently deuterium, halogen, —CN, —$NO_2$, —OH, —$OR^a$—OC(═O)$R^a$, —OC(═O)$OR^b$, —OC(═O)$NR^cR^d$-SH, —$SR^a$—S(═O)$R^a$-S(═O)$R^a$, —S(═O) —$NR^cR^d$—$NR^cR^d$—$NR^c$C(═O)$NR^cR^d$—$NR^c$C(═O)$R^a$, —$NR^c$C(═O)$OR^b$, —$NR^b$S $(═O)_3R^a$, —C(═O)$R^a$, —C(═O)C(═O)$R^a$, —C(═O)$OR^b$, —C(═O)$NR^cR^d$—C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl. $C_1$-$C_6$alkenyl, $C_2$-$C_6$alkynyl, cycloalkyl, heterocycloalkyl, aryl, or heteroaryl;

or two $R^{Ca}$ on the same atom are taken together to form an oxo:

p is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH. —$OCH_3$, —S(=O)$CH_3$, —S(=O)$_2CH_3$, —S(—O)$_3NH_2$, —S(=O)$_2NHCH_3$, —S(=O)—N$(CH_3)_2$, —$NH_2$, —$NHCH_3$, —N$(CH_3)_2$ , —C(=O)$CH_3$, —C(=O)OH, —C(=O)$OCH_3$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH. —$OCH_3$, —S(=O)$CH_3$, —S(—O)$_2CH_3$, —S(=O)$_2NH_2$, —S(=O)$_3NHCH_3$, —S(=O)$_3$N$(CH_3)_3$, —$NH_2$, —$NHCH_3$, —N$(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. $C_1$-$C_6$alkenyl. $C_1$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl). $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo. deuterium, halogen, —CN, —OH, —$OCH_3$, —S(=O)$CH_3$, —S(=O)$_2CH_3$, —S(—O)$_2NH_2$, —S(=O) ¿$NHCH_3$, —S(=O)$_2$N$(CH_3)_2$, —$NH_2$, —$NHCH_3$, —N$(CH_3)_2$, —C(=O)$CH_3$, —C(=O)OH, —C(=O)$OCH_3$, $C_1$-$C_6$alkyl. $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$NH_2$, —S(=O)$_2NHCH_3$, —S(=O)$_2$N$(CH_3)_2$, —$NH_2$, —$NHCH_3$, —N$(CH_3)_2$, —C(=O)$CH_3$, —C(=O)OH, —C(—O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

provided that the compound is not;

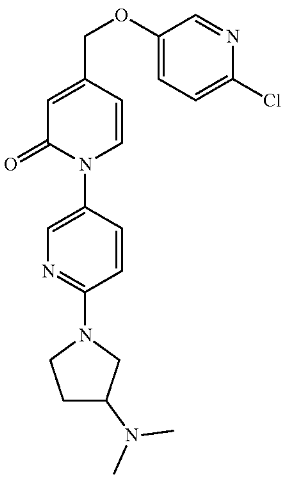

or

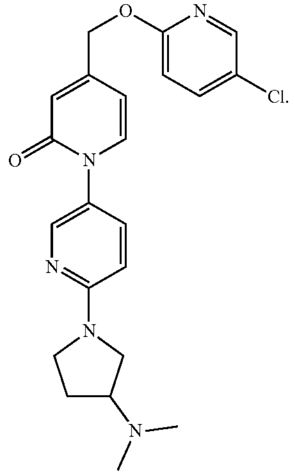

In some embodiments of a compound of Formula (VI), Ring A is heteroaryl. In some embodiments of a compound of Formula (VI), Ring A is pyridyl. In some embodiments of a compound of Formula (VI), Ring A is phenyl.

In some embodiments of a compound of Formula (VI), each $R^A$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (VI), each $R^A$ is independently halogen or $C_1$-$C_6$alkyl. In some embodiments of a compound of Formula (VI), each $R^A$ is independently halogen.

In some embodiments of a compound of Formula (VI), n is 1 or 2. In some embodiments of a compound of Formula (VI), n is 1-3. In some embodiments of a compound of Formula (VI), n is 2. In some embodiments of a compound of Formula (VI), n is 1.

In some embodiments of a compound of Formula (VI);

X is —C$(R^3)_2$—, —$NR^4$—, —O—, or —S—: Y is —CRIR2-;

$R^1$ halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^2$ is hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$, —C(=O)$CH_3$, —C(—O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^3$ are independently hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or two $R^3$ are taken together to form an oxo; and $R^4$ is hydrogen, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl.

In some embodiments of a compound of Formula (VI);

X is —$C(R^3)_2$—, —$NR^4$—, —O—, or —S—;

Y is —CR'$R^2$—;

$R^1$ halogen, $C_1$-$C_6$alkyl, $C_1$-$C_6$haloalkyl, or $C_1$-$C_6$deuteroalkyl;

$R^2$ is hydrogen, deuterium, halogen, or $C_1$-$C_6$alkyl;

or $R^1$ and $R^2$ are taken together to form a cycloalkyl or heterocycloalkyl;

each $R^3$ are independently hydrogen, deuterium, halogen, $C_1$-$C_6$alkyl, $C_1$-$C_6$haloalkyl, or $C_1$-$C_6$deuteroalkyl;

$R^4$ is hydrogen or $C_1$-$C_6$alkyl.

In some embodiments of a compound of Formula (VI);

X is —$C(R^3)_2$—, —NR4-, or —S—;

Y is —$CR^1R^2$—, —$NR^4$—, —O—, or —S—;

$R^1$ and $R^2$ are independently hydrogen, deuterium, halogen, —CN, —$NO_2$, —OH, —OR3, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^3$ are independently hydrogen, deuterium, halogen, —CN, —$NO_2$, —OH, —OR3, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or two $R^3$ are taken together to form an oxo; and $R^4$ is hydrogen, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl.

In some embodiments of a compound of Formula (VI);

X is —$C(R^3)_2$—;

Y is —$CR^1R^2$—, —$NR^4$—, —O—, or —S—;

$R^1$ and $R^2$ are independently hydrogen, deuterium, halogen, —OH, $C_1$-$C_6$alkyl, $C_1$-$C_6$haloalkyl, or $C_1$-$C_6$deuteroalkyl;

or $R^1$ and $R^2$ are taken together to form an oxo;

or $R^1$ and $R^2$ are taken together to form a cycloalkyl or heterocycloalkyl;

each $R^3$ are independently hydrogen, deuterium, halogen, —OH, $C_1$-$C_6$alkyl, $C_1$-$C_6$haloalkyl, or $C_1$-$C_6$deuteroalkyl;

or two $R^3$ are taken together to form an oxo; and $R^4$ is hydrogen or $C_1$-$C_6$alkyl.

In some embodiments of a compound of Formula (VI);

X is —$NR^4$—or —S—;

Y is —CRIR2;

$R^1$ and $R^2$ are independently hydrogen, deuterium, halogen, $C_1$-$C_6$alkyl, $C_1$-$C_6$haloalkyl, or $C_1$-$C_6$deuteroalkyl;

or $R^1$ and $R^2$ are taken together to form an oxo;

or $R^1$ and $R^2$ are taken together to form a cycloalkyl or heterocycloalkyl; and $R^4$ is hydrogen or $C_1$-$C_6$alkyl.

In some embodiments of a compound of Formula (VI), $R^5$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (VI), $R^5$ is hydrogen, deuterium, halogen, —CN, or $C_1$-$C_6$alkyl.

In some embodiments of a compound of Formula (VI), $R^6$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (VI), $R^6$ is hydrogen, deuterium, halogen, —CN, or $C_1$-$C_6$alkyl.

In some embodiments of a compound of Formula (VI), $R^7$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (VI), $R^7$ is hydrogen, deuterium, halogen, —CN, or $C_1$-$C_6$alkyl.

In some embodiments of a compound of Formula (VI), Ring B is a 6-membered heteroaryl. In some embodiments of a compound of Formula (VI), Ring B is pyridinyl.

In some embodiments of a compound of Formula (VI), each $R^B$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (VI), each $R^B$ is independently $C_1$-$C_6$alkyl.

In some embodiments of a compound of Formula (VI), m is 1 or 2. In some embodiments of a compound of Formula (VI), m is 1-4. In some embodiments of a compound of Formula (VI), m is 2-4. In some embodiments of a compound of Formula (VI), m is 1. In some embodiments of a compound of Formula (VI), m is 2.

In some embodiments of a compound of Formula (VI), Ring C is a 5- or 6-membered heteroaryl. In some embodiments of a compound of Formula (VI), Ring C is a pyrimidinyl.

In some embodiments of a compound of Formula (VI), each $R^C$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (VI), each $R^C$ is independently $C_1$-$C_6$hydroxyalkyl.

In some embodiments of a compound of Formula (VI), p is 1 or 2. In some embodiments of a compound of Formula (VI), p is 1-3. In some embodiments of a compound of Formula (VI), p is 1. In some embodiments of a compound of Formula (VI), p is 2.

Also disclosed herein is a compound of Formula (VII), or a pharmaceutically acceptable salt, solvate, N-oxide, or stereoisomer thereof:

Formula (VII)

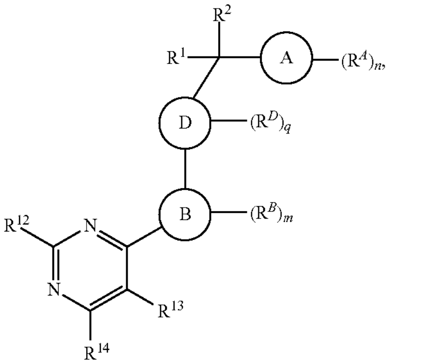

wherein;

Ring A is phenyl or heteroaryl;

each $R^A$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$NR^cR^d$, —$NR^cR^d$, —$NR^c$C(═O)$NR^cR^d$, —$NR^c$C(═O)$R^a$, —$NR^c$C(═O)$OR^b$, —$NR^b$S(═O)$R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Aa}$;

or two $R^A$ on the same atom are taken together to form an oxo;

each $R^{Aa}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$R^a$, —S(═O)$NR^cR^d$, —$NR^cR^d$, —$NR^c$C(═O)$NR^cR^d$, —$NR^c$C(═O)$R^a$, —$NR^c$C(═O)$OR^b$, —NR'S(═O)$R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Aa}$ on the same atom are taken together to form an oxo;

n is 0-4:

$R^1$ and $R^2$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; or $R^1$ and $R^2$ are taken together to form an oxo;

or $R^1$ and R' are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

Ring B is pyridinyl;

each $R^B$ is independently hydrogen, deuterium, halogen, —CN, —$NO_2$, —OH, —$OR^a$, —OC(═O)$R^a$, —OC(═O)$OR^b$. —OC(═O)$NR^cR^d$, —SH, —$SR^a$, —S(═O)$R^a$, —S(═O)$R^a$, —S(═O)$NR^cR^d$, —$NR^cR^d$, —$NR^c$C(═O)$NR^cR^d$—$NR^c$C(═O)$R^a$, —$NR^c$C (═O)$OR^b$, —NR'S (═O)$_3R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

each $R^{Ba}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_3R^a$, —S(═O)$_2NR^cR^d$, —$NR^cR^d$—$NR^c$C(═O)$NR^cR^d$—$NR^c$C(═O)$R^a$, —$NR^c$C (═O)$OR^b$, —$NR^b$S (═O)$_3R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ba}$ on the same atom are taken together to form an oxo:

m is 0-3;

Ring D is a bicyclic ring;

each $R^D$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_3R^a$, —S(═O)$_3NR^cR^d$, —$NR^cR^d$, —$NR^c$C(═O)$NR^cR^d$, —$NR^c$C(═O)$R^a$, —$NR^c$C(═O)$OR^b$, —$NR^b$S (═O)$_3R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Da}$;

or two $R^D$ on the same atom are taken together to form an oxo;

each $R^{Da}$ is independently deuterium, halogen, —CN, —$NO_2$, —OH, —$OR^a$, —OC(═O)$R^a$, —OC(═O)

$OR^b$, —OC(=O)$NR^cR^d$, —SH, —$SR^a$, —S(=O)$R^a$-S(=O)$_3R^a$, —S(=O)—$NR^cR^d$, —$NR^cR^d$, —$NR^c$C(=O)$NR^cR^d$, —$NR^c$C(=O)$R^a$, —$NR^c$C(=O)$OR^b$, —$NR^b$S(=O)$R^a$, —C(=O)$R^a$, —C(=O)C(=O)$R^a$, —C(=O)$OR^b$, —C(=O)$NR^cR^d$, —C(=O)C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Da}$ on the same atom are taken together to form an oxo;

q is 0-6;

$R^{12}$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)¿$R^a$, —S(=O)$_2NR^cR^d$, —S(=O)(=$NR^b$)$R^a$, —SiR-CRdOR$^b$, —$NR^cR^d$—$NR^c$C(=O)$NR^cR^d$, —$NR^c$C(=O)$R^a$—$NR^c$C(=O)$OR^b$, —NR'S(=O)$_3R^a$—C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl) aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{12a}$;

each $R^{12a}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$R^a$, —S(=O)$NR^cR^d$, —$NR^cR^d$, —$NR^c$C(=O)$NR^cR^d$, —$NR^c$C(=O)$R^a$, —$NR^c$C(=O)$OR^b$, —$NR^b$S(=O)$_3R^a$, —C(=O)$R^a$, —C(=O)C(=O)$R^a$, —C(=O)$OR^b$, —C(=O)$NR^cR^d$—C(=O)C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{12a}$ on the same atom are taken together to form an oxo;

$R^{13}$ is hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_1$-$C_6$alkenyl, $C_2$-$C_6$alkynyl, cycloalkyl, or heterocycloalkyl;

$R^{14}$ is hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$NH_2$, —S(=O)$NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH. —$OCH_3$, —S(=O)$CH_3$, —S(=O)$_2CH_3$, —S(=O)$_3NH_2$, —S(=O)$_2NHCH_3$, —S(=O), $N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl). $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo. deuterium, halogen, —CN, —OH, —$OCH_3$, —S(=O)$CH_3$, —S(=O)$_2CH_3$, —S(=O)—$NH_2$, —S(=O),$NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, or $C_1$-$C_6$heteroalkyl.

In some embodiments of a compound of Formula (VII). Ring A is heteroaryl. In some embodiments of a compound of Formula (VII). Ring A is pyridyl. In some embodiments of a compound of Formula (VII). Ring A is phenyl.

In some embodiments of a compound of Formula (VII), each $R^A$ is independently deuterium, halogen, —CN, —OH, —$OR^a$—$NR^cR^d$, $C_1$-$C_6$alkyl, $C_1$-$C_6$haloalkyl, or $C_1$-$C_6$deuteroalkyl. In some embodiments of a compound of Formula (I), each $R^A$ is independently halogen or $C_1$-$C_6$alkyl. In some embodiments of a compound of Formula (VII), each $R^A$ is independently halogen.

In some embodiments of a compound of Formula (VII), n is 1 or 2. In some embodiments of a compound of Formula (VII), n is 1-3. In some embodiments of a compound of Formula (VII), n is 2. In some embodiments of a compound of Formula (VII), n is 1.

In some embodiments of a compound of Formula (VII). $R^1$ and $R^2$ are independently hydrogen. deuterium, halogen, $C_1$-$C_6$alkyl, $C_1$-$C_6$haloalkyl, or $C_1$-$C_6$deuteroalkyl. In some embodiments of a compound of Formula (VII). $R^1$ and $R^2$ are independently hydrogen, deuterium, halogen, or $C_1$-$C_6$alkyl. In some embodiments of a compound of Formula (VII). $R^1$ and $R^2$ are hydrogen.

In some embodiments of a compound of Formula (VII). Ring D is a 6- to 12-membered bicyclic ring optionally comprising 1-4 heteroatoms selected from the group consisting of O, S, N, P, or B. In some embodiments of a compound of Formula (VII). Ring D is a 6- to 12-membered bicyclic ring optionally comprising 1-4 heteroatoms selected from the group consisting of O, S, or N. In some embodiments of a compound of Formula (VII). Ring D is a 6- to 12-membered bicyclic ring optionally comprising 1-4 heteroatoms selected from the group consisting of O and N. In some embodiments of a compound of Formula (VII), Ring D is a 6- to 12-membered bicyclic ring optionally comprising 1-4 heteroatoms selected from the group consisting of O and N. In some embodiments of a compound of Formula (VII), Ring D is a 6- to 12-membered bicyclic ring comprising 1-3 heteroatoms selected from the group consisting of O and N. In some embodiments of a compound of Formula (VII), Ring D is a 6- to 10-membered bicyclic ring comprising 1-3 heteroatoms that are N.

In some embodiments of a compound of Formula (VII), each $R^D$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl; or two $R^D$ on the same atom are taken together to form an oxo. In some embodiments of a compound of Formula (VII), each $R^D$ is independently hydrogen, deuterium, halogen, —CN, —$OR^a$, $C_1$-$C_6$alkyl, $C_1$-$C_6$haloalkyl, $C_2$-$C_6$alkynyl, or cycloalkyl; or two $R^D$ on the same atom are taken together to form an oxo.

In some embodiments of a compound of Formula (VII), q is 1-4. In some embodiments of a compound of Formula (VII), q is 1-3. In some embodiments of a compound of Formula (VII), q is 2-4.

In some embodiments of a compound of Formula (VII),

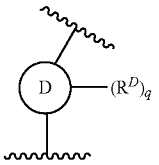

is

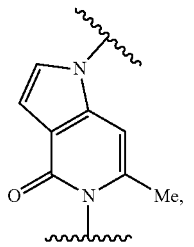

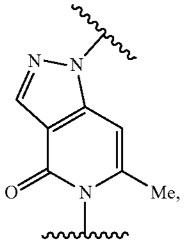

or

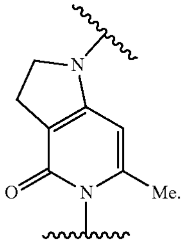

In some embodiments of a compound of Formula (VII), each $R^B$ is independently deuterium, halogen, —CN, —OH, —$OR^a$, $C_1$-$C_6$alkyl, $C_1$-$C_6$haloalkyl, $C_1$-$C_6$deuteroalkyl, $C_2$-$C_6$alkynyl, or cycloalkyl. In some embodiments of a compound of Formula (VII), each $R^B$ is independently deuterium, —CN, —OH, —$OR^a$, $C_1$-$C_6$alkyl, $C_1$-$C_6$haloalkyl, $C_1$-$C_6$deuteroalkyl, $C_2$-$C_6$alkynyl, or cycloalkyl. In some embodiments of a compound of Formula (VII), each $R^B$ is independently $C_1$-$C_6$alkyl.

In some embodiments of a compound of Formula (VII), m is 1 or 2. In some embodiments of a compound of Formula (VII), m is 1. In some embodiments of a compound of Formula (VII), m is 2.

In some embodiments of a compound of Formula (VII), $R^{12}$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (VII), $R^{12}$ is $C_1$-$C_6$hydroxyalkyl.

In some embodiments of a compound of Formula (VII), $R^{13}$ is hydrogen, deuterium, halogen, or $C_1$-$C_6$alkyl.

In some embodiments of a compound of Formula (VII), $R^{14}$ is hydrogen, deuterium, halogen, or $C_1$-$C_6$alkyl.

Also disclosed herein is a compound of Formula (VIII), or a pharmaceutically acceptable salt, solvate, N-oxide, or stereoisomer thereof:

Formula (VIII)

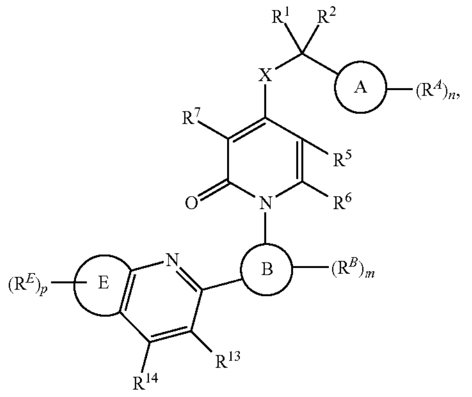

wherein;

Ring A is phenyl or heteroaryl;

each $R^A$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$R^a$, —S(=O)$NR^cR^d$, —$NR^cR^d$, —$NR^c$C(=O) $NR^cR^d$, —$NR^c$C(=O)$R^a$, —$NR^c$C(=O)$OR^b$, —$NR^b$S(=O)$R^a$, —C(=O)$R^a$, —C(=O)$OR^b$, —C(=O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Aa}$;

or two $R^A$ on the same atom are taken together to form an oxo;

each $R^{Aa}$ is independently deuterium, halogen, —CN, —$NO_2$, —OH, —$OR^a$, —OC(=O)$R^a$, —OC(=O)$OR^b$, —OC(=O) $NR^cR^d$, —SH, —$SR^a$, —S(=O)$R^a$, —S(=O)$R^a$, —S(=O)—$NR^cR^d$, —$NR^cR^d$, —$NR^c$C(=O) $NR^cR^d$, —$NR^c$C(=O)$R^a$, —$NR^c$C(=O)$OR^b$, —$NR^b$S(=O)$R^a$, —C(=O)$R^a$, —C(=O)C(=O)$R^a$, —C(=O)$OR^b$, —C(=O) $NR^cR^d$, —C(=O)C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Aa}$ on the same atom are taken together to form an oxo;

n is 0-4: $R^1$ and $R^2$ are independently hydrogen, deuterium, halogen, —CN, —$NO_2$, —OH, —$OR^a$, —$NR^cR^d$, —C(═O)$R^a$, —C(═O)$OR^b$, —C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —$OCH_3$, —$NH_2$, —$NHCH_3$, —$N(CH_3)_2$, —C(═O)$CH_3$, —C(═O)OH, —C(═O) $OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

X is —$C(R^3)_2$—, —$NR^4$—, —O—, or —S—;

each $R^3$ are independently hydrogen, deuterium, halogen, —CN, —$NO_2$, —OH, —$OR^a$, —$NR^cR^d$, —C(═O)$R^a$, —C(═O)$OR^b$, —C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or two $R^3$ are taken together to form an oxo;

$R^4$ is hydrogen, —C(═O)$R^a$, —C(═O)$OR^b$, —C(═O) $NR^cR^d$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^5$ is hydrogen, deuterium, halogen, —CN, —$NO_2$, —OH, —$OR^a$, —$NR^cR^d$, —C(═O)$R^a$, —C(═O) $OR^b$, —C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —$NR^cR^d$, —C(═O)$R^a$, —C(═O) $OR^b$, —C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. $C_2$-$C_6$alkenyl, $C_2$-$C_6$alkynyl, cycloalkyl, or heterocycloalkyl;

$R^7$ is hydrogen, deuterium, halogen, —CN, —$NO_2$, —OH, —$OR^a$, —$NR^cR^d$, —C(═O)$R^a$, —C(═O) $OR^b$, —C(═O) $NR^cR^d$. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Ring B is cycloalkyl, heterocycloalkyl, aryl, or heteroaryl;

each $R^B$ is independently hydrogen, deuterium, halogen, —CN, —$NO_2$, —OH, —$OR^a$, —OC(═O)$R^a$, —OC (═O)$OR^b$, —OC(═O) $NR^cR^d$, —SH, —$SR^a$, —S(═O)$R^a$, —S(═$O)_3R^a$, —S(═O)$NR^cR^d$, —$NR^cR^d$, —$NR^c$C(═O) $NR^cR^d$, —$NR^c$C(═O)$R^a$, —$NR^c$C(═O)$OR^b$, —$NR^b$S (═$O)_3R^a$, —C(═O)$R^a$, —C(═O)$OR^b$, —C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

or two $R^B$ on the same atom are taken together to form an oxo;

each $R^{Ba}$ is independently deuterium, halogen, —CN, —$NO_2$, —OH, —$OR^a$, —OC(═O)$R^a$, —OC(═O) $OR^b$, —OC(═O) $NR^cR^d$, —SH, —$SR^a$, —S(═O)$R^a$, —S(═$O)_3R^a$, —S(—$O)_3NR^cR^d$—$NR^cR^d$, —$NR^c$C (═O) $NR^cR^d$, —$NR^c$C(═O)$R^a$, —$NR^c$C(═O)$OR^b$, —$NR^b$S(═O)$R^a$, —C(═O)$R^a$, —C(═O)C(═O)$R^a$, —C(═O)$OR^b$, —C(═O) $NR^cR^d$—C(═O)C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ba}$ on the same atom are taken together to form an oxo;

m is 0-4;

Ring E is cycloalkyl, heterocycloalkyl, aryl, or heteroaryl;

each $R^E$ is independently hydrogen, deuterium, halogen, —CN, —$NO_2$, —OH, —$OR^a$, —OC(═O)$R^a$, —OC (═O)$OR^b$, —OC(═O) $NR^cR^d$, —SH, —$SR^a$, —S(═O)$R^a$, —S(═O)$R^a$, —S(═$O)^aNR^cR^d$, —S(═O) (═$NR^b$)$R^a$, —Si$R^c$RdO$R^b$, —$NR^cR^d$, —$NR^c$C(═O)$NR^cR^d$—$NR^c$C(═O)$R^a$—$NR^c$C (═O) $OR^b$, —$NR^c$S(═$O)^aR^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl) aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ea}$;

each $R^{Fa}$ is independently deuterium, halogen, —CN, —$NO_2$, —OH, —$OR^a$, —OC(═O)$R^a$, —OC(═O) ORh, —OC(═O) $NR^cR^d$, —SH, —$SR^a$, —S(═O)$R^a$, —S(═O)$R^a$, —S(═$O)_3NR^cR^d$, —$NR^cR^d$, —$NR^c$C (═O) $NR^cR^d$—$NR^c$C(═O)$R^a$, —$NR^c$C(═O)$OR^b$, —$NR^b$S (═$O)_3R^a$, —C(═O)$R^a$, —C(═O) C (═O) $R^a$—C(═O)$OR^b$, —C(═O) $NR^cR^d$, —C(═O)C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Fa}$ on the same atom are taken together to form an oxo;

$R^{13}$ is hydrogen, deuterium, halogen, —CN, —$NO_2$, —OH, —$OR^a$, —$NR^cR^d$, —C(═O)$R^a$, —C(═O) ORh, —C(—O) $NR^cR^d$. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_1$-$C_6$alkenyl, $C_2$-$C_6$alkynyl, cycloalkyl, or heterocycloalkyl;

$R^{14}$ is hydrogen, deuterium, halogen, —CN, —$NO_2$, —OH, —$OR^a$, —$NR^cR^d$, —C(═O)$R^a$, —C(═O) $OR^b$, —C(═O) $NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

p is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O),$NHCH_3$, —S(=O)N($CH_3$)$_2$ , —$NH_2$, —$NHCH_3$, —N($CH_3$)$_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl. $C_1$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)N($CH_3$)$_2$ , —$NH_2$, —$NHCH_3$, —N($CH_3$)$_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl). $C_1$-$C_6$alkyl (aryl), or $C_1$-$C_6$alkyl (heteroaryl); wherein each alkyl, alkenyl, alkynyl, cycloalkyl, heterocycloalkyl, aryl, and heteroaryl is independently optionally substituted with one or more oxo. deuterium, halogen, —CN, —OH, —$OCH_3$, —S(=O)$CH_3$, —S(=O)$_2CH_3$, —S(=O)$_2NH_2$, —S(=O)—$NHCH_3$, —S(=O)$_2$N($CH_3$)$_2$ , —$NH_2$, —$NHCH_3$, —N($CH_3$)$_2$ , —C(=O)$CH_3$, —C(=O)OH, —C(=O)$OCH_3$, $C_1$-$C_6$alkyl. $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(—O)$CH_3$, —S(=O)$_2CH_3$, —S(=O)$_3NH_2$, —S(=O),$NHCH_3$, —S(=O)N($CH_3$)$_2$, —$NH_2$, —$NHCH_3$, —N($CH_3$)$_2$, —C(=O)$CH_3$, —C(=O)OH, —C(—O)$OCH_3$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, or $C_1$-$C_6$heteroalkyl.

In some embodiments of a compound of Formula (VIII). Ring A is heteroaryl. In some embodiments of a compound of Formula (VIII). Ring A is pyridyl. In some embodiments of a compound of Formula (VIII). Ring A is phenyl.

In some embodiments of a compound of Formula (VIII), each $R^A$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (VIII), each $R^A$ is independently halogen or $C_1$-$C_6$alkyl. In some embodiments of a compound of Formula (VIII), each $R^A$ is independently halogen.

In some embodiments of a compound of Formula (VIII), n is 1 or 2. In some embodiments of a compound of Formula (VIII), n is 1-3. In some embodiments of a compound of Formula (VIII), n is 2. In some embodiments of a compound of Formula (VIII), n is 1.

In some embodiments of a compound of Formula (VIII). $R^1$ and $R^2$ are independently hydrogen. deuterium, halogen, $C_1$-$C_6$alkyl, $C_1$-$C_6$haloalkyl, or $C_1$-$C_6$deuteroalkyl. In some embodiments of a compound of Formula (VIII). $R^1$ and $R^2$ are independently hydrogen, deuterium, halogen, or $C_1$-$C_6$alkyl. In some embodiments of a compound of Formula (VIII). $R^1$ and $R^2$ are hydrogen.

In some embodiments of a compound of Formula (VIII). X is —O—.

In some embodiments of a compound of Formula (VIII). $R^5$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl. $C_1$-$C_6$heteroalkyl, $C_2$-$C_6$alkynyl, or cycloalkyl. In some embodiments of a compound of Formula (VIII), $R^5$ is hydrogen, deuterium, halogen, —CN, or $C_1$-$C_6$alkyl.

In some embodiments of a compound of Formula (VIII). $R^6$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl. $C_1$-$C_6$heteroalkyl, $C_2$-$C_6$alkynyl, or cycloalkyl. In some embodiments of a compound of Formula (VIII). $R^6$ is hydrogen, deuterium, halogen, —CN, or $C_1$-$C_6$alkyl, In some embodiments of a compound of Formula (VIII), $R^7$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (VIII), $R^7$ is hydrogen, deuterium, halogen, —CN, or $C_1$-$C_6$alkyl.

In some embodiments of a compound of Formula (VIII). Ring B is a 6-membered heteroaryl. In some embodiments of a compound of Formula (VIII). Ring B is pyridinyl.

In some embodiments of a compound of Formula (VIII), each $R^B$ is independently hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl, $C_2$-$C_6$alkynyl, or cycloalkyl. In some embodiments of a compound of Formula (VIII), each $R^B$ is independently $C_1$-$C_6$alkyl.

In some embodiments of a compound of Formula (VIII), m is 1 or 2. In some embodiments of a compound of Formula (VIII), m is 1-4. In some embodiments of a compound of Formula (VIII), m is 2-4. In some embodiments of a compound of Formula (VIII), m is 1. In some embodiments of a compound of Formula (VIII), m is 2.

In some embodiments of a compound of Formula (VIII). Ring E is cycloalkyl.

In some embodiments of a compound of Formula (VIII), each $R^E$ is independently hydrogen. deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, or $C_1$-$C_6$heteroalkyl. In some embodiments of a compound of Formula (VIII), each $R^E$ is independently-OH or $C_1$-$C_6$alkyl.

In some embodiments of a compound of Formula (VIII), p is 1 or 2. In some embodiments of a compound of Formula (VIII), p is 1 or 3. In some embodiments of a compound of Formula (VIII), p is 1. In some embodiments of a compound of Formula (VIII), p is 2.

In some embodiments of a compound of Formula (VIII). $R^{13}$ is hydrogen, deuterium, halogen, or $C_1$-$C_6$alkyl.

In some embodiments of a compound of Formula (VIII). $R^{14}$ is hydrogen, deuterium, halogen, or $C_1$-$C_6$alkyl.

In some embodiments of a compound disclosed herein, each $R^a$ is independently $C_1$-$C_6$alkyl. $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —$OCH_3$. —S(=O)$CH_3$, —S(=O)$_2CH_3$, —S(=O)$NH_2$, —S(=O),$NHCH_3$, —S(=O)N$(CH_3)_2$ , —$NH_2$, —$NHCH_3$, —N$(CH_3)_2$. —C(=O)$CH_3$, —C(=O)OH, —C(=O) $OCH_3$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl. In some embodiments of a compound disclosed herein, each $R^a$ is independently $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2$N$(CH_3)_2$, —$NH_2$, —$NHCH_3$, —N$(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl. $C_1$-$C_6$hydroxyalkyl, $C_1$-$C_6$aminoalkyl, $C_1$-$C_6$heteroalkyl. In some embodiments of a compound disclosed herein, each $R^a$ is independently $C_1$-$C_6$alkyl, $C_1$-$C_6$haloalkyl, cycloalkyl, or heterocycloalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl.

In some embodiments of a compound disclosed herein, each $R^b$ is independently hydrogen. $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH. —$OCH_3$, —S(=O)$CH_3$, —S(=O)$_2CH_3$, —S(=O)$_2NH_2$, —S(=O)$_2NHCH_3$, —S(=O)$_2$N$(CH_3)_2$ , —$NH_2$, —$NHCH_3$, —N$(CH_3)_2$. —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl. In some embodiments of a compound disclosed herein, each $R^b$ is independently hydrogen, $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —$OCH_3$, —S(=O)$CH_3$, —S(=O)$_2CH_3$, —S(=O)—$NH_2$, —S(=O),$NHCH_3$, —S(=O),N$(CH_3)_2$, —$NH_2$. —$NHCH_3$, —N$(CH_3)_2$ , —C(=O)$CH_3$, —C(=O)OH, —C(=O) $OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^b$ is independently hydrogen, $C_1$-$C_6$alkyl, $C_1$-$C_6$haloalkyl, cycloalkyl, or heterocycloalkyl. In some embodiments of a compound disclosed herein, each $R^b$ is independently hydrogen, $C_1$-$C_6$alkyl, or $C_1$-$C_6$haloalkyl. In some embodiments of a compound disclosed herein, each $R^b$ is independently hydrogen or $C_1$-$C_6$alkyl.

In some embodiments of a compound disclosed herein, each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl. $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo. deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2$N$(CH_3)_2$ , —$NH_2$, —$NHCH_3$, —N$(CH_3)_2$ , —C(=O) $CH_3$, —C(=O)OH, —C(=O)$OCH_3$, $C_1$-$C_6$alkyl. $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^c$ and $R^d$ are independently hydrogen, $C_1$-$C_6$alkyl. $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —$OCH_3$. —S(=O)$CH_3$, —S(=O)$_2CH_3$, —S(=O),$NH_2$, —S(=O)$_3NHCH_3$, —S(=O)N$(CH_3)_2$ , —$NH_2$, —$NHCH_3$, —N$(CH_3)_3$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl. $C_1$-$C_6$aminoalkyl, $C_1$-$C_6$heteroalkyl. In some embodiments of a compound disclosed herein, each $R^c$ and $R^d$ are independently hydrogen, $C_1$-$C_6$alkyl, $C_1$-$C_6$haloalkyl, cycloalkyl, or heterocycloalkyl. In some embodiments of a compound disclosed herein, each $R^c$ and $R^d$ are independently hydrogen, $C_1$-$C_6$alkyl, or $C_1$-$C_6$haloalkyl. In some embodiments of a compound disclosed herein, each $R^c$ and $R^d$ are independently hydrogen or $C_1$-$C_6$alkyl.

In some embodiments of a compound disclosed herein, $R^c$ and $R^d$ are taken together with the atom to which they are attached to form a heterocycloalkyl optionally substituted with one or more oxo, deuterium, halogen, —CN, —OH, —$OCH_3$, —$NH_2$, —$NHCH_3$, —N$(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound disclosed herein, each $R^A$, $R^B$, $R^C$, $R^D$, $R^E$, $R^{12}$, $R^a$, $R^b$, $R^c$, $R^d$, and the heterocycloalkyl formed when $R^c$ and $R^d$ are taken together is independently substituted with one, two, three, or four substituents as defined herein. In some embodiments of a compound disclosed herein, each $R^A$, $R^B$, $R^C$, $R^D$, $R^E$, $R^{12}$, $R^a$, $R^b$, $R^c$, $R^d$, and the heterocycloalkyl formed when $R^c$ and $R^d$ are taken together is independently substituted with one, two, or three substituents as defined herein. In some embodiments of a compound disclosed herein, each $R^A$, $R^B$, $R^C$, $R^D$, $R^E$, $R^{12}$, $R^a$, $R^b$, $R^c$, $R^d$, and the heterocycloalkyl formed when $R^c$ and $R^d$ are taken together is independently substituted with one or two substituents as defined herein. In some embodiments of a compound disclosed herein, each $R^A$, $R^B$, $R^C$, $R^D$, $R^E$, $R^{12}$, $R^a$, $R^b$, $R^c$, $R^d$, and the heterocycloalkyl formed when $R^c$ and $R^d$ are taken together is independently substituted with one substituent as defined herein.

Any combination of the groups described above for the various variables is contemplated herein. Throughout the specification, groups and substituents thereof are chosen by one skilled in the field to provide stable moieties and compounds.

In some embodiments the compound disclosed herein, or a pharmaceutically acceptable salt, solvate, N-oxide, or stereoisomer thereof, is one of the compounds in Table 1.

TABLE 1
| Ex. | Structure |
| --- | --- |
| 1 | 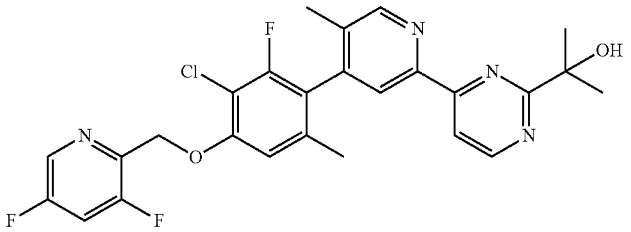 [SMILES: Cc1cnc(-c2ccnc(C(C)(C)O)n2)cc1-c1c(C)cc(OCc2ncc(F)cc2F)c(Cl)c1F] |
| 2* | 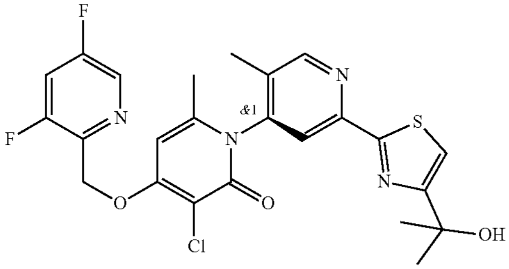 |
| 3* | 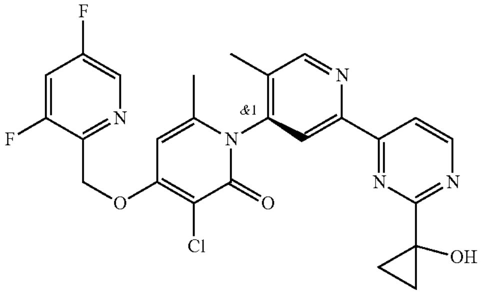 |
| 3A* | 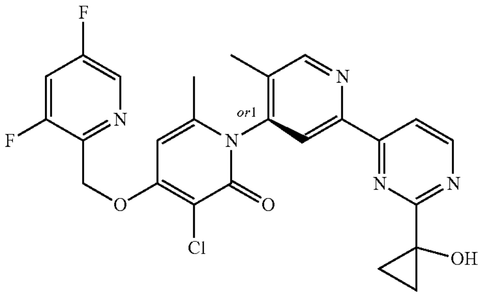 |
| 3B* | 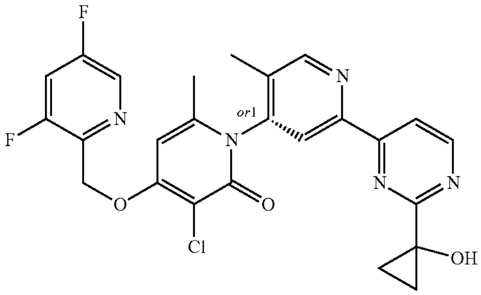 |

TABLE 1-continued
| Ex. | Structure |
|---|---|
| 4* | 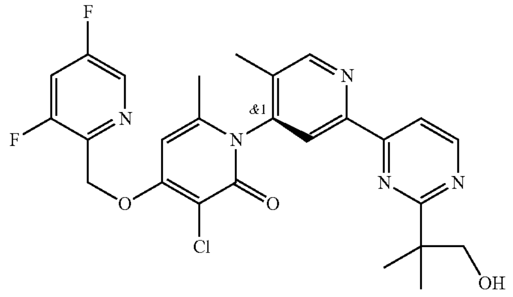 |
| 4A* | 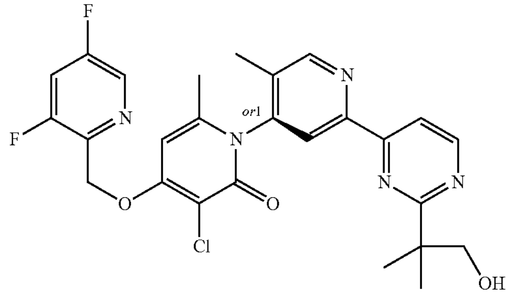 |
| 4B* | 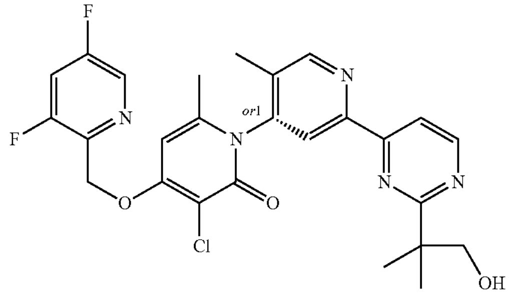 |
| 5* | 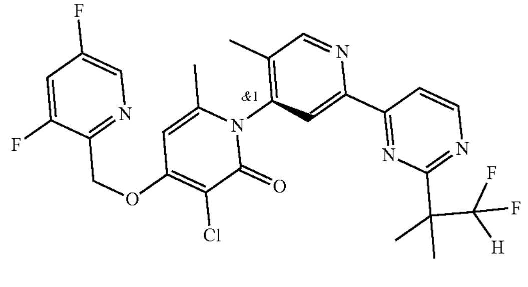 |
| 5A* | 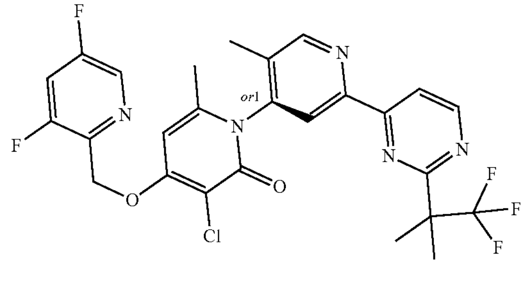 |

TABLE 1-continued
| Ex. | Structure |
| --- | --- |
| 5B* | 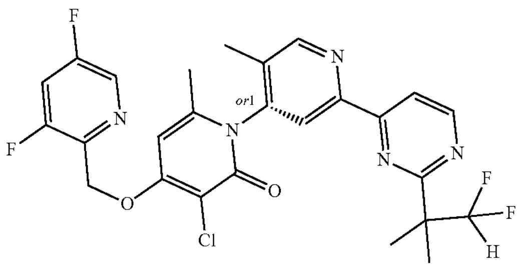 |
| 6* | 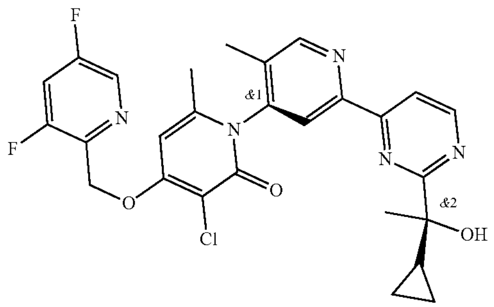 |
| 6A* | 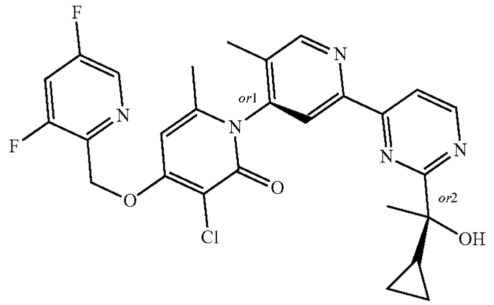 |
| 6B* | 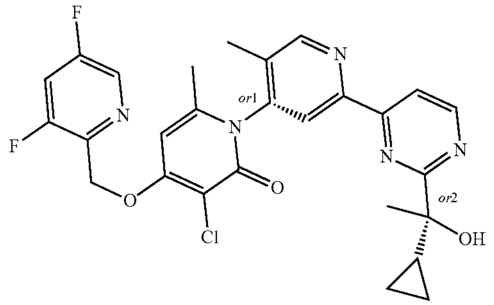 |
| 6C* | 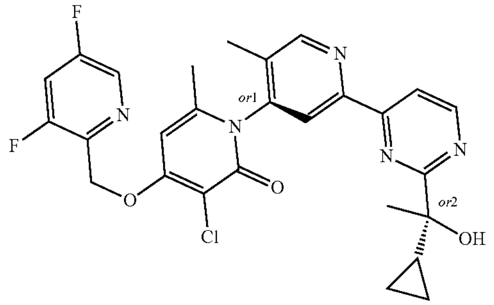 |

TABLE 1-continued
| Ex. | Structure |
|---|---|
| 6D* | 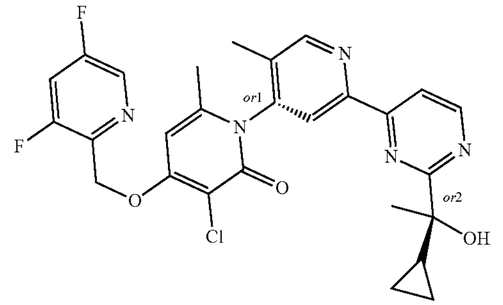 |
| 7* | 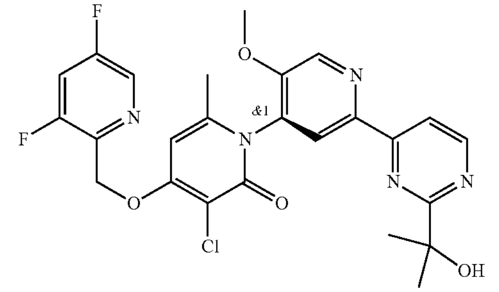 |
| 8* | 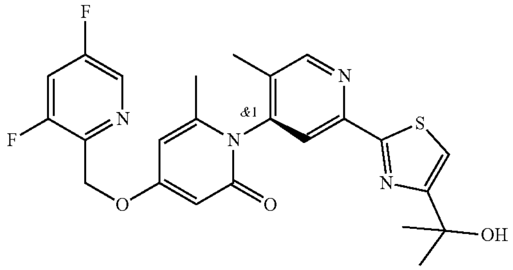 |
| 9A* | 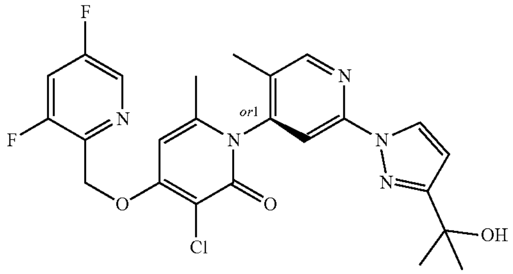 |
| 9B* | 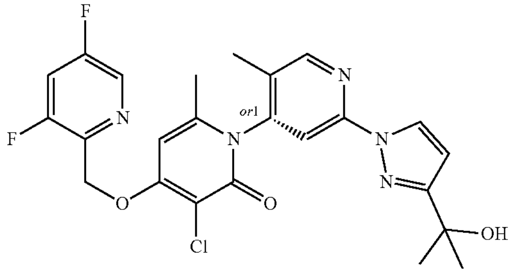 |

TABLE 1-continued
| Ex. | Structure |
|---|---|
| 10* | 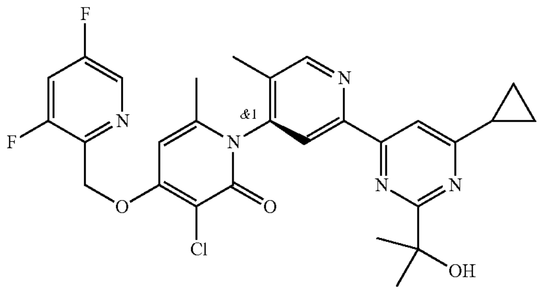 |
| 11* | 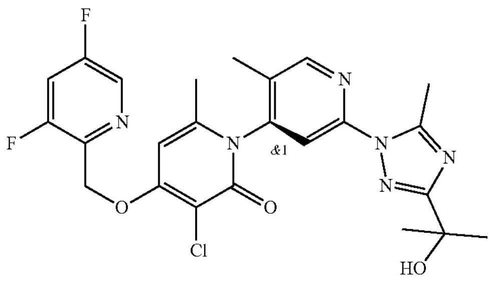 |
| 12* | 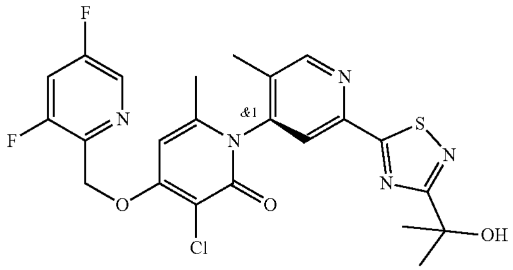 |
| 13* | 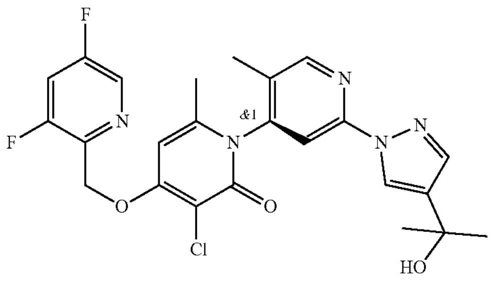 |
| 14* | 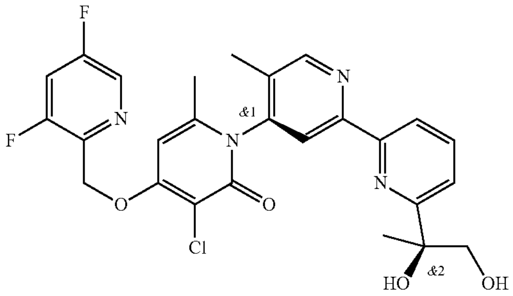 |

TABLE 1-continued
| Ex. | Structure |
| --- | --- |
| 15* | 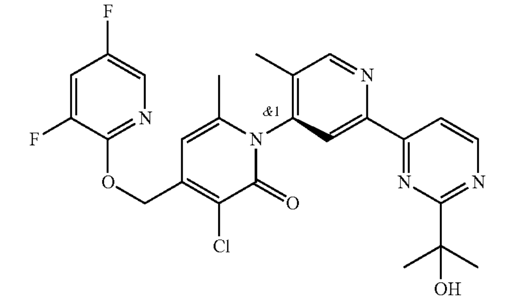 |
| 16* | 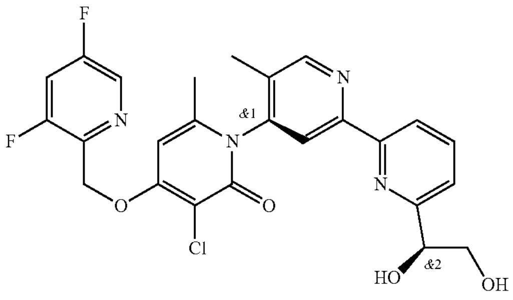 |
| 17* | 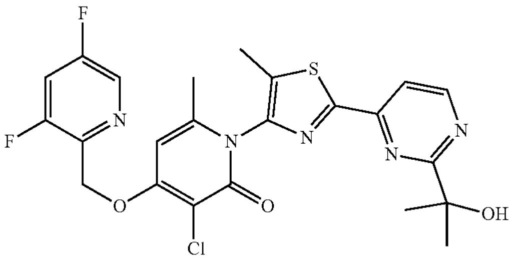 [SMILES: Cc1sc(-c2ccnc(C(C)(C)O)n2)nc1-n1c(C)cc(OCc2ncc(F)cc2F)c(Cl)c1=O] |
| 18A* | 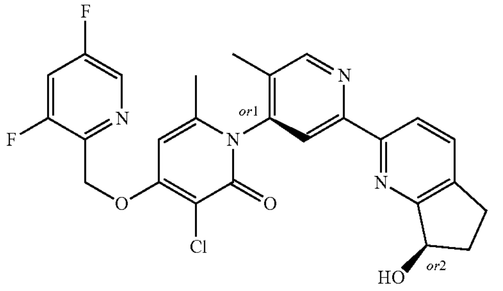 |
| 18B* | 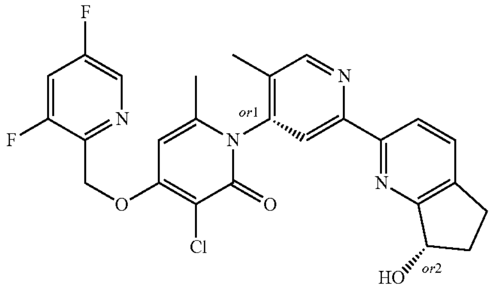 |

TABLE 1-continued
| Ex. | Structure |
| --- | --- |
| 18C* | 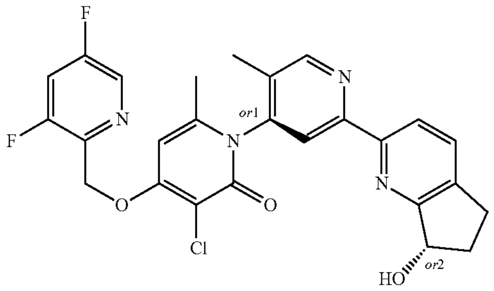 |
| 18D* | 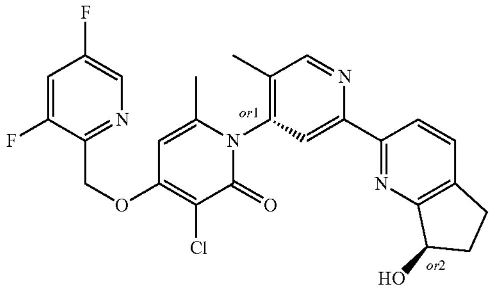 |
| 19A* | 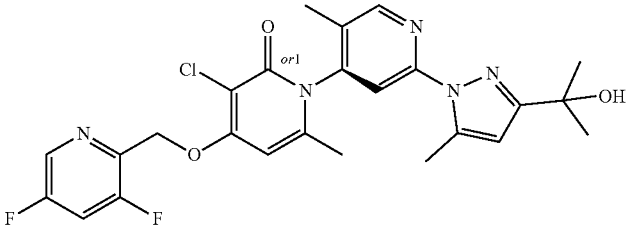 |
| 19B* | 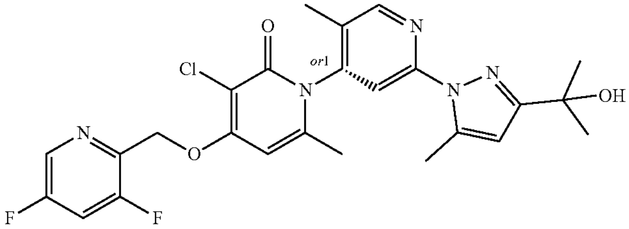 |
| 20A* | 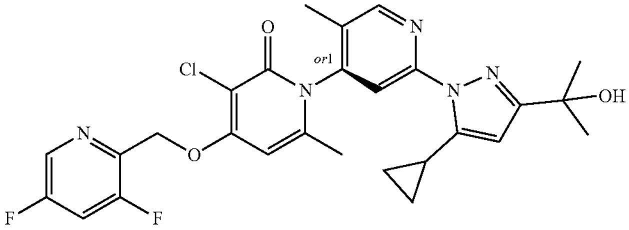 |
| 20B* | 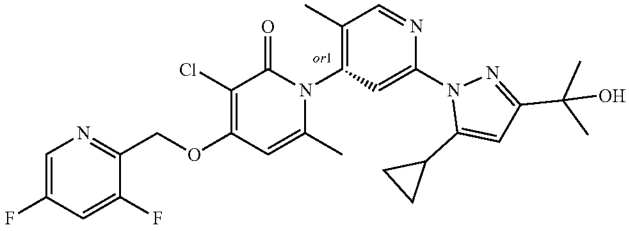 |

TABLE 1-continued
| Ex. | Structure |
|---|---|
| 21A* | 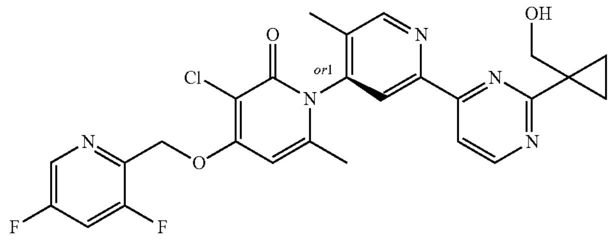 |
| 21B* | 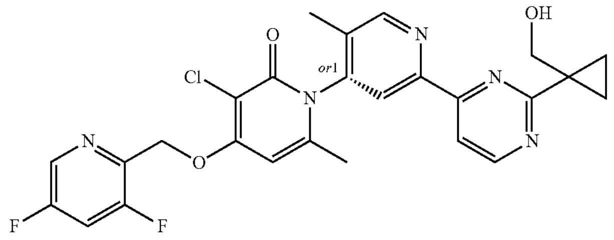 |
| 22A* | 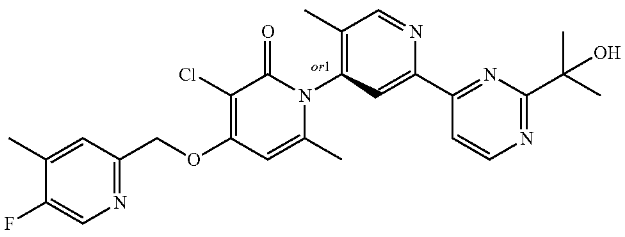 |
| 22B* | 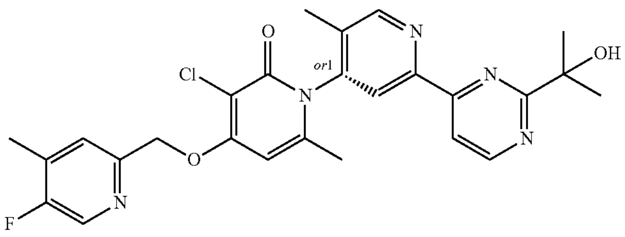 |
| 23A* | 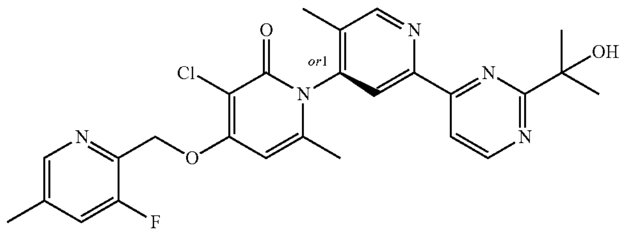 |
| 23B* | 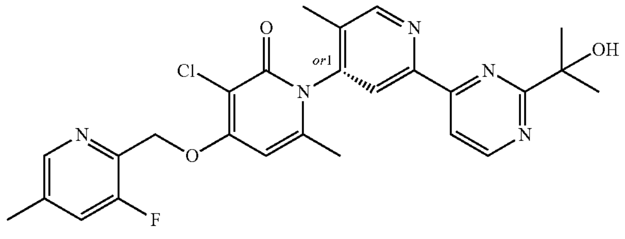 |

TABLE 1-continued
| Ex. | Structure |
|---|---|
| 24A* | 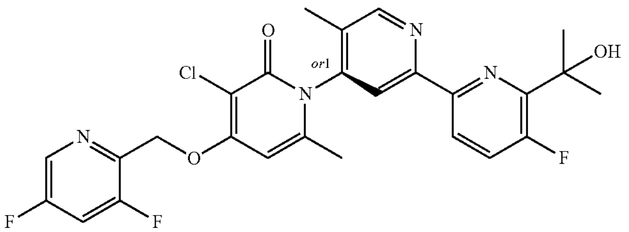 |
| 24B* | 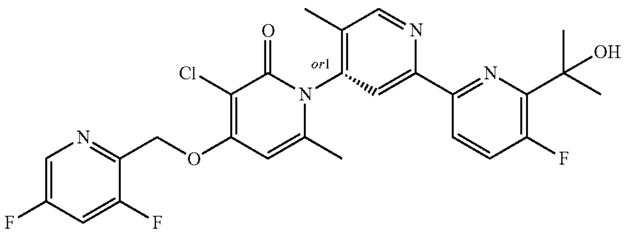 |
| 25* | 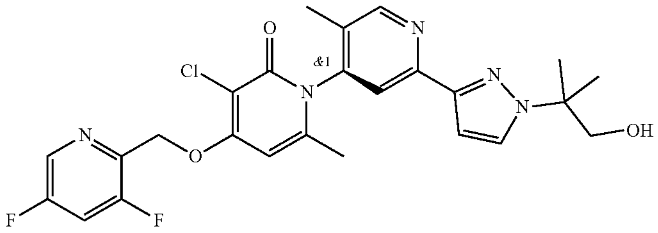 |
| 25A* | 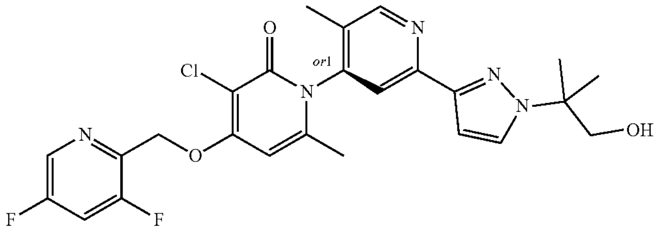 |
| 25B* | 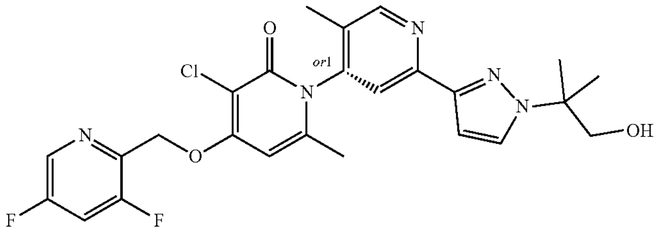 |
| 26A* | 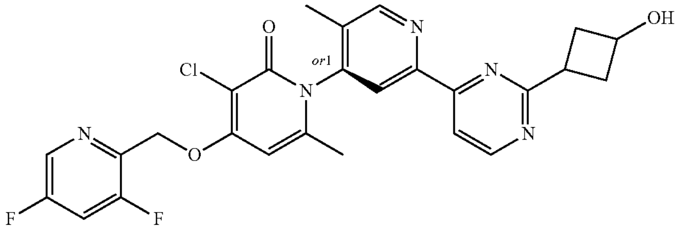 |

TABLE 1-continued
| Ex. | Structure |
|---|---|
| 26B* | 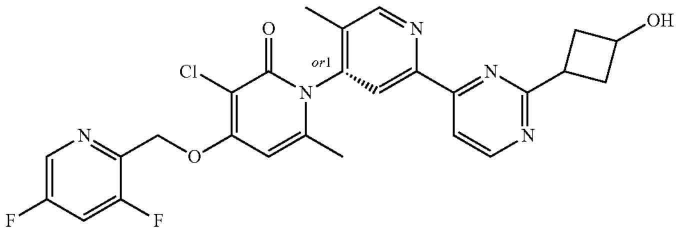 |
| 27A* | 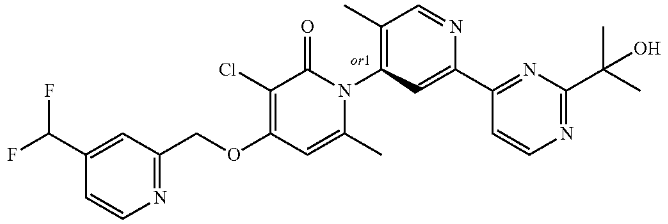 |
| 27B* | 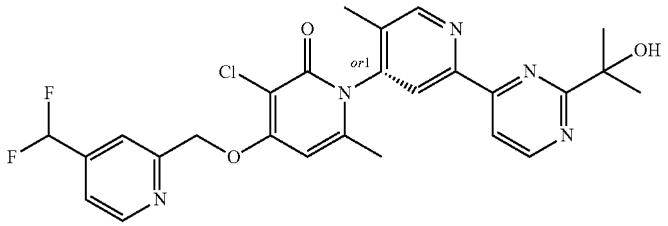 |
| 28A* | 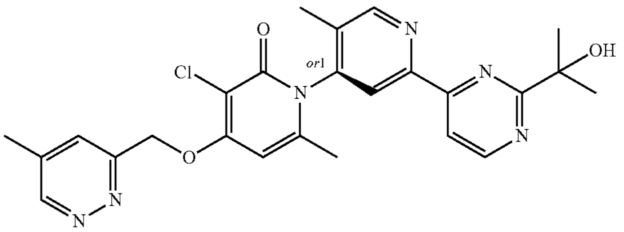 |
| 28B* | 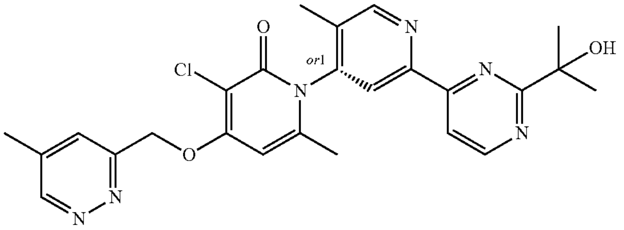 |
| 29A* | 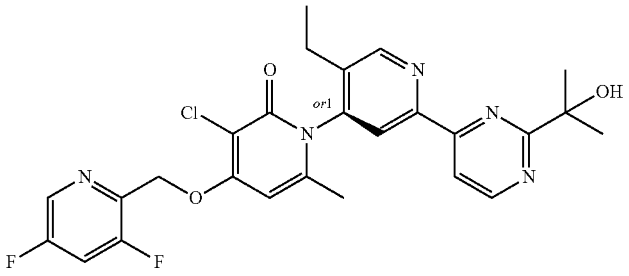 |

TABLE 1-continued
| Ex. | Structure |
| --- | --- |
| 29B* | 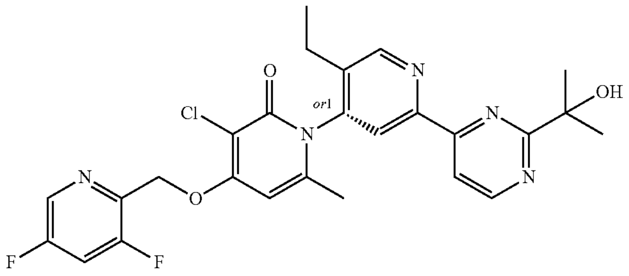 |
| 30* | 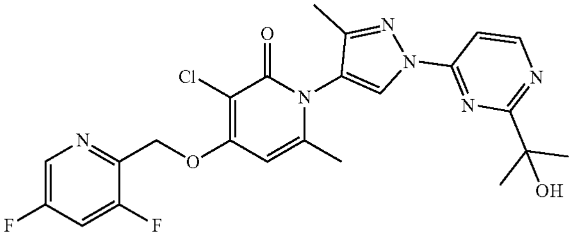 [SMILES: Cc1nn(-c2ccnc(C(C)(C)O)n2)cc1-n1c(C)cc(OCc2ncc(F)cc2F)c(Cl)c1=O] |
| 31A* | 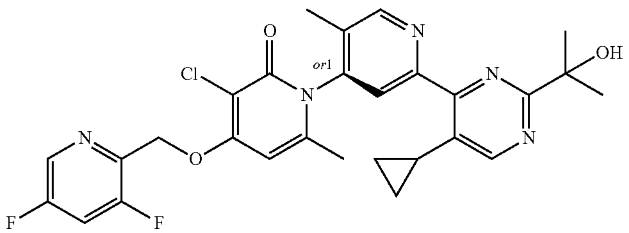 |
| 31B* | 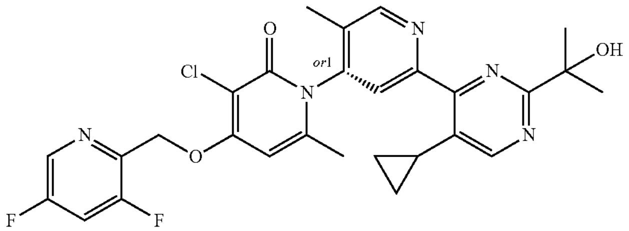 |
| 32A* | 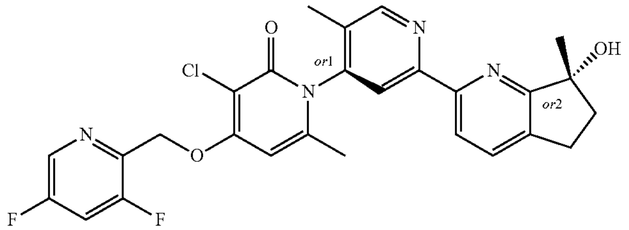 |
| 32B* | 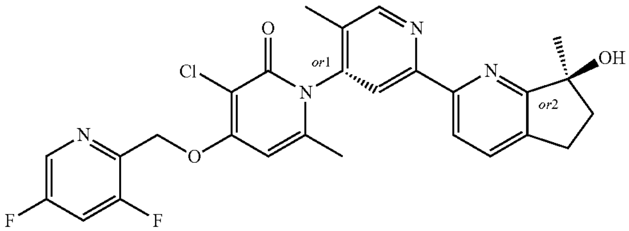 |

TABLE 1-continued
| Ex. | Structure |
|---|---|
| 32C* | 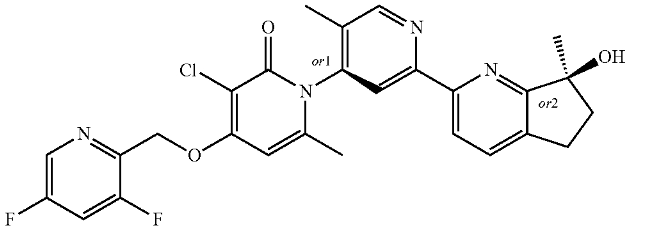 |
| 32D* | 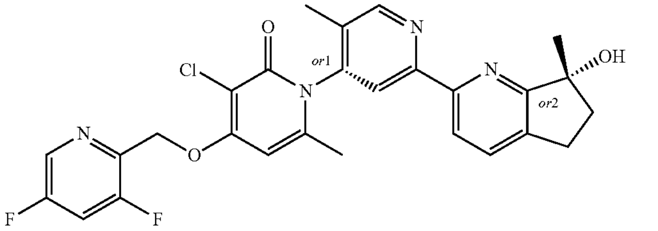 |
| 33A* | 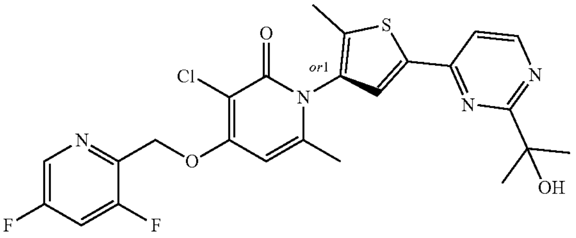 |
| 33B* | 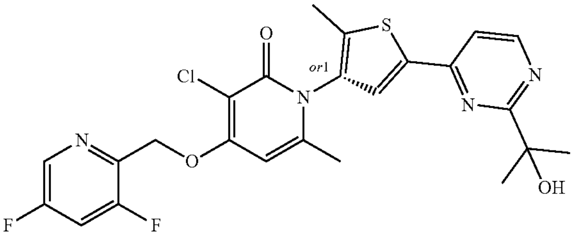 |
| 34A* | 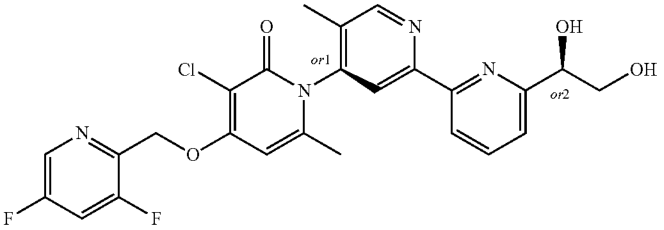 |
| 34B* | 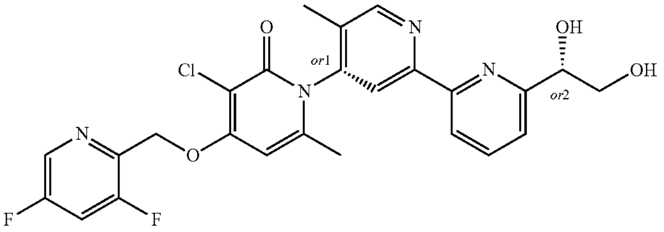 |

TABLE 1-continued
| Ex. | Structure |
| --- | --- |
| 34C* | 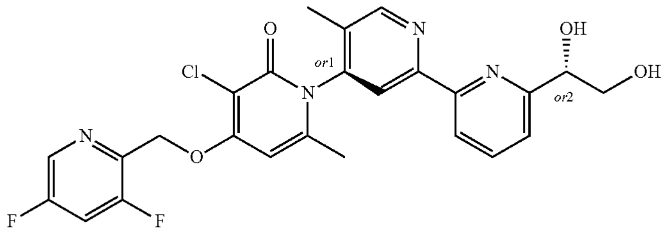 |
| 34D* | 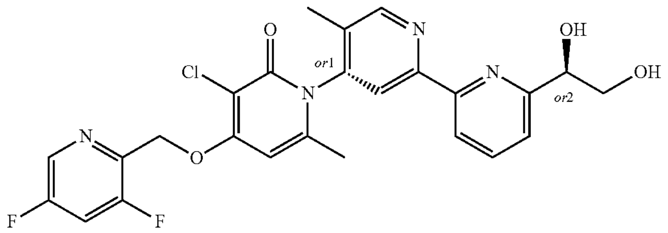 |
| 35A* | 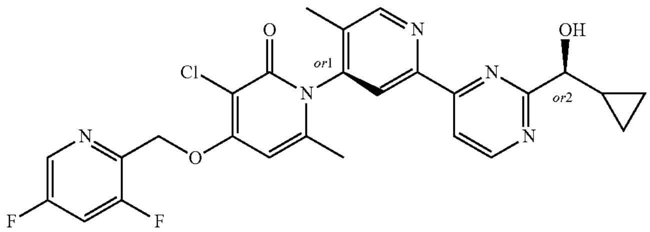 |
| 35B* | 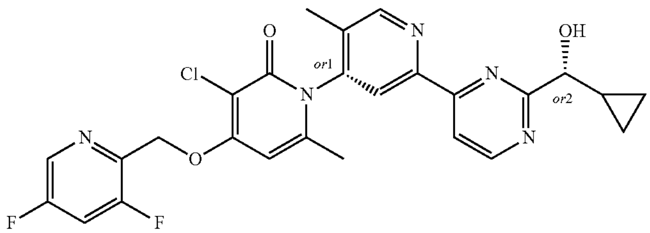 |
| 35C* | 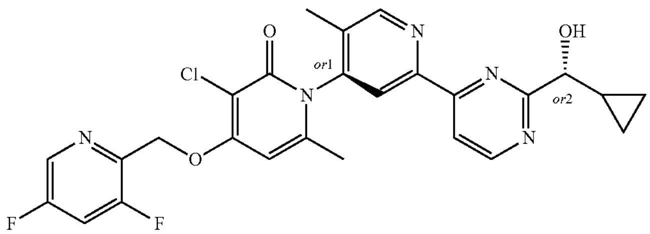 |
| 35D* | 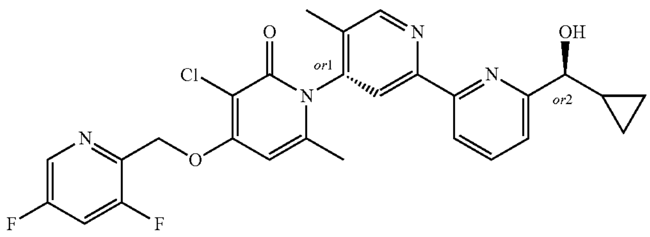 |

TABLE 1-continued
| Ex. | Structure |
|---|---|
| 36A* | 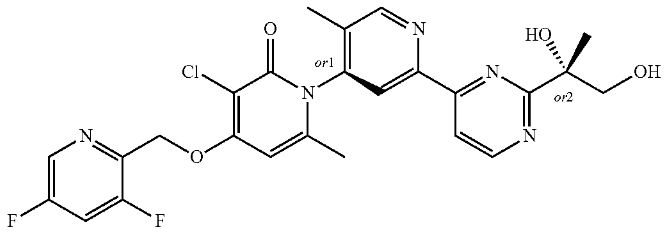 |
| 36B* | 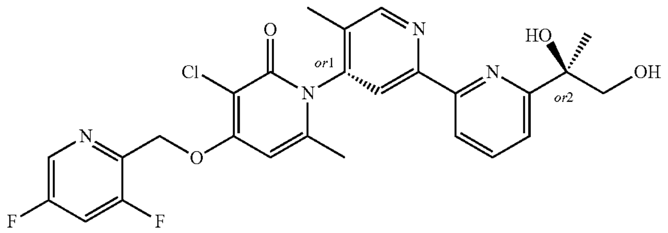 |
| 36C* | 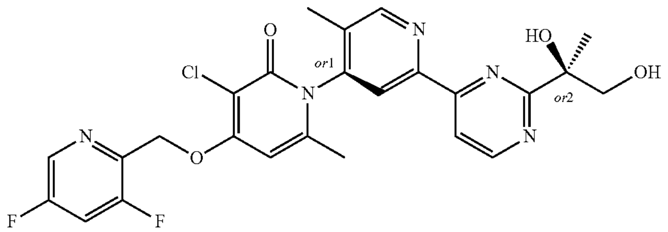 |
| 36D* | 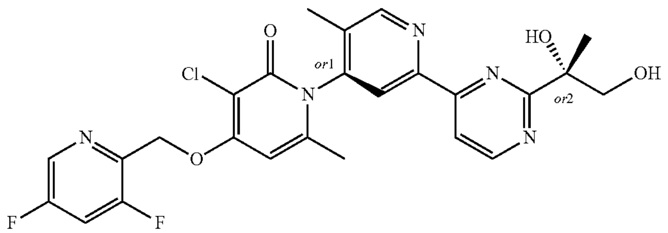 |
| 37A* | 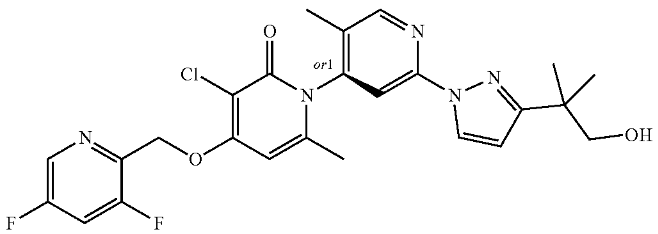 |
| 37B* | 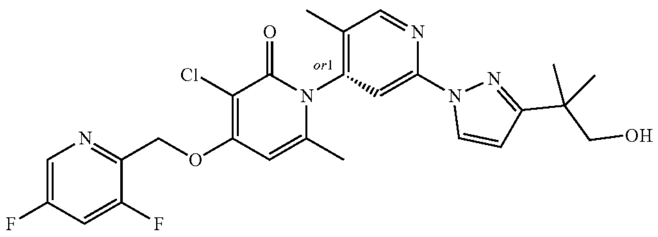 |

TABLE 1-continued
| Ex. | Structure |
|---|---|
| 38A* | 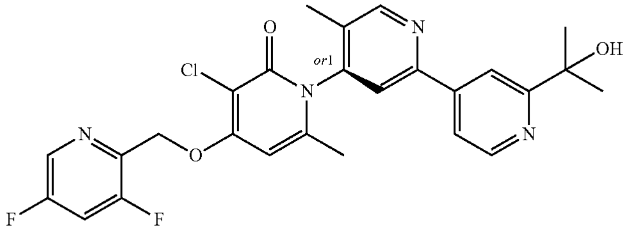 |
| 38B* | 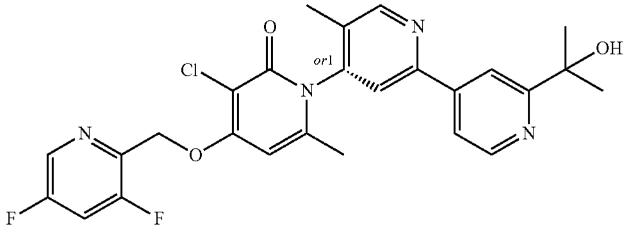 |
| 39A* | 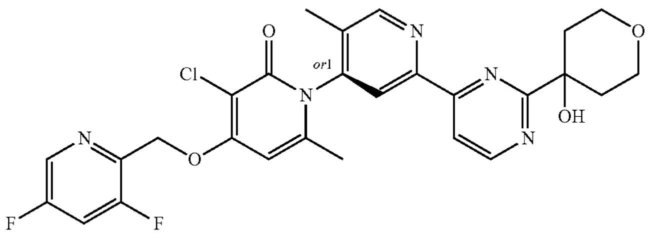 |
| 39B* | 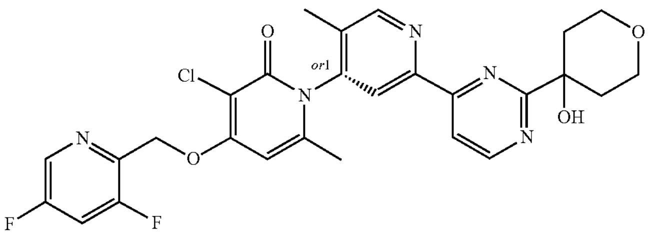 |
| 40A* | 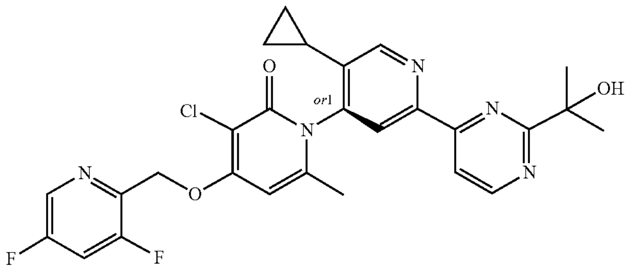 |
| 40B* | 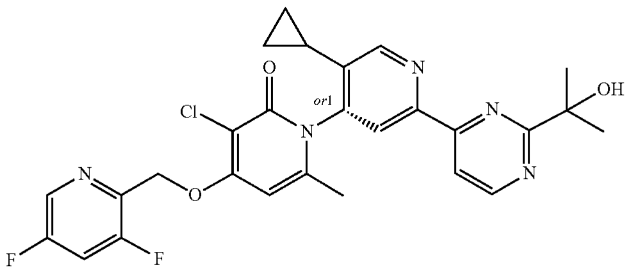 |

TABLE 1-continued
| Ex. | Structure |
|---|---|
| 41A* | 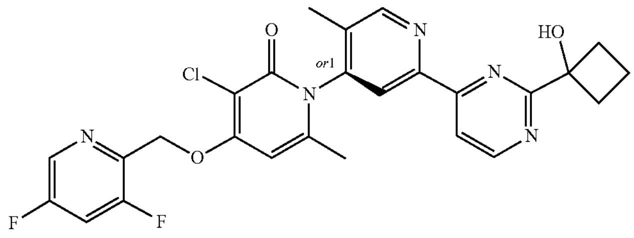 |
| 41B* | 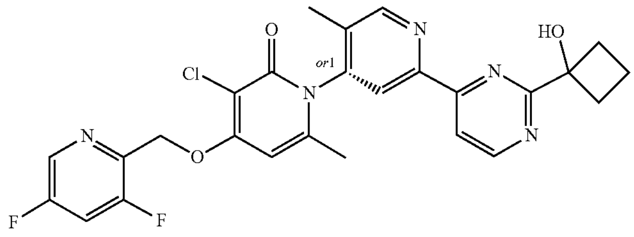 |
| 42A* | 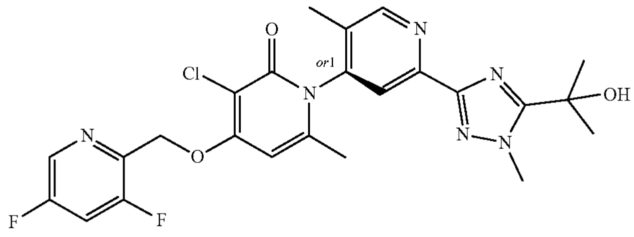 |
| 42B* | 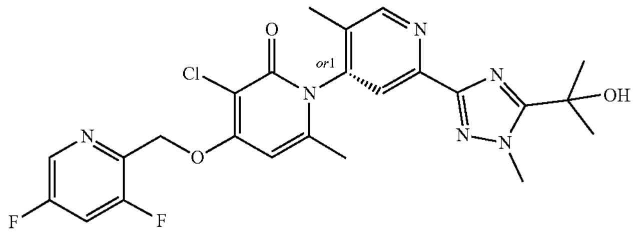 |
| 43A* | 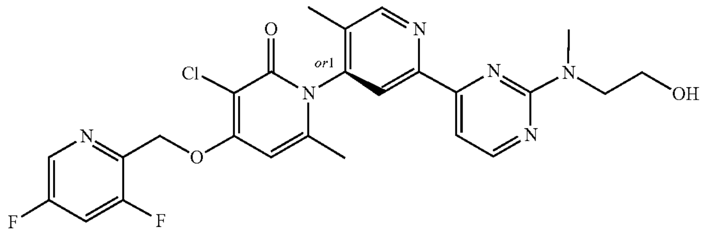 |
| 43B* | 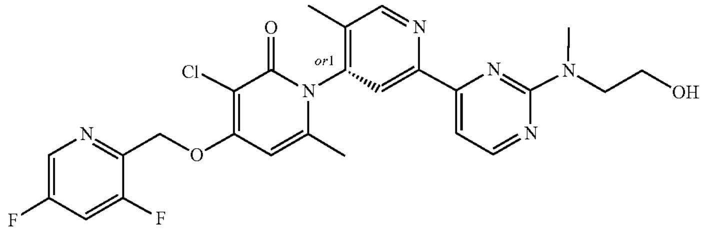 |

TABLE 1-continued
| Ex. | Structure |
| --- | --- |
| 44A* | 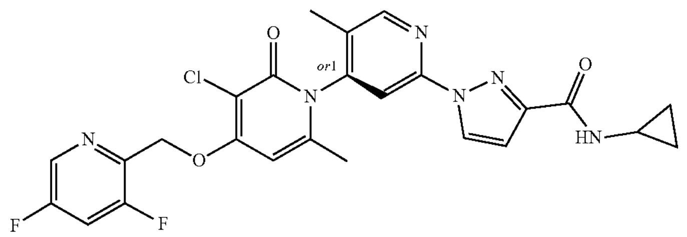 |
| 44B* | 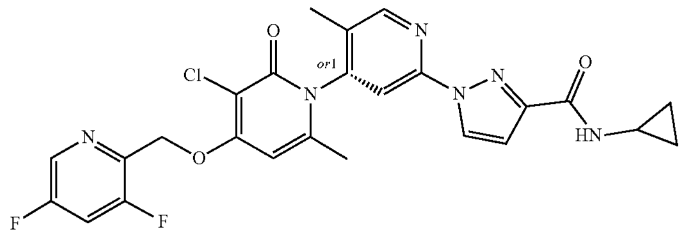 |
| 45A* | 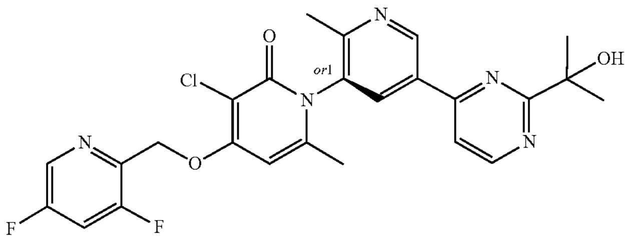 |
| 45B* | 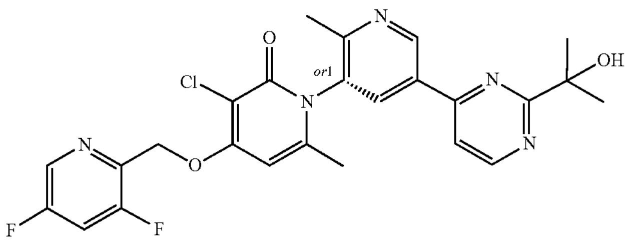 |
| 46A* | 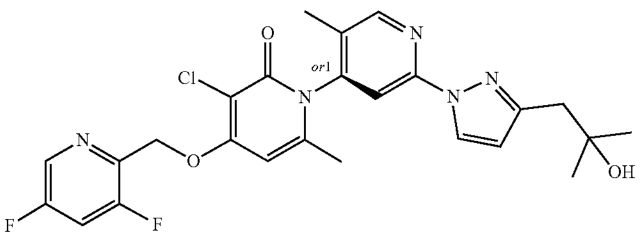 |
| 46B* | 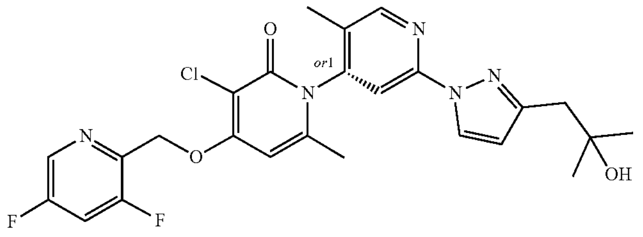 |

TABLE 1-continued
| Ex. | Structure |
|---|---|
| 47A* | 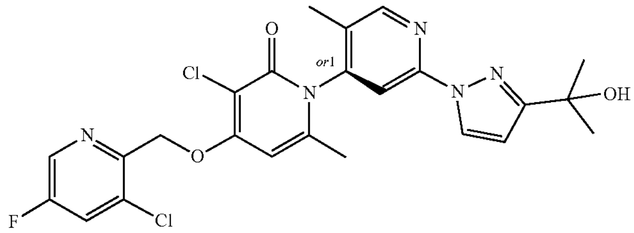 |
| 47B* | 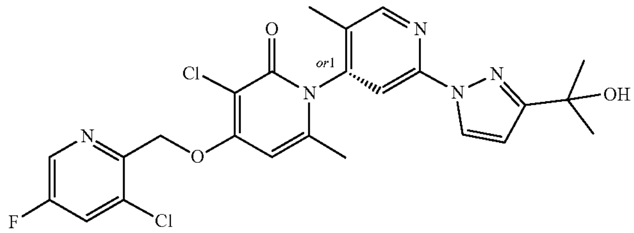 |
| 48A* | 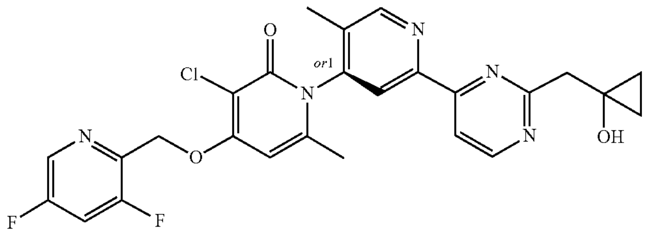 |
| 48B* | 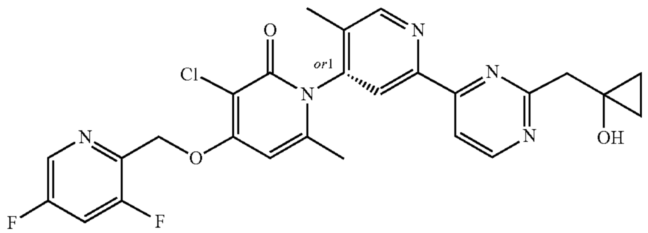 |
| 49A* | 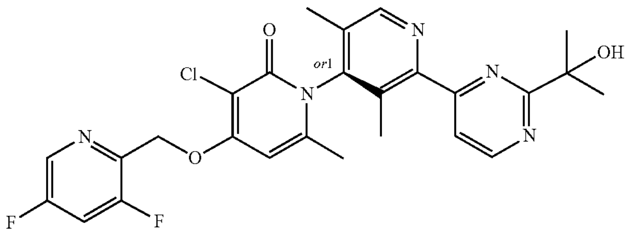 |
| 49B* | 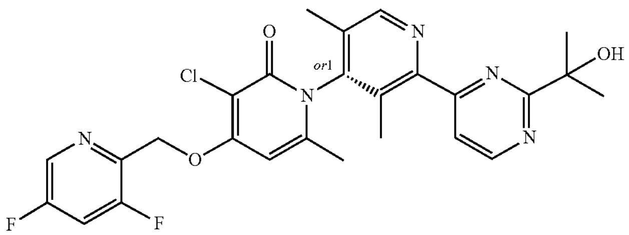 |

TABLE 1-continued
| Ex. | Structure |
|---|---|
| 50A* | 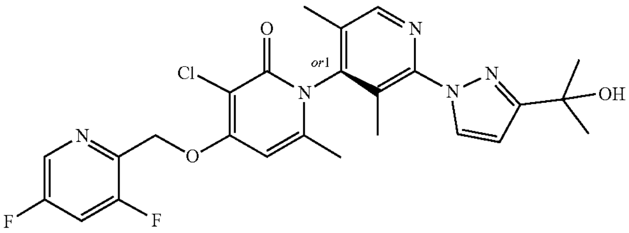 |
| 50B* | 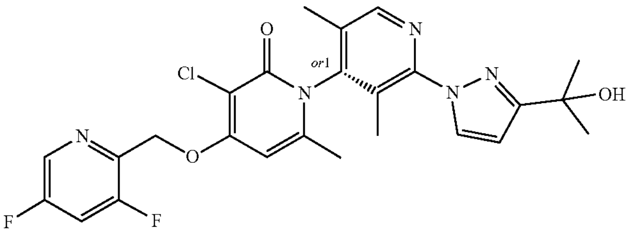 |
| 51A* | 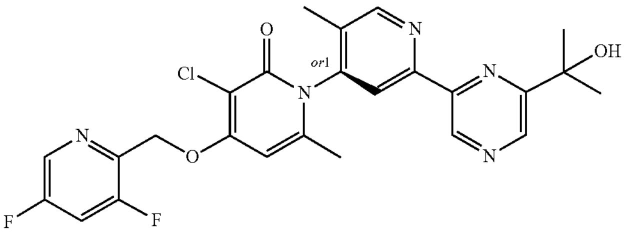 |
| 51B* | 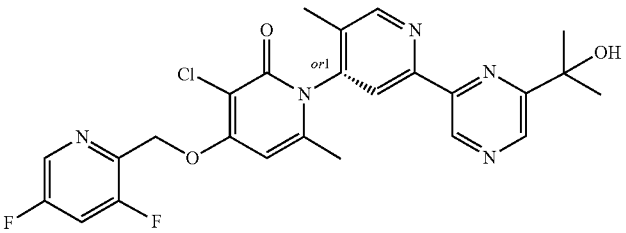 |
| 52A* | 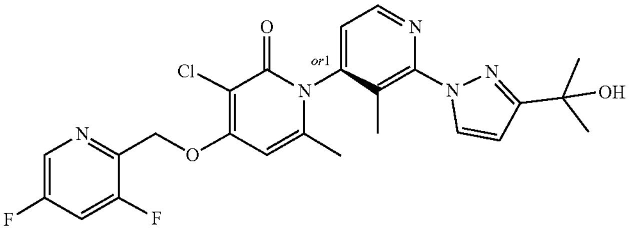 |
| 52B* | 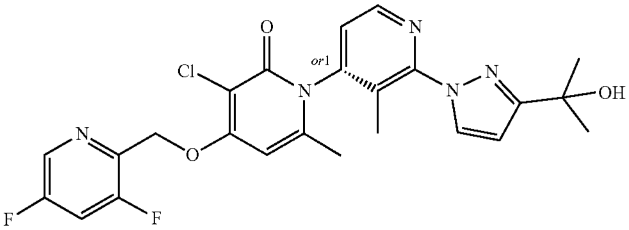 |

TABLE 1-continued
| Ex. | Structure |
| --- | --- |
| 53A* | 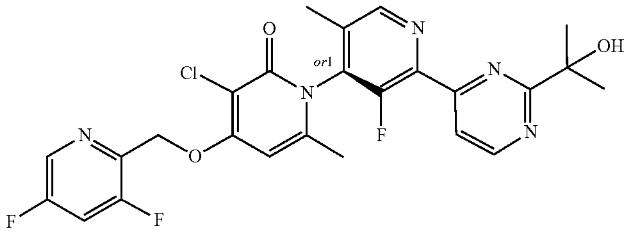 |
| 53B* | 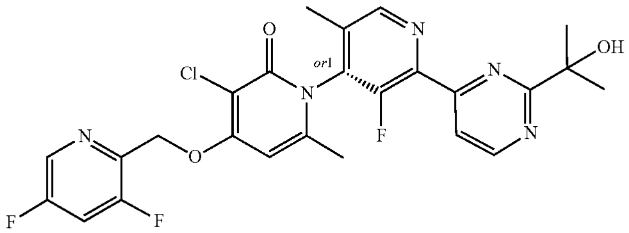 |
| 54A* | 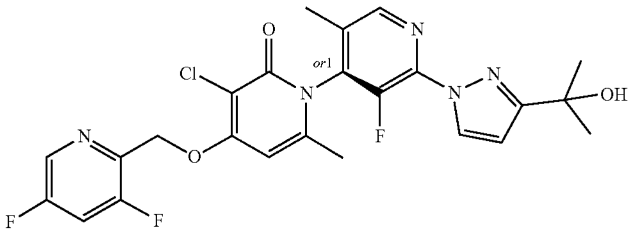 |
| 54B* | 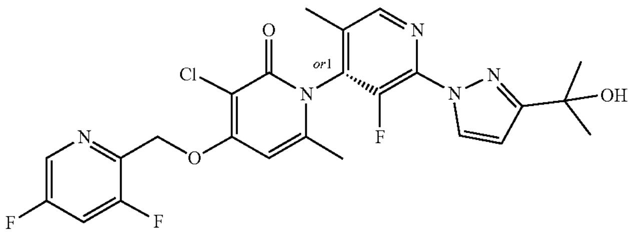 |
| 55* | 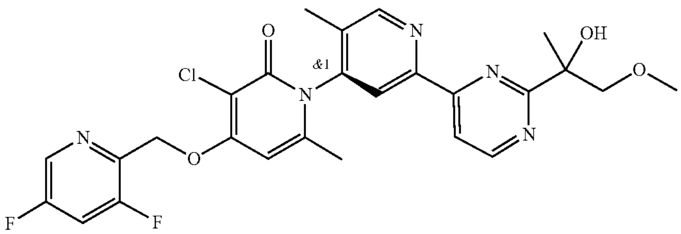 |
| 56A* | 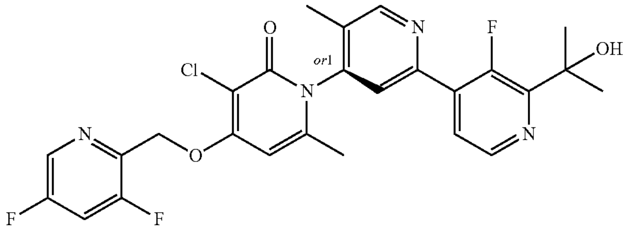 |

TABLE 1-continued
| Ex. | Structure |
|---|---|
| 56B* | 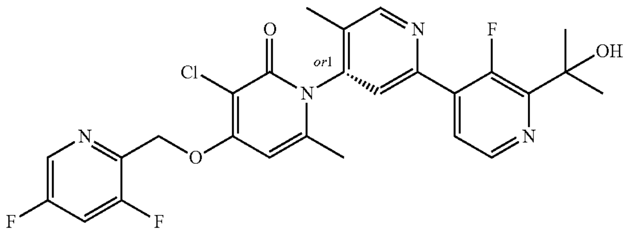 |
| 57A* | 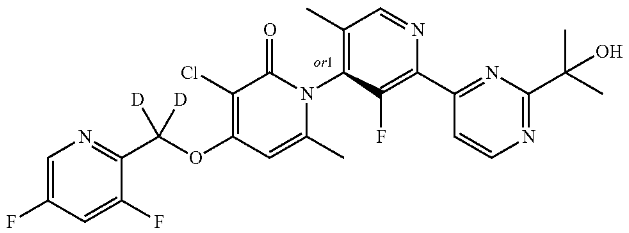 |
| 57B* | 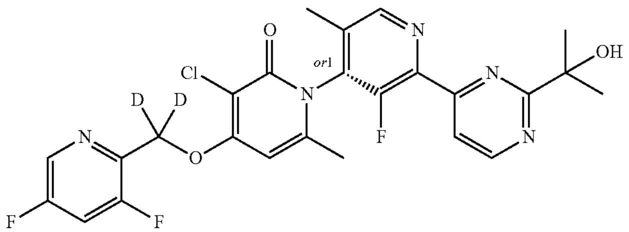 |
| 58A* | 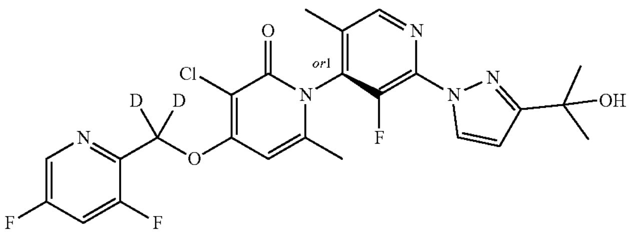 |
| 58B* | 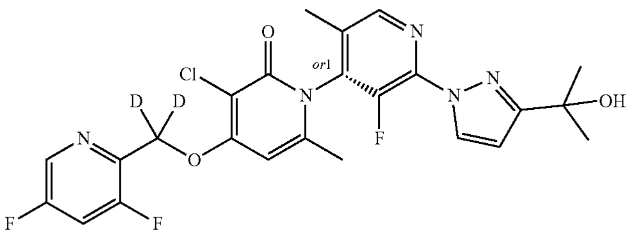 |
| 59A* | 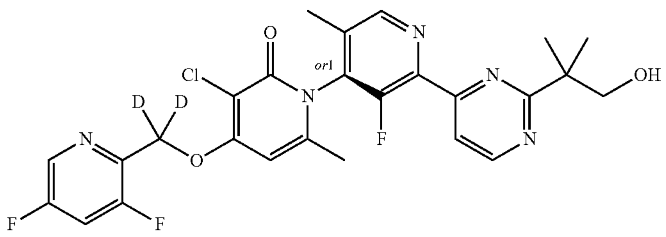 |

TABLE 1-continued
| Ex. | Structure |
|---|---|
| 59B* | 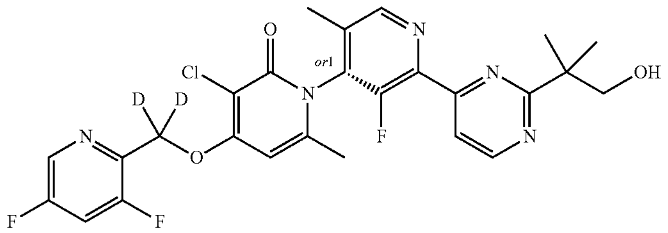 |
| 60A* | 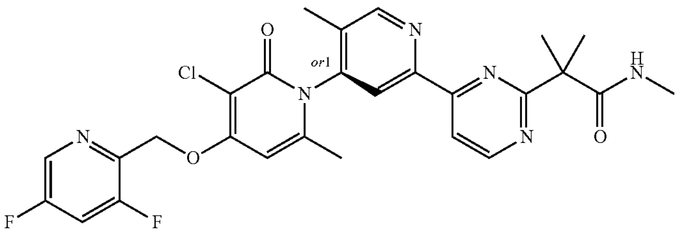 |
| 60B* | 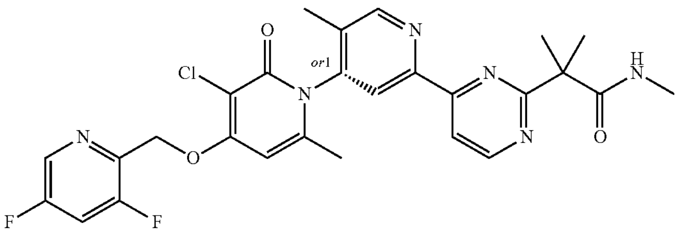 |
| 61A* | 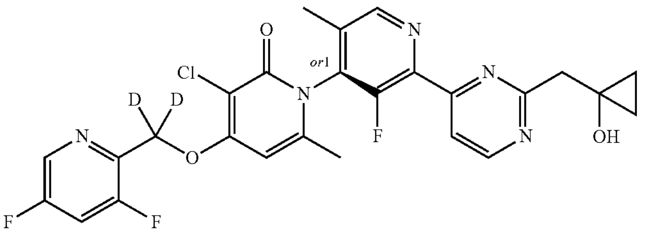 |
| 61B* | 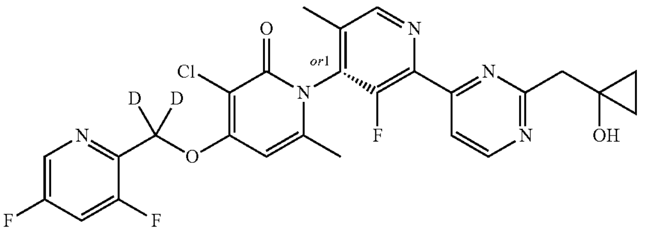 |
| 62A* | 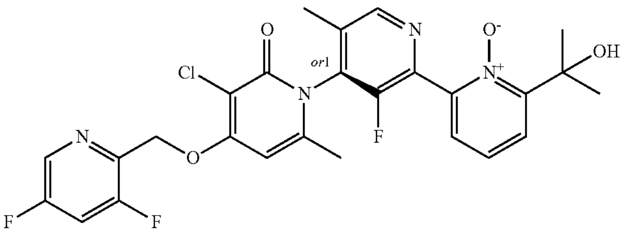 |

TABLE 1-continued
| Ex. | Structure |
| --- | --- |
| 62B* | 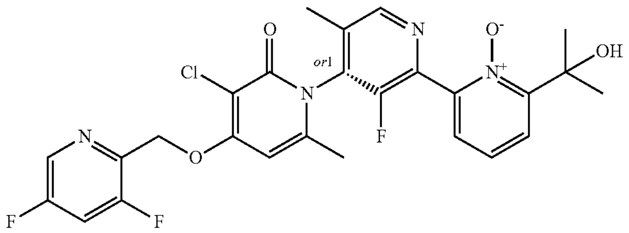 |
| 63A* | 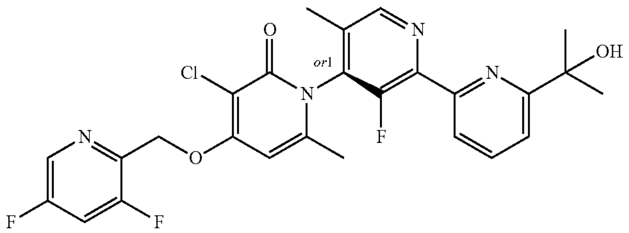 |
| 63B* | 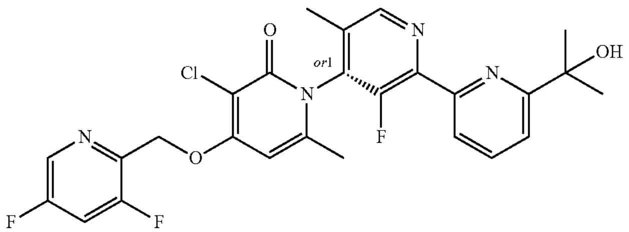 |
| 64A* | 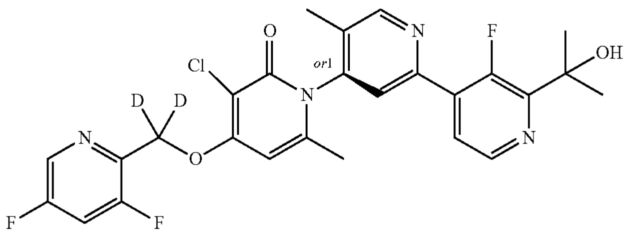 |
| 64B* | 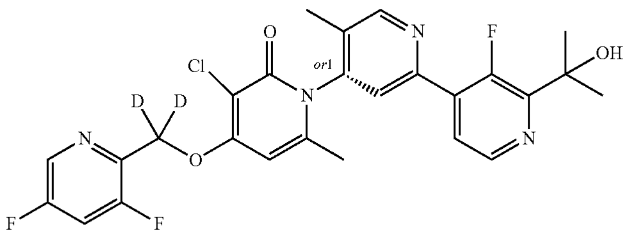 |
| 65A* | 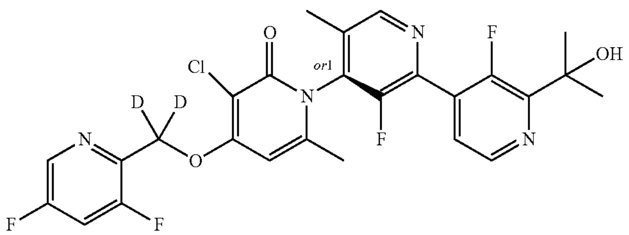 |

TABLE 1-continued
| Ex. | Structure |
| --- | --- |
| 65B* | 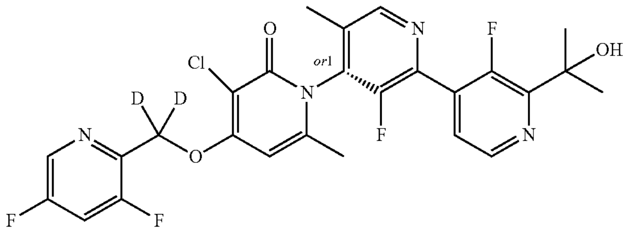 |
| 66A* | 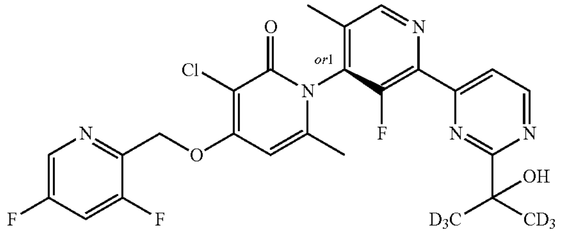 |
| 66B* | 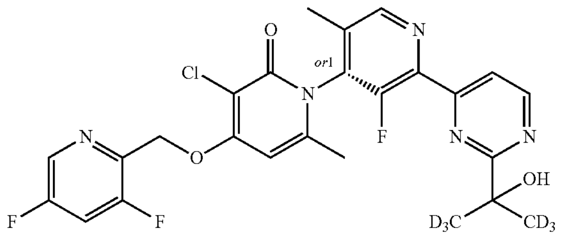 |
| 67A* | 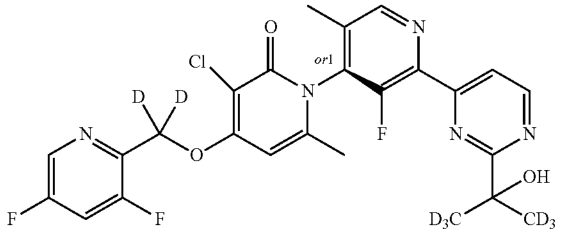 |
| 67B* | 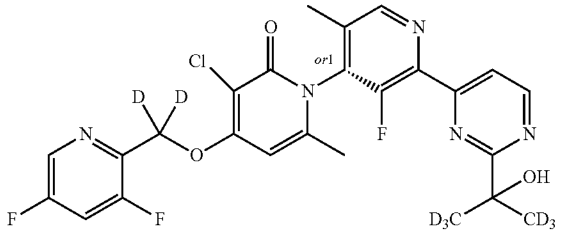 |
| 68A* | 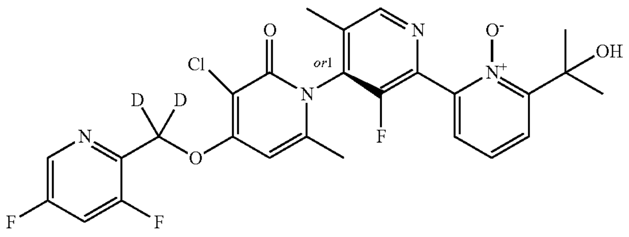 |

TABLE 1-continued
| Ex. | Structure |
| --- | --- |
| 68B* | 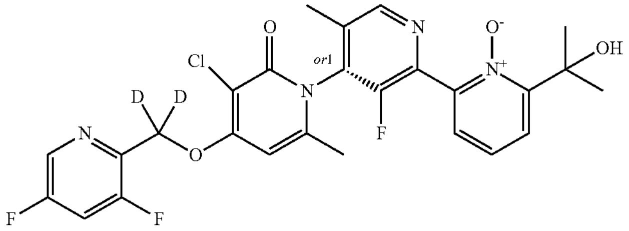 |
*stereochemistry arbitrarily assigned.
In some embodiments the compound of Formula (I) is selected from:
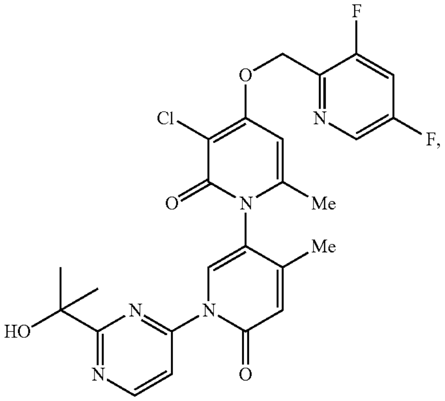
,
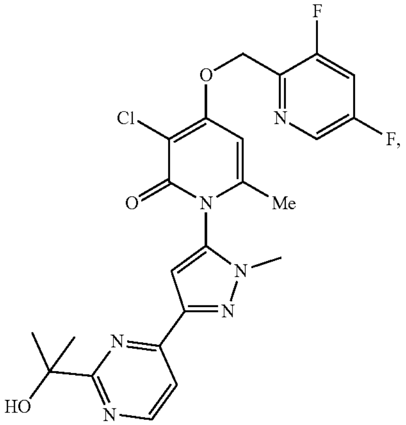
,
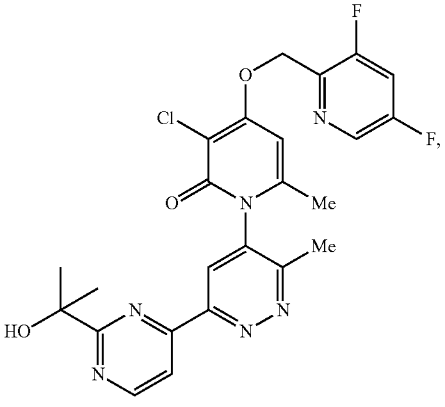
,
-continued
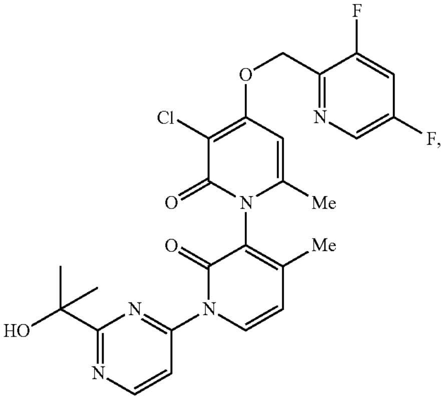
,
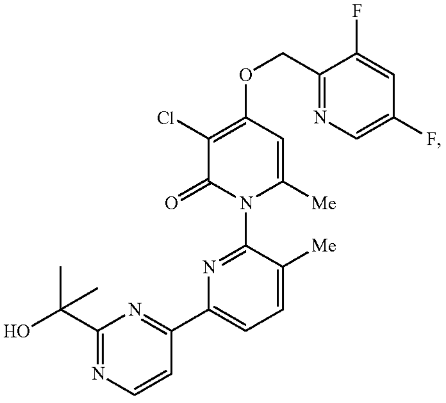
,
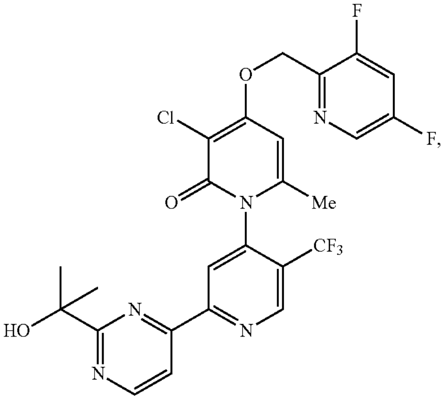
, -continued
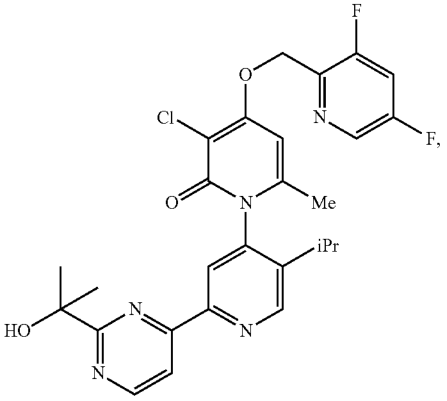
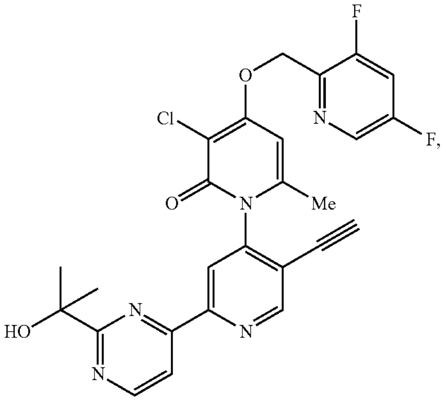
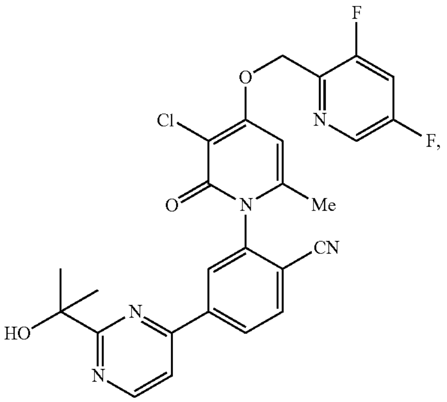
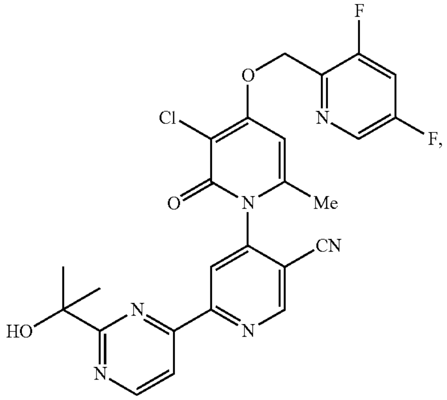
and
-continued
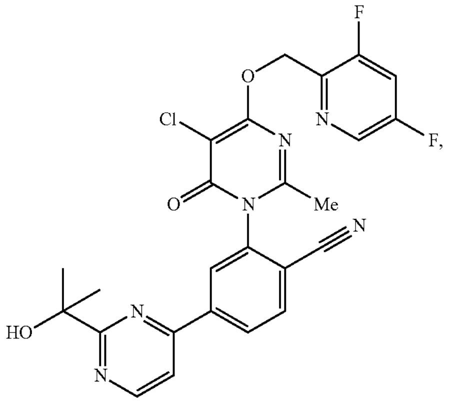
or a pharmaceutically acceptable salt, solvate. N-oxide, or stereoisomer thereof.
In some embodiments the compound of Formula (II) is selected from;
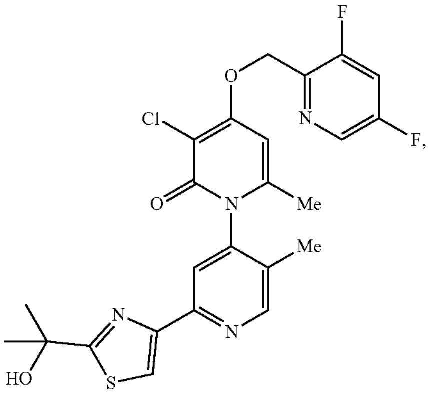
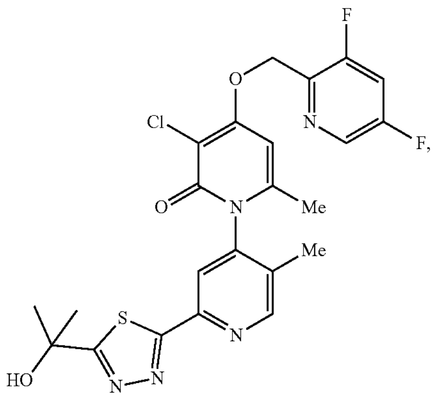

-continued
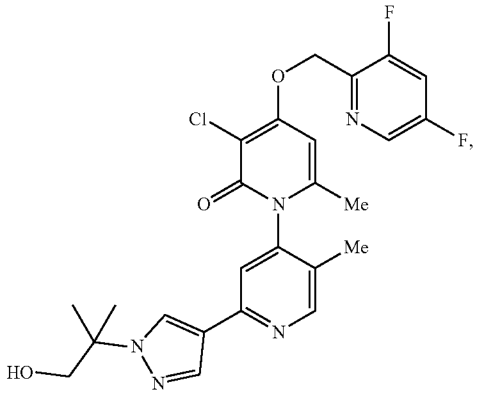
and
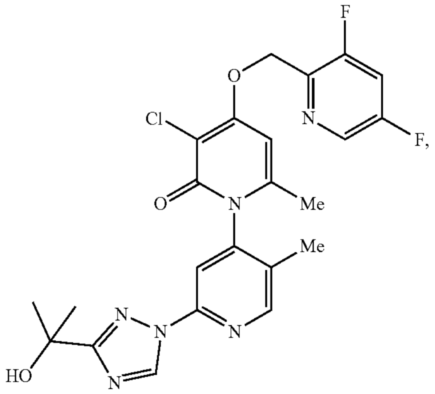
or a pharmaceutically acceptable salt, solvate. N-oxide, or stereoisomer thereof.
In some embodiments the compound of Formula (III) is selected from:
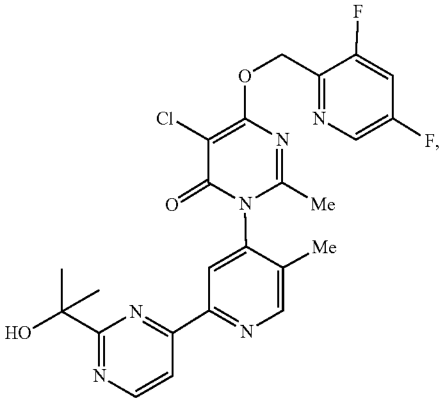
-continued
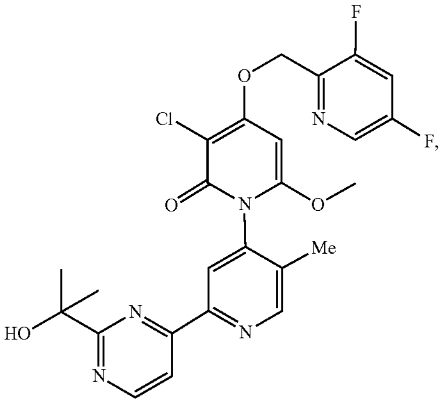
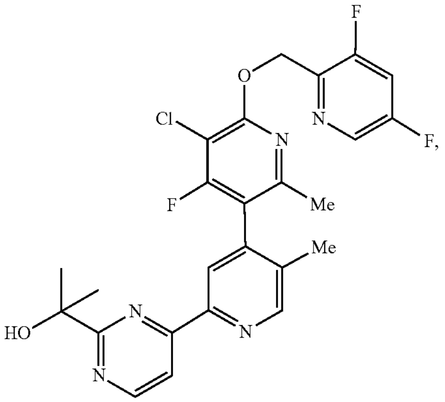
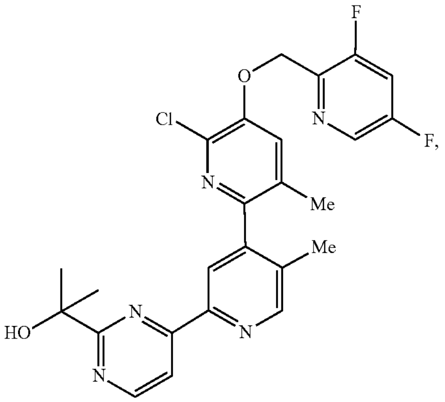
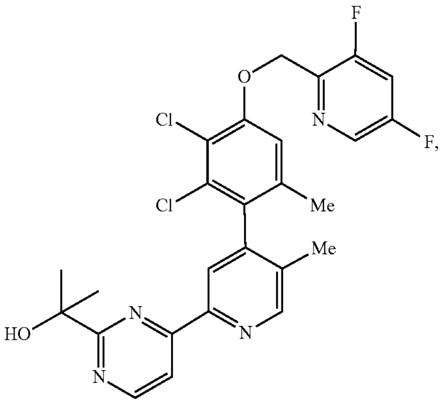

-continued
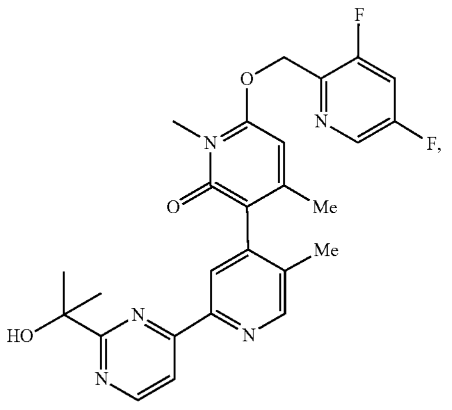
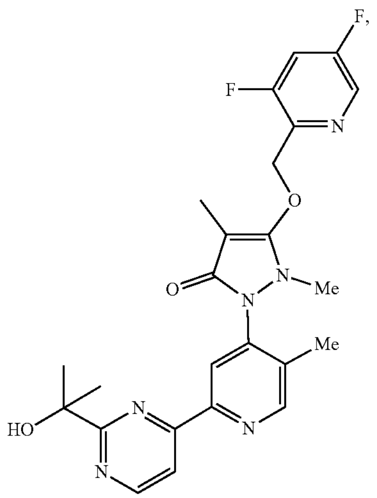
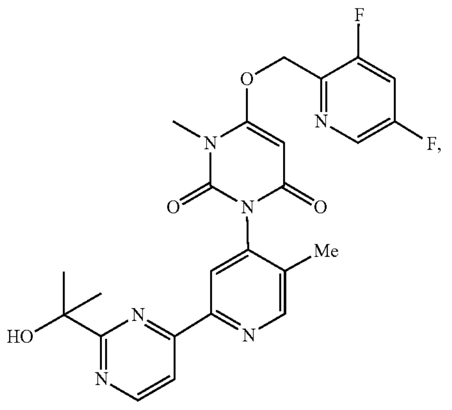
-continued
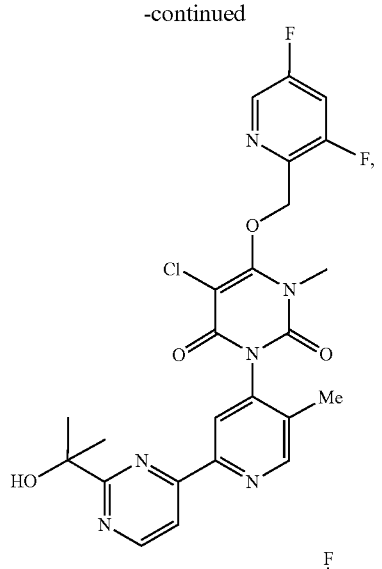
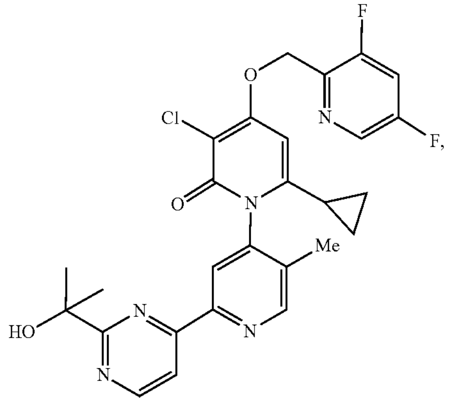
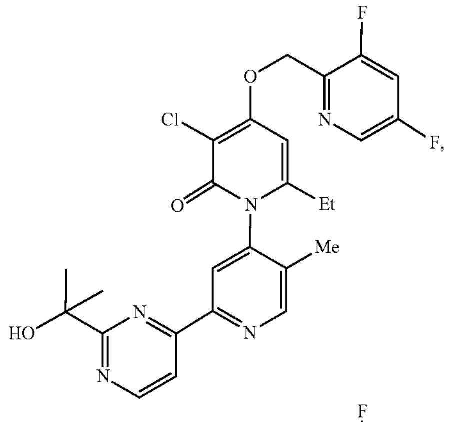
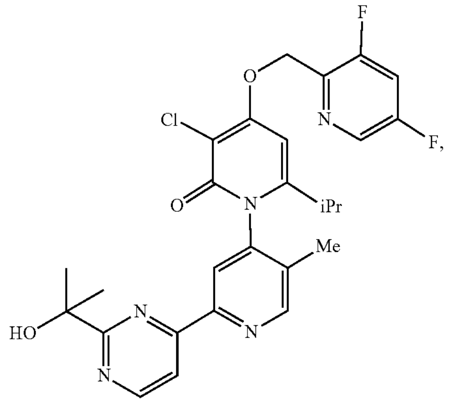

-continued
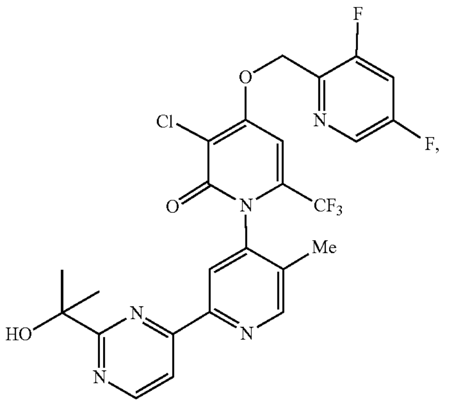
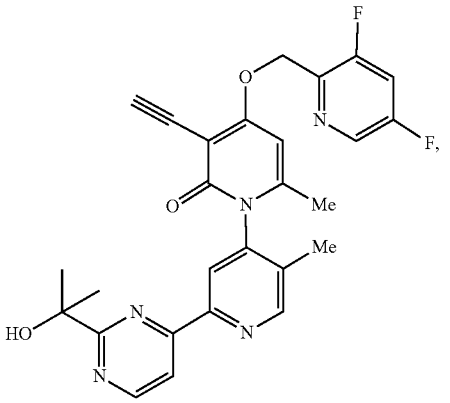
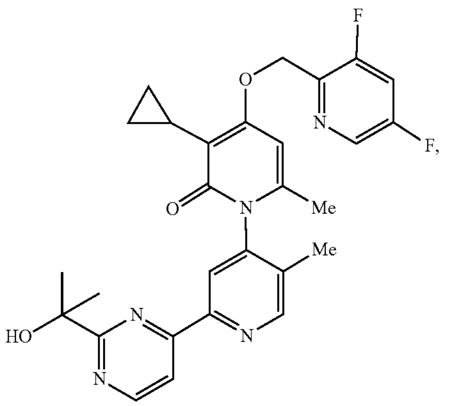
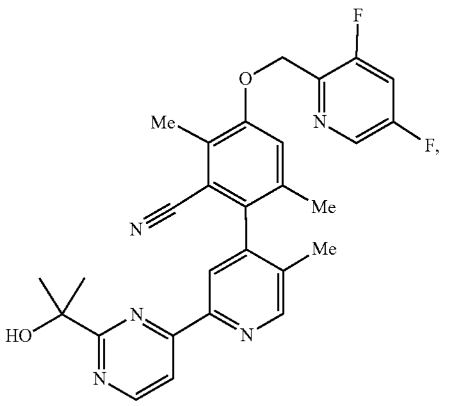
-continued
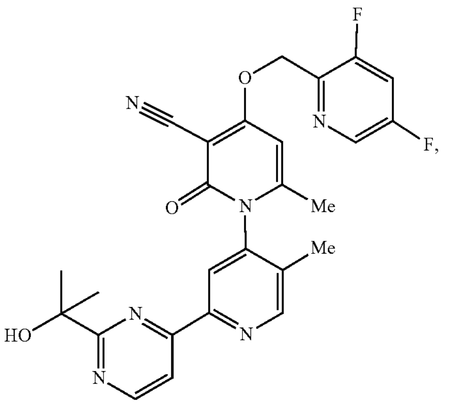
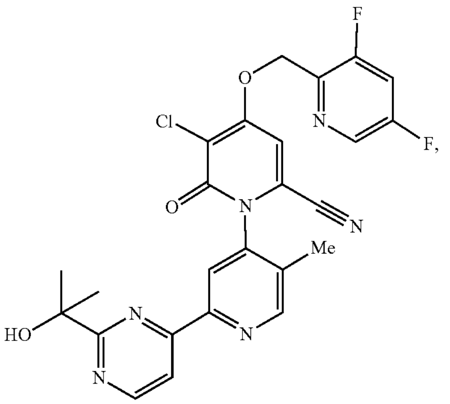
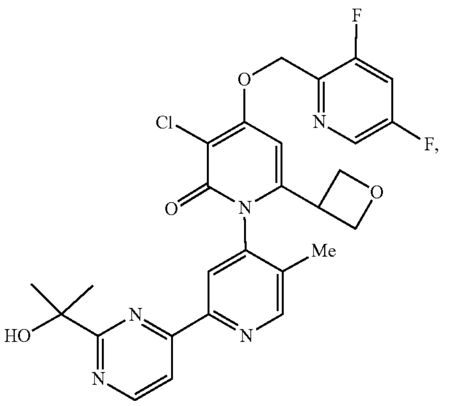
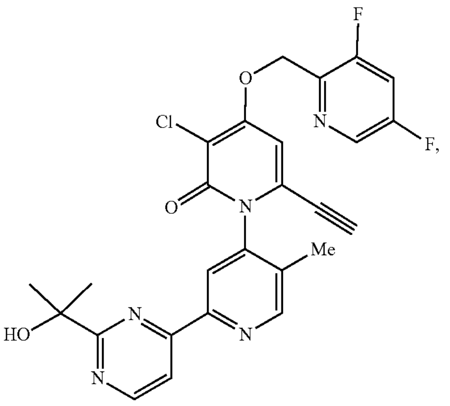

-continued
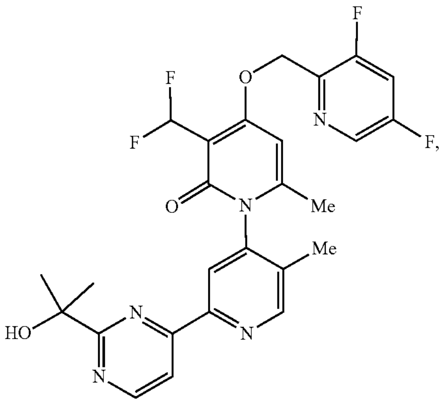
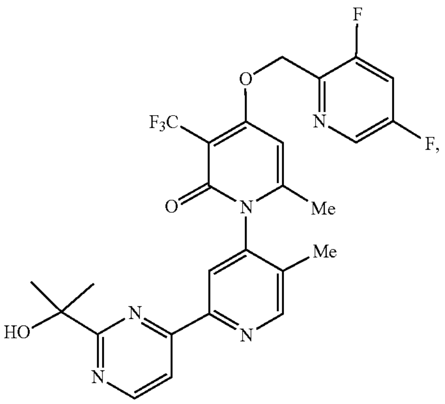
and
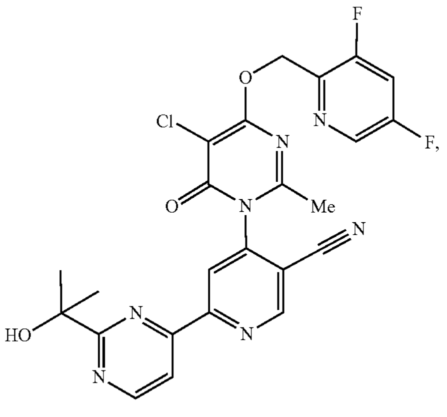
or a pharmaceutically acceptable salt, solvate. N-oxide, or stereoisomer thereof.
In some embodiments the compound of Formula (IV) is selected from:
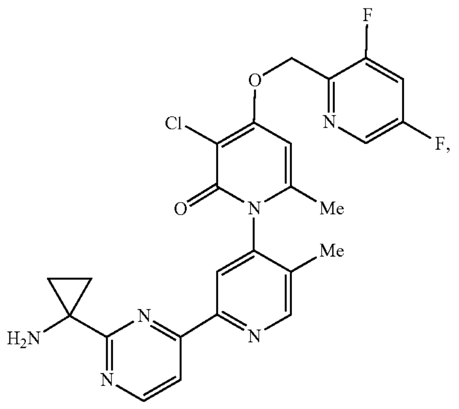
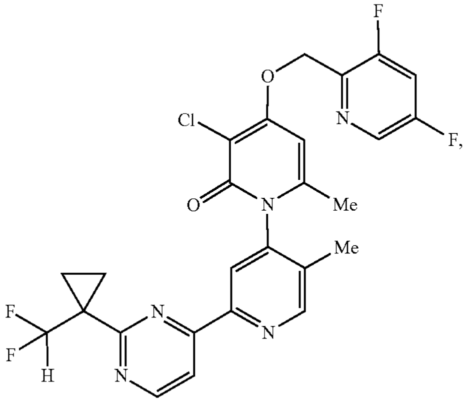
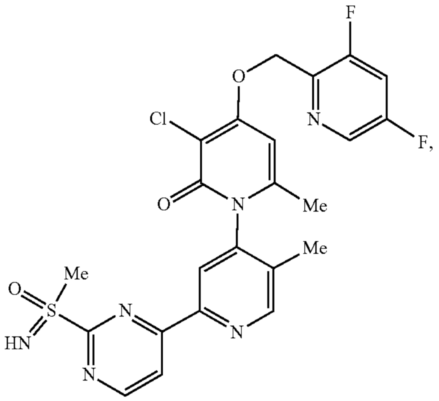
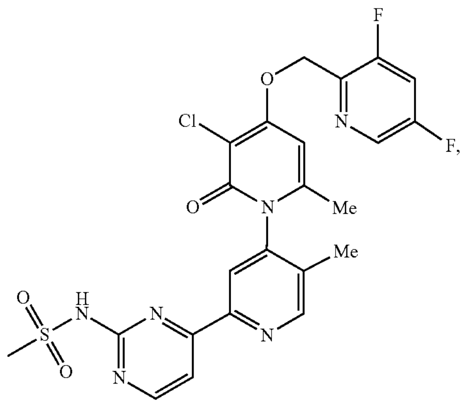

-continued
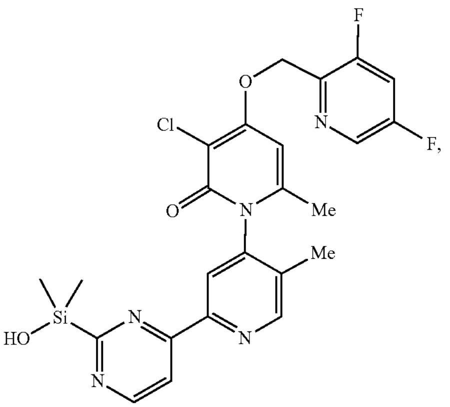
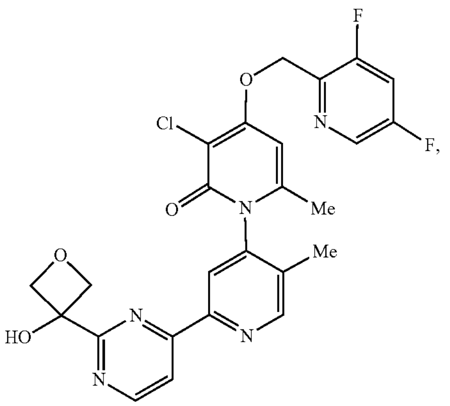
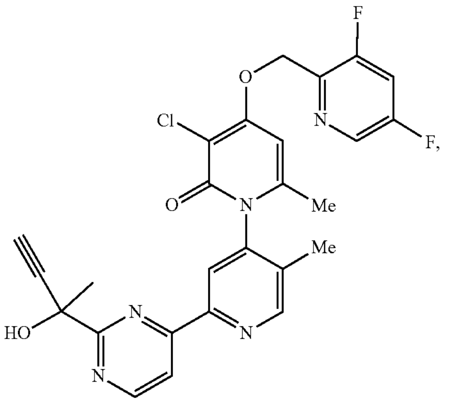
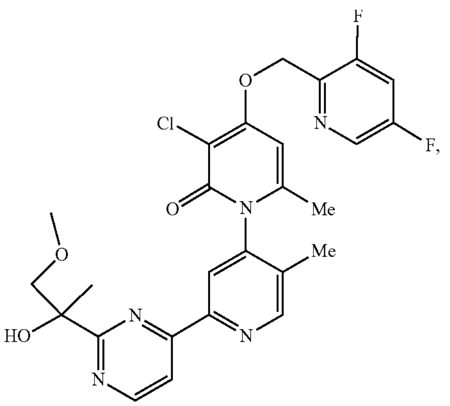
-continued
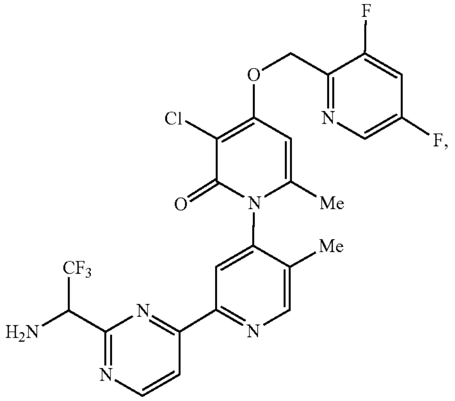
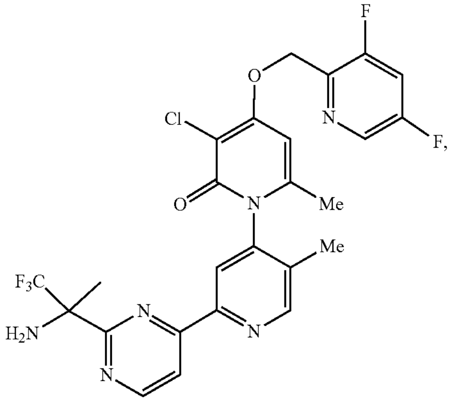
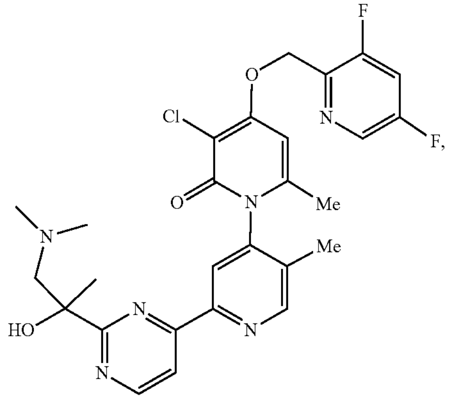
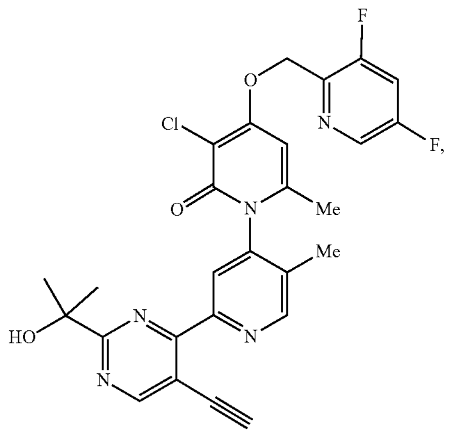

-continued
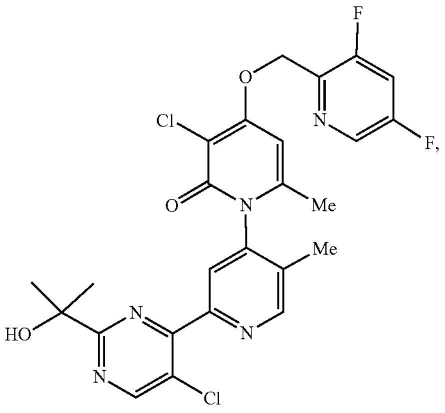
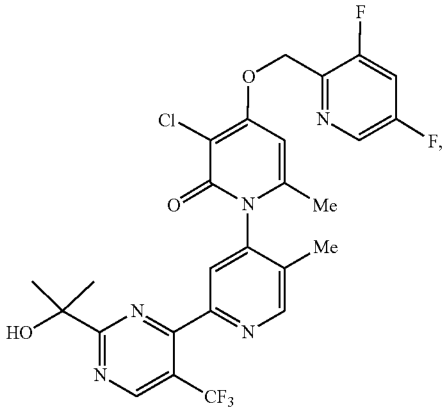
and
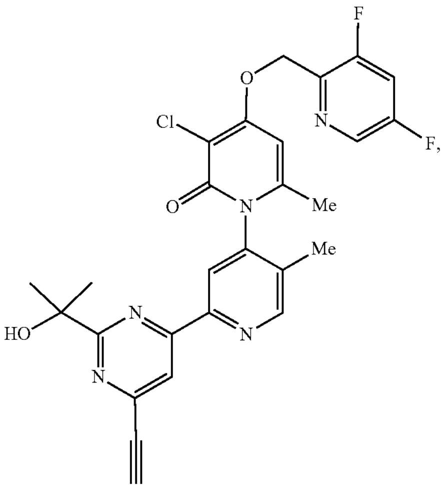
or a pharmaceutically acceptable salt, solvate. N-oxide, or stereoisomer thereof.
In some embodiments the compound of Formula (V) is selected from:
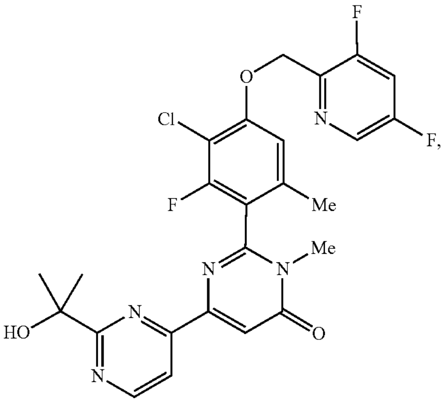
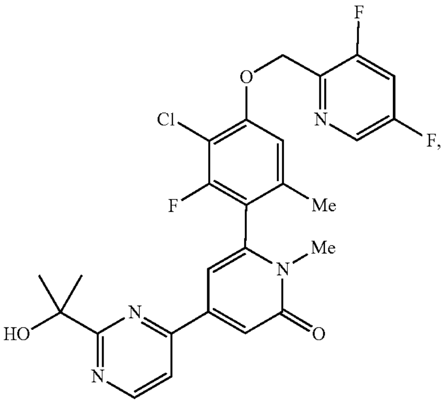
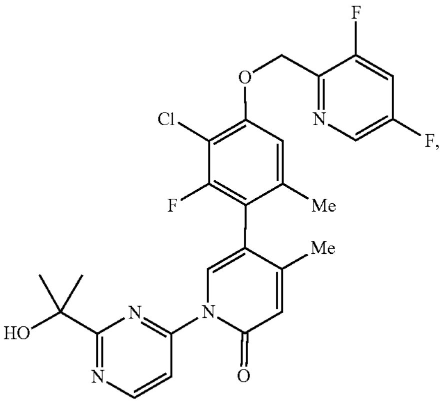
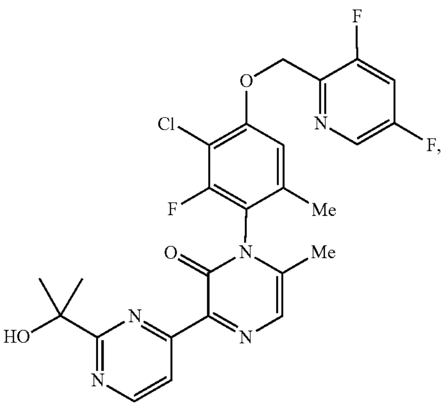

-continued
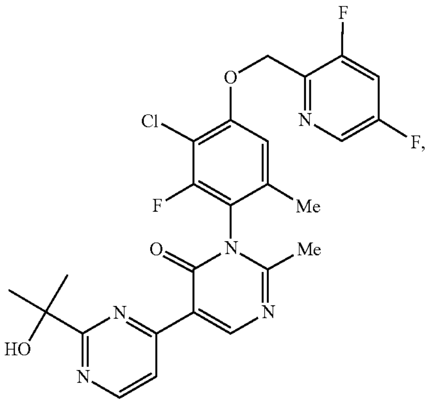
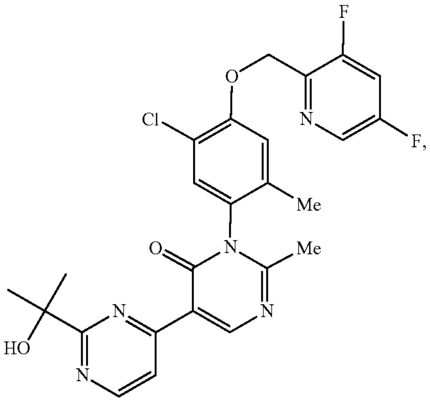
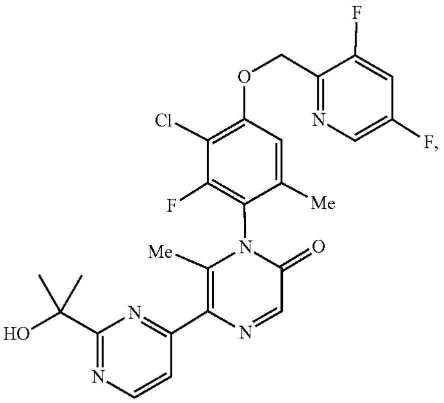
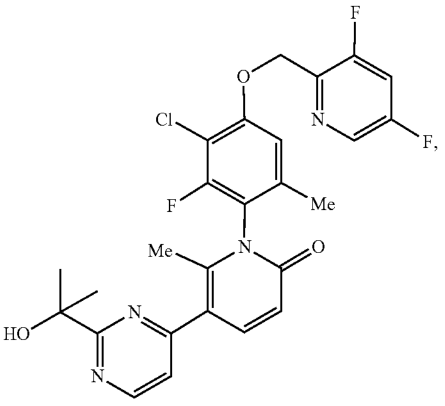
and
-continued
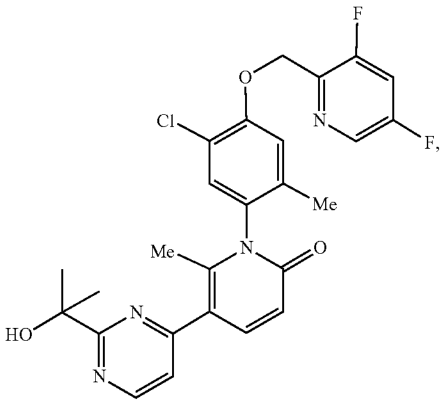 [SMILES: Cc1cc(OCc2ncc(F)cc2F)c(Cl)cc1-n1c(C)c(-c2ccnc(C(C)(C)O)n2)ccc1=O]
or a pharmaceutically acceptable salt, solvate, N-oxide, or stereoisomer thereof.
In some embodiments the compound of Formula (VI) is selected from:
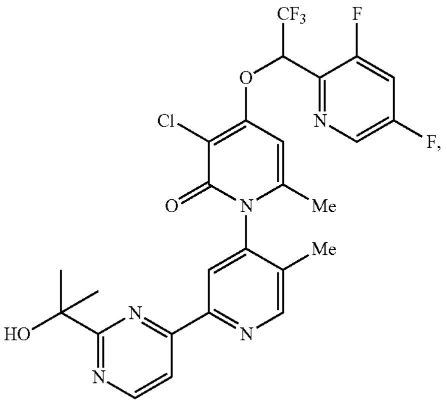
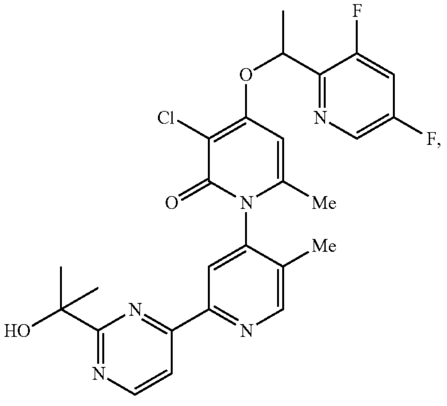

-continued
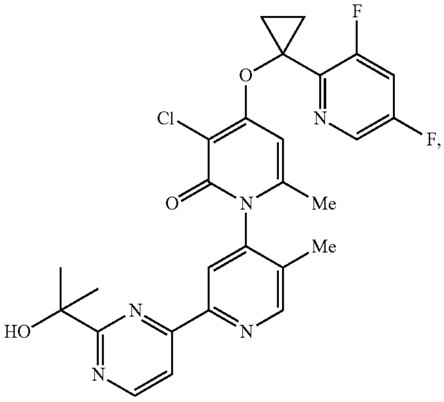
,
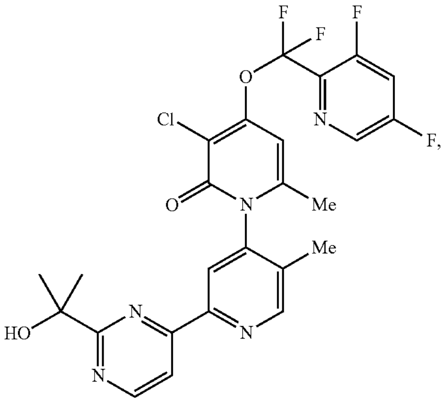
,
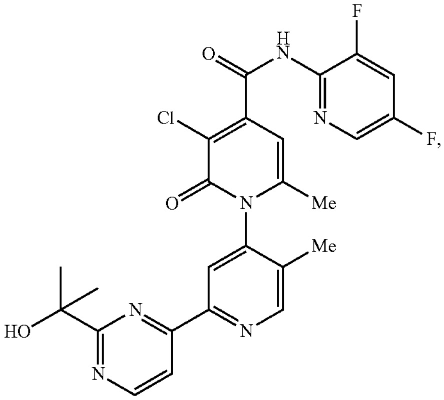
,
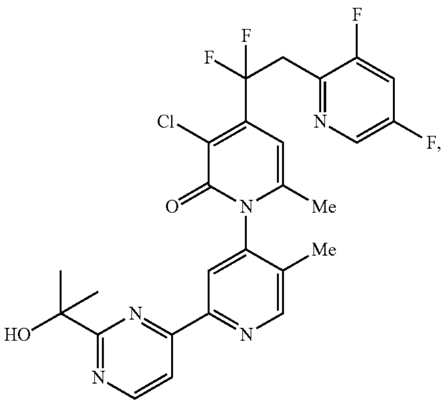
,
-continued
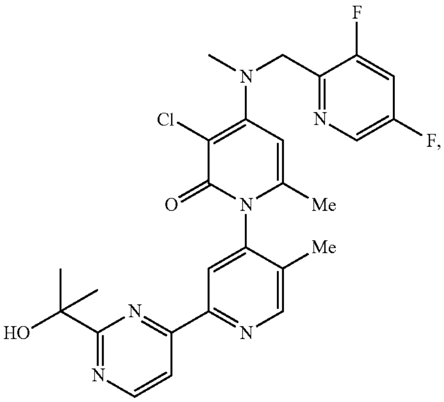
,
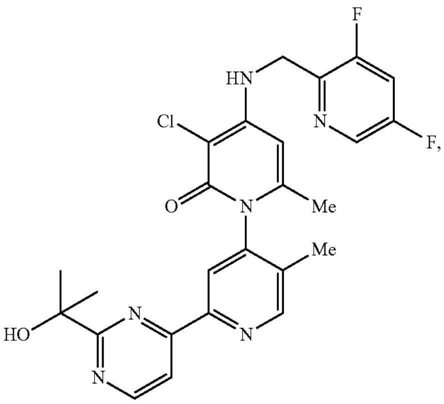
,
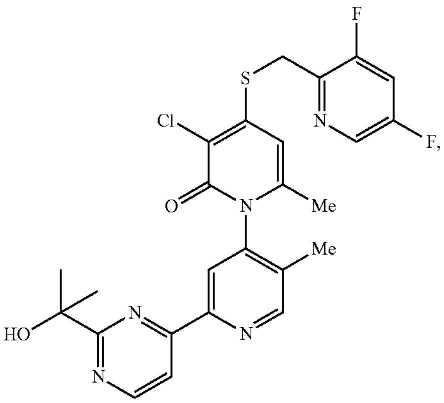
,
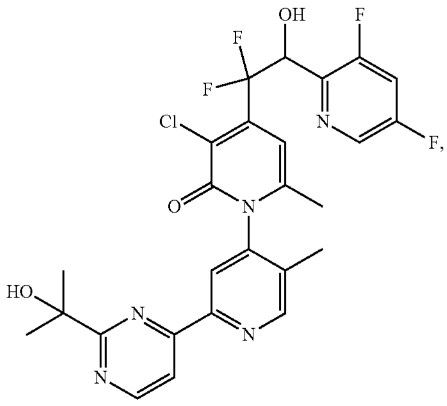
, and -continued

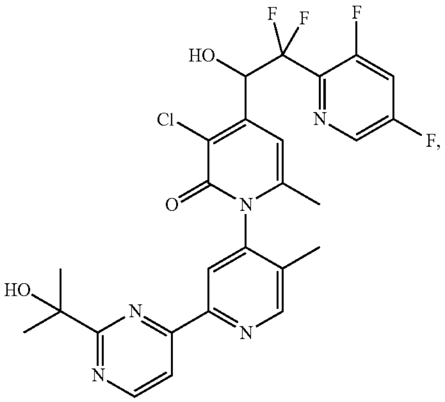

or a pharmaceutically acceptable salt, solvate, N-oxide, or stereoisomer thereof.

In some embodiments the compound of Formula (VII) is selected from:

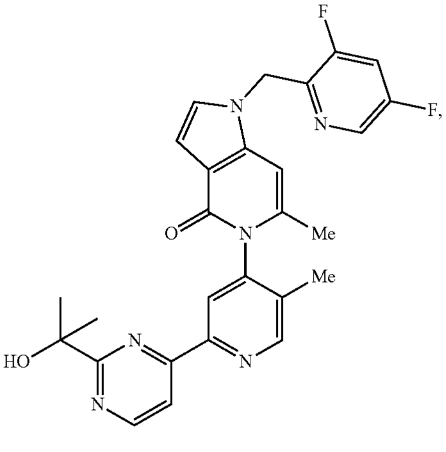

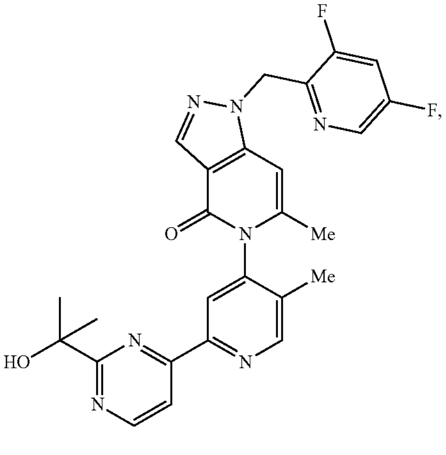

and

-continued

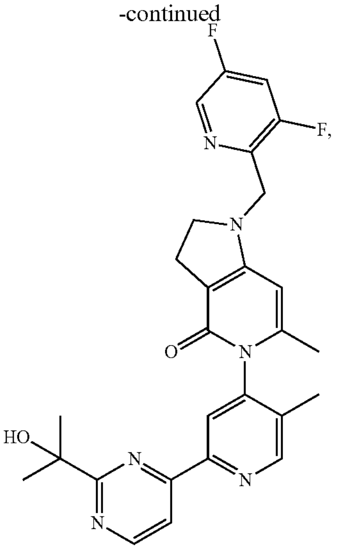

or a pharmaceutically acceptable salt, solvate, N-oxide, or stereoisomer thereof.

Further Forms of Compounds Disclosed Herein

Isomers Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

In some embodiments, the compounds described herein contain bonds with hindered rotation such that two separate rotamers or atropisomers can be isolated. In some embodiments the atropisomers are

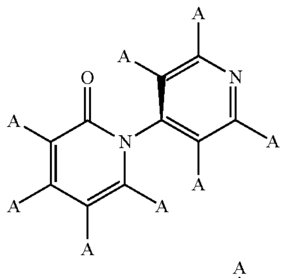

and

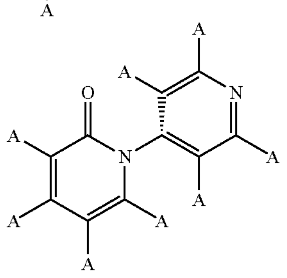

wherein each A correspond to the appropriate R group as defined in each of Formula (I) to (VIII). In some embodiments, these atropisomer are separated and are found to have different biological activity which may be advantageous. In some embodiments atropisomer is

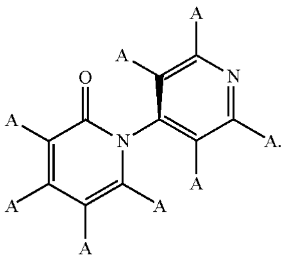

In some embodiments atropisomer is

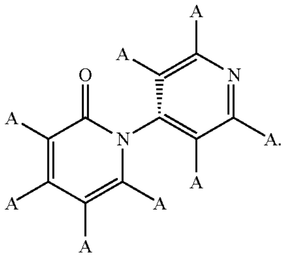

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as 3H and 14C are incorporated, are useful in drug and/or substrate tissue distribution assays. Tritiated, i.e., $^{3}H$ and carbon-14, i.e., $^{14}C$, isotopes are particularly preferred for their case of preparation and detectability. Further, substitution with heavy isotopes such as deuterium, i.e., $^{2}H$, produces certain therapeutic advantages resulting from greater metabolic stability, for example increased in vivo half-life or reduced dosage requirements.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acctatc, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1.6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate. 1-napthalenesulfonate, 2-napthalenesulfonate, nicotinate, nitrate, palmoatc, pectinate, persulfate, 3-phenylpropionate, phosphate, picrate, pivalate, propionate, pyrosulfate, pyrophosphatc, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid. 3-(4-hydroxybenzoyl)benzoic acid, cinnamic acid, mandelic acid, arylsulfonic acid, methanesulfonic acid, ethanesulfonic acid. 1.2-ethanedisulfonic acid. 2-hydroxyethanesulfonic acid, benzenesulfonic acid. 2-naphthalencsulfonic acid. 4-methylbicyclo-[2.2.2]oct-2-ene-1-carboxylic acid, glucoheptonic acid. 4.4-methylenebis —(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate. $N^+(C_{1-4}\text{ alkyl})_4$, and the like.

Representative organic amines useful for the formation of base addition salts include cthylamine. diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Described herein are compounds and compositions generally useful for the inhibition of kinase activity of one or more enzymes. Examples of kinases that are inhibited by the compounds and compositions described herein and against which the methods described herein are useful include p38 MAP kinase, MK2, or a mutant thereof.

MAP kinase-activated protein kinase 2 ("MK2") is an enzyme that in humans is encoded by the MAPKAPK2 gene. This gene encodes a member of the Ser/Thr protein kinase family. This kinase is regulated through direct phosphorylation by p38 MAP kinase. In conjunction with p38 MAP kinase, this kinase is known to be involved in many cellular processes including stress and inflammatory responses. nuclear export, gene expression regulation and cell proliferation. Heat shock protein HSP27 was shown to be one of the substrates of this kinase in vivo. Two transcript variants encoding two different isoforms have been found for this gene.

MK2 is a multi-domain protein consisting of an N-terminal proline-rich domain, a catalytic domain, an autoinhibitory domain and at the C-terminus a nuclear export signal (NES) and nuclear localization signal (NLS). Two isoforms of human MK2 have been characterized. One isoform consists of 400 amino acids and the other isoform 370 residues which is thought to be a splice variant missing the C-terminal NLS. MK2 is located in the nucleus of the cell and upon binding and phosphorylation by p38, the MK2 NES becomes functional and both kinases are co-transported out of the nucleus to the cytoplasm. Interestingly, transport of the MK2/p38 complex does not require catalytically active MK2, as the active site mutant. Asp207Ala, is still transported to the cytoplasm. Phosphorylation of human MK2 by p38 on residues T222. S272 and T334 is thought to activate the enzyme by inducing a conformational change of the autoinhibitory domain thus exposing the active site for substrate binding. Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity.

Diseases or disorders associated with MK2 that are treated by compounds disclosed herein include autoimmune disorders, chronic inflammatory disorders, acute inflammatory disorders, auto-inflammatory disorders, fibrotic disorders, metabolic disorders, neoplastic disorders, and cardiovascular or cerebrovascular disorders.

In some embodiments, the MK2-mediated disease or disorder is an autoimmune disorder, chronic and/or acute inflammatory disorder, and/or auto-inflammatory disorder. Exemplary autoimmune and/or inflammatory and/or auto-inflammatory disorders include: inflammatory bowel diseases (for example. ulcerative colitis or Crohn's disease), multiple sclerosis, psoriasis, arthritis, rheumatoid arthritis, osteoarthritis. juvenile arthritis, psoriatic arthritis, reactive arthritis, ankylosing spondylitis, cryopyrin associated periodic syndromes. Muckle-Wells syndrome, familial cold auto-inflammatory syndromc. neonatal-onset multisystem inflammatory disease. TNF receptor associated periodic syndrome, acute and chronic pancreatitis, atherosclerosis, gout, ankylosing spondylitis, fibrotic disorders (for example, hepatic fibrosis or idiopathic pulmonary fibrosis), nephropathy, sarcoidosis, scleroderma, anaphylaxis, diabetes (for example, diabetes mellitus type 1 or diabetes mellitus type 2), diabetic retinopathy. Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease. Sjogren's syndrome, familial Mediterranean fever, systemic lupus erythematosus, vasculitis syndromes (for example, temporal. Takayasu's and giant cell arteritis. Behçet's disease or Wegener's granulomatosis), vitiligo, secondary hematologic manifestation of autoimmune diseases (for example, anemias), drug-induced autoimmunity. Hashimoto's thyroiditis, hypophysitis, idiopathic thrombocytic purpura, metal-induced autoimmunity, myasthenia gravis, pemphigus, autoimmune deafness (for example, Meniere's disease), Goodpasture's syndrome, Graves' disease, HW-related autoimmune syndromes, Guillain-Barre disease, Addison's disease, anti-phospholipid syndrome, asthma, atopic dermatitis, Celiac disease, Cushing's syndrome, dermatomyositis, idiopathic adrenal atrophy, idiopathic thrombocytopenia, Kawasaki syndrome, Lambert-Eaton Syndrome, pernicious anemia, pollinosis, polyarteritis nodosa, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs, host reaction (for example, graft vs, host disease), allograft rejections (for example, acute allograft rejection or chronic allograft rejection), early transplantation rejection (for example, acute allograft rejection), reperfusion injury, pain (for example, acute pain, chronic pain, neuropathic pain, or fibromyalgia), chronic infections, meningitis, encephalitis, myocarditis, gingivitis, post-surgical trauma, tissue injury, traumatic brain injury, enterocolitis, sinusitis, uveitis, ocular inflammation, optic neuritis. gastric ulcers, esophagitis, peritonitis, periodontitis, dermatomyositis, gastritis, myositis, polymyalgia, pneumonia and bronchitis.

In some embodiments, the MK2-mediated disease or disorder is a fibrotic disorder. Exemplary fibrotic disorders include systemic sclerosis/scleroderma, lupus nephritis, connective tissue disease, wound healing, surgical scarring, spinal cord injury. CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension-induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation-induced fibrosis (for example, head and neck, gastrointestinal or pulmonary), primary sclerosing cholangitis, restenosis, cardiac fibrosis (for example, endomyocardial fibrosis or atrial fibrosis), ophthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the MK2-mediated disease or disorder is a metabolic disorder. Exemplary metabolic disorders include obesity, steroid-resistance, glucose intolerance, and metabolic syndrome.

In some embodiments, the MK2-mediated disease or disorder is a neoplastic disease or disorder. Exemplary neoplastic diseases or disorders include cancers. In some embodiments, exemplary neoplastic diseases or disorders include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example. B-cell lymphoma. T-cell lymphoma, mantle cell lymphoma, hairy cell lymphoma. Burkitt's lymphoma, mast cell tumors. Hodgkin's disease or non-Hodgkin's disease), myelodysplastic syndrome, fibrosarcoma, rhabdomyosarcoma: astrocytoma, neuroblastoma, glioma and schwannomas: melanoma, seminoma, teratocarcinoma, osteosarcoma, xenoderma pigmentosum, keratoctanthoma, thyroid follicular cancer. Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the MK2-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component. Alzheimer's disease. Parkinson's disease. Huntington's disease, amyotrophic lateral sclerosis, spinal cord injury, neuronal ischemia and peripheral neuropathy.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only. 2 days, 3 days. 4 days. 5 days. 6 days. 7 days. 10 days. 12 days. 15 days. 20 days. 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including. but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the LD10 and the ED90. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (c) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day: or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose: (ii) the time between multiple administrations is every 6 hours: (iii) the compound is administered to the mammal every 8 hours: (iv) the compound is administered to the subject every 12 hours: (v) the compound is administered to the subject every 24 hours. In further or alternative embodiments, the method comprises a drug holiday, wherein the administration of the compound is temporarily suspended or the dose of the compound being administered is temporarily reduced: at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In vet other embodiments, the compound described herein is administered topically.

Pharmaceutical Compositions/Formulations

The compounds described herein are administered to a subject in need thereof, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

In another aspect, provided herein are pharmaceutical compositions comprising a compound described herein, or a pharmaceutically acceptable salt, solvate. N-oxide, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton. Pa.: Mack Publishing Company. 1995): Hoover. John E. . . . Remington's Pharmaceutical Sciences. Mack Publishing Co. . . . Easton, Pennsylvania 1975; Liberman, H.A, and Lachman. L., Eds., Pharmaceutical Dosage Forms. Marcel Decker. New York. N.Y . . . 1980; and Pharmaceutical Dosage Forms and Drug Delivery Systems. Seventh Ed. (Lippincott Williams & Wilkins 1999), herein incorporated by reference for such disclosure.

In some embodiments, the pharmaceutically acceptable excipient is selected from carriers. binders, filling agents, suspending agents, flavoring agents, sweetening agents, disintegrating agents. dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, clixirs, slurrics, suspensions, self-emulsifying dispersions, solid solutions, liposomal dispersions, aerosols, solid oral dosage forms, powders, immediate release formulations, controlled release formulations. fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate. N-oxide, or stereoisomer thereof are manufactured in a conventional manner, such as, by way of example only, by means of conventional mixing, dissolving, granulating, dragcc-making. levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol: cellulose preparations such as, for example, maize starch, wheat starch, rice starch, potato starch. gelatin, gum tragacanth, methylcellulose, microcrystalline cellulose, hydroxypropylmethylcellulose, sodium carboxymethylcellulose: or others such as polyvinylpyrrolidone (PVP or povidone) or calcium phosphate. If desired, disintegrating agents are added, such as the cross-linked croscarmellose sodium. polyvinylpyrrolidone, agar, or alginic acid or a salt thereof such as sodium alginate. In some embodiments. dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate. N-oxide, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are methods of treating an autoimmune disorder, a chronic inflammatory disorder, an acute inflammatory disorder, an auto-inflammatory disorder, a fibrotic disorder, a metabolic disorder, a neoplastic disorder, or a cardiovascular or a cerebrovascular disorder using a compound disclosed herein, or a pharmaceutically acceptable salt, solvate. N-oxide, or stereoisomer thereof, in combination with an additional therapeutic agent.

In some embodiments, the additional therapeutic agent is selected from the group consisting of anti-inflammatory drugs, anti-atherosclerotic drugs, immunosuppressive drugs, immunomodulatory drugs. cytostatic drugs, anti-proliferative agents, angiogenesis inhibitors. kinase inhibitors, cytokine blockers, and inhibitors of cell adhesion molecules.

In some embodiments, the additional therapeutic agent is selected from the group consisting of NSAIDs, immunosuppressive drugs, immunomodulatory drugs, cytostatic drugs, antiproliferative agents, angiogenesis inhibitors, biological agents, steroids, vitamin D3 analogs, retinoids, other kinase inhibitors. cytokine blockers, corticosteroids, and inhibitors of cell adhesion molecules. In some embodiments, the additional therapeutic agent is selected from the group consisting of torcetrapib, aspirin, niacin, HMG CoA reductase inhibitors (e.g., atorvastatin, fluvastatin, lovastatin, pravastatin, rosuvastatin and simvastatin). colesevelam, cholestyramine, colestipol, gemfibrozil, probucol, and clofibrate.

In some embodiments, the additional therapeutic agent is selected from the group consisting of corticosteroids, non-steroidal anti-inflammatory drugs (NSAID) (e.g, ibuprofen, naproxen, acetaminophen, aspirin, Fenoprofen (Nalfon), Flurbiprofen (Ansaid), Ketoprofen, Oxaprozin (Daypro), Diclofenac sodium (Voltaren), Diclofenac potassium (Cataflam), Etodolac (Lodine), Indomethacin (Indocin), Ketorolac (Toradol), Sulindac (Clinoril), Tolmetin (Tolectin), Meclofenamate (Meclomen), Mefenamic acid (Ponstel), Nabumetone (Relafen), Piroxicam (Feldene), cox-2 inhibitors (e.g., celecoxib (Celebrex))), immunosuppressants (e.g., methotrexate (Rheumatrex), leflunomide (Arava), azathioprine (Imuran), cyclosporine (Neoral, Sandimmune), tacrolimus and cyclophosphamide (Cytoxan), $CD_{20}$ blockers (Rituximab), Tumor Necrosis Factor (TNF) blockers (e.g., etanercept (Enbrel), infliximab (Remicade) and adalimumab (Humira)), Abatacept (CTLA4-Ig) and interleukin-1 receptor antagonists (e.g. Anakinra (Kineret), interleukin 6 inhibitors (e.g., Actemra), interleukin 17 inhibitors (e.g., AlN457), Janus kinase inhibitors (e.g., Tasocitinib), syk inhibitors (e.g. $R^{788}$), and chloroquine and its derivatives.

In some embodiments, the additional therapeutic agent is selected from the group consisting of an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist. Raf protein kinase family inhibitor, angiogenesis inhibitor, Erb2 inhibitor, mTOR inhibitor, IGF-IR antibody, NFkB inhibitor, proteosome inhibitor, chemotherapy agent, and glucose reduction agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

EXAMPLE

Intermediates 1, 2, 3

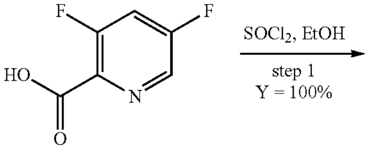

-continued

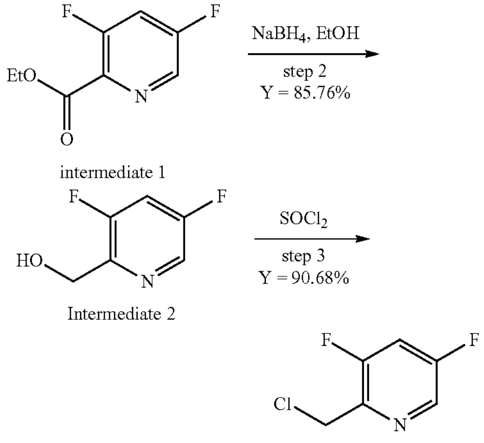

intermediate 1

Intermediate 2

Intermediate 3

Step 1: Preparation of ethyl 3,5-difluoropicolinate

A solution of 3,5-difluoropyridine-2-carboxylic acid (50.00 g, 314.28 mmol, 1.00 equiv) in ethanol (200 ml) was cooled using an ice bath, followed by the addition of SOCI2 (50 mL, 689.25 mmol, 2.20 equiv) dropwise at 0° C. The resulting mixture was stirred for 3 h at 60° C., under nitrogen atmosphere. The reaction was monitored by LCMS. The mixture was allowed to r.t. The resulting mixture was concentrated under vacuum. The residue was purified by silica gel column chromatography to afford ethyl 3,5-difluoropicolinate (59 g, 100%) as a colorless liquid. LC-MS: (ES+H, m/z): $[M+H]^+$=188.1.

Step 2: Preparation of (3,5-difluoropyridin-2-yl) methanol

To a stirred solution of ethyl 3,5-difluoropyridine-2-carboxylate (40.00 g, 213.74 mmol, 1.00 equiv) in ethanol (300 ml) was added $NaBH_4$ (20.22 g, 534.34 mmol, 2.50 equiv) in portions at 0° C., under nitrogen atmosphere. The resulting mixture was stirred for 30 min at 0° C., under nitrogen atmosphere. The resulting mixture was stirred for additional 2 h at room temperature under nitrogen atmosphere. The reaction was monitored by LCMS. The reaction was quenched with sat. $NH_4Cl$ (aq.) at 0° C. EtOH was removed under reduced pressure. The aqueous layer was basified to pH 10 with saturated $Na_2CO_3$ (aq., 300 mL), followed by extracted with EtOAc (3×300 mL). The combined organic layers were washed with brine, dried over anhydrous $Na_2SO_4$. After filtration, the filtrate was concentrated under vacuum to afford (3,5-difluoropyridin-2-yl) methanol (26.6 g, 85.76%) as a colorless liquid. LC-MS: (ES+H, m/z): $[M+H]^+$=146.1.

Step 3: Preparation of 2-(chloromethyl)-3,5-difluoropyridine

To a stirred solution of (3,5-difluoropyridin-2-yl) methanol (34.00 g, 234.31 mmol, 1.00 equiv) in DCM (500 ml) was added DMF (160 mg), and then cooled using ice water bath. To the above mixture was added SOCI2 (40 mL, 551.40 mmol, 2.35 equiv) dropwise under nitrogen atmosphere. The resulting mixture was stirred for 2 h at room temperature under nitrogen atmosphere. The reaction was monitored by LCMS The resulting mixture was concentrated under vacuum to afford 2-(chloromethyl)-3,5-difluoropyridine (34.75 g, 90.68%) as a brown-yellow semi-solid. LC-MS: (ES+H, m/z): $[M+H]^+$=164.0. $^1H$ NMR (400 MHz, Chloroform-d) δ 8.35 (d, 1H), 7.28 (td, 1H), 4.73 (d, 2H).

Intermediate 4-7

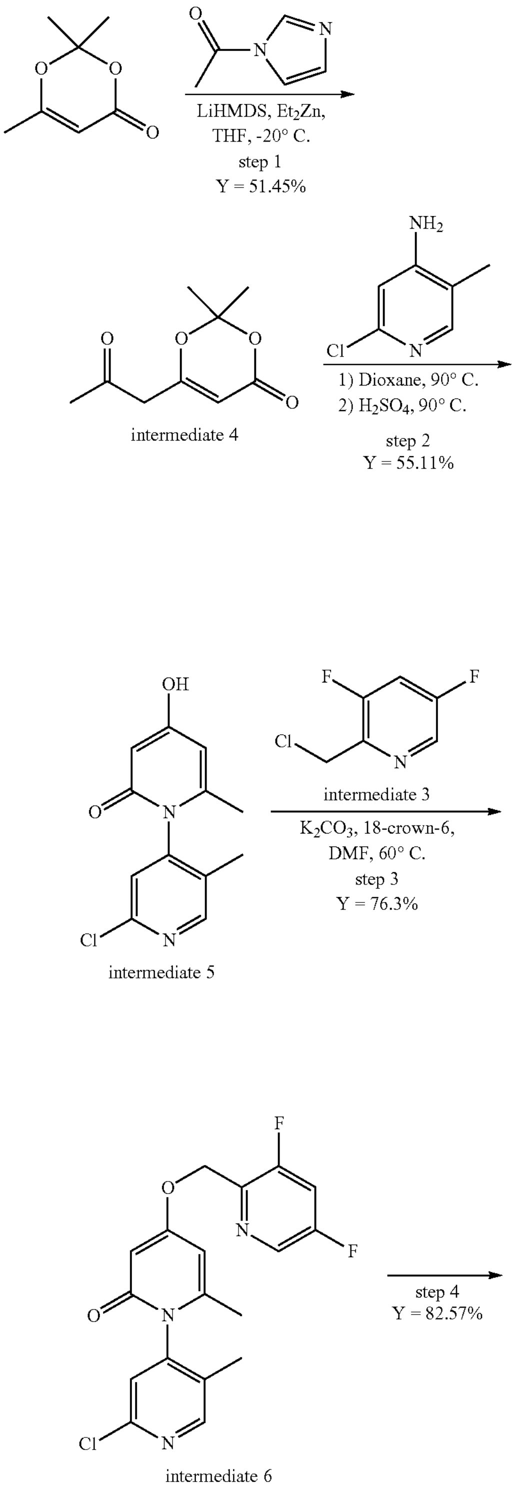

-continued

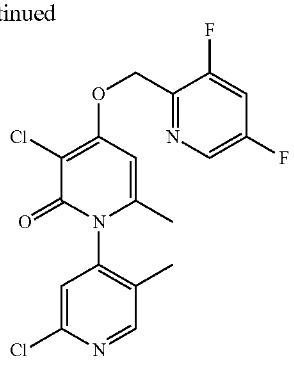

intermediate 7

Step 1: Preparation of 2,2-dimethyl-6-(2-oxopropyl)-1,3-dioxin-4-one

A solution of LiHMDS (3.16 L, 3.16 mol, 1.50 equiv, 1M in THF) in THF (1000 mL) was treated with 2,2,6-trimethyl-1,3-dioxin-4-one (300 g, 2.11 mol, 1.00 equiv) for 1 h at −20° C., under nitrogen atmosphere followed by the addition of ZnEt, (3.16 L, 3.16 mol, 1.50 equiv, 1M in hexane) dropwise over 2 h at −20° C. The resulting mixture was stirred for 30 min at −20° C., under nitrogen atmosphere. To the above mixture was added acetylimidazole (348.58 g, 3.16 mol, 1.50 equiv) at −10° C. The resulting mixture was stirred for additional overnight at room temperature. The reaction was monitored by LCMS. The reaction was quenched by the addition of IL Water/THF (1:1) at −10° C. The mixture was acidified to pH 1-2 with 2M HCl (aq.). The resulting mixture was extracted with EtOAc (3×5 L). The combined organic layers were washed with brine (3×5L), dried over anhydrous $Na_2SO_4$. After filtration, the filtrate was concentrated under reduced pressure. The residue was purified by silica gel column chromatography to afford 2,2-dimethyl-6-(2-oxopropyl)-1,3-dioxin-4-one (200 g, 51.45%) as a Brown yellow solid. LC-MS: (ES+H, m/z): $[M+H]^{+=}$185.0. $^1H$ NMR (400 MHZ, DMSO-$d_6$) δ 5.35 (s, 1H), 3.35 (s, 2H), 2.25 (s, 3H), 1.72 (d, 6H). Step 2: Preparation of 2'-chloro-4-hydroxy-5',6-dimethyl-[1,4'-bipyridin]-2-one A solution of 2,2-dimethyl-6-(2-oxopropyl)-1,3-dioxin-4-one (200.00 g, 1.08 mol, 1.00 equiv) and 2-chloro-5-methylpyridin-4-amine (154.83 g, 1.08 mol, 1.00 equiv) in dioxane (2000 mL) was stirred for 3.5 h at 90° C., under nitrogen atmosphere. The mixture was allowed to cool down to room temperature. The reaction was monitored by LCMS. To the above mixture was added $H_2SO_4$ (60 mL, 1.12 mol, 1.05 equiv) dropwise. The resulting mixture was stirred for additional 1 h at 90° C. The mixture was allowed to cool down to room temperature. The reaction was monitored by LCMS. The resulting mixture was concentrated under reduced pressure. The resulting mixture was added HO (1000 mL) and stirred for 30 min. The precipitated solids were collected by filtration and washed with Et,O (3×50 mL). This resulted in 2'-chloro-4-hydroxy-5',6-dimethyl-[1,4'-bipyridin]-2-one (150 g, 55.11%) as a yellow solid. LC-MS: (ES+H, m/z): $[M+H]^+$=251.0. $^1H$ NMR (300 MHz, DMSO-$d_6$) δ 10.82 (s, 1H), 8.48 (s, 1H), 7.57 (s, 1H), 5.98 (d, 1H), 5.58 (d, 1H), 1.97 (s, 3H), 1.84 (s, 3H).

Step 3: Preparation of 2'-chloro-4-((3,5-difluoropyridin-2-yl)methoxy)-5',6-dimethyl-2H-[1,4'-bipyridin]-2-one To a stirred mixture of 2'-chloro-4-hydroxy-5',6-dimethyl-[1,4'-bipyridin]-2-one (20.00 g, 79.78 mmol, 1.00 equiv), 2-(chloromethyl)-3,5-difluoropyridine (15.66 g, 95.74 mmol, 1.20 equiv), $K_2CO_3$ (33.08 g, 239.35 mmol, 3.00 equiv) and 18-Crown-6 (2.11 g. 7.98 mmol, 0.10 equiv) in DMF (50 ml). The resulting mixture was stirred for 3 h at 60° C., under nitrogen atmosphere. The reaction was monitored by LCMS. The residue was dissolved in EA (1500 mL). The organic layer was washed with water (3×400 mL). The organic layer was concentrated under reduced pressure. The residue was purified by silica gel column chromatography to afford 2'-chloro-4-[(3,5-difluoropyridin-2-yl)methoxy]-5',6-dimethyl-[1,4'-bipyridin]-2-one (23 g, 76.3%) as a yellow solid. LC-MS: (ES+H, m/z): $[M+H]^+$=378.0. $^1H$ NMR (400 MHZ, DMSO-$d_6$) δ 8.59 (s, 1H), 8.49 (s, 1H), 8.13-8.01 (m, 1H), 7.61 (s, 1H), 6.13 (d, 1H), 6.03 (d, 1H), 5.25 (s, 2H), 1.99 (s, 3H), 1.85 (s, 3H).

Step 4: Preparation of 2',3-dichloro-4-[(3,5-difluoropyridin-2-yl)methoxy]-5',6-dimethyl-[1,4'-bipyridin]-2-one To a stirred solution of 2'-chloro-4-[(3,5-difluoropyridin-2-yl)methoxy]-5',6-dimethyl-[1,4'-bipyridin]-2-one (1.00 g, 2.65 mmol, 1.00 equiv) and NCS (0.37 g, 2.78 mmol, 1.05 equiv) in ACN(25 mL) was added 2,2-dichloroacetic acid (0.17 g. 1.32 mmol, 0.50 equiv) dropwise at room temperature under nitrogen atmosphere. The resulting mixture was stirred for 2 h at 60° C., under nitrogen atmosphere. The reaction was monitored by LCMS. The resulting mixture was diluted with ethyl acetate (300 mL). The resulting mixture was washed with 2×100 mL of water and brine (100 mL), dried over anhydrous $Na_2SO_4$. After filtration, the filtrate was concentrated under reduced pressure. The residue was purified by silica gel column chromatography, he pure fraction was concentrated under reduced pressure to afford 2',3-dichloro-4-[(3,5-difluoropyridin-2-yl)methoxy]-5',6-dimethyl-[1,4'-bipyridin]-2-one (901 mg, 82.57%) as a yellow solid. LC-MS: (ES+H, m/z): $[M+H]^+$=411.9.

Intermediate 8-10

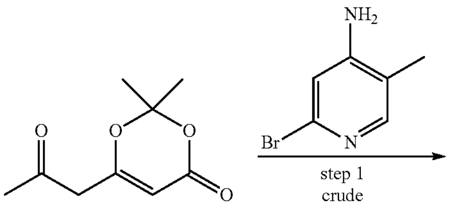

intermediate 4

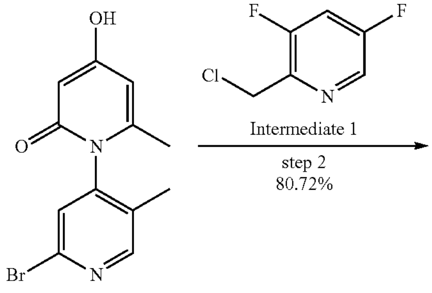

intermediate 8

-continued

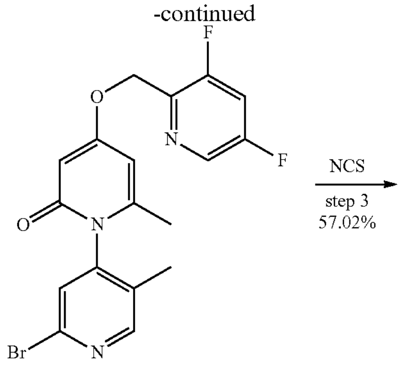

intermediate 9

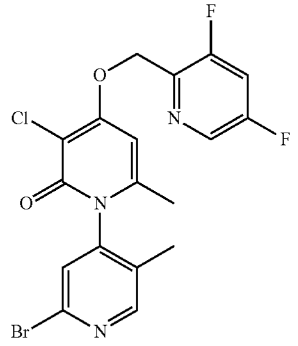

intermediate 10

Step 1: Preparation of 2'-bromo-4-hydroxy-5',6-dimethyl-[1,4'-bipyridin]-2-one A mixture of 2,2-dimethyl-6-(2-oxopropyl)-1,3-dioxin-4-one (22.16 g, 120.296 mmol, 1.5 equiv) and 2-bromo-5-methylpyridin-4-amine (15 g, 80.197 mmol, 1.00 equiv) in 1,4-dioxane (200 mL) was stirred for 2 h at 90° C., to the above mixture was added $H_2SO_4$ (7.87 g, 80.197 mmol, 1 equiv) dropwise at room temperature under air atmosphere. The resulting mixture was stirred for additional 1 h at 90° C. The reaction was monitored by LCMS. The resulting mixture was concentrated under reduced pressure. To the resulting mixture was added $H_2O$ (40 mL) and the slurry was stirred for 10 min. The precipitated solids were collected by filtration and washed with Et.O (3×10 mL), then dried under vacuum to afford 2'-bromo-4-hydroxy-5',6-dimethyl-[1,4'-bipyridin]-2-one (22.7 g, crude) as a yellow solid. The crude resulting mixture was used in the next step directly without further purification. LC-MS: (ES+H, m/z): $[M+H]^+$=294.9.

Step 2: 2'-chloro-4-[(4-methoxyphenyl)methoxy]-5',6-dimethyl-[1,4'-bipyridin]-2-one To a stirred mixture of 2'-bromo-4-hydroxy-5',6-dimethyl-[1,4'-bipyridin]-2-one (42.00 g, 142.307 mmol, 1 equiv) and 2-(chloromethyl)-3,5-difluoropyridine (46.55 g, 284.614 mmol, 2 equiv) in DMF (450 mL) were added $K_2CO_3$ (98.34 g, 711.535 mmol, 5.00 equiv) and 18-Crown-6 (3.76 g, 14.231 mmol, 0.10 equiv) at room temperature under nitrogen atmosphere. The resulting mixture was stirred for 2 h at 60° C. under nitrogen atmosphere. The reaction was monitored by LCMS. Desired product could be detected by LCMS. The reaction mixture was partitioned between EA (1000 mL) and water (500 mL). The organic layer was washed with water (500 mL) and brine (500 mL), and then dried over $Na_2SO_4$. The solution was concentrated under reduced pressure. The residue was purified by silica gel column chromatography to afford 2'-bromo-4-[(3,5-difluoropyridin-2-yl)methoxy]-5',6-dimethyl-[1,4'-bipyridin]-2-one (48.5 g, 80.72%) as a yellow oil. LC-MS: (ES+H, m/z): $[M+H]^+$=424.0.

Step 3: Preparation of 2'-bromo-3-chloro-4-[(3,5-difluoropyridin-2-yl)methoxy]-5',6-dimethyl-[1,4'-bipyridin]-2-one To a stirred mixture of 2'-bromo-4-[(3,5-difluoropyridin-2-yl)methoxy]-5',6-dimethyl-[1,4'-bipyridin]-2-one (12 g. 28.421 mmol, 1 equiv) and NCS (3.79 g, 28.421 mmol, 1 equiv) in 2-Propanol (21 mL) were added 2,2-dichloroacetic acid (1.2 mL, 2.870 mmol, 0.10 equiv) dropwise at room temperature under nitrogen atmosphere. The resulting mixture was stirred for 2 h at 60° C., under nitrogen atmosphere. The reaction was monitored by LCMS. Desired product could be detected by LCMS. The precipitated solids were collected by filtration and washed with 2-propanol to afford 2'-bromo-3-chloro-4-[(3,5-difluoropyridin-2-yl)methoxy]-5',6-dimethyl-[1,4'-bipyridin]-2-one (7.40 g, 57.02%) as a white solid. LC-MS: (ES+H, m/z): $[M+H]^+$=457.9. $^1$H NMR (300 MHz, DMSO-$d_6$) δ 8.60 (d, J=2.4 Hz, 1H), 8.52 (s, 1H), 8.10 (ddd, J=10.0, 8.9, 2.4 Hz, 1H), 7.81 (s, 1H), 6.80 (s, 1H), 5.48 (d, J=2.0 Hz, 2H), 1.98-1.94 (m, 6H).

Intermediate 11-16

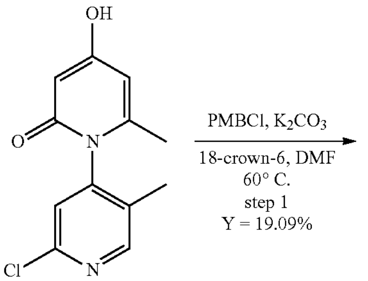

intermediate 5

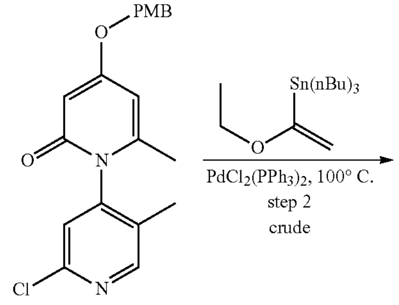

intermediate 11

-continued

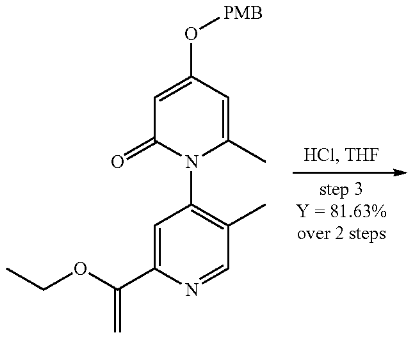

intermediate 12

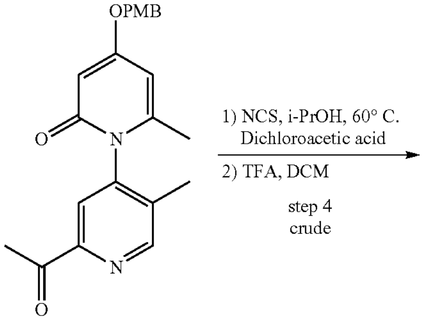

intermediate 13

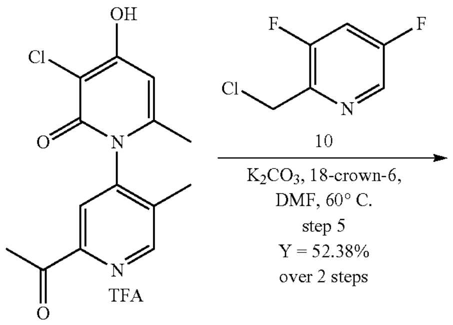

Intermeidate 14

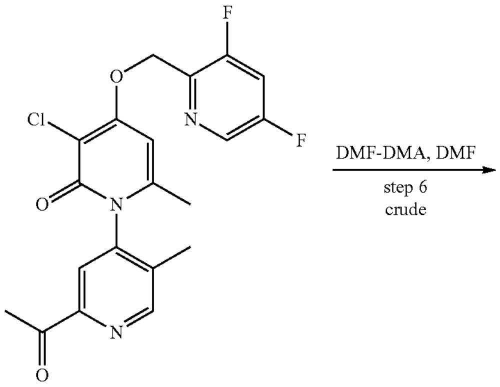

Intermeidate 15

-continued

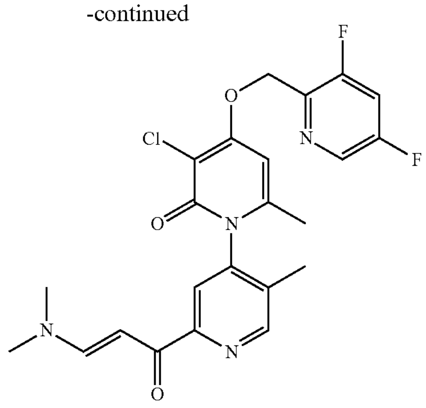

Intermeidate 16

Step 1: 2'-chloro-4-[(4-methoxyphenyl)methoxy]-5',6-dimethyl-[1,4'-bipyridin]-2-one To a solution of 2'-chloro-4-hydroxy-5',6-dimethyl-[1,4'-bipyridin]-2-one (85.00 g, 339.08 mmol, 1.00 equiv) in DMF (300 mL) was added 4-methoxybenzyl chloride (159.31 g, 1017.23 mmol, 3.00 equiv), $K_2CO_3$ (187.45 g, 1356.31 mmol, 4.00 equiv) and 18-crown-6 (4.48 g, 16.95 mmol, 0.05 equiv). The mixture was heated at 60° C., for 3 h. The reaction was monitored by LCMS. The mixture was allowed to cool down to r.t. The reaction mixture was partitioned between EA (1000 mL) and water (500 mL). The organic layer was washed with water (500 mL) and brine (500 mL), and then dried over $Na_2SO_4$. The solution was concentrated under reduced pressure. The residue was purified by silica gel column chromatography to afford 2'-chloro-4-[(4-methoxyphenyl)methoxy]-5',6-dimethyl-[1,4'-bipyridin]-2-one (24 g, 19.09%) as an off-white solid. LC-MS: (ES+H, m/z): $[M+H]^+$=371.0.

Step 2: Preparation of 2'-(1-ethoxyethenyl)-4-[(4-methoxyphenyl)methoxy]-5',6-dimethyl-[1,4'-bipyridin]-2-one To a stirred solution of 2'-chloro-4-[(4-methoxyphenyl)methoxy]-5',6-dimethyl-[1,4'-bipyridin]-2-one (24.00 g, 64.72 mmol, 1.00 equiv) and tributyl (1-ethoxyethenyl) stannane (28.05 g, 77.67 mmol, 1.20 equiv) in dioxane (200 mL) was added Pd(PPh3): Cl2 (2.27 g, 3.23 mmol, 0.05 equiv). The resulting mixture was stirred for 10 h at 100° C., under nitrogen atmosphere. The reaction was monitored by LCMS. The mixture was allowed to cool down to r.t. The resulting mixture was filtered, the filter cake was washed with EA (100 mL). The filtrate was concentrated under reduced pressure. The crude product 2'-(1-ethoxyethenyl)-4-[(4-methoxyphenyl)methoxy]-5'0.6-dimethyl-[1,4'-bipyridin]-2-one (32 g) was used in the next step directly without further purification. LC-MS: (ES+H, m/z): $[M+H]^+$=407.1.

Step 3: Preparation of 2'-acetyl-4-[(4-methoxyphenyl)methoxy]-5',6-dimethyl-[1,4'-bipyridin]-2-one To a stirred solution 2'-(1-ethoxyethenyl)-4-[(4-methoxyphenyl)methoxy]-5'0.6-dimethyl-[1,4'-bipyridin]-2-one (32 g. 78.72 mmol. 1.00 equiv) in THF (200 mL) was added conc. HCl (20 mL) dropwise at 0° C., under nitrogen atmosphere. The resulting mixture was stirred for 2 h at r.t, under nitrogen atmosphere. The reaction was monitored by LCMS. The mixture was basified to pH 10 with saturated $Na_2CO_3$ aq, under 0° C. The resulting mixture was extracted with EA (2×100 mL). The combined organic layers were washed with saturated NaCl aq. (200 mL), dried over anhydrous $Na_2SO_4$. After filtration, the filtrate was concentrated under reduced pressure. The residue was purified by silica gel column chromatography to afford 2'-acetyl-4-[(4-methoxyphenyl)methoxy]-5'0.6-dimethyl-[1,4'-bipyridin]-2-one (20 g. 81.63%, two steps) as an off-white solid. LC-MS: (ES+H, m z): $[M+H]^+$=379.1.

Step 4: Preparation of 2'-acetyl-3-chloro-4-hydroxy-5',6-dimethyl-[1,4'-bipyridin]-2-one To a stirred mixture of 2'-acetyl-4-[(4-methoxyphenyl)methoxy]-5',6-dimethyl-[1,4'-bipyridin]-2-one (19.00 g. 50.21 mmol. 1.00 equiv) and NCS (7.44 g. 55.72 mmol. 1.10 equiv) in i-PrOH (100.00 mL) was added 2.2-dichloroacetic acid (0.39 g. 3.02 mmol. 0.06 equiv) at room temperature. And the mixture was stirred for 5 h at 60° C., under nitrogen atmosphere. The reaction was monitored by LCMS. The mixture was allowed to cool down to r.t. The precipitated solids were collected by filtration and washed with cold i-PrOH (10 mL). The resulted solid was dissolved in DCM (100 mL). To the above mixture was added TFA (100 mL) at 0° C. The resulting mixture was stirred for additional 2 h at r.t . . . . The reaction was monitored by LCMS. The resulting mixture was concentrated under reduced pressure. The residue was purified by trituration with Et.O (50 mL). This resulted in 2'-acetyl-3-chloro-4-hydroxy-5'0.6-dimethyl-]1,4'-bipyridin]-2-one (14 g, crude. TFA salt) as a light-yellow solid. LC-MS: (ES+H, m z): $[M+H]^+$=293.0.

Step 5: Preparation of 2'-acetyl-3-chloro-4-[(3,5-difluoropyridin-2-yl)methoxy]-5',6-dimethyl-[1,4'-bipyridin]-2-one A mixture of 2'-acetyl-3-chloro-4-hydroxy-5'0.6-dimethyl-[1,4'-bipyridin]-2-one. TFA salt (14.00 g. 34.42 mmol. 1.00 equiv). $K_2CO_3$ (14.27 g. 103.25 mmol. 3.00 equiv), 18-crown-6 (0.91 g. 3.44 mmol. 0.10 equiv) and 2-(chloromethyl)-3.5-difluoropyridine (8.44 g. 51.60 mmol. 1.50 equiv) in DMF (100.00 mL) was stirred for 10 h at 60° C., under nitrogen atmosphere. The reaction was monitored by LCMS. The resulting mixture was concentrated under reduced pressure. The residue was purified by silica gel column chromatography to afford 2'-acetyl-3-chloro-4-[(3.5-difluoropyridin-2-yl)methoxy]-5'0.6-dimethyl-[1,4'-bipyridin]-2-one (11 g. 52.38%, two steps) as an off-white solid. LC-MS: (ES+H, m z): $[M+H]^+$=420.0.

Step 6: Preparation of 3-chloro-4-[(3,5-difluoropyridin-2-yl)methoxy]-2'-[(2E)-3-(dimethylamino) prop-2-enoyl]-5',6-dimethyl-[1,4'-bipyridin]-2-one A solution of 2'-acetyl-3-chloro-4-[(3.5-difluoropyridin-2-yl)methoxy]-5'0.6-dimethyl-[1,4'-bipyridin]-2-one (11.00 g. 26.20 mmol. 1.00 equiv) in DMF-DMA (50 mL) was stirred for 12 h at 100° C. under nitrogen atmosphere. The reaction was monitored by LCMS. The mixture was allowed to cool down to r.t. The resulting mixture was concentrated under reduced pressure.

Intermediate 17-22

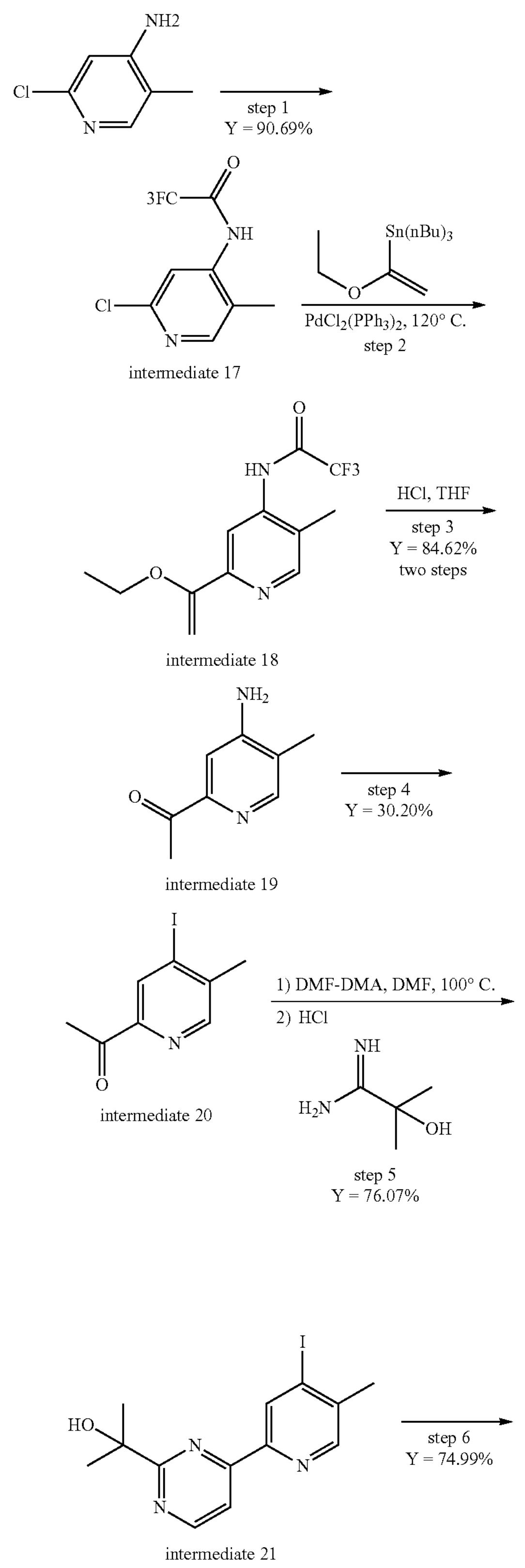

-continued

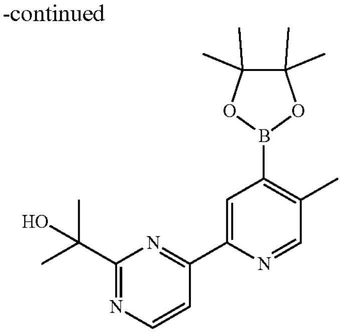

Intermediate 22

Step 1: Preparation of N-(2-chloro-5-methylpyridin-4-yl)-2,2,2-trifluoroacetamide To a stir solution of 2-chloro-5-methylpyridin-4-amine (5.00 g, 35.07 mmol, 1.00 equiv) and Trifluoroacetic anhydride (14.73 g, 70.13 mmol, 2.00 equiv) in DCM (100 mL) was added TEA (14.19 g, 140.26 mmol, 4.00 equiv) dropwise at 0° C., under nitrogen atmosphere. The resulting mixture was stirred overnight at room temperature under nitrogen atmosphere. The reaction was monitored by LCMS. The resulting mixture was diluted with water (200 mL). The resulting mixture was extracted with EtOAc (3×100 mL). The combined organic layers were washed with brine (3×100 mL), dried over anhydrous $Na_2SO_4$. After filtration, the filtrate was concentrated under reduced pressure. The residue was purified by silica gel column chromatography to afford N-(2-chloro-5-methylpyridin-4-yl)-2,2,2-trifluoroacetamide (7.60 g, 90.69%) as a light-yellow solid. LC-MS: (ES+H, m z): $[M+H]^+$=239.1.

Step 2: Preparation of N-(2-(1-ethoxyvinyl)-5-methylpyridin-4-yl)-2,2,2-trifluoroacetamide To a stirred solution of N-(2-chloro-5-methylpyridin-4-yl)-2,2,2-trifluoroacetamide (7.50 g, 31.44 mmol, 1.00 equiv) and tributyl (1-ethoxyethenyl) stannane (34.06 g, 94.30 mmol, 3.00 equiv) in dioxane (100 mL) was added palladium chloride: bis(triphenylphosphine) (1.10 g, 1.57 mmol, 0.05 equiv) in portions at room temperature under nitrogen atmosphere. The resulting mixture was stirred overnight at 120° C., under nitrogen atmosphere. The reaction was monitored by LCMS. The mixture was allowed to cool down to room temperature. The resulting mixture was filtered, the filter cake was washed with EA (100 mL). The filtrate was concentrated under reduced pressure. The crude product was used in the next step directly without further purification. LC-MS: (ES+H, m z): $[M+H]^+$=275.0.

Step 3: Preparation of 1-(4-amino-5-methylpyridin-2-yl)ethanone

To a stirred solution of N-[2-(1-ethoxyethenyl)-5-methylpyridin-4-yl]-2,2,2-trifluoroacetamide (11 g, 40.11 mmol, 1.00 equiv) in THF (120 mL) was added conc. HCl (10 mL) dropwise at room temperature. The resulting mixture was stirred for 2 h at room temperature. The reaction was monitored by LCMS. The resulting mixture was diluted with water (200 mL). The resulting mixture was washed with Et,O (8×200 mL). The aqueous layer was basified to pH 8 with saturated NaHCO; (aq.). The resulting mixture was extracted with EtOAc (3×200 mL). The combined organic layers were washed with brine (3×200 mL). dried over anhydrous $Na_2SO_4$. After filtration, the filtrate was concentrated under reduced pressure. The residue was purified by silica gel column chromatography to afford 1-(4-amino-5-methylpyridin-2-yl)ethanone (4.00 g. 84.62%, two steps) as a brown solid. LC-MS: (ES+H, m z): $[M+H]^+$=151.1. $^1$H NMR (300 MHz. DMSO-$d_6$) δ 8.02 (s, 1H), 7.16 (s.1H), 6.07 (s, 2H), 2.52 (s, 3H), 2.07 (s, 3H).

Step 4: Preparation of 1-(4-iodo-5-methylpyridin-2-yl)ethanone

To a stirred solution of 1-(4-amino-5-methylpyridin-2-yl) ethanone (4.00 g. 26.64 mmol. 1.00 equiv) and triiodomethane (31.46 g. 79.90 mmol. 3.00 equiv) in THF (50 mL) was added tert-butylnitrite (5.49 g. 53.27 mmol. 2.00 equiv) dropwise at room temperature under nitrogen atmosphere. The resulting mixture was stirred for 3 h at 80° C., under nitrogen atmosphere. The reaction was monitored by LCMS. The mixture was allowed to cool down to room temperature. The resulting mixture was diluted with water (200 mL). The resulting mixture was extracted with EtOAc (3×200 mL). The combined organic layers were washed with brine (3×200 mL), dried over anhydrous $Na_2SO_4$. After filtration, the filtrate was concentrated under reduced pressure. The residue was purified by silica gel column chromatography to afford 1-(4-iodo-5-methylpyridin-2-yl)ethanone (2.1 g. 30.20%) as a brown solid. LC-MS: (ES+H, m z): $[M+H]^+$=261.9. 1H NMR (400 MHz. DMSO-$d_6$) δ 8.54 (s, 1H), 8.27 (s.1H), 2.60 (s, 3H), 2.42 (s, 3H).

Step 5: Preparation of 2-[4-(4-iodo-5-methylpyridin-2-yl)pyrimidin-2-yl]propan-2-ol A mixture of 1-(4-iodo-5-methylpyridin-2-yl)ethanone (2.00 g. 7.66 mmol. 1.00 equiv) in DMF-DMA (20 mL) was stirred for 4 h at 100° C., under nitrogen atmosphere. The reaction was monitored by LCMS. The mixture was allowed to cool down to room temperature. The resulting mixture was concentrated under reduced pressure. The residue was diluted with DMF (20 mL). To the above mixture was added 2-hydroxy-2-methylpropanimidamide (1.17 g. 11.49 mmol. 1.50 equiv) in portions under nitrogen atmospherc. The resulting mixture was stirred for additional 1.5h at 100° C., under nitrogen atmosphere. The reaction was monitored by LCMS. The mixture was allowed to cool down to room temperature. The resulting mixture was diluted with water (150 mL). The resulting mixture was extracted with EtOAc (3×150 mL). The combined organic layers were washed with brine (3×150 mL), dried over anhydrous $Na_2SO_4$. After filtration, the filtrate was concentrated under reduced pressure. The residue was purified by silica gel column chromatography to afford 2-[4-(4-iodo-5-methylpyridin-2-yl)pyrimidin-2-xl]propan-2-ol (2.07 g. 76.07%) as an off-white solid. LC-MS: (ES+H, m z): $[M+H]^+$=355.9. $^1$H NMR (300 MHz. DMSO-$d_6$) δ 9.09 (s, 1H). 8.93 (d, 1H), 8.58 (s, 1H), 8.17 (d, 1H), 5.31 (s, 1H), 2.44 (s, 3H), 1.56 (s. 6H).

Step 6: Preparation of 2-{4-[5-methyl-4-(4,4,5,5-tetramethyl-1,3,2-dioxaborolan-2-yl)pyridin-2-yl]pyrimidin-2-yl}propan-2-ol To a stirred solution of 2-[4-(4-iodo-5-methylpyridin-2-yl)pyrimidin-2-yl]propan-2-ol (200 mg. 0.56 mmol. 1.00 equiv) and bis (pinacolato)diboron (357 mg, 1,41 mmol. 2.50 equiv) in dioxane (5 mL) was added Pd(dppf)$Cl_2$ (16 mg, 0.03 mmol. 0.05 equiv) and KOAc (221 mg. 2.25 mmol. 4.00 equiv) in portions at room temperature under nitrogen atmosphere. The resulting mixture was stirred overnight at 120° C., under nitrogen atmosphere. The reaction was monitored by LCMS. The mixture was allowed to cool down to room temperature. The resulting mixture was diluted with water (25 mL). The resulting mixture was extracted with EtOAc (3×25 mL). The combined organic layers were washed with brine (3×25 mL), dried over anhydrous $Na_2SO_4$. After filtration, the filtrate was concentrated under reduced pressure. The residue was purified by silica gel column chromatography to afford 2-{4-[5-methyl-4-(4,4,5,5-tetramethyl-1,3,2-dioxaborolan-2-yl)pyridin-2-xl]pyrimidin-2-yl}propan-2-ol (150 mg. 74.99%) as a brown solid. LC-MS: (ES+H, m z): $[M+H]^+$=274.1 (the mass signal of Boric acid). $^1$H NMR (300 MHz, DMSO-$d_6$) δ 8.92 (d, 1H), 8.62-8.66 (m, 2H), 8.19 (d, 1H), 5.19 (s, 1H), 2.53 (s, 3H), 1.57 (s, 6H), 1.36 (s, 12H).

Intermediate 24

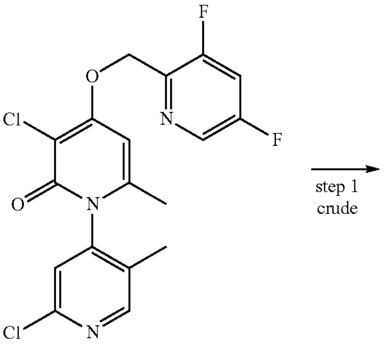

intermediate 7

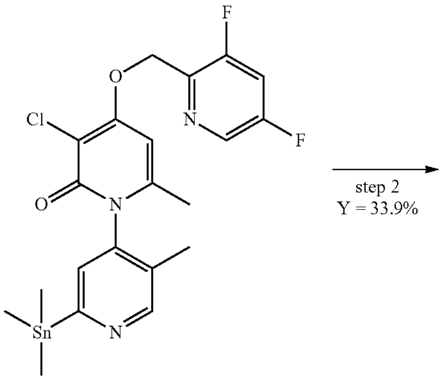

intermediate 23

-continued

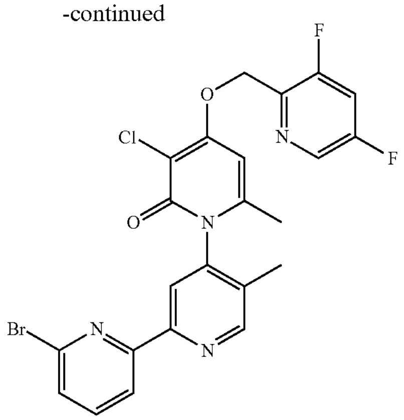

intermediate 24

Step 1: Preparation of 3-chloro-4-[(3,5-difluoropyridin-2-yl)methoxy]-3',6-dimethyl-2'-(trimethylstannyl)-[1,4'-bipyridin]-2-one To a stirred solution of 2',3-dichloro-4-[(3,5-difluoropyridin-2-yl)methoxy]-3',6-dimethyl-[1,4'-bipyridin]-2-one (1.00 g. 2.42 mmol. 1.00 equiv), Sn2Me6 (6.36 g. 19.40 mmol, 8.00 equiv) in 1,4-dioxane (20 mL) were added Pd(PPh3): Cl2 (681 mg, 0.97 mmol, 0.40 equiv) and AsPh3 (0.29 g, 0.97 mmol, 0.40 equiv). The resulting mixture was stirred for 12 h at 100° C., under nitrogen atmosphere. The reaction was monitored by LCMS. The mixture was allowed to cool down to room temperature. The resulting mixture was diluted with EA (200 mL). The combined organic layers were washed with KF (aq.) (3×100 mL), The organic layer was dried over anhydrous $Na_2SO_4$. After filtration, the filtrate was concentrated under reduced pressure. The crude product (1.78 g) was used in the next step directly without further purification. LC-MS: (ES+H, m/z): $[M+H]^+$=542.3.

Step 2: Preparation of 2'-(6-bromopyridin-2-yl)-3-chloro-4-[(3,5-difluoropyridin-2-yl)methoxy]-5',6-dimethyl-[1,4'-bipyridin]-2-one To a stirred solution 3-chloro-4-[(3,5-difluoropyridin-2-yl)methoxy]-5',6-dimethyl-2'-(trimethylstannyl)-[1,4'-bipyridin]-2-one (2.00 g. 3.70 mmol, 1.00 equiv) and 2,6-dibromo-pyridine (2.63 g, 11.10 mmol, 3.00 equiv) in 1,4-dioxane (20 mL) were added $Pd(PPh_3)$: $Cl_2$ (0.52 g. 0.74 mmol, 0.20 equiv), the resulting mixture was stirred at 80° C., for 2 h under nitrogen atmosphere. The reaction was monitored by LCMS. The mixture was allowed to cool down to room temperature. The resulting mixture was diluted with water (200 mL). The resulting mixture was extracted with EtOAc (3×100 mL). The combined organic layers were washed with brine (100 mL), dried over anhydrous $Na_2SO_4$. After filtration, the filtrate was concentrated under reduced pressure. The residue was purified by silica gel column chromatography to afford 2'-(6-bromopyridin-2-yl)-3-chloro-4-[(3,5-difluoropyridin-2-yl)methoxy]-5',6-dimethyl-[1,4'-bipyridin]-2-one (670 mg, 33.9%) as a yellow solid. LC-MS: (ES+H, m/z): $[M+H]^+$=535.1. $^1H$ NMR (300 MHz, DMSO-$d_6$) δ 8.82 (s, 1H), 8.61 (d, J=2.4 Hz, 1H), 8.42 (dd, J=7.7, 0.9 Hz, 1H), 8.16-8.04 (m, 2H), 7.95 (t, J=7.8 Hz, 1H), 7.74 (dd, J=7.9, 0.9 Hz, 1H), 6.81 (s, 1H), 5.49 (d, J=2.0 Hz, 2H), 2.09 (s, 3H), 1.98 (s, 3H). $^{19}F$ NMR (282 MHz, DMSO-$d_6$) δ-120.14,-120.17,-122.36,-122.39.

Intermediate 25-30

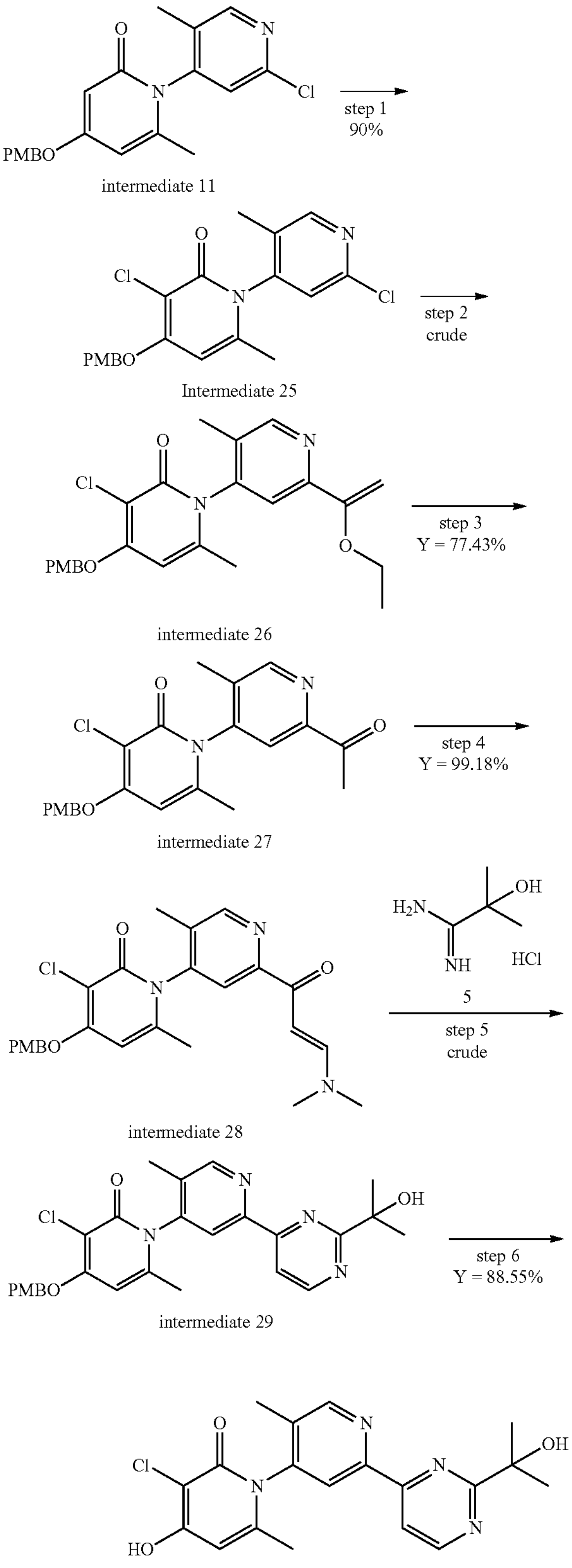

intermediate 30

Step 1: Preparation of 2',3-dichloro-4-[(4-methoxyphenyl)methoxy]-5',6-dimethyl-[1,4'-bipyridin]-2-one To a stirred mixture of2'-chloro-4-[(4-methoxyphenyl) methoxy]-5',6-dimethyl-[1,4'-bipyridin]-2-one (5 g, 13.483 mmol, 1 equiv) and 2,2-dichloroacetic acid (0.17 mL, 1.348 mmol, 0.1 equiv) in i-PrOH (20.00 mL, 261.705 mmol, 19.41 equiv) were added NCS (1.80 g, 13.483 mmol, 1 equiv) at room temperature under nitrogen atmosphere. The resulting mixture was stirred for 2 h at 60° C., under nitrogen atmosphere. The reaction was monitored by LCMS. The mixture was allowed to cool down to room temperature. This resulted in 2',3-dichloro-4-[(4-methoxyphenyl) methoxy]-5',6-dimethyl-[1,4'-bipyridin]-2-one (4.9 g. 90%) as a yellow solid. LC-MS: (ES+H, m/z): $[M+H]^+$=405.1.

Step 2:3-chloro-2'-(1-ethoxyethenyl)-4-[(4-methoxyphenyl)methoxy]-5',6-dimethyl-[1,4'-bipyridin]-2-one To a stirred solution of 2',3-dichloro-4-[(4-methoxyphenyl)methoxy]-5',6-dimethyl-[1,4'-bipyridin]-2-one (5 g, 12.33 mmol, 1.00 equiv) and dibutyl (1-ethoxyethenyl) propylstannane (12.85 g, 37.01 mmol, 3.00 equiv) in 1,4-dioxane (55 mL) were added Pd(PPh3): Cl2 (0.26 g, 0.37 mmol, 0.03 equiv) at room temperature under nitrogen atmosphere. The resulting mixture was stirred for 3 h at 120° C., under nitrogen atmosphere. The reaction was monitored by LCMS. The resulting mixture was concentrated under reduced pressure. The crude product was used in the next step directly without further purification. LC-MS: (ES+H, m/z): $[M+H]^+$=441.1.

Step 3: 2'-acetyl-3-chloro-4-[(4-methoxyphenyl) methoxy]-5',6-dimethyl-[1,4'-bipyridin]-2-one To a stirred mixture of 3-chloro-2'-(1-ethoxyethenyl)-4-[(4-methoxyphenyl)methoxy]-5',6-dimethyl-[1,4'-bipyridin]-2-one (4.00 g, 9.07 mmol, 1.00 equiv) in THF (200 mL) was added HCl (4 mL) dropwise at room temperature under nitrogen atmosphere. The resulting mixture was stirred for 1 h at room temperature under nitrogen atmosphere. The reaction was monitored by LCMS. The resulting mixture was diluted with EtOAc (200 mL). The resulting mixture was washed with 2×200 mL brine. The organic layers were dried over anhydrous $Na_2SO_4$. After filtration, the filtrate was concentrated under reduced pressure. The residue was purified by silica gel column chromatography to afford 2'-acetyl-3-chloro-4-[(4-methoxyphenyl)methoxy]-5'0.6-dimethyl-[1,4'-bipyridin]-2-one (2.90 g. 77.43%) as a yellow solid. LC-MS: (ES+H, m/z): $[M+H]^+$=413.1. $^1$H NMR (300 MHz, DMSO-$d_6$) δ 8.83 (s, 1H), 7.88 (s, 1H), 7.48-7.40 (m. 2H), 7.07-6.95 (m, 2H), 6.79-6.73 (m, 1H), 5.27 (s, 2H), 3.79 (s, 3H), 2.67 (s, 3H), 2.09 (s, 3H), 1.92 (s. 3H).

Step 4:3-chloro-2'-[(2E)-3-(dimethylamino) prop-2-enoyl]-4-[(4-methoxyphenyl)methoxy]-5',6-dimethyl-[1,4'-bipyridin]-2-one To a stirred mixture of 2'-acetyl-3-chloro-4-[(4-methoxyphenyl)methoxy]-5'0.6-dimethyl-[1,4'-bipyridin]-2-one (2.90 g. 7.02 mmol. 1.00 equiv) in DMF-DMA (25 mL) at room temperature under nitrogen atmosphere. The resulting mixture was stirred overnight at 100° C., under nitrogen atmosphere. The reaction was monitored by LCMS. The resulting mixture was concentrated under reduced pressure to afford 3-chloro-2'-[(2E)-3-(dimethylamino) prop-2-cnov1]-4-[(4-methoxyphenyl)methoxy]-5'0.6-dimethyl-[1, 4'-bipyridin]-2-one (3.26 g. 99.18%) as a yellow solid. LC-MS: (ES+H, m/z): $[M+H]^+$=470.1.

Step 5:3-chloro-2'-[2-(2-hydroxypropan-2-yl)pyrimidin-4-yl]-4-[(4-methoxyphenyl)methoxy]-5',6-dimethyl-[1,4'-bipyridin]-2-one To a stirred mixture of 3-chloro-2'-[(2E)-3-(dimethylamino) prop-2-cnov1]-4-[(4-methoxyphenyl)methoxy]-5'0.6-dimethyl-] 1,4'-bipyridin]-2-one (3.30 g. 7.05 mmol. 1.00 equiv) and $K_2CO_3$ (2.92 g. 21.15 mmol. 3.00 equiv) in IPA (33 mL) was added 2-hydroxy-2-methylpropanimidamide hydrochloride (1.95 g. 14.10 mmol. 2.00 equiv) at room temperature under nitrogen atmosphere. The resulting mixture was stirred for 2 h at 80° C., under nitrogen atmosphere. The reaction was monitored by LCMS. The resulting mixture was diluted with EtOAc (200 mL). The resulting mixture was washed with 2×200 ml brinc. The organic layers were dried over anhydrous $Na_2SO_4$. After filtration, the filtrate was concentrated under reduced pressure. The resulting mixture was concentrated under reduced pressure. The crude product was used in the next step directly without further purification. LC-MS: (ES+H, m/z): [M+H]=507.0.

Step 6:3-chloro-4-hydroxy-2'-[2-(2-hydroxypropan-2-yl)pyrimidin-4-yl]-5',6-dimethyl-[1,4'-bipyridin]-2-one To a stirred solution of 3-chloro-2'-[2-(2-hydroxypropan-2-yl)pyrimidin-4-yl]-4-[(4-methoxyphenyl)methoxy]-5'0.6-dimethyl-[1,4'-bipyridin]-2-one (3.70 g. 7.29 mmol. 1.00 equiv) in $CH_2Cl_2$ (50 mL) was added TFA (15 mL) at room temperature under nitrogen atmosphere. The resulting mixture was stirred for 2 h at room temperature under nitrogen atmosphere. The reaction was monitored by LCMS. The resulting mixture was diluted with EtOAc (200 mL). The resulting mixture was washed with 2×200 ml brine. The organic layers were dried over anhydrous $Na_2SO_4$. After filtration, the filtrate was concentrated under reduced pressure. The residue was purified by silica gel column chromatography to afford 3-chloro-4-hydroxy-2'-]2-(2-hydroxypropan-2-yl)pyrimidin-4-yl]-5'0.6-dimethyl-] 1,4'-bipyridin]-2-one (2.50 g. 88.55%) as a yellow solid. LC-MS: (ES+H, m/z): $[M+H]^+$=387.1. $^1$H NMR (400 MHZ. DMSO-$d_6$) δ 11.62 (br. 1H), 8.97 (d, 1H), 8.84 (s, 1H), 8.64 (s, 1H), 8.24 (d, 1H), 6.22 (d, 1H), 5.76 (s, 1H), 2.10 (s, 3H), 1.88 (s. 3H), 1.53 (s. 6H).

Intermediate 31-33

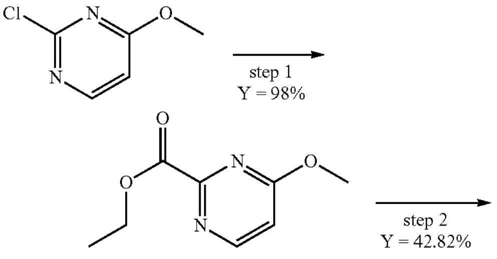

intermediate 31

-continued

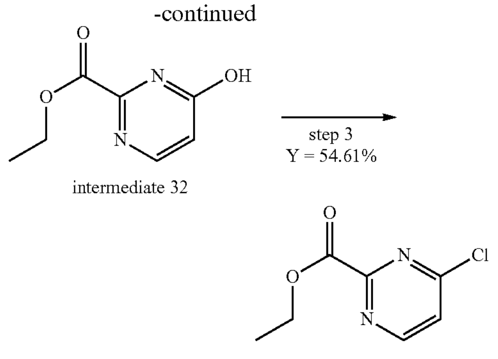

intermediate 32 intermediate 33

Step 1: Preparation of ethyl 4-methoxypyrimidine-2-carboxylate

To a stirred solution of 2-chloro-4-methoxypyrimidine (100.00 g. 691.75 mmol. 1.00 equiv) in EtOH (6.00 L) was added $Et_3N$(140.00 g. 1383.50 mmol. 2.00 equiv) and Pd(dppf) $C_1$; (10.00 g. 13.66 mmol. 0.05 equiv) in a pressure tank. The mixture was purged with nitrogen for 2 min and then was pressurized to 50 atm with carbon monoxide at 100° C., for 12 h. The reaction mixture was cooled to room temperature. The reaction was monitored by LCMS. The resulting mixture was concentrated under reduced pressure. The residue was purified by silica gel column chromatography to afford ethyl 4-methoxypyrimidine-2-carboxylate (123.50 g. 98.00%) as a yellow solid. LC-MS: (ES+H, m/z): $[M+H]^+$=183.0. $^1$H NMR (300 MHz. DMSO-$d_6$) δ 8.66 (d, 1H), 7.16 (d, 1H), 4.36 (q. 2H), 3.98 (s, 3H), 1.34 (t. 3H).

Step 2: Preparation of ethyl 4-hydroxypyrimidine-2-carboxylate

To a stirred solution of ethyl 4-methoxypyrimidine-2-carboxylate (83.50 g. 458.34 mmol. 1.00 equiv) in MeCN (1.00 L) was added TMSI (262 mL. 1833.36 mmol. 4.00 equiv) dropwise at room temperature under nitrogen atmosphere over 1 h. The resulting mixture was stirred overnight at 50° C. Desired product could be detected by LCMS. The mixture was allowed to cool down to room temperature. The resulting mixture was concentrated under reduced pressure. The residue was re-dissolved in DCM (500 mL) and then concentrated under reduced pressure. Repeat the above steps three times. The residue was purified by trituration with hexane (800 mL). The resulting mixture was concentrated under reduced pressure. This resulted in ethyl 4-hydroxypyrimidine-2-carboxylate (33.00 g. 42.82%) as a yellow solid. LC-MS: (ES+H, m/z): $[M+H]^+$=169.1. $^1$H NMR (300 MHz. DMSO-$d_6$) δ 8.14 (d, 1H), 6.60 (d, 1H), 4.34 (q. 2H), 1.32 (t. 3H).

Step 3: Preparation of ethyl 4-chloropyrimidine-2-carboxylate

To a stirred mixture of ethyl 4-hydroxypyrimidine-2-carboxylate (33.00 g. 196.25 mmol. 1.00 equiv) in DCE (1.20 L) were added $POCl_3$ (73 mL. 785.00 mmol. 4.00 equiv) dropwise at 0° C., under nitrogen atmosphere over 2 h. The resulting mixture was stirred additional overnight at 50° C. Desired product could be detected by LCMS. The mixture was allowed to cool down to room temperature. The reaction was quenched by the addition of Water/Ice (600 mL) at 0° C. The mixture was basified to pH 7-8 with saturated $Na_2CO_3$ (aq.). The resulting mixture was extracted with $CH.Cl_2$ (3×800 mL). The combined organic layers were washed with brine (2×800 mL), dried over anhydrous $Na_2SO_4$. After filtration, the filtrate was concentrated under reduced pressure. The residue was purified by silica gel column chromatography to afford ethyl 4-chloropyrimidine-2-carboxylate (20.00 g. 54.61%) as a yellow oil. LC-MS: (ES+H, m/z): $[M+H]^+$=187.0. $^1$H NMR (400 MHZ, DMSO-$d_6$) δ 8.98 (d, 1H), 7.97 (d, 1H), 4.40 (q, 2H), 1.34 (t, 3H).

Intermediate 34

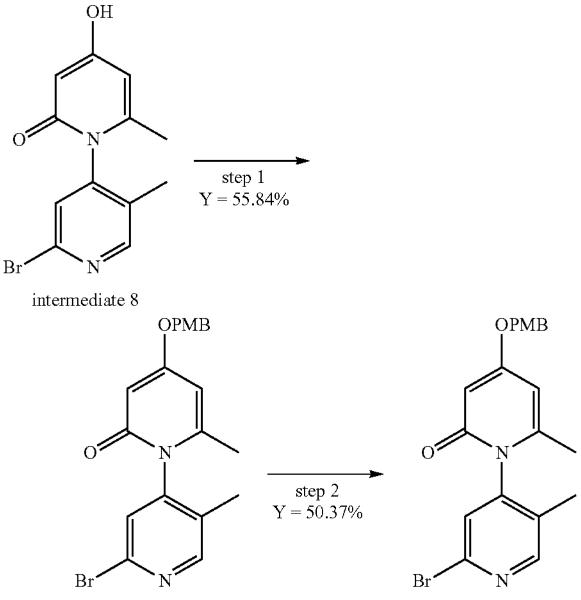

intermediate 8 intermediate 34

Step 1: Preparation of 2'-bromo-4-[(4-methoxyphenyl)methoxy]-5',6-dimethyl-[1,4'-bipyridin]-2-one To a solution of 2'-bromo-4-hydroxy-5',6-dimethyl-[1,4'-bipyridin]-2-one (7.00 g, 23.72 mmol, 1.00 equiv) in DMF (50 mL) was added PMBCl (11.14 g, 71.15 mmol, 3.00 equiv), $K_2CO_3$ (13.11 g, 94.872 mmol, 4.00 equiv) and 18-Crown-6 (310 mg, 1.19 mmol, 0.05 equiv). The mixture was stirred at 60° C., for 3 h. The reaction was monitored by LCMS. The mixture was allowed to cool down to room temperature. The reaction mixture was partitioned between EA (500 mL) and water (200 mL). The organic layer was washed with water (200 mL) and brine (200 mL), and then dried over $Na_2SO_4$. The solution was concentrated under reduced pressure. The residue was purified by silica gel column chromatography to afford 2'-bromo-4-[(4-methoxyphenyl)methoxy]-5',6-dimethyl-[1,4'-bipyridin]-2-one (5.5 g, 55.84%) as an off-white solid. LC-MS: (ES+H, m/z): $[M+H]^+$=415.0/417.0. $^1$H NMR (300 MHz, DMSO-$d_6$) δ 8.48 (s, 1H), 7.71 (s, 1H), 7.44-7.35 (m, 2H), 7.03-6.92 (m, 2H), 6.12 (dd, 1H), 5.93 (d, 1H), 5.04 (s, 2H), 3.78 (s, 3H), 1.96 (s, 3H), 1.85 (s, 3H).

Step 2: Preparation of 2'-bromo-3-chloro-4-[(4-methoxyphenyl)methoxy]-5',6-dimethyl-[1,4'-bipyridin]-2-one To a stirred mixture of 2'-bromo-4-[(4-methoxyphenyl)methoxy]-5',6-dimethyl-[1,4'-bipyridin]-2-one (5.50 g, 13.24 mmol, 1.00 equiv) and NCS (1.95 g, 14.57 mmol, 1.10 equiv) in IPA (20 mL) was added 2,2-dichloroacetic acid (100 mg, 0.80 mmol, 0.06 equiv) at room temperature. The mixture was stirred for 3 h at 60° C., under nitrogen atmosphere. The reaction was monitored by LCMS. The mixture was allowed to cool down to room temperature. The precipitated solids were collected by filtration to afford 2'-bromo-3-chloro-4-[(4-methoxyphenyl)methoxy]-5',6-dimethyl-[1,4'-bipyridin]-2-one (3 g, 50.37%) as a white solid. LC-MS: (ES+H, m/z): $[M+H]^+$=451.1. $^1H$ NMR (400 MHZ, DMSO-$d_6$) δ 8.51 (s, 1H), 7.79 (s, 1H), 7.47-7.39 (m, 2H), 7.04-6.96 (m, 2H), 6.76 (s, 1H), 5.26 (s, 2H), 3.78 (s, 3H), 1.95 (s, 3H), 1.95 (s, 3H).

Intermediate 35-37

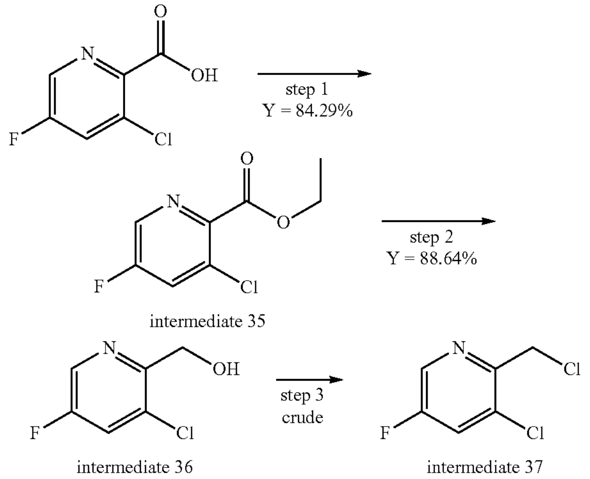

intermediate 35
intermediate 36
intermediate 37

Step 1: Preparation of ethyl 3-chloro-5-fluoropyridine-2-carboxylate

A solution of 3-chloro-5-fluoropyridine-2-carboxylic acid (4.50 g, 25.63 mmol, 1.00 equiv) in EtOH (100 mL) was cooled with an ice bath. To the above mixture was added SOCI, (6.13 g, 51.53 mmol, 2.01 equiv) dropwise over 3 min at 0° C. The resulting mixture was stirred for additional 3 h at room temperature. The reaction was monitored by LCMS. The mixture was allowed to r.t. The resulting mixture was concentrated under vacuum. The residue was purified by silica gel column chromatography to afford ethyl 3-chloro-5-fluoropyridine-2-carboxylate (4.40 g, 84.29%) as a colorless liquid. LC-MS: (ES+H, m/z): $[M+H]^+$=203.9.

Step 2: Preparation of (3-chloro-5-fluoropyridin-2-yl) methanol

To a stirred solution of ethyl 3-chloro-5-fluoropyridine-2-carboxylate (2.10 g, 10.31 mmol, 1.00 equiv) in EtOH (30 mL) was added NaBH+ (0.98 g, 25.90 mmol, 2.51 equiv) in portions at 0° C., under nitrogen atmosphere. The resulting mixture was stirred for 30 min at 0° C., under nitrogen atmosphere. The resulting mixture was stirred for additional 2 h at room temperature under nitrogen atmosphere. The reaction was monitored by LCMS. The reaction was quenched with sat. $NH_4Cl$ (aq.) at 0° C. The resulting mixture was concentrated under reduced pressure to remove EtOH, then extracted with EA (3×30 ml). The combined organic layers were washed with brine, dried over anhydrous $Na_2SO_4$. After filtration, the filtrate was concentrated under vacuum to afford (3-chloro-5-fluoropyridin-2-yl) methanol (2 g, 95.24%) as a yellow oil. LC-MS: (ES+H, m/z): $[M+H]^+$=162.0.

Step 3: Preparation of 3-chloro-2-(chloromethyl)-5-fluoropyridine

To a stirred solution of (3-chloro-5-fluoropyridin-2-yl) methanol (2.10 g, 12.99 mmol, 1.00 equiv) in DCM (30 mL) was added DMF (0.1 mL, 1.30 mmol, 0.10 equiv) at 0° C., under nitrogen atmosphere. The SOCI2 (2.3 mL, 32.49 mmol, 2.50 equiv) was added dropwise under nitrogen atmosphere. The resulting mixture was stirred for 2 h at room temperature. The reaction was monitored by LCMS. The resulting mixture was concentrated under vacuum, to afford 3-chloro-2-(chloromethyl)-5-fluoropyridine (2.00 g, crude) as a brown yellow oil. The crude product was used in the next step directly without further purification. LC-MS: (ES+H, m/z): $[M+H]^+$=179.90.

Intermediate 38-41

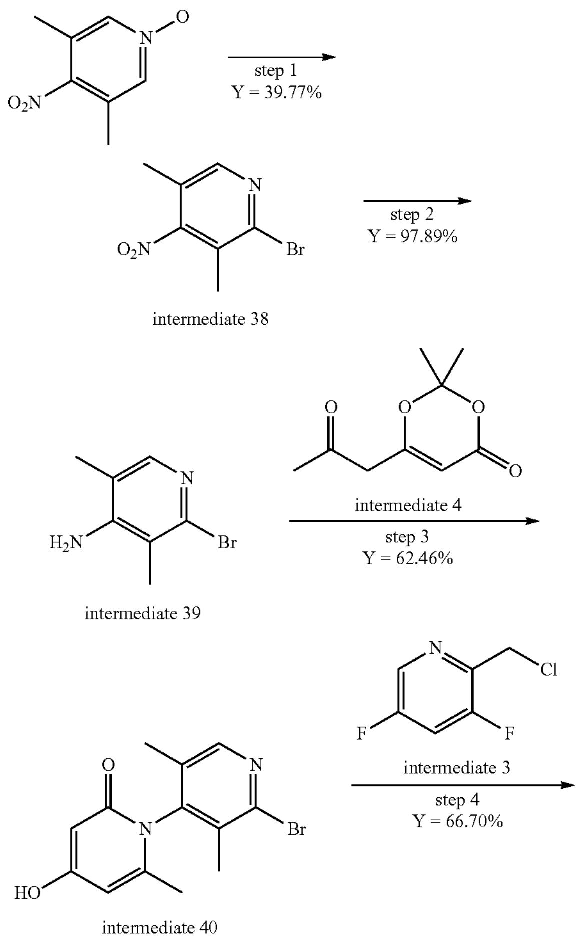

intermediate 38
intermediate 39
intermediate 40

-continued

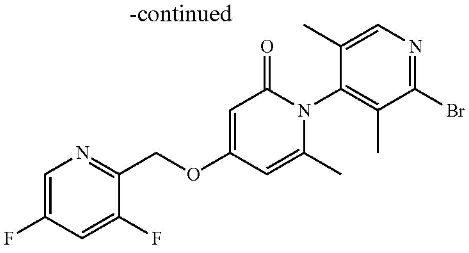

intermediate 41

Step 1: Preparation of 2-bromo-3,5-dimethyl-4-nitropyridine

To a stirred solution of 3.5-dimethyl-4-nitropyridin-1-ol (5.00 g. 29.38 mmol. 1.00 equiv) in DCE (100 mL) was added POBr; (12.64 g. 44.07 mmol. 1.50 equiv) dropwise at 0° C., under nitrogen atmosphere. The resulting mixture was stirred for 2 h at 60° C., under nitrogen atmosphere. The reaction was monitored by LCMS. The mixture was allowed to r.t. The residue was basified to pH 10 with saturated $Na_2CO$; (aq.) at 0° C. The reaction was poured into water (100 mL) at room temperature. The resulting mixture was extracted with EtOAc (3×300 mL). The combined organic layers were concentrated under reduced pressure. The residue was purified by silica gel column chromatography to afford 2-bromo-3.5-dimethyl-4-nitropyridinc (5.40 g. 39.77%) as a white solid. LC-MS: (ES+H, m/z): $[M+H]^+$=231.1/233. $^1$H NMR (400 MHZ. Chloroform-d) δ 8.24 (s, 1H), 2.35 (s, 3H), 2.25 (s, 3H).

Step 2: Preparation of 2-bromo-3,5-dimethylpyridin-4-amine

A mixture of 2-bromo-3.5-dimethyl-4-nitropyridine (5.40 g. 23.37 mmol. 1.00 equiv). Fc (2.61 g. 46.74 mmol. 5.00 equiv) and CaCl, (12.97 g. 116.86 mmol. 5.00 equiv) in EtOH (60 mL) was stirred for 3 h at 90° C., under nitrogen atmosphere. The reaction was monitored by LCMS. The mixture was allowed to r.t. The resulting mixture was filtered, the filter cake was washed with ethanol (500 mL). The filtrate was concentrated under reduced pressure. The residue was dissolved in EtOAc (500 mL). The EtOAc layer was washed with sat. Na.CO; (aq.) (2×300 mL). The organic layers dried over anhydrous $Na_2SO_4$. After filtration, the filtrate was concentrated under reduced pressure. To afford 2-bromo-3.5-dimethylpyridin-4-amine (4.60 g. 97.89%) as a white solid. LC-MS: (ES+H, m/z): $[M+H]^+$=201.0/203.0. $^1$H NMR (400 MHZ. DMSO-$d_6$) δ 7.57 (s, 1H), 5.90 (s, 2H), 2.14 (s, 3H), 1.99 (s, 3H).

Step 3: Preparation of 2'-bromo-4-hydroxy-3',5',6-trimethyl-[1,4'-bipyridin]-2-one A solution of 2-bromo-3.5-dimethylpyridin-4-amine (2.30 g. 11.43 mmol. 1.00 equiv) and 2.2-dimethyl-6-(2-oxopropyl)-1,3-dioxin-4-one (2.11 g. 11.43 mmol. 1.00 equiv) in dioxane (15 mL) was stirred for 3.5 h at 90° C., under nitrogen atmosphere. The mixture was allowed to cool down to room temperature. The reaction was monitored by LCMS. To the above mixture was added $H_2SO_4$ (1.12 g. 11.43 mmol, 1.00 equiv) dropwise at 0° C. The resulting mixture was stirred for additional 1 h at 90° C. The reaction was monitored by LCMS. The mixture was allowed to cool down to r.t. The resulting mixture was concentrated under reduced pressure. The residue was purified by reverse flash chromatography to afford 2'-bromo-4-hydroxy-3'0.5'0.6-trimethyl-[1,4'-bipyridin]-2-one (1.70 g. 62.46%) as a Brown yellow oil. LC-MS: (ES+H, m/z): $[M+H]^+$=309.2/311.2. $^1$H NMR (400 MHz. Chloroform-d) δ 8.25 (s, 1H), 7.69-7.57 (m. 1H), 6.14 (d, 1H), 6.06 (d, 1H), 2.13 (s, 3H), 2.02 (s, 3H), 1.85 (s, 3H).

Step 4: Preparation of 2'-bromo-4-[(3,5-difluoropyridin-2-yl)methoxy]-3',5',6-trimethyl-[1,4'-bipyridin]-2-one A mixture of 2'-bromo-4-hydroxy-3'0.5'0.6-trimethyl-[1,4'-bipyridin]-2-one (1.70 g. 5.49 mmol, 1.00 equiv), 2-(chloromethyl)-3.5-difluoropyridine (1.35 g. 8.24 mmol. 1.50 equiv), 18-Crown-6 (0.15 g. 0.55 mmol. 0.10 equiv) and $K_2CO_3$ (3.04 g. 21.99 mmol. 4.00 equiv) in DMF (15 mL) was stirred for 4 h at 60° C. under nitrogen atmosphere. The reaction was monitored by LCMS. The mixture was allowed to cool down to r.t. The residue was dissolved in EA (400 mL). The mixture was washed with water (3×200 mL), dried over anhydrous $Na_2SO_4$. After filtration, the filtrate was concentrated under reduced pressure. The residue was purified by silica gel column chromatography to afford 2'-bromo-4-[(3,5-difluoropyridin-2-yl)methoxy]-3',5',6-trimethyl-[1,4'-bipyridin]-2-one (1.60 g, 66.70%) as a yellow green solid. LC-MS: (ES+H, m/z): $[M+H]^+$=436.2/438.2. $^1$H NMR (400 MHZ, DMSO-$d_6$) δ 8.60 (d, 1H), 8.34 (s, 1H), 8.14-8.02 (m, 1H), 6.20 (d, 1H), 6.08 (d, 1H), 5.26 (d, 2H), 2.04 (s, 3H), 1.95 (s, 3H), 1.81 (s, 3H).

Intermediate 42-56

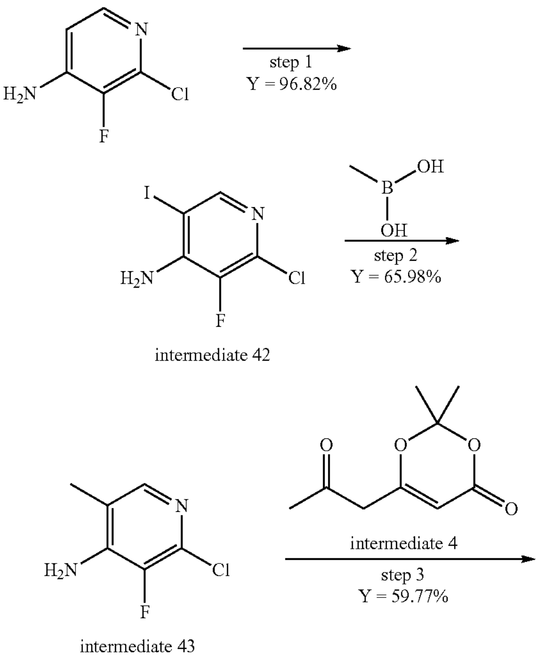

-continued

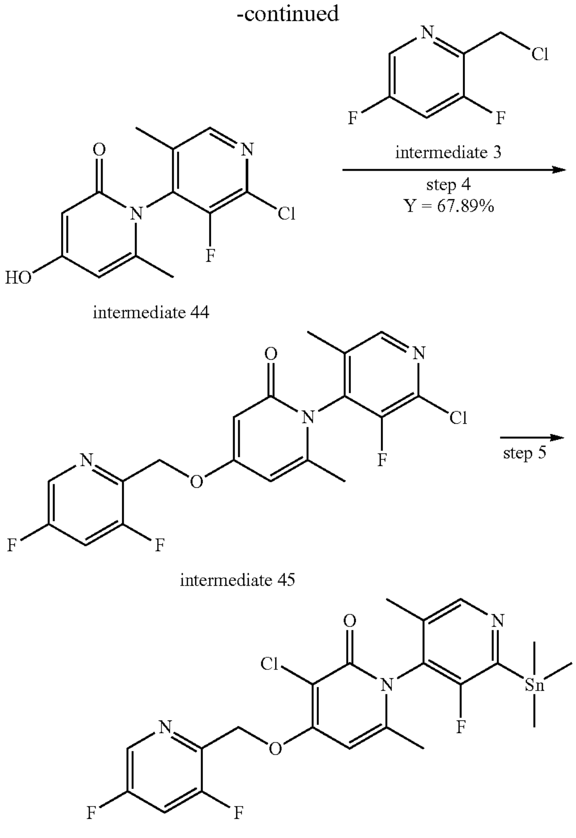

intermediate 44 intermediate 45 intermediate 46

Step 1: Preparation of 2-chloro-3-fluoro-5-iodopyridin-4-amine

To a stirred solution of 2-chloro-3-fluoropyridin-4-amine (5.00 g, 34.11 mmol, 1.00 equiv) in $CH_3CN$(150 mL) were added NIS (9.21 g, 40.94 mmol, 1.20 equiv) and 4-methylbenzene-1-sulfonic acid hydrate (0.32 g. 1.70 mmol, 0.05 equiv) in portions at room temperature under nitrogen atmosphere. The resulting mixture was stirred overnight at 70° C., under nitrogen atmosphere. The reaction was monitored by LCMS. The mixture was allowed to cool down to room temperature. The resulting mixture was diluted with water (300 mL). The resulting mixture was extracted with EtOAc (3×150 mL). The combined organic layers were washed with brine (3×150 mL), dried over anhydrous $Na_2SO_4$. After filtration, the filtrate was concentrated under reduced pressure to afford 2-chloro-3-fluoro-5-iodopyridin-4-amine (9.00 g, 96.82%) as a brown solid. LC-MS: (ES+H, m/z): $[M+H]^+$=272.9. $^1$H NMR (300 MHz, DMSO-$d_6$) δ 8.10 (s, 1H), 6.69 (s, 2H).

Step 2: Preparation of 2-chloro-3-fluoro-5-methylpyridin-4-amine

To a stirred mixture of 2-chloro-3-fluoro-5-iodopyridin-4-amine (9.00 g, 33.03 mmol, 1.00 equiv) and methylboronic acid (3.95 g, 66.06 mmol, 2.00 equiv) in Toluene (200 mL) and $H_2O$ (20 mL) were added $Cs_2CO_3$ (16.14 g, 49.55 mmol, 1.50 equiv), PCy3 (0.46 g, 1.65 mmol, 0.05 equiv) and Pd(OAc) 2 (0.37 g, 1.65 mmol, 0.05 equiv) at room temperature under nitrogen atmosphere. The resulting mixture was stirred overnight at 100° C., under nitrogen atmosphere. The reaction was monitored by LCMS. The mixture was allowed to cool down to room temperature. The resulting mixture was diluted with water (500 mL). The resulting mixture was extracted with EtOAc (3×200 mL). The combined organic layers were washed with brine (3×200 mL), dried over anhydrous $Na_2SO_4$. After filtration, the filtrate was concentrated under reduced pressure. The residue was purified by silica gel column chromatography, the filtrate was concentrated under reduced pressure to afford 2-chloro-3-fluoro-5-methylpyridin-4-amine (3.50 g, 65.98%) as a yellow solid. LC-MS: (ES+H, m/z): $[M+H]^+$=161.00. $^1$H NMR (300 MHz, Chloroform-d) δ 7.75 (s. 1H), 4.36 (s, 2H), 2.15 (s, 3H).

Step 3: Preparation of 2'-chloro-3'-fluoro-4-hydroxy-5',6-dimethyl-[1,4'-bipyridin]-2-one To a stirred solution of 2-chloro-3-fluoro-5-methylpyridin-4-amine (3.00 g. 18.68 mmol. 1.00 equiv) in 1,4-dioxane (100 mL) were added 2.2-dimethyl-6-(2-oxopropyl)-1,3-dioxin-4-one (6.88 g. 37.36 mmol. 2.00 equiv) at room temperature under nitrogen atmosphere. The resulting mixture was stirred for 2 h at 90° C., under nitrogen atmosphere. The mixture was allowed to cool down to room temperature. To the above mixture was added $H_2SO_4$ (1.83 g. 18.68 mmol. 1.00 equiv) dropwise at room temperature. The resulting mixture was stirred for additional 2 h at 90° C. The reaction was monitored by LCMS. The mixture was allowed to cool down to room temperature. The resulting mixture was concentrated under reduced pressure. The residue was purified by trituration with water (200 mL). The solid was collected by filtration and further purified by trituration with hexane (200 mL) to afford 2'-chloro-3'-fluoro-4-hydroxy-5'0.6-dimethyl-[1,4'-bipyridin]-2-one (3.00 g. 59.77%) as a brown solid. LC-MS: (ES+H, m/z): $[M+H]^+$=269.1. $^1$H NMR (300 MHz. DMSO-$d_6$) δ 11.03 (s, 1H), 8.42 (s, 1H), 6.05 (d, 1H), 5.61 (d, 1H), 2.06 (s, 3H), 1.89 (s. 3H).

Step 4: Preparation of 2'-chloro-4-[(3,5-difluoropyridin-2-yl)methoxy]-3'-fluoro-5',6-dimethyl-[1,4'-bipyridin]-2-one To a stirred mixture of 2'-chloro-3'-fluoro-4-hydroxy-5'0.6-dimethyl-] 1,4'-bipyridin]-2-one (2.00 g. 7.44 mmol. 1.00 equiv) and 2-(chloromethyl)-3.5-difluoropyridine (1.83 g. 11.16 mmol. 1.50 equiv) in DMF (60 mL) were added $Cs_2CO_3$ (7.28 g. 22.33 mmol. 3.00 equiv) and 18-Crown-6 (196.7 mg, 0.74 mmol. 0.10 equiv) at room temperature under nitrogen atmosphere. The resulting mixture was stirred overnight at 70° C. under nitrogen atmosphere. The reaction was monitored by LCMS. The mixture was allowed to cool down to room temperature. The resulting mixture was diluted with water (150 mL). The resulting mixture was extracted with EtOAc (3×100 mL). The combined organic layers were washed with brine (3×100 mL). dried over anhydrous $Na_2SO_4$. After filtration, the filtrate was concentrated under reduced pressure. The residue was purified by silica gel column chromatography, the filtrate was concentrated under reduced pressure to afford 2'-chloro-4-[(3.5-difluoropyridin-2-yl)methoxy]-3'-fluoro-5'0.6-dimethyl-[1, 4'-bipyridin]-2-one (2.00 g. 67.89%) as a yellow solid. LC-MS: (ES+H, m/z): $[M+H]^+$=396.1. $^1$H NMR (300 MHz. DMSO-d6) δ 8.60 (d, 1H), 8.44 (s, 1H), 8.12-8.04 (m. 1H), 6.22 (d, 1H), 6.09 (d, 1H), 5.27 (d, 2H), 2.08 (s, 3H). 1.92 (s, 3H).

Step 5: Preparation of 3-chloro-4-[(3,5-difluoropyridin-2-yl)methoxy]-3'-fluoro-5',6-dimethyl-2'-(trimethylstannyl)-[1,4'-bipyridin]-2-one To a stirred solution of 2'0.3-dichloro-4-[(3.5-difluoropyridin-2-yl)methoxy]-3'-fluoro-5'0.6-dimethyl-[1,4'-bipyridin]-2-one (500 mg, 1.16 mmol. 1.00 equiv) and Sn2Me6 (761.56 mg. 2.32 mmol. 2.00 equiv) in dioxane (8 mL) were added $Pd(PPh_3)_2Cl_2$ (163.15 mg, 0.23 mmol. 0.20 equiv) and AsPh; (71.18 mg. 0.23 mmol. 0.20 equiv) at room temperature under nitrogen atmosphere. The resulting mixture was stirred for 1 h at 80° C., under nitrogen atmosphere. The reaction was monitored by LCMS. The mixture was allowed to cool down to room temperature. The resulting mixture was used in the next step directly without further purification. LC-MS: (ES+H, m/z): $[M+H]^+$=560.0.

Intermediate 47-48

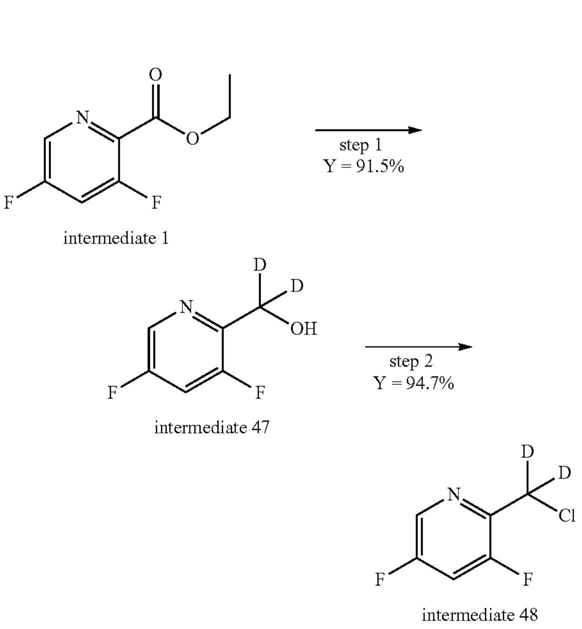

Step 1: Preparation of (3,5-difluoropyridin-2-yl) methan-d2-ol

To a stirred solution of ethyl 5-chloro-3-fluoropyridine-2-carboxylate (500.00 g, 2671.71 mmol, 1.00 equiv) in $CD_3OD$ (500 mL) and THF (1000 mL) was added NaBD+ (111.84 g, 2671.71 mmol, 1.00 equiv) in portions at 0° C., under nitrogen air. The resulting mixture was stirred for 2 hours at room temperature under nitrogen atmosphere. The reaction was monitored by LCMS. The resulting mixture was quenched by the addition of D.O (200 mL) at 0° C., and stirred for 30 min at 0° C. The mixture was diluted with EtOAc (2000 mL) and washed with water (2000 ml) and brine (2000 ml). The organic layers were dried over anhydrous $Na_2SO_4$. After filtration, the filtrate was concentrated under reduced pressure, to afford (3,5-difluoropyridin-2-yl) methan-d2-ol methanol (360.00 g, 91.5%) as a yellow oil. LC-MS: (ES+H, m/z): $[M+H]^+$=148.1. $^1$H NMR (300 MHz, DMSO-$d_6$) δ 8.44 (d, 1H), 7.88 (ddd, 1H), 5.37 (s, 1H).

Step 2: Preparation of 2-(chloromethyl-d2)-3,5-difluoropyridine

To a stirred solution of (3,5-difluoropyridin-2-yl) methan-d2-ol (300.00 g, 2039.13 mmol, 1.00 equiv) in DCM (1000 mL) was added DMF (14.91 g, 203.91 mmol, 0.10 equiv) and SOCI2 (606.44 g, 5097.84 mmol, 2.50 equiv) dropwise under nitrogen atmosphere at 0° C. The resulting mixture was stirred for 2 h at room temperature under nitrogen atmosphere. The reaction was monitored by LCMS. The resulting mixture was concentrated under vacuum to afford 2-(chloromethyl-d2)-3,5-difluoropyridine (320.00 g, 94.7%) as a yellow oil which was used directly in next step without further purification. LC-MS: (ES+H, m/z): $[M+H]^+$=166.1. $^1$H NMR (300 MHz, DMSO-$d_6$) δ 8.48 (d, 1H), 8.04-7.93 (m, 1H).

Intermediate 49-53

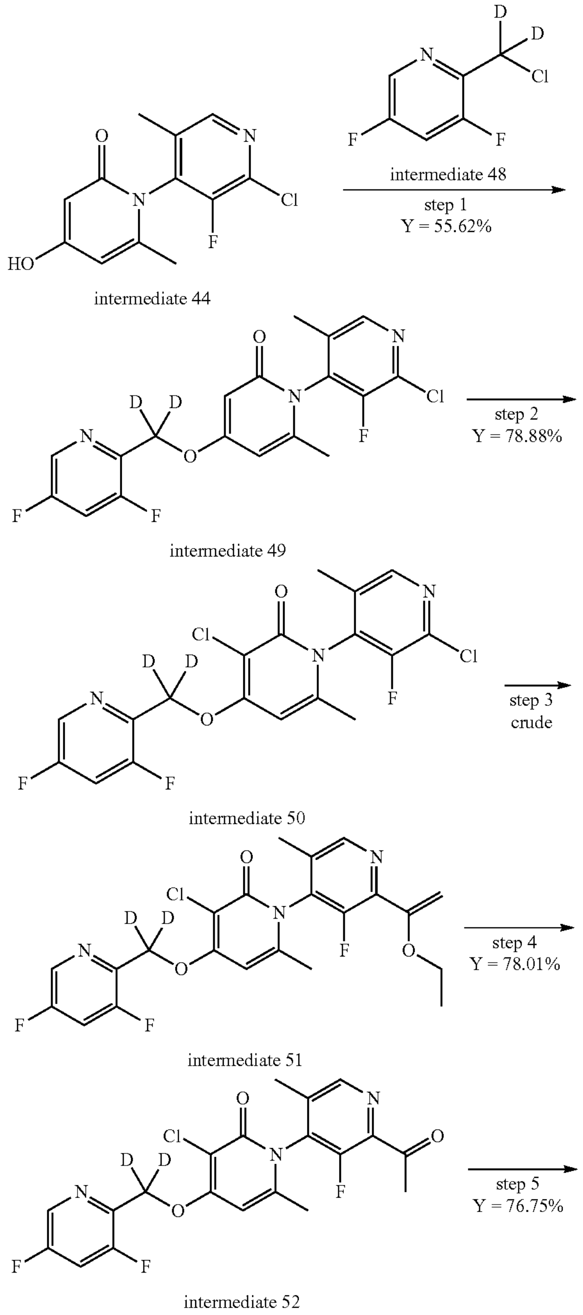

-continued

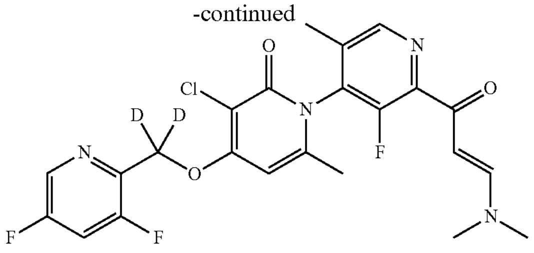

intermediate 53

Step 1: Preparation of 2'-chloro-4-[(3,5-difluoro-pyridin-2-yl) ($^2H_2$)methoxy]-3'-fluoro-5',6-dimethyl-[1,4'-bipyridin]-2-one To a stirred mixture of 2'-chloro-3'-fluoro-4-hydroxy-5'0.6-dimethyl-[1,4'-bipyridin]-2-one (1.70 g. 6.32 mmol. 1.00 equiv) and 2-[chloro ($^2H_2$) methyl]-3.5-difluoropyridine (1.57 g. 9.49 mmol. 1.50 equiv) in DMF (60 mL) were added $Cs_2CO_3$ (6.18 g. 18.98 mmol. 3.00 equiv) and 18-Crown-6 (0.17 g. 0.63 mmol, 0.10 equiv) at room temperature under nitrogen atmosphere. The resulting mixture was stirred for 2 h at 70° C., under nitrogen atmosphere. The reaction was monitored by LCMS. The mixture was allowed to cool down to room temperature. The resulting mixture was diluted with water (150 mL). The resulting mixture was extracted with EtOAc (3×100 mL). The combined organic layers were washed with brine (3×100 mL). dried over anhydrous $Na_2SO_4$. After filtration, the filtrate was concentrated under reduced pressure. The residue was purified by silica gel column chromatography, the filtrate was concentrated under reduced pressure to afford 2'-chloro-4-[(3.5-difluoropyridin-2-yl) ($^2H_2$)methoxy]-3'-fluoro-5'0.6-dimethyl-[1,4'-bipyridin]-2-one (1,40 g. 55.62%) as a yellow solid. LC-MS: (ES+H, m/z): $[M+H]^+$=398.1.

Step 2: Preparation of 2',3-dichloro-4-[(3,5-difluoropyridin-2-yl) ($^2H_2$)methoxy]-3'-fluoro-5',6-dimethyl-[1,4'-bipyridin]-2-one To a stirred solution of 2'-chloro-4-[(3.5-difluoropyridin-2-yl) ($^2H_2$)methoxy]-3'-fluoro-5'0.6-dimethyl-[1,4'-bipyridin]-2-one (1,40 g. 3.52 mmol. 1.00 equiv) and NCS (0.61 g. 4.57 mmol. 1.30 equiv) in i-PrOH was added dichloroacetic acid (0.05 g. 0.35 mmol. 0.10 equiv) dropwise at room temperature under nitrogen atmosphere. The resulting mixture was stirred 2 h at 60° C., under nitrogen atmosphere. The reaction was monitored by LCMS. The resulting mixture was diluted with water (100 mL). The resulting mixture was extracted with EtOAc (3×50 mL). The combined organic layers were washed with brine (3×50 mL), dried over anhydrous $Na_2SO_4$. After filtration, the filtrate was concentrated under reduced pressure. The residue was purified by silica gel column chromatography, the filtrate was concentrated under reduced pressure to afford 2'0.3-dichloro-4-[(3.5-difluoropyridin-2-yl) ($H_2$)methoxy]-3'-fluoro-5'0.6-dimethyl-[1,4'-bipyridin]-2-one (1.2 g. 78.88%) as a yellow solid. LC-MS: (ES+H, m/z): $[M+H]^+$=432.0. $^1H$ NMR (400 MHz. DMSO-do) δ 8.59 (d, 1H), 8.43 (d, 1H), 8.12-8.03 (m, 1H), 6.21 (s, 1H), 6.08 (d, 1H), 2.07 (s, 3H), 1.91 (s, 3H).

Step 3:3-chloro-4-[(3,5-difluoropyridin-2-yl) ($^2H_2$) methoxy]-2'-(1-ethoxyethenyl)-3'-fluoro-5',6-dimethyl-[1,4'-bipyridin]-2-one To a stirred solution of 2'.3-dichloro-4- [(3.5-difluoropyridin-2-yl) ($^2H_2$)methoxy]-3'-fluoro-5'.6-dimethyl-[1,4'-bipyridin]-2-one (1.20 g. 2.77 mmol. 1.00 equiv) and tributyl (1-ethoxyethenyl) stannane (2.01 g. 5.55 mmol. 2.00 equiv) in dioxane 24.00 mL were added Pd(PPh3): $Cl_2$ (0.10 g. 0.14 mmol. 0.05 equiv) at room temperature under nitrogen atmosphere. The resulting mixture was stirred for 2 h at 120° C., under nitrogen atmosphere. The reaction was monitored by LCMS. Desired product could be detected by LCMS. The mixture was allowed to cool down to room temperature. The resulting mixture was used in the next step directly without further purification. LC-MS: (ES+H, m/z): $[M+H]^+$=468.1.

Step 4: Preparation of 2'-acetyl-3-chloro-4-[(3,5-difluoropyridin-2-yl) ($^2H_2$)methoxy]-3'-fluoro-5',6-dimethyl-[1,4'-bipyridin]-2-one The above mixture was diluted with 1,4-dioxane (80 mL), then was added HCl (0.94 g. 25.65 mmol. 10.00 equiv) dropwise at 0° C. The resulting mixture was stirred for additional 30 min at room temperature. Desired product could be detected by LCMS. The mixture was basified to pH 8 with saturated NaHCO; (aq.). The resulting mixture was extracted with EtOAc (3×100 mL). The combined organic layers were washed with brine (3×10 mL), dried over anhydrous $Na_2SO_4$. After filtration. The residue was purified by silica gel column chromatography, the filtrate was concentrated under reduced pressure to afford 2'-acetyl-3-chloro-4-[(3.5-difluoropyridin-2-yl) ($^2H_2$)methoxy]-3'-fluoro-5'0.6-dimethyl-[1,4'-bipyridin]-2-one (880 mg. 78.01%) as a yellow solid. LC-MS: (ES+H, m/z): $[M+H]^+$=440.20.

Step 5: Preparation of 3-chloro-4-[(3,5-difluoropyridin-2-yl) ($^2H_2$)methoxy]-2'-[(2E)-3-(dimethylamino) prop-2-enoyl]-3'-fluoro-5',6-dimethyl-[1,4'-bipyridin]-2-one A solution of 2'-acetyl-3-chloro-4-[(3.5-difluoropyridin-2-yl) (2H.)methoxy]-3'-fluoro-5'0.6-dimethyl-[1,4'-bipyridin]-2-one (880 mg. 2.00 mmol. 1.00 equiv) in DMF-DMA (6 mL) was stirred for 2 h at 100° C., under nitrogen atmosphere. Desired product could be detected by LCMS. The mixture was allowed to cool down to room temperature. The precipitated solids were collected by filtration and washed with hexane (3×2 mL). This resulted in 3-chloro-4-[(3.5-difluoropyridin-2-yl) ($^2H_2$)methoxy]-2'-[(2E)-3-(dimethylamino) prop-2-enoyl]-3'-fluoro-5'0.6-dimethyl-[1,4'-bipyridin]-2-one (760 mg. 76.75%) as a yellow solid. LC-MS: (ES+H, m/z): $[M+H]^+$=495.1.

Intermediate 54-55

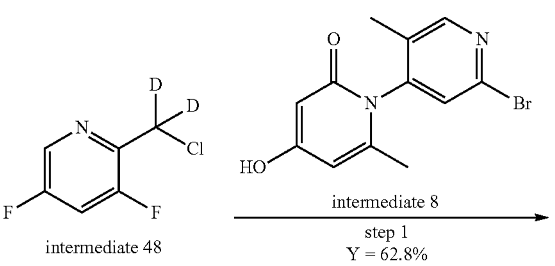

intermediate 48

-continued

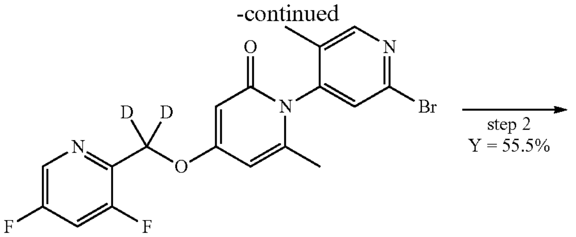

intermediate 54

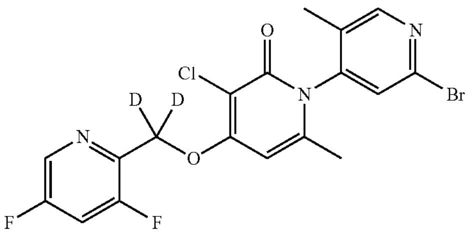

intermediate 55

Step 1: Preparation of 2'-bromo-4-((3,5-difluoro-pyridin-2-yl)methoxy-d2)-5',6-dimethyl-2H-[1,4'-bipyridin]-2-one To a stirred mixture of 2'-bromo-4-hydroxy-5'0.6-dimethyl-] 1,4'-bipyridin]-2-one (100.00 g. 338.82 mmol. 1.00 equiv), 18-Crown-6 (5.37 g. 3.00 mmol. 0.40 equiv) and $K_2CO_3$ (42.14 g. 304.94 mmol. 3.00 equiv) in DMF (200 mL) was added 2-(chloromethyl-d2)-3.5-difluoropyridine (27.75 g. 152.47 mmol. 1.50 equiv) at r.t . . . . The resulting mixture was stirred for 2.5 h at 60° C., under nitrogen atmosphere. The reaction was monitored by LCMS. The resulting mixture was filtered, the filter cake was washed with EtOAc (3×500 mL). The filtrate was diluted with EA (3000 mL). The resulting mixture was washed with brine (3×2000 mL) and water (5×2000 mL). The organic layer was dried over anhydrous $Na_2SO_4$. After filtration, the filtrate was concentrated under reduced pressure. The residue was purified by trituration with Et.O (3×250 ml) and dried under reduced pressure to afford 2'-bromo-4-((3.5-difluoropyridin-2-yl)methoxy-d2)-5'0.6-dimethyl-2H-[1,4'-bipyridin]-2-one (90 g. 62.8%) as a white solid. LC-MS: (ES+H, m/z): $[M+H]^+$=424.0. $^1$H NMR (300 MHz. DMSO-$d_6$) δ 8.59 (d, 1H), 8.48 (s, 1H), 8.08 (ddd. 1H), 7.73 (s, 1H), 6.13 (dd. 1H), 6.03 (d, 1H), 1.97 (s.3H), 1.85 (s, 3H).

Step 2: Preparation of 2'-bromo-3-chloro-4-((3,5-difluoropyridin-2-yl)methoxy-d2)-5',6-dimethyl-2H-[1,4'-bipyridin]-2-one To a stirred solution of 2'-bromo-4-((3,5-difluoropyridin-2-yl)methoxy-d2)-5',6-dimethyl-2H-[1,4'-bipyridin]-2-one (100.00 g, 235.71 mmol, 1.00 equiv) and NCS (37.77 g, 282.85 mmol, 1.20 equiv) in IPA (500 mL) was added 2,2-dichloroacetic acid (3.04 g, 23.57 mmol, 0.10 equiv) dropwise at room temperature. The resulting mixture was stirred for 1 h at 60° C., under nitrogen atmosphere. The reaction was monitored by LCMS. The mixture was allowed to cool down to r.t. The precipitated solids were collected by filtration and washed with cold IPA (4×30 mL), to afford 2'-bromo-3-chloro-4-((3,5-difluoropyridin-2-yl)methoxy-d2)-5',6-dimethyl-2H-[1,4'-bipyridin]-2-one (60.00 g, 55.5%) as a white solid. LC-MS: (ES+H, m/z): $[M+H]^+$=458.0. $^1$H NMR 300 MHz, DMSO-$d_6$) δ 8.60 (d, 1H), 8.52 (s, 1H), 8.10 (ddd, 1H), 7.81 (s. 1H), 6.80 (d, 1H), 1.96 (s, 6H).

Intermediate 56-57

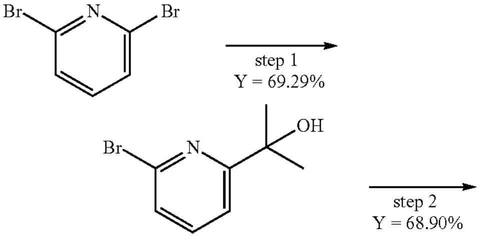

intermediate 56

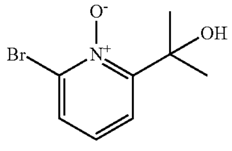

intermediate 57

Step 1: Preparation of 2-(6-bromopyridin-2-yl) propan-2-ol

To a stirred solution of 2,6-dibromo-pyridine, (25.00 g, 105.53 mmol, 1.00 equiv) in toluene (50 ml) was added n-BuLi (46.43 mL, 116.08 mmol, 1.10 equiv, 2.5M in THF) dropwise at −50° C., under nitrogen atmosphere. The resulting mixture was stirred for 30 min at −50° C., under nitrogen atmosphere. To the above mixture was added acetone (9.19 g. 158.29 mmol, 1.5 equiv) dropwise over 10 min at −50° C. The resulting mixture was stirred for additional 1 h at −50° C. The reaction was monitored by LCMS. The reaction was quenched with sat. $NH_4Cl$ (aq.) at −10° C. The resulting mixture was extracted with EtOAc (3×300 mL). The combined organic layers were concentrated under reduced pressure. The residue was purified by silica gel column chromatography to afford 2-(6-bromopyridin-2-yl) propan-2-ol (15.80 g, 69.29%) as a colorless liquid. LC-MS: (ES+H, m/z): $[M+H]^+$=216.2/218.2. $^1$H NMR (400 MHZ, DMSO-$d_6$) δ 7.73 (t, 1H), 7.68 (dd, 1H), 7.46 (dd, 1H), 5.33 (s, 1H), 1,43 (s, 6H).

Step 2: Preparation of 2-bromo-6-(2-hydroxypropan-2-yl)pyridin-1-ium-1-olate

To a stirred solution of 2-(6-bromopyridin-2-yl) propan-2-ol (5.00 g, 23.14 mmol, 1.00 equiv) in DCM (50 ml) was added m-CPBA (11.98 g, 69.42 mmol, 3.00 equiv) in portions at 0° C., under nitrogen atmosphere. The resulting mixture was stirred for 24 h at 50° C., under nitrogen atmosphere. The reaction was monitored by LCMS. The mixture was allowed to r.t. The resulting mixture was concentrated under reduced pressure. The residue was purified by silica gel column chromatography, to afford 2-bromo-6-(2-hydroxypropan-2-yl)pyridin-1-ium-1-olate (3.70 g, 68.90%) as a white solid. LC-MS: (ES+H, m/z): $[M+H]^+$=232.3/234.3. $^1$H NMR (300 MHz, DMSO-$d_6$) δ 7.91 (dd, 1H), 7.69 (dd, 1H), 7.33 (t, 1H), 6.70-6.04 (m, 1H), 1.58 (s, 6H).

EXAMPLE 1

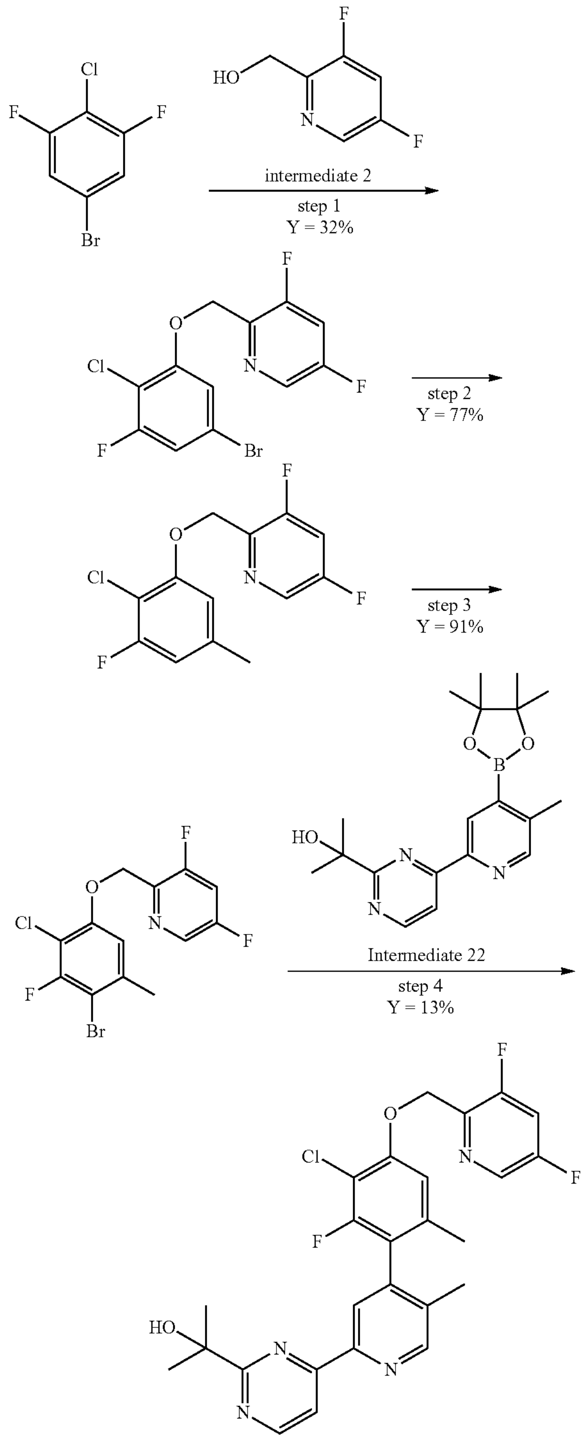

Example 1

Step 1: Preparation of 2-(5-bromo-2-chloro-3-fluorophenoxymethyl)-3,5-difluoropyridine A mixture of 5-bromo-2-chloro-1,3-difluorobenzene (6.00 g, 26.38 mmol, 1.00 equiv), (3,5-difluoropyridin-2-yl)

methanol (3.83 g, 26.38 mmol, 1.00 equiv), 18-Crown-6 (0.70 g, 2.64 mmol, 0.10 equiv) and $K_2CO_3$ (10.94 g, 79.15 mmol, 3.00 equiv) in DMF (100 mL) was stirred overnight at 80° C., under nitrogen atmosphere. The reaction was monitored by LCMS. The resulting mixture was concentrated under reduced pressure. The residue was purified by silica gel column chromatography, and the pure fraction was concentrated under reduced pressure to afford 2-(5-bromo-2-chloro-3-fluorophenoxymethyl)-3,5-difluoropyridine (3.00 g, 32%) as a white solid. LC-MS: (ES+H, m z): $[M+H]^+$=351.9/353.9. $^1H$ NMR (400 MHz, DMSO-$d_6$) δ 8.58 (d, 1H), 8.07 (td, 1H), 7.49 (t, 1H), 7.42 (dd, 1H), 5.41 (d, 2H).

Step 2: Preparation of 2-(2-chloro-3-fluoro-5-methylphenoxymethyl)-3,5-difluoropyridine A mixture of 2-(5-bromo-2-chloro-3-fluorophenoxymethyl)-3,5-difluoropyridine (3.00 g. 8.51 mmol, 1.00 equiv), methylboronic acid (0.76 g. 12.77 mmol, 1.50 equiv), Pd(dppf) $Cl_2$ (313 mg, 0.43 mmol, 0.05 equiv) and $K_2CO_3$ (3.53 g, 25.53 mmol, 3.00 equiv) in dioxane: $H_2O$=10:1 (100 mL) was stirred overnight at 80° C., under nitrogen atmosphere. The reaction was monitored by LCMS. The resulting mixture was concentrated under reduced pressure. The residue was purified by silica gel column chromatography and the pure fraction was concentrated under reduced pressure to afford 2-(2-chloro-3-fluoro-5-methylphenoxymethyl)-3,5-difluoropyridine (1.90 g, 77%) as a white solid. LC-MS: (ES+H, m z): $[M+H]^+$=288.1. $^1H$ NMR (400 MHZ, DMSO-$d_6$) δ 8.57 (d, 1H), 8.08-8.03 (m, 1H), 7.06 (s, 1H), 6.88 (dd, 1H), 5.30 (d, 2H), 2.32 (s, 3H).

Step 3: Preparation of 2-(4-bromo-2-chloro-3-fluoro-5-methylphenoxymethyl)-3,5-difluoropyridine A mixture of 2-(2-chloro-3-fluoro-5-methylphenoxymethyl)-3,5-difluoropyridine (1.30 g, 4.52 mmol, 1.00 equiv) and NBS (804 mg, 4.52 mmol, 1.00 equiv) in MeCN was stirred overnight at 80° C., under nitrogen atmosphere. The reaction was monitored by LCMS. The resulting mixture was concentrated under reduced pressure. The residue was purified by silica gel column chromatography and the pure fraction was concentrated under reduced pressure to afford 2-(4-bromo-2-chloro-3-fluoro-5-methylphenoxymethyl)-3,5-difluoropyridine (1.50 g. 91%) as a white solid. LC-MS: (ES+H, m z): $[M+H]^+$=365.9/367.9. $^1H$ NMR (400 MHz, DMSO-$d_6$) δ 8.57 (d, 1H), 8.09-8.04 (m, 1H), 7.32 (d, 1H), 5.36 (d, 2H), 2.39 (s, 3H).

Step 4: Preparation of 3-{5-chloro-4-[(2,4-difluorophenyl)methoxy]-2-methyl-6-oxopyrimidin-1-yl}-N-methoxy-N,4-dimethylbenzamide A mixture of 2-{4-[5-methyl-4-(4,4,5,5-tetramethyl-1,3,2-dioxaborolan-2-yl)pyridin-2-yl] pyrimidin-2-yl}propan-2-ol (50 mg, 0.18 mmol, 1.00 equiv), 2-(4-bromo-2-chloro-3-fluoro-5-methylphenoxymethyl)-3,5-difluoropyridine (62 mg, 0.17 mmol, 1.20 equiv), Pd(dppf) $Cl_2$ (10 mg, 0.01 mmol, 0.10 equiv) and $Cs_2CO_3$ (138 mg, 0.42 mmol, 3.00 equiv) in dioxane: $H_2O$=20:1 (1 mL) was stirred for 3 h at 100° C., under nitrogen atmosphere. The reaction was monitored by LCMS. The resulting mixture was concentrated under reduced pressure. The residue was purified by Prep-TLC to afford 2-[4-(4-{3-chloro-4-[(3,5-difluoropyridin-2-yl)methoxy]-2-fluoro-6-methylphenyl}-5-methylpyridin-2-yl)pyrimidin-2-yl] propan-2-ol (50 mg, crude) as an off-white solid. The crude product (50 mg) was purified by Prep-HPLC and the pure fractions were concentrated and lyophilized to afford 2-[4-(4-{3-chloro-4-[(3,5-difluoropyridin-2-yl)methoxy]-2-fluoro-6-methylphenyl}-5-methylpyridin-2-yl)pyrimidin-2-yl]propan-2-ol (13 mg, 13%) as an off-white solid. LC-MS: (ES+H, m z): $[M+H]^+$=515.15. $^1$H NMR (400 MHZ, DMSO-$d_6$) δ 8.95 (d, 1H), 8.78 (s, 1H), 8.61 (d, 1H), 8.53 (s, 1H), 8.24 (d, 1H), 8.10 (td, 1H), 7.33 (s, 1H), 5.42 (s, 2H), 5.23 (s, 1H), 2.13 (s, 3H), 2.06 (s, 3H), 1.52 (s, 6H). $^{19}$F NMR (377 MHz, DMSO) δ-115.32,-120.15,-122.47.

EXAMPLE 2

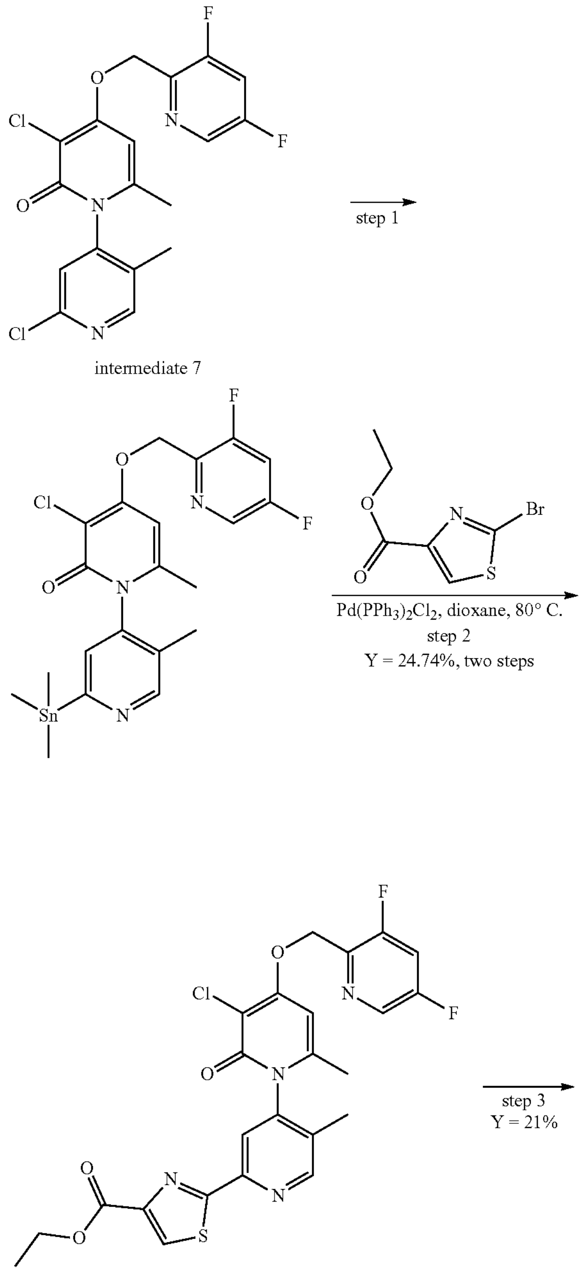

-continued

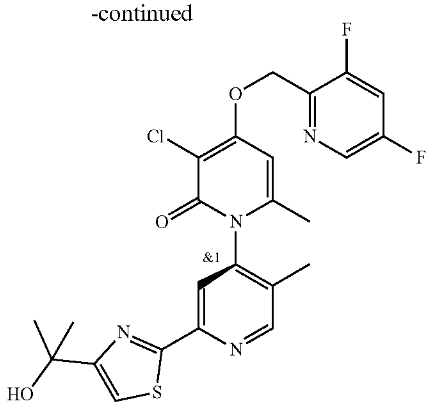

Example 2

Step 1: Preparation of 3-chloro-4-((3,5-difluoropyridin-2-yl)methoxy)-5',6-dimethyl-2'-(trimethylstannyl)-2H-[1,4'-bipyridin]-2-one To a mixture of 2',3-dichloro-4-[(3,5-difluoropyridin-2-yl)methoxy]-5',6-dimethyl-[1,4'-bipyridin]-2-one (500 mg, 1.21 mmol, 1.00 equiv) and hexamethyldistannane (477 mg, 1,46 mmol, 1.20 equiv) in dioxane (10 mL) was added Pd(PPh3): $C_1$: (170 mg, 0.24 mmol, 0.20 equiv) and AsPh3 (74 mg, 0.24 mmol, 0.20 equiv) at room temperature under nitrogen. The mixture was stirred overnight at 80° C. under nitrogen atmosphere. The reaction was monitored by LCMS. Desired product could be detected by LCMS. The mixture was used directly on the next step. LC-MS: (ES+H, m z): $[M+H]^+$=542.1.

Step 2: Preparation of ethyl 2-{3-chloro-4-[(3,5-difluoropyridin-2-yl)methoxy]-5',6-dimethyl-2-oxo-[1,4'-bipyridin]-2'-yl}-1,3-thiazole-4-carboxylate To the last step of reaction mixture was added ethyl 2-bromo-1,3-thiazole-4-carboxylate (432.59 mg, 1.833 mmol, 1.50 equiv), Pd($PPh_3$): $Cl_2$ (170 mg, 0.24 mmol, 0.20 equiv) at room temperature under nitrogen. The mixture was stirred overnight at 80° C., under nitrogen atmosphere. The reaction was monitored by LCMS. The mixture was allowed to cool down to room temperature. The resulting mixture was firstly purified by silica gel column chromatography to afford a crude product (210 mg). The crude product (210 mg) was further purified by Prep-HPLC and the pure fractions were concentrated to afford ethyl 2-{3-chloro-4-[(3,5-difluoropyridin-2-yl)methoxy]-5', 6-dimethyl-2-oxo-[1,4'-bipyridin]-2'-yl}-1,3-thiazole-4-carboxylate (160 mg. 24.74%, two steps) as a white solid. LC-MS: (ES+H, m z): $[M+H]^+$=533.1.

Step 3: Preparation of 3-chloro-4-[(3,5-difluoropyridin-2-yl)methoxy]-2'-[4-(2-hydroxypropan-2-yl)-1,3-thiazol-2-yl]-5',6-dimethyl-[1,4'-bipyridin]-2-one To a mixture of ethyl 2-{3-chloro-4-[(3,5-difluoropyridin-2-yl)methoxy]-5',6-dimethyl-2-oxo-[1,4'-bipyridin]-2'-yl}-1,3-thiazole-4-carboxylate (100 mg, 0.19 mmol, 1.00 equiv) in THF (5 mL) was added $CH_3MgBr$ (0.6 mL, 0.56 mmol, 3.00 equiv) dropwise at 0° C., under nitrogen. The mixture was stirred for 3 h at room temperature under nitrogen atmosphere. The reaction was monitored by LCMS. The reaction was quenched by MeOH (1 mL). The resulting mixture was concentrated under reduced pressure. The residue was directly purified by Prep-HPLC and the pure fractions were concentrated and lyophilized to afford 3-chloro-4-[(3,5-difluoropyridin-2-yl)methoxy]-2'-[4-(2-hydroxypropan-2-yl)-1,3-thiazol-2-yl]-5',6-dimethyl-[1,4'-bipyridin]-2-one (20.3 mg. 21%) as a white solid. LC-MS: (ES+H, m z): $[M+H]^+$=518.8. 1H NMR (400 MHZ, DMSO-$d_6$) δ 8.72 (s, 1H), 8.61 (d, 1H), 8.10 (ddd, 1H), 8.01 (s, 1H), 7.54 (s, 1H), 6.81 (s, 1H), 5.49 (s, 2H), 5.23 (s, 1H), 2.05 (s, 3H), 1.99 (s, 3H), 1.50 (s, 6H). $^{19}F$ NMR (377 MHz, DMSO) δ-120.15,-122.34.

EXAMPLE 3 AND EXAMPLE 3A AND EXAMPLE 3B

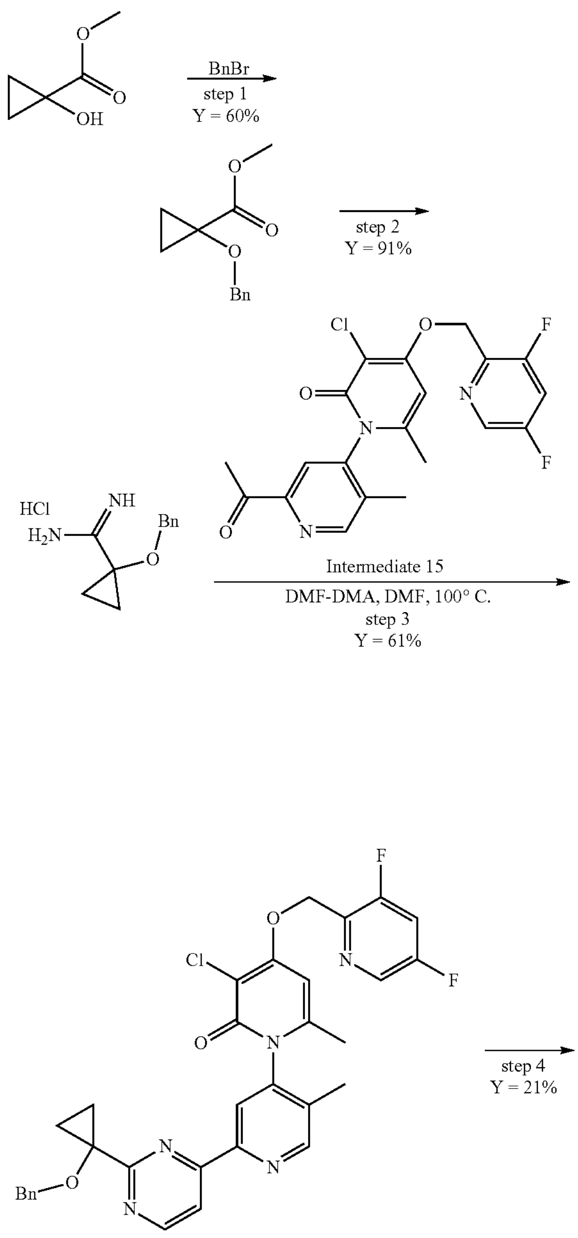

-continued

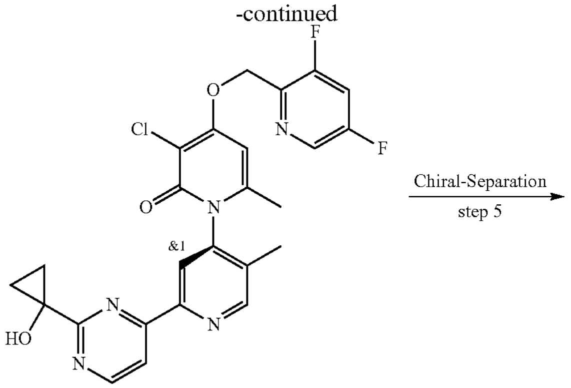

Example 3

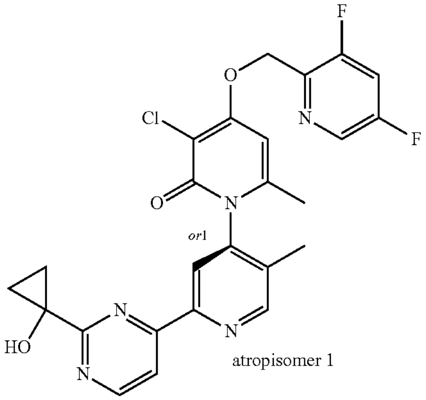

atropisomer 1

Example 3A

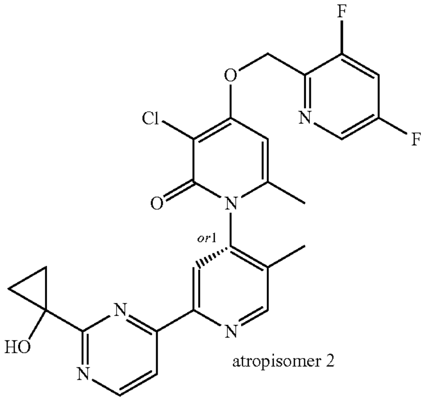

atropisomer 2

Example 3B

Step 1: Preparation of methyl 1-(benzyloxy)cyclopropane-1-carboxylate

A solution of methyl 1-hydroxycyclopropane-1-carboxylate (3.00 g. 25.84 mmol. 1.00 equiv) in DMF (20 mL) was treated with NaH (0.93 g. 38.75 mmol. 1.50 equiv, 60% wt) for 30 min at 0° C., under nitrogen atmosphere followed by the addition of benzyl bromide (8.84 g. 51.67 mmol. 2.00 equiv) dropwise at 0° C. The resulting mixture was stirred for 2 h at room temperature under nitrogen atmosphere. The reaction was monitored by LCMS and TLC. The reaction was quenched by the addition of Water/Ice (150 mL) at 0° C. The resulting mixture was extracted with EtOAc (3×150 mL). The combined organic layers were washed with brine (1×150 mL), dried over anhydrous $Na_2SO_4$. After filtration, the filtrate was concentrated under reduced pressure. The residue was purified by silica gel column chromatography to afford methyl 1-(benzyloxy)cyclopropane-1-carboxylate (3.20 g. 60%) as a colorless oil. $^1$H NMR (300 MHz. DMSO-$d_6$) δ 7.47-7.23 (m. 5H), 4.60 (s, 2H), 3.69 (s, 3H), 1.37-1.16 (m, 4H).

Step 2: Preparation of 1-(benzyloxy)cyclopropane-1-carboximidamide hydrochloride To a stirred mixture of $NH_4Cl$ (2.50 g. 46.74 mmol. 9.64 equiv) in Toluene (20 mL. 188.00 mmol. 38.77 equiv) was added trimethylaluminium (19.25 mL. 534.09 mmol. 110.15 equiv) dropwise at 0° C., under nitrogen atmosphere. The resulting mixture was stirred for 30 min at room temperature under nitrogen atmosphere. To the above mixture was added methyl 1-(benzyloxy)cyclopropane-1-carboxylate (1.00 g. 4.85 mmol. 1.00 equiv) in toluene (10 mL) dropwise over 10 min at room temperature. The resulting mixture was stirred for additional overnight at 80° C. The reaction was monitored by LCMS. The reaction was quenched by the addition of MeOH (10 mL) at 0° C. The resulting mixture was filtered, the filter cake was washed with EtOH (5×20 mL). The filtrate was concentrated under reduced pressure. This resulted in 1-(benzyloxy)cyclopropane-1-carboximidamide hydrochloride (1.00 g. 91%) as a white solid. LC-MS: (ES+H, m z): $[M+H]^+$=191.1. $^1$H NMR (300 MHz. DMSO-$d_6$) δ 8.85 (d, 4H), 7.56-7.23 (m. 5H), 4.57 (s, 2H), 1,48 (s. 4H).

Step 3: Preparation of 2'-{2-[1-(benzyloxy)cyclopropyllpyrimidin-4-yl}-3-chloro-4-[(3,5-difluoropyridin-2-yl)methoxy]-5',6-dimethyl-[1,4'-bipyridin]-2-one A solution of 2'-acetyl-3-chloro-4-[(3.5-difluoropyridin-2-yl)methoxy]-5'0.6-dimethyl-l 1,4'-bipyridin]-2-one (200 mg, 0.48 mmol. 1.00 equiv) in DMF-DMA (5 mL) was stirred overnight at 100° C. under nitrogen atmosphere. The resulting mixture was concentrated under vacuum. To the above mixture was added 1-(benzyloxy)cyclopropane-1-carboximidamide hydrochloride (324 mg, 1,43 mmol. 3.00 equiv) and $K_2CO_3$ (395 mg. 2.86 mmol. 6 equiv) in IPA (5 mL). The resulting mixture was stirred for additional overnight at 100° C. The reaction was monitored by LCMS. The resulting mixture was concentrated under reduced pressure. The residue was purified by Prep-TLC (PE/EA=1:3) to afford 2'-{2-[1-(benzyloxy)cyclopropyllpyrimidin-4-yl}-3-chloro-4-[(3.5-difluoropyridin-2-yl)methoxy]-5'0.6-dimethyl-[1,4'-bipyridin]-2-one (185 mg. 65%) as a white solid. LC-MS: (ES+H, m z): $[M+H]^+$=602.2. Step 4: Preparation of 3-chloro-4-[(3,5-difluoropyridin-2-yl)methoxy]-2'-[2-(1-hydroxycyclopropyl)pyrimidin-4-yl]-5',6-dimethyl-[1,4'-bipyridin]-2-one A mixture of 2'-{2-[1-(benzyloxy)cyclopropyllpyrimidin-4-yl}-3-chloro-4-[(3.5-difluoropyridin-2-yl)methoxy]-5'0.6-dimethyl-[1,4'-bipyridin]-2-one (150 mg, 0.25 mmol. 1.00 equiv) and AlCl3 (199 mg. 1,49 mmol, 6.00 equiv) in Toluene (10 mL) was stirred for 4 h at room temperature under nitrogen atmosphere. The reaction was monitored by LCMS. The resulting mixture was filtered, the filter cake was washed with DCM:MeOH=5:1 (3×10 mL). The filtrate was concentrated under reduced pressure. The crude product (100 mg) was purified by Prep-HPLC, the pure fractions were concentrated and lyophilized to afford 3-chloro-4-[(3,5-difluoropyridin-2-yl)methoxy]-2'-[2-(1-hydroxycyclopropyl)pyrimidin-4-yl]-5',6-dimethyl-[1,4'-bipyridin]-2-one (26.3 mg, 21%) as a white solid. LC-MS: (ES+H, m z): $[M+H]^+$=511.85. 1H NMR (400 MHZ, DMSO-$d_6$) δ 8.91-8.84 (m, 2H), 8.61 (d, 1H), 8.57 (s, 1H), 8.18-8.07 (m, 2H), 6.84 (s, 1H), 6.05 (s, 1H), 5.50 (d, 2H), 2.11 (s, 3H), 1.98 (s, 3H), 1,43-1.31 (m, 2H), 1.21-1.18 (m, 2H). $^{19}$F NMR (377 MHz, DMSO) δ-120.14-122.34.

Step 5: Preparation of rel-3-chloro-4-[(3,5-difluoropyridin-2-yl)methoxy]-2'-[2-(1-hydroxycyclopropyl)pyrimidin-4-yl]-5',6-dimethyl-[1,4'-bipyridin]-2-one and rel-3-chloro-4-[(3,5-difluoropyridin-2-yl)methoxy]-2'-[2-(1-hydroxycyclopropyl)pyrimidin-4-yl]-5',6-dimethyl-[1,4'-bipyridin]-2-one 3-chloro-4-[(3,5-difluoropyridin-2-yl)methoxy]-2'-[2-(1-hydroxycyclopropyl)pyrimidin-4-yl]-5',6-dimethyl-[1,4'-bipyridin]-2-one (30 mg, 0.059 mmol, 1.00 equiv) was isolated by prep-Chiral-HPLC. The pure fraction was concentrated and lyophilized to afford rel-3-chloro-4-[(3,5-difluoropyridin-2-yl)methoxy]-2'-[2-(1-hydroxycyclopropyl)pyrimidin-4-yl]-5',6-dimethyl-[1,4'-bipyridin]-2-one (isomer 1, 13.6 mg, ee %=100%) as a white solid and rel-3-chloro-4-[(3,5-difluoropyridin-2-yl)methoxy]-2'-[2-(1-hydroxycyclopropyl)pyrimidin-4-yl]-5',6-dimethyl-[1,4'-bipyridin]-2-one (isomer 2, 11.8 mg, ee %=99.8%) as a white solid.

EXAMPLE 3A (isomer 1)

LC-MS: (ES+H, m/z): $[M+H]^+$=511.80. $^1$H NMR (400 MHZ, DMSO-$d_6$) δ 8.90-8.83 (m, 2H), 8.61 (d, 1H), 8.57 (s, 1H), 8.15 (d, 1H), 8.11 (td, 1H), 6.85 (s, 1H), 6.05 (s, 1H), 5.50 (d, 2H), 2.11 (s, 3H), 1.98 (s, 3H), 1,43-1.30 (m, 2H), 1.18 (d, 2H). $^{19}$F NMR (377 MHz, DMSO) δ-120.14,-122.35.

EXAMPLE 3B (isomer 2)

LC-MS: (ES+H, m/z): $[M+H]^+$=511.80. $^1$H NMR (400 MHZ, DMSO-$d_6$) δ 8.90-8.83 (m, 2H), 8.61 (d, 1H), 8.57 (s, 1H), 8.15 (d, 1H), 8.11 (td, 1H), 6.85 (s, 1H), 6.05 (s, 1H), 5.50 (d, 2H), 2.11 (s, 3H), 1.98 (s, 3H), 1,43-1.30 (m, 2H), 1.18 (d, 2H). $^{19}$F NMR (377 MHz, DMSO) δ-120.13,-122.35.

EXAMPLE 4, 4A, 4B

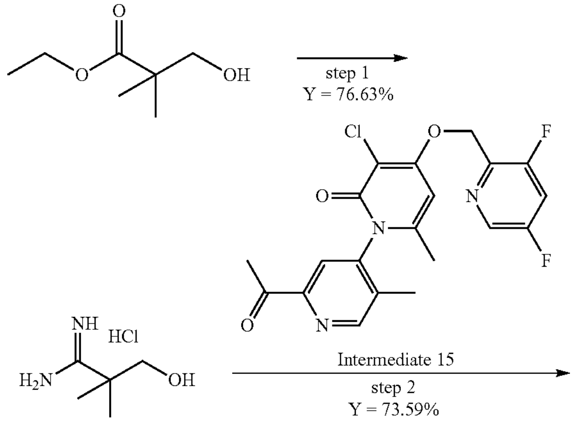

-continued

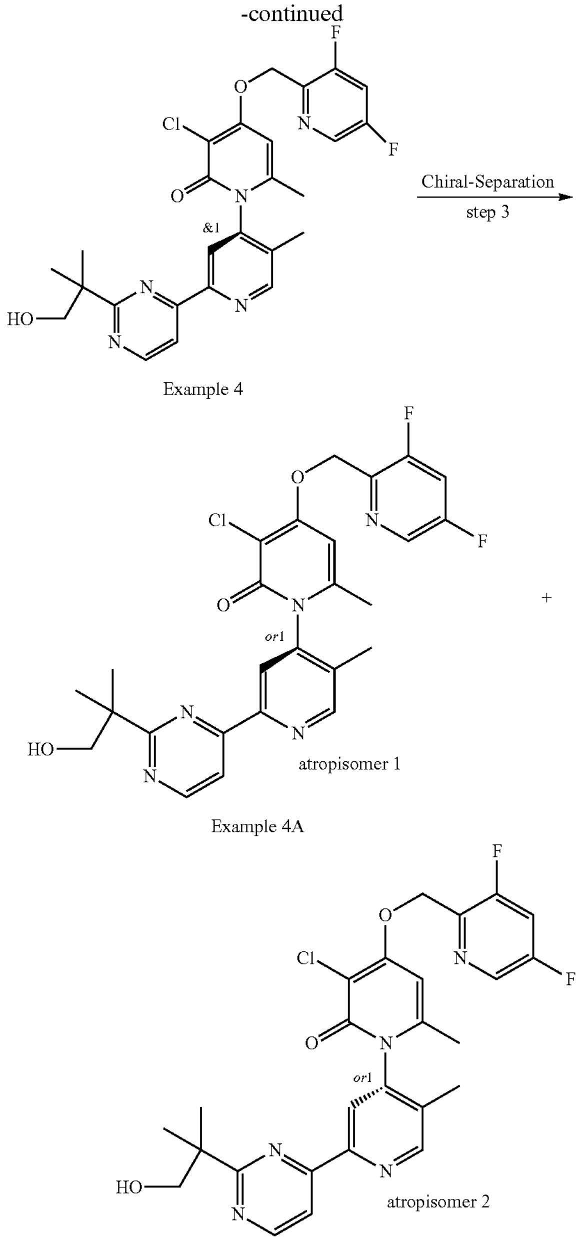

Example 4

Example 4A

Example 4B

Step 1: Preparation of 3-hydroxy-2,2-dimethylpropanimidamide hydrochloride

To a stirred mixture of $NH_4Cl$ (9.15g. 171.02 mmol, 5.00 equiv) in Toluene (40 mL) was added $AlMe_3$ (85.51 mL, 2 M in Toluene, 171.02 mmol, 5.00 equiv) dropwise at 0° C., under nitrogen atmosphere. The resulting mixture was stirred for 10 min at 0° C., under nitrogen atmosphere, and then was stirred at room temperature until no generation of gas. To the above mixture was added a solution of ethyl 3-hydroxy-2,2-dimethylpropanoate (5.00 g, 34.20 mmol, 1.00 equiv) in toluene dropwise at r.t. The resulting mixture was stirred for additional overnight at 80° C. The reaction was monitored by LCMS. The reaction was quenched by the addition of MeOH (30 mL) at 0° C. The resulting mixture was filtered, the filter cake was washed with MeOH (500 mL). The filtrate was concentrated under reduced pressure. The residue was dissolved in EtOH (30 mL). The resulting mixture was filtered, the filter cake was washed with EtOH (15 mL). The filtrate was concentrated under reduced pressure. This resulted in 3-hydroxy-2,2-dimethylpropanimidamide hydrochloride) (4 g, crude) as a white solid. $^1$H NMR (400 MHZ, DMSO-$d_6$) δ 9.04 (s, 2H), 8.62 (s, 2H), 5.43 (t, 1H), 3.48 (d, 2H), 1.18 (s, 6H).

Step 2: Preparation of 3-chloro-4-[(3,5-difluoropyridin-2-yl)methoxy]-2'-[2-(1-hydroxy-2-methylpropan-2-yl)pyrimidin-4-yl]-5',6-dimethyl-[1,4'-bipyridin]-2-one A solution of 2'-acetyl-3-chloro-4-[(3,5-difluoropyridin-2-yl)methoxy]-5',6-dimethyl-[1,4'-bipyridin]-2-one (450 mg, 0.95 mmol, 1.00 equiv) in DMF-DMA (6 mL) was stirred overnight at 100° C. under nitrogen atmosphere. The reaction was monitored by LCMS. The resulting mixture was allowed to r.t, and concentrated under reduced pressure. The crude product (550 mg) was used in the next step directly without further purification. To a solution of the above crude product in IPA (20 mL) was added 3-hydroxy-2,2-dimethylpropanimidamide, HCl salt (1.80 g crude 2, 11.58 mmol, 10.00 equiv) and $K_2CO_3$ (1.60 g, 11.58 mmol, 10.00 equiv), and then the mixture was stirred overnight at 80° C., under nitrogen atmosphere. The reaction was monitored by LCMS. The resulting mixture allowed to r.t, and diluted with EtOAc (100 mL). The combined organic layers were washed with brine (3×100 mL), dried over anhydrous $Na_2SO_4$. After filtration, the filtrate was concentrated under reduced pressure. The residue was purified by silica gel column chromatography to afford 3-chloro-4-[(3,5-difluoropyridin-2-yl)methoxy]-2'-[2-(1-hydroxy-2-methylpropan-2-yl)pyrimidin-4-yl]-5',6-dimethyl-[1,4'-bipyridin]-2-one (450 mg, 73.59%) as an off-white solid. LC-MS: (ES+H, m/z): $[M+H]^+$=528.25. $^1$H NMR (300 MHz, DMSO-$d_6$) δ 8.93 (d, 1H), 8.86 (s, 1H), 8.62 (d, 1H), 8.36 (s, 1H), 8.17 (d, 1H), 8.11 (ddd, 1H), 6.84 (s, 1H), 5.50 (d, 2H), 4.56 (t, 1H), 3.73 (d, 2H), 2.10 (s, 3H), 1.98 (s, 3H), 1.35 (s, 6H). $^{19}$F NMR (377 MHz, DMSO) δ-120.11,-120.14,-122.31,-122.336.

Step 3: Preparation of rel-3-chloro-4-[(3,5-difluoropyridin-2-yl)methoxy]-2'-[2-(1-hydroxy-2-methylpropan-2-yl)pyrimidin-4-yl]-5',6-dimethyl-[1,4'-bipyridin]-2-one and rel-3-chloro-4-[(3,5-difluoropyridin-2-yl)methoxy]-2'-[2-(1-hydroxy-2-methylpropan-2-yl)pyrimidin-4-yl]-5',6-dimethyl-[1,4'-bipyridin]-2-one The racemate 3-chloro-4-[(3,5-difluoropyridin-2-yl)methoxy]-2'-[2-(1-hydroxy-2-methylpropan-2-yl)pyrimidin-4-yl]-5',6-dimethyl-[1,4'-bipyridin]-2-one (65 mg) was separated by Prep-Chiral HPLC to afford rel-3-chloro-4-[(3,5-difluoropyridin-2-yl)methoxy]-2'-[2-(1-hydroxy-2-methylpropan-2-yl)pyrimidin-4-yl]-5',6-dimethyl-[1,4'-bipyridin]-2-one (Example 4A, 18 mg, ee %=99.5%) and rel-3-chloro-4-[(3,5-difluoropyridin-2-yl)methoxy]-2'-[2-(1-hydroxy-2-methylpropan-2-yl)pyrimidin-4-yl]-5',6-dimethyl-[1,4'-bipyridin]-2-one (Example 4B, 23 mg, ee %-99.4%) as a white solid.

EXAMPLE 4A

LC-MS: (ES+H, m/z): $[M+H]^+$=528.2. $^1$H NMR (400 MHZ, DMSO-$d_6$) δ 8.92 (d, 1H), 8.85 (s, 1H), 8.61 (d, 1H), 8.35 (s, 1H), 8.16 (d, 1H), 8.12-8.05 (m, 1H), 6.83 (s, 1H), 5.49 (d, 2H), 4.59 (t, 1H), 3.73 (d, 2H), 2.10 (s, 3H), 1.98 (s, 3H), 1.34 (s, 6H). $^{19}F$ NMR (377 MHz, DMSO) δ-120.06,-120.08,-122.20,-122.22.

EXAMPLE 4B

LC-MS: (ES+H, m/z): $[M+H]^+$=528.2. $^1H$ NMR (400 MHZ, DMSO-$d_6$) δ 8.92 (d, 1H), 8.85 (s, 1H), 8.60 (d, 1H), 8.34 (s, 1H), 8.16 (d, 1H), 8.10-8.03 (m, 1H), 6.82 (s, 1H), 5.48 (d, 2H), 4.62 (t, 1H), 3.72 (d, 2H), 2.09 (s, 3H), 1.97 (s, 3H), 1.33 (s, 6H). $^{19}F$ NMR (377 MHz, DMSO) δ-120.03,-120.05,-122.11,-122.13.

EXAMPLE 5, 5A, 5B

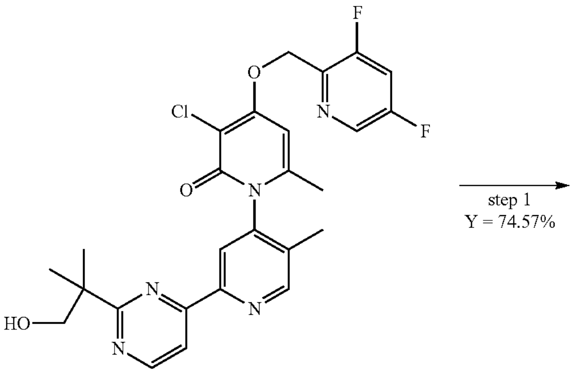

Example 4

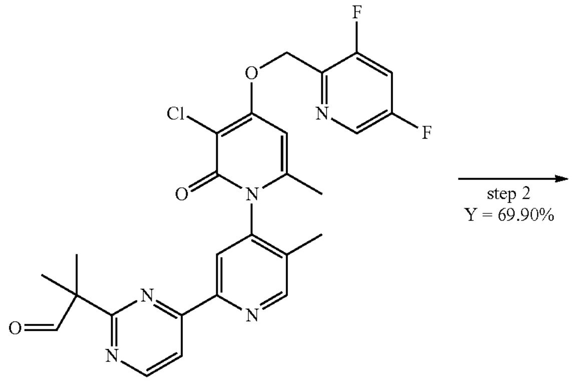

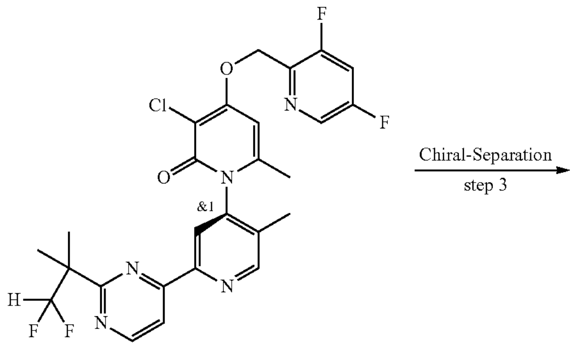

Example 5

-continued

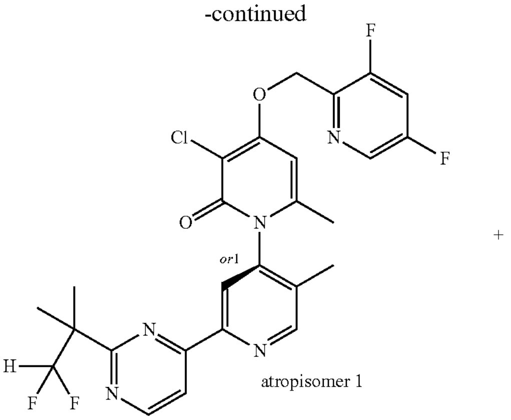

Example 5A

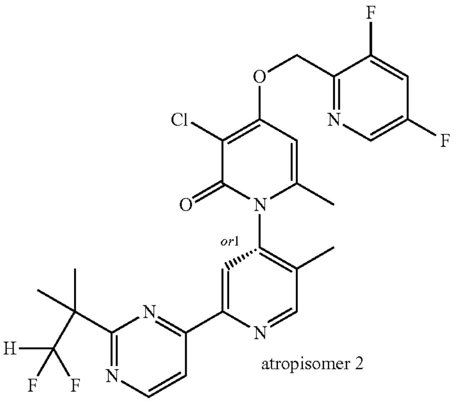

Example 5B

Step 1: Preparation of 2-(4-{3-chloro-4-[(3,5-difluoropyridin-2-yl)methoxy]-5',6-dimethyl-2-oxo-[1,4'-bipyridin]-2'-yl}pyrimidin-2-yl)-2-methylpropanal To a stirred mixture of Dess-Martin (422 mg, 1.00 mmol, 1.50 equiv) in DCM (10 mL) was added a solution of 3-chloro-4-[(3,5-difluoropyridin-2-yl)methoxy]-2'-[2-(1-hydroxy-2-methylpropan-2-yl)pyrimidin-4-yl]-5',6-dimethyl-[1,4'-bipyridin]-2-one (350 mg, 0.66 mmol, 1.00 equiv) in DCM (5 mL) dropwise at room temperature under nitrogen atmosphere. The resulting mixture was stirred for 3 h at room temperature under nitrogen atmosphere. The reaction was monitored by LCMS. The solvent was removed under reduce pressure. The resulting mixture was diluted with EtOAc (100 mL). The resulting mixture was washed with 3×100 mL of saturated solution of $NaHCO_3$. The combined organic layers were washed with brine (1×100 mL), dried over anhydrous $Na_2SO_4$. After filtration, the filtrate was concentrated under reduced pressure. The residue was purified by silica gel column chromatography to afford 2-(4-{3-chloro-4-[(3,5-difluoropyridin-2-yl)methoxy]-5',6-dimethyl-2-oxo-[1,4'-bipyridin]-2'-yl}pyrimidin-2-yl)-2-methylpropanal (260 mg, 74.57%) as a white solid. LC-MS: (ES+H, m/z): $[M+H]^+$=526.2.

Step 2: Preparation of 3-chloro-2'-[2-(1,1-difluoro-2-methylpropan-2-yl)pyrimidin-4-yl]-4-[(3,5-difluoropyridin-2-yl)methoxy]-5',6-dimethyl-[1,4'-bipyridin]-2-one To a solution of 2-(4-{3-chloro-4-[(3,5-difluoropyridin-2-yl)methoxy]-5',6-dimethyl-2-oxo-[1,4'-bipyridin]-2'- yl}pyrimidin-2-yl)-2-methylpropanal (260 mg, 0.49 mmol, 1.00 equiv) in DCE (10 mL) was added BAST (547 mg, 2.47 mmol, 5.00 equiv) dropwise at 0° C., under nitrogen atmosphere, the mixture was then stirred overnight at 80° C. The reaction was monitored by LCMS. The resulting mixture was allowed to r.t, and diluted with EtOAc (100 mL). The combined organic layers were washed with brine (3×100 mL), dried over anhydrous $Na_2SO_4$. After filtration, the filtrate was concentrated under reduced pressure. The residue was purified by silica gel column chromatography to afford 3-chloro-2'-[2-(1,1-difluoro-2-methylpropan-2-yl)pyrimidin-4-yl]-4-[(3,5-difluoropyridin-2-yl)methoxy]-5',6-dimethyl-[1,4'-bipyridin]-2-one (195 mg, 69.90%) as a white solid. LC-MS: (ES+H, m/z): $[M+H]^+$=548.2. $^1$H NMR (400 MHZ, DMSO-$d_6$) δ 9.00 (d, 1H), 8.87 (s, 1H), 8.62 (d, 1H), 8.51 (s, 1H), 8.27 (d, 1H), 8.11 (ddd, 1H), 6.85 (s, 1H), 6.75 (t, 1H), 5.50 (d, 2H), 2.10 (s, 3H), 1.98 (s, 3H), 1,45 (d, 6H). $^{19}$F NMR (377 MHz, DMSO) δ-120.11,-120.13,-122.29,-122.31,-128.77.

Step 3: Preparation of rel-3-chloro-2'-[2-(1,1-difluoro-2-methylpropan-2-yl)pyrimidin-4-yl]-4-[(3,5-difluoropyridin-2-yl)methoxy]-5',6-dimethyl-[1,4'-bipyridin]-2-one and rel-3-chloro-2'-[2-(1,1-difluoro-2-methylpropan-2-yl)pyrimidin-4-yl]-4-[(3,5-difluoropyridin-2-yl)methoxy]-5',6-dimethyl-[1,4'-bipyridin]-2-one The racemate 3-chloro-2'-[2-(1,1-difluoro-2-methylpropan-2-yl)pyrimidin-4-yl]-4-[(3,5-difluoropyridin-2-yl)methoxy]-5',6-dimethyl-[1,4'-bipyridin]-2-one (135 mg) was separated by Prep-Chiral HPLC to afford rel-3-chloro-2'-[2-(1,1-difluoro-2-methylpropan-2-yl)pyrimidin-4-yl]-4-[(3,5-difluoropyridin-2-yl)methoxy]-5',6-dimethyl-[1,4'-bipyridin]-2-one (Example 5A, 53 mg, ee %=100%) and rel-3-chloro-2'-[2-(1,1-difluoro-2-methylpropan-2-yl)pyrimidin-4-yl]-4-[(3,5-difluoropyridin-2-yl)methoxy]-5',6-dimethyl-[1,4'-bipyridin]-2-one (Example 5B, 50 mg, ee %=100%) as a white solid.

EXAMPLE 5A

LC-MS: (ES+H, m/z): $[M+H]^+$=548.2. $^1$H NMR (400 MHZ, DMSO-$d_6$) δ 9.00 (d, 1H), 8.88 (s, 1H), 8.62 (d, 1H), 8.51 (s, 1H), 8.28 (d, 1H), 8.18-8.05 (m, 1H), 6.98-6.54 (m, 2H), 5.50 (d, 2H), 2.11 (s, 3H), 1.98 (s, 3H), 1,45 (s, 6H). $^{19}$F NMR (377 MHz, DMSO) δ-120.12,-120.14,-122.29,-122.31,-128.77.

EXAMPLE 5B

LC-MS: (ES+H, m/z): $[M+H]^+$=548.2. $^1$H NMR (400 MHZ, DMSO-$d_6$) δ 9.00 (d, 1H), 8.88 (s, 1H), 8.62 (d, 1H), 8.51 (s, 1H), 8.28 (d, 1H), 8.16-8.07 (m, 1H), 6.95-6.55 (m, 2H), 5.50 (d, 2H), 2.11 (s, 3H), 1.98 (s, 3H), 1,45 (s, 6H). $^{19}$F NMR (377 MHz, DMSO) δ-120.11,-120.14,-122.28,-122.31,-128.77.

EXAMPLE 6, 6A, 6B, 6C, 6D

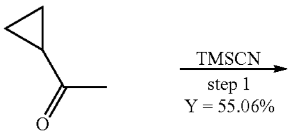

-continued

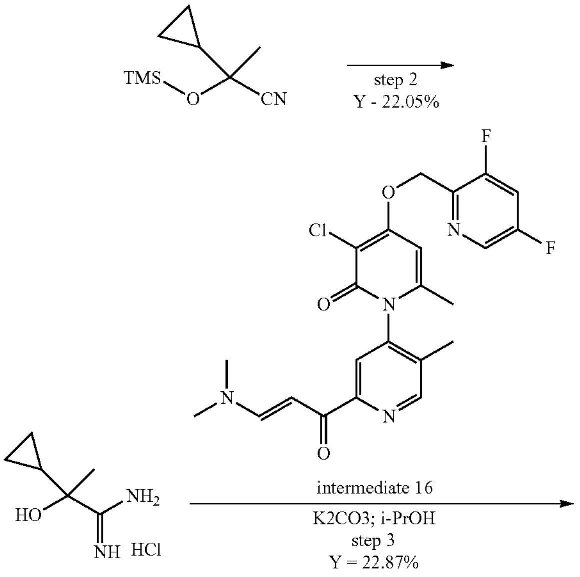

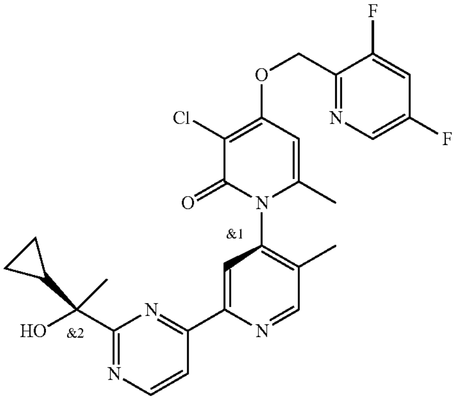

Example 6

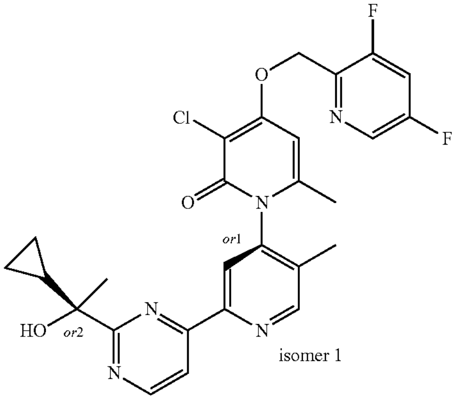

isomer 1

Example 6A

-continued

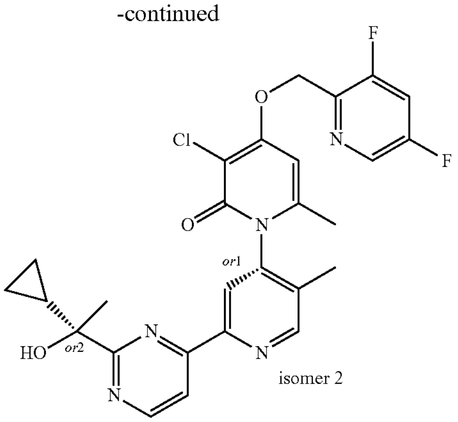

isomer 2

Example 6B

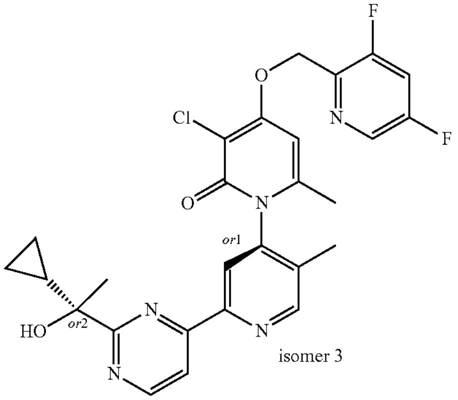

isomer 3

Example 6C

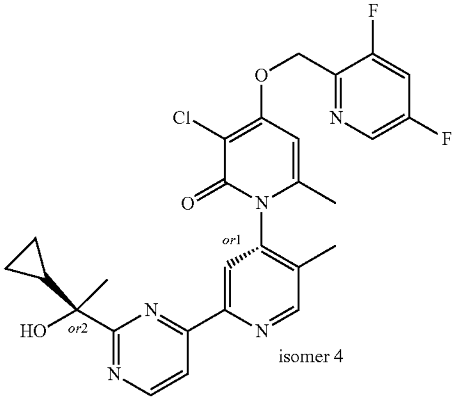

isomer 4

Example 6D

Step 1: Preparation of 2-cyclopropyl-2-[(trimethylsilyl)oxylpropanenitrile

To a stirred solution of cyclopropyl methyl ketone (10.00 g. 118.90 mmol. 1.00 equiv) and trimethylsilyl cyanide (14.15 g. 142.60 mmol. 1.20 equiv) in THF (150 mL) was added ZnI: (1.90 g. 5.90 mmol. 0.05 equiv) in portions at room temperature under nitrogen atmosphere. The mixture was stirred overnight at room temperature under nitrogen atmosphere. The reaction was monitored by TLC. The resulting mixture was concentrated under reduced pressure. The mixture was diluted with water (50 mL). The resulting mixture was extracted with $CH_2Cl_2$ (3×200 mL). The combined organic layers were washed with brine (2×50 mL), dried over anhydrous $Na_2SO_4$. After filtration, the filtrate was concentrated under reduced pressure. The residue was purified by silica gel column chromatography to afford 2-cyclopropyl-2-[(trimethylsilyl) oxy]propanenitrile (12.00 g. 55.06%) as a colorless oil. $^1$H NMR (300 MHz, Chloroform-d) § 1.65 (s, 3H), 1.25-1.11 (m, 1H), 0.70-0.49 (m, 4H), 0.24 (s, 9H).

Step 2: Preparation of methyl 2-carbamimidoyl-2,2-dimethylacetate HCl salt

To a stirred solution of methyl 2-cyano-2.2-dimethylacetate (12.00 g. 94.40 mmol. 1.00 equiv) in McOH (30 mL) was added HCl (236 mL. 944.0 mmol. 10.00 equiv. 4M in $CH_3OH$) dropwise at 0° C., under nitrogen atmosphere. The mixture was stirred for 7 h at room temperature under nitrogen atmosphere. The resulting mixture was concentrated under vacuum. To the above mixture in $CH_3OH$ (30.00 mL) added $NH_3$ solution (470 mL. 1.88 mol. 20.00 equiv. 4M in $CH_3OH$) dropwise over 20 min at 0° C. The resulting mixture was stirred for additional overnight at room temperature. The reaction was monitored by LCMS. The resulting mixture was concentrated under reduced pressure. The product was precipitated by the addition of EtOH (30 mL). The resulting mixture was filtered, the filter cake was washed with EtOH (2×30 mL). The filtrate was concentrated under reduced pressure. The residue was purified by trituration with Et-O (3×20 mL). This resulted in methyl 2-carbamimidoyl-2.2-dimethylacetate HCl salt (3 g. 22.05%) as a yellow semi-solid. LC-MS: (ES+H, m/z): $[M+H]^+$=129.3. $^1$H NMR (300 MHz. DMSO-$d_6$) δ 5.94 (s, 1H). 1.50 (s, 3H), 1,40-1.24 (m. 1H), 0.58-0.30 (m, 4H).

Step 3: Preparation of 3-chloro-2'-[2-(1-cyclopropyl-1-hydroxyethyl)pyrimidin-4-yl]-4-[(3,5-difluoropyridin-2-yl)methoxy]-5',6-dimethyl-[1,4'-bipyridin]-2-one To a stirred mixture of 3-chloro-4-[(3.5-difluoropyridin-2-yl)methoxy]-2'-[(2E)-3-(dimethylamino) prop-2-enoyl]-5'0.6-dimethyl-l1,4'-bipyridin]-2-one (50 mg, 0.10 mmol. 1.00 equiv) and 2-cyclopropyl-2-hydroxypropanimidamide. HCl salt (108 mg, 0.84 mmol. 8.00 equiv) in i-PrOH (1 mL) were added $K_2CO_3$ (291 mg. 2.10 mmol. 20.00 equiv) in portions at room temperature under nitrogen atmosphere. The resulting mixture was stirred overnight at 80° C., under nitrogen atmosphere. The reaction was monitored by LCMS. The mixture was allowed to cool down to room temperature. The resulting mixture was diluted with water (10 mL). The resulting mixture was extracted with EtOAc (3×30 mL). The combined organic layers were washed with brine (2×5 mL), dried over anhydrous $Na_2SO_4$. After filtration, the filtrate was concentrated under reduced pressure. The residue was purified by reversed combi-flash chromatography. The pure fraction was concentrated under vacuum to afford 3-chloro-2'-[2-(1-cyclopropyl-1-hydroxyethyl)pyrimidin-4-yl]-4-[(3.5-difluoropyridin-2-yl)methoxy]-5',6-dimethyl-[1,4'-bipyridin]-2-one (13.0 mg. 22.87%) as a white solid. LC-MS: (ES+H, m/z): $[M+H]^+$=539.90. $^1$H NMR (400 MHZ. DMSO-$d_6$) δ 9.00 (d, 1H), 8.86 (s.1H), 8.78 (d, 1H), 8.61 (d, 1H), 8.26 (d, 1H), 8.13-8.08 (m, 1H), 6.85 (s.1H). 5.50 (s, 2H), 4.92 (d, 1H), 2.11 (s, 3H), 1.98 (d, 3H), 1.56 (s, 3H), 1,43-1.36 (m, 1H), 0.48-0.37 (m. 1H), 0.41-0.29 (m, 2H), 0.17-0.11 (m, 1H). $^{19}$F NMR (377 MHz. DMSO) δ-120.13, -122.30.

Step 4: Preparation of rel-3-chloro-2'-[2-(1-cyclopropyl-1-hydroxyethyl)pyrimidin-4-yl]-4-[(3,5-difluoropyridin-2-yl)methoxy]-5',6-dimethyl-[1,4'-bipyridin]-2-one, rel-3-chloro-2'-[2-(1-cyclopropyl-1-hydroxyethyl)pyrimidin-4-yl]-4-[(3,5-difluoropyridin-2-yl)methoxy]-5',6-dimethyl-[1,4'-bipyridin]-2-one, rel-3-chloro-2'-[2-(1-cyclopropyl-1-hydroxyethyl)pyrimidin-4-yl]-4-[(3,5-difluoropyridin-2-yl)methoxy]-5',6-dimethyl-[1,4'-bipyridin]-2-one, rel-3-chloro-2'-[2-(1-cyclopropyl-1-hydroxyethyl)pyrimidin-4-yl]-4-[(3,5-difluoropyridin-2-yl)methoxy]-5',6-dimethyl-[1,4'-bipyridin]-2-one The racemate 3-chloro-2'-[2-(1-cyclopropyl-1-hydroxyethyl)pyrimidin-4-yl]-4-[(3.5-difluoropyridin-2-yl)methoxy]-5'0.6-dimethyl-[1,4'-bipyridin]-2-one (200 mg) was separated by Prep-Chiral-HPLC to afford the first cluted peak (80 mg. Example 6A&B) and second eluted peak (80 mg. Example 6C&D).

The first eluted peak was further separated by Prep-Chiral-HPLC to afford rel-3-chloro-2'-[2-(1-cyclopropyl-1-hydroxyethyl)pyrimidin-4-yl]-4-[(3.5-difluoropyridin-2-yl)methoxy]-5'0.6-dimethyl-[1,4'-bipyridinl-2-one (Example 6A. 29.3 mg, ce=95.3%) and rel-3-chloro-2'-[2-(1-cyclopropyl-1-hydroxyethyl)pyrimidin-4-yl]-4-[(3.5-difluoropyridin-2-yl)methoxy]-5'0.6-dimethyl-[1,4'-bipyridin]-2-one (Example 6B. 32.3 mg, ee=98.7%) as white solid.

EXAMPLE 6A

LC-MS: (ES+H, m/z): [M+H]+=539.90. $^{1}$H NMR (300 MHz. DMSO-$d_6$) δ 9.01 (d, 1H), 8.86 (s. 1H), 8.80 (s.1H), 8.62 (d, 1H), 8.27 (d. 1H), 8.11 (td. 1H), 6.85 (s.1H), 5.50 (s, 2H), 4.93 (s, 1H), 2.11 (s. 3H), 1.99 (s, 3H), 1.57 (s, 3H), 1,42-1.36 (m, 1H), 0.49-0.46 (m. 1H), 0.41-0.37 (m, 2H), 0.13-0.12 (m. 1H). $^{19}$F NMR (282 MHz, DMSO) δ-120.13, —120.15, —122.30,-122.33.

EXAMPLE 6B

LC-MS: (ES+H, m/z): $[M+H]^+$=540.10. $^{1}$H NMR (300 MHz. DMSO-$d_6$) δ 9.00 (d, 1H), 8.86 (s. 1H), 8.78 (s.1H), 8.61 (d, 1H), 8.26 (d, 1H), 8.10 (td. 1H), 6.85 (s.1H), 5.50 (s, 2H), 4.91 (s, 1H), 2.11 (s. 3H), 1.98 (s, 3H), 1.56 (s, 3H), 1,44-1.38 (m. 1H), 0.49-0.46 (m. 1H), 0.41-0.37 (m, 2H), 0.13-0.12 (m. 1H). $^{19}$F NMR (282 MHz. DMSO) δ-120.14, —120.16, —122.31, —122.33.

The second eluted peak above was further separated by Prep-Chiral-HPLC to afford rel-3-chloro-2'-[2-(1-cyclopropyl-1-hydroxyethyl)pyrimidin-4-yl]-4-[(3.5-difluoropyridin-2-yl)methoxy]-5'0.6-dimethyl-[1,4'-bipyridin]-2-one (Example 6C. 28.0 mg, ee=99.5%) and rel-3-chloro-2'-[2-(1-cyclopropyl-1-hydroxyethyl)pyrimidin-4-yl]-4-[(3.5-difluoropyridin-2-yl)methoxy]-5'0.6-dimethyl-[1,4'-bipyridin]-2-one (Example 6D. 28.8 mg, ee=95.1%) as white solid.

EXAMPLE 6C

LC-MS: (ES+H, m/z): $[M+H]^+$=540.2. $^{1}$H NMR (300 MHz, DMSO-$d_6$) δ 9.00 (d, 1H), 8.86 (s, 1H), 8.79 (s, 1H), 8.61 (d, 1H), 8.26 (d, 1H), 8.10 (td, 1H), 6.84 (s, 1H), 5.50 (s, 2H), 4.94 (s, 1H), 2.11 (s, 3H), 1.98 (s, 3H), 1.56 (s, 3H), 1,42-1.35 (m, 1H), 0.48-0.44 (m, 1H), 0.40-0.38 (m, 2H), 0.13-0.12 (m, 1H). $^{19}$F NMR (282 MHz, DMSO) δ-120.14,-120.16,-122.32,-122.34.

EXAMPLE 6D

LC-MS: (ES+H, m/z): $[M+H]^+$=540.2. $^{1}$H NMR (300 MHz, DMSO-$d_6$) δ 9.00 (d, 1H), 8.86 (s, 1H), 8.78 (s, 1H), 8.61 (d, 1H), 8.26 (d, 1H), 8.10 (td, 1H), 6.85 (s, 1H), 5.50 (s, 2H), 4.94 (s, 1H), 2.11 (s, 3H), 1.98 (s, 3H), 1.56 (s, 3H), 1,44-1.38 (m, 1H), 0.50-0.48 (m, 1H), 0.39-0.34 (m, 2H), 0.13-0.12 (m, 1H). $^{19}$F NMR (282 MHz, DMSO) δ-120.14,-120.16,-122.31,-122.33.

EXAMPLE 7

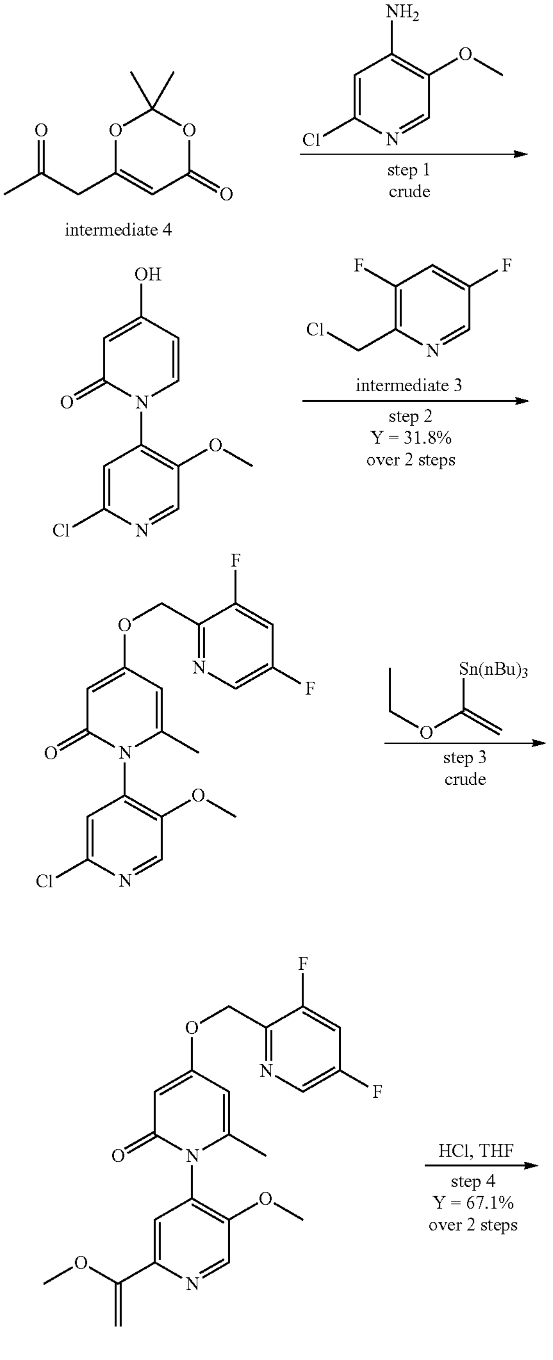

-continued

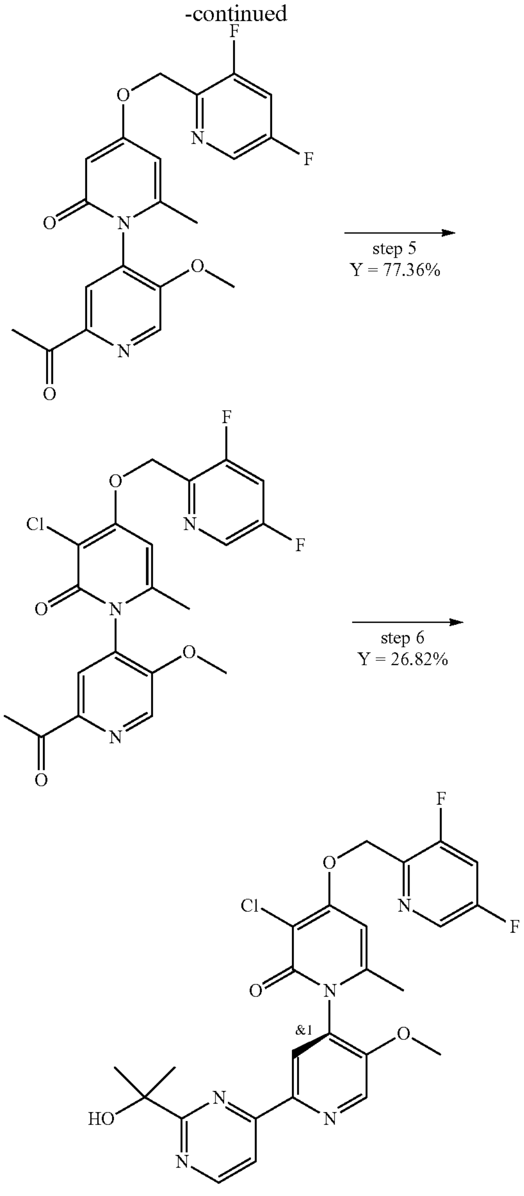

Example 7

Step 1: Preparation of 2'-chloro-4-hydroxy-5'-methoxy-6-methyl-[1,4'-bipyridin]-2-one To a stirred solution of 2,2-dimethyl-6-(2-oxopropyl)-1,3-dioxin-4-one (1.16 g, 6.31 mmol, 1.00 equiv) in 1,4-dioxane (17 mL) was added 2-chloro-5-methoxypyridin-4-amine (1.00 g, 6.31 mmol, 1.00 equiv) at rt. The resulting mixture was stirred for 3 h at 90° C., under nitrogen atmosphere. The reaction was monitored by LCMS. The mixture was allowed to cool down to RT. To the above mixture was added $H_2SO_4$ (0.5 mL) at RT. The resulting mixture was stirred for 1 h at 90° C., under nitrogen atmosphere. The reaction was monitored by LCMS. The mixture was allowed to cool down to RT. To the above mixture was added $H_2O$ (10 mL) at RT. The resulting mixture was filtered, and the filter cake was washed with diethyl ether (2×10 mL). The filter cake was concentrated under reduced pressure to afford 2'-chloro-4-hydroxy-5'-methoxy-6-methyl-[1,4'-bipyridin]-2-one (990 mg, crude) as a Brown yellow solid. LC-MS: (ES+H, m/z): $[M+H]^+$=267.1.

Step 2: Preparation of 2'-chloro-4-[(3,5-difluoro-pyridin-2-yl)methoxy]-5'-methoxy-6-methyl-[1,4'-bipyridin]-2-one To a stirred solution of 2'-chloro-4-hydroxy-5'-methoxy-6-methyl-[1,4'-bipyridin]-2-one (990 mg, crude) and 2-(chloromethyl)-3,5-difluoropyridine (911 mg, 5.57 mmol, 1.50 equiv) in DMF (20 mL) were added 18-Crown-6 (10 mg, 0.04 mmol, 0.01 equiv) and $K_2CO_3$ (1.54 g, 11.14 mmol, 3.00 equiv) at RT. The resulting mixture was stirred for 4 h at 60° C., under nitrogen atmosphere. The reaction was monitored by LCMS. The mixture was allowed to cool down to RT. The resulting mixture was concentrated under reduced pressure. The residue was purified by flash chromatography to afford 2'-chloro-4-[(3.5-difluoropyridin-2-yl)methoxy]-5'-methoxy-6-methyl-[1,4'-bipyridin]-2-one (790 mg. 31.8% over 2steps) as a light yellow solid. LC-MS: (ES+H, m/z): $[M+H]^+$=394.0.

Step 3: Preparation of 4-[(3,5-difluoropyridin-2-yl)methoxy]-2'-(1-ethoxyethenyl)-5'-methoxy-6-methyl-[1,4'-bipyridin]-2-one To a stirred solution of 2'-chloro-4-[(3.5-difluoropyridin-2-yl)methoxy]-5'-methoxy-6-methyl-[1,4'-bipyridin]-2-one (790 mg. 2.01 mmol. 1.00 equiv) and tributyl (1-ethoxyethenyl) stannanc (1,45 g. 4.01 mmol. 2.00 equiv) in 1,4-dioxane (20 mL) were added Pd(PPh;): $C_1$, (141 mg, 0.20 mmol. 0.10 equiv) at rt. The resulting mixture was stirred for 2 h at 100° C., under nitrogen atmosphere. The reaction was monitored by LCMS. The mixture was allowed to cool down to RT. The resulting mixture was filtered, and the filter cake was washed with EA (2×20 mL). The filtrate was concentrated under reduced pressure to afford 4-[(3.5-difluoropyridin-2-yl)methoxy]-2'-(1-ethoxyethenyl)-5'-methoxy-6-methyl-[1,4'-bipyridin]-2-one (860 mg, crude) as a yellow oil. LC-MS: (ES+H, m/z): $[M+H]^+$=430.0.

Step 4: Preparation of 2'-acetyl-4-[(3,5-difluoropyridin-2-yl)methoxy]-5'-methoxy-6-methyl-[1,4'-bipyridin]-2-one To a stirred solution of 4-[(3.5-difluoropyridin-2-yl)methoxy]-2'-(1-ethoxyethenyl)-5'-methoxy-6-methyl-[1,4'-bipyridin]-2-one (860 mg, crude) in THF (10 mL) were added HCl (0.20 mL. 6.59 mmol, 28.27 equiv) dropwise at 0° C. . . . The resulting mixture was stirred for Ih at rt under nitrogen atmosphere. The reaction was monitored by LCMS. The mixture was basified with saturated sodium carbonate solution. The resulting mixture was extracted with EA (3×50 mL). The combined organic layers were washed with brine (50 mL), and the combined organic layers were concentrated under reduced pressure. The residue was purified by flash chromatography to afford 2'-acetyl-4-[(3.5-difluoropyridin-2-yl)methoxy]-5'-methoxy-6-methyl-[1,4'-bipyridin]-2-one (540 mg. 67.1% over 2steps) as white solid. LC-MS: (ES+H, m z): $[M+H]^+$=402.0.

Step 5: Preparation of 2'-acetyl-3-chloro-4-[(3,5-difluoropyridin-2-yl)methoxy]-5'-methoxy-6-methyl-[1,4'-bipyridin]-2-one To a stirred solution of 2'-acetyl-4-[(3.5-difluoropyridin-2-yl)methoxy]-5'-methoxy-6-methyl-[1,4'-bipyridin]-2-one (500 mg, 1.25 mmol. 1.00 equiv) and NCS (175 mg, 1.31 mmol. 1.05 equiv) in MeCN (10 mL) were added 2.2-dichloroacetic acid (16 mg, 0.12 mmol. 0.10 equiv) at RT. The resulting mixture was stirred for 1 h at 60° C., under nitrogen atmosphere. The reaction was monitored by LCMS. The mixture was allowed to cool down to RT. The resulting mixture was concentrated under reduced pressure. The residue was purified by flash chromatography to afford 2'-acetyl-3-chloro-4-[(3.5-difluoropyridin-2-yl)methoxy]-5'-methoxy-6-methyl-[1,4'-bipyridin]-2-one (420 mg. 77.36%). LC-MS: (ES+H, m z): $[M+H]^+$=436.1. $^1H$ NMR (300 MHz. DMSO-$d_6$) δ 8.76 (s, 1H), 8.60 (d, 1H), 8.16-8.03 (m, 1H), 7.96 (s, 1H), 6.73 (s.1H), 5.48 (d, 2H), 4.02 (s, 3H), 2.65 (s, 3H), 1.94 (s, 3H).

Step 6: Preparation of 3-chloro-4-[(3,5-difluoropyridin-2-yl)methoxy]-2'-[2-(2-hydroxypropan-2-yl) pyrimidin-4-yl]-5'-methoxy-6-methyl-[1,4'-bipyridin]-2-one A solution of 2'-acetyl-3-chloro-4-[(3,5-difluoropyridin-2-yl)methoxy]-5'-methoxy-6-methyl-[1,4'-bipyridin]-2-one (370 mg, 0.85 mmol, 1.00 equiv) in DMF-DMA (3 mL) was stirred for 12 h at 100° C., under nitrogen atmosphere. The reaction was monitored by LCMS. The mixture was allowed to cool down to RT. The resulting mixture was concentrated under reduced pressure. To the above mixture in DMF (5 mL) was added 2-hydroxy-2-methylpropanimidamide hydrochloride (353 mg, 2.55 mmol, 3.00 equiv) and $K_2CO_3$ (587 mg. 4.25 mmol, 5.00 equiv) at rt. The resulting mixture was stirred for additional 4 h at 80° C., under nitrogen atmosphere. The reaction was monitored by LCMS. The mixture was allowed to cool down to RT. The resulting mixture was concentrated under reduced pressure. The residue was purified by flash chromatography to afford crude product. The crude product was further purified by Prep-HPLC to afford pure fractions. The pure fractions were concentrated under vacuum and then lyophilized to afford 3-chloro-4-[(3,5-difluoropyridin-2-yl)methoxy]-2'-[2-(2-hydroxypropan-2-yl)pyrimidin-4-yl]-5'-methoxy-6-methyl-[1,4'-bipyridin]-2-one (120.9 mg, 26.82%) as a white solid. LC-MS: (ES+H, m z): $[M+H]^+$=529.90. 1H NMR (400 MHZ, DMSO-$d_6$) δ 8.93 (d, 1H), 8.80 (s, 1H), 8.73 (s, 1H), 8.61 (d, 1H), 8.18 (d, 1H), 8.10 (ddd, 1H), 6.77 (s, 1H), 5.50 (s, 2H), 5.23 (s, 1H), 4.01 (s, 3H), 2.00 (s, 3H), 1.53 (d, 6H). $^{19}F$ NMR (377 MHz, DMSO) δ-120.16,-122.38.

EXAMPLE 8

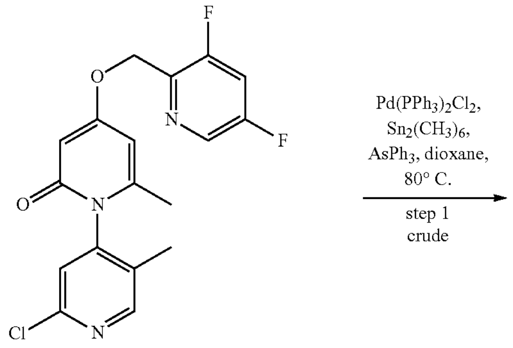

intermediate 6

-continued

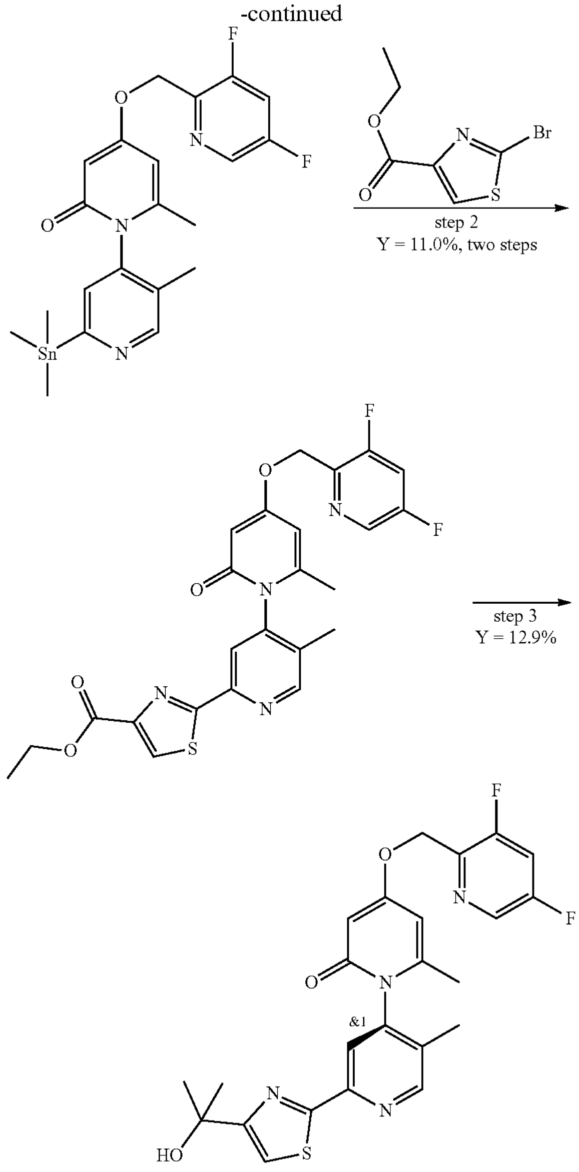

Example 8

Step 1: Preparation of 4-((3,5-difluoropyridin-2-yl) methoxy)-5',6-dimethyl-2'-(trimethylstannyl)-2H-[1,4'-bipyridin]-2-one To a mixture of 2'-chloro-4-[(3,5-difluoropyridin-2-yl) methoxy]-5',6-dimethyl-[1,4'-bipyridin]-2-one (1.10 g. 2.91 mmol, 1.00 equiv) and hexamethyldistannane (1.14 g, 3.48 mmol, 1.20 equiv) in dioxane (20 mL) was added $Pd(PPh_3)_2Cl_2$ (0.41 g, 0.58 mmol, 0.20 equiv) and $AsPh_3$ (0.18 g, 0.58 mmol, 0.20 equiv) at room temperature under nitrogen. The mixture was stirred overnight at 80° C., under nitrogen atmosphere. The reaction was monitored by LCMS. Desired product could be detected by LCMS. The mixture was used directly on the next step. LC-MS: (ES+H, m z): $[M+H]^+$=508.1.

Step 2: Preparation of 2-(4-bromo-2-chloro-3-fluoro-5-methylphenoxymethyl)-3,5-difluoropyridine To the last step of reaction mixture was added ethyl 2-bromothiazole-4-carboxylate (680 mg, 2.91 mmol, 1.00 equiv)), $Pd(PPh_3)$: $Cl_2$ (0.41 g, 0.58 mmol, 0.20 equiv) at room temperature under nitrogen. The mixture was stirred overnight at 80° C., under nitrogen atmosphere. The reaction was monitored by LCMS. The mixture was allowed to cool down to room temperature. The resulting mixture was firstly purified by silica gel column chromatography to afford a crude product (300 mg). The crude product (300 mg) was further purified by Prep-HPLC and the pure fractions were concentrated to afford ethyl 2-{4-[(3,5-difluoropyridin-2-yl) methoxy]-2,5'-dimethyl-6-oxo-[1,4'-bipyridin]-2'-yl}-1,3-thiazole-4-carboxylate (160 mg, 11.0%, two steps) as a white solid. LC-MS: (ES+H, m z): $[M+H]^+$=499.0.

Step 3: Preparation of 4-[(3,5-difluoropyridin-2-yl) methoxy]-2'-[4-(2-hydroxypropan-2-yl)-1,3-thiazol-2-yl]-5',6-dimethyl-[1,4'-bipyridin]-2-one To a mixture of ethyl 2-{4-[(3,5-difluoropyridin-2-yl) methoxy]-2,5'-dimethyl-6-oxo-[1,4'-bipyridin]-2'-yl}-1,3-thiazole-4-carboxylate (160 mg, 0.32 mmol, 1.00 equiv) in THF (5 mL) was added $CH_3MgBr$ in THF (1.0 mL, 0.96 mmol, 3.00 equiv, 1M) dropwise at 0° C., under nitrogen. The mixture was stirred for 3 h at room temperature under nitrogen atmosphere. The reaction was monitored by LCMS. The reaction was quenched by MeOH (1 mL). The resulting mixture was concentrated under reduced pressure. The residue was directly purified by Prep-HPLC, and the pure fractions were concentrated and lyophilized to afford 4-[(3,5-difluoropyridin-2-yl)methoxy]-2'-[4-(2-hydroxypropan-2-yl)-1,3-thiazol-2-yl]-5',6-dimethyl-[1,4'-bipyridin]-2-one (20 mg, 12.9%) as a white solid. LC-MS: (ES+H, m z): $[M+H]^+$=485.0. 1H NMR (400 MHZ, DMSO-$d_6$) δ 8.68 (s, 1H), 8.60 (d, 1H), 8.11-8.06 (m, 1H), 7.91 (s, 1H), 7.53 (s, 1H), 6.16 (d, 1H), 6.05 (d, 1H), 5.26 (s, 2H), 5.22 (s, 1H), 2.06 (s, 3H), 1.88 (s, 3H), 1.50 (s, 6H). $^{19}$F NMR (377 MHz, DMSO) δ-120.29,-122.43.

EXAMPLE 9, 9A, 9B

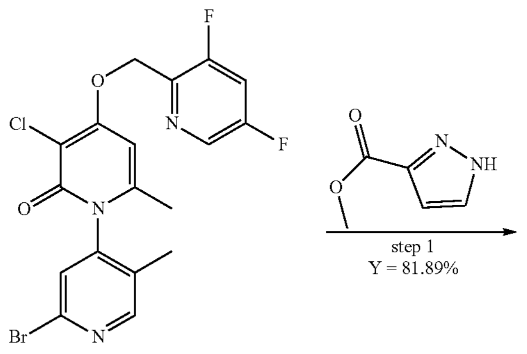

intermediate 10

-continued

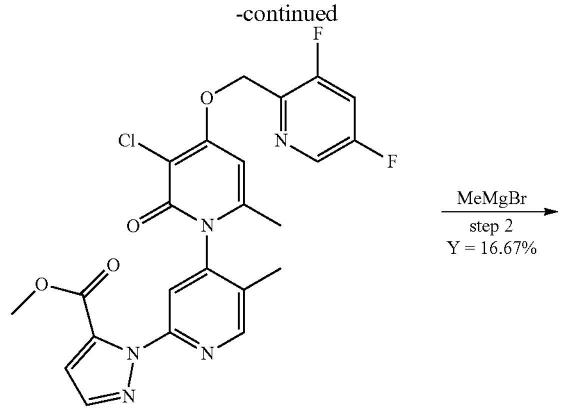

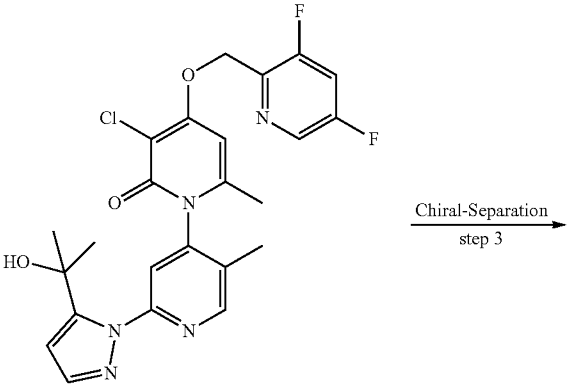

Example 9

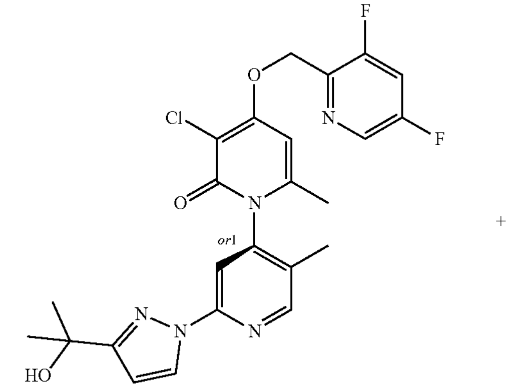

atropisomer 1
Example 9A

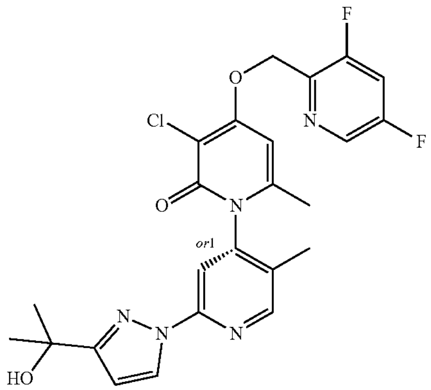

atropisomer 2
Example 9B

Step 1: Preparation of methyl 1-(3-chloro-4-((3,5-difluoropyridin-2-yl)methoxy)-5',6-dimethyl-2-oxo-2H-[1,4'-bipyridin]-2'-yl)-1H-pyrazole-5-carboxylate To a stirred solution of 2'-bromo-3-chloro-4-[(3.5-difluoropyridin-2-yl)methoxy]-5'0.6-dimethyl-[1,4'-bipyridin]-2-one (200 mg, 0.44 mmol. 1.00 equiv) and methyl 1H-pyrazole-3-carboxylate (110 mg. 0.88 mmol. 2.00 equiv) in 1,4-dioxane (5 mL) were added $K_2CO_3$ (121 mg, 0.88 mmol. 2.00 equiv). CuI (17 mg. 0.09 mmol. 0.20 equiv) and N1.N2-dimethylcyclohexane-1.2-diamine (25 mg, 0.18 mmol. 0.40 equiv) at rt. The resulting mixture was stirred overnight at 90° C., under nitrogen atmosphere. The reaction was monitored by LCMS. The mixture was directly purified by reversed combi-flash chromatography. The pure fractions were concentrated under vacuum to afford methyl 1-(3-chloro-4-((3.5-difluoropyridin-2-yl)methoxy)-5'0.6-dimethyl-2-oxo-2H-[1,4'-bipyridin]-2'-yl)-1H-pyrazole-5-carboxylate (180 mg. 81.89%) as a light yellow solid. LC-MS: (ES+H, m/z): $[M+H]^+$=502.10. $^1$H NMR (400 MHZ. DMSO-$d_6$) δ 8.76 (d, 1H). 8.67-8.58 (m, 2H), 8.14-8.05 (m, 1H), 8.01 (s.1H), 7.05 (d, 1H), 6.80 (s, 1H), 5.49 (s, 2H), 3.86 (s, 3H). 2.06 (s, 3H), 2.00 (s, 3H).

Step 2: Preparation of 3-chloro-4-((3,5-difluoropyridin-2-yl)methoxy)-2'-(5-(2-hydroxypropan-2-yl)-1H-pyrazol-1-yl)-5',6-dimethyl-2H-[1,4'-bipyridin]-2-one To a stirred solution of methyl 1-{3-chloro-4-[(3.5-difluoropyridin-2-yl)methoxy]-5'0.6-dimethyl-2-oxo-[1,4'-bipyridin]-2'-yl}pyrazole-3-carboxylate (150 mg, 0.30 mmol. 1.00 equiv) in THF (8 mL) were added MeMgBr (3 mL. 2.99 mmol. 10.00 equiv. IM in THF) dropwise at −30° C., under nitrogen atmosphere. The resulting mixture was warmed to rt and stirred for 30 min under nitrogen atmosphere. The reaction was monitored by LCMS. The reaction was quenched with sat. $NH_4Cl$ (aq.) at room temperature. The residue was purified by reversed flash chromatography to afford a crude product. The crude product was further purified by Prep-HPLC. The pure fractions were concentrated under vacuum and then lyophilized to afford 3-chloro-4-((3.5-difluoropyridin-2-yl)methoxy)-2'-(5-(2-hydroxypropan-2-yl)-1H-pyrazol-1-yl)-5'0.6-dimethyl-2H-[1,4'-bipyridin]-2-one (25 mg, 16.67%) as a white solid. LC-MS: (ES+H, m/z): $[M+H]^+$=502.14 1H NMR (400 MHz. DMSO-$d_6$) δ 8.61 (d, 1H), 8.57-8.49 (m, 2H), 8.14-8.05 (m, 1H), 7.79 (s. 1H), 6.81 (s.1H), 6.57 (d, 1H), 5.49 (s, 2H), 5.11 (s, 1H), 2.01 (d, 6H), 1,48 (s. 6H), $^{19}$F NMR (377 MHz. DMSO) δ-120.15, —122.32.

Step 3: Preparation of rel-3-chloro-4-((3,5-difluoropyridin-2-yl)methoxy)-2'-(3-(2-hydroxypropan-2-yl)-1H-pyrazol-1-yl)-5',6-dimethyl-2H-[1,4'-bipyridin]-2-one and rel-3-chloro-4-((3,5-difluoropyridin-2-yl)methoxy)-2'-(3-(2-hydroxypropan-2-yl)-1H-pyrazol-1-yl)-5',6-dimethyl-2H-[1,4'-bipyridin]-2-one The racemate 3-chloro-4-((3.5-difluoropyridin-2-yl) methoxy)-2'-(3-(2-hydroxypropan-2-yl)-1H-pyrazol-1-yl)-5'0.6-dimethyl-2H-[1,4'-bipyridin]-2-one (80 mg) was separated by Chiral Prep-HPLC. The pure fraction was concentrated under reduced pressure to afford rel-3-chloro-4-((3.5-difluoropyridin-2-yl)methoxy)-2'-(3-(2-hydroxypropan-2-yl)-1H-pyrazol-1-yl)-5'0.6-dimethyl-2H-[1,4'-bipyridin]-2-one (Example 9A. 34 mg, ee=100%) and rel-3-chloro-4-((3.5-difluoropyridin-2-yl)methoxy)-2'-(3-(2-hydroxypropan-2-yl)-1H-pyrazol-1-yl)-5', 6-dimethyl-2H-[1,4'-bipyridin]-2-one (Example 9B, 32.9 mg, ee=100%) as a white solid.

EXAMPLE 9A

LC-MS: (ES+H, m/z): $[M+H]^+$=502.2. $^1$H NMR (300 MHz, DMSO-$d_6$) δ 8.60 (d, 1H), 8.54 (s, 1H), 8.51 (d, 1H), 8.14-8.08 (m, 1H), 7.78 (s, 1H), 6.80 (d, 1H), 6.56 (d, 1H), 5.48 (d, 2H), 5.09 (s, 1H), 2.01 (s, 3H), 2.00 (s, 3H), 1,48 (s, 6H). $^{19}$F NMR (282 MHz, DMSO) δ-120.15,-120.17,-120.34,-122.37.

EXAMPLE 9B

LC-MS: (ES+H, m/z): $[M+H]^+$=502.2. $^1$H NMR (300 MHz, DMSO-$d_6$) δ 8.60 (d, 1H), 8.54 (s, 1H), 8.51 (d, 1H), 8.14-8.08 (m, 1H), 7.78 (s, 1H), 6.80 (d, 1H), 6.56 (d, 1H), 5.48 (d, 2H), 5.09 (s, 1H), 2.01 (s, 3H), 2.00 (s, 3H), 1,48 (s, 6H). $^{19}$F NMR (282 MHz, DMSO) δ-120.15,-120.17,-120.34,-122.37.

EXAMPLE 10

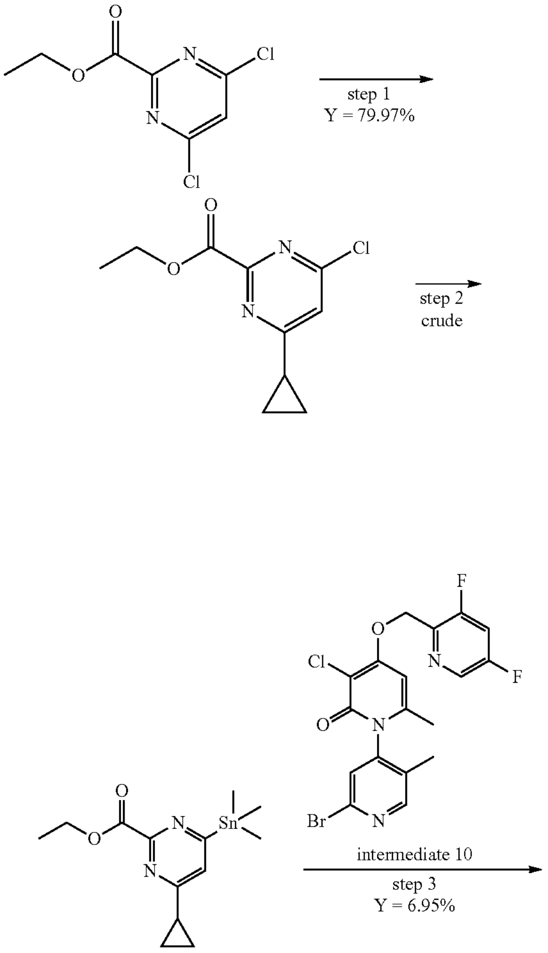

-continued

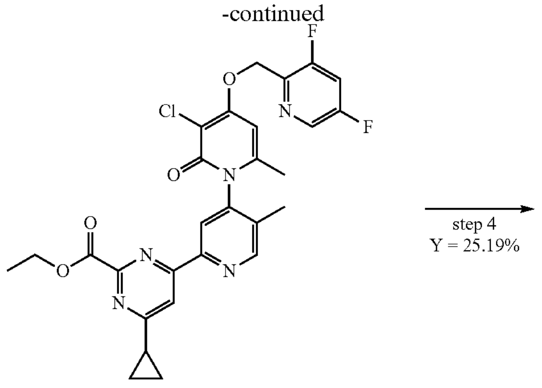

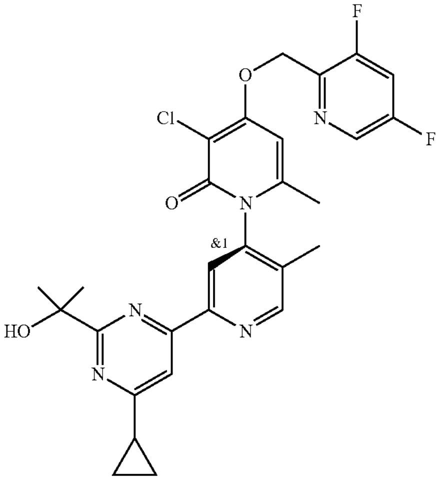

Example 10

Step 1: Preparation of ethyl 4-chloro-6-cyclopropylpyrimidine-2-carboxylate

To a stirred solution of ethyl 4,6-dichloropyrimidine-2-carboxylate (500 mg, 2.262 mmol, 1.00 equiv) and cyclopropylboronic acid (194.30 mg, 2.262 mmol, 1 equiv) in in Toluene (5 mL) and $H_2O$ (0.5 mL) was added Pd(dppf) $Cl_2$ (37.48 mg, 0.068 mmol, 0.03 equiv) and $Cs_2CO_3$ (1474.03 mg, 4.524 mmol, 2 equiv) at room temperature under nitrogen atmosphere. The resulting mixture was stirred for 1 h at 100° C. under nitrogen atmosphere. The reaction was monitored by LCMS. The resulting mixture was diluted with water (2 mL). The aqueous layer was extracted with EtOAc (3×5 mL). The residue was purified by silica gel column chromatography to afford ethyl 4-chloro-6-cyclopropylpyrimidine-2-carboxylate (410 mg, 79.97%) as a yellow oil. MS: (ES+H, m/z): $[M+H]^+$=227.0

Step 2: Preparation of ethyl 4-cyclopropyl-6-(trimethylstannyl)pyrimidine-2-carboxylate To a stirred solution of ethyl 4-chloro-6-cyclopropylpyrimidine-2-carboxylate (400 mg, 1.765 mmol, 1.00 equiv) and Sn2Me6 (636.01 mg, 1.942 mmol, 1.10 equiv) in 1,4-dioxane (2 ml) was added $Pd(PPh_3)$: $Cl_2$ (247.74 mg, 0.353 mmol, 0.2 equiv) and $AsPh_3$ (162.13 mg, 0.529 mmol, 0.3 equiv) at room temperature under nitrogen atmosphere. The resulting mixture was stirred for overnight at 80° C., under nitrogen atmosphere. The reaction was monitored by LCMS. The resulting mixture was used in the next step directly without further purification. MS: (ES+H, m/z): $[M+H]^+$=357.0

Step 3: Preparation of ethyl 4-{3-chloro-4-[(3,5-difluoropyridin-2-yl)methoxy]-5',6-dimethyl-2-oxo-[1,4'-bipyridin]-2'-yl}-6-cyclopropylpyrimidine-2-carboxylate To a stirred solution of ethyl 4-cyclopropyl-6-(trimethylstannyl)pyrimidine-2-carboxylate (630 mg. 1.775 mmol. 1.00 equiv) in 1,4-dioxane (5 ml) was added 2'-bromo-3-chloro-4-[(3,5-difluoropyridin-2-yl)methoxy]-5',6-dimethyl-[1,4'-bipyridin]-2-one (405.19 mg, 0.887 mmol, 0.50 equiv) and $AsPh_3$ (108.68 mg. 0.355 mmol. 0.2 equiv), $Pd(PPh_3)$: $Cl_2$ (373.66 mg, 0.532 mmol. 0.3 equiv) at room temperature under nitrogen atmosphere. The resulting mixture was stirred for 2 days at 80° C., under nitrogen atmosphere. The reaction was monitored by LCMS. The resulting mixture was diluted with water (5 mL). The aqueous layer was extracted with EtOAc (3×10 mL). The resulting mixture was concentrated under reduced pressure. The residue was purified by Prep-TLC (PE/EA 1:1) to afford ethyl 4-{3-chloro-4-[(3,5-difluoropyridin-2-yl)methoxy]-5',6-dimethyl-2-oxo-[1,4'-bipyridin]-2'-yl}-6-cyclopropylpyrimidine-2-carboxylate (70 mg, 6.95%) as a yellow solid. MS: (ES+H, m/z): $[M+H]^+$=568.3

Step 4: Preparation of 3-chloro-2'-[6-cyclopropyl-2-(2-hydroxypropan-2-yl)pyrimidin-4-yl]-4-[(3,5-difluoropyridin-2-yl)methoxy]-5',6-dimethyl-[1,4'-bipyridin]-2-one To a stirred solution of ethyl 4-{3-chloro-4-[(3,5-difluoropyridin-2-yl)methoxy]-5',6-dimethyl-2-oxo-[1,4'-bipyridin]-2'-yl}-6-cyclopropylpyrimidine-2-carboxylate (70 mg, 0.123 mmol, 1.00 equiv) in THF (1 ml) was added MeMgBr (44.09 mg, 0.369 mmol, 3 equiv) at 0° C., under nitrogen atmosphere. The resulting mixture was stirred for 1 h at 0° C., under nitrogen atmosphere. The reaction was monitored by LCMS. The reaction was quenched with sat. $NH_4Cl$ (aq.) at 0° C. The resulting mixture was extracted with EtOAc (3×5 mL). After filtration, the filtrate was concentrated under reduced pressure. The crude product (60 mg) was purified by Prep-HPLC to afford 3-chloro-2'-[6-cyclopropyl-2-(2-hydroxypropan-2-yl)pyrimidin-4-yl]-4-[(3,5-difluoropyridin-2-yl)methoxy]-5',6-dimethyl-[1,4'-bipyridin]-2-one (17.2 mg, 25.19%) as a white solid. MS: (ES+H, m/z): $[M+H]^+$=554.1 1H NMR (300 MHz, DMSO-$d_6$) δ 8.84 (s, 1H), 8.63 (s, 1H), 8.61 (d, 1H), 8.15 (s, 1H), 8.10 (t, 1H), 6.84 (s, 1H), 5.58-5.41 (m, 2H), 5.14 (s, 1H), 2.38-2.25 (m, 1H), 2.10 (s, 3H), 1.98 (s, 3H), 1,48 (s, 3H), 1,47 (s, 3H), 1.18-1.08 (m, 4H). $^{19}F$ NMR (282 MHZ, DMSO) δ-120.10,-120.13,-122.24,-122.27.

EXAMPLE 11

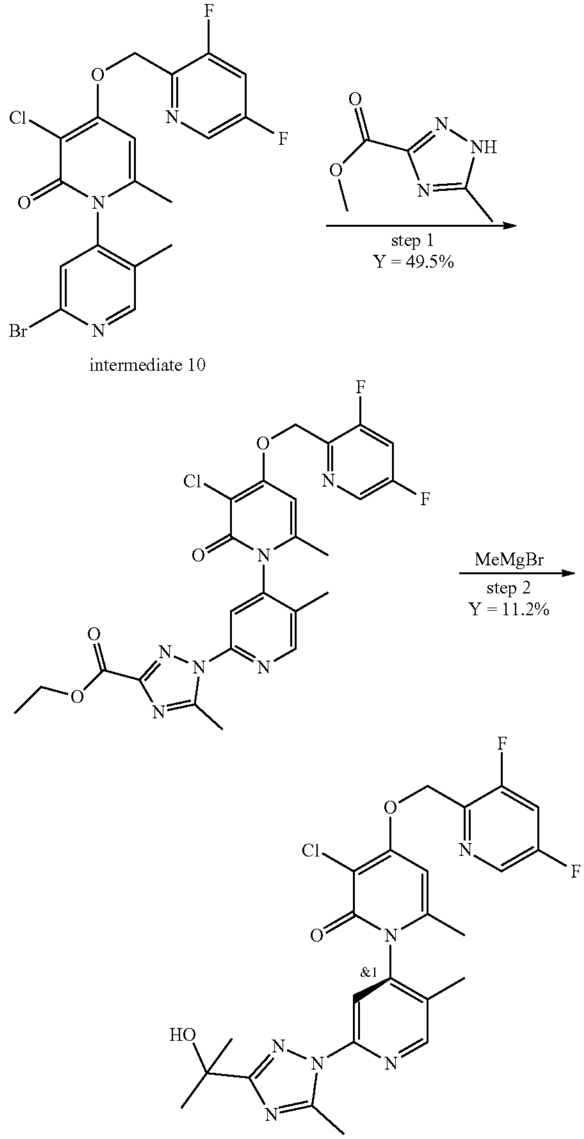

Example 11

Step 1: Preparation of ethyl 1-{3-chloro-4-[(3,5-difluoropyridin-2-yl)methoxy]-5',6-dimethyl-2-oxo-[1,4'-bipyridin]-2'-yl}-5-methyl-1,2,4-triazole-3-carboxylate A mixture of 2'-bromo-3-chloro-4-[(3.5-difluoropyridin-2-yl)methoxy]-5'0.6-dimethyl-[1,4'-bipyridin]-2-one (400 mg, 0.876 mmol. 1.00 equiv), ethyl 5-methyl-1H-1.2.4-triazole-3-carboxylate (271.8 mg. 1.752 mmol. 2 equiv). $K_2CO_3$ (242.12 mg, 1.752 mmol. 2 equiv). (1R.2R)-N1.N2-dimethylcyclohexane-1.2-diamine (249.18 mg, 1.752 mmol. 2.00 equiv) and CuI (41.7 mg, 0.220 mmol. 0.25 equiv) in 1. 4-dioxane (6 mL) was stirred for overnight at 100° C., under nitrogen atmosphere. The reaction was monitored by LCMS. The reaction was allowed to cool down to room temperature. The resulting mixture was poured into 20 ml of water. The resulting mixture was extracted with EtOAc (3×20 mL). The combined organic layers were washed with brine (20 ml), dried over anhydrous $Na_2SO_4$. After filtration, the filtrate was concentrated under reduced pressure. The residue was purified by silica gel column chromatography to afford ethyl 1-{3-chloro-4-[(3.5-difluoropyridin-2-yl) methoxy]-5'0.6-dimethyl-2-oxo-[1,4'-bipyridin]-2'-yl}-5-methyl-1.2.4-triazole-3-carboxylate (240 mg. Y=49.03%) as a yellow solid. LC-MS: (ES+H, m/z): $[M+H]^+$=531.1. $^1H$ NMR (400 MHZ. DMSO-$d_6$) δ 8.72 (s, 1H), 8.60 (d, 1H), 8.10 (t. 1H), 7.96 (s, 1H), 6.81 (s, 1H), 5.49 (s, 2H), 4.35 (q. 2H), 2.82 (s, 3H), 2.09 (s, 3H), 1.99 (s, 3H), 1.32 (t. 3H).

Step 2: Preparation of 3-chloro-4-[(3,5-difluoropyridin-2-yl)methoxy]-2'-[3-(2-hydroxypropan-2-yl)-5-methyl-1,2,4-triazol-1-yl]-5',6-dimethyl-[1,4'-bipyridin]-2-one To a stirred solution of ethyl 1-{3-chloro-4-[(3.5-difluoropyridin-2-yl)methoxy]-5'0.6-dimethyl-2-oxo-[1,4'-bipyridin]-2'-yl}-5-methyl-1.2.4-triazole-3-carboxylate (200 mg, 0.377 mmol. 1.00 equiv) in THF (10 mL) was added bromo (methyl) magnesium (3.77 mL. 10 equiv. IM in THF) dropwise at −30° C. under $N_2$ atmosphere. The resulting mixture was stirred at room temperature under $N_2$ atmosphere. The reaction was monitored by LCMS. The reaction was quenched by the addition of saturated $NH_4Cl$ (20 mL) at room temperature. The resulting mixture was extracted with EtOAc (3×20 mL). The combined organic layers were washed with brine, dried over anhydrous $Na_2SO_4$. After filtration, the filtrate was concentrated under reduced pressure. The crude product was purified by Prep-HPLC to afford 3-chloro-4-[(3,5-difluoropyridin-2-yl)methoxy]-2'-[3-(2-hydroxypropan-2-yl)-5-methyl-1.2.4-triazol-1-yl]-5'0.6-dimethyl-[1,4'-bipyridin]-2-one (22.4 mg. Y=11.2%) as a white solid. LC-MS: (ES+H, m/z): $[M+H]^+$=517.25. 1H NMR (400 MHZ. DMSO-$d_6$) δ 8.66 (s, 1H), 8.61 (d, 1H), 8.14-8.07 (m, 1H), 7.84 (s, 1H), 6.82 (s, 1H), 5.50 (d, 2H), 5.15 (s, 1H), 2.78 (s, 3H), 2.07 (s, 3H), 2.00 (s, 3H), 1.51 (s. 6H). $^{19}F$ NMR (282 MHz. DMSO) δ-120.127, —120.151, —122.289, —122.313.

EXAMPLE 12

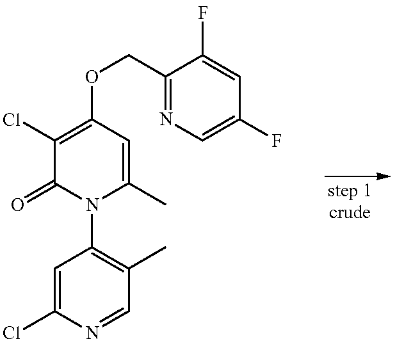

intermediate 7

-continued

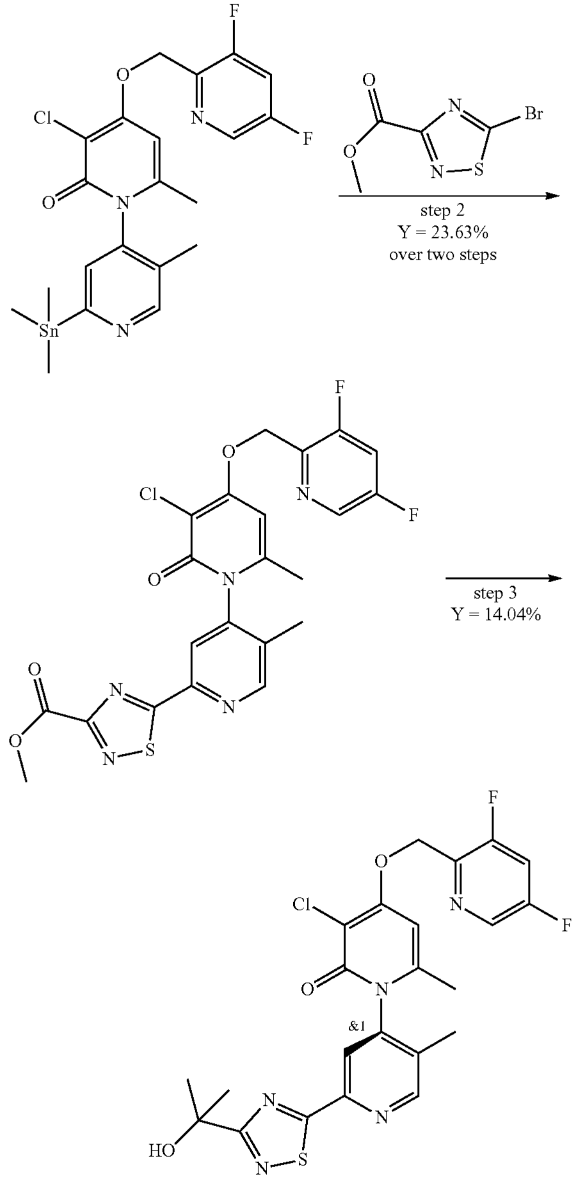

Example 12

Step 1: Preparation of 3-chloro-4-((3,5-difluoropyridin-2-yl)methoxy)-5',6-dimethyl-2'-(trimethylstannyl)-2H-[1,4'-bipyridin]-2-one To a solution of 2'0.3-dichloro-4-[(3.5-difluoropyridin-2-yl)methoxy]-5'0.6-dimethyl-[1,4'-bipyridin |-2-one (500 mg, 1.213 mmol. 1.00 equiv) and hexamethyldistannane (476.88 mg, 1,456 mmol, 1.2 equiv) in 1,4-dioxane (10 ml) was added Pd($PPh_3$): $C_1$: (170.27 mg, 0.243 mmol. 0.2 equiv) and AsPh; (74.29 mg. 0.243 mmol. 0.2 equiv) at room temperature. The resulting mixture was stirred for overnight at 80° C. under nitrogen atmosphere. The reaction was monitored by LCMS. The resulting mixture was used in the next step directly without further purification. LC-MS: (ES+H, m/z): $[M+H]^+$=542.1.

Step 2: Preparation of methyl 5-(3-chloro-4-((3,5-difluoropyridin-2-yl)methoxy)-5',6-dimethyl-2-oxo-2H-[1,4'-bipyridin]-2'-yl)-1,2,4-thiadiazole-3-carboxylate Methyl 5-bromo-1.2.4-thiadiazole-3-carboxylate (136.16 mg, 0.611 mmol. 0.50 equiv). CuI (232.52 mg, 1.221 mmol, 1 equiv) and Pd(PPh;): $Cl_2$ (171.39 mg, 0.244 mmol. 0.2 equiv) were added to the reaction solution (assumed 100% yield) in the previous step at room temperature. The resulting mixture was stirred for 2 h at 80° C., under nitrogen atmosphere. The reaction was monitored by LCMS. The mixture was allowed to cool down to room temperature. The resulting mixture was concentrated under vacuum. The residue was purified by silica gel column chromatography to afford methyl 5-(3-chloro-4-((3.5-difluoropyridin-2-yl)methoxy)-5'0.6-dimethyl-2-oxo-2H-[1,4'-bipyridin]-2'-yl)-1.2.4-thiadiazole-3-carboxylate (150 mg. 23.63%, over two steps) as a yellow solid. LC-MS: (ES+H, m/z): $[M+H]^+$=520.0.

Step 3: Preparation of 3-chloro-4-((3,5-difluoropyridin-2-yl)methoxy)-2'-(3-(2-hydroxypropan-2-yl)-1,2,4-thiadiazol-5-yl)-5',6-dimethyl-2H-[1,4'-bipyridin]-2-one To a stirred solution of methyl 5-(3-chloro-4-((3.5-difluoropyridin-2-yl)methoxy)-5'0.6-dimethyl-2-oxo-2H-[1,4'-bipyridin]-2'-yl)-1.2.4-thiadiazole-3-carboxylate (150 mg, 0.289 mmol. I equiv) in THF (5 mL) was added CH;MgBr (0.58 mL. 0.578 mmol. 2 equiv. 1 M in THF) dropwise at 0° C., under nitrogen atmosphere. The resulting mixture was stirred for 1 h at 0° C., under nitrogen atmosphere. The reaction was monitored by LCMS. The reaction was quenched by the addition of MeOH (5 mL) at 0° C. The resulting mixture was concentrated under reduced pressure. The mixture was purified by Prep-HPLC to afford crude product (50 mg). The crude product was further purified by Prep-HPLC to afford 3-chloro-4-((3.5-difluoropyridin-2-yl)methoxy)-2'-(3-(2-hydroxypropan-2-yl)-1.2.4-thiadiazol-5-yl)-5'0.6-dimethyl-2H-[1,4'-bipyridin]-2-one (21.3 mg, 14.04%) as a white solid. LC-MS: (ES+H, m/z): $[M+H]^+$=520.1. $^1$H NMR (400 MHz. DMSO-$d_6$) δ 8.85 (s, 1H), 8.61 (d, 1H), 8.16 (s, 1H), 8.11 (td. 1H), 6.82 (s, 1H), 5.49 (s, 2H), 5.46 (s. 1H), 2.11 (s, 3H), 1.99 (s, 3H), 1.61 (s, 3H), 1.60 (s, 3H). $^{19}$F NMR (377 MHz, DMSO) δ-120.13,-120.15,-122.31,-122.33.

EXAMPLE 13

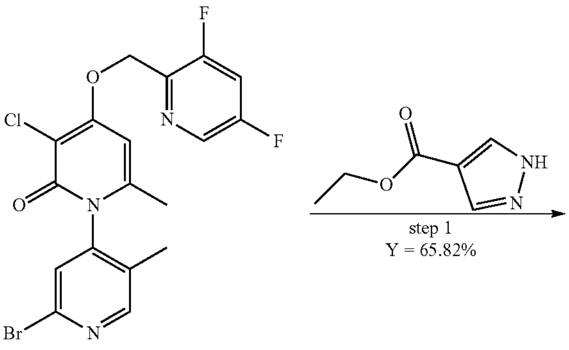

intermediate 10

-continued

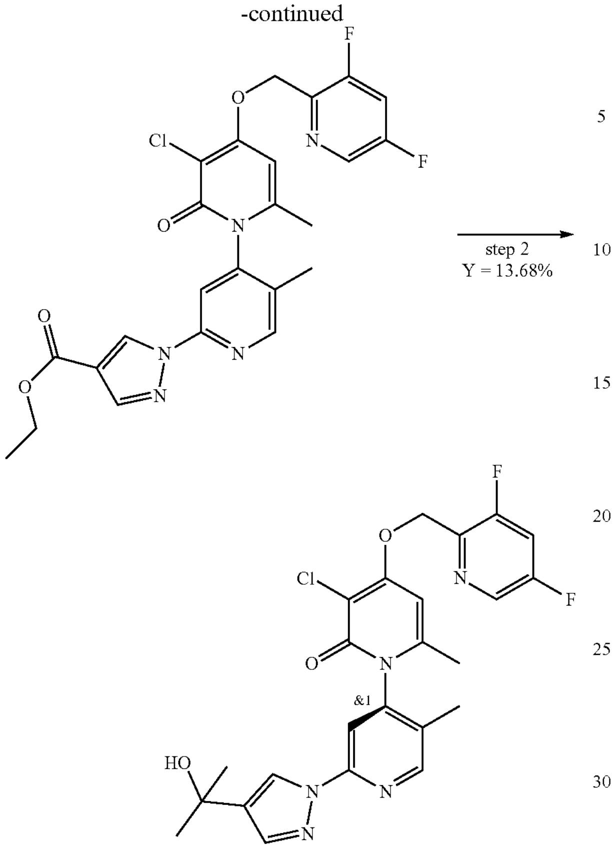

Example 13

Step 1: Preparation of ethyl 1-{3-chloro-4-[(3,5-difluoropyridin-2-yl)methoxy]-5',6-dimethyl-2-oxo-[1,4'-bipyridin]-2'-yl}pyrazole-4-carboxylate To a stirred solution of 3-chloro-4-[(3,5-difluoropyridin-2-yl)methoxy]-2',5',6-trimethyl-[1,4'-bipyridin]-2-one (300 mg, 0.766 mmol, 1 equiv), ethyl 1H-pyrazole-4-carboxylate (215 mg, 1.534 mmol, 2.00 equiv), $K_2CO_3$ (212 mg, 1.534 mmol, 2.00 equiv) and CuI (36.5 mg, 0.192 mmol, 0.25 equiv) in 1,4-dioxane (4 mL) were added (1S,2S)-N1,N2-dimethylcyclohexane-1,2-diamine (218 mg, 1.533 mmol, 2.00 equiv) room temperature under nitrogen atmosphere. The reaction was monitored by LCMS. Desired product could be detected by LCMS. The resulting mixture was concentrated under reduced pressure. The residue was purified by silica gel column chromatography to afford ethyl 1-{3-chloro-4-[(3,5-difluoropyridin-2-yl)methoxy]-5',6-dimethyl-2-oxo-[1,4'-bipyridin]-2'-yl}pyrazole-4-carboxylate (260 mg, 65.82%) as a yellow solid. LC-MS: (ES+H, m/z): $[M+H]^+$=516.1. $^1$H NMR (400 MHZ, DMSO-$d_6$) δ 9.03 (s, 1H), 8.65 (s, 1H), 8.61 (d, 1H), 8.23 (s, 1H), 8.14-8.06 (m, 1H), 7.96 (s, 1H), 6.81 (s, 1H), 5.50-5.57 (m, 2H), 4.28 (q, 2H), 2.05 (s, 3H), 1.99 (s, 3H), 1.32 (t, 3H).

Step 2: Preparation of 3-chloro-4-[(3,5-difluoropyridin-2-yl)methoxy]-2'-[4-(2-hydroxypropan-2-yl)pyrazol-1-yl]-5',6-dimethyl-[1,4'-bipyridin]-2-one Into a 3-necked round-bottom flask were added ethyl 1-{3-chloro-4-[(3,5-difluoropyridin-2-yl)methoxy]-5',6-dimethyl-2-oxo-[1,4'-bipyridin]-2'-yl}pyrazole-4-carboxylate (200 mg, 0.388 mmol, 1 equiv) in THF (5 mL). After nitrogen replacement, the temperature of the reaction system was reduced to-10° C. To the above mixture was added MeMgBr (4 mL, 34.719 mmol, 10 equiv) dropwise at −10° C. The resulting mixture was stirred for additional Ih at room temperature. The reaction was monitored by LCMS. Desired product could be detected by LCMS. The crude product was purified by Prep-HPLC to afford 3-chloro-4-[(3,5-difluoropyridin-2-yl)methoxy]-2'-[4-(2-hydroxypropan-2-yl)pyrazol-1-yl]-5',6-dimethyl-[1,4'-bipyridin]-2-one (28.4 mg, 13.68%) as a white solid. LC-MS: (ES+H, m/z): $[M+H]^+$=502.10. $^1$H NMR (400 MHz, DMSO-$d_6$) δ 8.60 (d, 1H), 8.55 (s, 1H), 8.44 (d, 1H), 8.15-8.05 (m, 1H), 7.82-7.74 (m, 2H), 6.82-6.77 (m, 1H), 5.48 (d, 2H), 5.05 (s, 1H), 2.06-1.96 (m, 6H), 1,47 (s, 6H). $^{19}$F NMR (377 MHz, DMSO) δ-120.13,-120.15,-122.32,-122.34.

EXAMPLE 14

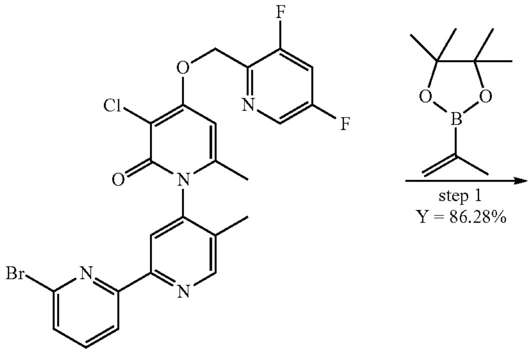

intermediate 24

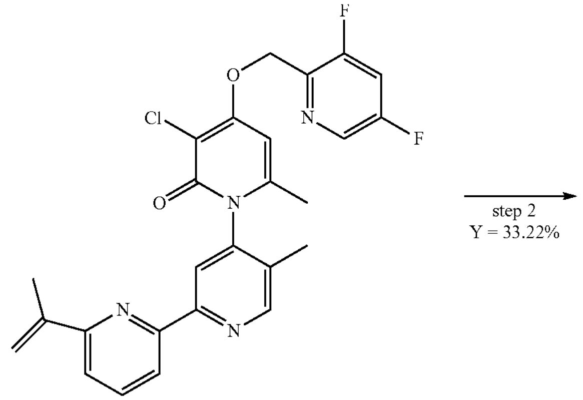

-continued

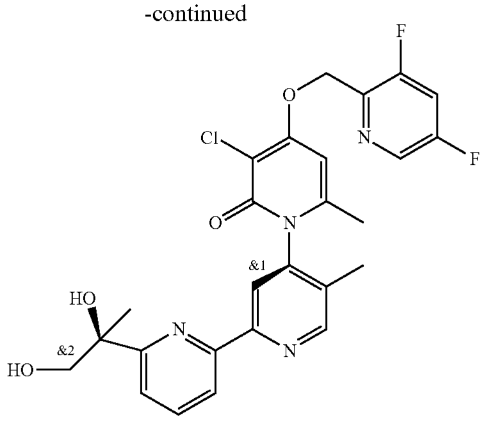

Example 14

Step 1: Preparation of 3-chloro-4-[(3,5-difluoropyridin-2-yl)methoxy]-5',6-dimethyl-2'-[6-(prop-1-en-2-yl)pyridin-2-yl]-[1,4'-bipyridin]-2-one To a stirred solution of 2'-(6-bromopyridin-2-yl)-3-chloro-4-[(3,5-difluoropyridin-2-yl)methoxy]-5',6-dimethyl-[1,4'-bipyridin]-2-one (150 mg, 0.281 mmol, 1 equiv) and 4,4,5,5-tetramethyl-2-(prop-1-en-2-yl)-1,3,2-dioxaborolane (70.84 mg, 0.422 mmol. 1.5 equiv) in dioxane (2 mL) and $H_2O$ (0.2 mL) were added CsF (85.38 mg, 0.562 mmol, 2 equiv) and $Pd(PPh_3)+$ (64.95 mg, 0.056 mmol, 0.2 equiv) at room temperature under nitrogen atmosphere. The resulting mixture was stirred for 2 h at 90° C., under nitrogen atmosphere. The reaction was monitored by LCMS. The mixture was allowed to cool down to room temperature. The reaction was quenched with saturating $NH_4Cl$ (aq.) (10 mL) at room temperature. The resulting mixture was extracted with EtOAc (3×40 mL). The combined organic layers were washed with brine (1×50 mL), dried over anhydrous $Na_2SO_4$. After filtration, the filtrate was concentrated under reduced pressure. The residue was purified by Prep-TLC (PE/EA 1:1) to afford 3-chloro-4-[(3,5-difluoropyridin-2-yl)methoxy]-5',6-dimethyl-2'-[6-(prop-1-en-2-yl)pyridin-2-yl]-[1,4'-bipyridin]-2-one (200 mg. 86.28%) as a white solid. LC-MS: (ES+H, m/z): $[M+H]^+$=495.2.

Step 2: Preparation of 3-chloro-4-[(3,5-difluoropyridin-2-yl)methoxy]-2'-[6-(1,2-dihydroxypropan-2-yl)pyridin-2-yl]-5',6-dimethyl-[1,4'-bipyridin]-2-one To a stirred solution of 3-chloro-4-[(3,5-difluoropyridin-2-yl)methoxy]-5',6-dimethyl-2'-[6-(prop-1-en-2-yl)pyridin-2-yl]-[1,4'-bipyridin]-2-one (200 mg, 0.242 mmol, 1 equiv, 60%) and NMO (56.81 mg. 0.485 mmol, 2.00 equiv) in THF (3 mL) and t-BuOH (1 mL) were added $K_2Os04.2H_2O$ (44.67 mg, 0.121 mmol, 0.50 equiv) at room temperature under nitrogen atmosphere. The resulting mixture was stirred for 3 h at room temperature under nitrogen atmosphere. The reaction was monitored by LCMS. The resulting mixture was filtered: the filter cake was washed with THF (2×3 mL). The filtrate was concentrated under reduced pressure. The residue was purified by reverse flash chromatography. This resulted in 3-chloro-4-[(3,5-difluoropyridin-2-yl)methoxy]-2'-[6-(1,2-dihydroxypropan-2-yl)pyridin-2-yl]-5',6-dimethyl-[1,4'-bipyridin]-2-one (42.6 mg. 33.22%) as a white solid. LC-MS: (ES+H, m/z): $[M+H]^+$=529.10. $^1$H NMR (400 MHz, DMSO-$d_6$) δ 8.77 (s, 1H), 8.61 (d, 1H), 8.36 (d, 1H), 8.25 (m, 1H), 8.10 (m, 1H), 7.93 (m, 1H), 7.67 (m, 1H), 6.82 (s, 1H), 5.49 (s, 2H), 5.20-5.16 (m, 1H), 4.59-4.55 (m, 1H), 3.69-3.48 (m, 2H), 2.06 (s, 3H), 1.98 (s, 3H), 1,43 (s, 3H). $^{19}$F NMR (377 MHz, DMSO) δ-120.12,-120.14,-122.33,-122.35.

EXAMPLE 15

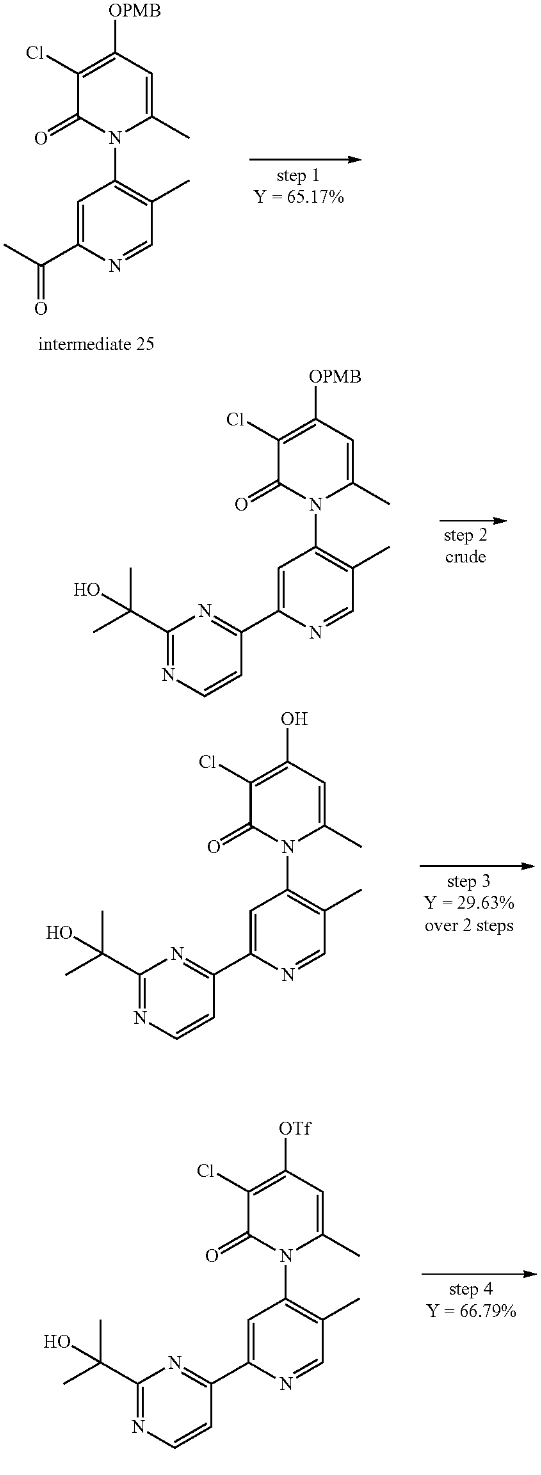

intermediate 25

-continued

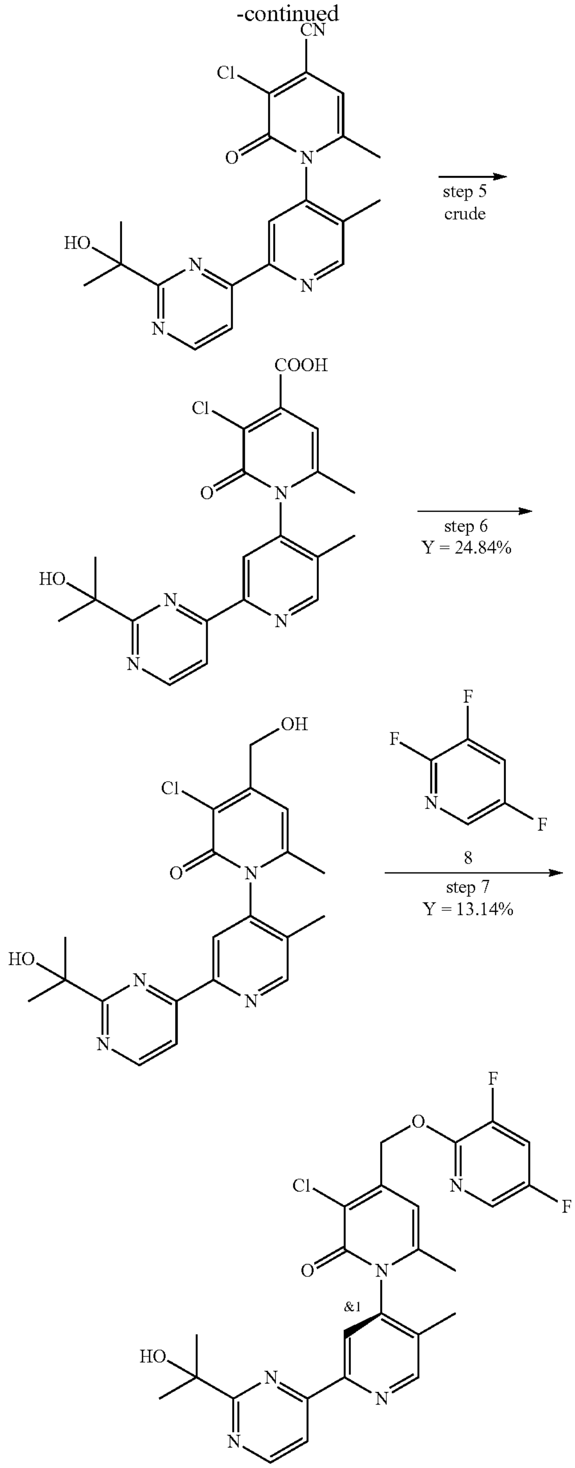

Example 15

Step 1: Preparation of 3-chloro-2'-[2-(2-hydroxy-propan-2-yl)pyrimidin-4-yl]-4-[(4-methoxyphenyl) methoxy]-5',6-dimethyl-[1,4'-bipyridin]-2-one To a stirred solution of 2'-acetyl-3-chloro-4-[(4-methoxy-phenyl)methoxy]-5',6-dimethyl-[1,4'-bipyridin]-2-one (2 g, 4.84 mmol, 1.00 equiv) in DMF-DMA (30 mL). The resulting mixture was stirred for 12 h at 100° C., under nitrogen atmosphere. The reaction was monitored by LCMS. The mixture was allowed to cool down to RT. The resulting mixture was concentrated under reduced pressure. To a stirred solution of the above mixture was added $K_2CO_3$ (3.35 g, 24.22 mmol, 5 equiv) and 2-hydroxy-2-methylpropanimidamide hydrochloride (2.01 g, 14.53 mmol, 3 equiv) in DMF (30 mL) at RT. The resulting mixture was stirred for 4 h at 80° C., under nitrogen atmosphere. The reaction was monitored by LCMS. The resulting mixture was concentrated under reduced pressure. The residue was purified by reverse flash chromatography to afford 3-chloro-2'-[2-(2-hydroxypropan-2-yl)pyrimidin-4-yl]-4-[(4-methoxyphenyl) methoxy]-5',6-dimethyl-[1,4'-bipyridin]-2-one (1.6 g, 65.17%) as a white solid. LC-MS: (ES+H, m z): $[M+H]^+$=507.1.

Step 2: Preparation of 3-chloro-4-hydroxy-2'-[2-(2-hydroxypropan-2-yl)pyrimidin-4-yl]-5',6-dimethyl-[1,4'-bipyridin]-2-one To a stirred solution of 3-chloro-2'-[2-(2-hydroxypropan-2-yl)pyrimidin-4-yl]-4-[(4-methoxyphenyl)methoxy]-5',6-dimethyl-[1,4'-bipyridin]-2-one (1.6 g, 3.16 mmol, 1.00 equiv) and TFA (5 mL, 67.32 mmol, 21.33 equiv) in DCM (10 mL) at RT. The resulting mixture was stirred for 2 h at RT under nitrogen atmosphere. The reaction was monitored by LCMS. The resulting mixture was concentrated under reduced pressure, The residue was purified by trituration with diethyl ether (10 mL) to afford 3-chloro-4-hydroxy-2'-[2-(2-hydroxypropan-2-yl)pyrimidin-4-yl]-5',6-dimethyl-[1,4'-bipyridin]-2-one (1 g, yellow semi-solid, TFA salt). LC-MS: (ES+H, m z): $[M+H]^+$=387.0.

Step 3: Preparation of 3-chloro-2'-[2-(2-hydroxy-propan-2-yl)pyrimidin-4-yl]-5',6-dimethyl-2-oxo-[1,4'-bipyridin]-4-yl trifluoromethanesulfonate To a stirred solution of 3-chloro-4-hydroxy-2'-[2-(2-hydroxypropan-2-yl)pyrimidin-4-yl]-5'0.6-dimethyl-[1,4'-bipyridin]-2-one (1 g, assumed 100% yield. 2.58 mmol. 1.00 equiv) lutidine (415.6 mg. 3.88 mmol. 1.5 equiv) and DMAP (31.6 mg, 0.26 mmol, 0.1 equiv) in DCM (10 mL) were added Tf: O (948.2 mg. 3.36 mmol. 1.3 equiv) dropwise at 0° C. The resulting mixture was stirred for 2 h at RT under nitrogen atmosphere. The reaction was monitored by LCMS. The resulting mixture was concentrated under reduced pressure. The residue was purified by flash chromatography to afford 3-chloro-2'-]2-(2-hydroxypropan-2-yl)pyrimidin-4-yl]-5'0.6-dimethyl-2-oxo-[1,4'-bipyridin]-4-yltrifluoromethanesulfonate (486 mg. 29.63% over 2 steps) as a yellow oil. LC-MS: (ES+H, m z): $[M+H]^+$=519.0.

Step 4: Preparation of 2-{3-chloro-2'-[2-(2-hydroxypropan-2-yl)pyrimidin-4-yl]-5',6-dimethyl-2-oxo-[1,4'-bipyridin]-4-yl}acetonitrile To a stirred solution of 3-chloro-2'-[2-(2-hydroxypropan-2-yl)pyrimidin-4-yl]-5'0.6-dimethyl-2-oxo-[1,4'-bipyridin]-4-yl trifluoromethanesulfonate (360 mg, 0.69 mmol. 1.00 equiv) and Zn (CN): (48.89 mg. 0.42 mmol. 0.6 equiv) in DMF (4 mL) were added Pd($PPh_3$) 4 (80.17 mg, 0.07 mmol, 0.1 equiv) at RT. The resulting mixture was stirred for 2 h at 100° C., under nitrogen atmosphere. The reaction was monitored by LCMS. The resulting mixture was concentrated under reduced pressure. The residue was purified by flash chromatography to afford 2-{3-chloro-2'-[2-(2-hydroxypropan-2-yl)pyrimidin-4-yl]-5'0.6-dimethyl-2-oxo-[1, 4'-bipyridin]-4-yl}acetonitrile (190 mg.66.79%) as a yellow solid. LC-MS: (ES+H, m z): $[M+H]^+$=396.0.

Step 5: Preparation of 3-chloro-2'-[2-(2-hydroxypropan-2-yl)pyrimidin-4-yl]-5',6-dimethyl-2-oxo-[1,4'-bipyridine]-4-carboxylic acid To a stirred solution of 3-chloro-2'-[2-(2-hydroxypropan-2-yl)pyrimidin-4-yl]-5'0.6-dimethyl-2-oxo-[1,4'-bipyridine]-4-carbonitrile (190 mg, 0.48 mmol. 1.00 equiv) in EtOH (10 mL) was added NaOH (96 mg. 2.40 mmol. 5.00 equiv) in at room temperature under nitrogen atmosphere. The resulting mixture was stirred for additional 2 h at 100° C. The reaction was monitored by LCMS. The mixture was acidified by using citric acid. The resulting mixture was diluted with EA (3×50 mL). The resulting mixture was washed with NaCl aq. (50 mL). The organic layers were dried over anhydrous $Na_2SO_4$. After filtration, the filtrate was concentrated under reduced pressure to afford 3-chloro-2'-[2-(2-hydroxypropan-2-yl)pyrimidin-4-yl]-5'0.6-dimethyl-2-oxo-[1,4'-bipyridine]-4-carboxylic acid (290 mg, crude) as a white solid, used without further purification. LC-MS: (ES+H, m z): $[M+H]^+$=415.1.

Step 6: Preparation of 3-chloro-4-(hydroxymethyl)-2'-[2-(2-hydroxypropan-2-yl)pyrimidin-4-yl]-5',6-dimethyl-[1,4'-bipyridin]-2-one To a stirred solution of 3-chloro-2'-[2-(2-hydroxypropan-2-yl)pyrimidin-4-yl]-5'0.6-dimethyl-2-oxo-[1,4'-bipyridine]-4-carboxylic acid (250 mg, 0.603 mmol. 1.00 equiv) in THF (10 mL) was added CDI (117.26 mg, 0.724 mmol. 1.20 equiv) in portions at r.t, under nitrogen atmosphere. The resulting mixture was stirred for 1 h at r.t . . . . The above mixture was added to a solution of $NaBH_4$ (68.40 mg, 1.809 mmol. 3.00 equiv) in THF (10 mL) and $H_2O$ (4 mL) dropwise over 5 min at 0° C. The resulting mixture was stirred for additional 1 h at r.t. The reaction was quenched by the addition of sat. NaHCO; (20 mL) at 0° C. The resulting mixture was extracted with DCM (3×20 mL). The combined organic layers were concentrated under reduced pressure. The residue was purified by reverse flash chromatography to afford 3-chloro-4-(hydroxymethyl)-2'-[2-(2-hydroxypropan-2-yl)pyrimidin-4-yl]-5'0.6-dimethyl-] 1,4'-bipyridin]-2-one (60 mg. 24.84%) as a brown solid. LC-MS: (ES+H, m z): $[M+H]^+$=401.1. $^1H$ NMR (400 MHZ. DMSO-$d_6$) δ 8.98 (d, 1H), 8.87 (s, 1H), 8.69 (s, 1H), 8.25 (d, 1H), 6.66 (s, 1H), 5.74-5.65 (m, 1H), 5.26 (s, 1H), 4.60-4.50 (m. 2H), 2.10 (s, 3H), 1.98 (s, 3H), 1.53 (s, 3H), 1.52 (s, 3H).

Step 7: Preparation of 3-chloro-4- {[(3,5-difluoropyridin-2-yl)oxy]methyl}-2'-[2-(2-hydroxypropan-2-yl)pyrimidin-4-yl]-5',6-dimethyl-[1,4'-bipyridin]-2-one A mixture of 3-chloro-4-(hydroxymethyl)-2'-[2-(2-hydroxypropan-2-yl)pyrimidin-4-yl]-5'0.6-dimethyl-[1,4'-bipyridin]-2-one (40 mg, 0.100 mmol, 1 equiv), 2.3.5-trifluoropyridine (26.56 mg, 0.200 mmol. 2 equiv) and $Cs_2CO_3$ (97.54 mg, 0.300 mmol, 3 equiv) in dioxane (4 mL) was stirred for 5 h at 80° C. under nitrogen atmosphere. The reaction was monitored by LCMS. The resulting mixture was diluted with EA (50 mL). The resulting mixture was washed with 2×50 mL of NaCl (aq.). The organic layers were dried over anhydrous $Na_2SO_4$. After filtration, the filtrate was concentrated under reduced pressure. The crude product was purified by Prep-HPLC to afford 3-chloro-4-{[(3.5-difluoropyridin-2-yl)oxy]methyl}-2'-[2-(2-hydroxypropan-2-yl)pyrimidin-4-yl]-5'0.6-dimethyl-[1,4'-bipyridin]-2-one (7 mg, 13.14%) as a grey solid. LC-MS: (ES+H, m z): $[M+H]^+$=514.10. $^1H$ NMR (400 MHZ. DMSO-$d_6$) δ 8.98 (d, 1H), 8.88 (s, 1H), 8.72 (s. 1H), 8.31-8.21 (m. 1H), 8.13 (d, 1H), 8.07 (ddd. 1H), 6.56 (s, 1H), 5.60-5.43 (m, 2H), 5.26 (s, 1H). 2.11 (s, 3H), 1.96 (s, 3H), 1.53 (s, 3H), 1.52 (s, 3H). $^{19}F$ NMR (377 MHz. DMSO) δ-133.74, —134.05.

EXAMPLE 16

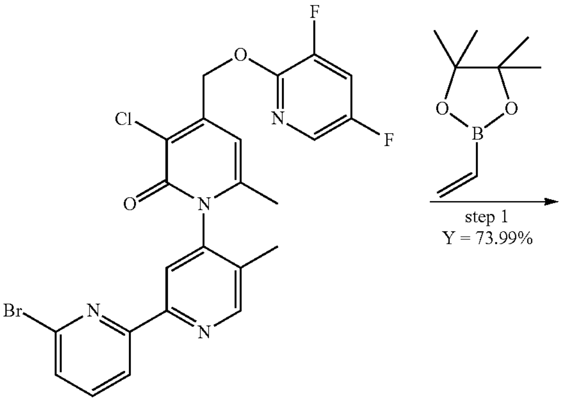

intermediate 24

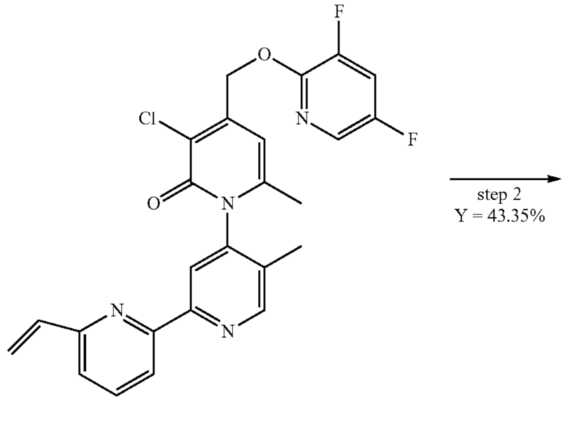

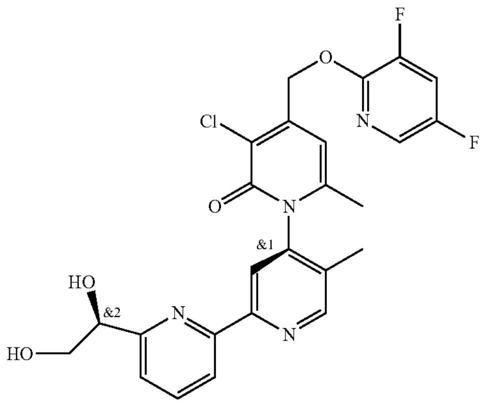

Example 16

Step 1: Preparation of 3-chloro-4-[(3,5-difluoropyridin-2-yl)methoxy]-2'-(6-ethenylpyridin-2-yl)-5',6-dimethyl-[1,4'-bipyridin]-2-one To a stirred mixture of 2'-(6-bromopyridin-2-yl)-3-chloro-4-[(3.5-difluoropyridin-2-yl)methoxy]-5'0.6-dimethyl-[1,4'-bipyridin]-2-one (150 mg, 0.281 mmol, 1 equiv). $K_2CO_3$ (77.68 mg, 0.562 mmol. 2 equiv) and 2-ethenyl-4.4.5.5-tetramethyl-1.3.2-dioxaborolane (86.57 mg, 0.562 mmol. 2 equiv) in 1,4-dioxane (2.5 mL) and $H_2O$ (0.5 mL) was added Pd(dppf) $C_1$, —$CH_2C_1$. (22.89 mg, 0.028 mmol, 0.1 equiv) at room temperature. The resulting mixture was stirred for 2 h at 100° C., under nitrogen atmosphere. The reaction was monitored by LCMS. The reaction was allowed to cool down to room temperature. The crude product was purified by reverse phase combi-flash to afford 3-chloro-4-[(3.5-difluoropyridin-2-yl)methoxy]-2'-(6-ethenylpyridin-2-yl)-5',6-dimethyl-[1,4'-bipyridin]-2-one (100 mg, 73.99%) as a white solid. LC-MS: (ES+H, m/z): $[M+H]^+$=481.12. $^1$H NMR (400 MHZ, DMSO-$d_6$) δ 8.79 (d, 1H), 8.61 (d, 1H), 8.33 (d, 1H), 8.30 (d, 1H), 8.15-8.05 (m, 1H), 8.00-7.91 (m, 1H), 7.60-7.53 (m, 1H), 6.94-6.85 (m, 1H), 6.82 (s, 1H), 6.47-6.37 (m, 1H), 5.56-5.45 (m, 3H), 2.07 (s, 3H), 1.98 (s, 3H).

Step 2: Preparation of 3-chloro-4-[(3,5-difluoropyridin-2-yl)methoxy]-2'-[6-(1,2-dihydroxyethyl)pyridin-2-yl]-5',6-dimethyl-[1,4'-bipyridin]-2-one To a stirred mixture of NMO (48.72 mg, 0.416 mmol, 2 equiv) and 3-chloro-4-[(3,5-difluoropyridin-2-yl)methoxy]-2'-(6-ethenylpyridin-2-yl)-5',6-dimethyl-[1,4'-bipyridin]-2-one (100 mg, 0.208 mmol, 1 equiv) in THF (1.5 mL) and t-BuOH (0.5 mL) was added KOs04.2$H_2O$ (38.31 mg, 0.104 mmol, 0.5 equiv) at room temperature under nitrogen atmosphere. The resulting mixture was stirred for 15 h at room temperature under nitrogen atmosphere. The reaction was monitored by LCMS. The reaction was quenched with sat, sodium thiosulfate (aq.) (40 ml), extracted with EtOAc (3 ×40 mL). The combined organic layers were dried over anhydrous $Na_2SO_4$. After filtration, the filtrate was concentrated under reduced pressure. The crude product (100 mg) was purified by Prep-HPLC to afford 3-chloro-4-[(3,5-difluoropyridin-2-yl)methoxy]-2'-[6-(1,2-dihydroxyethyl)pyridin-2-yl]-5',6-dimethyl-[1,4'-bipyridin]-2-one (46.6 mg, 43.35%) as a white solid. LC-MS: (ES+H, m/z): $[M+H]^+$=515.12. $^1$H NMR (400 MHz, DMSO-d6) δ 8.77 (s, 1H), 8.61 (d, 1H), 8.32-8.22 (m, 2H), 8.15-8.06 (m, 1H), 7.94 (t, 1H), 7.54 (d, 1H), 6.82 (s, 1H), 5.49 (s, 2H), 5.44 (t, 1H), 4.72-4.58 (m, 2H), 3.81-3.68 (m, 1H), 3.62-3.48 (m, 1H), 2.07 (s, 3H), 1.98 (s, 3H). $^{19}$F NMR (377 MHz, DMSO) δ-120.136,-120.154,-122.345,-122.364.

EXAMPLE 17

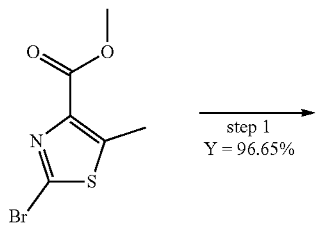

-continued

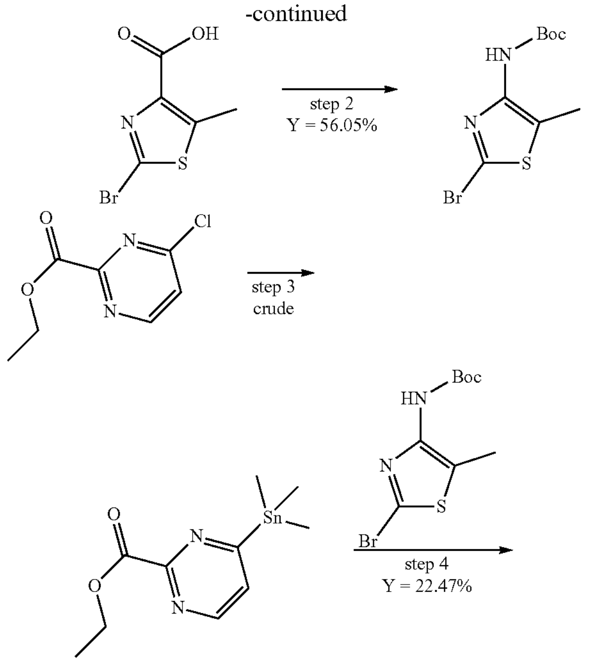

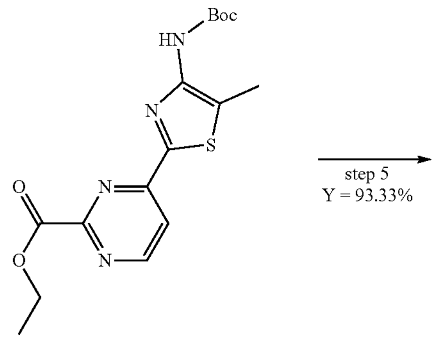

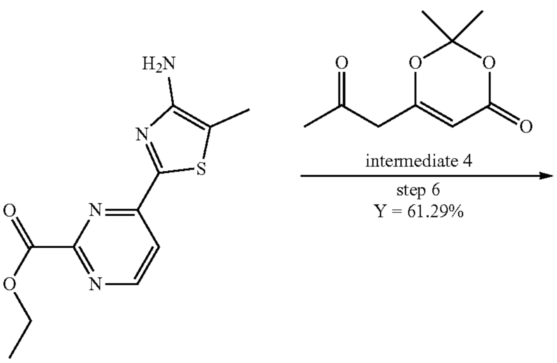

-continued

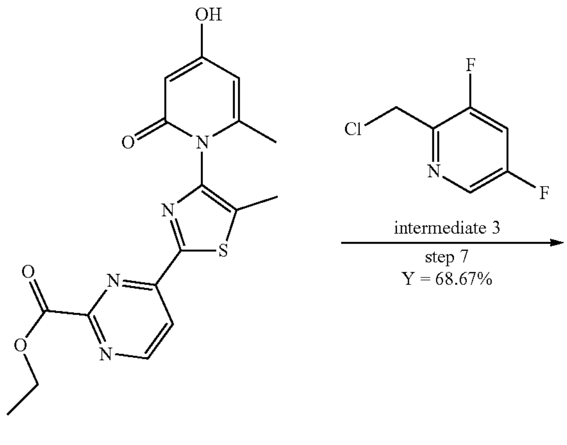

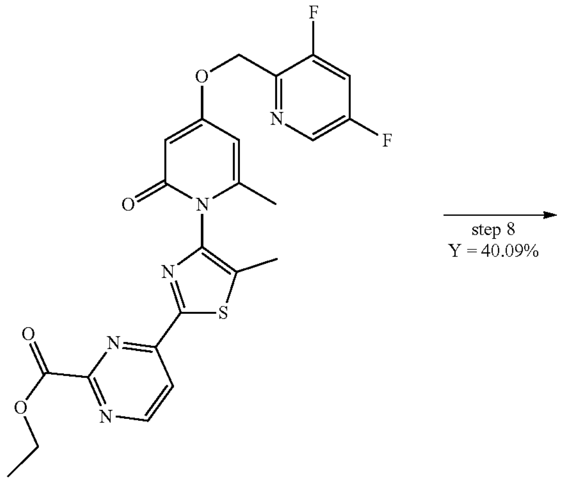

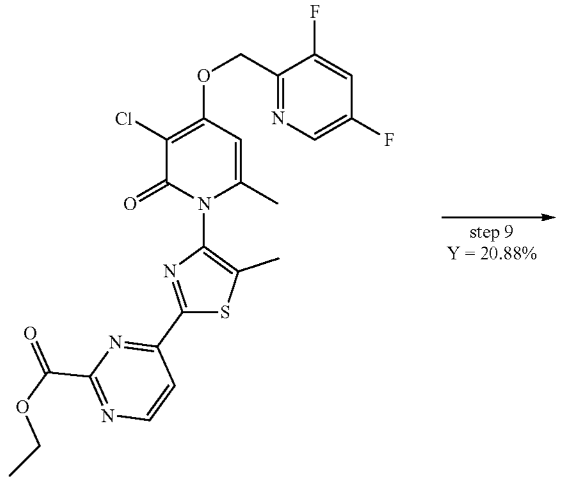

-continued

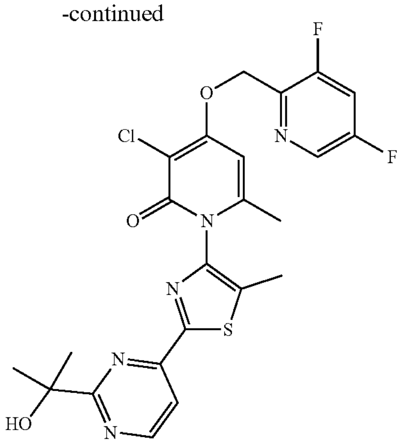

Example 17

Step 1: Preparation of 2-bromo-5-methyl-1,3-thiazole-4-carboxylic acid

To a stirred solution of methyl 2-bromo-5-methyl-1,3-thiazole-4-carboxylate (5.5 g, 23.297 mmol, 1.00 equiv) in THF (25 ml) was added LiOH (1.12 g, 46.768 mmol, 2.01 equiv) in water (25 ml) at room temperature under nitrogen atmosphere. The resulting mixture was stirred for 30 min at 50° C., under nitrogen atmosphere. The reaction was monitored by LCMS. The mixture was acidified to pH 4 with conc. HCl. The resulting mixture was extracted with EtOAc (3 ×100 mL), dried over anhydrous $Na_2SO_4$. After filtration, the filtrate was concentrated under reduced pressure, to afford 2-bromo-5-methyl-1,3-thiazole-4-carboxylic acid (5 g. 96.65%) as a red solid. LC-MS: (ES+H, m/z): $[M+H]^+$=221.9. $^1H$ NMR (400 MHZ. DMSO-$d_6$) δ 13.17 (s.1H), 2.67 (s, 3H).

Step 2: Preparation of tert-butyl N-(2-bromo-5-methyl-1,3-thiazol-4-yl) carbamate To a stirred solution of 2-bromo-5-methyl-1,3-thiazole-4-carboxylic acid (5 g. 22.516 mmol. 1.00 equiv) and 2-methylpropan-2-ol (16.69 g. 225.160 mmol. 10.00 equiv) in 1.2-dimethoxyethane (50 mL) was added DPPA (6.82 g. 24.768 mmol. 1.1 equiv) dropwise at 0° C., under nitrogen atmosphere. The resulting mixture was stirred for overnight at 90° C., under nitrogen atmosphere. The reaction was monitored by LCMS. The resulting mixture was diluted with EA (100 mL). The resulting mixture was washed with water (3 ×100 mL) and NaCl (aq.) (100 mL), the mixture was concentrated under reduced pressure. The residue was purified by silica gel column chromatography to afford tert-butyl N-(2-bromo-5-methyl-1,3-thiazol-4-vl) carbamate (3.7 g. 56.05%) as a white solid. LC-MS: (ES+H, m/z): [M+H−56]=238.9. $^1H$ NMR (300 MHz. DMSO-$d_6$) δ 9.07 (s, 1H), 2.19 (d, 3H), 1,43 (s, 9H).

Step 3: Preparation of ethyl 4-(trimethylstannyl)pyrimidine-2-carboxylate

To a stirred solution of ethyl 4-chloropyrimidine-2-carboxylate (1.5 g. 8.039 mmol. 1.00 equiv) and $Sn_2Me_6$ (6.58 g. 20.084 mmol. 2.50 equiv) in 1,4-dioxane (10 ml) was added Pd(PPh;): $Cl_2$ (1.69 g. 2.412 mmol. 0.30 equiv) and $AsPh_3$ (0.49 g. 1.608 mmol. 0.2 equiv) at room temperature under nitrogen atmosphere. The resulting mixture was stirred for overnight at 80° C., under nitrogen atmosphere. The reaction was monitored by LCMS. The resulting mixture was diluted with EA (100 mL) and washed with 5×100 ml of water and NaCl (aq.) (100 mL), dried over anhydrous $Na_2SO_4$. After filtration, the filtrate was concentrated under reduced pressure. The crude product was used in the next step directly without further purification. LC-MS: (ES+H, m/z): $[M+H]^+$=317.0

Step 4: Preparation of 4-{4-[(tert-butoxycarbonyl) amino]-5-methyl-1,3-thiazol-2-yl}pyrimidine-2-carboxylate To a stirred solution of ethyl 4-(trimethylstannyl)pyrimidine-2-carboxylate (2.5 g. 7.938 mmol. 1.00 equiv) and tert-butyl N-(2-bromo-5-methyl-1,3-thiazol-4-yl) carbamate (1.86 g. 6.350 mmol. 0.8 equiv) in 1,4-dioxane (20 ml) was added CuI (1.51 g. 7.938 mmol, 1 equiv) and $Pd(PPh_3)$: $Cl_2$ (1.11 g. 1.588 mmol. 0.2 equiv) at room temperature under nitrogen atmosphere. The resulting mixture was stirred for 2 h at 80° C. under nitrogen atmosphere. The mixture was allowed to cool down to room temperature. The reaction was monitored by LCMS. The reaction mixture was partitioned between EA (100 mL) and water (100 mL). The organic layer was extracted with EtOAc (2×200 mL) the resulting mixture was concentrated under reduced pressure. The residue was purified by silica gel column chromatography to afford ethyl 4-{4-] (tert-butoxycarbonyl)amino]-5-methyl-1, 3-thiazol-2-yl}pyrimidine-2-carboxylate (650 mg. 22.47%) as a white solid. LC-MS: (ES+H, m/z): [M+H−56]=309.1.

Step 5: Preparation of ethyl 4-(4-amino-5-methyl-1, 3-thiazol-2-yl)pyrimidine-2-carboxylate To a stirred solution of ethyl 4-{4-] (tert-butoxycarbonyl) amino]-5-methyl-1,3-thiazol-2-vl} pyrimidine-2-carboxylate (650 mg, 1.784 mmol, 1 equiv) in DCM (2 ml) was added HCl (gas) in 1,4-dioxane (2 ml) at room temperature under nitrogen atmosphere. The resulting mixture was stirred for 30 min at room temperature under nitrogen atmosphere. The reaction was monitored by LCMS. The resulting mixture was diluted with EA (100 mL). The resulting mixture was washed with water (3 ×100 mL), dried over anhydrous $Na_2SO_4$. After filtration, the filtrate was concentrated under reduced pressure to afford ethyl 4-(4-amino-5-methyl-1,3-thiazol-2-yl)pyrimidine-2-carboxylate (440 mg. 93.33%) as a yellow solid. LC-MS: (ES+H, m/z): $[M+H]^+$=265.1.

Step 6: Preparation of ethyl 4-[4-(4-hydroxy-2-methyl-6-oxopyridin-1-yl)-5-methyl-1,3-thiazol-2-yl]pyrimidine-2-carboxylate A solution of ethyl 4-(4-amino-5-methyl-1,3-thiazol-2-yl) pyrimidine-2-carboxylate (440 mg. 1.665 mmol. I equiv) and 2.2-dimethyl-6-(2-oxopropyl)-1,3-dioxin-4-one (613.27 mg. 3.330 mmol. 2 equiv) in dioxane (5 mL) was stirred for 3 h at 90° C., under nitrogen atmosphere. The mixture was allowed to cool down to room temperature. The reaction was monitored by LCMS. To the above mixture was added $H_2SO_4$ (163.28 mg, 1.665 mmol. I equiv) dropwise. The resulting mixture was stirred for additional 1 h at 90° C. The mixture was allowed to cool down to room temperature. The reaction was monitored by LCMS. The resulting mixture was concentrated under reduced pressure. The resulting mixture was added $H_2O$ (25 mL) and stirred for 30 min. The precipitated solids were collected by filtration and washed with Et2O (3 ×50 mL). This resulted in ethyl 4-[4-(4-hydroxy-2-methyl-6-oxopyridin-1-yl)-5-methyl-1,3-thiazol-2-yl]pyrimidine-2-carboxylate (380 mg. 61.29%) as a yellow solid.

Step 7: Preparation of ethyl 4-(4-{4-[(3,5-difluoropyridin-2-yl)methoxy]-2-methyl-6-oxopyridin-1-yl}-5-methyl-1,3-thiazol-2-yl)pyrimidine-2-carboxylate To a stirred solution of ethyl 4-[4-(4-hydroxy-2-methyl-6-oxopyridin-1-yl)-5-methyl-1,3-thiazol-2-yl]pyrimidine-2-carboxylate (380 mg, 1.020 mmol. I equiv) and 2-(chloromethyl)-3.5-difluoropyridinc (417.22 mg. 2.550 mmol. 2.5 equiv) in DMF (10 ml) was added 18-Crown-6 (80.91 mg, 0.306 mmol. 0.3 equiv) and $K_2CO_3$ (423.08 mg. 3.060 mmol, 3 equiv) at room temperature under nitrogen atmosphere. The resulting mixture was stirred for 2 h at 60° C., under nitrogen atmosphere. The mixture was allowed to cool down to room temperature. The reaction was monitored by LCMS. The reaction mixture was partitioned between EA (100 mL) and water (100 mL). The organic layer was washed with water (200 mL), and then dried over $Na_2SO_4$. The solution was concentrated under reduced pressure. The residue was purified by silica gel column chromatography to afford ethyl 4-(4-{4-[(3.5-difluoropyridin-2-yl)methoxy]-2-methyl-6-oxopyridin-1-yl}-5-methyl-1,3-thiazol-2-yl)pyrimidine-2-carboxylate (350 mg. 68.67%) as a white solid. LC-MS: (ES+H, m z): $[M+H]^+$=500.1.

Step 8: Preparation of ethyl 4-(4-{3-chloro-4-[(3,5-difluoropyridin-2-yl)methoxy]-6-methyl-2-oxopyridin-1-yl}-5-methyl-1,3-thiazol-2-yl)pyrimidine-2-carboxylate To a stirred solution of ethyl 4-(4-{4-[(3.5-difluoropyridin-2-yl)methoxy]-2-methyl-6-oxopyridin-1-yl}-5-methyl-1,3-thiazol-2-yl)pyrimidine-2-carboxylate (350 mg, 0.701 mmol, 1 equiv) and NCS (121.64 mg, 0.911 mmol, 1.3 equiv) in IPA (5 ml) at room temperature under nitrogen atmosphere. The resulting mixture was stirred for 2 h at 50° C., under nitrogen atmosphere. The reaction was monitored by LCMS. The mixture was allowed to cool down to room temperature. The reaction mixture was partitioned between EA (10 mL) and water (10 mL). The organic layer was extracted with EtOAc (3 ×50 mL). The resulting mixture was concentrated under reduced pressure. The crude product (300 mg) was purified by Prep-HPLC to afford ethyl 4-(4-{3-chloro-4-[(3,5-difluoropyridin-2-yl)methoxy]-6-methyl-2-oxopyridin-1-yl}-5-methyl-1,3-thiazol-2-yl)pyrimidine-2-carboxylate (150 mg, 40.09%) as a yellow oil. LC-MS: (ES+H, m z): $[M+H]^+$=534.1. $^1$H NMR (300 MHz, DMSO-$d_6$) δ 9.11 (d, 1H), 8.61 (d, 1H), 8.21 (d, 1H), 8.18-8.04 (m, 1H), 6.79 (s, 1H), 5.52 (d, 2H), 4.44 (q,2H), 2.34 (s, 3H), 2.05 (s, 3H), 1.38 (t, 3H).

Step 9: Preparation of 3-chloro-4-[(3,5-difluoropyridin-2-yl)methoxy]-1-{2-[2-(2-hydroxypropan-2-yl) pyrimidin-4-yl]-5-methyl-1,3-thiazol-4-yl}-6-methylpyridin-2-one To a stirred solution of ethyl 4-(4-{3-chloro-4-[(3,5-difluoropyridin-2-yl)methoxy]-6-methyl-2-oxopyridin-1-yl}-5-methyl-1,3-thiazol-2-yl)pyrimidine-2-carboxylate (150 mg, 0.281 mmol, 1 equiv) in THF was added MeMgBr (335.00 mg, 2.810 mmol, 10 equiv) at 0° C., under nitrogen atmosphere The resulting mixture was stirred for 30 min at 0° C., under nitrogen atmosphere. The reaction was monitored by LCMS. The reaction was quenched with MeOH at 0° C. The resulting mixture was concentrated under reduced pressure. The crude product (150 mg) was purified by Prep-HPLC to afford 3-chloro-4-[(3,5-difluoropyridin-2-yl)methoxy]-1-{2-[2-(2-hydroxypropan-2-yl)pyrimidin-4-yl]-5-methyl-1,3-thiazol-4-yl}-6-methylpyridin-2-one (30.5 mg, 20.88%) as a white solid. LC-MS: (ES+H, m z): $[M+H]^+$=520.1. $^1H$ NMR (300 MHz, DMSO-$d_6$) δ 8.97 (d, 1H), 8.61 (d, 1H), 8.17-8.04 (m, 1H), 7.89 (d, 1H), 6.78 (s, 1H), 5.52 (d, 2H), 5.17 (s, 1H), 2.32 (s, 3H), 2.05 (d, 3H), 1.57 (s, 6H). $^{19}F$ NMR (282 MHz, DMSO) δ-120.21,-120.24,-122.44,-122.46.

EXAMPLE 18A, 18B, 18C, 18D

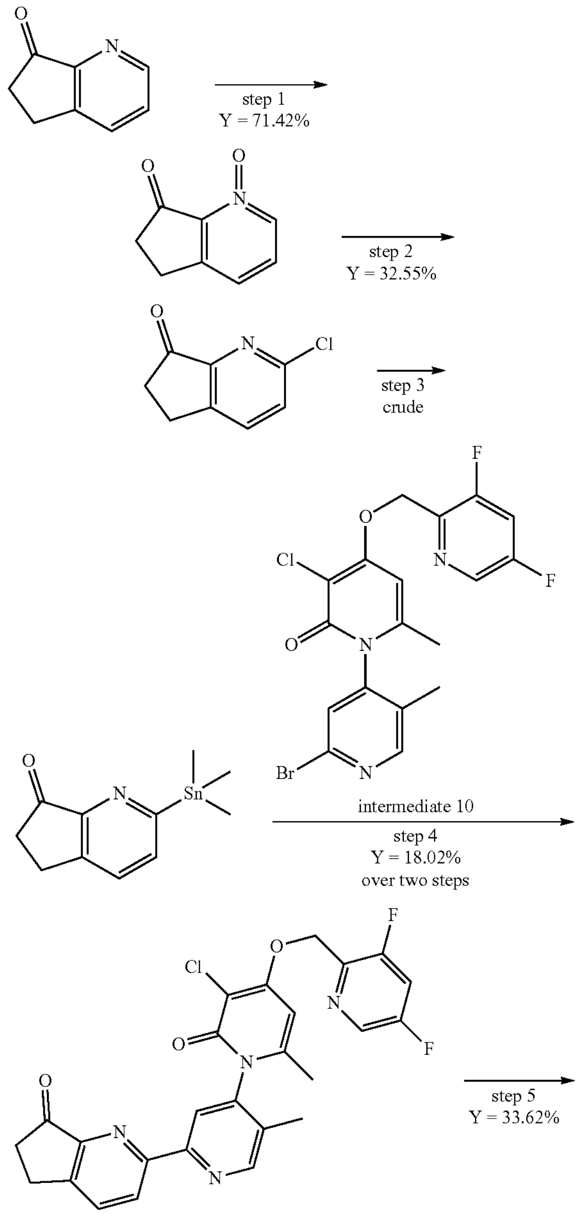

-continued

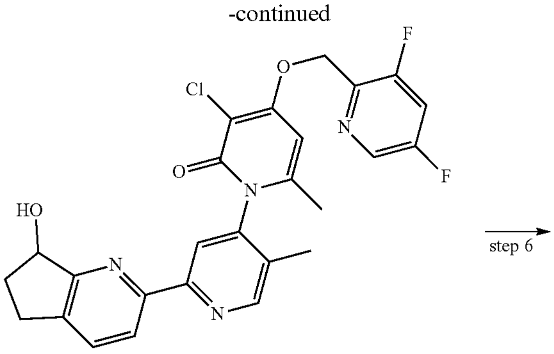

Example 18

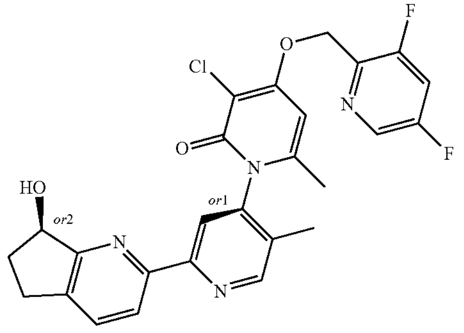

isomer 1
Example 18A

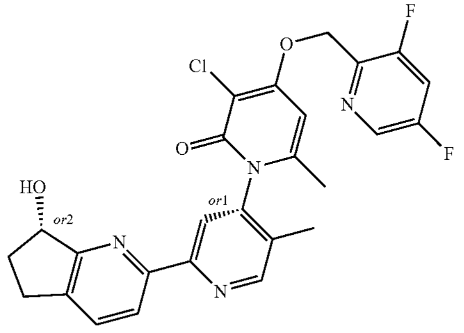

isomer 2
Example 18B

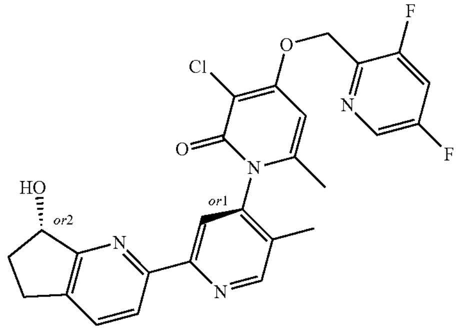

isomer 3
Example 18C

-continued

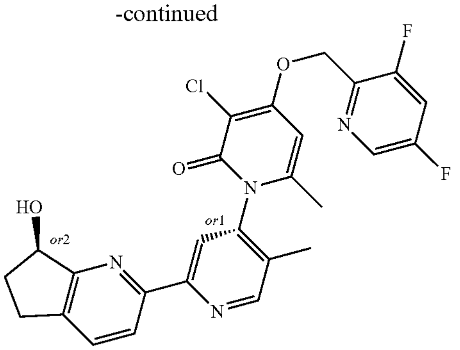

isomer 4
Ecample 18D

Step 1: Preparation of 5H,6H-1lambda5-cyclopenta[b] pyridine-1,7-dione

To a stirred solution of 5H.6H-cyclopenta]b]pyridin-7-one (5 g. 37.552 mmol. 1.00 equiv) in DCM (150 ml) was added m-CPBA (12.96 g. 75.104 mmol. 2.00 equiv) in portions at 0° C., under nitrogen atmosphere. The resulting mixture was stirred for 18 h at room temperature under nitrogen atmosphere. The reaction was monitored by LCMS. The resulting mixture was concentrated under reduced pressure. The residue was purified by silica gel column chromatography to afford 5H.6H-1lambda5-cyclopenta]b]pyridine-1.7-dione (4 g. 71.42%) as a black solid. LC-MS: (ES+H, m/z): $[M+H]^+$=150.1. 1H NMR (400 MHZ. DMSO-$d_6$) § 8.17 (d, 1H), 7.55 (t. 1H), 7.44 (d, 1H), 3.02 (t. 2H), 2.64 (t. 2H).

Step 2: Preparation of 2-chloro-5H,6H-cyclopenta[b] pyridin-7-one

To a stirred solution of 5H.6H-1lambda5-cyclopenta]b] pyridine-1.7-dione (3.5 g. 23.466 mmol. 1.00 equiv) in DCE (80 mL) was added $POCl_3$ (17.99 g. 117.330 mmol. 5 equiv) dropwise at 0° C., under nitrogen atmosphere. The resulting mixture was stirred for 2 h at 80° C., under nitrogen atmosphere. The reaction was monitored by LCMS. The mixture was allowed to r.t. The resulting mixture was concentrated under reduced pressure. The residue was purified by silica gel column chromatography to afford 2-chloro-5H.6H-cyclopenta[b] pyridin-7-one (1.28 g. 32.55%) as a black solid. LC-MS: (ES+H, m/z): $[M+H]^+$=168.0. $^1$H NMR (400 MHz. DMSO-$d_6$) δ 8.15 (d, 1H), 7.72 (d, 1H), 3.09 (t. 2H), 2.71 (t. 2H).

Step 3: Preparation of 2-(trimethylstannyl)-5H,6H-cyclopenta[b] pyridin-7-one

A mixture of 2-chloro-5H.6H-cyclopenta[b] pyridin-7-one (250 mg, 1,492 mmol. I equiv).

$Pd(PPh_3)$: $C_1$: (209.41 mg, 0.298 mmol. 0.20 equiv). AsPh; (91.36 mg, 0.298 mmol. 0.2 equiv) and Sn_Mco (488.74 mg, 1,492 mmol, 1 equiv) in dioxane (8 mL) was stirred for overnight at 80° C., under nitrogen atmosphere. The reaction was monitored by LCMS. The resulting mixture was used in the next step directly without further purification. LC-MS: (ES+H, m/z): $[M+H]^+$=298.0.

Step 4: Preparation of 3-chloro-4-[(3,5-difluoropyridin-2-yl)methoxy]-5',6-dimethyl-2'-{7-oxo-5H,6H-cyclopenta[b] pyridin-2-yl}-[1,4'-bipyridin]-2-one 2'-bromo-3-chloro-4-[(3.5-difluoropyridin-2-yl) methoxy]-5'0.6-dimethyl-[1,4'-bipyridin]-2-one (328.67 mg, 0.719 mmol. 0.6 equiv). $Pd(PPh_3)$: $Cl_2$ (168.39 mg, 0.240 mmol. 0.20 equiv) and CuI (228.44 mg, 1.199 mmol. I equiv) was added to the reaction solution in the previous step at room temperature. The resulting mixture was stirred for 2 h at 80° C., under nitrogen atmosphere. The reaction was monitored by LCMS. The mixture was allowed to r.t. The resulting mixture was diluted with EA (200 mL), washed with 3 ×150 mL of sat. $NaHCO_3$(aq.). The organic layers were concentrated under reduced pressure. And purified by silica gel column chromatography to afford crude product. The crude product was purified by reverse flash chromatography to afford 3-chloro-4-[(3.5-difluoro-pyridin-2-yl)methoxy]-5'0.6-dimethyl-2'-{7-oxo-5H.6H-cyclopenta]b]pyridin-2-yl}-[1,4'-bipyridin]-2-one (110 mg, 18.02%, over two steps) as a white solid. LC-MS: (ES+H, m/z): $[M+H]^+$=508.8. $^1$H NMR (300 MHz. Chloroform-d) δ 8.71 (s. 1H), 8.68 (d, 1H), 8.43 (s.1H), 8.40 (s, 1H), 8.02 (d, 1H), 7.39-7.31 (m, 1H), 6.39 (s, 1H), 5.46 (s, 2H). 3.22 (t. 2H), 2.84 (t. 2H), 2.19 (s, 3H), 2.01 (s, 3H).

Step 5: Preparation of 3-chloro-4-[(3,5-difluoropyridin-2-yl)methoxy]-2'-{7-hydroxy-5H,6H,7H-cyclopenta[b] pyridin-2-yl}-5',6-dimethyl-[1,4'-bipyridin]-2-one To a stirred solution of 3-chloro-4-[(3.5-difluoropyridin-2-yl)methoxy]-5'0.6-dimethyl-2'-{7-oxo-5H.6H-cyclopenta]b]pyridin-2-yl}-] 1,4'-bipyridin]-2-one (400 mg, 0.786 mmol. I equiv) in THF (10 ml) was added $NaBH_4$ (59.47 mg, 1.572 mmol. 2 equiv) in portions at 0° C., under nitrogen atmosphere. The resulting mixture was stirred for 1 h at room temperature under nitrogen atmosphere. The reaction was monitored by LCMS. The reaction was quenched with sat. $NH_4Cl$ (aq.) at 0° C. The resulting mixture was extracted with EtOAc. The combined organic layers were concentrated under reduced pressure. The residue was purified by silica gel column chromatography to afford 3-chloro-4-[(3.5-difluoropyridin-2-yl)methoxy]-2'-{7-hydroxy-5H.6H.7H-cyclopenta]b]pyridin-2-yl}-5',6-dimethyl-] 1,4'-bipyridin]-2-one (135 mg. 33.62%) as a white solid. LC-MS: (ES+H, m/z): $[M+H]^+$=510.8.

Step 6: Preparation of rel-(R)-3-chloro-4-((3,5-difluoropyridin-2-yl)methoxy)-2'-(7-hydroxy-6,7-dihydro-5H-cyclopenta[b] pyridin-2-yl)-5',6-dimethyl-2H-[1,4'-bipyridin]-2-one, rel-(R)-3-chloro-4-((3,5-difluoropyridin-2-yl)methoxy)-2'-(7-hydroxy-6,7-dihydro-5H-cyclopenta[b] pyridin-2-yl)-5',6-dimethyl-2H-[1,4'-bipyridin]-2-one, rel-(R)-3-chloro-4-((3,5-difluoropyridin-2-yl)methoxy)-2'-(7-hydroxy-6, 7-dihydro-5H-cyclopenta[b] pyridin-2-yl)-5',6-dimethyl-2H-[1,4'-bipyridin]-2-one and rel-(R)-3-chloro-4-((3,5-difluoropyridin-2-yl)methoxy)-2'-(7-hydroxy-6,7-dihydro-5H-cyclopenta[b] pyridin-2-yl)-5',6-dimethyl-2H-[1,4'-bipyridin]-2-one 3-chloro-4-[(3.5-difluoropyridin-2-yl)methoxy]-2'-{7-hydroxy-5H.6H.7H-cyclopenta]b]pyridin-2-yl}-5'0.6-dimethyl-]1,4'-bipyridin]-2-one (135 mg, 0.264 mmol. I equiv) was isolated by PREP-HPLC to afford 2 peaks. The first peak (53 mg) was separated by prep-chiral-HPLC to afford Example 18A (18.3 mg) and Example 18B (16.9 mg) as a white solid. The second peak (45 mg) was separated by prep-chiral-HPLC to afford Example 18C (14.1 mg) and Example 18D (14.3 mg) as a white solid.

EXAMPLE 18A

LC-MS: (ES+H, m/z): $[M+H]^+$=510.80. $^1H$ NMR (400 MHZ. DMSO-$d_6$) δ 8.77 (s.1H), 8.61 (d. 1H), 8.26 (d. 1H), 8.24 (s.1H), 8.15-8.01 (m. 1H), 7.82 (d, 1H), 6.80 (d, 1H), 5.50 (d, 2H), 5.42 (d, 1H), 5.07-4.93 (m. 1H), 3.05-2.91 (m. 1H), 2.88-2.71 (m. 1H), 2.45-2.33 (m. 1H), 2.08 (s, 3H), 1.99 (s. 3H), 1.91-1.78 (m, 1H), $^{19}F$ NMR (377 MHz. DMSO) δ-120.15, —120.17, —122.34, —122.36.

EXAMPLE 18B

LC-MS: (ES+H, m/z): $[M+H]^+$=510.85. $^1H$ NMR (400 MHZ. DMSO-$d_6$) δ 8.76 (s. 1H), 8.60 (d, 1H), 8.25 (d, 1H), 8.23 (s.1H), 8.13-8.02 (m. 1H), 7.82 (d. 1H), 6.79 (d, 1H), 5.49 (d, 2H). 5.41 (d, 1H), 5.06-4.92 (m. 1H), 3.04-2.93 (m. 1H), 2.87-2.74 (m. 1H), 2.46-2.34 (m. 1H), 2.07 (s. 3H), 1.99 (s, 3H), 1.91-1.79 (m. 1H), $^{19}F$ NMR (377 MHz. DMSO) δ-120.15, —120.17, —122.36, —122.37.

EXAMPLE 18C

LC-MS: (ES+H, m/z): $[M+H]^+$=510.85. $^1H$ NMR (400 MHz. DMSO-$d_6$) δ 8.76 (s.1H), 8.61 (d, 1H), 8.26 (d. 1H), 8.24 (s.1H), 8.13-8.05 (m. 1H), 7.82 (d. 1H), 6.80 (d, 1H), 5.49 (d. 2H), 5.37 (d, 1H), 5.02-4.93 (m. 1H), 3.06-2.94 (m. 1H), 2.85-2.73 (m, 1H), 2.45-2.33 (m. 1H), 2.07 (s. 3H), 1.98 (s, 3H), 1.93-1.82 (m. 1H), $^{19}F$ NMR (377 MHz. DMSO) δ-120.14, —120.16, —122.34.-122.36

EXAMPLE 18D

LC-MS: (ES+H, m/z): $[M+H]^+$=510.85. $^1H$ NMR (400 MHZ, DMSO-$d_6$) δ 8.76 (s, 1H), 8.61 (d, 1H), 8.26 (d, 1H), 8.25 (s, 1H), 8.13-8.06 (m, 1H), 7.83 (d, 1H), 6.80 (d, 1H), 5.49 (d, 2H), 5.39 (d, 1H), 5.02-4.93 (m, 1H), 3.06-2.94 (m, 1H), 2.85-2.73 (m, 1H), 2.45-2.33 (m, 1H), 2.07 (s, 3H), 1.98 (s, 3H), 1.91-1.86 (m, 1H). $^{19}F$ NMR (377 MHz, DMSO) δ-120.12,-120.15,-122.31,-122.33.

EXAMPLE 19A, 19B

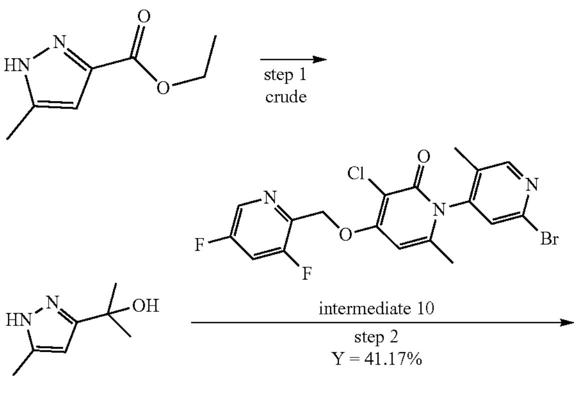

-continued

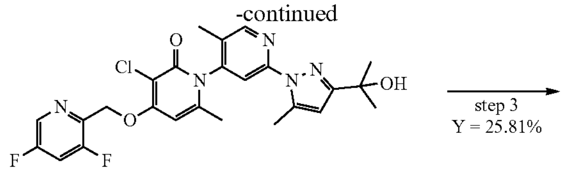

Exapmle 19

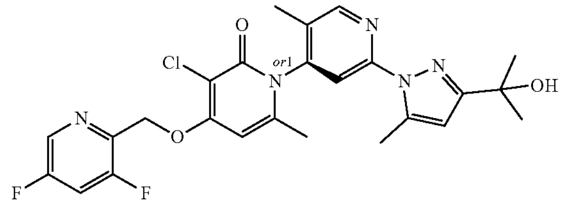

isomer 1
Example 19A

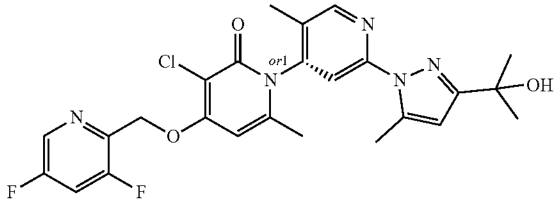

isomer 2
Example 19B

Step 1: Preparation of 2-(5-methyl-1H-pyrazol-3-yl) propan-2-ol

To a stirred solution of ethyl 5-methyl-1H-pyrazole-3-carboxylate (3 g. 19.459 mmol, 1 equiv) in THF (100 mL) were added MeMgBr (97.30 mL, 97.295 mmol, 5 equiv) dropwise at 0° C., under nitrogen atmosphere.

The reaction was monitored by LCMS. The reaction was quenched with sat. $NH_4Cl$ (aq.) at 0° C., extracted with EtOAc (3 ×1L), dried over anhydrous $Na_2SO_4$. After filtration, the filtrate was concentrated under reduced pressure. The crude product 2-(5-methyl-1H-pyrazol-3-yl) propan-2-ol (2.9 g, 88.24%) was used in the next step directly without further purification. LC-MS: (ES+H, m/z): $[M+H]^+$=141.09. Step 2: Preparation of 3-chloro-4-((3,5-difluoropyridin-2-yl) methoxy)-2'-(3-(2-hydroxypropan-2-yl)-5-methyl-1H-pyrazol-1-yl)-5',6-dimethyl-2H-[1,4'-bipyridin]-2-one To a stirred mixture of 2-(5-methyl-1H-pyrazol-3-yl) propan-2-ol (184.18 mg, 1.314 mmol, 2 equiv), $K_2CO_3$ (181.58 mg, 1.314 mmol, 2 equiv) and 2'-bromo-3-chloro-4-[(3,5-difluoropyridin-2-yl)methoxy]-5',6-dimethyl-[1,4'-bipyridin]-2-one (300 mg, 0.657 mmol, 1.00 equiv) in 1,4-dioxane (5 mL) were added (1S,2S)-N1,N2-dimethylcyclohexane-1, 2-diamine (37.38 mg, 0.263 mmol, 0.4 equiv) and CuI (25.02 mg, 0.131 mmol, 0.2 equiv) at room temperature under nitrogen atmosphere. The resulting mixture was stirred for overnight at 100° C., under nitrogen atmosphere. After cooling down to r.t., the resulting mixture was poured into water (100 mL), then extracted with EtOAc (3 ×100 mL). The combined organic layers were dried over anhydrous $Na_2SO_4$. After filtration, the filtrate was concentrated under reduced pressure. The residue was purified by silica gel column chromatography to afford 240 mg of crude product, which was further purified by Prep-HPLC to afford 3-chloro-4-[(3,5-difluoropyridin-2-yl)methoxy]-2'-[3-(2-hydroxypropan-2-yl)-5-methylpyrazol-1-yl]-5',6-dimethyl-

[1,4'-bipyridin]-2-one (140 mg, 41.17%) as a white solid. LC-MS: (ES+H, m/z): $[M+H]^+$=516.1.

Step 3: Preparation of rel-3-chloro-4-((3,5-difluoropyridin-2-yl)methoxy)-2'-(3-(2-hydroxypropan-2-yl)-5-methyl-1H-pyrazol-1-yl)-5',6-dimethyl-2H-[1,4'-bipyridin]-2-one and rel-3-chloro-4-((3,5-difluoropyridin-2-yl)methoxy)-2'-(3-(2-hydroxypropan-2-yl)-5-methyl-1H-pyrazol-1-yl)-5',6-dimethyl-2H-[1,4'-bipyridin]-2-one The racemate (3-chloro-4-[(3,5-difluoropyridin-2-yl)methoxy]-2'-[3-(2-hydroxypropan-2-yl)-5-methylpyrazol-1-yl]-5',6-dimethyl-[1,4'-bipyridin]-2-one (140 mg) was separated by Prep-Chiral-HPLC to afford rel-3-chloro-4-((3,5-difluoropyridin-2-yl)methoxy)-2'-(3-(2-hydroxypropan-2-yl)-5-methyl-1H-pyrazol-1-yl)-5',6-dimethyl-2H-[1,4'-bipyridin]-2-one (Example 19A, 27.7 mg) and rel-3-chloro-4-((3,5-difluoropyridin-2-yl)methoxy)-2'-(3-(2-hydroxypropan-2-yl)-5-methyl-1H-pyrazol-1-yl)-5',6-dimethyl-2H-[1,4'-bipyridin]-2-one (Example 19B, 35.0 mg) as a white solid.

EXAMPLE 19A

LC-MS: (ES+H, m/z): $[M+H]^+$=516.1. $^1H$ NMR (400 MHZ, DMSO-$d_6$) δ 8.60 (d, 1H), 8.54 (s, 1H), 8.16-8.05 (m, 1H), 7.75 (s, 1H), 6.80 (s, 1H), 6.30 (s, 1H), 5.48 (d, 2H), 4.98 (s, 1H), 2.63 (s, 3H), 2.01 (s, 3H), 1.99 (s, 3H), 1,44 (s, 6H). $^{19}F$ NMR (377 MHz, DMSO) δ-120.155,-120.173,-122.342,-122.361.

EXAMPLE 19B

LC-MS: (ES+H, m/z): $[M+H]^+$=516.1. $^1H$ NMR (400 MHZ, DMSO-$d_6$) δ 8.60 (d, 1H), 8.54 (s, 1H), 8.16-8.05 (m, 1H), 7.75 (s, 1H), 6.80 (s, 1H), 6.30 (s, 1H), 5.48 (d, 2H), 4.98 (s, 1H), 2.63 (s, 3H), 2.01 (s, 3H), 1.99 (s, 3H), 1,44 (s, 6H). $^{19}F$ NMR (377 MHz, DMSO) δ-120.150,-120.176,-122.336,-122.362.

EXAMPLE 20A, 20B

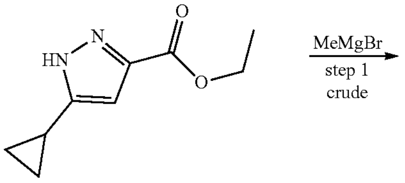

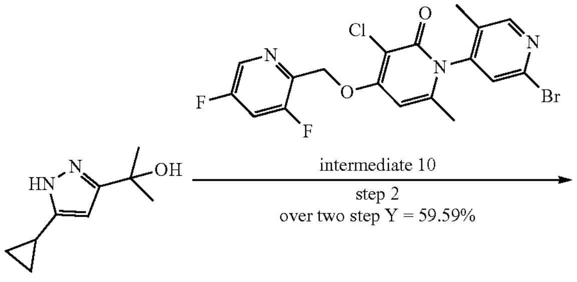

-continued

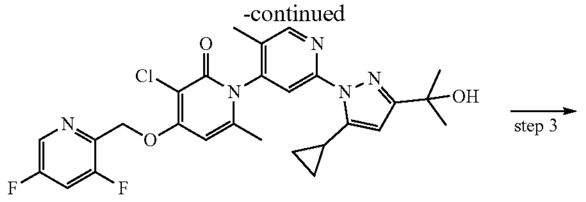

Eample 20

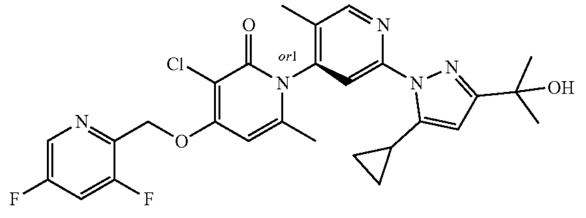

isomer 1
Example 20A

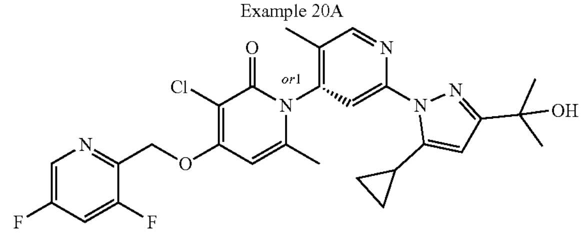

isomer 2
Example 20B

Step 1: Preparation of 2-(5-cyclopropyl-1H-pyrazol-3-yl) propan-2-ol

To a stirred solution of ethyl 5-cyclopropyl-1H-pyrazole-3-carboxylate (500 mg. 2.775 mmol, 1 equiv) in THF (10 mL) was added bromo (methyl) magnesium (13.87 mL, 5 equiv, 1 M in THF) dropwise at −30° C., under $N_2$ atmosphere. The resulting mixture was stirred for 1 h at r.t, under $N_2$ atmosphere. The reaction was monitored by LCMS. The reaction was quenched by the addition of Saturated $NH_4Cl$ (10 mL) at r.t. The resulting mixture was extracted with EtOAc (3 ×10 mL). The combined organic layers were washed with brinc, dried over anhydrous $Na_2SO_4$. After filtration, the filtrate was concentrated under reduced pressure to afford 2-(5-cyclopropyl-1H-pyrazol-3-yl) propan-2-ol (517 mg, crude) as a yellow solid. LC-MS: (ES+H, m/z): $[M+H]^+$=167.2.

Step 2: Preparation of racemate 3-chloro-2'-[5-cyclopropyl-3-(2-hydroxypropan-2-yl)pyrazol-1-yl]-4-[(3,5-difluoropyridin-2-yl)methoxy]-5',6-dimethyl-[1,4'-bipyridin]-2-one A mixture of 2'-bromo-3-chloro-4-[(3.5-difluoropyridin-2-yl)methoxy]-5'0.6-dimethyl-[1,4'-bipyridin]-2-one (300 mg, 0.657 mmol, 1 equiv), 2-(5-cyclopropyl-1H-pyrazol-3-yl) propan-2-ol (218.39 mg. 1.314 mmol. 2 equiv). (IR.2R)-N1.N2-dimethylcyclohexane-1.2-diamine (186.89 mg, 1.314 mmol. 2 equiv). $K_2CO$; (181.58 mg, 1.314 mmol. 2 equiv) and CuI (31.28 mg, 0.164 mmol. 0.25 equiv) in 1,4-dioxane (3 mL) was stirred for 2 h at 100° C., under nitrogen atmosphere. The reaction was monitored by LCMS. The resulting mixture was cooled down to r.t, and poured into 10 ml of water. The resulting mixture was extracted with EtOAc (3 ×10 mL). The combined organic layers were washed with brine (20 mL), dried over anhydrous $Na_2SO_4$. After filtration, the filtrate was concentrated under reduced pressure. The residue was purified by silica gel column chromatography to afford crude product, which was further purified by Prep-HPLC to afford 3-chloro-2'-[5-cyclopropyl-3-(2-hydroxypropan-2-yl)pyrazol-1-yl]-4-[(3.5-difluoro-pyridin-2-yl)methoxy]-5'0.6-dimethyl-[1,4'-bipyridin]-2-one (230 mg. 59.59%) as a white solid. LC-MS: (ES+H, m/z): $[M+H]^+$=542.2.

Step 3: Preparation of rel-3-chloro-2'-[5-cyclopropyl-3-(2-hydroxypropan-2-yl)pyrazol-1-yl]-4-[(3,5-difluoropyridin-2-yl)methoxy]-5',6-dimethyl-[1,4'-bipyridin]-2-one (Example 20A) and rel-3-chloro-2'-[5-cyclopropyl-3-(2-hydroxypropan-2-yl)pyrazol-1-yl]-4-[(3,5-difluoropyridin-2-yl)methoxy]-5',6-dimethyl-[1,4'-bipyridin]-2-one (Example 20B)

The racemate (230 mg) was separated by Prep-Chiral-HPLC to afford Example 20A (78.4 mg) as white solid and Example 20B (90.2 mg.) as white solid.

EXAMPLE 20A

LC-MS: (ES+H, m/z): $[M+H]^+$=541.90. $^1H$ NMR (300 MHz. DMSO-$d_6$) δ 8.61 (d, 1H), 8.57 (s. 1H), 8.15-8.06 (m. 1H), 7.74 (s.1H), 6.81 (s.1H), 6.12 (s.1H), 5.49 (d, 2H), 4.96 (s.1H), 2.81-2.73 (m. 1H), 2.03 (s, 3H), 2.01 (s, 3H), 1,42 (s. 6H), 1.04-0.93 (m, 2H), 0.74-0.62 (m, 2H). $^{19}F$ NMR (282 MHz. DMSO) δ-120.14, —120.17, —122.33, —122.36.

EXAMPLE 20B

LC-MS: (ES+H, m/z): $[M+H]^+$=541.90. $^1H$ NMR (300 MHz. DMSO-$d_6$) δ 8.61 (d, 1H), 8.57 (s. 1H), 8.19-8.03 (m. 1H), 7.74 (s, 1H), 6.81 (s.1H), 6.12 (s, 1H), 5.49 (d, 2H), 4.96 (s.1H), 2.81-2.73 (m. 1H), 2.03 (s, 3H), 2.01 (s, 3H), 1,42 (s. 6H), 1.03-0.94 (m, 2H), 0.78-0.61 (m, 2H), $^{19}F$ NMR (282 MHz. DMSO) δ-120.14, —120.17, —122.33, —122.35.

EXAMPLE 21A, 21B

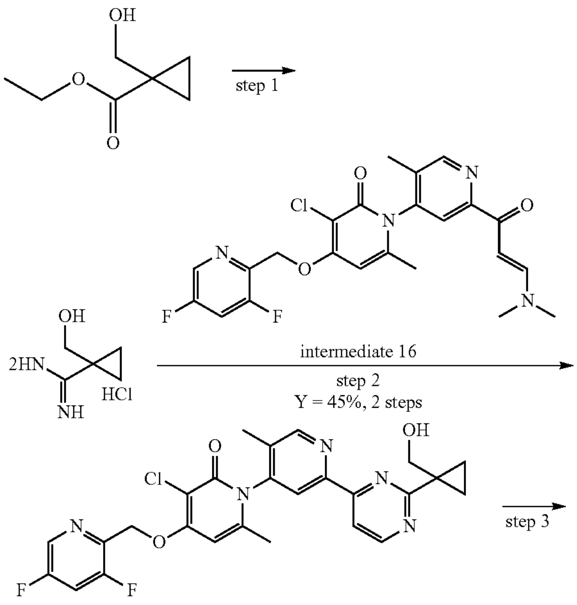

Example 21

-continued

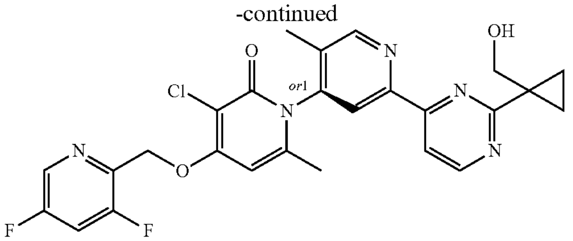

isomer 1
Example 21A

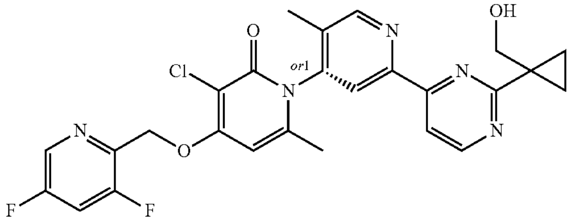

Example 21B

Step 1: Preparation of 1-(hydroxymethyl)cyclopropane-1-carboximidamide hydrochloride To a stirred mixture of $NH_4Cl$ (556.54 mg, 10.405 mmol, 5 equiv) in Toluene (10 mL) was added $AlMe_3$ (5.2 mL, 10.405 mmol, 5 equiv, 2 M in toluene) dropwise at 0° C., under nitrogen atmosphere. The resulting mixture was stirred for 10 min at 0° C., under nitrogen atmosphere, and then was stirred at room temperature until no generation of gas. To the above mixture was added a solution of ethyl 1-(hydroxymethyl)cyclopropane-1-carboxylate (300 mg, 2.081 mmol, 1 equiv) in toluene dropwise at room temperature. The resulting mixture was stirred for additional overnight at 80° C. The reaction was monitored by LCMS. The reaction was quenched by the addition of MeOH (10 mL) at 0° C. The resulting mixture was filtered, the filter cake was washed with MeOH (50 mL). The filtrate was concentrated under reduced pressure. The residue was dissolved in MeOH (30 mL). The resulting mixture was filtered, the filter cake was washed with MeOH (15 mL). The filtrate was concentrated under reduced pressure. This resulted in 1-(hydroxymethyl)cyclopropane-1-carboximidamide hydrochloride (230 mg, crude) as a white solid. $^1H$ NMR (300 MHz, DMSO-$d_6$) δ 8.99 (s, 2H), 8.72 (s, 2H), 5.41 (t, 1H), 3.52 (d, 2H), 1.21-1.12 (m, 2H), 0.99-0.90 (m, 2H).

Step 2: Preparation of 3-chloro-4-[(3,5-difluoropyridin-2-yl)methoxy]-2'-{2-[1-(hydroxymethyl)cyclopropyl] pyrimidin-4-yl}-5',6-dimethyl-[1,4'-bipyridin]-2-one To a stirred mixture of 3-chloro-4-[(3,5-difluoropyridin-2-yl)methoxy]-2'-[(2E)-3-(dimethylamino) prop-2-enoyl]-5',6-dimethyl-[1,4'-bipyridin]-2-one (150 mg, 0.316 mmol, 1.00 equiv) and 1-(hydroxymethyl)cyclopropane-1-carboximidamide hydrochloride (216.33 mg, 1.896 mmol, 6 equiv, assumed 100% yield) in IPA (3 mL) was added $K_2CO_3$ (436.53 mg, 1.896 mmol, 10 equiv) at room temperature under nitrogen atmosphere. The resulting mixture was stirred for overnight at 80° C., under nitrogen atmosphere. The mixture was allowed to cool down to room temperature. The resulting mixture was filtered, the filter cake was washed with MeOH (3 ×10 mL). The filtrate was concentrated under reduced pressure. The residue was purified by Prep-TLC (PE/EA 1:4) to afford 3-chloro-4-[(3,5-difluoropyridin-2-yl)methoxy]-2'-{2-[1-(hydroxymethyl)cyclopropyl] pyrimidin-4-yl}-5',6-dimethyl-[1,4'-bipyridin]-2-one (75 mg, 45%) as a light yellow solid. LC-MS: (ES+H, m/z): $[M+H]^+$=526.1.

Step3: Preparation of (isomer 1) rel-3-chloro-4-((3,5-difluoropyridin-2-yl)methoxy)-2'-(2-(1-(hydroxymethyl)cyclopropyl)pyrimidin-4-yl)-5',6-dimethyl-2H-[1,4'-bipyridin]-2-one and (isomer 2) rel-3-chloro-4-((3,5-difluoropyridin-2-yl)methoxy)-2'-(2-(1-(hydroxymethyl)cyclopropyl)pyrimidin-4-yl)-5',6-dimethyl-2H-[1,4'-bipyridin]-2-one 3-chloro-4-[(3,5-difluoropyridin-2-yl)methoxy]-2'-{2-[1-(hydroxymethyl)cyclopropyl] pyrimidin-4-yl}-5',6-dimethyl-[1,4'-bipyridin]-2-one (70 mg) was separated by Prep-CHIRAL-HPLC to afford rel-3-chloro-4-((3,5-difluoropyridin-2-yl)methoxy)-2'-(2-(1-(hydroxymethyl) cyclopropyl)pyrimidin-4-yl)-5',6-dimethyl-2H-[1,4'-bipyridin]-2-one (Example 21A, isomer 1, 18.4 mg, ee=100%) as a white solid and rel-3-chloro-4-((3,5-difluoropyridin-2-yl)methoxy)-2'-(2-(1-(hydroxymethyl)cyclopropyl)pyrimidin-4-yl)-5',6-dimethyl-2H-[1,4'-bipyridin]-2-one (Example 21B, isomer 2, 19.1 mg, ee=99.1%) as a white solid.

EXAMPLE 21A

LC-MS: (ES+H, m/z): $[M+H]^+$=526.15. $^1$H NMR (400 MHZ, DMSO-$d_6$) δ 8.85 (t, 2H), 8.62 (d, 1H), 8.36 (s, 1H), 8.15-8.06 (m, 2H), 6.84 (s, 1H), 5.49 (d, 2H), 4.56 (t, 1H), 3.97 (d, 2H), 2.09 (s, 3H), 1.97 (s, 3H), 1.38-1.32 (m, 1H), 1.26-1.20 (m, 1H), 1.10-1.04 (m, 2H). $^{19}$F NMR (377 MHz, DMSO) δ -120.10,-120.12,-122.31,-122.33.

EXAMPLE 21B

LC-MS: (ES+H, m/z): $[M+H]^+$=526.15. $^1$H NMR (400 MHZ, DMSO-$d_6$) δ 8.85 (t, 2H), 8.62 (d, 1H), 8.36 (s, 1H), 8.15-8.06 (m, 2H), 6.84 (s, 1H), 5.49 (d, 2H), 4.56 (t, 1H), 3.97 (d, 2H), 2.09 (s, 3H), 1.97 (s, 3H), 1.38-1.31 (m, 1H), 1.27-1.17 (m, 1H), 1.10-1.05 (m, 2H). $^{19}$F NMR (377 MHz, DMSO) δ-120.10,-120.12,-122.31,-122.32.

EXAMPLE 22A, 22B

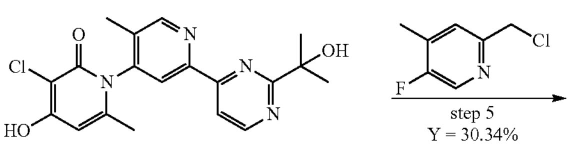

intermediate 30

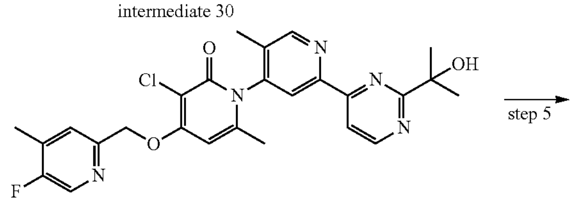

Example 22

-continued

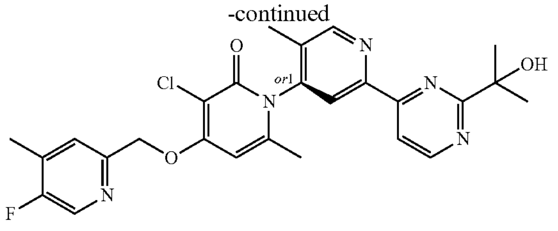

isomer 1
Example 22A

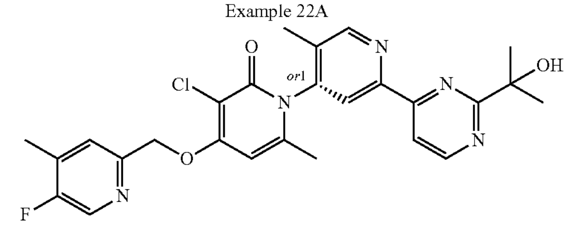

isomer 2
Example 22B

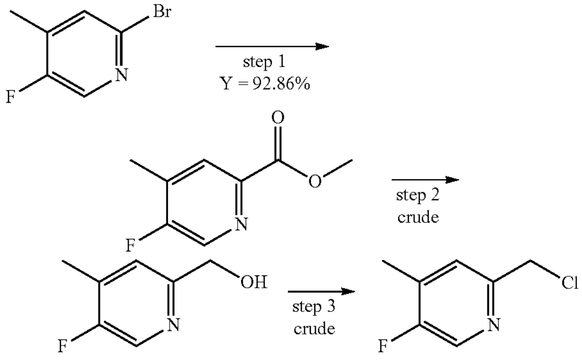

Step 1: methyl 5-fluoro-4-methylpyridine-2-carboxylate

To a stirred mixture of 2-bromo-3-fluoro-5-methylpyridine (3.00 g. 15.78 mmol. 1.00 equiv) and DIEA (10.20 g. 78.94 mmol. 5.00 equiv) in MeOH (14 mL) were added Pd(dppf) $Cl_2$ (0.58 g. 0.78 mmol. 0.05 equiv) at room temperature under air atmosphere. The resulting mixture was stirred for 5 h at 110° C. under carbon monoxide atmosphere (30 atm). The reaction was monitored by LCMS. Desired product could be detected by LCMS. The resulting mixture was concentrated under reduced pressure. The residue was purified by silica gel column chromatography to afford ethyl 3-fluoro-5-methylpyridine-2-carboxylate (2.48 g. 92.86%) as an off-white solid. LC-MS: (ES+H, m/z): $[M+H]^+$=170.2. $^1$H NMR (400 MHZ, DMSO-$d_6$) δ 8.58 (d, 1H), 8.08 (d, 1H), 3.89 (s, 3H), 2.36 (s, 3H).

Step 2: (5-fluoro-4-methylpyridin-2-yl) methanol

To a stirred solution of methyl 5-fluoro-4-methylpyridine-2-carboxylate (1.00 g. 5.91 mmol. 1.00 equiv) in THF (8 mL) and MeOH (2 mL) were added $NaBH_4$ (1.12 g. 29.56 mmol. 5.00 equiv) in portions at room temperature under nitrogen atmosphere. The resulting mixture was stirred for 2 h at room temperature under nitrogen atmosphere. The reaction was monitored by LCMS. Desired product could be detected by LCMS. The reaction was quenched with water (50 mL) at room temperature. The resulting mixture was extracted with EtOAc (100 mL). The combined organic layers were washed with brine (100 mL), dried over anhydrous $Na_2SO_4$. After filtration, the filtrate was concentrated under reduced pressure. The crude product (700 mg) was used in the next step directly without further purification. LC-MS: (ES+H, m/z): $[M+H]^+$=142.2. $^1$H NMR (300 MHz. DMSO-$d_6$) δ 8.33 (d, 1H), 7.42-7.38 (m, 1H), 5.44 (t. 1H), 4.51 (d, 2H), 2.29 (s. 3H).

Step 3:2-(chloromethyl)-5-fluoro-4-methylpyridine

To a stirred solution of (5-fluoro-4-methylpyridin-2-yl) methanol (700 mg. 2.80 mmol. 1.00 equiv) in DCM (6 mL) were added SOCI: (1.5 mL) and DMF (362 mg. 2.80 mmol. 1.00 equiv) dropwisc at room temperature under nitrogen atmosphere. The resulting mixture was stirred for 2 h at room temperature under nitrogen atmosphere. The reaction was monitored by LCMS. Desired product could be detected by LCMS. The resulting mixture was concentrated under reduced pressure. The crude product (838 mg) was used in the next step directly without further purification. LC-MS: (ES+H, m/z): $[M+H]^+$=160.0.

Step 4:3-chloro-4-[(5-fluoro-4-methylpyridin-2-yl) methoxy]-2'-[2-(2-hydroxypropan-2-yl)pyrimidin-4-yl]-5',6-dimethyl-[1,4'-bipyridin]-2-one To a stirred mixture of 3-chloro-4-hydroxy-2'-[2-(2-hydroxypropan-2-yl)pyrimidin-4-yl]-5'0.6-dimethyl-[1,4'-bipyridin]-2-one (500 mg, 1.29 mmol. 1.00 equiv) and 2-(chloromethyl)-5-fluoro-4-methylpyridinc (778 mg. 4.87 mmol. 4.00 equiv) in DMF (4 ml) were added $K_2CO_3$ (891 mg. 6.44 mmol. 4.99 equiv) and 18-Crown-6 (34 mg, 0.13 mmol. 0.10 equiv) at room temperature under nitrogen atmosphere. The resulting mixture was stirred for 2 h at 60° C., under nitrogen atmosphere. The reaction was monitored by LCMS. Desired product could be detected by LCMS. The residue was purified by silica gel column chromatography to afford crude product (280 mg), which was further purified by Prep-HPLC to afford 3-chloro-4-[(5-fluoro-4-methylpyridin-2-yl)methoxy]-2'-[2-(2-hydroxypropan-2-yl)pyrimidin-4-yl]-5',6-dimethyl-[1,4'-bipyridin]-2-one (200 mg, 30.34%) as a white solid. LC-MS: (ES+H, m/z): $[M+H]^+$=510.2.

Step 5: rel-3-chloro-4-[(5-fluoro-4-methylpyridin-2-yl)methoxy]-2'-[2-(2-hydroxypropan-2-yl)pyrimidin-4-yl]-5',6-dimethyl-[1,4'-bipyridin]-2-one and rel-3-chloro-4-[(5-fluoro-4-methylpyridin-2-yl)methoxy]-2'-[2-(2-hydroxypropan-2-yl)pyrimidin-4-yl]-5',6-dimethyl-[1,4'-bipyridin]-2-one The racemate (200 mg) was separated by Prep-Chiral-HPLC to afford Example 22A (73 mg, 99.4%, ee=100%) as a white solid and Example 22B (69.8 mg, 99.4%, ee=98.8%) as a white solid.

EXAMPLE 22A

LC-MS: (ES+H, m/z): $[M+H]^+$=510.15. $^1$H NMR (400 MHZ, DMSO-$d_6$) δ 8.97 (d, 1H), 8.86 (s, 1H), 8.68 (s, 1H), 8.51 (d, 1H), 8.24 (d, 1H), 7.58 (d, 1H), 6.81 (s, 1H), 5.38 (d, 2H), 5.25 (s, 1H), 2.35 (d, 3H), 2.11 (s, 3H), 1.98 (s, 3H), 1.53 (s, 6H). $^{19}$F NMR (377 MHz, DMSO) δ-133.88.

EXAMPLE 22B

LC-MS: (ES+H, m/z): $[M+H]^+$=510.10. $^1$H NMR (400 MHZ, DMSO-$d_6$) δ 8.97 (d, 1H), 8.86 (s, 1H), 8.68 (s, 1H), 8.51 (d, 1H), 8.24 (d, 1H), 7.58 (d, 1H), 6.83-6.78 (m, 1H), 5.38 (d, 2H), 5.25 (s, 1H), 2.35 (d, 3H), 2.11 (s, 3H), 1.98 (s, 3H), 1.53 (s, 6H). $^{19}$F NMR (377 MHz, DMSO) δ-133.88.

EXAMPLE 23A, 23B

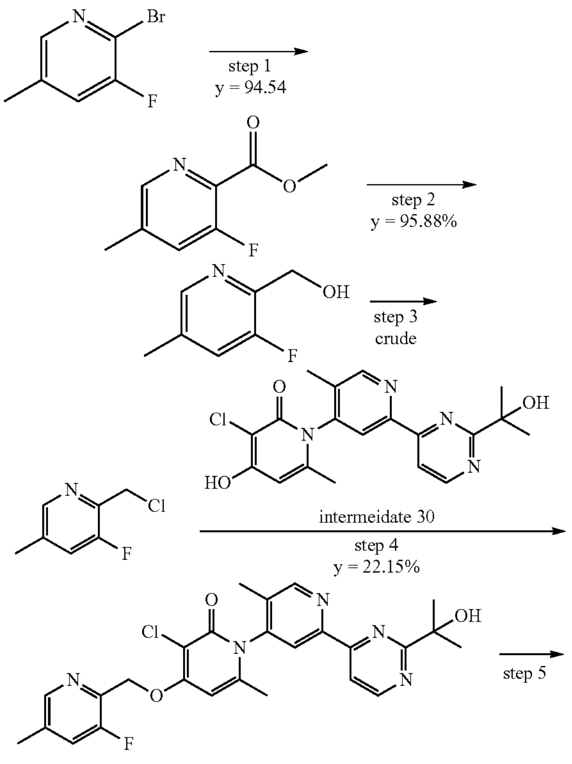

Example 23

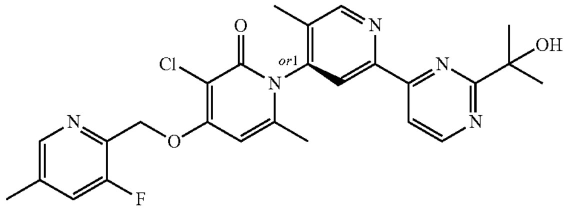

isomer 1
Example 23A

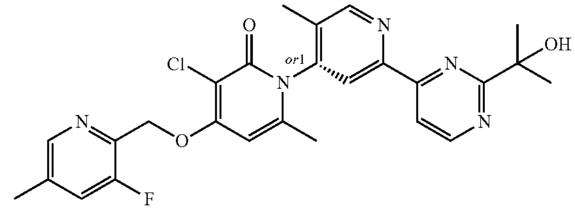

isomer 2
Example 23B

Step 1: Preparation of methyl 3-fluoro-5-methylpyridine-2-carboxylate

A mixture of 2-bromo-3-fluoro-5-methylpyridine (3 g, 15.788 mmol, 1 equiv), Pd(dppf) $Cl_2$ (1.16 g. 1.579 mmol, 0.1 equiv) and DIEA (10.20 g. 78.940 mmol, 5 equiv) in MeOH (30 mL) was stirred for 3 h at 110° C., under carbon monoxide atmosphere (30 atm). The reaction was monitored by LCMS. The resulting mixture was concentrated under reduced pressure. The residue was purified by silica gel column chromatography to afford methyl 3-fluoro-5-methylpyridine-2-carboxylate (2.54 g, 94.54%) as an off-white solid. LC-MS: (ES+H, m/z): $[M+H]^+$=170.1. $^1$H NMR (300 MHz, DMSO-$d_6$) δ 8.43-8.34 (m, 1H), 7.80-7.70 (m, 1H), 3.88 (s, 3H), 2.40 (t, 3H).

Step 2: Preparation of (3-fluoro-5-methylpyridin-2-yl) methanol

A mixture of methyl 3-fluoro-5-methylpyridine-2-carboxylate (500 mg, 2.956 mmol, 1 equiv) and $NaBH_4$ (447.32 mg, 11.824 mmol, 4 equiv) in THF (4 mL) and methanol (1 mL) was stirred for 2 h at r.t. The reaction was monitored by LCMS. The reaction was quenched with water at r, t. The resulting mixture was extracted with EtOAc (3 ×10 mL). The combined organic layers were washed with brine (30 mL), dried over anhydrous $Na_2SO_4$. After filtration, the filtrate was concentrated under reduced pressure to afford (3-fluoro-5-methylpyridin-2-yl) methanol (400 mg. 95.88%) as a yellow solid. LC-MS: (ES+H, m/z): $[M+H]^+$=142.1. $^1$H NMR (300 MHz. DMSO-$d_6$) δ 8.22 (d, 1H), 7.56-7.43 (m, 1H), 5.23 (t. 1H), 4.59-4.48 (m, 2H). 2.32 (s, 3H).

Step 3: Preparation of 2-(chloromethyl)-3-fluoro-5-methylpyridine

A mixture of (3-fluoro-5-methylpyridin-2-yl) methanol (387 mg. 2.742 mmol. I equiv). DMF (20.04 mg, 0.274 mmol, 0.1 equiv) and SOCI: (1.5 mL. 20.677 mmol. 7.54 equiv) in $CH_2Cl_2$ (3 mL) was stirred for 2 h at r.t. The reaction was monitored by LCMS. The resulting mixture was concentrated under reduced pressure to afford 2-(chloromethyl)-3-fluoro-5-methylpyridinc (638 mg, crude) as a yellow solid. LC-MS: (ES+H, m/z): $[M+H]^+$=160.0.

Step 4: Preparation of 3-chloro-4-[(3-fluoro-5-methylpyridin-2-yl)methoxy]-2'-[2-(2-hydroxypropan-2-yl)pyrimidin-4-yl]-5',6-dimethyl-[1,4'-bipyridin]-2-one A mixture of 2-(chloromethyl)-3-fluoro-5-methylpyridine (412.55 mg. 2.586 mmol. 2 equiv), 3-chloro-4-hydroxy-2'-[2-(2-hydroxypropan-2-yl)pyrimidin-4-yl]-5'0.6-dimethyl-] 1,4'-bipyridin]-2-one (500 mg. 1.293 mmol. 1.00 equiv). $K_2CO$; (893.17 mg. 6.465 mmol. 5 equiv) and 18-Crown-6 (34.16 mg, 0.129 mmol. 0.1 equiv) in DMF was stirred for overnight at 60° C., under nitrogen atmosphere. The reaction was monitored by LCMS. The resulting mixture was cooled down to r.t, and poured into 10 mL of water. The resulting mixture was extracted with EtOAc (3 ×10 mL). The combined organic layers were washed with brine (20 mL), dried over anhydrous $Na_2SO_4$. After filtration, the filtrate was concentrated under reduced pressure. The residue was purified by silica gel column chromatography to afford crude product, which was further purified by Prep-HPLC to afford 3-chloro-4-[(3-fluoro-5-methylpyridin-2-yl)methoxy]-2'-[2-(2-hydroxypropan-2-yl)pyrimidin-4-yl]-5'0.6-dimethyl-[1, 4'-bipyridin]-2-one (149 mg. 22.15%) as a white solid. LC-MS: (ES+H, m/z): $[M+H]^+$=510.1.

Step 5: Preparation of rel-3-chloro-4-[(3-fluoro-5-methylpyridin-2-yl)methoxy]-2'-[2-(2-hydroxypropan-2-yl)pyrimidin-4-yl]-5',6-dimethyl-[1,4'-bipyridin]-2-one and rel-3-chloro-4-[(3-fluoro-5-methylpyridin-2-yl)methoxy]-2'-[2-(2-hydroxypropan-2-yl)pyrimidin-4-yl]-5',6-dimethyl-[1,4'-bipyridin]-2-one The racemate (149 mg) was separated by Prep-Chiral-HPLC to afford Example 23A (64.4 mg. 99.2%, ee=100%) as a white solid and Example 23B (57.6 mg. 99.5%, ee=99.8%) as a white solid.

EXAMPLE 23A

LC-MS: (ES+H, m/z): $[M+H]^+$=510.10. $^1$H NMR (400 MHz. DMSO-$d_6$) δ 8.97 (d, 1H), 8.86 (s. 1H), 8.69 (s, 1H), 8.36 (s, 1H), 8.24 (d, 1H), 7.75-7.67 (m, 1H), 6.85 (s, 1H), 5.45 (d, 2H), 5.25 (s.1H). 2.39 (s, 3H), 2.11 (s, 3H), 1.98 (s, 3H), 1.54 (s, 3H), 1.53 (s, 3H). $^{19}$F NMR (377 MHz. DMSO) δ-126.190.

EXAMPLE 23B

LC-MS: (ES+H, m/z): $[M+H]^+$=510.10. $^1$H NMR (400 MHZ, DMSO-$d_6$) δ 8.97 (d, 1H), 8.86 (s, 1H), 8.69 (s, 1H), 8.36 (s, 1H), 8.24 (d, 1H), 7.74-7.69 (m, 1H), 6.85 (s, 1H), 5.45 (d, 2H), 5.25 (s, 1H), 2.39 (s, 3H), 2.11 (s, 3H), 1.98 (s, 3H), 1.54 (s, 3H), 1.53 (s, 3H). $^{19}$F NMR (282 MHZ, DMSO) δ-126.192.

EXAMPLE 24A, 24B

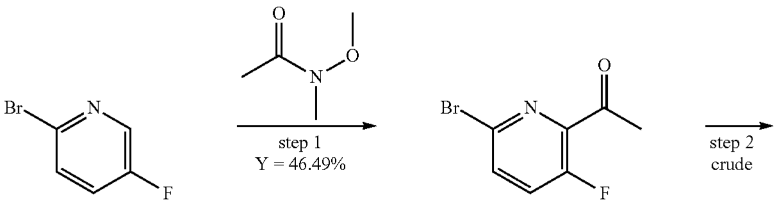

-continued

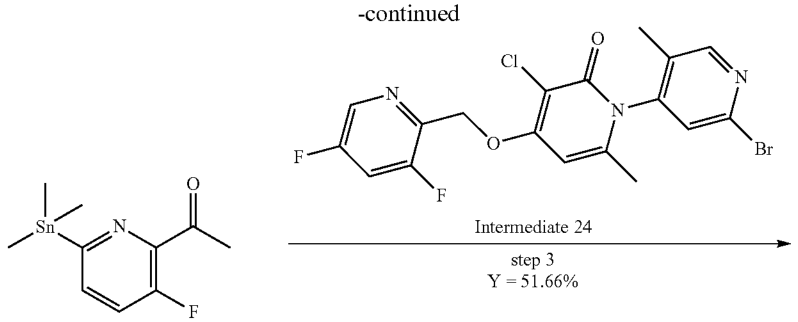

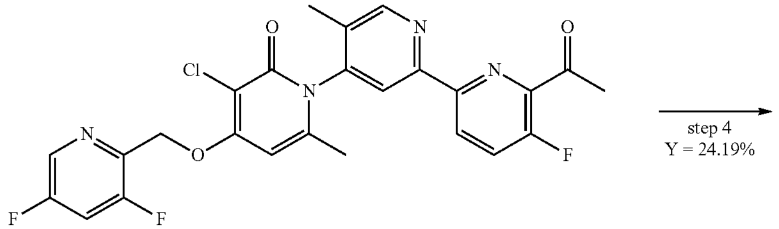

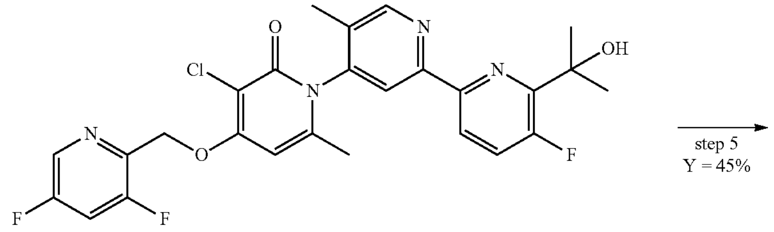

Example 24

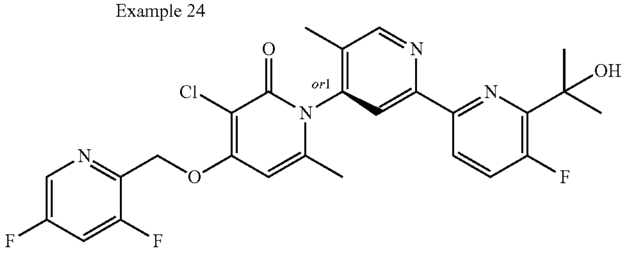

isomer 1
Example 24A

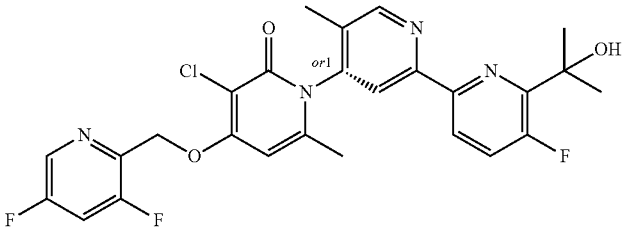

isomer 2
Example 24B

Step 1: Preparation of 1-(6-bromo-3-fluoropyridin-2-yl)ethanone

To a stirred solution of 2-bromo-5-fluoropyridine (20 g, 113.644 mmol, 1 equiv) in Et,O (500 mL) was added t-BuLi (50.00 mL, 125.008 mmol, 1.1 equiv) dropwise at −78° C., under nitrogen atmosphere. The resulting mixture was stirred for 2 h at −78° C., under nitrogen atmosphere. N-methoxy-N-methylacetamide (12.89 g, 125.008 mmol, 1.1 equiv) was added dropwise to the above solution at −78° C., under nitrogen atmosphere. The resulting mixture was stirred for 1 h at −78° C., under nitrogen atmosphere. The mixture was allowed to warm up to room temperature. The reaction was monitored by LCMS. The reaction was quenched by the addition of sat. $NH_4Cl$ (aq.) (500 mL). The organic phase was collected. The aqueous layer was extracted with EtOAc (2×500 mL). The combined organic layers were dried over anhydrous $Na_2SO_4$. After filtration, the filtrate was concentrated under reduced pressure. The residue was purified by silica gel column chromatography to afford 1-(6-bromo-3-fluoropyridin-2-yl)ethanone (12 g, 46.49%) as a reddish semi-solid. LC-MS: (ES+H, m/z): $[M+H]^+$=220.0. $^1H$ NMR (400 MHZ, DMSO-$d_6$) δ 8.03-7.95 (m, 1H), 7.94-7.85 (m, 1H), 2.58 (s, 3H).

Step 2: Preparation of 1-[3-fluoro-6-(trimethylstannyl)pyridin-2-yl]ethanone

To a stirred mixture of 1-(6-bromo-3-fluoropyridin-2-yl) ethanone (1.2 g, 5.504 mmol, 1 equiv) and $Sn_2Me_6$ (7.21 g, 22.016 mmol, 4 equiv) in 1,4-dioxane (20 mL) was added $Pd(PPh_3)_2Cl_2$ (0.77 g, 1.101 mmol, 0.2 equiv) and $AsPh_3$ (0.34 g, 1.101 mmol, 0.2 equiv) at room temperature. The resulting mixture was stirred for overnight at 80° C., under nitrogen atmosphere. The reaction was monitored by LCMS. The mixture was allowed to cool down to room temperature. The resulting mixture was poured into EA (200 ml) and washed with 5×200 mL of KF (aq.). The organic layer was dried over anhydrous $Na_2SO_4$. After filtration, the filtrate was concentrated under reduced pressure to afford 1-[3-fluoro-6-(trimethylstannyl)pyridin-2-yllethanone (crude). The crude product was used in the next step directly without further purification. LC-MS: (ES+H, m/z): $[M+H]^+$=304.0

Step 3: Preparation of 1-{6'-acetyl-5'-fluoro-5-methyl-[2,2'-bipyridin]-4-yl}-3-chloro-4-[(3,5-difluoropyridin-2-yl)methoxy]-6-methylpyridin-2-one To a stirred solution of 1-[3-fluoro-6-(trimethylstannyl) pyridin-2-yllethanone (1190.10 mg. 3.942 mmol. 3 equiv) and 2'-bromo-3-chloro-4-[(3.5-difluoropyridin-2-yl) methoxy]-5',6-dimethyl-] 1,4'-bipyridin]-2-one (600 mg, 1.314 mmol. 1.00 equiv) in 1,4-dioxane (15 mL) were added $Pd(PPh_3)$: Cl: (92.22 mg, 0.131 mmol. 0.1 equiv) and CuI (250.22 mg, 1.314 mmol. I equiv) at room temperature. The resulting mixture was stirred for 3 h at 80° C., under nitrogen atmosphere. The mixture was allowed to cool down to room temperature. The reaction was monitored by LCMS. The resulting mixture was poured into water (200 ml), and extracted with EtOAc (3 ×200 mL). The combined organic layers were dried over anhydrous $Na_2SO_4$. After filtration, the filtrate was concentrated under reduced pressure. The residue was purified by silica gel column chromatography to afford 1-{6'-acetyl-5'-fluoro-5-methyl-[2.2'-bipyridin]-4-yl}-3-chloro-4-[(3.5-difluoropyridin-2-yl)methoxy]-6-methylpyridin-2-one (500 mg. 51.66%) as a white solid. LC-MS: (ES+H, m/z): $[M+H]^+$=515.1. $^1H$ NMR (400 MHZ. DMSO-$d_6$) δ 8.81 (s.1H), 8.70-8.64 (m. 1H), 8.64-8.59 (m. 1H), 8.34 (s.1H), 8.15-8.07 (m. 1H), 8.07-8.00 (m. 1H), 6.83 (s.1H), 5.49 (s, 2H), 2.73 (s, 3H), 2.08 (s. 3H), 1.98 (s, 3H).

Step 4: Preparation of 3-chloro-4-[(3,5-difluoropyridin-2-yl)methoxy]-1-[5'-fluoro-6'-(2-hydroxypropan-2-yl)-5-methyl-[2,2'-bipyridin]-4-yl]-6-methylpyridin-2-one To a stirred mixture of 1-{6'-acetyl-5'-fluoro-5-methyl-[2.2'-bipyridin]-4-yl}-3-chloro-4-[(3.5-difluoropyridin-2-yl)methoxy]-6-methylpyridin-2-one (450 mg, 0.874 mmol. I equiv) in THF (6 mL) was added MeMgBr (2.91 mL. 8.740 mmol. 10 equiv) dropwise at 0° C., under nitrogen atmosphere. The resulting mixture was stirred for 1 h at 0° C., under nitrogen atmosphere. The reaction was monitored by LCMS. The reaction was quenched with sat. $NH_4Cl$ (aq.) at 0° C. The resulting mixture was extracted with EtOAc (3 ×100 mL). The combined organic layers were dried over anhydrous $Na_2SO_4$. After filtration, the filtrate was concentrated under reduced pressure. The crude product was purified by Prep-HPLC to afford 3-chloro-4-[(3.5-difluoropyridin-2-yl)methoxy]-1-[5'-fluoro-6'-(2-hydroxypropan-2-yl)-5-methyl-]2.2'-bipyridin]-4-yl]-6-methylpyridin-2-one (80 mg. 24.19%) as a white solid. LC-MS: (ES+H, m/z): $[M+H]^+$=531.1. Step 5: Preparation of rel-3-chloro-4-[(3,5-difluoropyridin-2-yl)methoxy]-1-[5'-fluoro-6'-(2-hydroxypropan-2-yl)-5-methyl-[2,2'-bipyridin]-4-yl]-6-methylpyridin-2-one and rel-3-chloro-4-[(3,5-difluoropyridin-2-yl) methoxy]-1-[5'-fluoro-6'-(2-hydroxypropan-2-yl)-5-methyl-[2,2'-bipyridin]-4-yl]-6-methylpyridin-2-one The racemate 3-chloro-4-[(3.5-difluoropyridin-2-yl) methoxy]-1-[5'-fluoro-6'-(2-hydroxypropan-2-yl)-5-methyl-[2.2'-bipyridin]-4-yl]-6-methylpyridin-2-one (80 mg) was separated by Prep-Chiral-HPLC to afford rel-3-chloro-4-[(3.5-difluoropyridin-2-yl)methoxy]-1-[5'-fluoro-6'-(2-hydroxypropan-2-yl)-5-methyl-[2.2'-bipyridin]-4-yl]-6-methylpyridin-2-one (Example 24A. 18.6 mg. 98.8%, ce=100%) as a white solid and rel-3-chloro-4-[(3.5-difluoropyridin-2-yl)methoxy]-1-[5'-fluoro-6'-(2-hydroxypropan-2-yl)-5-methyl-[2.2'-bipyridin]-4-yl]-6-methylpyridin-2-one (Example 24B. 17.5 mg. 99.7%, ce=98.6% %) as a white solid.

EXAMPLE 24A

LC-MS: (ES+H, m/z): $[M+H]^+$=531.25. $^1H$ NMR (400 MHZ, DMSO-$d_6$) δ 8.77 (s, 1H), 8.62 (d, 1H), 8.49 (s, 1H), 8.43-8.35 (m, 1H), 8.17-8.05 (m, 1H), 7.90-7.78 (m, 1H), 6.83 (s, 1H), 5.49 (s, 2H), 5.46 (s, 1H), 2.07 (s, 3H), 1.99 (s, 3H), 1.55 (s, 6H). $^{19}F$ NMR (377 MHz, DMSO) δ-119.955,-120.122,-120.148,-122.312,-122.337.

EXAMPLE 24B

LC-MS: (ES+H, m/z): $[M+H]^+$=531.25. $^1H$ NMR (400 MHZ, DMSO-$d_6$) δ 8.77 (s, 1H), 8.62 (d, 1H), 8.49 (s, 1H), 8.43-8.35 (m, 1H), 8.17-8.05 (m, 1H), 7.90-7.78 (m, 1H), 6.83 (s, 1H), 5.49 (s, 2H), 5.46 (s, 1H), 2.06 (s, 3H), 1.99 (s, 3H), 1.55 (s, 6H). $^{19}F$ NMR (377 MHz, DMSO) δ-119.954,-120.119,-120.144,-122.307,-122.332.

EXAMPLE 25, 25A, 25B

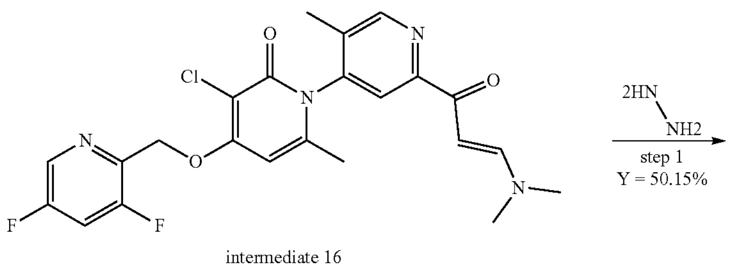

intermediate 16

-continued

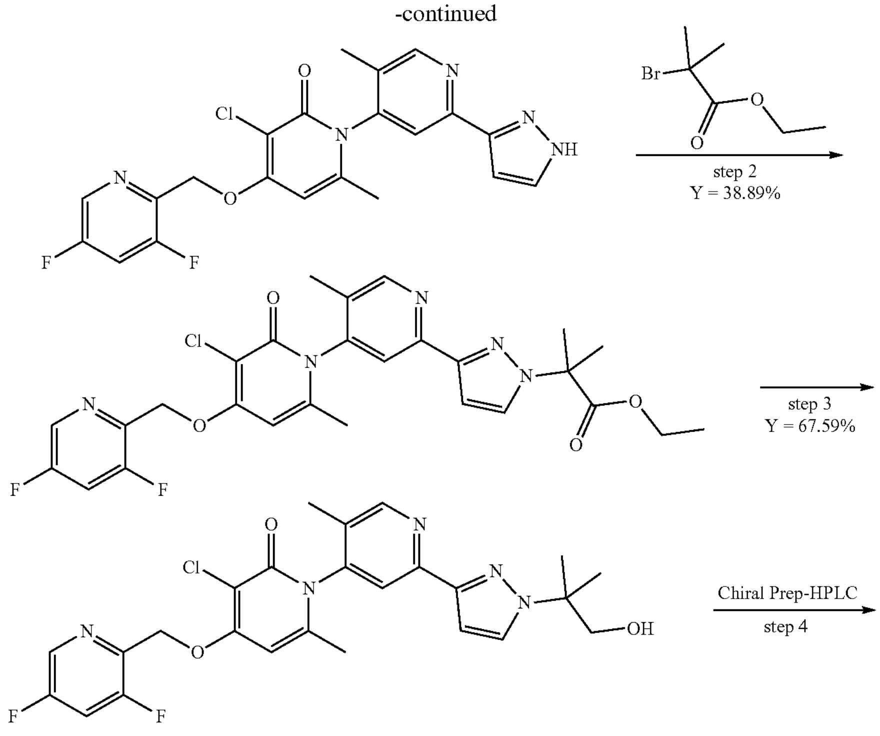

Example 25

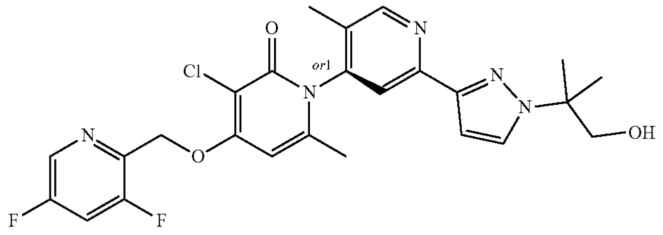

Isomer 1
Example 25A

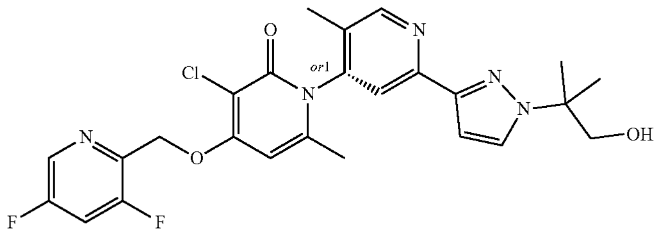

isomer 2
Example 25B

Step 1:3-chloro-4-((3,5-difluoropyridin-2-yl) methoxy)-5',6-dimethyl-2'-(1H-pyrazol-3-yl)-2H-[1,4'-bipyridin]-2-one To a stirred solution of 3-chloro-4-[(3,5-difluoropyridin-2-yl)methoxy]-2'-[(2E)-3-(dimethylamino) prop-2-enoyl]-5',6-dimethyl-[1,4'-bipyridin]-2-one (960 mg, 2.022 mmol, 1.00 equiv) and $K_2CO_3$ (558.77 mg, 4.044 mmol, 2 equiv) in ACN(10 mL) was added hydrazine (20 mL, IM in THF, 20.220 mmol, 10 equiv) at room temperature. The resulting mixture was stirred for overnight at 80° C., under nitrogen atmosphere. The reaction was monitored by LCMS. Desired product could be detected by LCMS. The resulting mixture was diluted with water (20 mL). The resulting mixture was extracted with EtOAc (2x20 mL). The combined organic layers were dried over anhydrous $Na_2SO_4$. After filtration, the filtrate was concentrated under reduced pressure. The residue was purified by reverse flash chromatography to afford 3-chloro-4-[(3,5-difluoropyridin-2-yl)methoxy]-5',6-dimethyl-2'-(1H-pyrazol-3-yl)-[1,4'-bipyridin]-2-one (450 mg, 50.15%) as a yellow solid. LC-MS: (ES+H, m/z): $[M+H]^+$=444.1. 1H NMR (400 MHZ, DMSO-$d_6$) δ 13.11 (s, 1H), 8.67 (s, 1H), 8.61 (d, 1H), 8.16-8.05 (m, 1H), 7.81 (s, 2H), 6.87 (d, 1H), 6.80 (s, 1H), 5.49 (s, 2H), 2.02 (s, 3H), 1.98 (s, 3H).

Step 2: ethyl 2-(3-(3-chloro-4-((3,5-difluoropyridin-2-yl)methoxy)-5',6-dimethyl-2-oxo-2H-[1,4'-bipyridin]-2'-yl)-1H-pyrazol-1-yl)-2-methylpropanoate To a stirred solution of 3-chloro-4-[(3,5-difluoropyridin-2-yl)methoxy]-5',6-dimethyl-2'-(1H-pyrazol-3-yl)-[1,4'-bipyridin]-2-one (450 mg, 1.014 mmol, 1 equiv) and $K>CO_3$ (280.25 mg, 2.028 mmol, 2 equiv) in DMF (5 mL) was added ethyl α-bromoisobutyrate (988.82 mg. 5.070 mmol. 5 equiv) dropwisc at room temperature. The resulting mixture was stirred for overnight at 80° C., under nitrogen atmosphere. The reaction was monitored by LCMS. LCMS was ok. The resulting mixture was diluted with water (20 mL) and extracted with EtOAc (2×20 mL). The combined organic layers were dried over anhydrous $Na_2SO_4$. After filtration, the filtrate was concentrated under reduced pressure. The residue was purified by reverse flash chromatography to afford ethyl 2-(3-{3-chloro-4-[(3.5-difluoropyridin-2-yl)methoxy]-5'0.6-dimethyl-2-oxo-[1,4'-bipyridin]-2'-yl}pyrazol-1-yl)-2-methylpropanoate (220 mg. 38.89%) as a yellow solid. LC-MS: (ES+H, m/z): $[M+H]^+$=558.3. $^1H$ NMR (400 MHZ. DMSO-$d_6$) δ 8.66 (s, 1H), 8.61 (d, 1H), 8.13-8.06 (m. 1H), 8.02 (d, 1H), 7.75 (s, 1H), 6.89 (d, 1H), 6.79 (s, 1H), 5.48 (s. 2H), 4.18-4.00 (m, 2H), 2.01 (s, 3H), 1.96 (s, 3H), 1.82 (s. 6H), 1.11 (t. 3H).

Step 3:3-chloro-4-((3,5-difluoropyridin-2-yl)methoxy)-2'-(1-(1-hydroxy-2-methylpropan-2-yl)-1H-pyrazol-3-yl)-5',6-dimethyl-2H-[1,4'-bipyridin]-2-one To a stirred solution of ethyl 2-(3-{3-chloro-4-[(3.5-difluoropyridin-2-yl)methoxy]-5'0.6-dimethyl-2-oxo-[1,4'-bipyridin]-2'-yl}pyrazol-1-yl)-2-methylpropanoate (160 mg, 0.287 mmol, 1 equiv) in THF (3 mL) and MeOH (1 mL) was added $NaBH_4$ (54.24 mg, 1,435 mmol. 5 equiv) at room temperature. The resulting mixture was stirred for 4 h at room temperature under nitrogen atmosphere. The reaction was monitored by LCMS. LCMS was ok. The resulting mixture was quenched by addition of saturated NH,CI aq . . , then poured into water (20 mL). The resulting mixture was extracted with EtOAc (2×15 mL). The combined organic layers were dried over anhydrous $Na_2SO_4$. After filtration, the filtrate was concentrated under reduced pressure to afford 3-chloro-4-[(3.5-difluoropyridin-2-yl)methoxy]-2'-[1-(1-hydroxy-2-methylpropan-2-yl)pyrazol-3-yl]-5'0.6-dimethyl-[1,4'-bipyridin]-2-one (100 mg. 67.59%) as a pale yellow solid. LC-MS: (ES+H, m/z): $[M+H]^+$=515.9.

Step 4: rel-3-chloro-4-((3,5-difluoropyridin-2-yl)methoxy)-2'-(1-(1-hydroxy-2-methylpropan-2-yl)-1H-pyrazol-3-yl)-5',6-dimethyl-2H-[1,4'-bipyridin]-2-one and rel-3-chloro-4-((3,5-difluoropyridin-2-yl)methoxy)-2'-(1-(1-hydroxy-2-methylpropan-2-yl)-1H-pyrazol-3-yl)-5',6-dimethyl-2H-[1,4'-bipyridin]-2-one The racemate was separated by Chiral Prep-HPLC to afford rel-3-chloro-4-[(3.5-difluoropyridin-2-yl)methoxy]-2'-[1-(1-hydroxy-2-methylpropan-2-yl)pyrazol-3-yl]-5'0.6-dimethyl-] 1,4'-bipyridin]-2-onc (Example 25A. 41.6 mg, ee=100%) as a white solid and rel-3-chloro-4-[(3.5-difluoropyridin-2-yl)methoxy]-2'-[1-(1-hydroxy-2-methylpropan-2-yl)pyrazol-3-yl]-5'0.6-dimethyl-[1,4'-bipyridin]-2-one (Example 25B. 47.3 mg, ee=99.9%) as a white solid.

EXAMPLE 25A

LC-MS: (ES+H, m/z): $[M+H]^+$=516.10. $^1H$ NMR (300 MHz. DMSO-$d_6$) δ 8.65 (s.1H), 8.61 (d. 1H), 8.16-8.07 (m. 1H), 7.88 (d, 1H), 7.77 (s.1H), 6.87-6.73 (m, 2H), 5.49 (s, 2H), 4.99 (t. 1H), 3.70-3.57 (m, 2H), 2.01 (s, 3H), 1.98 (s, 3H), 1.51 (s. 6H), 10F NMR (282 MHz. DMSO) δ-120.16,-120.18.-122.36, —122.39.

EXAMPLE 25B

LC-MS: (ES+H, m/z): $[M+H]^+$=516.15. $^1H$ NMR (400 MHZ, DMSO-$d_6$) δ 8.64 (s, 1H), 8.61 (d, 1H), 8.15-8.06 (m, 1H), 7.87 (d, 1H), 7.77 (s, 1H), 6.84-6.75 (m, 2H), 5.52-5.45 (m, 2H), 4.97 (t, 1H), 3.66-3.58 (m, 2H), 2.00 (s, 3H), 1.98 (s, 3H), 1.50 (s, 6H). $^{19}F$ NMR (377 MHz, DMSO) δ-120.16,-120.18,-122.37,-122.39.

EXAMPLE 26A, 26B

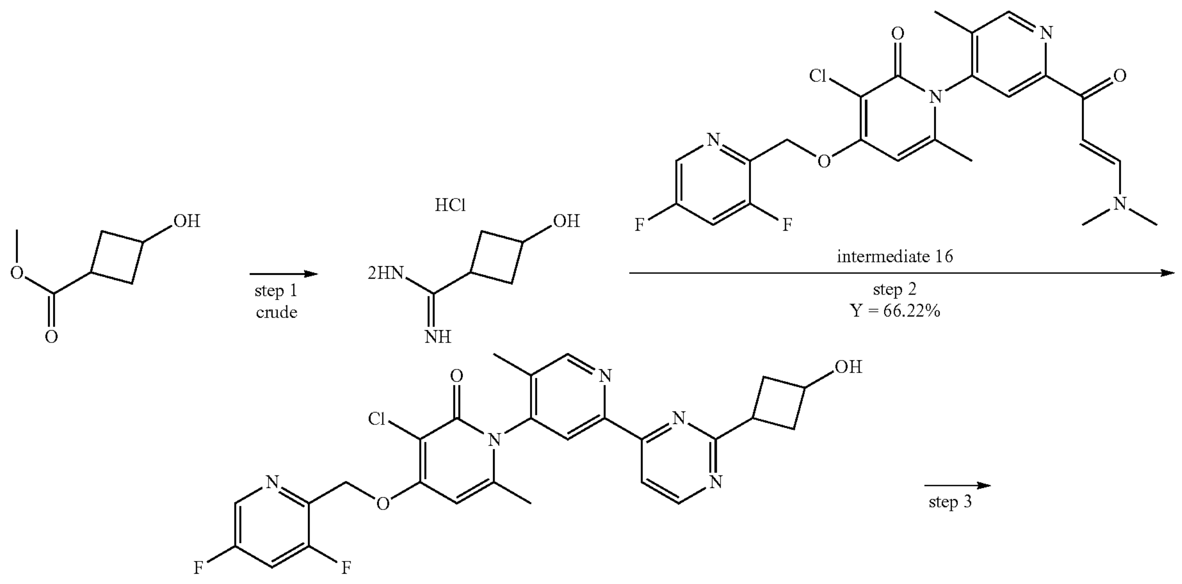

Example 26

-continued

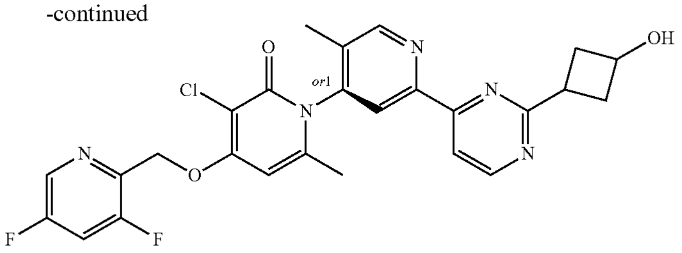

isomer 1
Example 26A

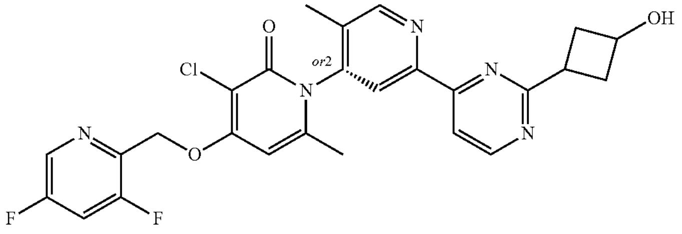

isomer 2
Example 26B

Step 1: Preparation of 3-hydroxycyclobutane-1-carboximidamide

To a stirred mixture of $NH_4Cl$ (2.06 g, 38.420 mmol, 5 equiv) in Toluene (10 mL) was added $AlMe_3$ (19.21 mL, 38.420 mmol, 5 equiv) dropwise at 0° C., under nitrogen atmosphere. The resulting mixture was stirred for 10 min at 0° C., under nitrogen atmosphere, and then was stirred at room temperature until no generation of gas. To the above mixture was added a solution of methyl 3-hydroxycyclobutane-1-carboxylate (1 g. 7.684 mmol, 1 equiv) in toluene dropwise at r.t . . . . The resulting mixture was stirred for overnight at 80° C. The reaction was monitored by LCMS. The reaction was quenched by the addition of MeOH (20 mL) at 0° C. The resulting mixture was filtered, the filter cake was washed with MeOH (150 mL). The filtrate was concentrated under reduced pressure. The residue was dissolved in EtOH (20 mL). The resulting mixture was filtered, the filter cake was washed with EtOH (10 mL). The filtrate was concentrated under reduced pressure. This resulted in 3-hydroxycyclobutane-1-carboximidamide (1.1 g, crude) as a white solid. $^1H$ NMR (400 MHZ, DMSO-$d_6$) δ 8.93 (s, 1H), 8.82 (s, 2H), 5.42 (d, 1H), 4.43-4.33 (m, 1H), 2.79-2.71 (m, 1H), 2.49-2.42 (m, 2H), 2.11-2.06 (m, 2H).

Step 2: Preparation of 3-chloro-4-[(3,5-difluoropyridin-2-yl)methoxy]-2'-[2-(3-hydroxycyclobutyl)pyrimidin-4-yl]-5',6-dimethyl-[1,4'-bipyridin]-2-one A mixture of 3-chloro-4-[(3,5-difluoropyridin-2-yl) methoxy]-2'-[(2E)-3-(dimethylamino) prop-2-enoyl]-5',6-dimethyl-[1,4'-bipyridin]-2-one (150 mg, 0.316 mmol, 1.00 equiv), $K_2CO_3$ (873.08 mg, 6.320 mmol, 20 equiv) and 3-hydroxycyclobutane-1-carboximidamide (360.55 mg, 3.160 mmol, 10 equiv) in IPA (8 mL) was stirred for overnight at 80° C., under nitrogen atmosphere. The reaction was monitored by LCMS. The resulting mixture was allowed to r.t . . . . The resulting mixture was diluted with EA (200 mL). The resulting mixture was washed with 2×100 mL of water. The organic layers were concentrated under reduced pressure. The residue was purified by Prep-TLC (EA) to afford3-chloro-4-[(3,5-difluoropyridin-2-yl) methoxy]-2'-[2-(3-hydroxycyclobutyl)pyrimidin-4-yl]-5',6-dimethyl-[1,4'-bipyridin]-2-one (150 mg, crude). The crude product was further purified by reversed combi-flash chromatography. The pure fraction was concentrated under reduce pressure to afford 3-chloro-4-[(3,5-difluoropyridin-2-yl)methoxy]-2'-[2-(3-hydroxycyclobutyl)pyrimidin-4-yl]-5',6-dimethyl-[1,4'-bipyridin]-2-one (110 mg, 66.22%) as a white solid. LC-MS: (ES+H, m/z): $[M+H]^+$=526.3.

Step 3: Preparation of rel-3-chloro-4-((3,5-difluoropyridin-2-yl)methoxy)-2'-(2-(3-hydroxycyclobutyl) pyrimidin-4-yl)-5',6-dimethyl-2H-[1,4'-bipyridin]-2-one & rel-3-chloro-4-((3,5-difluoropyridin-2-yl) methoxy)-2'-(2-(3-hydroxycyclobutyl)pyrimidin-4-yl)-5',6-dimethyl-2H-[1,4'-bipyridin]-2-one 3-chloro-4-[(3,5-difluoropyridin-2-yl)methoxy]-2'-[2-(3-hydroxycyclobutyl)pyrimidin-4-yl]-5',6-dimethyl-[1,4'-bipyridin]-2-one (100 mg, 0.190 mmol, 1 equiv) was isolated by Prep-Chiral-HPLC to afford rel-3-chloro-4-((3,5-difluoropyridin-2-yl)methoxy)-2'-(2-(3-hydroxycyclobutyl)pyrimidin-4-yl)-5',6-dimethyl-2H-[1,4'-bipyridin]-2-one (Example 26A, 40.4 mg, 40.40%) and rel-3-chloro-4-((3,5-difluoropyridin-2-yl)methoxy)-2'-(2-(3-hydroxycyclobutyl) pyrimidin-4-yl)-5',6-dimethyl-2H-[1,4'-bipyridin]-2-one (Example 26B, 32.3 mg, 32.3%) as a light pink solid. [the cis/trans=4/1 in the cyclobutene ring]

EXAMPLE 26A: LC-MS: (ES+H, m/z): $[M+H]^+$=525.85. $^1H$ NMR (400 MHZ, DMSO-$d_6$) δ 8.92

(d, 1H), 8.87 (s, 1H), 8.61 (d, 1H), 8.32 (s, 1H), 8.18 (d, 1H), 8.13-8.04 (m, 1H), 6.83 (d, 1H), 5.50 (d, 2H), 5.18 (d, 1H), 4.14-4.04 (m, 1H), 3.23-3.14 (m, 1H), 2.60-2.55 (m, 2H), 2.33-2.23 (m, 2H), 2.10 (s, 3H), 1.98 (s, 3H). $^{19}F$ NMR (377 MHz, DMSO) δ-120.10,-120.12,-122.28,-122.30.

EXAMPLE 26B: LC-MS: (ES+H, m/z): $[M+H]^+$=525.85. $^1H$ NMR (400 MHZ, DMSO-$d_6$) δ 8.92

(d, 1H), 8.87 (s, 1H), 8.61 (d, 1H), 8.33 (s, 1H), 8.18 (d, 1H), 8.14-8.02 (m, 1H), 6.83 (d, 1H), 5.50 (d, 2H), 5.16 (d,

1H), 4.15-4.04 (m, 1H), 3.23-3.15 (m, 1H), 2.63-2.55 (m, 2H), 2.33-2.22 (m, 2H), 2.10 (s, 3H), 1.98 (s, 3H). $^{19}$F NMR (377 MHz, DMSO) δ-120.11,-120.13,-122.32,-122.34.

EXAMPLE 27A, 27B

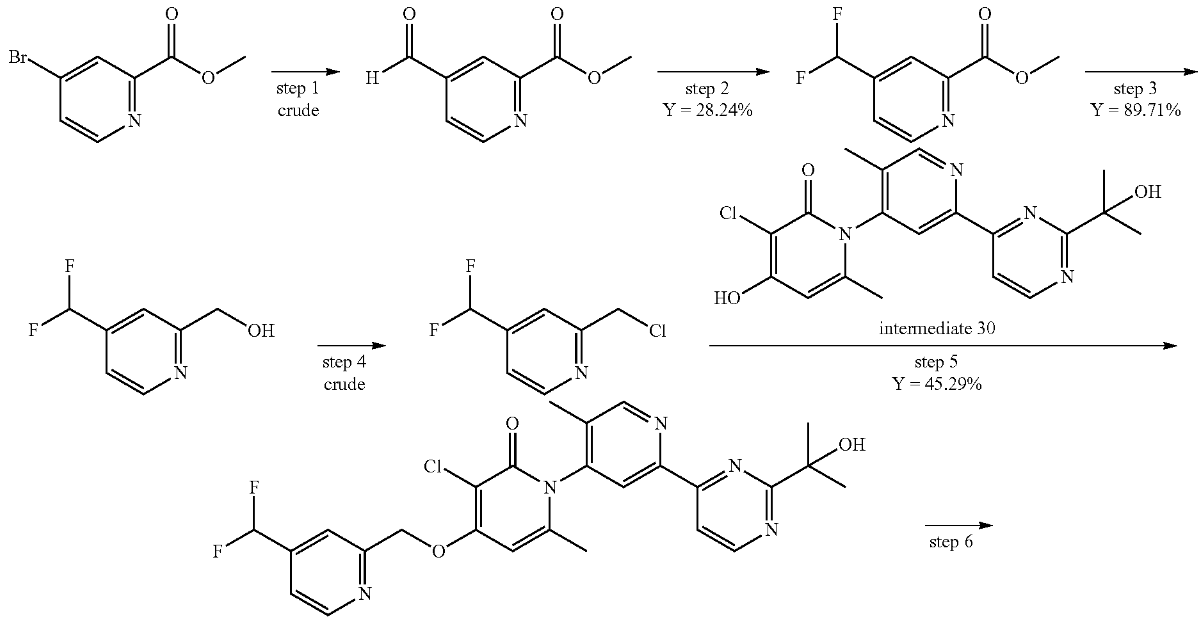

Example 27

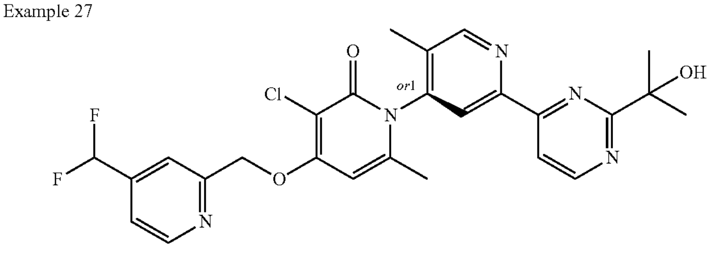

isomer 1
Example 27A

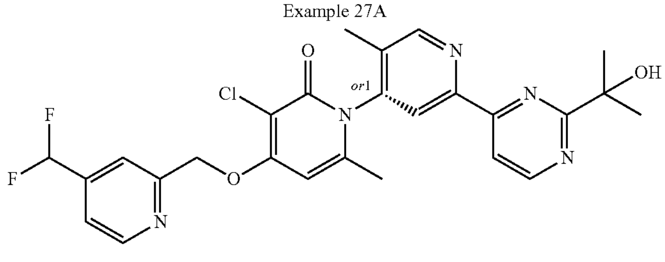

isomer 2
Example 27B

Step 1: Preparation of methyl 4-formylpyridine-2-carboxylate

To a stirred solution of methyl 4-bromopyridine-2-carboxylate (10 g, 46.28 mmol, 1.00 equiv) and TMEDA (10.76 g, 92.57 mmol, 2.00 equiv) in Toluene (130 mL) were added Pd(AcO)$_2$ (1.04 g, 4.62 mmol, 0.10 equiv) and bis (adamantan-1-yl) (butyl) phosphane (3.32 g, 9.25 mmol, 0.20 equiv) at room temperature under nitrogen atmosphere. The resulting mixture was stirred overnight at 100° C., under carbon monoxide/hydrogen (15 atm/15 atm) atmosphere. Desired product could be detected by LCMS. The resulting mixture was cooled down to r.t. The resulting mixture was concentrated under reduced pressure. The resulting mixture was filtered, the filter cake was washed with EtOAc (3 ×20 mL). The filtrate was concentrated under reduced pressure. The residue was purified by silica gel column chromatography to afford methyl 4-formylpyridine-2-carboxylate (1.70 g, crude) as a yellow solid. LC-MS: (ES+H, m/z): [M+H+$H_2O$]$^+$=183.8

Step 2: Preparation of methyl 4-(difluoromethyl)pyridine-2-carboxylate

To a stirred solution of methyl crude 4-formylpyridine-2-carboxylate (1.50 g, 9.08 mmol, 1.00 equiv) in DCM (8 mL) was added BAST (6.03 g, 27.24 mmol, 3.00 equiv) dropwise at room temperature under nitrogen atmosphere.

The resulting mixture was stirred for 2 h at room temperature under nitrogen atmosphere. The reaction was monitored by LCMS. The resulting mixture was slowly poured into ice water (50 mL). The resulting mixture was extracted with $CH_2Cl_2$ (3 ×20 mL). The combined organic layers were dried over anhydrous $Na_2SO_4$. After filtration, the filtrate was concentrated under reduced pressure. The residue was purified by silica gel column chromatography to afford methyl 4-(difluoromethyl)pyridine-2-carboxylate (480 mg, 28.24%) as a light yellow oil. LC-MS: (ES+H, m/z): $[M+H]^+$=188.1. $^1$H NMR (300 MHz, DMSO-$d_6$) δ 8.94-8.86 (m, 1H), 8.19 (s, 1H), 7.90-7.82 (m, 1H), 7.22 (t, 1H), 3.92 (s, 3H).

Step 3: Preparation of [4-(difluoromethyl)pyridin-2-yl]methanol

A mixture of methyl 4-(difluoromethyl)pyridine-2-carboxylate (430 mg. 2.29 mmol. 1.00 equiv) and $NaBH_4$ (347 mg. 9.19 mmol. 4.00 equiv) in THF (4 mL) and methanol (1 mL) was stirred for 2 h at room temperature under nitrogen atmosphere. The reaction was monitored by LCMS. The reaction was quenched with water (10 mL) at r.t. The resulting mixture was extracted with EtOAc (3 ×30 mL). The combined organic layers were washed with brine (30 mL), dried over anhydrous $Na_2SO_4$. After filtration, the filtrate was concentrated under reduced pressure to afford [4-(difluoromethyl)pyridin-2-yl]methanol (328 mg. 89.71%) as a yellow solid. LC-MS: (ES+H, m/z): $[M+H]^+$=160.1. $^1$H NMR (400 MHZ. DMSO-$d_6$) ¿ 8.65 (d, 1H), 7.64 (s.1H), 7.43 (d, 1H), 7.13 (t. 1H), 5.59 (t. 1H), 4.63 (d, 2H)

Step 4: Preparation of 2-(chloromethyl)-4-(difluoromethyl)pyridine

A mixture of [4-(difluoromethyl)pyridin-2-yl]methanol (328 mg. 2.06 mmol. 1.00 equiv). DMF (15 mg, 0.20 mmol, 0.1 equiv) and SOCI: (1.5 mL) in CH-$Cl_2$ (3 mL) was stirred for 2 h at r.t. The reaction was monitored by LCMS. The resulting mixture was concentrated under reduced pressure to afford 2-(chloromethyl)-4-(difluoromethyl)pyridine (700 mg, crude) as a yellow solid. LC-MS: (ES+H, m/z): $[M+H]^+$=178.0.

Step 5: Preparation of 3-chloro-4-{[4-(difluoromethyl)pyridin-2-yl]methoxy}-2'-[2-(2-hydroxypropan-2-yl)pyrimidin-4-yl]-5',6-dimethyl-[1,4'-bipyridin]-2-one A mixture of 2-(chloromethyl)-4-(difluoromethyl)pyridine (201 mg, 1.13 mmol. 2.00 equiv), 3-chloro-4-hydroxy-2'-[2-(2-hydroxypropan-2-yl)pyrimidin-4-yl]-5'0.6-dimethyl-[1,4'-bipyridin]-2-one (220) mg. 0.57 mmol. 1.00 equiv). $K_2CO$; (392 mg. 2.84 mmol. 5.00 equiv) and 18-Crown-6 (15 mg, 0.06 mmol. 0.10 equiv) in DMF (3 mL) was stirred overnight at 60° C., under nitrogen atmosphere. The reaction was monitored by LCMS. The resulting mixture was cooled down to r.t, and poured into 10 ml of water. The resulting mixture was extracted with EtOAc (3 ×30 mL). The combined organic layers were washed with brine (20 mL), dried over anhydrous $Na_2SO_4$. After filtration, the filtrate was concentrated under reduced pressure. The residue was purified by silica gel column chromatography to afford crude product, which was further purified by Prep-HPLC to afford 3-chloro-4-{[4-(difluoromethyl)pyridin-2-yl]methoxy}-2'-]2-(2-hydroxypropan-2-yl)pyrimidin-4-yl]-5'0.6-dimethyl-] 1,4'-bipyridin]-2-one (136 mg. 45.29%). LC-MS: (ES+H, m/z): $[M+H]^+$=528.2.

Step 6: Preparation of rel-3-chloro-4-{[4-(difluoromethyl)pyridin-2-yl]methoxy}-2'-[2-(2-hydroxypropan-2-yl)pyrimidin-4-yl]-5',6-dimethyl-[1,4'-bipyridin]-2-one and rel-3-chloro-4-{[4-(difluoromethyl)pyridin-2-yl]methoxy}-2'-[2-(2-hydroxypropan-2-yl)pyrimidin-4-yl]-5',6-dimethyl-[1,4'-bipyridin]-2-one The racemate (136 mg) was separated by Prep-Chiral-HPLC to afford Example 27A (56.3 mg. 99.6%, ee=100%) as a white solid and Example 27B (53.3 mg. 99.4%, ee=99.2%) as a white solid.

EXAMPLE 27A

LC-MS: (ES+H, m/z): $[M+H]^+$=528.10. $^1$H NMR (300 MHz. DMSO-$d_6$) δ 8.98 (d, 1H), 8.87 (s. 1H), 8.82 (d, 1H), 8.70 (s, 1H), 8.25 (d, 1H), 7.79 (s.1H), 7.61 (d, 1H), 7.42-7.02 (t. 1H) 6.84 (s, 1H), 5.54 (s, 2H), 5.26 (s, 1H), 2.11 (s, 3H), 1.99 (s, 3H), 1.54 (s, 3H), 1.53 (s, 3H). $^{19}$F NMR (282 MHZ, DMSO) δ-115.08.

EXAMPLE 27B

LC-MS: (ES+H, m/z): $[M+H]^+$=528.10. $^1$H NMR (300 MHz, DMSO-$d_6$) δ 8.98 (d, 1H), 8.87 (s, 1H), 8.82 (d, 1H), 8.70 (s, 1H), 8.25 (d, 1H), 7.79 (s, 1H), 7.61 (d, 1H), 7.41-7.02 (t, 1H), 6.84 (s, 1H), 5.54 (s, 2H), 5.26 (s, 1H), 2.11 (s, 3H), 1.99 (s, 3H), 1.54 (s, 3H), 1.53 (s, 3H). $^{19}$F NMR (282 MHz, DMSO) δ-115.08.

EXAMPLE 28A, 28B

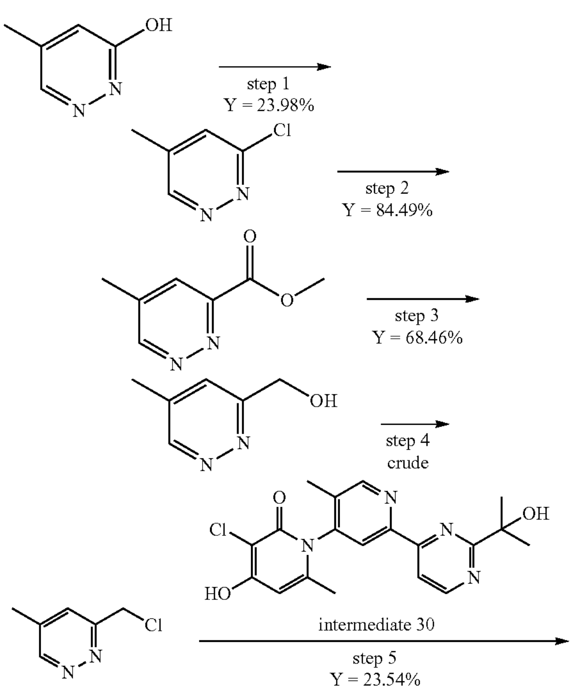

-continued

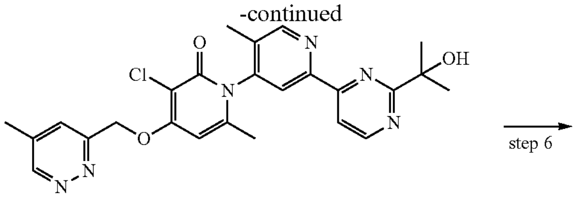

Example 28

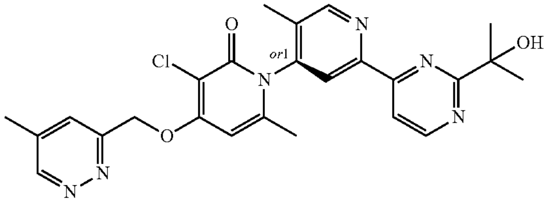

isomer 1
Example 28A

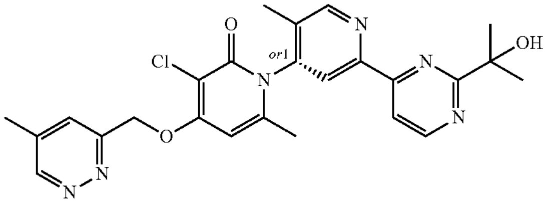

isomer 2
Example 28B

Step 1: Preparation of 3-chloro-5-methylpyridazine

A solution of 5-methylpyridazin-3-ol (5.00 g) in $POCl_3$ (50 mL) was stirred for 3 h at 80° C., under nitrogen atmosphere. The reaction was monitored by LCMS. The reaction was quenched with ice at room temperature. The mixture was basified to pH 9 with NaOH aq. The resulting mixture was extracted with EtOAc (3 ×100 mL). The combined organic layers were dried over anhydrous $Na_2SO_4$. After filtration, the filtrate was concentrated under reduced pressure. The residue was purified by silica gel column chromatography to afford 3-chloro-5-methylpyridazine (1,4 g, 23.98%) as a brown liquid. LC-MS: (ES+H, m/z): $[M+H]^+$=129.1. $^1$H NMR (400 MHZ, DMSO-$d_6$) δ 9.14 (d, 1H), 7.81 (d, 1H), 2.37 (s, 3H). Step 2: Preparation of methyl 5-methylpyridazine-3-carboxylate To a stirred solution of DIEA (2.01 g, 15.55 mmol, 2.00 equiv) and 3-chloro-5-methylpyridazine (1.00 g, 7.77 mmol, 1.00 equiv) in MeOH (10 mL) was added Pd(dppf) $C_1$;$CH_2Cl_2$ (0.63 g, 0.77 mmol, 0.10 equiv) at room temperature under nitrogen atmosphere. The resulting mixture was stirred overnight at 100° C., under carbon monoxide atmosphere. The reaction was monitored by LCMS. The resulting mixture was cooled down to r.t. The resulting mixture was concentrated under vacuum. The residue was purified by silica gel column chromatography to afford methyl 5-methylpyridazine-3-carboxylate (1.00 g, 84.49%) as a light-yellow solid. LC-MS: (ES+H, m/z): $[M+H]^+$=153.2. $^1$H NMR (400 MHZ. DMSO-$d_6$) δ 9.32 (d, 1H). 8.12-8.06 (m. 1H), 3.96 (s, 3H), 2.42 (s, 3H).

Step 3: Preparation of (5-methylpyridazin-3-yl) methanol

To a stirred solution of methyl 5-methylpyridazine-3-carboxylate (500 mg. 3.28 mmol. 1.00 equiv) in THF (3 mL) and MeOH (1 mL) was added $NaBH_4$ (621 mg, 16.43 mmol. 5.00 equiv) at room temperature. The resulting mixture was stirred for 2 h at room temperature. The reaction was monitored by LCMS. The resulting mixture was diluted with water (10 mL). The resulting mixture was extracted with CHCI; and isopropanol (3:1) (3 ×10 mL). The combined organic layers were dried over anhydrous $Na_2SO_4$. After filtration, the filtrate was concentrated under reduced pressure to afford (5-methylpyridazin-3-yl) methanol (280 mg. 68.64%) as pale yellow solid. LC-MS: (ES+H, m/z): $[M+H]^+$=125.2. $^1$H NMR (400 MHz. DMSO-$d_6$) δ 8.98 (d, 1H), 7.54 (d, 1H), 5.60 (s, 1H), 4.72 (s, 2H), 2.34 (s, 3H).

Step 4: Preparation of 3—(chloromethyl)-5-methylpyridazine

A mixture of (5-methylpyridazin-3-yl) methanol (280 mg. 2.25 mmol. 1.00 equiv). DMF (16 mg. 0.22 mmol. 0.10 equiv) and SOCI, (1.5 mL) in $CH_2Cl$, (3 mL) was stirred for 2 h at r.t. The reaction was monitored by LCMS. The resulting mixture was concentrated under reduced pressure to afford 3-(chloromethyl)-5-methylpyridazine (280 mg, crude) as a yellow solid. LC-MS: (ES+H, m/z): $[M+H]^+$=143.1.

Step 5: Preparation of 3-chloro-2'-[2-(2-hydroxypropan-2-yl)pyrimidin-4-yl]-5',6-dimethyl-4-[(5-methylpyridazin-3-yl)methoxy]-[1,4'-bipyridin]-2-one A mixture of 3—(chloromethyl)-5-methylpyridazine (147 mg, 1.03 mmol. 2 equiv), 3-chloro-4-hydroxy-2'-[2-(2-hydroxypropan-2-yl)pyrimidin-4-yl]-5'0.6-dimethyl-] 1,4'-bipyridin]-2-one (200 mg, 0.51 mmol. 1.00 equiv). K.CO; (357 mg. 2.58 mmol. 5.00 equiv) and 18-Crown-6 (13 mg, 0.05 mmol. 0.10 equiv) in DMF (2 mL) was stirred overnight at 60° C., under nitrogen atmosphere. The reaction was monitored by LCMS. The resulting mixture was cooled down to r.t, and poured into 10 ml of water. The resulting mixture was extracted with EtOAc (3 ×10 mL). The combined organic layers were washed with brine (20 mL), dried over anhydrous $Na_2SO_4$. After filtration, the filtrate was concentrated under reduced pressure. The residue was purified by silica gel column chromatography, to afford crude product, which was further purified by Prep-HPLC to afford 3-chloro-2'-[2-(2-hydroxypropan-2-yl)pyrimidin-4-yl]-5'0.6-dimethyl-4-[(5-methylpyridazin-3-yl)methoxy]-] 1,4'-bipyridin]-2-one (60 mg. 23.54%) as a white solid. LC-MS: (ES+H, m/z): $[M+H]^+$=493.1.

Step 6: Preparation of rel-3-chloro-2'-[2-(2-hydroxypropan-2-yl)pyrimidin-4-yl]-5',6-dimethyl-4-[(5-methylpyridazin-3-yl)methoxy]-[1,4'-bipyridin]-2-one and rel-3-chloro-2'-[2-(2-hydroxypropan-2-yl) pyrimidin-4-yl]-5',6-dimethyl-4-[(5-methylpyridazin-3-yl)methoxy]-[1,4'-bipyridin]-2-one The racemate (60 mg) was separated by Prep-Chiral-HPLC to afford Example 28A (19.1 mg. 98.7%, ee=100%) as a white solid and Example 28B (18.4 mg. 98.7%, ee=100%) as a white solid.

EXAMPLE 28A

LC-MS: (ES+H, m/z): $[M+H]^+$=493.20. $^1$H NMR (400 MHZ, DMSO-$d_6$) δ 9.15 (s, 1H), 8.97 (d, 1H), 8.87 (s, 1H), 8.69 (s, 1H), 8.24 (d, 1H), 7.71 (s, 1H), 6.86 (s, 1H), 5.63 (s, 2H), 5.27 (s, 1H), 2.41 (s, 3H), 2.11 (s, 3H), 1.99 (s, 3H), 1.54 (s, 3H), 1.53 (s, 3H).
EXAMPLE 28B
LC-MS: (ES+H, m/z): $[M+H]^+$=493.25. $^1$H NMR (400 MHZ, DMSO-$d_6$) δ 9.15 (s, 1H), 8.98 (d, 1H), 8.87 (s, 1H), 8.69 (s, 1H), 8.24 (d, 1H), 7.71 (s, 1H), 6.86 (s, 1H), 5.63 (s, 2H), 5.27 (s, 1H), 2.42 (s, 3H), 2.11 (s, 3H), 1.99 (s, 3H), 1.54 (s, 3H), 1.53 (s, 3H).
EXAMPLE 29A, 28B
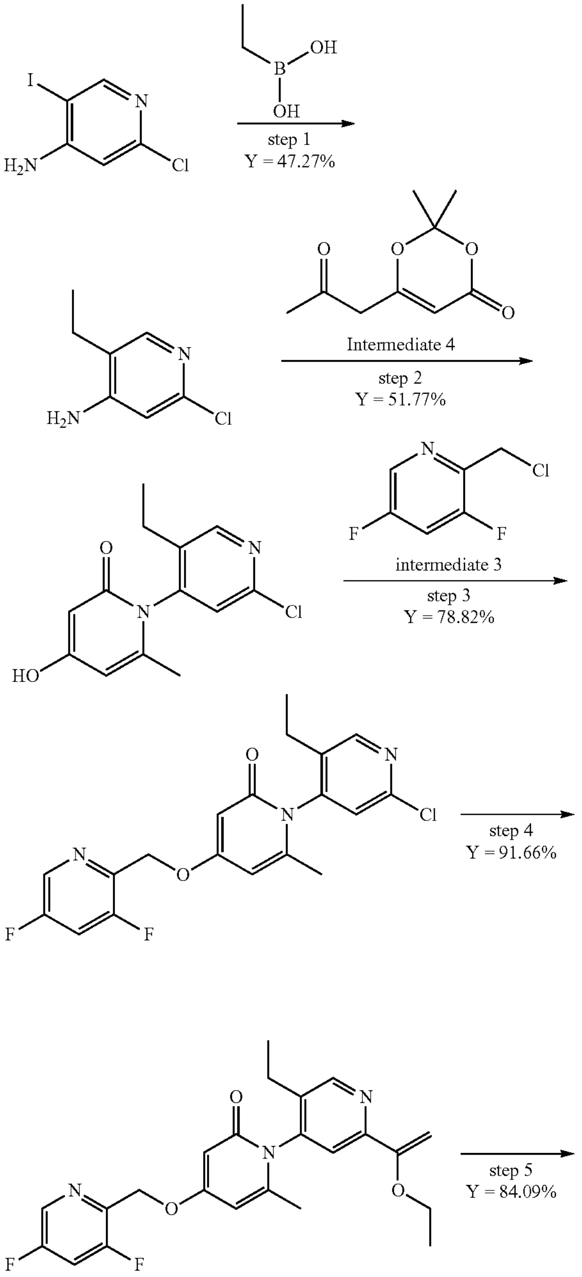
-continued
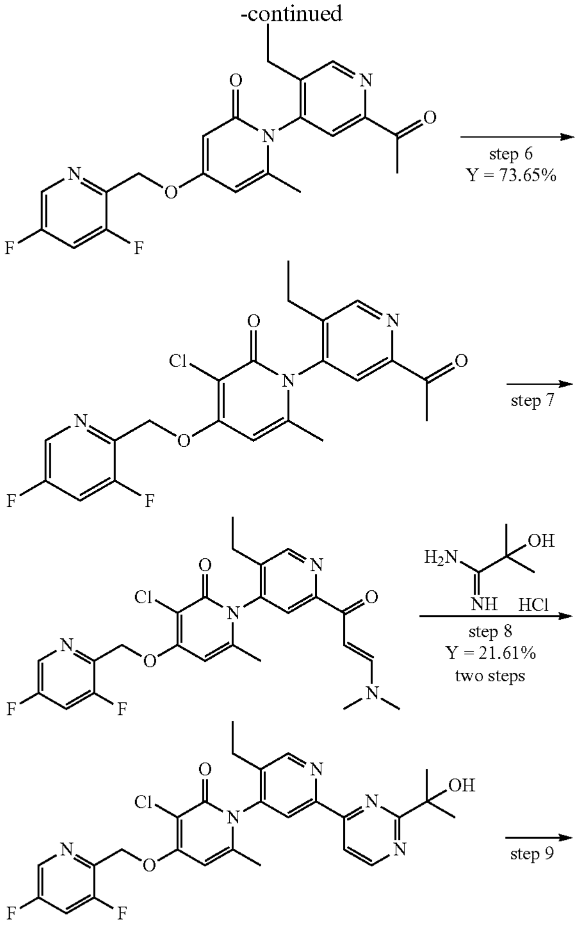
Example 29
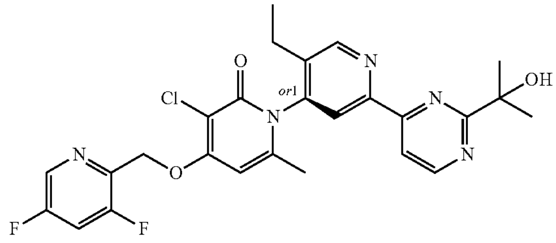
Isomer 1
Example 29A
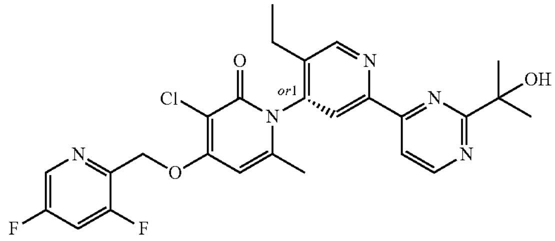
Isomer 2
Example 29B
Step1: Preparation of 2-chloro-5-ethylpyridin-4-amine
To a stirred mixture of 2-chloro-5-iodopyridin-4-amine (5.50 g, 21.61 mmol, 1.00 equiv) and boronic acid, ethyl- (3.19 g, 43.22 mmol, 2.00 equiv) in Toluene (500 mL) and $H_2O$ (50 mL) were added $Cs_2CO_3$ (21.13 g, 64.84 mmol, 3.00 equiv) and Pd(dppf) $Cl_2$ (880.38 mg, 1.08 mmol, 0.05 equiv) at room temperature under nitrogen atmosphere. The resulting mixture was stirred overnight at 100° C., under nitrogen atmosphere. The reaction was monitored by LCMS. The mixture was allowed to cool down to room temperature. The reaction was poured into water (1.5L) at room temperature. The resulting mixture was extracted with EtOAc (2×500 mL). The combined organic layers were washed with brine (500 mL), dried over anhydrous $Na_2SO_4$. After filtration, the filtrate was concentrated under reduced pressure. The residue was purified by silica gel column chromatography the pure fraction was concentrated under reduced pressure to afford 2-chloro-5-ethylpyridin-4-amine (1.60 g, 47.27%) as a white solid. LC-MS: (ES+H, m z): $[M+H]^+$ =157.1. $^1$H NMR (400 MHZ, Chloroform-d) § 7.87 (s, 1H), 6.55 (s, 1H), 4.33 (br, 2H), 2.46 (q, 2H), 1.24 (t, 3H).

Step2: Preparation of 2'-chloro-5'-ethyl-4-hydroxy-6-methyl-[1,4'-bipyridin]-2-one To a stirred solution of 2-chloro-5-ethylpyridin-4-amine (1.60 g, 10.21 mmol, 1.00 equiv) in 1,4-dioxane (40 mL) was added 2,2-dimethyl-6-(2-oxopropyl)-1,3-dioxin-4-one (3.76 g, 20.43 mmol, 2.00 equiv) at room temperature under nitrogen atmosphere. The resulting mixture was stirred for 2 h at 90° C. under nitrogen atmosphere. The mixture was allowed to cool down to room temperature. To the above mixture was added conc. $H_2SO_4$ (1.00 g. 10.21 mmol. 1.00 equiv) dropwise at room temperature. The resulting mixture was stirred for additional 2 h at 90° C. The reaction was monitored by LCMS. The mixture was allowed to cool down to room temperature. The resulting mixture was concentrated under reduced pressure. The resulting mixture was diluted with water (50 mL). The precipitated solids were collected by filtration and washed with water (3 ×20 mL). The residue was purified by trituration with hexane (200 mL) to afford 2'-chloro-5'-ethyl-4-hydroxy-6-methyl-[1,4'-bipyridin]-2-one (1,4 g. 51.77%) as a brown solid. LC-MS: (ES+H, m z): $[M+H]^+$=265.2. $^1$H NMR (300 MHz. DMSO-$d_6$) δ 10.86 (br. 1H), 8.50 (s, 1H), 7.55 (s. 1H), 5.98 (d, 1H), 5.59 (d, 1H), 2.41-2.26 (m, 2H), 1.84 (s, 3H), 1.07 (t. 3H).

Step3: Preparation of 2'-chloro-4-[(3,5-difluoropyridin-2-yl)methoxy]-5'-ethyl-6-methyl-[1,4'-bipyridin]-2-one To a stirred solution of 2'-chloro-5'-ethyl-4-hydroxy-6-methyl-]1,4'-bipyridin]-2-one (1.20 g. 4.53 mmol. 1.00 equiv) and 2-(chloromethyl)-3.5-difluoropyridine (1.11 g. 6.80 mmol. 1.50 equiv) in DMF (50 mL) were added 18-Crown-6 (0.12 g. 0.45 mmol. 0.10 equiv) and $K_2CO_3$ (1.25 g. 9.06 mmol. 2.00 equiv) at room temperature under nitrogen atmosphere. The resulting mixture was stirred overnight at 60° C., under nitrogen atmosphere. The reaction was monitored by LCMS. The mixture was allowed to cool down to room temperature. The reaction was quenched with water (50 mL) at room temperature. The resulting mixture was extracted with EtOAc (3 ×50 mL). The combined organic layers were washed with brine (50 mL), dried over anhydrous $Na_2SO_4$. After filtration, the filtrate was concentrated under reduced pressure. The residue was purified by silica gel column chromatography the pure fraction was concentrated under reduced pressure to afford 2'-chloro-4-[(3.5-difluoropyridin-2-yl)methoxy]-5'-ethyl-6-methyl-[1, 4'-bipyridin]-2-one (1,40 g. 78.82%) as a yellow solid. LC-MS: (ES+H, m z): $[M+H]^+$=392.1. $^1$H NMR (300 MHz.

DMSO-$d_6$) § 8.60 (d, 1H), 8.53 (s.1H), 8.12-8.04 (m. 1H), 7.60 (s.1H), 6.14 (d. 1H), 6.04 (d, 1H), 5.25 (d, 2H), 2.45-2.23 (m. 2H), 1.86 (s, 3H), 1.08 (t. 3H).

Step 4: Preparation of 4-[(3,5-difluoropyridin-2-yl)methoxy]-2'-(1-ethoxyethenyl)-5'-ethyl-6-methyl-[1,4'-bipyridin]-2-one To a stirred solution of 2'-chloro-4-[(3.5-difluoropyridin-2-yl)methoxy]-5'-ethyl-6-methyl-[1,4'-bipyridin]-2-one (1,40 g. 3.57 mmol. 1.00 equiv) and tributyl (1-ethoxyethenyl) stannane (2.58 g. 7.14 mmol. 2.00 equiv) in 1,4-dioxane (20 mL) were added $Pd(PPh_3)_2Cl_2$ (125 mg, 0.18 mmol. 0.05 equiv) at room temperature under nitrogen atmosphere. The resulting mixture was stirred overnight at 100° C., under nitrogen atmosphere. The reaction was monitored by LCMS. The mixture was allowed to cool down to room temperature. The reaction was quenched with water (100 mL) at room temperature. The resulting mixture was extracted with EtOAc (3 ×50 mL). The combined organic layers were washed with brine (100 mL). dried over anhydrous $Na_2SO_4$. After filtration, the filtrate was concentrated under reduced pressure. The residue was purified by silica gel column chromatography the pure fraction was concentrated under reduced pressure to afford 4-[(3.5-difluoropyridin-2-yl) methoxy]-2'-(1-ethoxyethenyl)-5'-ethyl-6-methyl-[1,4'-bipyridin]-2-one (1,40 g. 91.66%) as a yellow solid. LC-MS: (ES+H, m z): $[M+H]^+$=428.1.

Step 5: Preparation of 2'-acetyl-4-[(3,5-difluoropyridin-2-yl)methoxy]-5'-ethyl-6-methyl-[1,4'-bipyridin]-2-one To a stirred solution of 4-[(3.5-difluoropyridin-2-yl) methoxy]-2'-(1-ethoxyethenyl)-5'-ethyl-6-methyl-] 1,4'-bipyridin]-2-one (1,40 g. 3.27 mmol. 1.00 equiv) in THF (10 mL) was added conc. HCl (1 mL) dropwise at 0° C. The resulting mixture was stirred for 1 h at room temperature. The reaction was monitored by LCMS. The reaction was poured into water (50 mL) at room temperature. The resulting mixture was extracted with EtOAc (3 ×30 mL). The combined organic layers were washed with brine (40 mL). The resulting mixture was concentrated under vacuum. The residue was purified by silica gel column chromatography the pure fraction was concentrated under vacuum to afford 2'-acetyl-4-[(3.5-difluoropyridin-2-yl)methoxy]-5'-ethyl-6-methyl-[1,4'-bipyridin]-2-one (1.10 g. 84.09%) as a brown oil. LC-MS: (ES+H, m/z): $[M+H]^+$=400.1. $^1$H NMR (400 MHZ. DMSO-$d_6$) δ 8.84 (s, 1H), 8.59 (d, 1H), 8.10-8.05 (m. 1H), 7.77 (s.1H), 6.14 (d, 1H), 6.04 (d, 1H), 5.25 (d, 2H), 2.67 (s, 3H), 2.48-2.34 (m, 2H), 1.81 (s. 3H), 1.12 (t. 3H).

Step 6: Preparation of 2'-acetyl-3-chloro-4-[(3,5-difluoropyridin-2-yl)methoxy]-5'-ethyl-6-methyl-[1,4'-bipyridin]-2-one To a stirred solution of 2'-acetyl-4-[(3.5-difluoropyridin-2-yl)methoxy]-5'-ethyl-6-methyl-[1,4'-bipyridin]-2-one (1.00 g. 2.50 mmol. 1.00 equiv) in isopropyl alcohol (20 mL) were added NCS (0.37 g. 2.75 mmol. 1.10 equiv) and dichloroacetic acid (0.02 g. 0.15 mmol. 0.06 equiv) dropwise at room temperature under nitrogen atmosphere. The resulting mixture was stirred for 1.5 h at 60° C., under nitrogen atmosphere. The reaction was monitored by LCMS. The reaction was quenched by the addition of water (60 mL) at room temperature. The resulting mixture was extracted with EtOAc (3 ×25 mL). The combined organic layers were washed with brine (30 mL). The resulting mixture was concentrated under reduced pressure. The residue was purified by silica gel column chromatography, the pure fraction was concentrated under vacuum to afford 2'-acetyl-3-chloro-4-[(3.5-difluoropyridin-2-yl)methoxy]-5'-ethyl-6-methyl-[1,4'-bipyridin]-2-one (800 mg. 73.65%) as a yellow solid. LC-MS: (ES+H, m/z): $[M+H]^+$=434.2. $^1$H NMR (300 MHz. DMSO-$d_6$) δ 8.88 (s.1H), 8.61 (d, 1H), 8.14-8.07 (m, 1H), 7.88 (s, 1H), 6.80 (s, 1H), 5.48 (d, 2H). 2.68 (s, 3H), 2.47-2.30 (m, 2H), 1.91 (s, 3H), 1.12 (t. 3H).

Step 7: Preparation of 3-chloro-4-[(3,5-difluoropyridin-2-yl)methoxy]-2'-[(2E)-3-(dimethylamino) prop-2-enoyl]-5'-ethyl-6-methyl-[1,4'-bipyridin]-2-one Into DMF-DMA (4 mL) was added 2'-acetyl-3-chloro-4-[(3.5-difluoropyridin-2-yl)methoxy]-5'-ethyl-6-methyl-[1,4'-bipyridin]-2-one (400 mg, 0.92 mmol. 1.00 equiv) at room temperature under nitrogen atmosphere. The resulting mixture was stirred overnight at 100° C., under nitrogen atmosphere. The reaction was monitored by LCMS. The mixture was allowed to cool down to room temperature. The resulting mixture was concentrated under reduced pressure. The crude product was used in the next step directly without further purification.LC-MS: (ES+H, m/z): $[M+H]^+$=489.2.

Step 8: Preparation of 3-chloro-4-[(3,5-difluoropyridin-2-yl)methoxy]-5'-ethyl-2'-[2-(2-hydroxypropan-2-yl)pyrimidin-4-yl]-6-methyl-[1,4'-bipyridin]-2-one To a stirred solution of 3-chloro-4-[(3.5-difluoropyridin-2-yl)methoxy]-2'-[(2E)-3-(dimethy lamino) prop-2-enoyl]-5'-ethyl-6-methyl- [1,4'-bipyridin]-2-one (450 mg, 0.92 mmol, assumed 100% yield. 1.00 equiv) in dimethylformamide (10 mL) were added 2-hydroxy-2-methylpropanimidamide hydrochloride (1.27 g. 2.76 mmol. 10.00 equiv) and $K_2CO_3$ (1.28 g. 2.76 mmol. 10.00 equiv) at room temperature under nitrogen atmosphere. The resulting mixture was stirred overnight at 80° C., under nitrogen atmosphere. The reaction was monitored by LCMS. The reaction was poured into water (100 mL) at room temperature. The resulting mixture was extracted with EtOAc (3 ×100 mL). The combined organic layers were washed with brine (5×100 mL). The resulting mixture was concentrated under reduced pressure. The residue was purified by Prep-TLC, the residue was concentrated under reduced pressure. The crude product was purified by Prep-HPLC, the pure fraction was concentrated under reduced pressure to afford 3-chloro-4-[(3.5-difluoropyridin-2-yl)methoxy]-5'-ethyl-2'-]2-(2-hydroxypropan-2-yl)pyrimidin-4-yl]-6-methyl-[1,4'-bipyridin]-2-one (105 mg. 21.61%) as a white solid. LC-MS: (ES+H, m/z): $[M+H]^+$=528.3. $^1$H NMR (300 MHz. DMSO-$d_6$) δ 8.98 (d, 1H), 8.90 (s, 1H), 8.68 (s, 1H), 8.61 (d, 1H), 8.25 (d, 1H), 8.16-8.03 (m. 1H), 6.85 (s.1H), 5.50 (s, 2H), 5.27 (s, 1H), 2.50-2.35 (m, 2H), 1.99 (s, 3H), 1.54 (s, 3H), 1.53 (s, 3H), 1.15 (s. 3H)

Step 9: Preparation of (Example 29A, isomer 1) rel-3-chloro-4-((3,5-difluoropyridin-2-yl)methoxy)-5'-ethyl-2'-(2-(2-hydroxypropan-2-yl)pyrimidin-4-yl)-6-methyl-2H-[1,4'-bipyridin]-2-one and (Example 28B, isomer 2) rel-3-chloro-4-((3,5-difluoropyridin-2-yl)methoxy)-5'-ethyl-2'-(2-(2-hydroxypropan-2-yl)pyrimidin-4-yl)-6-methyl-2H-[1,4'-bipyridin]-2-one The race-mixture (100 mg) was separated by Prep-CHIRAL-HPLC, the pure fraction was concentrated under reduced pressure and then lyophilized to afford rel-3-chloro-4-((3.5-difluoropyridin-2-yl)methoxy)-5'-ethyl-2'-(2-(2-hydroxypropan-2-yl)pyrimidin-4-yl )-6-methyl-2H-[1,4'-bipyridin]-2-onc (Example 29A, isomer 1. 36.2 mg, ee=100%) as a white solid and rel-3-chloro-4-((3.5-difluoropyridin-2-yl)methoxy)-5'-ethyl-2'-(2-(2-hydroxypropan-2-yl)pyrimidin-4-yl)-6-methyl-2H-[1,4'-bipyridin]-2-onc (Example 29B, isomer 2. 32.3 mg, ee=100%) as a white solid.

EXAMPLE 29A

LC-MS: (ES+H, m z): $[M+H]^+$=528.10. $^1$H NMR (300 MHz. DMSO-$d_6$) δ 8.98 (d, 1H), 8.90 (s. 1H), 8.68 (s, 1H), 8.61 (d, 1H), 8.24 (d, 1H), 8.16-8.03 (m, 1H), 6.85 (s, 1H), 5.50 (s, 2H), 5.25 (s, 1H). 2.50-2.34 (m, 2H), 1.98 (s, 3H), 1.54 (s, 3H), 1.53 (s, 3H), 1.15 (t. 3H). $^{19}$F NMR (282 MHz. DMSO) δ-120.12, —120.15, —122.31, —122.34.

EXAMPLE 29B

LC-MS: (ES+H, m z): $[M+H]^+$=528.10. $^1$H NMR (300 MHz. DMSO-$d_6$) δ 8.98 (d, 1H), 8.90 (s. 1H), 8.68 (s, 1H), 8.61 (d, 1H), 8.24 (d, 1H), 8.16-8.03 (m. 1H), 6.85 (s, 1H), 5.50 (s, 2H), 5.25 (s, 1H). 2.51-2.37 (m, 2H), 1.98 (s, 3H), 1.54 (s, 3H), 1.53 (s, 3H), 1.15 (t. 3H). $^{19}$F NMR (282 MHz. DMSO) δ-120.12, —120.15, —122.32, —122.34.

EXAMPLE 30

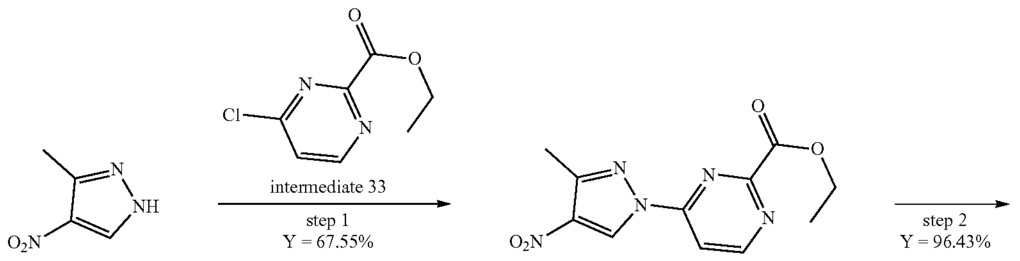

-continued

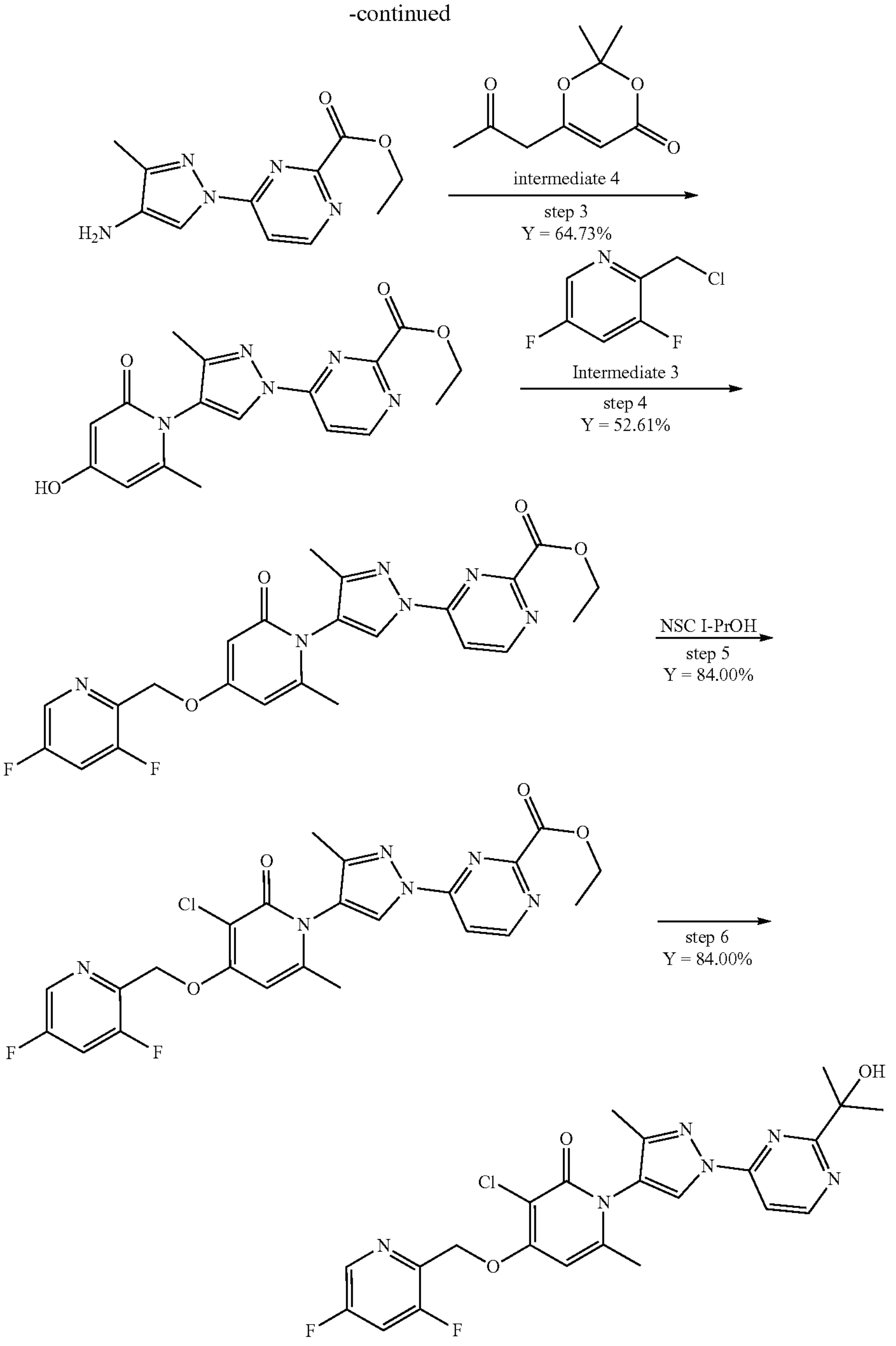

Example 30

Step 1: Preparation of ethyl 4-(3-methyl-4-nitropyrrol-1-yl)pyrimidine-2-carboxylate To a stirred solution of ethyl 4-chloropyrimidine-2-carboxylate (1.00 g. 5.35 mmol, 1.00 equiv) and 3-methyl-4-nitro-1H-pyrazole (0.89 g. 7.02 mmol, 1.31 equiv) in DMF (10 mL) was added $Cs_2CO_3$ (3.49 g. 10.71 mmol, 2.00 equiv) at room temperature under nitrogen atmosphere. The resulting mixture was stirred for 3 h at 50° C., under nitrogen atmosphere. The mixture was allowed to cool down to room temperature. The reaction was quenched with saturating $NH_4Cl$ (aq.) at room temperature. The resulting mixture was extracted with EtOAc (3 ×20 mL). The combined organic layers were washed with brine (30 mL), dried over anhydrous $Na_2SO_4$. After filtration, the filtrate was concentrated under reduced pressure. The residue was purified by silica gel column chromatography to afford ethyl 4-(3-methyl-4-nitropyrrol-1-yl)pyrimidine-2-carboxylate (1.00 g. 67.55%) as a white solid. LC-MS: (ES+H, m/z): $[M+H]^+$=278.1. Step 2: Preparation of ethyl 4-(4-amino-3-methylpyrazol-1-yl)pyrimidine-2-carboxylate To a solution of ethyl 4-(3-methyl-4-nitropyrazol-1-yl)pyrimidine-2-carboxylate (1.00 g. 3.60 mmol, 1.00 equiv) in 15 mL EtOH was added Pd/C (0.38 g, enough, 10 wt %) in a pressure tank. The mixture was hydrogenated at room temperature under 30 atm of hydrogen pressure for 40 min, the reaction was monitored by LCMS. The resulting mixture was filtered through a Celite pad and concentrated under reduced pressure. The residue was purified by trituration with diethyl ether (5 mL). The precipitated solids were collected by filtration. This resulted in ethyl 4-(4-amino-3-methylpyrazol-1-yl)pyrimidine-2-carboxylate (0.86 g. 96.43%) as a yellow solid. LC-MS: (ES+H, m/z): $[M+H]^+$ =248.1. $^1$H NMR (300 MHz. DMSO-$d_6$) δ 8.76 (d, 1H), 7.79 (d, 1H), 7.77 (s, 1H), 4.54 (br, 2H), 4.38 (q, 2H), 2.19 (s, 3H), 1.35 (t, 3H). Step 3: Preparation of ethyl 4-[4-(4-hydroxy-2-methyl-6-oxopyridin-1-yl)-3-methylpyrazol-1-yl]pyrimidine-2-carboxylate;

A solution of ethyl 4-(4-amino-3-methylpyrazol-1-yl)pyrimidine-2-carboxylate (0.86 g. 3.47 mmol, 1.00 equiv) and 2.2-dimethyl-6-(2-oxopropyl)-1,3-dioxin-4-one (1.60 g, 8.69 mmol, 2.50 equiv) in dioxane (10 mL) was stirred for 3 h at 80° C., under nitrogen atmosphere. The mixture was allowed to cool down to room temperature. To the above mixture was added conc. $H_2SO_4$ (0.29 mL, 35.48 mmol, 1.00 equiv) dropwise at room temperature. The resulting mixture was stirred for additional 1 h at 80° C. The mixture was allowed to cool down to room temperature. The resulting mixture was concentrated under vacuum. The residue was dissolved in water (1 mL). The residue was purified by reverse combi-flash chromatography. This resulted in ethyl 4-[4-(4-hydroxy-2-methyl-6-oxopyridin-1-yl)-3-methylpyrazol-1-yl]pyrimidine-2-carboxylate (0.80 g. 64.73%) as a brown solid. LC-MS: (ES+H, m/z): $[M+H]^+$=356.1. 1H NMR (300 MHz. DMSO-$d_6$) δ 10.75 (br. 1H), 9.02 (d, 1H), 8.81 (s, 1H), 8.07 (d, 1H), 5.94 (s, 1H), 5.57 (d. 1H), 4.40 (q. 2H), 2.07 (s, 3H), 2.00 (s, 3H), 1.36 (t. 3H).

Step 4: Preparation of ethyl 4-(4-{4-[(3,5-difluoropyridin-2-yl)methoxy]-2-methyl-6-oxopyridin-1-yl}-3-methylpyrazol-1-yl)pyrimidine-2-carboxylate To a stirred solution of ethyl 4-[4-(4-hydroxy-2-methyl-6-oxopyridin-1-yl)-3-methylpyrazol-1-yl]pyrimidine-2-carboxylate (0.70 g. 1.97 mmol. 1.00 equiv) and $Na_2CO_3$ (0.42 g. 3.94 mmol. 2.00 equiv) in DMF (5 mL) were added 2-(chloromethyl)-3.5-difluoropyridine (0.48 g. 2.95 mmol. 1.50 equiv) and 18 Crown-6 (0.20 g. 0.78 mmol. 0.40 equiv) at room temperature under nitrogen atmosphere. The resulting mixture was stirred for 2 h at 60° C., under nitrogen atmosphere. The mixture was allowed to cool down to room temperature. The reaction was quenched with saturating $NH_4Cl$ (aq.) at room temperature. The resulting mixture was extracted with EtOAc (3 ×20 mL). The combined organic layers were washed with brine (30 mL), dried over anhydrous $Na_2SO_4$. After filtration, the filtrate was concentrated under reduced pressure. The residue was purified by silica gel column chromatography to afford ethyl 4-(4-{4-[(3.5-difluoropyridin-2-yl)methoxy]-2-methyl-6-oxopyridin-1-yl}-3-methylpyrazol-1-yl)pyrimidine-2-carboxylate (0.50 g. 52.61%) as a yellow solid. LC-MS: (ES+H, m/z): $[M+H]^+$ =483.2

Step 5: Preparation of ethyl 4-(4-{3-chloro-4-[(3,5-difluoropyridin-2-yl)methoxy]-6-methyl-2-oxopyridin-1-yl}-3-methylpyrazol-1-yl)pyrimidine-2-carboxylate To a stirred solution of ethyl 4-(4-{4-[(3.5-difluoropyridin-2-yl)methoxy]-2-methyl-6-oxopyridin-1-yl}-3-methylpyrazol-1-yl)pyrimidine-2-carboxylate (0.50 g. 1.03 mmol. 1.00 equiv) and dichloroacetic acid (13 mg, 0.10 mmol. 0.10 equiv) in propan-2-ol (2 mL) was added NCS (0.15 g. 1.14 mmol. 1.10 equiv) at room temperature under nitrogen atmosphere. The resulting mixture was stirred for 2 h at 60° C., under nitrogen atmosphere. The mixture was allowed to cool down to room temperature. The precipitated solids were collected by filtration and washed with 2-propanol (3 ×1 mL). This resulted in ethyl 4-(4-{3-chloro-4-[(3.5-difluoropyridin-2-yl)methoxy]-6-methyl-2-oxopyridin-1-yl}-3-methylpyrazol-1-yl)pyrimidine-2-carboxylate (0.45 g. 84.00%) as a white solid. LC-MS: (ES+H, m/z): $[M+H]^+$=517.1

Step 6: Preparation of 3-chloro-4-[(3,5-difluoropyridin-2-yl)methoxy]-1-{1-[2-(2-hydroxypropan-2-yl)pyrimidin-4-yl]-3-methylpyrazol-4-yl}-6-methylpyridin-2-one To a stirred solution of ethyl 4-(4-{3-chloro-4-[(3.5-difluoropyridin-2-yl)methoxy]-6-methyl-2-oxopyridin-1-yl}-3-methylpyrazol-1-yl)pyrimidine-2-carboxylate (330 mg, 0.64 mmol. 1.00 equiv) in THF (2 mL) was added MeMgBr (3.2 mL. 6.40 mmol. 10 equiv. 2M in THF) dropwise at −10° C., under nitrogen atmosphere. The resulting mixture was stirred for 20 min at 0° C., under nitrogen atmosphere. The reaction was quenched with saturating NH,CI (aq.) at room temperature. The resulting mixture was extracted with EtOAc (3 ×10 mL). The combined organic layers were washed with brine (10 mL), dried over anhydrous $Na_2SO_4$. After filtration, the filtrate was concentrated under reduced pressure. The residue was purified by reverse combi-flash chromatography. This resulted in 3-chloro-4-[(3.5-difluoropyridin-2-yl)methoxy]-1-{1-[2-(2-hydroxypropan-2-yl)pyrimidin-4-yl]-3-methylpyrazol-4-yl}-6-methylpyridin-2-one (77 mg, 24.08%) as a white solid. LC-MS: (ES+H, m/z): $[M+H]^+$=503.05. $^1$H NMR (300 MHz, DMSO-$d_6$) δ 9.20 (s, 1H), 8.90 (d, 1H), 8.60 (d, 1H), 8.10 (m, 1H), 7.76 (d, 1H), 6.77 (s, 1H), 5.49 (d, 2H), 5.17 (s, 1H), 2.13 (s, 3H), 2.10 (s, 3H), 1.53 (s, 3H), 1.52 (s, 3H). $^{19}$F NMR (282 MHz, DMSO) δ-120.19,-120.21,-122.42,-122.44.

EXAMPLE 31A, 31B

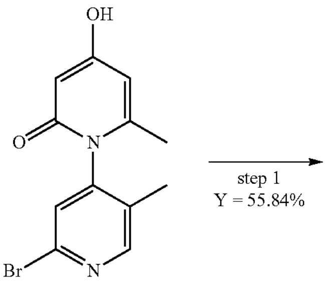

intermediate 8

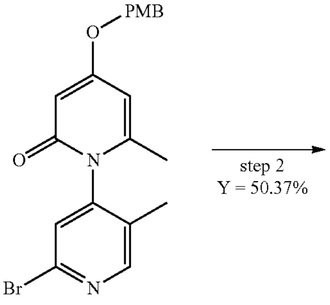

-continued
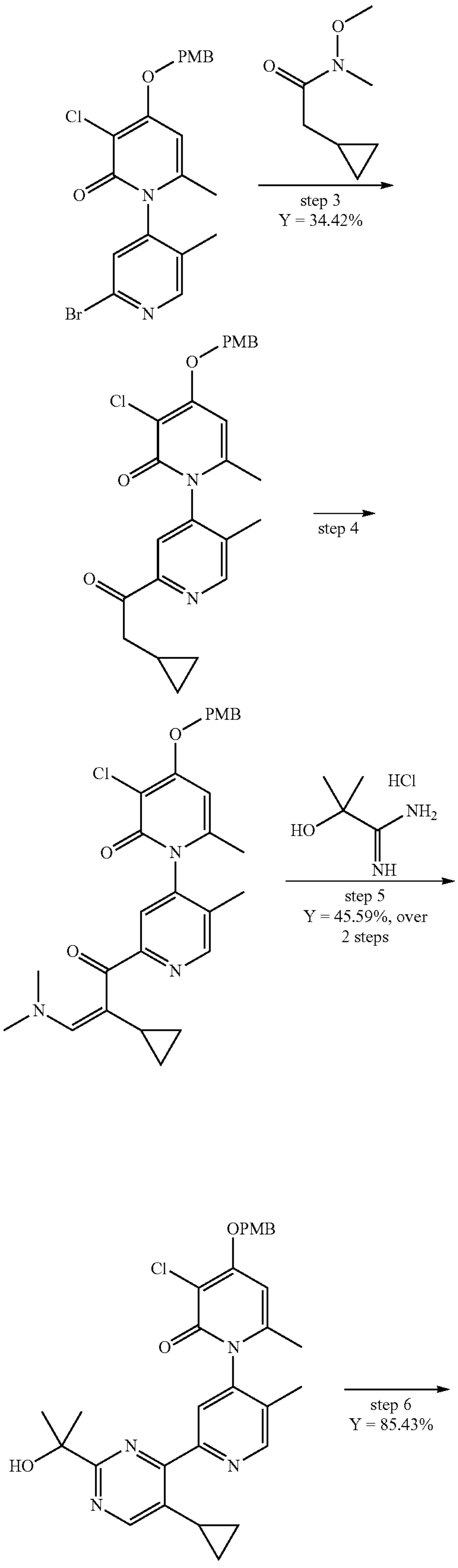
-continued
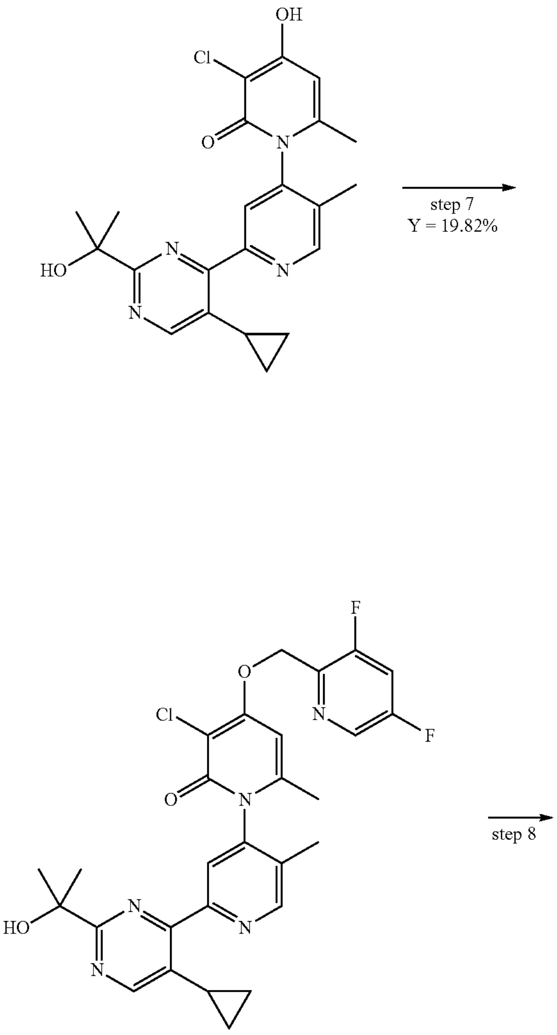
Example 31
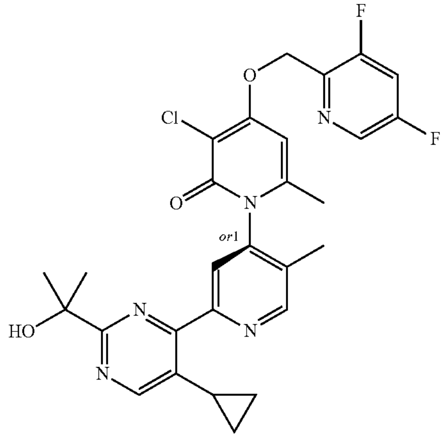
Isomer 1
Example 31A -continued

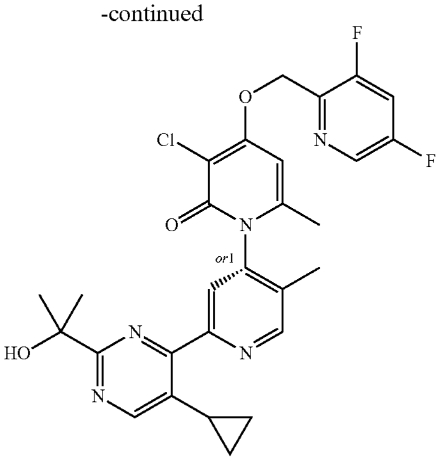

Isomer 2
Example 31B

Step 1: Preparation of 2'-bromo-4-[(4-methoxyphenyl)methoxy]-5',6-dimethyl-[1,4'-bipyridin]-2-one To a solution of 2'-bromo-4-hydroxy-5',6-dimethyl-[1,4'-bipyridin]-2-one (7.00 g, 23.72 mmol, 1.00 equiv) in DMF (50 mL) was added PMBCl (11.14 g, 71.15 mmol, 3.00 equiv), $K_2CO_3$ (13.11 g, 94.872 mmol, 4.00 equiv) and 18-Crown-6 (310 mg, 1.19 mmol, 0.05 equiv). The mixture was stirred at 60° C., for 3 h. The reaction was monitored by LCMS. The mixture was allowed to cool down to room temperature. The reaction mixture was partitioned between EA (500 mL) and water (200 mL). The organic layer was washed with water (200 mL) and brine (200 mL), and then dried over $Na_2SO_4$. The solution was concentrated under reduced pressure. The residue was purified by silica gel column chromatography to afford 2'-bromo-4-[(4-methoxyphenyl)methoxy]-5',6-dimethyl-[1,4'-bipyridin]-2-one (5.5 g, 55.84%) as an off-white solid. LC-MS: (ES+H, m/z): $[M+H]^+$=415.0/417.0. $^1H$ NMR (300 MHz, DMSO-$d_6$) δ 8.48 (s, 1H), 7.71 (s, 1H), 7.44-7.35 (m, 2H), 7.03-6.92 (m, 2H), 6.12 (dd, 1H), 5.93 (d, 1H), 5.04 (s, 2H), 3.78 (s, 3H), 1.96 (s, 3H), 1.85 (s, 3H).

Step 2: Preparation of 2'-bromo-3-chloro-4-[(4-methoxyphenyl)methoxy]-5',6-dimethyl-[1,4'-bipyridin]-2-one To a stirred mixture of 2'-bromo-4-[(4-methoxyphenyl)methoxy]-5',6-dimethyl-[1,4'-bipyridin]-2-one (5.50 g, 13.24 mmol, 1.00 equiv) and NCS (1.95 g, 14.57 mmol, 1.10 equiv) in IPA (20 mL) was added 2,2-dichloroacetic acid (100 mg, 0.80 mmol, 0.06 equiv) at room temperature. The mixture was stirred for 3 h at 60° C., under nitrogen atmosphere. The reaction was monitored by LCMS. The mixture was allowed to cool down to room temperature. The precipitated solids were collected by filtration to afford 2'-bromo-3-chloro-4-[(4-methoxyphenyl)methoxy]-5',6-dimethyl-[1,4'-bipyridin]-2-one (3 g, 50.37%) as a white solid. LC-MS: (ES+H, m/z): $[M+H]^+$=451.1. $^1H$ NMR (400 MHZ, DMSO-$d_6$) δ 8.51 (s, 1H), 7.79 (s, 1H), 7.47-7.39 (m, 2H), 7.04-6.96 (m, 2H), 6.76 (s, 1H), 5.26 (s, 2H), 3.78 (s, 3H), 1.95 (s, 3H), 1.95 (s, 3H).

Step3: Preparation of 3-chloro-2'-(2-cyclopropylacetyl)-4-[(4-methoxyphenyl)methoxy]-5',6-dimethyl-[1,4'-bipyridin]-2-one To a stirred mixture of 2'-bromo-3-chloro-4-[(4-methoxyphenyl)methoxy]-5'0.6-dimethyl-] 1,4'-bipyridin]-2-one (1.50 g. 3.34 mmol. 1.00 equiv) in Toluene (50 mL) were added i-PrMgCl (3.34 mL. 6.67 mmol. 2 equiv. 2M in THF) at room temperature under nitrogen atmosphere. The resulting mixture was stirred for 2 h at room temperature under nitrogen atmosphere. To the above mixture was added 2-cyclopropyl-N-methoxy-N-methylacetamide (22.39 g. 16.68 mmol. 5.00 equiv) dropwise over 5 min at room temperature. The resulting mixture was stirred overnight at room temperature. The reaction was monitored by LCMS. The reaction was quenched by the addition of sat. $NH_4Cl$ (aq.) (10 mL) at 0° C. The resulting mixture was extracted with EtOAc (3 ×100 mL). The combined organic layers were washed with brine (2×100 mL), dried over anhydrous $Na_2SO_4$. After filtration, the filtrate was concentrated under reduced pressure. The residue was purified by silica gel column chromatography to afford 3-chloro-2'-(2-cyclopropylacetyl)-4-[(4-methoxyphenyl)methoxy]-5'0.6-dimethyl-] 1,4'-bipyridin]-2-one (520 mg. 34.42%) as a yellow solid. LC-MS: (ES+H, m/z): $[M+H]^+$=453.2.

Step 4/5: Preparation of 3-chloro-2'-[5-cyclopropyl-2-(2-hydroxypropan-2-yl)pyrimidin-4-yl]-4-[(4-methoxyphenyl)methoxy]-5',6-dimethyl-[1,4'-bipyridin]-2-one A solution of 3-chloro-2'-(2-cyclopropylacetyl)-4-[(4-methoxyphenyl)methoxy]-5'0.6-dimethyl-[1,4'-bipyridin]-2-one (520 mg, 1.15 mmol. 1.00 equiv) in DMF-DMA (4 mL) was stirred overnight at 100° C., under nitrogen atmosphere. The reaction was monitored by LCMS. The mixture was allowed to cool down to room temperature. The resulting mixture was concentrated under reduced pressure, to afford 3-chloro-2'-[(2Z)-2-cyclopropyl-3-(dimethylamino)prop-2-enoyl]-4-[(4-methoxyphenyl)methoxy]-5'0.6-dimethyl-[1,4'-bipyridin]-2-one (550 mg, crude). The crude product was used in the next step directly without further purification.

The above crude (assumed 100% yield. 1.00 equiv) was re-dissolved in IPA (3 mL) and added 2-hydroxy-2-methylpropanimidamide hydrochloride (1.11 g. 10.83 mmol. 10.00 equiv) and $K_2CO$; (1.50 g. 10.83 mmol. 10.00 equiv). The resulting mixture was stirred for 12 h at 80° C. The reaction was monitored by LCMS. The mixture was allowed to cool down to room temperature. The resulting mixture was filtered, the filter cake was washed with MeOH (3 ×10 mL). The filtrate was concentrated under reduced pressure. The residue was purified by silica gel column chromatography to afford 3-chloro-2'-[5-cyclopropyl-2-(2-hydroxypropan-2-yl)pyrimidin-4-yl]-4-[(4-methoxyphenyl)methoxy]-5'0.6-dimethyl-[1,4'-bipyridin]-2-one (270 mg. 45.59%) as a light yellow solid. LC-MS: (ES+H, m/z): $[M+H]^+$=547.2.

Step 6: Preparation of 3-chloro-2'-[5-cyclopropyl-2-(2-hydroxypropan-2-yl)pyrimidin-4-yl]-4-hydroxy-5',6-dimethyl-[1,4'-bipyridin]-2-one To a stirred solution of 3-chloro-2'-[5-cyclopropyl-2-(2-hydroxypropan-2-yl)pyrimidin-4-yl]-4-[(4-methoxyphenyl)methoxy]-5'0.6-dimethyl-[1,4'-bipyridin]-2-one (270 mg, 0.49 mmol. 1.00 equiv) in DCM (3 mL) was added TFA (1 mL) at room temperature under nitrogen atmosphere. The resulting mixture was stirred for 1 h at room temperature under nitrogen atmosphere. The reaction was monitored by LCMS. The resulting mixture was concentrated under reduced pressure. The residue was purified by trituration with hexane (10 mL) to afford 3-chloro-2'-[5-cyclopropyl-2-(2-hydroxypropan-2-yl)pyrimidin-4-yl]-4-hydroxy-5'0.6-dimethyl-[1,4'-bipyridin]-2-one (180 mg. 85.43%) as a yellow oil. LC-MS: (ES+H, m/z): $[M+H]^+$=427.2.

Step 7: Preparation of 3-chloro-2'-[5-cyclopropyl-2-(2-hydroxypropan-2-yl)pyrimidin-4-yl]-4-[(3,5-difluoropyridin-2-yl)methoxy]-5',6-dimethyl-[1,4'-bipyridin]-2-one To a stirred mixture of 3-chloro-2'-[5-cyclopropyl-2-(2-hydroxypropan-2-yl)pyrimidin-4-yl]-4-hydroxy-5'0.6-dimethyl-[1,4'-bipyridin]-2-one (175 mg, 0.41 mmol. 1.00 equiv) and 2-(chloromethyl)-3.5-difluoropyridinc (74 mg, 0.45 mmol. 1.10 equiv) in DMF (2 mL) was added 18-Crown-6 (5.42 mg, 0.02 mmol. 0.05 equiv) and $K_2CO_3$ (169.96 mg, 1.23 mmol. 3.00 equiv) at room temperature under nitrogen atmosphere. The resulting mixture was stirred overnight at 60° C., under nitrogen atmosphere. The mixture was allowed to cool down to room temperature. The resulting mixture was diluted with EA (20 mL), then washed with $H_2O$ (3 ×20 mL), the organic layer was concentrated under reduced pressure. The resulting mixture was purified by Prep-HPLC to afford 3-chloro-2'-[5-cyclopropyl-2-(2-hydroxypropan-2-yl)pyrimidin-4-yl]-4-[(3.5-difluoropyridin-2-yl)methoxy]-5'0.6-dimethyl-[1,4'-bipyridin]-2-one (45 mg. 19.82%) as a light yellow solid. LC-MS: (ES+H, m/z): $[M+H]^+$=554.1.

Step 8: Preparation of (Example 31A, isomer 1) rel-3-chloro-2'-(5-cyclopropyl-2-(2-hydroxypropan-2-yl)pyrimidin-4-yl)-4-((3,5-difluoropyridin-2-yl)methoxy)-5',6-dimethyl-2H-[1,4'-bipyridin]-2-one and rel-3-chloro-2'-(5-cyclopropyl-2-(2-hydroxypropan-2-yl)pyrimidin-4-yl)-4-((3,5-difluoropyridin-2-yl)methoxy)-5',6-dimethyl-2H-[1,4'-bipyridin]-2-one 3-chloro-2'-[5-cyclopropyl-2-(2-hydroxypropan-2-yl)pyrimidin-4-yl]-4-[(3.5-difluoropyridin-2-yl)methoxy]-5'0.6-dimethyl-] 1,4'-bipyridin]-2-one (racemate. 40 mg) was separated by Prep-CHIRAL-HPLC to afford Example 31A (11.1 mg, cc-98.5%) as a light yellow solid and Example 31B (11.1 mg, ee=99.6%) as a light yellow solid.

EXAMPLE 31A

LC-MS: (ES+H, m/z): $[M+H]^+$=554.30. $^1H$ NMR (400 MHZ. DMSO-$d_6$) δ 8.81 (s, 1H), 8.60 (d. 1H), 8.57 (s, 1H), 8.18 (s.1H), 8.15-8.05 (m, 1H), 6.83 (s, 1H), 5.49 (d, 2H), 5.08 (s, 1H), 2.75 (td. 1H). 2.10 (s, 3H), 2.00 (s, 3H), 1.50 (s, 3H), 1.50 (s, 3H), 1.01-0.90 (m, 2H), 0.82-0.75 (m, 2H). $^{19}F$ NMR (377 MHz, DMSO) δ-120.14, —120.16, —122.33, —122.35.

EXAMPLE 31B

LC-MS: (ES+H, m/z): $[M+H]^+$=554.10. $^1H$ NMR (400 MHZ. DMSO-$d_6$) δ 8.81 (s, 1H), 8.60 (d. 1H), 8.57 (s, 1H), 8.18 (s, 1H), 8.10 (ddd. 1H), 6.83 (s.1H), 5.49 (d, 2H), 5.08 (s.1H), 2.81-2.70 (m, 1H). 2.10 (s, 3H), 2.00 (s, 3H), 1.50 (s, 3H), 1.50 (s, 3H), 1.02-0.88 (m, 2H), 0.84-0.73 (m, 2H). $^{19}F$ NMR (377 MHz. DMSO) δ-120.14, —120.16, —122.34, —122.36.

EXAMPLE 32A, 32B, 32C, 32D

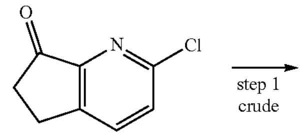

-continued

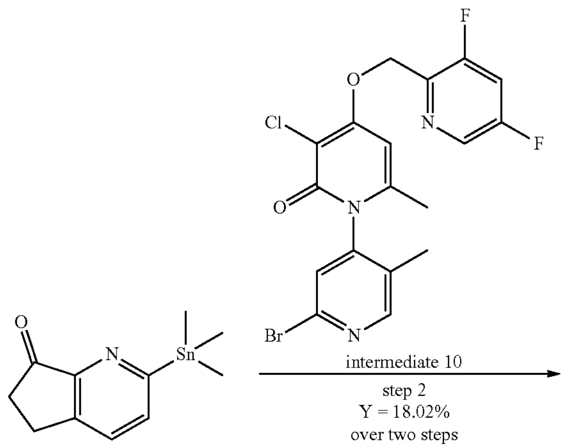

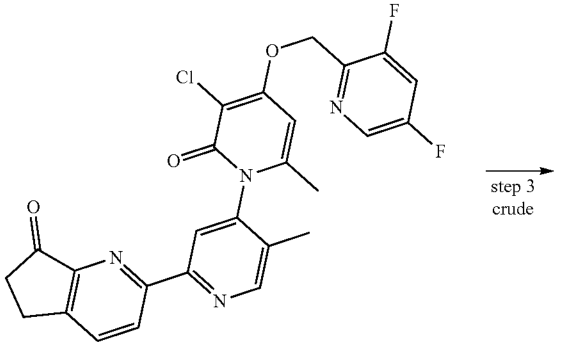

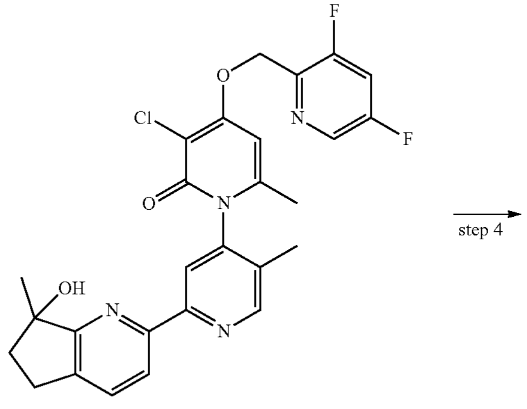

Example 32

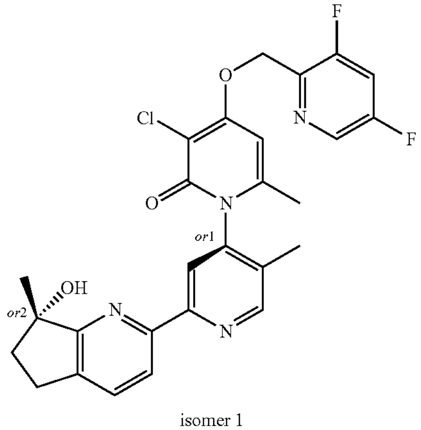

isomer 1
Example 32A

-continued

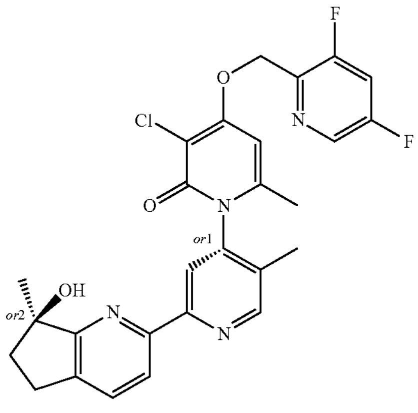

isomer 2
Example 32B

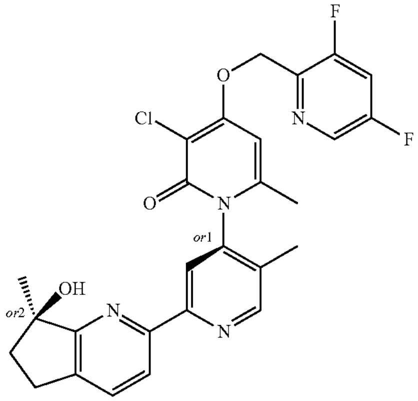

isomer 3
Example 32C

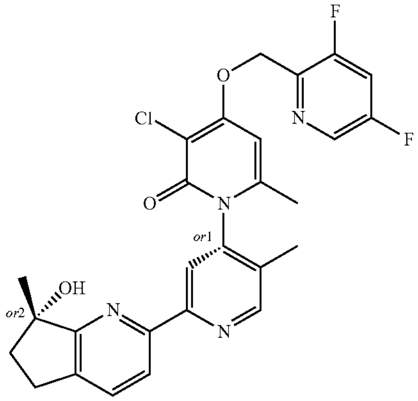

isomer 4
Example 32D

Step 1: Preparation of 2-(trimethylstannyl)-5H,6H-cyclopenta[b] pyridin-7-one

A mixture of 2-chloro-5H,6H-cyclopenta[b] pyridin-7-one (250 mg, 1,492 mmol, 1.00 equiv), $Pd(PPh_3)$: $Cl_2$ (209 mg, 0.298 mmol, 0.20 equiv), $AsPh_3$ (91 mg, 0.298 mmol, 0.20 equiv) and $Sn_2Me_6$ (488 mg, 1,492 mmol, 1.00 equiv) in dioxane (8 mL) was stirred for overnight at 80° C., under nitrogen atmosphere. The reaction was monitored by LCMS. The resulting mixture was used in the next step directly without further purification. LC-MS: (ES+H, m/z): $[M+H]^+$=298.0.

Step 2: Preparation of 3-chloro-4-[(3,5-difluoropyridin-2-yl)methoxy]-5',6-dimethyl-2'-{7-oxo-5H,6H-cyclopenta[b] pyridin-2-yl}-[1,4'-bipyridin]-2-one 2'-bromo-3-chloro-4-[(3,5-difluoropyridin-2-yl) methoxy]-5',6-dimethyl-[1,4'-bipyridin]-2-one (328 mg, 0.719 mmol, 0.6 equiv), $Pd(PPh_3)$: $Cl_2$ (168 mg, 0.240 mmol, 0.20 equiv) and CuI (228 mg, 1.199 mmol, 1 equiv) was added to the reaction solution in the previous step at room temperature. The resulting mixture was stirred for 2 h at 80° C., under nitrogen atmosphere. The reaction was monitored by LCMS. The mixture was allowed to r.t . . . . The resulting mixture was diluted with EA (200 mL), washed with 3 ×150 mL of sat. $NaHCO_3$(aq.). The organic layers were concentrated under reduced pressure and purified by silica gel column chromatography to afford crude product. The crude product was further purified by reverse combi-flash chromatography to afford 3-chloro-4-[(3,5-difluoropyridin-2-yl)methoxy]-5',6-dimethyl-2'-{7-oxo-5H, 6H-cyclopenta[b] pyridin-2-yl}-[1,4'-bipyridin]-2-one (110 mg, 18.02%, over two steps) as a white solid. LC-MS: (ES+H, m/z): $[M+H]^+$=508.8. $^1$H NMR (300 MHz, Chloroform-d) δ 8.71 (s, 1H), 8.68 (d, 1H), 8.43 (s, 1H), 8.40 (s, 1H), 8.02 (d, 1H), 7.39-7.31 (m, 1H), 6.39 (s, 1H), 5.46 (s, 2H), 3.22 (t, 2H), 2.84 (t, 2H), 2.19 (s, 3H), 2.01 (s, 3H).

Step 3: Preparation of 3-chloro-4-[(3,5-difluoropyridin-2-yl)methoxy]-2'-{7-hydroxy-7-methyl-5H,6H-cyclopenta[b] pyridin-2-yl}-5',6-dimethyl-[1,4'-bipyridin]-2-one To a stirred solution of 3-chloro-4-[(3,5-difluoropyridin-2-yl)methoxy]-5',6-dimethyl-2'-{7-oxo-5H,6H-cyclopenta [b] pyridin-2-yl}-[1,4'-bipyridin]-2-one (200 mg, 0.393 mmol, 1.00 equiv) in THF (10 mL) was added MeMgBr (1.31 mL. 3.93 mmol. 10.00 equiv. 3M in THF) dropwise at −10° C., under nitrogen atmosphere. The resulting mixture was stirred for 1 h at −10° C., under nitrogen atmosphere. The reaction was monitored by LCMS. The reaction was quenched by addition of sat. $NH_4Cl$ (aq.) (20 mL) at −10° C. The resulting mixture was extracted with EtOAc (3 ×50 mL). The combined organic layers were dried over anhydrous $Na_2SO_4$. After filtration, the filtrate was concentrated under reduced pressure, to afford 3-chloro-4-[(3.5-difluoropyridin-2-yl)methoxy]-2'-{7-hydroxy-7-methyl-5H.6H-cyclopenta[b] pyridin-2-yl}-5'0.6-dimethyl-[1,4'-bipyridin]-2-one (220 mg, crude) as a yellow solid. LC-MS: (ES+H, m/z): $[M+H]^+$=525.2.

Step 4: Preparation of rel-(R)-3-chloro-4-((3,5-difluoropyridin-2-yl)methoxy)-2'-(7-hydroxy-7-methyl-6,7-dihydro-5H-cyclopenta[b] pyridin-2-yl)-5',6-dimethyl-2H-[1,4'-bipyridin]-2-one & rel-(R)-3-chloro-4-((3,5-difluoropyridin-2-yl)methoxy)-2'-(7-hydroxy-7-methyl-6,7-dihydro-5H-cyclopenta[b] pyridin-2-yl)-5',6-dimethyl-2H-[1,4'-bipyridin]-2-one & rel-(R)-3-chloro-4-((3,5-difluoropyridin-2-yl) methoxy)-2'-(7-hydroxy-7-methyl-6,7-dihydro-5H-cyclopenta[b] pyridin-2-yl)-5',6-dimethyl-2H-[1,4'-bipyridin]-2-one & rel-(R)-3-chloro-4-((3,5-difluoropyridin-2-yl)methoxy)-2'-(7-hydroxy-7-methyl-6,7-dihydro-5H-cyclopenta[b] pyridin-2-yl)-5',6-dimethyl-2H-[1,4'-bipyridin]-2-one 3-chloro-4-[(3.5-difluoropyridin-2-yl)methoxy]-2'-{7-hydroxy-7-methyl-5H.6H-cyclopenta/b] pyridin-2-yl}-5',6-dimethyl-[1,4'-bipyridin]-2-one (220 mg, crude) was isolated by Prep-HPLC to afford 2 fractions. The first peak (50 mg) was separated by prep-chiral-HPLC to afford Example 32A (17.8 mg. 95.7% purity, ee=100%) and Example 32B (17.3 mg. 95.0% purity, ee=97.17%) as a white solid. The second peak (60 mg) was separated by prep-chiral-HPLC to afford Example 32C (22.8 mg. 97.8% purity, ee=98.67%) and Example 32D (23.5 mg. 97.3% purity, ee=96.46%) as a white solid.

EXAMPLE 32A

LC-MS: (ES+H, m/z): $[M+H]^+$=525.1. $^1$H NMR (400 MHz. DMSO-$d_6$) δ 8.76 (s, 1H), 8.61 (d. 1H), 8.26 (d, 1H), 8.24 (d, 1H), 8.15-8.04 (m, 1H), 7.80 (d, 1H), 6.83 (d, 1H), 5.50 (d, 2H), 5.12 (s.1H). 3.03-2.88 (m. 1H), 2.86-2.73 (m, 1H), 2.19-2.09 (m, 2H), 2.07 (s, 3H), 1.98 (s, 3H), 1,47 (s, 3H), 1° F. NMR (377 MHz. DMSO) δ-120.13, —120.15, —122.31, —122.33.

EXAMPLE 32B

LC-MS: (ES+H, m/z): $[M+H]^+$=525.1. $^1$H NMR (400 MHZ. DMSO-$d_6$) δ 8.76 (s, 1H), 8.61 (d. 1H), 8.26 (d, 1H), 8.24 (d, 1H), 8.15-7.99 (m. 1H), 7.80 (d, 1H), 6.83 (d, 1H), 5.50 (d, 2H), 5.13 (s, 1H). 3.02-2.87 (m, 1H), 2.86-2.75 (m. 1H), 2.20-2.10 (m, 2H), 2.07 (s, 3H), 1.98 (s, 3H), 1,47 (s, 3H), 1° F. NMR (377 MHz. DMSO) δ-120.12, —120.14, —122.28, —122.30.

EXAMPLE 32C

LC-MS: (ES+H, m/z): [M+H]+=525.1. $^1$H NMR (400 MHZ. DMSO-$d_6$) δ 8.76 (s, 1H), 8.61 (d. 1H), 8.27 (d, 1H), 8.25 (d, 1H), 8.15-8.04 (m, 1H), 7.80 (d, 1H), 6.82 (d, 1H), 5.49 (d, 2H), 5.12 (s, 1H). 3.05-2.89 (m, 1H), 2.83-2.74 (m, 1H), 2.15-2.09 (m, 2H), 2.07 (s, 3H), 1.98 (s, 3H), 1.50 (s, 3H), 1° F. NMR (377 MHz. DMSO) δ-120.14, —120.16, —122.33, —122.35.

EXAMPLE 32D

LC-MS: (ES+H, m/z): $[M+H]^+$=525.1. $^1$H NMR (400 MHZ, DMSO-$d_6$) δ 8.76 (s, 1H), 8.61 (d, 1H), 8.27 (d, 1H), 8.25 (d, 1H), 8.13-8.04 (m, 1H), 7.80 (d, 1H), 6.82 (d, 1H), 5.49 (d, 2H), 5.12 (s, 1H), 3.03-2.87 (m, 1H), 2.85-2.73 (m, 1H), 2.19-2.08 (m, 2H), 2.07 (s, 3H), 1.98 (s, 3H), 1.50 (s, 3H), 19F NMR (377 MHz, DMSO) δ-120.14,-120.16,-122.33,-122.35.

EXAMPLE 33A, 33B

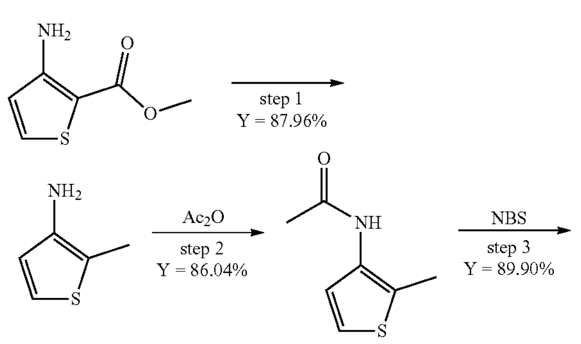

-continued

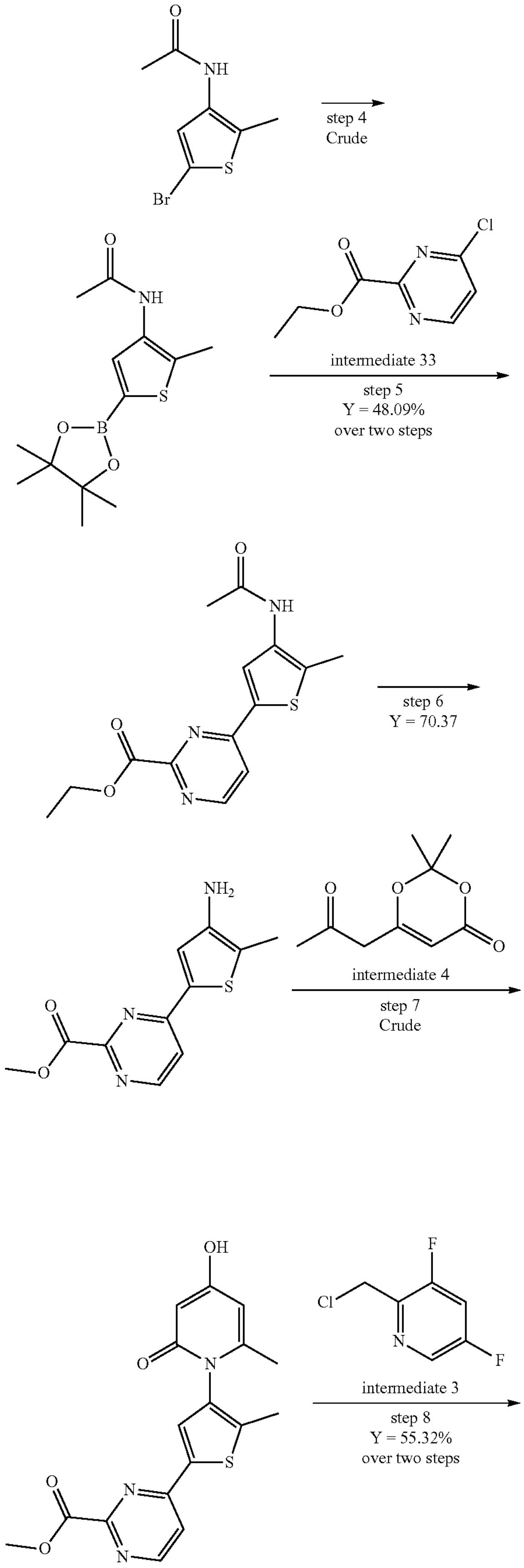

-continued

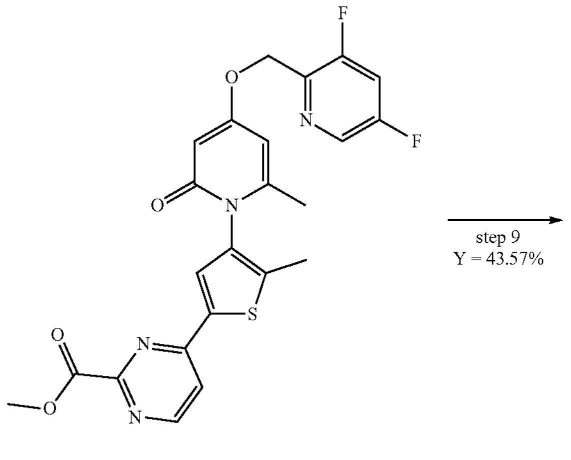

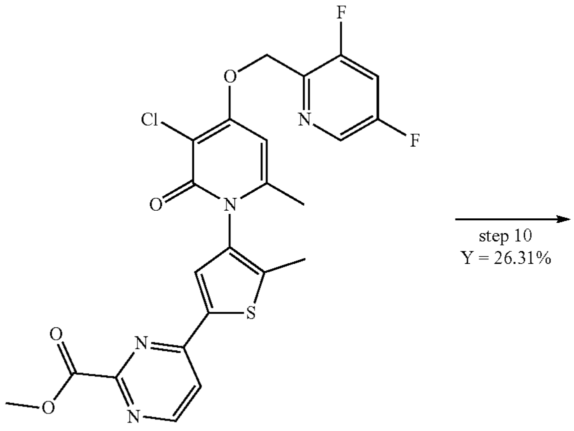

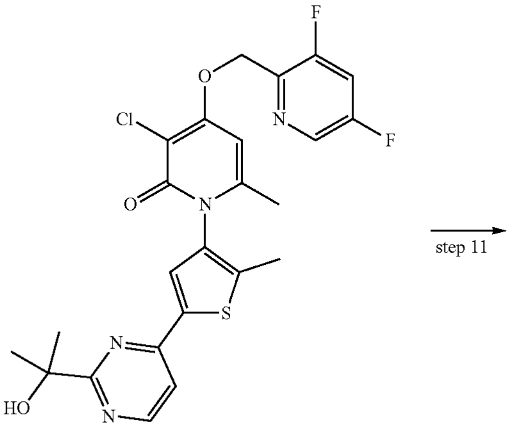

Example 33

-continued

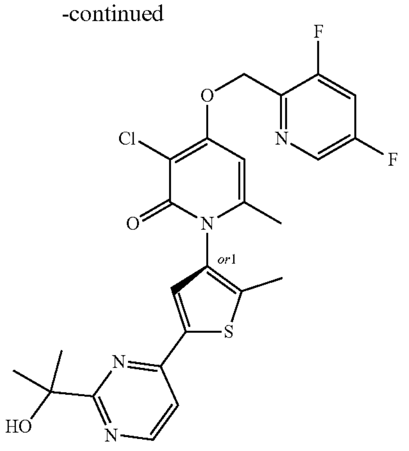

isomer 1
Example 33A

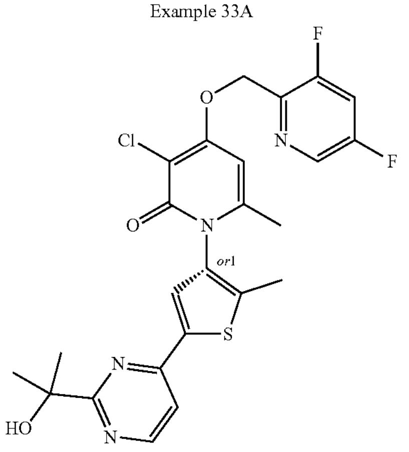

isomer 2
Example 33B

Step 1: Preparation of 2-methylthiophen-3-amine

To a stirred solution of LAH (14.49 g, 381.70 mmol, 2.00 equiv) in 1,4-dioxane was added methyl 3-aminothiophene-2-carboxylate (30.00 g, 190.85 mmol, 1.00 equiv) in 1,4-dioxane dropwise at 95° C., under nitrogen atmosphere. The resulting mixture was stirred for 1.5 h at 95° C., under nitrogen atmosphere. The mixture was allowed to cool down to room temperature. The reaction was monitored by LCMS. LCMS was OK. The mixture was allowed to cool down to 0° C. To the above mixture was added water (14.5 mL), 15% aqueous NaOH (43.5 ml) and water (14.5 ml), The resulting mixture was stirred for 1 h at room temperature, The resulting mixture was filtered, the filter cake was washed with EtOAc (3 ×50 mL). The filtrate was concentrated under reduced pressure.to afford 2-methylthiophen-3-amine (19.00 g, 87.96%) as a black oil. LC-MS: (ES+H, m/z): $[M+H]^+$=114.0. $^1H$ NMR (300 MHz, DMSO-$d_6$) δ 6.94 (d, 1H), 6.50 (d, 1H), 4.48 (br, 2H), 2.11 (s, 3H).

Step 2: Preparation of N-(2-methylthiophen-3-yl)acetamide

To a stirred solution of 2-methylthiophen-3-amine (10.00 g, 88.35 mmol, 1.00 equiv) and $CH_3COOK$ (11.27 g, 114.86 mmol, 1.30 equiv) in toluene was added Ac: O (10.86 mL, 114.86 mmol, 1.30 equiv) in portions at room temperature.

The resulting mixture was stirred for 1 h at room temperature. The resulting mixture was concentrated under reduced pressure. The residue was dissolved in DCM (30 mL). The combined organic layers were washed with brine (3 ×30 mL), dried over anhydrous $Na_2SO_4$. After filtration, the filtrate was concentrated under reduced pressure. The residue was purified by silica gel column chromatography to afford N-(2-methylthiophen-3-yl)acetamide (11.80 g. 86.04%) as a yellow solid. LC-MS: (ES+H, m/z): $[M+H]^+$=156.1. $^1H$ NMR (300 MHz. DMSO-$d_6$) δ 9.41 (s, 1H), 7.22-7.11 (m, 2H), 2.27 (s. 3H), 2.01 (s, 3H).

Step 3: Preparation of N-(5-bromo-2-methylthiophen-3-yl)acetamide

To a stirred solution of N-(2-methylthiophen-3-yl)acetamide (11.80 g. 76.02 mmol. 1.00 equiv) and 1-bromopyrrolidine-2.5-dione (13.53 g. 76.02 mmol. 1.00 equiv) in acetonitrile at room temperature under air atmosphere. The resulting mixture was stirred for 3 h at room temperature. The reaction was monitored by LCMS. The resulting mixture was concentrated under reduced pressure. The resulting mixture was diluted with brine (50 mL) and extracted with CH.$C_1$. (3 ×20 mL). Then organic layer was dried over anhydrous $Na_2SO_4$ and concentrated under reduced pressure. The residue was purified by silica gel column chromatography to afford N-(5-bromo-2-methylthiophen-3-yl) acetamide (16.00 g. 89.90%) as a yellow solid. LC-MS: (ES+H, m/z): $[M+H]^+$=233.9. $^1H$ NMR (400 MHZ. DMSO-$d_6$) δ 9.52 (s, 1H), 7.25 (s, 1H). 2.22 (s, 3H), 2.00 (s, 3H).

Step 4: Preparation of N-[2-methyl-5-(4,4,5,5-tetramethyl-1,3,2-dioxaborolan-2-yl) thiophen-3-ylacetamide To a stirred solution of N-(5-bromo-2-methylthiophen-3-yl)acetamide (10.00 g. 42.71 mmol. 1.00 equiv) and 4.4.5.5-tetramethyl-2-(tetramethyl-1.3.2-dioxaborolan-2-yl)-1.3.2-dioxaborolane (14.10 g. 55.53 mmol. 1.30 equiv) in 1,4-dioxane (50 mL) were added $CH_3COOK$ (12.58 g. 128.14 mmol. 3.00 equiv) and Pd(dppf)$Cl_2$(1.56 g. 2.13 mmol. 0.10 equiv) at room temperature under nitrogen atmosphere. The resulting mixture was stirred for 12 h at 100° C., under nitrogen atmosphere. The mixture was allowed to cool down to room temperature. The reaction was monitored by LCMS. The resulting mixture was filtered, the filter cake was washed with 1,4-dioxane (3 ×10 mL). The filtrate was concentrated under reduced pressure to afford N-]2-methyl-5-(4.4.5.5-tetramethyl-1.3.2-dioxaborolan-2-yl) thiophen-3-yl]acetamide (11.00 g, crude) as a black solid. The crude product was used in the next step directly without further purification. LC-MS: (ES+H, m/z): $[M+H]^+$=282.2.

Step 5: Preparation of ethyl 4-(4-acetamido-5-methylthiophen-2-yl)pyrimidine-2-carboxylate To a stirred solution of N-]2-methyl-5-(4.4.5.5-tetramethyl-1.3.2-dioxaborolan-2-yl) thiophen-3-yl]acetamide (9.00 g. 32.00 mmol, assumed 100% yield. 1.00 equiv) and ethyl 4-chloropyrimidine-2-carboxylate (7.76 g. 41.61 mmol. 1.30 equiv) in 1,4-dioxane/$H_2O$ (50 mL/10 mL) were added $K_2CO_3$ (13.27 g. 96.02 mmol. 3.00 equiv) and Pd(dppf) $Cl_2$.$CH_2Cl_2$ (2.61 g. 3.20 mmol. 0.10 equiv) at room temperature under nitrogen atmosphere. The resulting mixture was stirred for 2 h at 80° C., under nitrogen atmosphere. The reaction was monitored by LCMS. The resulting mixture was concentrated under reduced pressure. The resulting mixture was diluted with brine (50 mL) and extracted with DCM (3 ×50 mL). Then organic layer was dried over anhydrous $Na_2SO_4$ and concentrated under reduced pressure. The residue was purified by silica gel column chromatography to afford ethyl 4-(4-acetamido-5-methylthiophen-2-yl)pyrimidine-2-carboxylate (4.70 g. 48.09%) as a brown solid. LC-MS: (ES+H, m/z): $[M+H]^+$=306.1. $^1H$ NMR (300 MHz. DMSO-$d_6$) δ 9.64 (s, 1H), 8.85 (d, 1H), 8.18 (s, 1H), 8.03 (d, 1H), 4.44-4.32 (m, 2H), 2.38 (s, 3H), 2.07 (s. 3H), 1.38-1.31 (m, 3H).

Step 6: Preparation of methyl 4-(4-amino-5-methylthiophen-2-yl)pyrimidine-2-carboxylate To a stirred solution of ethyl 4-(4-acetamido-5-methylthiophen-2-yl)pyrimidine-2-carboxylate (4.70 g. 15.39 mmol. 1.00 equiv) HCl (g) in MeOH (10 mL. 4M in MeOH) at room temperature under nitrogen atmosphere. The resulting mixture was stirred for 2 h at room temperature under nitrogen atmosphere. The reaction was monitored by LCMS. The resulting mixture was concentrated under reduced pressure. The residue was purified by silica gel column chromatography to afford methyl 4-(4-amino-5-methylthiophen-2-yl)pyrimidine-2-carboxylate (2.70 g. 70.37%) as a brown solid. LC-MS: (ES+H, m/z): $[M+H]^+$=250.0. $^1H$ NMR (300 MHz. DMSO-$d_6$) δ 8.78 (d, 1H), 7.84 (d, 1H), 7.46 (s.1H), 4.81 (s, 2H), 3.91 (s. 3H), 2.22 (s, 3H).

Step 7: Preparation of methyl 4-[4-(4-hydroxy-2-methyl-6-oxopyridin-1-yl)-5-methylthiophen-2-yl] pyrimidine-2-carboxylate To a stirred solution of methyl 4-(4-amino-5-methylthiophen-2-yl)pyrimidine-2-carboxylate (1.70 g. 6.81 mmol. 1.00 equiv) and 2.2-dimethyl-6-(2-oxopropyl)-1,3-dioxin-4-one (1.63 g. 8.86 mmol. 1.30 equiv) in 1,4-dioxane (30 mL) at room temperature under nitrogen atmosphere. The resulting mixture was stirred for 2 h at 90° C., under nitrogen atmosphere. The mixture was allowed to cool down to room temperature. To the above mixture was added conc. $H_2SO_4$ (0.67 g. 6.81 mmol. 1.00 equiv) dropwise over Imin at room temperature. The resulting mixture was stirred for additional 1 h at 90° C. The mixture was allowed to cool down to room temperature. The reaction was monitored by LCMS. The resulting mixture was concentrated under reduced pressure. The residue was purified by trituration with Et.O (100 mL). The precipitated solid was collected by filtration and washed with Et.O (5×6 mL), to afford methyl 4-[4-(4-hydroxy-2-methyl-6-oxopyridin-1-yl)-5-methylthiophen-2-yl]pyrimidine-2-carboxylate (2.00 g. 82.06%) as a brown solid. LC-MS: (ES+H, m/z): $[M+H]^+$=358.0. $^1H$ NMR (400 MHZ, DMSO-$d_6$) δ 10.75 (s, 1H), 8.94-8.91 (m, 1H), 8.12-8.08 (m, 1H), 8.01 (d, 1H), 5.95 (d, 1H), 5.59 (d, 1H), 3.93 (s, 3H), 2.20 (s, 3H), 1.94 (s. 3H).

Step 8: Preparation of methyl 4-(4-{4-[(3,5-difluoropyridin-2-yl)methoxy]-2-methyl-6-oxopyridin-1-yl}-5-methylthiophen-2-yl)pyrimidine-2-carboxylate To a stirred solution of methyl 4-[4-(4-hydroxy-2-methyl-6-oxopyridin-1-yl)-5-methylthiophen-2-yl]pyrimidine-2-carboxylate (1.20 g. 3.35 mmol. 1.00 equiv) and 2-(chloromethyl)-3.5-difluoropyridinc (600.42 mg. 3.69 mmol. 1.10 equiv) in DMF (3 mL) were added 18-crown-6 (90.12 mg, 0.33 mmol. 0.10 equiv) and $K_2CO$; (2.32 g. 16.79 mmol. 5.00 equiv) at room temperature under nitrogen atmosphere. The resulting mixture was stirred for 3 h at 60°

C., under nitrogen atmosphere. The mixture was allowed to cool down to room temperature. The reaction was monitored by LCMS. The resulting mixture was poured into water (20 mL), then extracted with EtOAc (3 ×10 mL). The combined organic layers were washed with brine (20 mL), dried over anhydrous $Na_2SO_4$. After filtration, the filtrate was concentrated under reduced pressure. The residue was purified by silica gel column chromatography to afford methyl 4-(4-{4-[(3.5-difluoropyridin-2-yl)methoxy]-2-methyl-6-oxopyridin-1-yl}-5-methylthiophen-2-yl)pyrimidine-2-carboxylate (900 mg. 55.32%) as a brown solid. LC-MS: (ES+H, m z): $[M+H]^+$=485.0.

Step 9: Preparation of methyl 4-(4-{3-chloro-4-[(3, 5-difluoropyridin-2-yl)methoxy]-6-methyl-2-oxopyridin-1-yl}-5-methylthiophen-2-yl)pyrimidine-2-carboxylate To a stirred solution of methyl 4-(4-{4-[(3.5-difluoropyridin-2-yl)methoxy]-2-methyl-6-oxopyridin-1-yl}-5-methylthiophen-2-yl)pyrimidine-2-carboxylate (900 mg, 1.85 mmol. 1.00 equiv) and NCS (322 mg. 2.41 mmol. 1.30 equiv) in IPA (4 mL) was added 2.2-dichloroacetic acid (24 mg, 0.18 mmol. 0.10 equiv) dropwise at room temperature under nitrogen atmosphere. The resulting mixture was stirred for 1 h at 60° C., under nitrogen atmosphere. The mixture was allowed to cool down to room temperature. The reaction was monitored by LCMS. The resulting mixture was poured into brine (50 mL) and extracted with DCM (3 ×50 mL). Then organic layer was dried over anhydrous $Na_2SO_4$ and concentrated under reduced pressure. The residue was purified by reverse combi-flash chromatography to afford methyl 4-(4-{3-chloro-4-[(3.5-difluoropyridin-2-yl) methoxy]-6-methyl-2-oxopyridin-1-yl}-5-methylthiophen-2-yl)pyrimidine-2-carboxylate (420 mg. 43.57%) as a yellow solid. LC-MS: (ES+H, m z): $[M+H]^+$=519.0. $^1H$ NMR (400 MHz. DMSO-$d_6$) δ 8.94 (d, 1H), 8.60 (d, 1H), 8.13-8.08 (m. 1H), 8.08 (d. 1H), 8.07 (d, 1H), 6.77-6.74 (m. 1H), 5.48 (d, 2H), 3.94 (s, 3H), 2.23 (s, 3H), 2.06 (s, 3H).

Step 10: Preparation of 3-chloro-4-[(3,5-difluoropyridin-2-yl)methoxy]-1-{5-[2-(2-hydroxypropan-2-yl)pyrimidin-4-yl]-2-methylthiophen-3-yl}-6-methylpyridin-2-one To a stirred solution of methyl 4-(4-{3-chloro-4-[(3.5-difluoropyridin-2-yl)methoxy]-6-methyl-2-oxopyridin-1-yl}-5-methylthiophen-2-yl)pyrimidine-2-carboxylate (380 mg, 0.73 mmol. 1.00 equiv) in THF (3 mL) was added MeMgBr (3.66 mL. 7.32 mmol. 10.00 equiv. 2M in THF) dropwise at 0° C., under nitrogen atmosphere. The resulting mixture was stirred for 1 h at 0° C., under nitrogen atmosphere. The reaction was monitored by LCMS. The reaction was quenched by the addition of sat. $NH_4Cl$ (aq.) (20 mL) at 0° C. The resulting mixture was extracted with EtOAc (3 ×20 mL). The combined organic layers were washed with brine (40 mL), dried over anhydrous $Na_2SO_4$. After filtration, the filtrate was concentrated under reduced pressure. The residue was purified by reverse combi-flash chromatography to afford crude 3-chloro-4-1 (3.5-difluoropyridin-2-yl)methoxy]-1-{5-[2-(2-hydroxypropan-2-yl)pyrimidin-4-yl]-2-methylthiophen-3-yl}-6-methylpyridin-2-one (154 mg, crude) as a light yellow solid. The crude product (154 mg) was further purified by Prep-HPLC to afford 3-chloro-4-[(3.5-difluoropyridin-2-yl)methoxy]-1-{5—]2-(2-hydroxypropan-2-yl)pyrimidin-4-yl]-2-methylthiophen-3-yl}-6-methylpyridin-2-one (100 mg. 26.31%) as a light yellow solid. LC-MS: (ES+H, m z): $[M+H]^+$=519.1. $^1H$ NMR (300 MHz. DMSO-$d_6$) δ 8.80 (d, 1H), 8.60 (d, 1H), 8.16-8.03 (m. 1H), 7.99 (s.1H), 7.75 (d, 1H), 6.75 (s.1H), 5.48 (s, 2H), 5.03 (s.1H), 2.22 (s, 3H), 2.06 (s. 3H), 1.52 (s. 6H).

Step 11: Preparation of rel-3-chloro-4-[(3,5-difluoropyridin-2-yl)methoxy]-1-{5-[2-(2-hydroxypropan-2-yl)pyrimidin-4-yl]-2-methylthiophen-3-yl}-6-methylpyridin-2-one and rel-3-chloro-4-[(3,5-difluoropyridin-2-yl)methoxy]-1-{5-[2-(2-hydroxypropan-2-yl)pyrimidin-4-yl]-2-methylthiophen-3-yl}-6-methylpyridin-2-one The race-mixture (100.00 mg) was separated by Prep-HPLC to afford rel-3-chloro-4-[(3,5-difluoropyridin-2-yl) methoxy]-1-{5-[2-(2-hydroxypropan-2-yl)pyrimidin-4-yl]-2-methylthiophen-3-yl}-6-methylpyridin-2-one (Example 33A, isomer 1, 26.20 mg, ee=100%) as a light yellow solid and rel-3-chloro-4-[(3,5-difluoropyridin-2-yl)methoxy]-1-{5-[2-(2-hydroxypropan-2-yl)pyrimidin-4-yl]-2-methylthiophen-3-yl}-6-methylpyridin-2-one (Example 33B, isomer 2, 33.50 mg, ee=99.70%) as a white solid.

EXAMPLE 33A

LC-MS: (ES+H, m z): $[M+H]^+$=519.0. $^1H$ NMR (300 MHz, DMSO-$d_6$) δ 8.80 (d, 1H), 8.61 (d, 1H), 8.15-8.06 (m, 1H), 8.00 (s, 1H), 7.76 (d, 1H), 6.76 (s, 1H), 5.48 (s, 2H), 5.03 (s, 1H), 2.22 (s, 3H), 2.07 (s, 3H), 1.53 (s, 6H). $^{19}F$ NMR (282 MHz, DMSO) δ-120.17,-120.20,-122.40,-122.43.

EXAMPLE 33B

LC-MS: (ES+H, m z): $[M+H]^+$=519.0. $^1H$ NMR (300 MHz, DMSO-$d_6$) δ 8.80 (d, 1H), 8.61 (d, 1H), 8.17-8.04 (m, 1H), 8.00 (s, 1H), 7.75 (d, 1H), 6.76 (s, 1H), 5.48 (s, 2H), 5.03 (s, 1H), 2.22 (s, 3H), 2.07 (s, 3H), 1.53 (s, 6H). $^{19}F$ NMR (282 MHz, DMSO) δ-120.17,-120.20,-122.40,-122.43.

EXAMPLE 34A, 34B, 34C, 34D

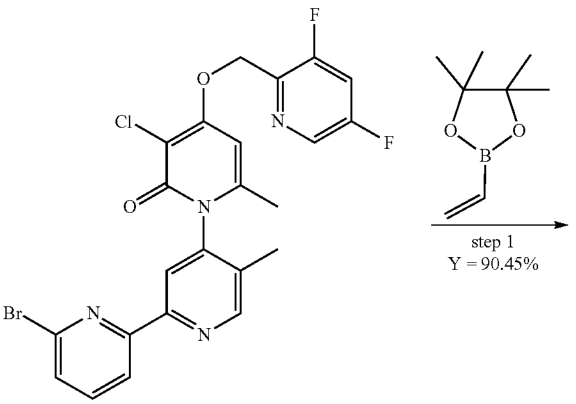

intermediate 24

-continued

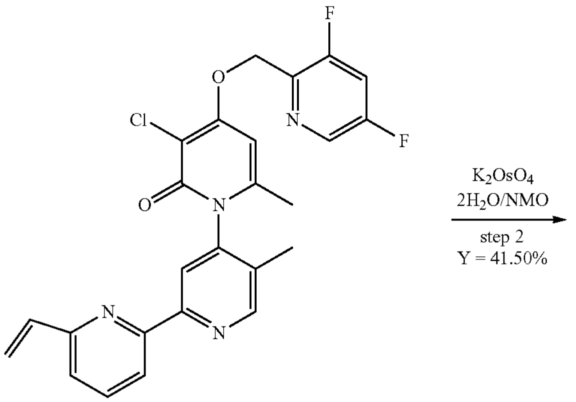

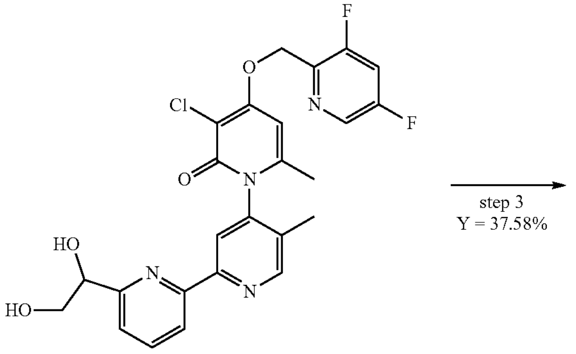

Example 34

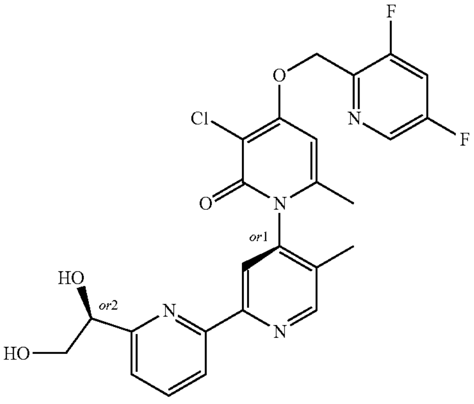

isomer 1
Example 34A

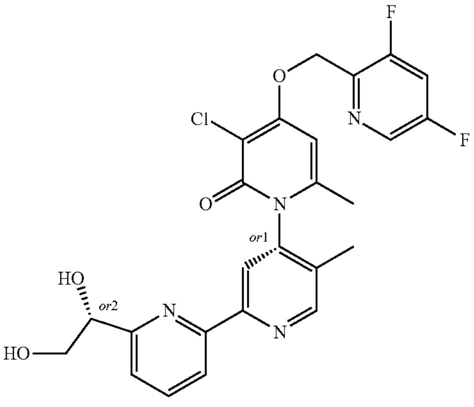

isomer 2
Example 34B

-continued

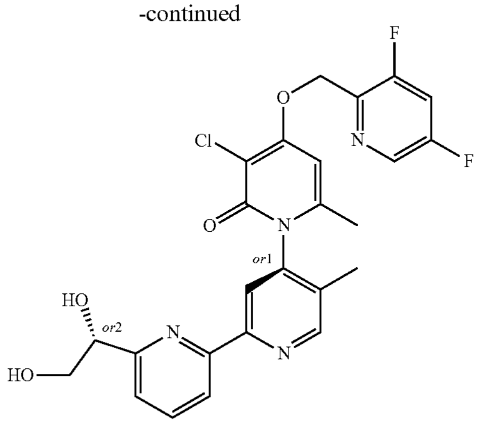

isomer 3
Example 34C

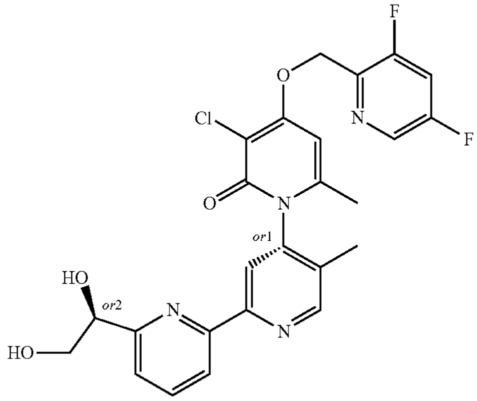

isomer 1
Example 34D

Step 1: Preparation of 3-chloro-4-[(3,5-difluoropyridin-2-yl)methoxy]-2'-(6-ethenylpyridin-2-yl)-5',6-dimethyl-[1,4'-bipyridin]-2-one To a stirred mixture of 2'-(6-bromopyridin-2-yl)-3-chloro-4-[(3,5-difluoropyridin-2-yl)methoxy]-5',6-dimethyl-[1,4'-bipyridin]-2-one (220 mg, 0.41 mmol, 1.00 equiv), $K_2CO_3$ (114 mg, 0.82 mmol, 2.00 equiv) and 2-ethenyl-4,4,5,5-tetramethyl-1,3,2-dioxaborolane (128 mg, 0.82 mmol, 2.00 equiv) in 1,4-dioxane (3.50 mL) and $H_2O$ (0.70 mL) was added Pd(dppf) $Cl_2CH_2Cl_2$ (35 mg, 0.04 mmol, 0.10 equiv) at room temperature. The resulting mixture was stirred for 2 h at 100° C., under nitrogen atmosphere. The mixture was allowed to cool down to room temperature. The reaction was monitored by LCMS. The mixture was purified by reverse phase combi-flash to afford 3-chloro-4-[(3,5-difluoropyridin-2-yl)methoxy]-2'-(6-ethenylpyridin-2-yl)-5',6-dimethyl-[1,4'-bipyridin]-2-one (180 mg, 90.45%) as a white solid. LC-MS: (ES+H, m/z): $[M+H]^+$=481.0.

Step 2: Preparation of 3-chloro-4-[(3,5-difluoropyridin-2-yl)methoxy]-2'-[6-(1,2-dihydroxyethyl)pyridin-2-yl]-5',6-dimethyl-[1,4'-bipyridin]-2-one To a stirred mixture of NMO (88 mg, 0.75 mmol. 2.00 equiv) and 3-chloro-4-[(3.5-difluoropyridin-2-yl)methoxy]-2'-(6-cthenylpyridin-2-yl)-5'0.6-dimethyl-[1,4'-bipyridin]-2-one (180 mg, 0.38 mmol. 1.00 equiv) in THF (2 mL) and t-BuOH (0.66 mL) was added K: Os04.2H-O (78 mg, 0.19 mmol. 0.50 equiv) at room temperature. The resulting mixture was stirred for 15 h at room temperature under nitrogen atmosphere. The reaction was monitored by LCMS. The reaction was quenched with sat, sodium thiosulfate (aq.) (30 ml), extracted with EtOAc (3 ×40 mL). The combined organic layers were dried over anhydrous $Na_2SO_4$. After filtration, the filtrate was concentrated under reduced pressure. The crude product (150 mg) was purified by Prep-HPLC to afford 3-chloro-4-[(3.5-difluoropyridin-2-yl) methoxy]-2'-[6-(1.2-dihydroxyethyl)pyridin-2-yl]-5'0.6-dimethyl-[1,4'-bipyridin]-2-one (80 mg. 41.50%) as a white solid. LC-MS: (ES+H, m/z): $[M+H]^+$=515.1.

Step 3: Preparation of rel-3-chloro-4-[(3,5-difluoro-pyridin-2-yl)methoxy]-2'-[6-(1,2-dihydroxyethyl) pyridin-2-yl]-5',6-dimethyl-[1,4'-bipyridin]-2-one and rel-3-chloro-4-[(3,5-difluoropyridin-2-yl) methoxy]-2'-[6-(1,2-dihydroxyethyl)pyridin-2-yl]-5', 6-dimethyl-[1,4'-bipyridin]-2-one and rel-3-chloro-4-[(3,5-difluoropyridin-2-yl)methoxy]-2'-[6-(1,2-dihydroxyethyl)pyridin-2-yl]-5',6-dimethyl-[1,4'-bipyridin]-2-one and rel-3-chloro-4-[(3,5-difluoropyridin-2-yl)methoxy]-2'-[6-(1,2-dihydroxyethyl)pyridin-2-yl]-5',6-dimethyl-[1,4'-bipyridin]-2-one The racemate 3-chloro-4-[(3.5-difluoropyridin-2-yl) methoxy]-2'-[6-(1.2-dihydroxyethyl)pyridin-2-yl]-5'0.6-dimethyl-[1,4'-bipyridin]-2-one (120 mg) was separated by Prep-Chiral-HPLC to afford two peaks. The first peak was separated by Prep-Chiral-SFC to afford Example 34A (10.2 mg, ee=99.32%) and Example 34B (8.3 mg, ce=96.92%) as a white solid. The second peak was separated by Prep-Chiral-SFC to afford Example 34C (16 mg, ee=100%) and Example 34D (10.6 mg, ce=98.18%) as a white solid.

EXAMPLE 34A

LC-MS: (ES+H, m/z): $[M+H]^+$=515.05. $^1H$ NMR (400 MHZ. DMSO-$d_6$) δ 8.77 (s, 1H), 8.61 (d. 1H), 8.30 (s, 1H), 8.26 (d, 1H), 8.11 (td. 1H), 7.94 (t. 1H), 7.54 (d, 1H), 6.82 (s, 1H), 5.49 (d, 2H), 5.45 (d. 1H), 4.74-4.58 (m, 2H), 3.83-3.69 (m. 1H), 3.62-3.48 (m, 1H), 2.07 (s, 3H), 1.97 (s, 3H). $^{19}F$ NMR (377 MHz. DMSO) δ-120.13, —120.15, —122.34,-122.36.

EXAMPLE 34B

LC-MS: (ES+H, m/z): $[M+H]^+$=515.10. $^1H$ NMR (400 MHZ. DMSO-$d_6$) δ 8.77 (s, 1H), 8.61 (d. 1H), 8.30 (s.1H), 8.26 (d, 1H), 8.11 (td. 1H), 7.94 (t. 1H), 7.54 (d, 1H), 6.82 (s, 1H), 5.49 (d, 2H), 5.45 (d. 1H), 4.74-4.58 (m, 2H), 3.83-3.69 (m, 1H), 3.62-3.48 (m, 1H), 2.07 (s, 3H), 1.97 (s, 3H), $^{19}F$ NMR (377 MHz. DMSO) δ-120.13, —120.15, —122.34, —122.36.

EXAMPLE 34C

LC-MS: (ES+H, m/z): $[M+H]^+$=515.10. $^1H$ NMR (300 MHz. DMSO-$d_6$) δ 8.78 (s, 1H), 8.62 (d. 1H), 8.30 (s, 1H), 8.29-8.23 (m, 1H), 8.11 (ddd. 1H), 7.95 (t. 1H), 7.55 (d, 1H), 6.83 (s, 1H), 5.50 (d, 2H). 5.45 (d, 1H), 4.74-4.55 (m, 2H), 3.83-3.72 (m, 1H), 3.66-3.47 (m, 1H), 2.07 (s, 3H), 1.98 (s, 3H), 19F NMR (377 MHz, DMSO) δ-120.13,-120.15,-122.34,-122.36.

EXAMPLE 34D

LC-MS: (ES+H, m/z): $[M+H]^+$=515.05. $^1H$ NMR (300 MHz, DMSO-$d_6$) δ 8.78 (s, 1H), 8.62 (d, 1H), 8.30 (s, 1H), 8.29-8.23 (m, 1H), 8.11 (ddd, 1H), 7.95 (t, 1H), 7.55 (d, 1H), 6.83 (s, 1H), 5.50 (d, 2H), 5.45 (d, 1H), 4.74-4.55 (m, 2H), 3.83-3.72 (m, 1H), 3.66-3.47 (m, 1H), 2.07 (s, 3H), 1.98 (s, 3H), 19F NMR (377 MHz, DMSO) δ-120.13,-120.15,-122.34,-122.36.

EXAMPLE 35A, 35B, 35C, 35D

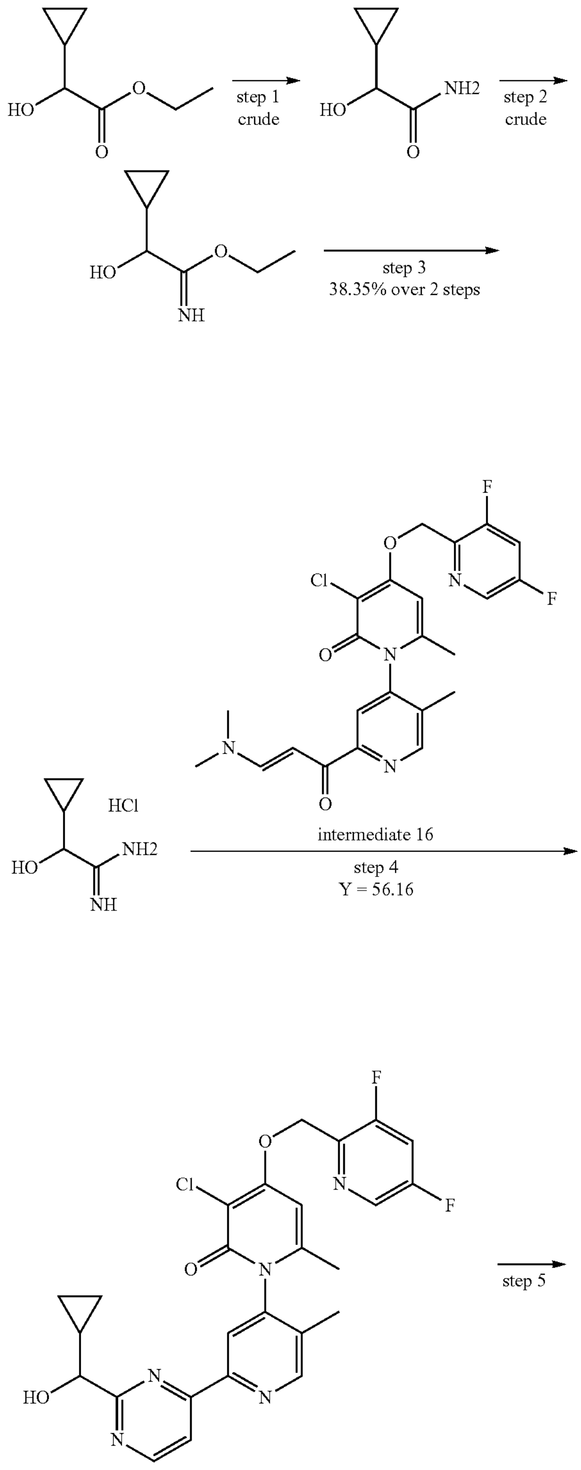

-continued

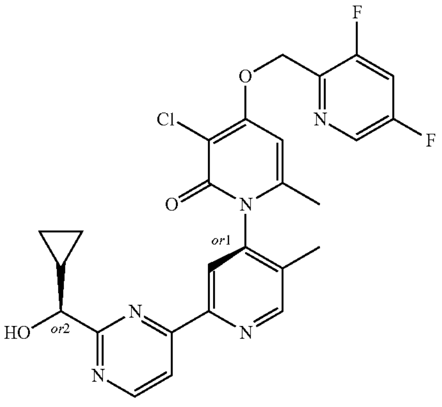

isomer 1
Example 35A

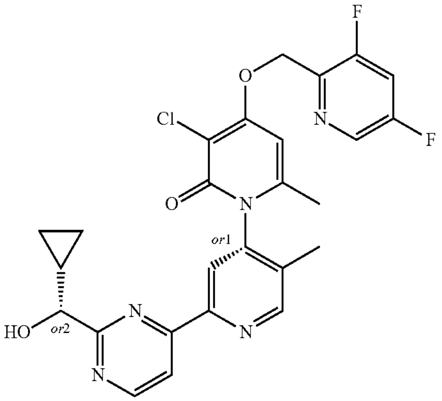

isomer 2
Example 35B

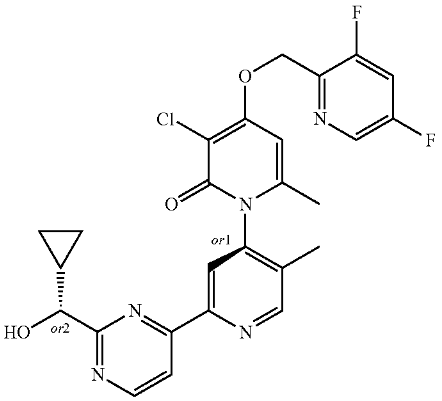

isomer 3
Example 35C

-continued

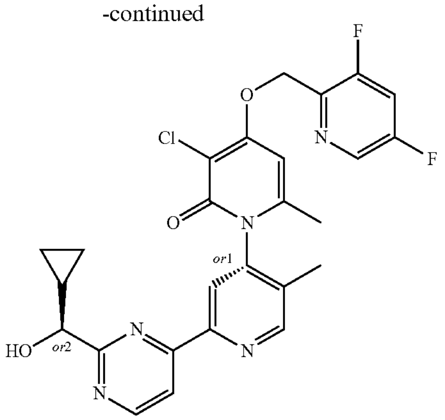

isomer 4
Example 35D

Step 1: Preparation of 2-cyclopropyl-2-hydroxyacetamide

To a stirred solution of ethyl 2-cyclopropyl-2-hydroxyacetate (1.20 g, 8.33 mmol, 1.00 equiv) in acetone (20 mL) and $H_2O$ (20 mL) was added MnO2 (1,45 g, 16.66 mmol, 2.00 equiv) at room temperature under nitrogen atmosphere. The resulting mixture was stirred overnight at room temperature under nitrogen atmosphere. The reaction was monitored by TLC (PE:EA=1:1, Rf=0.2). The resulting mixture was filtrated, and the filtrate was concentrated under vacuum to afford 2-cyclopropyl-2-hydroxyacetamide (1.00 g, crude) as white solid. $^1$H NMR (300 MHz, DMSO-$d_6$) δ 7.24-6.91 (m, 2H), 5.16 (s, 1H), 3.56-3.41 (m, 1H), 1.17-0.87 (m, 1H), 0.43-0.23 (m, 4H).

Step 2&3: Preparation of 2-cyclopropyl-2-hydroxyethanimidamide hydrochloride

To a stirred solution of 2-cyclopropyl-2-hydroxyacetamide (800 mg, 6.949 mmol, 1.00 equiv) in THF (10 mL) was added tetrafluoroboranuide: triethyloxidanium (1716 mg, 9.034 mmol, 1.30 equiv) at 0° C. under nitrogen atmosphere. The resulting mixture was stirred for 3 h at r.t, under nitrogen atmosphere. The resulting mixture was concentrated under reduced pressure to afford crude ethyl 2-cyclopropyl-2-hydroxyethanimidate. The above residue was dissolved in methanol (20 mL), To the above mixture was added $NH_3$ (g) in MeOH (20 mL) at 0° C., over 5 min. The resulting mixture was stirred for additional 1 h at r.t. The resulting mixture was concentrated under reduced pressure. The residue was dissolved in EA (20 mL). The resulting mixture was filtered, to the filtrate was added HCl (gas) in 1,4-dioxane (5 mL) at 0° C., the resulting mixture was stirred for 2 h at 0° C., under nitrogen atmosphere. The precipitated solids were collected by filtration and washed with EA (3 ×10 mL). This resulted in 2-cyclopropyl-2-hydroxyethanimidamide hydrochloride (400 mg. 38.35%) as a white solid. $^1$H NMR (300 MHz. DMSO-$d_6$) δ 9.21-8.54 (m, 4H), 6.69-5.55 (m, 1H), 3.94 (d, 1H), 1.21-1.01 (m. 1H), 0.68-0.52 (m, 1H), 0.54-0.25 (m, 3H).

Step 4: Preparation of 3-chloro-2'-{2-[cyclopropyl (hydroxy) methyl]pyrimidin-4-yl}-4-[(3,5-difluoropyridin-2-yl)methoxy]-5',6-dimethyl-[1,4'-bipyridin]-2-one A mixture of 2-cyclopropyl-2-hydroxyethanimidamide hydrochloride (285 mg, 1.89 mmol. 3.00 equiv), 3-chloro- 4-[(3.5-difluoropyridin-2-yl)methoxy]-2'-[(2E)-3-(dimethylamino) prop-2-cnoyl]-5',6-dimethyl-[1,4'-bipyridin]-2-one (300 mg, 0.63 mmol. 1.00 equiv) and $K_2CO$; (873 mg. 6.32 mmol. 10.00 equiv) in IPA was stirred overnight at 80° C., under nitrogen atmosphere. The reaction was monitored by LCMS. The resulting mixture was cooled down to r.t, and poured into 10 ml of water. The resulting mixture was extracted with EtOAc (3 ×10 mL). The combined organic layers were washed with brine (20 mL), dried over anhydrous $Na_2SO_4$. After filtration, the filtrate was concentrated under reduced pressure. The residue was purified by silica gel column chromatography to afford crude product, which was further purified by Prep-HPLC to afford 3-chloro-2'-{2-[cyclopropyl (hydroxy) methyl]pyrimidin-4-yl}-4-[(3.5-difluoropyridin-2-yl)methoxy]-5'0.6-dimethyl-[1,4'-bipyridin]-2-one (190 mg. 56.16%) as a white solid. LC-MS: (ES+H, m/z): $[M+H]^+$=526.0.

Step 5: Preparation of rel-3-chloro-2'-{2-[cyclopropyl (hydroxy) methyl]pyrimidin-4-yl}-4-[(3,5-difluoropyridin-2-yl)methoxy]-5',6-dimethyl-[1,4'-bipyridin]-2-one (Example 35A&B&C&D): The racemate (190 mg) was separated by Prep-Chiral-HPLC to afford a mixture of Example 35A&B (90 mg) as a white solid and a mixture of Example 35C&D (85 mg) as a white solid The first racemate (90 mg) was separated by Prep-Chiral-HPLC to afford Example 35A (33.4 mg. 99.2%. ee=100%) as a white solid and Example 35B (30.3 mg. 99.7%, ee=100%) as a white solid. The second racemate (85 mg) was separated by Prep-Chiral-HPLC to afford Example 35C (26.7 mg. 99.8%, ee=100%) as a white solid and Example 35D (23.8 mg. 99.4%, ee=100%) as a white solid.

EXAMPLE 35A

LC-MS: (ES+H, m/z): $[M+H]^+$=526.1. $^1$H NMR (300 MHz. DMSO-$d_6$) δ 8.97 (d, 1H), 8.87 (s. 1H), 8.62 (d, 1H), 8.59 (s, 1H), 8.26 (d, 1H), 8.16-8.06 (m, 1H), 6.85 (s, 1H), 5.50 (d, 2H), 5.22 (d, 1H). 4.20 (t. 1H), 2.12 (s, 3H), 1.98 (s, 3H), 1.39-1.29 (m, 1H), 0.50-0.37 (m, 4H). $^{19}$F NMR (282 MHz. DMSO) δ-120.14, —120.17, —122.32,-122.35.

EXAMPLE 35B

LC-MS: (ES+H, m/z): $[M+H]^+$=526.1. $^1$H NMR (300 MHz, DMSO-$d_6$) δ 8.97 (d, 1H), 8.87 (s. 1H), 8.62 (d, 1H), 8.56 (s, 1H), 8.26 (d, 1H), 8.16-8.06 (m, 1H), 6.85 (s, 1H), 5.50 (d, 2H), 5.23 (d, 1H). 4.20 (t, 1H), 2.12 (s, 3H), 1.99 (s, 3H), 1.38-1.24 (m, 1H), 0.49-0.34 (m, 4H). $^{19}$F NMR (282 MHZ, DMSO) δ-120.14,-120.16,-122.32,-122.34.

EXAMPLE 35C

LC-MS: (ES+H, m/z): $[M+H]^+$=526.1. $^1$H NMR (300 MHZ, DMSO-$d_6$) δ 8.97 (d, 1H), 8.87 (s, 1H), 8.61 (d, 1H), 8.56 (s, 1H), 8.26 (d, 1H), 8.16-8.04 (m, 1H), 6.84 (s, 1H), 5.50 (d, 2H), 5.23 (d, 1H), 4.20 (t, 1H), 2.11 (s, 3H), 1.98 (s, 3H), 1,40-1.29 (m, 1H), 0.49-0.36 (m, 4H). $^{19}$F NMR (282 MHZ, DMSO) δ-120.14,-120.16,-122.32,-122.34.

EXAMPLE 35D

LC-MS: (ES+H, m/z): $[M+H]^+$=526.1. $^1$H NMR (300 MHz, DMSO-$d_6$) δ 8.97 (d, 1H), 8.88 (s, 1H), 8.62 (d, 1H), 8.60 (s, 1H), 8.27 (d, 1H), 8.16-8.04 (m, 1H), 6.85 (s, 1H), 5.51 (d, 2H), 5.22 (d, 1H), 4.20 (t, 1H), 2.12 (s, 3H), 1.99 (s, 3H), 1.39-1.28 (m, 1H), 0.46-0.38 (m, 4H). $^{19}$F NMR (282 MHZ, DMSO) δ-120.14,-120.17,-122.32,-122.35.

EXAMPLE 36A, 36B, 36C, 36D

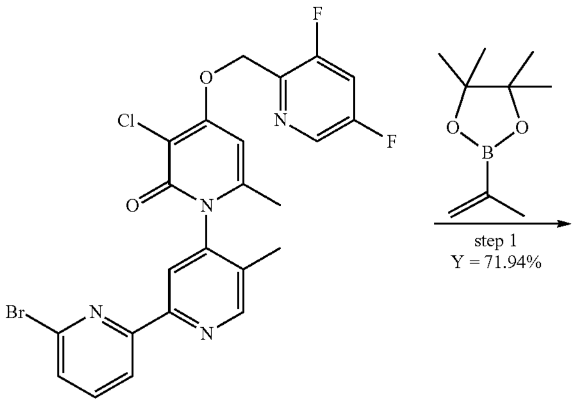

intermediate 24

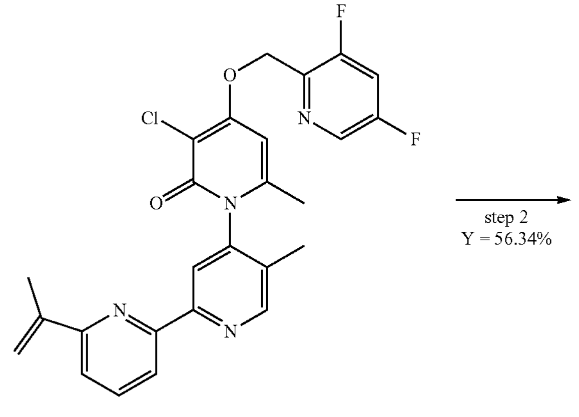

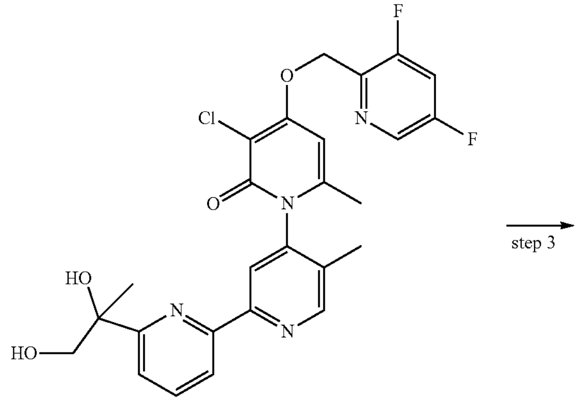

Example 36

-continued

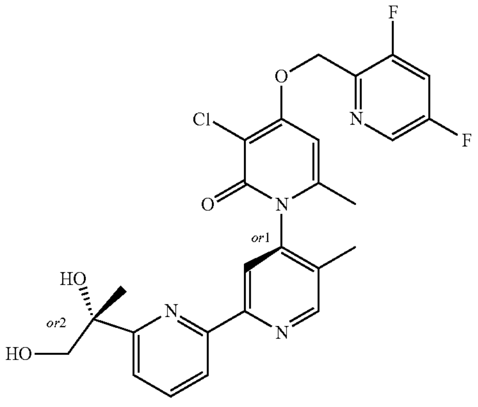

isomer 1
Example 36A

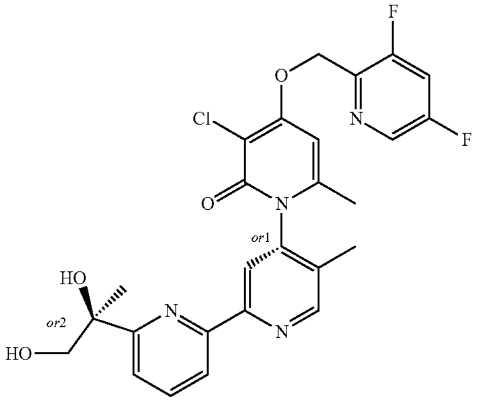

isomer 2
Example 36B

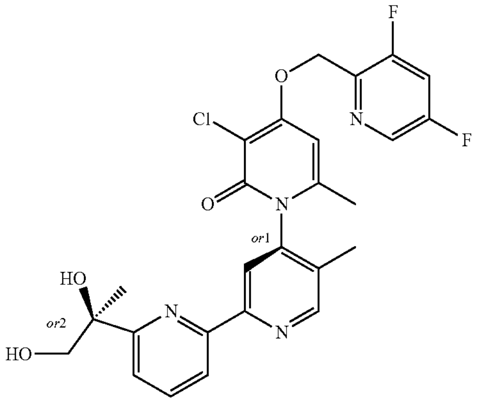

isomer 3
Example 36C

-continued

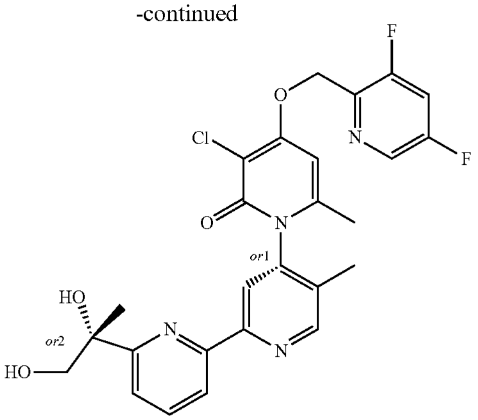

isomer 4
Example 36D

Step 1: Preparation of 3-chloro-4-[(3,5-difluoropyridin-2-yl)methoxy]-5',6-dimethyl-2'-[6—(prop-1-en-2-yl)pyridin-2-yl]-[1,4'-bipyridin]-2-one To a stirred solution of 2'-(6-bromopyridin-2-yl)-3-chloro-4-[(3,5-difluoropyridin-2-yl)methoxy]-5',6-dimethyl-[1,4'-bipyridin]-2-one (300 mg, 0.56 mmol, 1.00 equiv) and 4,4,5,5-tetramethyl-2-(prop-1-en-2-yl)-1,3,2-dioxaborolane (142 mg, 0.84 mmol, 1.50 equiv) in dioxane (4 mL) and $H_2O$ (0.4 mL) were added CsF (170 mg, 1.12 mmol, 2.00 equiv) and $Pd(PPh_3)+$ (130 mg, 0.11 mmol, 0.20 equiv) at room temperature under nitrogen atmosphere. The resulting mixture was stirred for 2 h at 90° C., under nitrogen atmosphere. The mixture was allowed to cool down to room temperature. The reaction was poured into sat. $NH_4Cl$ (aq.) (20 mL) at room temperature. The resulting mixture was extracted with EtOAc (3 ×20 mL). The combined organic layers were washed with brine (20 mL), dried over anhydrous $Na_2SO_4$. After filtration, the filtrate was concentrated under reduced pressure. The residue was purified by Prep-TLC to afford 3-chloro-4-[(3.5-difluoropyridin-2-yl)methoxy]-5'0.6-dimethyl-2'-[6—(prop-1-en-2-yl)pyridin-2-yl]-[1,4'-bipyridin]-2-one (200 mg. 71.94%) as a white solid. LC-MS: (ES+H, m/z): $[M+H]^+$=495.2

Step 2: Preparation of 3-chloro-4-[(3,5-difluoropyridin-2-yl)methoxy]-2'-[6-(1,2-dihydroxypropan-2-yl)pyridin-2-yl]-5',6-dimethyl-[1,4'-bipyridin]-2-one To a stirred solution of 3-chloro-4-[(3.5-difluoropyridin-2-yl)methoxy]-5'0.6-dimethyl-2'-[6—(prop-1-en-2-yl)pyridin-2-yl]-[1,4'-bipyridin]-2-one (200 mg, 0.24 mmol. 1.00 equiv.) and NMO (57 mg, 0.48 mmol. 2.00 equiv) in THF (3 mL) and t-BuOH (1 mL) were added K: $Os04.2H_2O$ (45 mg, 0.12 mmol, 0.50 equiv) at room temperature under nitrogen atmosphere. The resulting mixture was stirred for 3 h at room temperature under nitrogen atmosphere. The resulting mixture was filtered, the filter cake was washed with THF (2×3 mL). The filtrate was concentrated under reduced pressure. The residue was purified by reverse combi-flash chromatography. This resulted in 3-chloro-4-[(3.5-difluoropyridin-2-yl)methoxy]-2'-[6-(1.2-dihydroxypropan-2-yl)pyridin-2-yl]-5'0.6-dimethyl-[1,4'-bipyridin]-2-one (120 mg. 56.34%) as a white solid. LC-MS: (ES+H, m/z): $[M+H]^+$=529.10. $^1$H NMR (400 MHZ. DMSO-$d_6$) δ 8.77 (s, 1H), 8.61 (d. 1H), 8.36 (d, 1H), 8.25 (m. 1H), 8.10 (m. 1H), 7.93 (m. 1H), 7.67 (m. 1H), 6.82 (s.1H), 5.49 (s, 2H), 5.19 (d, 1H), 4.59 (m. 1H), 3.69-3.48 (m, 2H), 2.49 (s, 3H), 2.06 (s, 3H), 1,43 (s, 3H), $^{19}$F NMR (377 MHz. DMSO) ¿-120.12, —120.14, —122.33, —122.35.

Step 3: Preparation of rel-3-chloro-4-[(3,5-difluoropyridin-2-yl)methoxy]-2'-[6-(1,2-dihydroxypropan-2-yl)pyridin-2-yl]-5',6-dimethyl-[1,4'-bipyridin]-2-one & rel-3-chloro-4-[(3,5-difluoropyridin-2-yl)methoxy]-2'-[6-(1,2-dihydroxypropan-2-yl)pyridin-2-yl]-5',6-dimethyl-[1,4'-bipyridin]-2-one & rel-3-chloro-4-[(3,5-difluoropyridin-2-yl)methoxy]-2'-[6-(1,2-dihydroxypropan-2-yl)pyridin-2-yl]-5',6-dimethyl-[1,4'-bipyridin]-2-one & rel-3-chloro-4-[(3,5-difluoropyridin-2-yl)methoxy]-2'-[6-(1,2-dihydroxypropan-2-yl)pyridin-2-yl]-5',6-dimethyl-[1,4'-bipyridin]-2-one 3-chloro-4-[(3.5-difluoropyridin-2-yl)methoxy]-2'-[6-(1.2-dihydroxypropan-2-yl)pyridin-2-yl]-5'0.6-dimethyl-[1, 4'-bipyridin]-2-one (120 mg) was separated by Prep-Chiral-HPLC to afford Example 36A (11.6 mg, ce=100%). Example 36B (13.1 mg, ce=99.34%) and mixture of Example 36C&D (56.0 mg) as a white solid. The mixture of Example 36C&D (56.0 mg) was further separated by Prep-Chiral-HPLC to afford Example 36C (10.4 mg, ee=100%), and Example 36D (11.5 mg, ee=99.78%) as a white solid.

EXAMPLE 36A

LC-MS: (ES+H, m/z): [M+H]$^+$=529.05. $^1$H NMR (300 MHz. DMSO-$d_6$) δ 8.77 (s.1H), 8.62 (d. 1H), 8.36 (d, 1H), 8.26 (m. 1H), 8.11 (m. 1H), 7.94 (m. 1H), 7.67 (m. 1H), 6.83 (s.1H), 5.49 (d, 2H), 5.20 (d, 1H), 4.60 (m. 1H), 3.60 (m, 2H), 2.07 (s, 3H), 1.98 (s, 3H), 1,44 (s, 3H), $^{19}$F NMR (282 MHz. DMSO) δ -120.11, -120.14, -122.30.-122.33.

EXMAPLE 36B

LC-MS: (ES+H, m/z): [M+H]$^+$=529.05. $^1$H NMR (300 MHz. DMSO-$d_6$) δ 8.77 (s, 1H), 8.62 (d. 1H), 8.36 (d, 1H), 8.26 (m. 1H), 8.11 (m, 1H), 7.94 (m. 1H), 7.67 (m. 1H), 6.83 (s, 1H), 5.49 (d, 2H), 5.20 (d, 1H), 4.60 (m. 1H), 3.60 (m, 2H), 2.07 (s, 3H), 1.98 (s, 3H), 1,44 (s, 3H), $^{19}$F NMR (282 MHz. DMSO) ¿-120.11, -120.14, -122.31, -122.33.

EXAMPLE 36C

LC-MS: (ES+H, m/z): [M+H]$^+$=529.10. $^1$H NMR (300 MHz, DMSO-$d_6$) δ 8.76 (s, 1H), 8.60 (d, 1H), 8.35 (s, 1H), 8.25 (d, 1H), 8.16-7.98 (m, 1H), 7.94 (m, 1H), 7.66 (m, 1H), 6.82 (s, 1H), 5.48 (d, 2H), 5.24 (s, 1H), 4.64 (m, 1H), 3.60 (m, 2H), 2.06 (s, 3H), 1.98 (s, 3H), 1,43 (s, 3H). $^{19}$F NMR (282 MHZ, DMSO) δ-120.04,-120.06,-122.13,-122.16.

EXAMPLE 36D

LC-MS: (ES+H, m/z): [M+H]$^+$=529.10. $^1$H NMR (300 MHZ, DMSO-$d_6$) δ 8.76 (s, 1H), 8.60 (d, 1H), 8.35 (s, 1H), 8.25 (d, 1H), 8.16-7.98 (m, 1H), 7.94 (m, 1H), 7.66 (m, 1H), 6.82 (s, 1H), 5.48 (d, 2H), 5.24 (s, 1H), 4.64 (m, 1H), 3.60 (m, 2H), 2.06 (s, 3H), 1.98 (s, 3H), 1,43 (s, 3H). $^{19}$F NMR (282 MHZ, DMSO) δ-120.09,-120.11,-122.26,-122.28.

EXAMPLE 37A, 37B

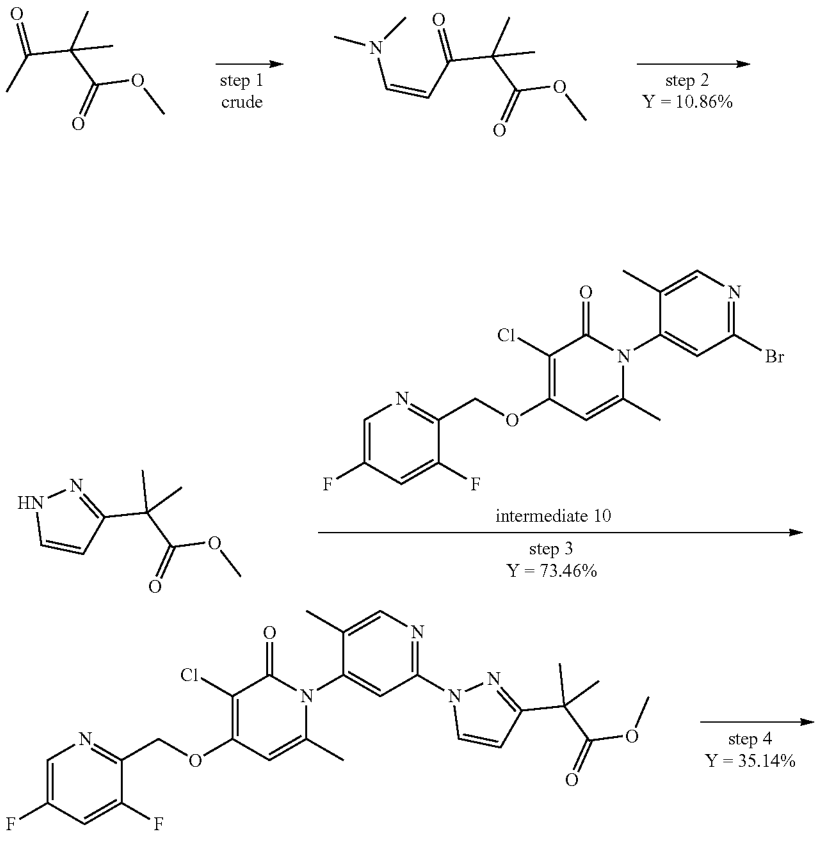

-continued

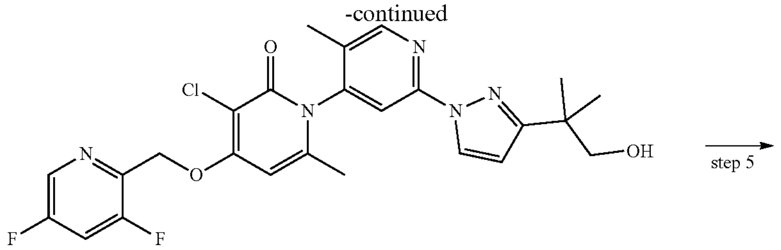

Example 37

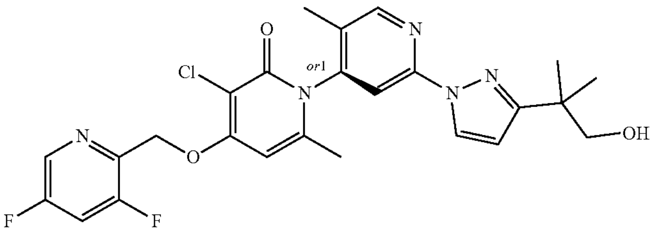

isomer 1
Example 37A

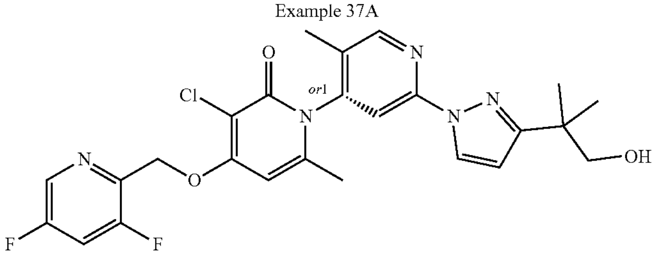

isomer 2
Example 37B

Step 1: Preparation of methyl (4Z)-5-(dimethylamino)-2,2-dimethyl-3-oxopent-4-enoate Into a 250 mL round-bottom flask were added methyl 2,2-dimethyl-3-oxobutanoate (4 g, 27.745 mmol, 1 equiv) and DMF-DMA (25 mL) at room temperature. The resulting mixture was stirred overnight at 100° C., under nitrogen atmosphere. The mixture was allowed to cool down to room temperature. The reaction was monitored by LCMS. The resulting mixture was concentrated under reduced pressure. The crude product was used in the next step directly without further purification. LC-MS: (ES+H, m/z): $[M+H]^+$ =200.1.

Step 2: Preparation of methyl 2-methyl-2-(1H-pyrazol-3-yl) propanoate

Into a 100 mL round-bottom flask were added methyl (4Z)-5-(dimethylamino)-2,2-dimethyl-3-oxopent-4-enoate (1.50 g, crude) and hydrazine (10 mL, 1M in THF) at room temperature. The resulting mixture was stirred overnight at room temperature under nitrogen atmosphere. The reaction was monitored by LCMS. The resulting mixture was concentrated under reduced pressure. The residue was purified by reverse combi-flash chromatography. This resulted in methyl 2-methyl-2-(1H-pyrazol-3-yl) propanoate (500 mg, 10.86%) as a colorless oil. LC-MS: (ES+H, m/z): $[M+H]^+$=169.2. $^1$H NMR (300 MHz, Chloroform-d) δ 7.60-7.53 (m, 1H), 7.25-6.98 (m, 1H), 6.30-6.21 (m, 1H), 3.72 (s, 3H), 1.64 (s, 6H).

Step 3: Preparation of methyl 2-(1-{3-chloro-4-[(3,5-difluoropyridin-2-yl)methoxy]-5',6-dimethyl-2-oxo-[1,4'-bipyridin]-2'-yl}pyrazol-3-yl)-2-methylpropanoate To a solution of methyl 2-methyl-2-(1H-pyrazol-3-yl) propanoate (220 mg, 1.31 mmol. 1.50 equiv) and 2'-bromo-3-chloro-4-[(3.5-difluoropyridin-2-yl)methoxy]-5'0.6-dimethyl-[1,4'-bipyridin]-2-one (400 mg. 0.87 mmol. 1.00 equiv) in 1,4-dioxane (6 mL) were added CuI (33 mg, 0.17 mmol. 0.20 equiv), $K_2CO_3$ (185 mg. 1.75 mmol. 2.00 equiv) and (1S.2S)-N1.N2-dimethylcyclohexane-1.2-diamine (49 mg, 0.35 mmol. 0.40 equiv) at room temperature. The resulting mixture was stirred for 3 h at 80° C., under nitrogen atmosphere. The reaction was monitored by LCMS. The mixture was allowed to cool down to room temperature. The reaction was poured into water (100 mL) and was extracted with EtOAc (3 ×100 mL). The combined organic layers were dried over anhydrous $Na_2SO_4$. After filtration, the filtrate was concentrated under reduced pressure. The residue was purified by silica gel column chromatography to afford methyl 2-(1-{3-chloro-4-[(3.5-difluoropyridin-2-yl)methoxy]-5'0.6-dimethyl-2-oxo-[1,4'-bipyridin]-2'-yl}pyrazol-3-yl)-2-methylpropanoate (350 mg. 73.46%) as a white solid. LC-MS: (ES+H, m/z): $[M+H]^+$=544.3. $^1$H NMR (400 MHz. Chloroform-d) δ 8.47-8.43 (m. 1H), 8.43-8.40 (m. 1H), 8.38 (s.1H), 7.73 (s, 1H), 7.36-7.30 (m. 1H), 6.43-6.35 (m, 2H), 5.45-5.40 (m, 2H), 3.68 (s, 3H), 2.09 (s, 3H), 2.03 (s, 3H), 1.62 (s, 3H), 1.60 (s. 3H).

Step 4: Preparation of 3-chloro-4-[(3,5-difluoropyridin-2-yl)methoxy]-2'-[3-(1-hydroxy-2-methylpropan-2-yl)pyrazol-1-yl]-5',6-dimethyl-[1,4'-bipyridin]-2-one To a stirred solution of methyl 2-(1-{3-chloro-4-[(3.5-difluoropyridin-2-yl)methoxy]-5'0.6-dimethyl-2-oxo-[1,4'-bipyridin]-2'-x1} pyrazol-3-yl)-2-methylpropanoate (300 mg, 0.55 mmol. 1.00 equiv) in DCM (3 mL) and MeOH (3 mL) was added NaBH+ (625 mg, 16.56 mmol. 30.00 equiv) in portions at 0° C. The resulting mixture was stirred overnight at room temperature. The reaction was poured into water (100 ml) and extracted with $CH_2Cl_2$ (3 ×100 mL). The combined organic layers were dried over anhydrous $Na_2SO_4$. After filtration, the filtrate was concentrated under reduced pressure. The residue was purified by silica gel column chromatography to afford 3-chloro-4-[(3.5-difluoropyridin-2-yl)methoxy]-2'-[3-(1-hydroxy-2-methylpropan-2-yl)pyrazol-1-yl]-5'0.6-dimethyl-]1,4'-bipyridin]-2-one (100 mg. 35.14%) as a white solid. LC-MS: (ES+H, m/z): $[M+H]^+$=516.3.

Step 5: Preparation of rel-3-chloro-4-[(3,5-difluoropyridin-2-yl)methoxy]-2'-[3-(1-hydroxy-2-methylpropan-2-yl)pyrazol-1-yl]-5',6-dimethyl-[1,4'-bipyridin]-2-one and rel-3-chloro-4-[(3,5-difluoropyridin-2-yl)methoxy]-2'-[3-(1-hydroxy-2-methylpropan-2-yl)pyrazol-1-yl]-5',6-dimethyl-[1,4'-bipyridin]-2-one The racemate 3-chloro-4-[(3.5-difluoropyridin-2-yl) methoxy]-2'-[3-(1-hydroxy-2-methylpropan-2-yl)pyrazol-1-yl]-5'0.6-dimethyl-[1,4'-bipyridin]-2-one (80 mg) was separated by Prep-Chiral-SFC to afford rel-3-chloro-4-[(3.5-difluoropyridin-2-yl)methoxy]-2'-[3-(1-hydroxy-2-methylpropan-2-yl)pyrazol-1-yl]-5'0.6-dimethyl-[1,4'-bipyridin]-2-one (Example 37A, 28.6 mg, ee=97.82%) as a white solid and rel-3-chloro-4-[(3.5-difluoropyridin-2-yl) methoxy]-2'-[3-(1-hydroxy-2-methylpropan-2-yl)pyrazol-1-yl]-5'0.6-dimethyl-[1,4'-bipyridin]-2-one (Example 37B, 22.8 mg, ee=98.44%) as a white solid.

EXAMPLE 37A

LC-MS: (ES+H, m/z): $[M+H]^+$=516.05. $^1H$ NMR (300 MHz, DMSO-$d_6$) δ 8.67-8.59 (m, 1H), 8.54 (s, 1H), 8.52-8.45 (m, 1H), 8.17-8.03 (m, 1H), 7.80 (s, 1H), 6.81 (s, 1H), 6.57-6.45 (m, 1H), 5.49 (s, 2H), 4.64 (t, 1H), 3.47 (d, 2H), 2.01 (s, 6H), 1.25 (s, 6H). $^{19}F$ NMR (377 MHz, DMSO) δ-120.148,-120.173,-122.343,-122.369.

EXAMPLE 37B

LC-MS: (ES+H, m/z): $[M+H]^+$=516.05. $^1H$ NMR (300 MHz, DMSO-$d_6$) δ 8.69-8.59 (m, 1H), 8.54 (s, 1H), 8.52-8.47 (m, 1H), 8.17-8.06 (m, 1H), 7.80 (s, 1H), 6.81 (s, 1H), 6.56-6.46 (m, 1H), 5.49 (s, 2H), 4.64 (t, 1H), 3.47 (d, 2H), 2.01 (s, 6H), 1.25 (s, 6H). $^{19}F$ NMR (377 MHz, DMSO) δ-120.145,-120.170,-122.340,-122.365.

EXAMPLE 38A, 38B

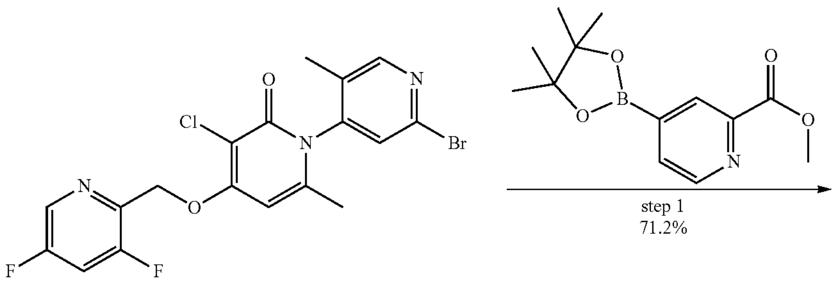

intermediate 10

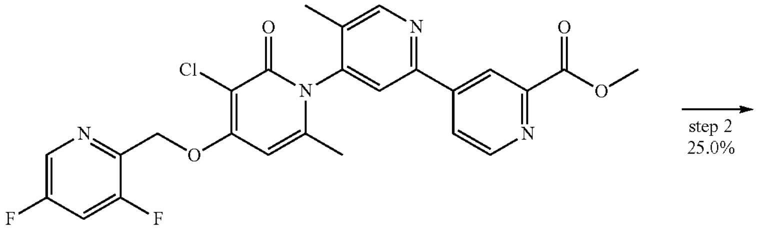

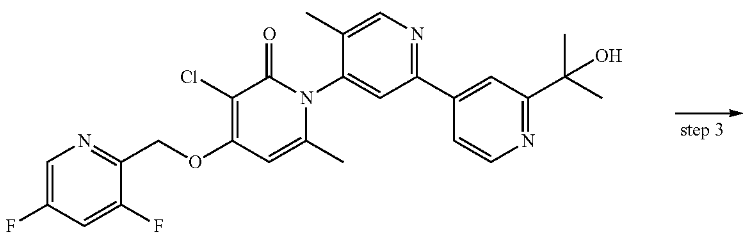

Example 38

-continued

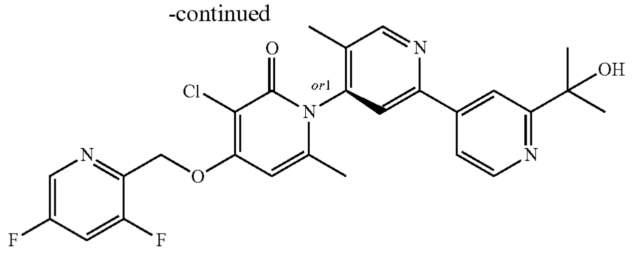

isomer 1
Example 38A

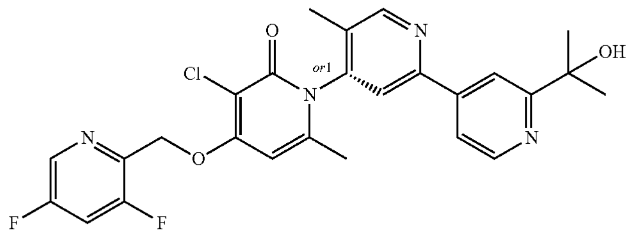

isomer 2
Example 38B

Step 1: Preparation of methyl 4-{3-chloro-4-[(3,5-difluoropyridin-2-yl)methoxy]-5',6-dimethyl-2-oxo-[1,4'-bipyridin]-2'-yl}pyridine-2-carboxylate To a stirred mixture of 2'-bromo-3-chloro-4-[(3,5-difluoropyridin-2-yl)methoxy]-5',6-dimethyl-[1,4'-bipyridin]-2-one (500 mg, 1.09 mmol, 1.00 equiv) and methyl 4-(4,4,5,5-tetramethyl-1,3,2-dioxaborolan-2-yl)pyridine-2-carboxylate (576 mg, 2.19 mmol, 2.00 equiv) in dioxane (15 mL) and $H_2O$ (3 ml) were added CsF (332 mg, 2.19 mmol, 2.00 equiv) and Pd(dppf) $Cl_2$ (80 mg, 0.11 mmol, 0.10 equiv) at room temperature under nitrogen atmosphere. The resulting mixture was stirred for additional 2 h at 100° C. The reaction was monitored by LCMS. The mixture was allowed to cool down to room temperature. The resulting mixture was filtered, the filter cake was washed with EtOAc (3 ×50 mL). The filtrate was concentrated under reduced pressure. The residue was purified by silica gel column chromatography to afford methyl 4-{3-chloro-4-[(3,5-difluoropyridin-2-yl)methoxy]-5',6-dimethyl-2-oxo-[1,4'-bipyridin]-2'-yl}pyridine-2-carboxylate (400 mg. 71.23%) as a yellow solid. LC-MS: (ES+H, m/z): $[M+H]^+$=513.1.

Step 2: Preparation of 3-chloro-4-[(3,5-difluoropyridin-2-yl)methoxy]-2'-[2-(2-hydroxypropan-2-yl)pyridin-4-yl]-5',6-dimethyl-[1,4'-bipyridin]-2-one To a stirred solution of methyl 4-{3-chloro-4-[(3,5-difluoropyridin-2-yl)methoxy]-5',6-dimethyl-2-oxo-[1,4'-bipyridin]-2'-yl}pyridine-2-carboxylate (400 mg, 0.78 mmol, 1.00 equiv) in THF (20 mL) was added MeMgBr (2.60 mL, 7.80 mmol, 10.00 equiv, 3M in THF) dropwise at 0° C., under nitrogen atmosphere. The resulting mixture was stirred forl h at 0° C., under nitrogen atmosphere. The reaction was quenched by the addition of sat. $NH_4Cl$ (aq.) (20 mL) at 0° C. The resulting mixture was extracted with EtOAc (3 ×40 mL). The combined organic layers were washed with brine (1×200 mL), dried over anhydrous $Na_2SO_4$. After filtration, the filtrate was concentrated under reduced pressure. The residue was purified by PREP-HPLC. This resulted in 3-chloro-4-[(3,5-difluoropyridin-2-yl)methoxy]-2'-[2-(2-hydroxypropan-2-yl)pyridin-4-yl]-5',6-dimethyl-[1,4'-bipyridin]-2-one (100 mg, 25.00%) as a white solid. LC-MS: (ES+H, m/z): $[M+H]^+$=512.9.

Step 3: Preparation of rel-3-chloro-4-[(3,5-difluoropyridin-2-yl)methoxy]-2'-[2-(2-hydroxypropan-2-yl)pyridin-4-yl]-5',6-dimethyl-[1,4'-bipyridin]-2-one & rel-3-chloro-4-[(3,5-difluoropyridin-2-yl)methoxy]-2'-[2-(2-hydroxypropan-2-yl)pyridin-4-yl]-5',6-dimethyl-[1,4'-bipyridin]-2-one 3-chloro-4-[(3,5-difluoropyridin-2-yl)methoxy]-2'-[2-(2-hydroxypropan-2-yl)pyridin-4-yl]-5',6-dimethyl-[1,4'-bipyridin]-2-one (140 mg) was separated by prep-chiral-HPLC to afford Example 38A (41.3 mg 'ee=100%) and Example 38B (43.8 mg, ee=100%) as a white solid.

EXAMPLE 38A

LC-MS: (ES+H, m/z): $[M+H]^+$=513.10. $^1$H NMR (300 MHz, DMSO-$d_6$) δ 8.84 (s, 1H), 8.65-8.57 (m, 2H), 8.39 (d, 1H), 8.18 (s, 1H), 8.11 (td, 1H), 7.92 (dd, 1H), 6.83 (s, 1H), 5.50 (d, 2H), 5.33 (s, 1H), 2.08 (s, 3H), 1.99 (s, 3H), 1.50 (s, 3H), 1,49 (s, 3H). $^{19}$F NMR (282 MHz, DMSO) δ-120.14,-120.16,-122.33,-122.36.

EXAMPLE 38B

LC-MS: (ES+H, m/z): $[M+H]^+$=513.10. $^1$H NMR (300 MHz, DMSO-$d_6$) δ 8.84 (s, 1H), 8.65-8.57 (m, 2H), 8.39 (t, 1H), 8.18 (s, 1H), 8.11 (ddd, 1H), 7.91 (dd, 1H), 6.83 (s, 1H), 5.50 (d, 2H), 5.32 (s, 1H), 2.08 (s, 3H), 1.99 (s, 3H), 1.50 (s, 3H), 1,49 (s, 3H). $^{19}$F NMR (282 MHz, DMSO) δ-120.14,-120.16,-122.33,-122.36.

EXAMPLE 39A, 39B

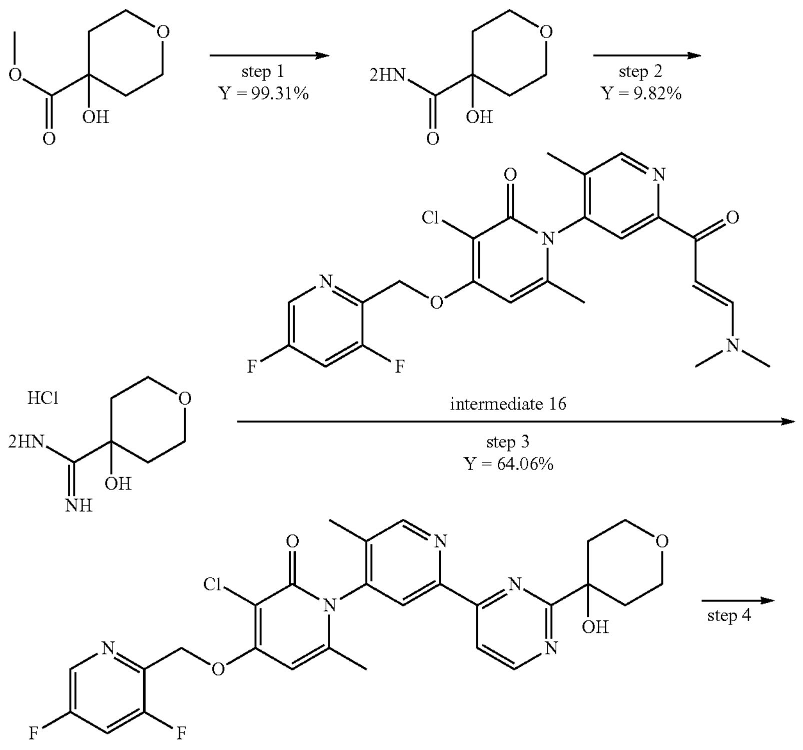

Example 39

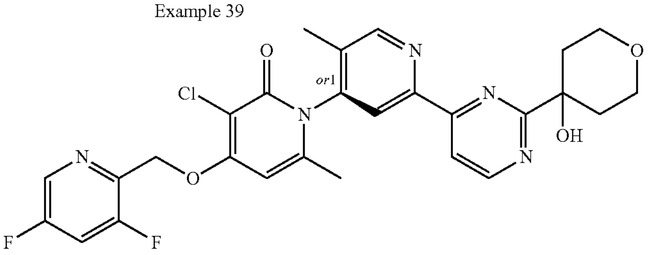

isomer 1
Example 39A

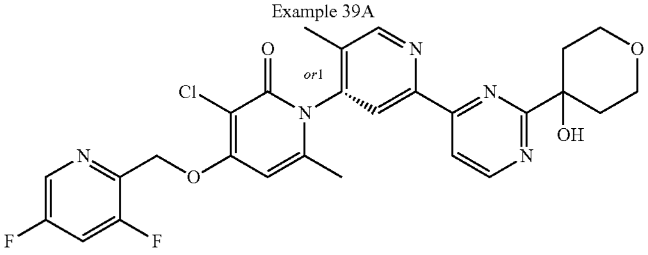

isomer 2
Example 39B

Step 1: Preparation of 4-hydroxyoxane-4-carboxamide

A solution of methyl 4-hydroxyoxane-4-carboxylate (3 g, 18.73 mmol, 1.00 equiv) in $NH_3$ (g) in MeOH (30 mL, 4M) was stirred for 2 h at 80° C., under nitrogen atmosphere. The resulting mixture was allowed to cool down to room temperature. The resulting mixture was concentrated under vacuum, to afford 4-hydroxyoxane-4-carboxamide (2.70 g. 99.31%) as a white solid. $^1$H NMR (400 MHZ. DMSO-$d_6$) δ 7.15 (d, 2H), 5.30 (s.1H), 3.83-3.48 (m, 4H), 2.09-1.75 (m, 2H), 1,42-1.17 (m, 2H).

Step 2: Preparation of 4-hydroxyoxane-4-carboximidamide hydrochloride

A solution of 4-hydroxyoxane-4-carboxamide (2.70 g. 18.60 mmol. 1.00 equiv) in THF (60 mL) was added tetrafluoroboranuide: triethyloxidanium (5.30 g. 27.90 mmol. 1.50 equiv) in portions at 0° C. under nitrogen atmosphere. The resulting mixture was stirred for 3 h at room temperature under nitrogen atmosphere. The resulting mixture was concentrated under reduced pressure. The residue was dissolved in MeOH (40 mL). To the above solution was added $NH_3$ (g) in MeOH (30 mL. 4M) dropwise at 0° C. The resulting mixture was stirred for additional 3 h at room temperature. The resulting mixture was concentrated under reduced pressure. The residue was dissolved in EA (50 mL). To the above solution was added HCl (gas) in 1,4-dioxane (10 mL. 7M) dropwise at 0° C. The resulting mixture was stirred for additional 30 min at room temperature. The precipitated solids were collected by filtration and washed with EA (10 mL). The filter cake was concentrated under vacuum. To afford 4-hydroxyoxane-4-carboximidamide hydrochloride (330 mg. 9.82%) as a white solid.

Step 3: Preparation of 3-chloro-4-[(3,5-difluoropyridin-2-yl)methoxy]-2'-[2-(4-hydroxyoxan-4-yl)pyrimidin-4-yl]-5',6-dimethyl-[1,4'-bipyridin]-2-one A mixture of 4-hydroxyoxane-4-carboximidamide hydrochloride (380 mg. 2.10 mmol. 5.00 equiv). KCO; (580 mg. 4.20 mmol. 10.00 equiv) and 3-chloro-4-[(3.5-difluoropyridin-2-yl)methoxy]-2'-[(2E)-3-(dimethylamino) prop-2-enov1]-5'0.6-dimethyl-]1,4'-bipyridin]-2-one (200 mg, 0.42 mmol. 1.00 equiv) in IPA (5 mL) was stirred overnight at 80° C., under nitrogen atmosphere. The reaction was monitored by LCMS. The resulting mixture was allowed to cool down to room temperature. The resulting mixture was diluted with EA (200 mL). The resulting mixture was washed with water (2×100 mL). The organic layers were concentrated under reduced pressure. The residue was purified by Prep-TLC (EA 0.1% Et;N) to afford 3-chloro-4-[(3.5-difluoropyridin-2-yl)methoxy]-2'-[2-(4-hydroxyoxan-4-yl)pyrimidin-4-yl]-5'0.6-dimethyl-[1,4'-bipyridin]-2-one (200 mg, crude). The crude product was further purified by Prep-HPLC to afford 3-chloro-4-[(3.5-difluoropyridin-2-yl)methoxy]-2'-[2-(4-hydroxyoxan-4-yl)pyrimidin-4-yl]-5'0.6-dimethyl-[1,4'-bipyridin]-2-one (150 mg. 64.06%) as a white solid. LC-MS: (ES+H, m/z): $[M+H]^+$=556.1. $^1$H NMR (400 MHz. DMSO-$d_6$) ¿ 9.07 (s, 2H), 8.76 (s, 2H), 6.29 (br. 1H), 3.81-3.70 (m, 2H), 3.69-3.64 (m, 2H). 2.20-1.95 (m, 2H), 1.58-1.52 (m, 2H).

Step 4: Preparation of rel-3-chloro-4-((3,5-difluoropyridin-2-yl)methoxy)-2'-(2-(4-hydroxytetrahydro-2H-pyran-4-yl)pyrimidin-4-yl)-5',6-dimethyl-2H-[1,4'-bipyridin]-2-one & rel-3-chloro-4-((3,5-difluoropyridin-2-yl)methoxy)-2'-(2-(4-hydroxytetrahydro-2H-pyran-4-yl)pyrimidin-4-yl)-5',6-dimethyl-2H-[1,4'-bipyridin]-2-one 3-chloro-4-[(3.5-difluoropyridin-2-yl)methoxy]-2'-]2-(4-hydroxyoxan-4-yl)pyrimidin-4-yl]-5'0.6-dimethyl-[1,4'-bipyridin]-2-one (150 mg) was isolated by Prep-CHIRAL-HPLC to afford rel-3-chloro-4-((3.5-difluoropyridin-2-yl)methoxy)-2'-(2-(4-hydroxytetrahydro-2H-pyran-4-yl)pyrimidin-4-yl)-5'0.6-dimethyl-2H-[1,4'-bipyridin]-2-one (Example 39A, isomer 1. 37.2 mg, ce=99.58%) and rel-3-chloro-4-((3,5-difluoropyridin-2-yl)methoxy)-2'-(2-(4-hydroxytetrahydro-2H-pyran-4-yl)pyrimidin-4-yl)-5',6-dimethyl-2H-[1,4'-bipyridin]-2-one (Example 39B, isomer 2, 35.3 mg, ee=99.63%) as a white solid.

EXAMPLE 39A

LC-MS: (ES+H, m/z): $[M+H]^+$=555.85. $^1$H NMR (400 MHZ, DMSO-$d_6$) δ 9.01 (d, 1H), 8.87 (s, 1H), 8.64 (d, 1H), 8.61 (d, 1H), 8.26 (d, 1H), 8.15-8.06 (m, 1H), 6.85 (d, 1H), 5.50 (d, 2H), 5.33 (s, 1H), 3.88-3.67 (m, 4H), 2.35-2.15 (m, 2H), 2.11 (s, 3H), 1.98 (s, 3H), 1.72-1.60 (m, 2H). $^{19}$F NMR (377 MHz, DMSO) δ-120.13,-120.15,-122.31,-122.32.

EXAMPLE 39B

LC-MS: (ES+H, m/z): $[M+H]^+$=555.90. $^1$H NMR (400 MHZ, DMSO-$d_6$) δ 9.01 (d, 1H), 8.87 (s, 1H), 8.64 (d, 1H), 8.61 (d, 1H), 8.26 (d, 1H), 8.14-8.06 (m, 1H), 6.85 (d, 1H), 5.50 (d, 2H), 5.33 (s, 1H), 3.85-3.67 (m, 4H), 2.35-2.16 (m, 2H), 2.11 (s, 3H), 1.98 (s, 3H), 1.75-1.60 (m, 2H). $^{19}$F NMR (377 MHz, DMSO) δ-120.13,-120.15,-122.30,-122.32.

EXAMPLE 40A, 40B

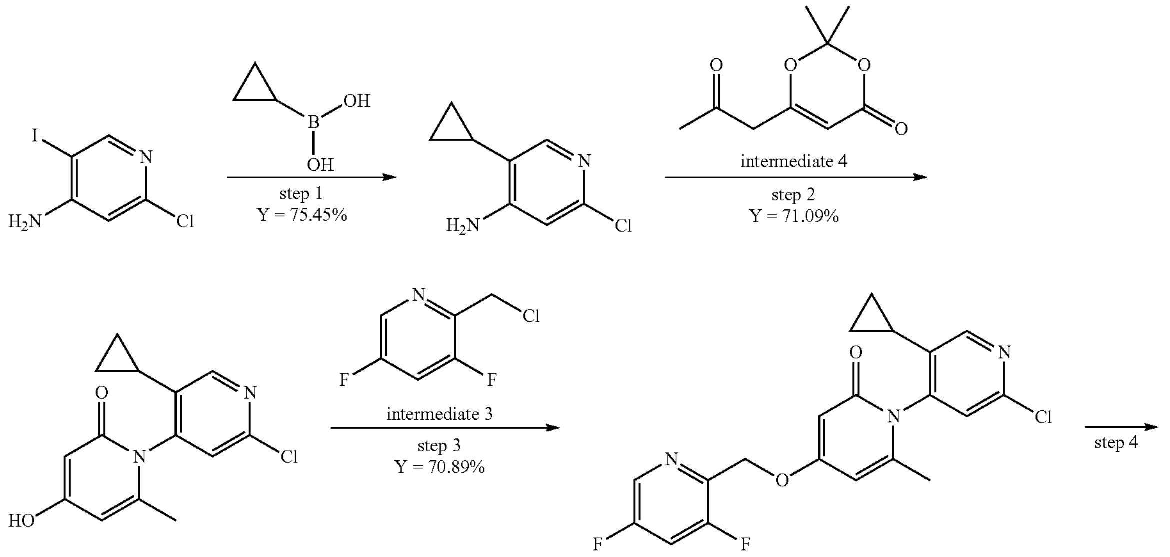

-continued
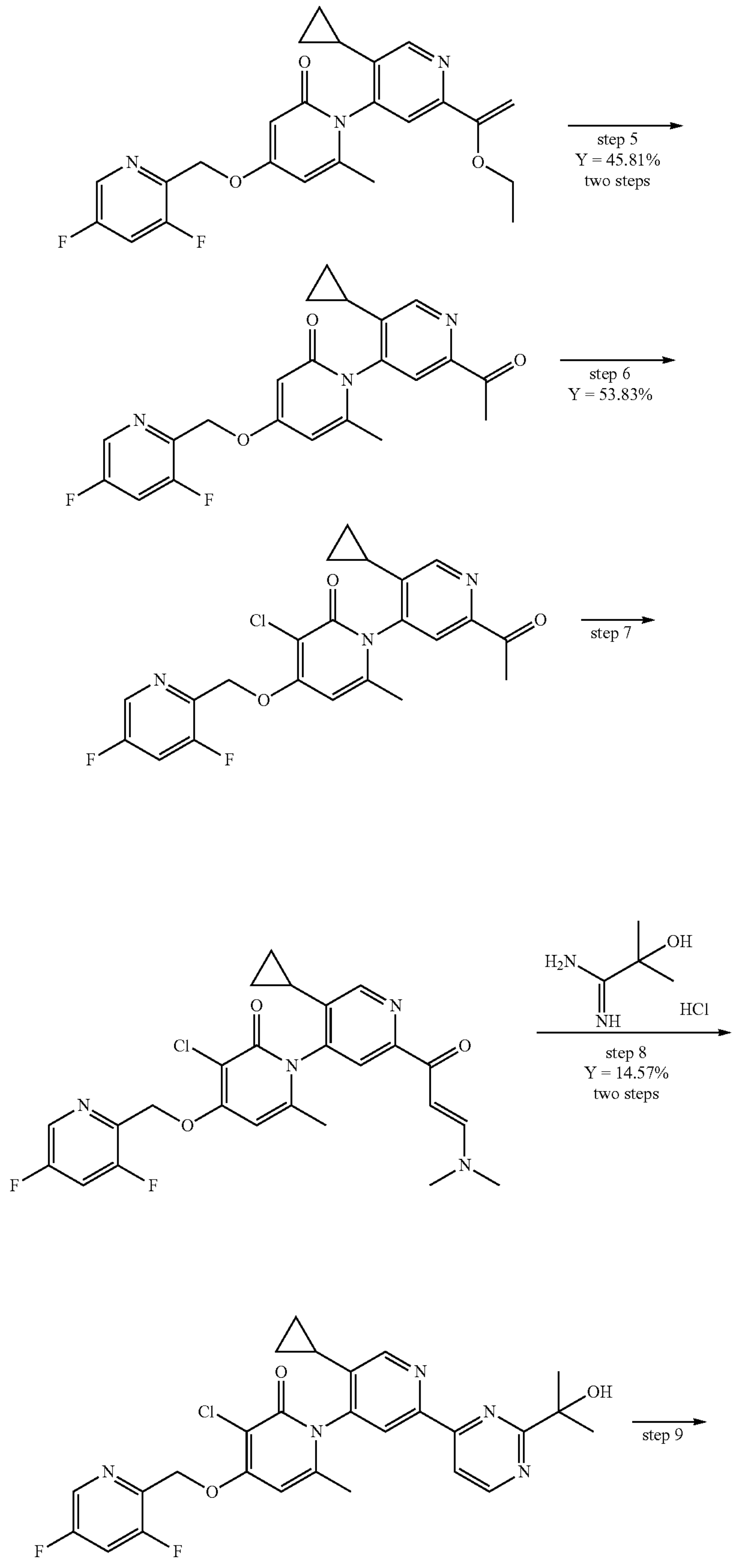
Example 40

-continued

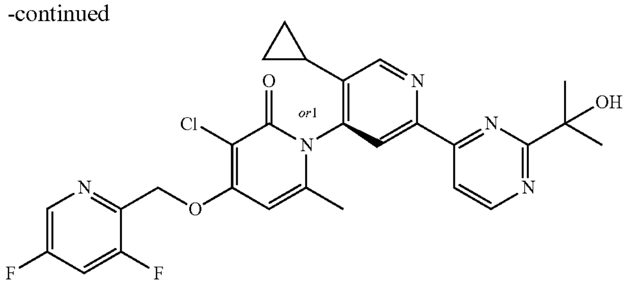

isomer 1
Example 40A

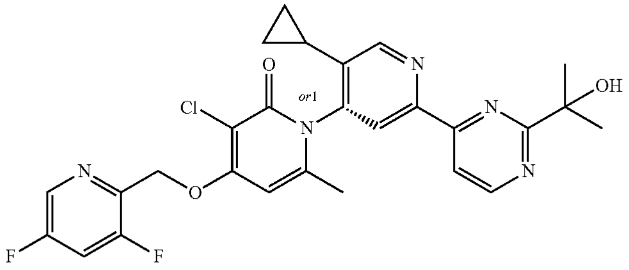

isomer 2
Example 40B

Step1: Preparation of 2-chloro-5-cyclopropylpyridin-4-amine

To a stirred solution of 2-chloro-5-iodopyridin-4-amine (5.00 g, 19.64 mmol, 1.00 equiv), cyclopropylboronic acid (1.69 g, 19.64 mmol, 1.00 equiv) in Toluene (30 mL) and $H_2O$ (3 mL) was added Pd(dppf) $Cl_2$ (0.72 g, 0.98 mmol, 0.05 equiv) at room temperature under nitrogen atmosphere. The resulting mixture was stirred overnight at 100° C., under nitrogen atmosphere. The reaction was monitored by TLC. The mixture was allowed to cool down to room temperature. The reaction was quenched by the addition of water (50 mL) at room temperature. The resulting mixture was extracted with EtOAc (3 ×30 mL). The combined organic layers were washed with brine (100 mL). The filtrate was concentrated under reduced pressure. The residue was purified by silica gel column chromatography, the pure fraction was concentrated under vacuum to afford 2-chloro-5-cyclopropylpyridin-4-amine (2.50 g. 75.45%) as a yellow oil. $^1$H NMR (300 MHz. DMSO-$d_6$) δ 7.60 (s.1H), 6.51 (s, 1H), 6.28 (s, 2H), 1.67-1,43 (m, 1H), 0.98-0.75 (m, 2H). 0.64-0.43 (m, 2H).

Step2: Preparation of 2'-chloro-5'-cyclopropyl-4-hydroxy-6-methyl-[1,4'-bipyridin]-2-one To a stirred solution of 2-chloro-5-cyclopropylpyridin-4-amine (2.40 g. 14.23 mmol. 1.00 equiv) and 2.2-dimethyl-6-(2-oxopropyl)-1,3-dioxin-4-one (5.24 g. 28.46 mmol. 2.00 equiv) in 1,4-dioxane (72 mL) at room temperature under nitrogen atmosphere. The resulting mixture was stirred for 2 h at 90° C., under nitrogen atmosphere. The mixture was allowed to cool down to room temperature. To the above mixture was added $H_2SO_4$ (1,40 g. 14.23 mmol. 1.00 equiv) dropwise at room temperature. The resulting mixture was stirred for additional 1 h at 90° C. The reaction was monitored by LCMS. The mixture was allowed to cool down to room temperature then concentrated to remove the solvent. followed by additions of water (20 ml). The precipitated solids were collected by filtration and washed with Et,O (3 ×10 mL) to afford 2'-chloro-5'-cyclopropyl-4-hydroxy-6-methyl-] 1,4'-bipyridin]-2-one (2.80 g. 71.09%) as a white solid. LC-MS: (ES+H, m z): $[M+H]^+$=277.1. $^1$H NMR (400 MHZ. DMSO-$d_6$) δ 10.84 (br. 1H), 8.20 (s, 1H), 7.52 (s.1H), 6.04-5.91 (m. 1H), 5.66-5.54 (m. 1H), 1.88 (s, 3H), 1.51-1.35 (m, 1H), 1.00-0.80 (m, 3H), 0.73-0.55 (m, 1H).

Step3: Preparation of 2'-chloro-5'-cyclopropyl-4-[(3,5-difluoropyridin-2-yl)methoxy]-6-methyl-[1,4'-bipyridin]-2-one To a stirred solution of 2'-chloro-5'-cyclopropyl-4-hydroxy-6-methyl-[1,4'-bipyridin]-2-one (2.90 g. 10.48 mmol. 1.00 equiv) and 2-(chloromethyl)-3.5-difluoropyridine (3.43 g. 20.96 mmol. 2.00 equiv) in DMF (50 mL) were added $K_2CO_3$ (5.79 g. 41.92 mmol. 4.00 equiv) and 18-Crown-6 (277 mg, 1.04 mmol. 0.10 equiv) at room temperature under nitrogen atmosphere. The resulting mixture was stirred for 1 h at 60° C. under nitrogen atmosphere. The reaction was monitored by LCMS. The mixture was allowed to cool down to room temperature. The reaction was poured into water (100 mL) at room temperature. The resulting mixture was extracted with EtOAc (3 ×50 mL). The combined organic layers were washed with brine (5×100 mL), the filtrate was concentrated under reduced pressure. The residue was purified by silica gel column chromatography the pure fraction was concentrated under vacuum to afford 2'-chloro-5'-cyclopropyl-4-[(3.5-difluoropyridin-2-yl)methoxy]-6-methyl-[1,4'-bipyridin]-2-one (3.00 g. 70.89%) as a yellow solid. LC-MS: (ES+H, m z): $[M+H]^+$=404.1. $^1$H NMR (400 MHz. DMSO-$d_6$) δ 8.62-8.57 (m, 1H), 8.22 (s, 1H), 8.13-8.02 (m. 1H), 7.57 (s, 1H), 6.19-6.11 (m. 1H), 6.08-6.01 (m, 1H), 5.29-5.17 (m, 2H), 1.90 (s, 3H), 1,48-1.34 (m. 1H), 0.99-0.90 (m, 1H), 0.91-0.82 (m, 2H), 0.74-0.60 (m, 1H).

Step4: Preparation of 5'-cyclopropyl-4-[(3,5-difluoropyridin-2-yl)methoxy]-2'-(1-ethoxyethenyl)-6-methyl-[1,4'-bipyridin]-2-one To a stirred solution of 2'-chloro-5'-cyclopropyl-4-[(3.5-difluoropyridin-2-yl)methoxy]-6-methyl-[1,4'-bipyridin]-2-one (3.00 g. 7.42 mmol. 1.00 equiv) and tributyl (1-ethoxyethenyl) stannane (5.37 g. 14.85 mmol. 2.00 equiv) in 1,4-dioxane (30 mL) were added Pd(PPh;) $C_1$, (260 mg, 0.37 mmol. 0.05 equiv) at room temperature under nitrogen atmosphere. The resulting mixture was stirred overnight at 100° C., under nitrogen atmosphere. The reaction was monitored by TLC. The mixture was allowed to cool down to room temperature. The resulting mixture was filtrated and concentrated under reduced pressure to afford 5'-cyclopropyl-4-[(3.5-difluoropyridin-2-yl)methoxy]-2'-(1-ethoxyethenyl)-6-methyl-] 1,4'-bipyridin]-2-one (1.80 g, crude) as a yellow solid.

Step 5: Preparation of 2'-acetyl-5'-cyclopropyl-4-[(3,5-difluoropyridin-2-yl)methoxy]-6-methyl-[1,4'-bipyridin]-2-one To a stirred solution of 5'-cyclopropyl-4-[(3.5-difluoropyridin-2-yl)methoxy]-2'-(1-ethoxyethenyl)-6-methyl-[1,4'-bipyridin]-2-one (1.80 g. 4.09 mmol. 1.00 equiv) in THF (20 mL) were added conc. HCl (2 mL) dropwise at 0° C., under nitrogen atmosphere. The resulting mixture was stirred for 2 h at room temperature under nitrogen atmosphere. The reaction was monitored by LCMS. The reaction was poured into Water (40 ml) at room temperature. The resulting mixture was extracted with EtOAc (3 ×30 mL). The combined organic layers were washed with brine (3 ×50 mL), the filtrate was concentrated under reduced pressure. The residue was purified by silica gel column chromatography, the pure fraction was concentrated under vacuum to afford 2'-acetyl-5'-cyclopropyl-4-[(3.5-difluoropyridin-2-yl) methoxy]-6-methyl-[1,4'-bipyridin]-2-one (1,40 g. 45.81%, two steps) as a yellow solid. LC-MS: (ES+H, m/z): $[M+H]^+$=412.1. $^1$H NMR (400 MHz. DMSO-$d_6$) δ 8.63-8.57 (m. 1H), 8.47 (s, 1H), 8.12-8.04 (m, 1H), 7.75 (s.1H). 6.18-6.11 (m, 1H), 6.08-6.02 (m. 1H), 5.24 (d, 2H), 2.64 (s, 3H), 1.86 (s, 3H), 1.56-1,43 (m, 1H), 1.14-0.94 (m, 3H), 0.88-0.76 (m, 1H).

Step 6: Preparation of 2 '-acetyl-3-chloro-5'-cyclopropyl-4-[(3,5-difluoropyridin-2-yl)methoxy]-6-methyl-[1,4'-bipyridin]-2-one To a stirred solution of 2'-acetyl-5'-cyclopropyl-4-[(3,5-difluoropyridin-2-yl)methoxy]-6-methyl-[1,4'-bipyridin]-2-one (1.20 g. 2.91 mmol. 1.00 equiv) and NCS (506 mg. 3.79 mmol. 1.30 equiv) in DCM (10 mL) were added 2.2-dichloroacetic acid (18 mg, 0.14 mmol. 0.05 equiv) at room temperature under nitrogen atmosphere. The resulting mixture was stirred overnight at room temperature under nitrogen atmosphere. The reaction was monitored by LCMS. The reaction was poured into Water (30 ml) at room temperature. The resulting mixture was extracted with CH $Cl_2$ (3×20 mL). The combined organic layers were washed with brine (3×30 mL), the filtrate was concentrated under reduced pressure. The residue was purified by silica gel column chromatography, the pure fraction was concentrated under vacuum to afford 2'-acetyl-3-chloro-5'-cyclopropyl-4-[(3.5-difluoropyridin-2-yl)methoxy]-6-methyl-[1,4'-bipyridin]-2-one (700 mg. 53.83%) as a yellow solid. LC-MS: (ES+H, m/z): $[M+H]^+$=446.0. $^1$H NMR (300 MHz. DMSO-$d_6$) δ 8.66-8.57 (m. 1H), 8.51 (s, 1H), 8.16-8.03 (m. 1H), 7.86 (s.1H), 6.81 (s.1H), 5.47 (s, 2H), 2.65 (s, 3H), 1.96 (s. 3H), 1.57-1,40 (m. 1H), 1.15-1.05 (m. 1H), 1.04-0.95 (m, 2H), 0.91-0.75 (m, 1H).

Step 7: Preparation of 3-chloro-5'-cyclopropyl-4-[(3,5-difluoropyridin-2-yl)methoxy]-2'-[(2E)-3-(dimethylamino) prop-2-enoyl]-6-methyl-[1,4'-bipyridin]-2-one To a stirred solution of 2'-acetyl-3-chloro-5'-cyclopropyl-4-[(3.5-difluoropyridin-2-yl)methoxy]-6-methyl-[1,4'-bipyridin]-2-one (680 mg, 1.52 mmol. 1.00 equiv) in DMF-DMA (20 mL) at room temperature under nitrogen atmosphere. The resulting mixture was stirred for 3 h at 100° C., under nitrogen atmosphere. The reaction was monitored by LCMS. The mixture was allowed to cool down to room temperature. The resulting mixture was concentrated under reduced pressure to afford 3-chloro-5'-cyclopropyl-4-[(3.5-difluoropyridin-2-yl)methoxy]-2'-] (2E)-3-(dimethylamino) prop-2-enoyl]-6-methyl-[1,4'-bipyridin]-2-onc (440 mg, crude) as a yellow solid. The crude product mixture was used in the next step directly without further purification. LC-MS: (ES+H, m/z): $[M+H]^+$=501.2.

Step 8: Preparation of 3-chloro-5'-cyclopropyl-4-[(3,5-difluoropyridin-2-yl)methoxy]-2'-[2-(2-hydroxypropan-2-yl)pyrimidin-4-yl]-6-methyl-[1,4'-bipyridin]-2-one To a stirred solution of 3-chloro-5'-cyclopropyl-4-[(3.5-difluoropyridin-2-yl)methoxy]-2'-[(2E)-3-(dimethylamino) prop-2-cnov1]-6-methyl-[1,4'-bipyridin]-2-one (440 mg, 0.87 mmol. 1.00 equiv) and 2-hydroxy-2-methylpropanimidamide hydrochloride (608 mg. 4.39 mmol. 5.00 equiv) in DMF (5 mL) were added $K_2CO_3$ (364 mg. 2.63 mmol. 3.00 equiv) at room temperature under nitrogen atmosphere. The resulting mixture was stirred overnight at 80° C., under nitrogen atmosphere. The reaction was monitored by LCMS. The mixture was allowed to cool down to room temperature. The resulting mixture was poured into water (40 mL) at 0° C. The resulting mixture was extracted with EtOAc (3×30 mL). The combined organic layers were washed with brine (5×50 mL), the filtrate was concentrated under reduced pressure. The residue was purified by Prep-TLC, the pure fraction was concentrated under vacuum to afford 3-chloro-5'-cyclopropyl-4-[(3.5-difluoropyridin-2-yl)methoxy]-2'-[2-(2-hydroxypropan-2-yl)pyrimidin-4-yl]-6-methyl-[1,4'-bipyridin]-2-one (120 mg, 14.57%, over two steps) as a white solid. LC-MS: (ES+H, m/z): $[M+H]^+$=540.1.

Step 9: Preparation of rel-3-chloro-5'-cyclopropyl-4-[(3,5-difluoropyridin-2-yl)methoxy]-2'-[2-(2-hydroxypropan-2-yl)pyrimidin-4-yl]-6-methyl-[1,4'-bipyridin]-2-one and rel-3-chloro-5'-cyclopropyl-4-[(3,5-difluoropyridin-2-yl)methoxy]-2'-[2-(2-hydroxypropan-2-yl)pyrimidin-4-yl]-6-methyl-[1,4'-bipyridin]-2-one The racemate (100 mg) was separated by Prep-Chiral-HPLC to afford Example 40A (30.9 mg. 98.2% purity, ee=100%) as a white solid and Example 40B (37.7 mg. 96.9% purity, ee=99.48%) as a white solid.

EXAMPLE 40A

LC-MS: (ES+H, m z): $[M+H]^+$=540.10. $^1$H NMR (300 MHz. DMSO-$d_6$) δ 9.00-8.93 (m, 1H). 8.66 (s.1H).8.63-8.60

(m. 1H), 8.56 (s.1H) 8.25-8.18 (m, 1H), 8.15-8.07 (m, 1H), 6.86 (s, 1H), 5.52-5.48 (m. 2H), 5.26 (s, 1H), 2.03 (s, 3H), 1.56-1.50 (m. 7H), 1.14-1.07 (m, 1H), 1.03-0.95 (m, 2H), 0.87-0.78 (m. 1H). $^{19}$F NMR (282 MHz. DMSO) δ-120.11, -120.13, -122.29.-122.31.
EXAMPLE 40B
LC-MS: (ES+H, m z): $[M+H]^+$=539.85. $^1$H NMR (300 MHz. DMSO-$d_6$) δ 8.99-8.94 (m, 1H). 8.66 (s.1H), 8.63-8.60 (m. 1H), 8.56 (s, 1H), 8.23-8.19 (m, 1H), 8.15-8.06 (m, 1H), 6.86 (s, 1H), 5.54-5.45 (m. 2H), 5.26 (s, 1H), 2.03 (s, 3H), 1.57-1.50 (m. 7H), 1.17-1.05 (m, 1H), 1.02-0.93 (m, 2H), 0.88-0.77 (m. 1H), $^{19}$F NMR (282 MHz. DMSO) δ-120.10, -120.12, -122.27, -122.29.
EXAMPLE 41A, 41B
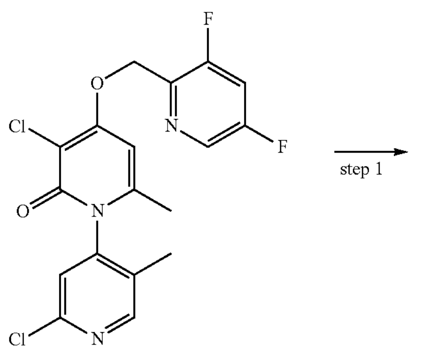
intermediate 7
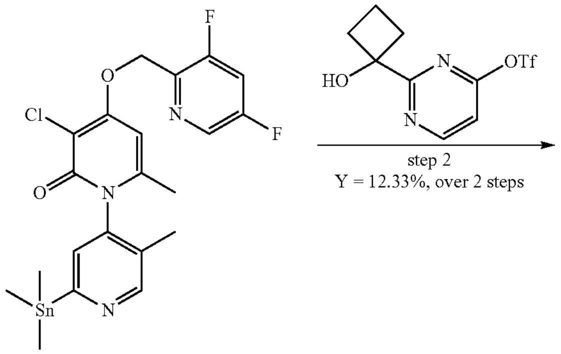
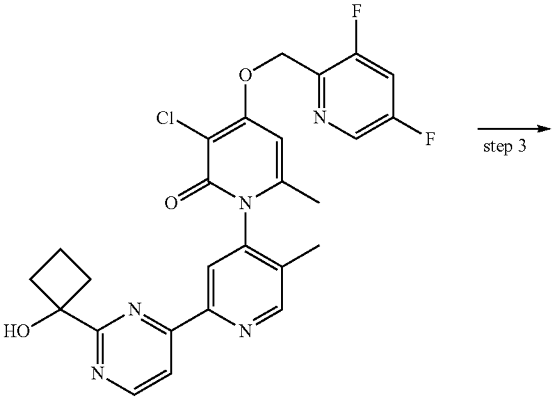
Example 41
-continued
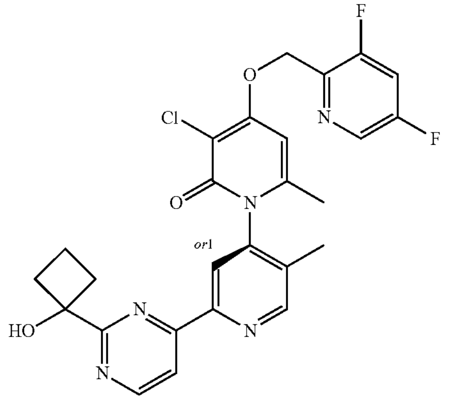
isomer 1
Example 41A
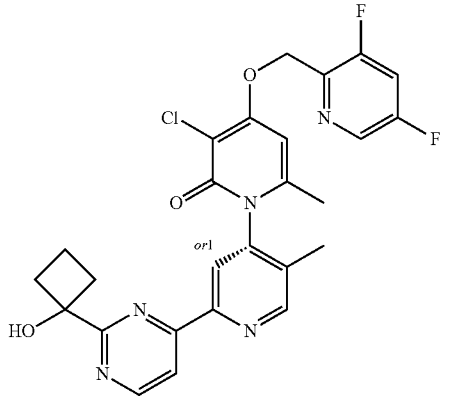
isomer 2
Example 41B
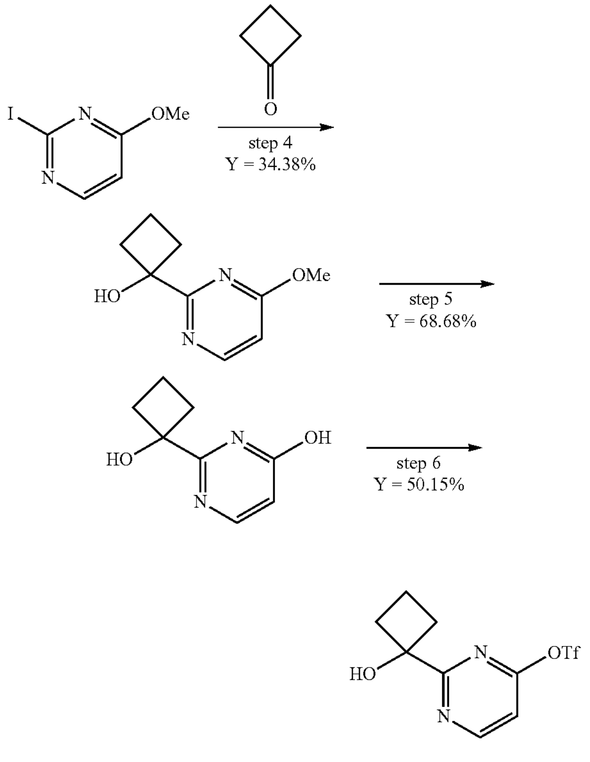

Step 1: Preparation of 3-chloro-4-[(3,5-difluoropyridin-2-yl)methoxy]-5',6-dimethyl-2'-(trimethylstannyl)-[1,4'-bipyridin]-2-one To a stirred mixture of 2',3-dichloro-4-[(3,5-difluoropyridin-2-yl)methoxy]-5',6-dimethyl-[1,4'-bipyridin]-2-one (500 mg, 1.21 mmol, 1.00 equiv) and $Sn_2Me_6$ (1.59 g, 4.85 mmol, 4.00 equiv) in dioxane (10 mL) was added $AsPh_3$ (185 mg, 0.61 mmol, 0.50 equiv) and $Pd(PPh_3)$: $Cl_2$ (170 mg, 0.24 mmol, 0.20 equiv) at room temperature under nitrogen atmosphere. The resulting mixture was stirred overnight at 80° C. under nitrogen atmosphere. The mixture was allowed to cool down to room temperature. The resulting mixture was diluted with ethyl acetate (50 mL). The resulting mixture was washed with 5×20 mL of sat. KF aq. . . . The combined organic layers were washed with brine (50 mL), dried over anhydrous $Na_2SO_4$. After filtration, the filtrate was concentrated under reduced pressure, to afford 3-chloro-4-[(3,5-difluoropyridin-2-yl)methoxy]-5',6-dimethyl-2'-(trimethylstannyl)-[1,4'-bipyridin]-2-one (700 mg, crude) as a brown semi-solid. LC-MS: (ES+H, m/z): $[M+H]^+$=541.9.

Step 2: Preparation of 3-chloro-4-[(3,5-difluoropyridin-2-yl)methoxy]-2'-[2-(1-hydroxycyclobutyl)pyrimidin-4-yl]-5',6-dimethyl-[1,4'-bipyridin]-2-one To a stirred mixture of 3-chloro-4-[(3,5-difluoropyridin-2-yl)methoxy]-5',6-dimethyl-2'-(trimethylstannyl)-[1,4'-bipyridin]-2-one (700 mg, assumed 100% yield, 0.93 mmol, 1.00 equiv) and 2-(1-hydroxycyclobutyl)pyrimidin-4-yl trifluoromethanesulfonate (827 mg, 2.78 mmol, 3.00 equiv) in dioxane (10 mL) was added $Pd(PPh_3)$: $Cl_2$ (194 mg, 0.29 mmol, 0.30 equiv) and CuI (176 mg, 0.96 mmol, 1.00 equiv) at room temperature under nitrogen atmosphere. The resulting mixture was stirred for 2 h at 100° C., under nitrogen atmosphere. The mixture was allowed to cool down to room temperature. The resulting mixture was diluted with water (50 mL). The resulting mixture was extracted with EtOAc (3×100 mL). The combined organic layers were washed with brine (100 mL), dried over anhydrous $Na_2SO_4$. After filtration, the filtrate was concentrated under reduced pressure. The residue was purified by silica gel column chromatography to afford the crude product (200 mg), which was further purified by Prep-HPLC to afford 3-chloro-4-[(3,5-difluoropyridin-2-yl)methoxy]-2'-[2-(1-hydroxycyclobutyl) pyrimidin-4-yl]-5',6-dimethyl-[1,4'-bipyridin]-2-one (60 mg, 12.33%, over 2 steps) as a white solid. LC-MS: (ES+H, m/z): $[M+H]^+$=526.2.

Step3: Preparation of rel-3-chloro-4-[(3,5-difluoropyridin-2-yl)methoxy]-2'-[2-(1-hydroxycyclobutyl) pyrimidin-4-yl]-5',6-dimethyl-[1,4'-bipyridin]-2-one and rel-3-chloro-4-[(3,5-difluoropyridin-2-yl) methoxy]-2'-[2-(1-hydroxycyclobutyl)pyrimidin-4-yl]-5', 6-dimethyl-[1,4'-bipyridin]-2-one The racemate 3-chloro-4-[(3.5-difluoropyridin-2-yl) methoxy]-2'-[2-(1-hydroxycyclobutyl)pyrimidin-4-yl]-5'0.6-dimethyl-[1,4'-bipyridin]-2-one (60 mg) was separated by Prep-Chiral-HPLC to afford Example 41A (21.6 mg, ee=100%) as an off-white solid and Example 41B (20.7 mg, ee=100%) as an off-white solid.

EXAMPLE 41A

LC-MS: (ES+H, m/z): $[M+H]^+$=526.20. $^1$H NMR (400 MHz. DMSO-$d_6$) δ 9.02 (d, 1H), 8.87 (s. 1H), 8.63 (s, 1H), 8.62-8.60 (d, 1H), 8.26 (d, 1H), 8.15-8.05 (m. 1H), 6.84 (s.1H), 5.68 (s, 1H), 5.50 (s. 2H), 2.72-2.58 (m, 2H), 2.34-2.24 (m, 2H), 2.11 (s, 3H), 1.98 (s, 3H), 1.96-1.76 (m, 2H), $^{19}$F NMR (377 MHz. DMSO) δ-120.13, -120.15, -122.30,-122.32.

EXAMPLE 41B

LC-MS: (ES+H, m/z): $[M+H]^+$=526.15. $^1$H NMR (400 MHZ. DMSO-$d_6$) δ 9.02 (d, 1H), 8.87 (s. 1H), 8.63 (s, 1H), 8.62-8.60 (d, 1H), 8.26 (d, 1H), 8.11 (ddd. 1H), 6.84 (s.1H), 5.68 (s, 1H), 5.50 (s, 2H). 2.71-2.59 (m, 2H), 2.35-2.54 (m, 2H), 2.11 (s, 3H), 1.98 (s, 3H), 1.96-1.78 (m, 2H). $^{19}$F NMR (377 MHz. DMSO) δ-120.13, -120.15, -122.31, -122.33.

Step 4: Preparation of 1-(4-methoxypyrimidin-2-yl)cyclobutan-1-ol

To a stirred solution of 2-iodo-4-methoxypyrimidine (8.00 g. 33.90 mmol. 1.00 equiv) in toluene (50 mL) was added i-PrMgCl (3.83 g. 37.29 mmol. 1.10 equiv. 2M in THF) dropwise at 0° C., under nitrogen atmosphere. The resulting mixture was stirred for 30 min at 0° C., under nitrogen atmosphere. To the above mixture was added cyclobutanone (3.09 g. 44.07 mmol. 1.30 equiv) in toluene (2 mL) dropwise over 2 min at 0° C. The resulting mixture was stirred for additional 1h at room temperature. The reaction was monitored by LCMS. The reaction was quenched with sat. $NH_4Cl$ (aq.) at 0° C. The resulting mixture was extracted with EtOAc (3×100 mL). The combined organic layers were washed with brine (2×100 mL), dried over anhydrous $Na_2SO_4$. After filtration, the filtrate was concentrated under reduced pressure. The residue was purified by silica gel column chromatography to afford 1-(4-methoxypyrimidin-2-yl)cyclobutan-1-ol (2.10 g. 34.38%) as a yellow oil. LC-MS: (ES+H, m/z): $[M+H]^+$=183.0.

Step 5: Preparation of 2-(1-hydroxycyclobutyl)pyrimidin-4-ol

To a stirred solution of 1-(4-methoxypyrimidin-2-yl)cyclobutan-1-ol (2.10 g. 11.65 mmol. 1.00 equiv) in MeCN(20 mL) was added TMSI (9.33 g. 46.61 mmol. 4.00 equiv) at room temperature under nitrogen atmosphere. The resulting mixture was stirred for overnight at room temperature under nitrogen atmosphere. The mixture was allowed to cool down to room temperature. The resulting mixture was concentrated under reduced pressure. The residue was purified by trituration with hexane/EA (3/1) (3×20 mL), to afford 2-(1-hydroxycyclobutyl)pyrimidin-4-ol (1.33 g, 68.68%) as a light yellow solid. LC-MS: (ES+H, m/z): $[M+H]^+$=167.1.

Step 6: Preparation of 2-(1-hydroxycyclobutyl)pyrimidin-4-yl trifluoromethanesulfonate To a stirred mixture of 2-(1-hydroxycyclobutyl)pyrimidin-4-ol (1 g. 6.018 mmol, 1 equiv) and Pyridine (1,43 g, 18.05 mmol, 3 equiv) in DCM (10 mL) was added Tf2O (3.40 g, 12.04 mmol, 2 equiv) dropwise at 0° C., under nitrogen atmosphere. The resulting mixture was stirred for 5 min at 0° C., under nitrogen atmosphere. The reaction was monitored by LCMS. The residue was purified by silica gel column chromatography, to afford 2-(1-hydroxycyclobutyl)

pyrimidin-4-yl trifluoromethanesulfonate (900 mg, 50.15%) as a yellow oil. LC-MS: (ES+H, m/z): $[M+H]^+$=299.1.

EXAMPLE 42A, 42B

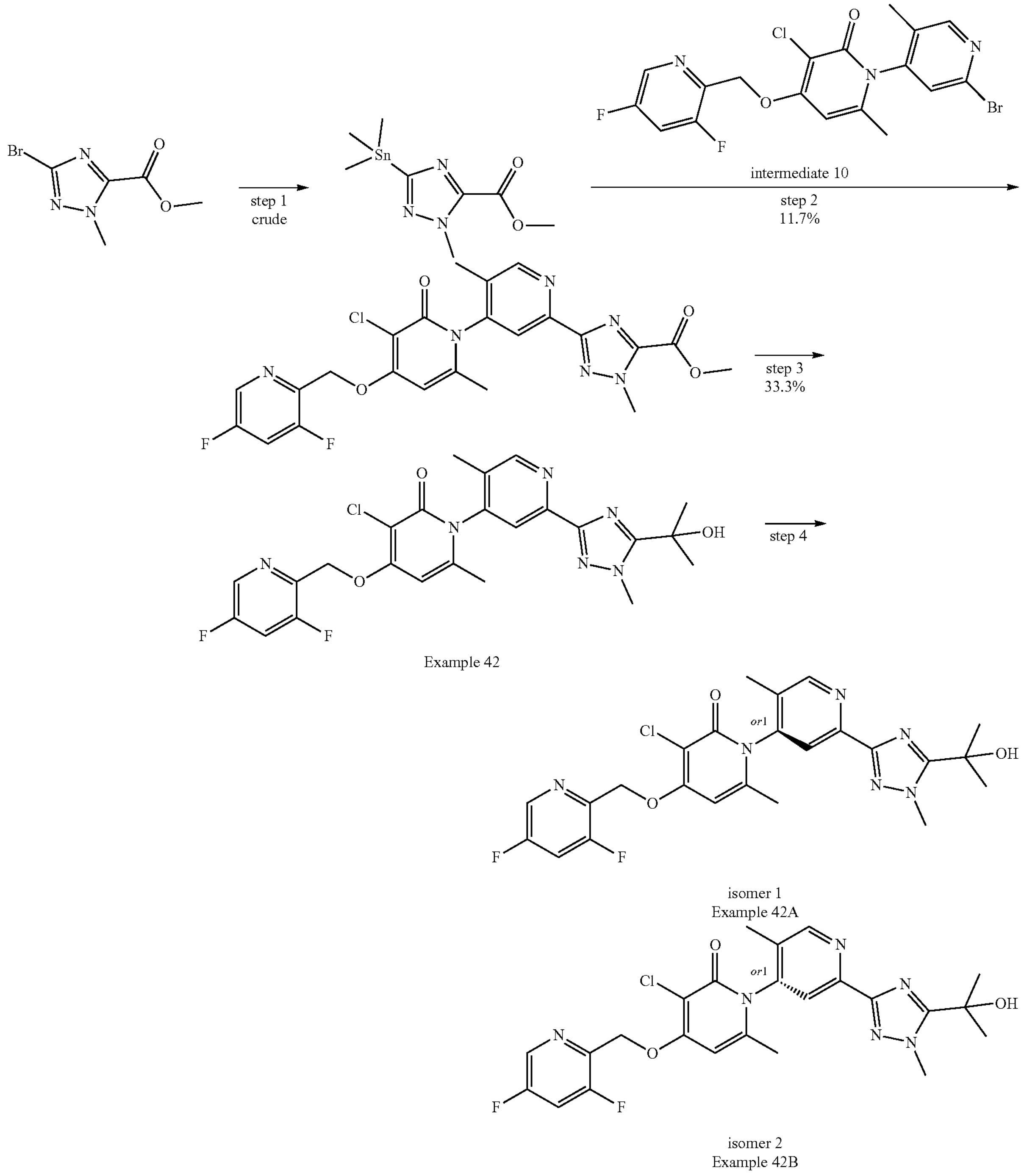

Step 1: Preparation of methyl 2-methyl-5-(trimethylstannyl)-1,2,4-triazole-3-carboxylate To a stirred solution of methyl 5-bromo-2-methyl-1,2,4-triazole-3-carboxylate (500 mg, 2.27 mmol, 1.00 equiv) and $Sn_2Me_6$ (2.98 g, 9.08 mmol, 4.00 equiv) in 1,4-dioxane was added $Pd(PPh_3)$: $Cl_2$ (478 mg, 0.68 mmol, 0.30 equiv) and AsPh; (208 mg, 0.68 mmol, 0.30 equiv) at room temperature under nitrogen atmosphere. The resulting mixture was stirred overnight at 80° C. The reaction was monitored by LCMS. The mixture was allowed to cool down to room temperature. The resulting mixture was diluted with EtOAc (100 mL). The residue was washed with KF (5×300 mL). The combined organic layers were washed with brine (200 mL), dried over anhydrous $Na_2SO_4$. After filtration, the filtrate was concentrated under reduced pressure. The crude product was used in the next step directly without further purification. LC-MS: (ES+H, m/z): $[M+H]^+$=306.1.

Step 2: Preparation of methyl 5-{3-chloro-4-[(3,5-difluoropyridin-2-yl)methoxy]-5',6-dimethyl-2-oxo-[1,4'-bipyridin]-2'-yl}-2-methyl-1,2,4-triazole-3-carboxylate To a stirred mixture of methyl 2-methyl-5-(trimethylstannyl)-1,2,4-triazole-3-carboxylate (500 mg, 1.64 mmol, 1.00 equiv) and 2'-bromo-3-chloro-4-[(3,5-difluoropyridin-2-yl)methoxy]-5',6-dimethyl-[1,4'-bipyridin]-2-one (450 mg, 0.98 mmol, 0.60 equiv) in dioxane (40 mL) were added $Pd(PPh_3)$: $Cl_2$ (230 mg, 0.32 mmol, 0.20 equiv) and CuI (313 mg, 1.64 mmol, 1.00 equiv) at room temperature under nitrogen atmosphere. The resulting mixture was stirred for 2 h at 80° C., under nitrogen atmosphere. The reaction was monitored by LCMS. The mixture was allowed to cool down to room temperature. The residue was purified by silica gel column chromatography to afford methyl 5-{3-chloro-4-[(3.5-difluoropyridin-2-yl)methoxy]-5'0.6-dimethyl-2-oxo-[1,4'-bipyridin]-2'-yl}-2-methyl-1.2.4-triazole-3-carboxylate (100 mg, 11.76%) as a yellow solid. LC-MS: (ES+H, m/z): $[M+H]^+$=517.2

Step 3: Preparation of 3-chloro-4-[(3,5-difluoropyridin-2-yl)methoxy]-2'-[5-(2-hydroxypropan-2-yl)-1-methyl-1,2,4-triazol-3-yl]-5',6-dimethyl-[1,4'-bipyridin]-2-one To a stirred solution of methyl 5-{3-chloro-4-[(3.5-difluoropyridin-2-yl)methoxy]-5'0.6-dimethyl-2-oxo-[1,4'-bipyridin]-2'-yl}-2-methyl-1.2.4-triazole-3-carboxylate (300 mg, 0.58 mmol. 1.00 equiv) in THF (30 mL) was added MeMgBr (1.93 mL. 5.80 mmol. 10.00 equiv) dropwise at 0° C., under nitrogen atmosphere. The resulting mixture was stirred for 1 h at 0° C., under nitrogen atmosphere. The reaction was monitored by LCMS. The reaction was quenched by the addition of sat. $NH_4Cl$ (aq.) (10 mL) at 0° C. The resulting mixture was extracted with EtOAc (3×100 mL). The combined organic layers were washed with brine (200 mL), dried over anhydrous $Na_2SO_4$. After filtration, the filtrate was concentrated under reduced pressure. The residue was purified by PREP-HPLC. This resulted in 3-chloro-4-[(3.5-difluoropyridin-2-yl)methoxy]-2'-[5-(2-hydroxypropan-2-yl)-1-methyl-1.2.4-triazol-3-yl]-5'0.6-dimethyl-[1,4'-bipyridin]-2-one (100 mg. 33.33%) as a white solid. LC-MS: (ES+H, m/z): $[M+H]^+$=517.4.

Step 3: Preparation of rel-3-chloro-4-[(3,5-difluoropyridin-2-yl)methoxy]-2'-[5-(2-hydroxypropan-2-yl)-1-methyl-1,2,4-triazol-3-yl]-5',6-dimethyl-[1,4'-bipyridin]-2-one & rel-3-chloro-4-[(3,5-difluoropyridin-2-yl)methoxy]-2'-[5-(2-hydroxypropan-2-yl)-1-methyl-1,2,4-triazol-3-yl]-5',6-dimethyl-[1,4'-bipyridin]-2-one The racemate 3-chloro-4-[(3.5-difluoropyridin-2-yl)methoxy]-2'-[5-(2-hydroxypropan-2-yl)-1-methyl-1.2.4-triazol-3-yl]-5'0.6-dimethyl-[1,4'-bipyridin]-2-one (55 mg) was separated by prep-chiral-HPLC to afford Example 42A (26.2 mg. 99.0% purity, ee=100%) and Example 42B (26.0 mg. 99.4% purity, ee=100%) as a white solid.

EXAMPLE 42A

LC-MS: (ES+H, m/z): $[M+H]^+$=517.10. $^1H$ NMR (300 MHz. DMSO-$d_6$) δ 8.70-8.76 (m, 1H). 8.56-8.66 (m, 1H), 8.11 (t. 1H), 7.84 (s, 1H), 6.80 (s, 1H), 5.73 (s, 1H), 5.49 (s, 2H), 4.09 (s, 3H), 2.05 (s. 3H), 1.96 (s, 3H), 1.59 (s. 6H). $^{19}F$ NMR (282 MHz. DMSO) δ-120.14, -120.16, -122.33, -122.36.

EXAMPLE 42B

LC-MS: (ES+H, m/z): $[M+H]^+$=517.10. $^1H$ NMR (300 MHz. DMSO-$d_6$) δ 8.73 (s, 1H), 8.61 (s. 1H), 8.10 (t. 1H), 7.84 (s, 1H), 6.80 (s, 1H), 5.73 (s, 1H), 5.48 (s, 2H), 4.09 (s, 3H), 2.05 (s, 3H), 1.96 (s. 3H), 1.58 (s. 6H). $^{19}F$ NMR (282 MHz. DMSO) δ-120.13, -120.16, -122.32, -122.35.

EXAMPLE 43A, 43B

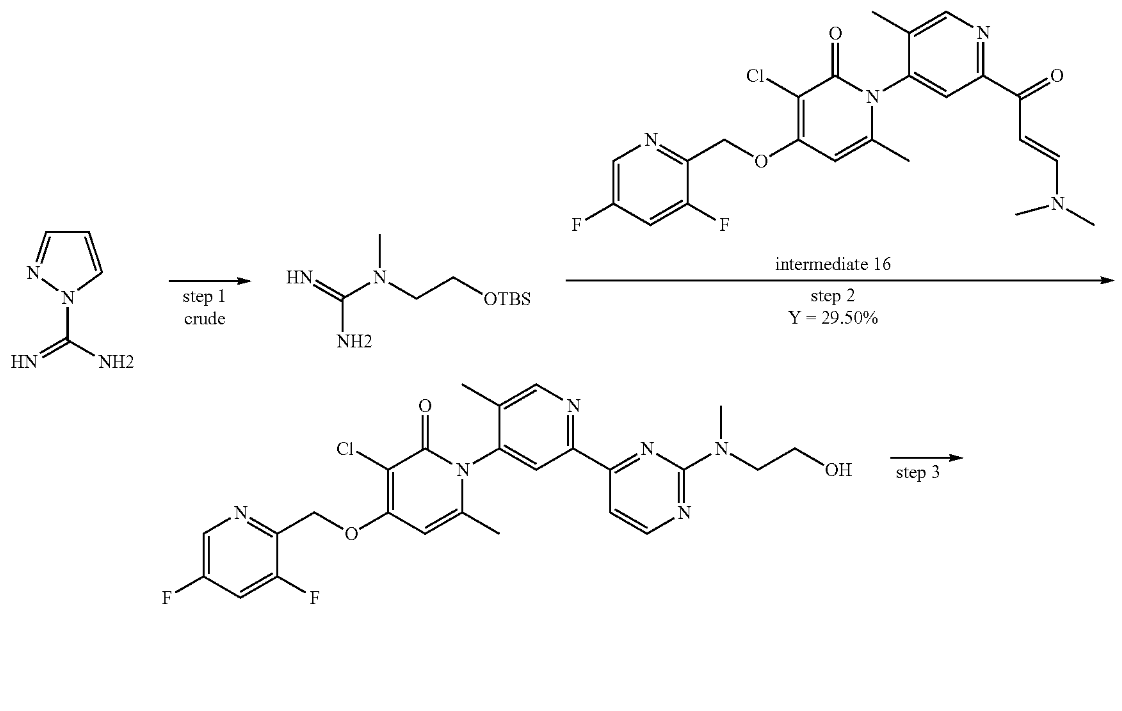

-continued

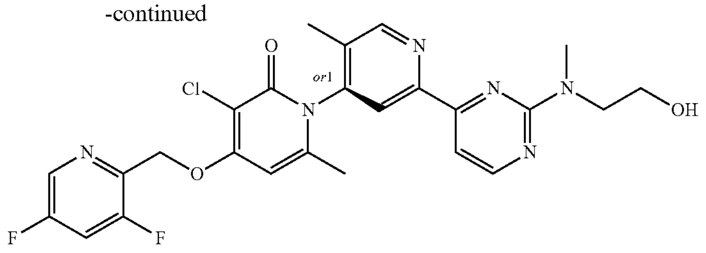

isomer 1
Example 43A

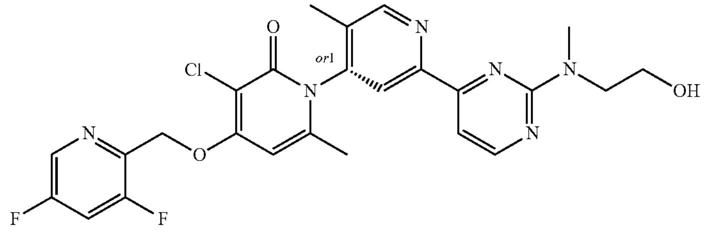

isomer 2
Example 43B

Step 1: Preparation of N-{2-[(tert-butyldimethylsilyl)oxy]ethyl}-N-methylguanidine To a mixture of pyrazole-1-carboximidamide (1.00 g, 9.08 mmol, 1.00 equiv) and {2-[(tert-butyldimethylsilyl) oxy Jethyl}(methyl) amine (1.72 g, 9.08 mmol, 1.00 equiv) in MeCN(15 mL) was added TEA (2.76 g, 27.24 mmol, 3.00 equiv) at room temperature. The resulting mixture was stirred overnight at 60° C., under nitrogen atmosphere. The mixture was allowed to cool down to room temperature. The reaction was monitored by LCMS. The resulting mixture was concentrated under reduced pressure. The crude product was used in the next step directly without further purification. LC-MS: (ES+H, m/z): $[M+H]^+$=232.1.

Step 2: Preparation of 3-chloro-4-[(3,5-difluoropyridin-2-yl)methoxy]-2'-{2-[(2-hydroxyethyl) (methyl) amino]pyrimidin-4-yl}-5',6-dimethyl-[1,4'-bipyridin]-2-one To a solution of N-{2-[(tert-butyldimethylsilyl)oxy] ethyl}-N-methylguanidine (682 mg, 2.94 mmol, 2.00 equiv) and 3-chloro-4-[(3,5-difluoropyridin-2-yl)methoxy]-2'-[(2E)-3-(dimethylamino) prop-2-enoyl]-5',6-dimethyl-[1,4'-bipyridin]-2-one (700 mg, 1,47 mmol, 1.00 equiv) in IPA (15 mL) was added $K_2CO_3$ (2037 mg, 14.74 mmol, 10.00 equiv) at room temperature. The resulting mixture was stirred overnight at 80° C., under nitrogen atmosphere. The mixture was allowed to cool down to room temperature. The reaction was monitored by LCMS. The reaction was poured into water (300 ml), extracted with $CH_2Cl_2$ (3×300 mL). The combined organic layers were dried over anhydrous $Na_2SO_4$. After filtration, the filtrate was concentrated under reduced pressure. The residue was purified by reverse flash chromatography to afford 3-chloro-4-[(3,5-difluoropyridin-2-yl)methoxy]-2'-{2-[(2-hydroxyethyl) (methyl) amino] pyrimidin-4-yl}-5',6-dimethyl-[1,4'-bipyridin]-2-one (230 mg, 29.50%) as a white solid. LC-MS: (ES+H, m/z): $[M+H]^+$ =529.2.

Step 3: Preparation of rel-3-chloro-4-[(3,5-difluoropyridin-2-yl)methoxy]-2'-{2-[(2-hydroxyethyl) (methyl) amino]pyrimidin-4-yl}-5',6-dimethyl-[1,4'-bipyridin]-2-one (Example 43A) and rel-3-chloro-4-[(3,5-difluoropyridin-2-yl)methoxy]-2'-{2-[(2-hydroxyethyl) (methyl) amino] pyrimidin-4-yl}-5',6-dimethyl-[1,4'-bipyridin]-2-one (Example 43B)

The racemate 3-chloro-4-[(3,5-difluoropyridin-2-yl) methoxy]-2'-{2-[(2-hydroxyethyl) (methyl) amino] pyrimidin-4-yl}-5',6-dimethyl-[1,4'-bipyridin]-2-one (230 mg) was separated by Prep-Chiral-SFC to afford rel-3-chloro-4-[(3,5-difluoropyridin-2-yl)methoxy]-2'-{2-[(2-hydroxyethyl) (methyl) amino] pyrimidin-4-yl}-5',6-dimethyl-[1,4'-bipyridin]-2-one (Example 43A, 90.1 mg, ee=100.00%) as a white solid and rel-3-chloro-4-[(3,5-difluoropyridin-2-yl) methoxy]-2'-{2-[(2-hydroxyethyl) (methyl) amino] pyrimidin-4-yl}-5',6-dimethyl-[1,4'-bipyridin]-2-one (Example 43B, 83.3 mg, ee=99.58%) as a white solid.

EXAMPLE 43A

LC-MS: (ES+H, m/z): $[M+H]^+$=529.1. $^1$H NMR (300 MHz, DMSO-$d_6$) δ 8.81 (s, 1H), 8.66-8.58 (m, 1H), 8.55-8.47 (m, 1H), 8.25 (s, 1H), 8.17-8.05 (m, 1H), 7.50 (d, 1H), 6.83 (s, 1H), 5.49 (s, 2H), 5.03-4.37 (br, 1H), 3.86-3.68 (m, 2H), 3.66-3.58 (m, 2H), 3.22 (s, 3H), 2.07 (s, 3H), 1.96 (s, 3H), 19F NMR (377 MHz, DMSO) δ-120.109,-120.134,-122.296,-122.322.

EXAMPLE 43B

LC-MS: (ES+H, m/z): $[M+H]^+$=529.1. $^1$H NMR (300 MHz, DMSO-$d_6$) δ 8.81 (s, 1H), 8.65-8.58 (m, 1H), 8.55-8.48 (m, 1H), 8.25 (s, 1H), 8.17-8.03 (m, 1H), 7.50 (d, 1H), 6.83 (s, 1H), 5.49 (s, 2H), 4.69 (br, 1H), 3.85-3.69 (m, 2H), 3.66-3.56 (m, 2H), 3.22 (s, 3H), 2.07 (s, 3H), 1.96 (s, 3H). $^{19}$F NMR (377 MHz, DMSO) δ-120.104,-120.130,-122.287,-122.312.

EXAMPLE 44A, 44B
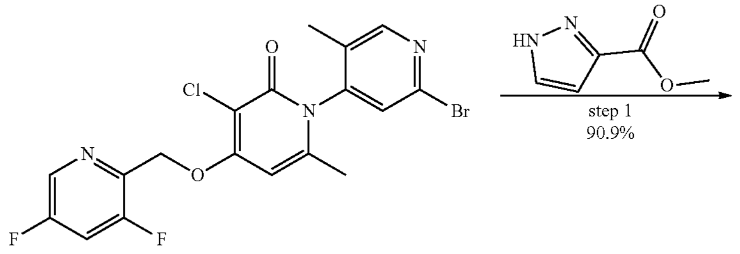
intermediate 10
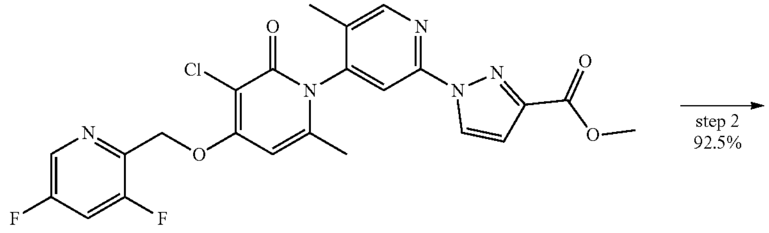
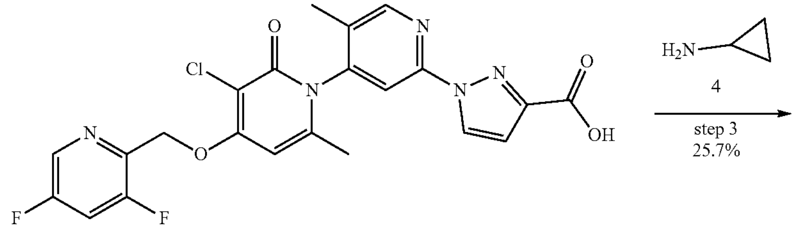
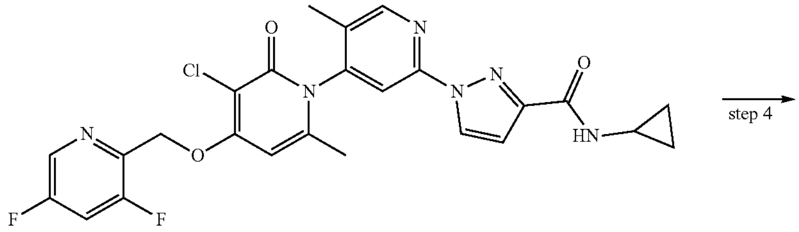
Example 44
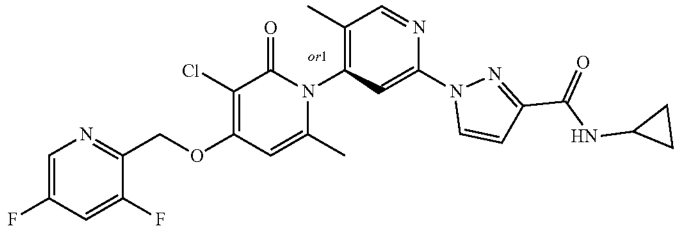
isomer 1
Example 44A
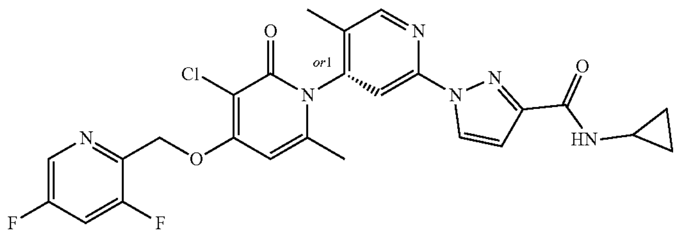
isomer 2
Example 44B Step 1: Preparation of methyl 1-{3-chloro-4-[(3,5-difluoropyridin-2-yl)methoxy]-5',6-dimethyl-2-oxo-[1,4'-bipyridin]-2'-yl}pyrazole-3-carboxylate To a stirred mixture of 2'-bromo-3-chloro-4-[(3,5-difluoropyridin-2-yl)methoxy]-5',6-dimethyl-[1,4'-bipyridin]-2-one (1.00 g, 2.19 mmol, 1.00 equiv) and methyl 1H-pyrazole-3-carboxylate (552 mg, 4.38 mmol, 2.00 equiv) in 1,4-dioxane (20 ml) were added CuI (83 mg, 0.43 mmol, 0.20 equiv), $K_2CO_3$ (605 mg, 4.38 mmol, 2.00 equiv) and N1,N2-dimethylcyclohexane-1,2-diamine (124 mg, 0.87 mmol, 0.40 equiv). The resulting mixture was stirred for 3 h at 90° C., under nitrogen atmosphere. The reaction was monitored by LCMS. The mixture was allowed to cool down to room atmosphere. The residue was purified by silica gel column chromatography to afford methyl 1-{3-chloro-4-[(3,5-difluoropyridin-2-yl)methoxy]-5',6-dimethyl-2-oxo-[1,4'-bipyridin]-2'-yl}pyrazole-3-carboxylate (1.00 g, 90.9%) as a white solid. LC-MS: (ES+H, m/z): $[M+H]^+$=502.1.

Step 2: Preparation of 1-{3-chloro-4-[(3,5-difluoropyridin-2-yl)methoxy]-5',6-dimethyl-2-oxo-[1,4'-bipyridin]-2'-yl}pyrazole-3-carboxylic acid A solution of methyl 1-{3-chloro-4-[(3.5-difluoropyridin-2-yl)methoxy]-5'0.6-dimethyl-2-oxo-[1,4'-bipyridin]-2'-yl}pyrazole-3-carboxylate (1.00 g. 1.99 mmol. 1.00 equiv) and LiOH (47 mg, 1.99 mmol. 1.00 equiv) in THF (6 mL) and $H_2O$ (6 mL) was stirred for 2 h at room temperature under nitrogen atmosphere. The reaction was monitored by LCMS. The resulting mixture was concentrated under reduced pressure to afford crude product (Li salt) 1-{3-chloro-4-[(3.5-difluoropyridin-2-yl)methoxy]-5'0.6-dimethyl-2-oxo-[1,4'-bipyridin]-2'-yl}pyrazole-3-carboxylic acid (0.90 g. 92.50%) as a white solid. LC-MS: (ES+H, m/z): $[M+H]^+$=488.0.

Step 3: Preparation of 1-{3-chloro-4-[(3,5-difluoropyridin-2-yl)methoxy]-5',6-dimethyl-2-oxo-[1,4'-bipyridin]-2'-yl}-N-cyclopropylpyrazole-3-carboxamide A mixture of 1-{3-chloro-4-[(3.5-difluoropyridin-2-yl)methoxy]-5'0.6-dimethyl-2-oxo-[1,4'-bipyridin]-2'-yl}pyrazole-3-carboxylic acid (900 mg, 1.84 mmol. 1.00 equiv), HATU (2.10 g. 5.53 mmol. 3.00 equiv). DIEA (1.19 g. 9.22 mmol. 5.00 equiv) in DMF (30 ml) was stirred for 15 min, then aminocyclopropane (105 mg, 1.84 mmol. 1.00 equiv) was added and the resulting mixture was stirred for additional 2 h at 80° C. The reaction was monitored by LCMS. The reaction was poured into water (300 mL) at room temperature. The resulting mixture was extracted with EtOAc (3×100 mL). The combined organic layers were washed with brine (5×300 mL), the filtrate was concentrated under reduced pressure. The residue was purified by PREP-HPLC. This resulted in 1-{3-chloro-4-[(3.5-difluoropyridin-2-yl)methoxy]-5'0.6-dimethyl-2-oxo-[1,4'-bipyridin]-2'-yl}-N-cyclopropylpyrazole-3-carboxamide (250 mg. 25.70%) as a white solid. LC-MS: (ES+H, m/z): $[M+H]^+$=527.1

Step 4: Preparation of rel-1-{3-chloro-4-[(3,5-difluoropyridin-2-yl)methoxy]-5',6-dimethyl-2-oxo-[1,4'-bipyridin]-2'-yl}-N-cyclopropylpyrazole-3-carboxamide and rel-1-{3-chloro-4-[(3,5-difluoropyridin-2-yl)methoxy]-5',6-dimethyl-2-oxo-[1,4'-bipyridin]-2'-yl}-N-cyclopropylpyrazole-3-carboxamide 1-{3-chloro-4-[(3.5-difluoropyridin-2-yl)methoxy]-5'0.6-dimethyl-2-oxo-[1,4'-bipyridin]-2'-yl}-N-cyclopropylpyrazole-3-carboxamide (200 mg) was separated by prep-chiral-HPLC to afford Example 44A (88.0 mg, ee=100.0%) and Example 44B (69.6 mg, ee=100.0%) as a white solid.

EXAMPLE 44A

LC-MS: (ES+H, m/z): $[M+H]^+$=527.05. $^1H$ NMR (300 MHz. DMSO-$d_6$) δ 8.68 (d, 1H), 8.65-8.58 (m, 2H), 8.38 (d, 1H), 8.11 (m, 1H), 8.00 (s, 1H), 6.91 (d, 1H), 6.85 (s, 1H), 5.51 (s, 2H), 2.83 (m. 1H), 2.06 (s, 3H), 2.02 (s, 3H), 0.75-0.61 (m, 2H), 0.64-0.56 (m, 2H), $^{19}F$ NMR (282 MHz. DMSO) δ-120.17, —120.20, -122.35, -122.37.

EXAMPLE 44B

LC-MS: (ES+H, m/z): $[M+H]^+$=527.05. $^1H$ NMR (300 MHz. DMSO-$d_6$) δ 8.68 (d, 1H), 8.65-8.58 (m, 2H), 8.38 (d, 1H), 8.16-8.04 (m, 1H), 8.00 (s.1H), 6.91 (d, 1H), 6.85 (s, 1H), 5.51 (s, 2H), 2.83 (m. 1H), 2.06 (s, 3H), 2.02 (s, 3H), 0.75-0.63 (m, 2H), 0.64-0.56 (m, 2H). $^{19}F$ NMR (282 MHz. DMSO) δ-120.17, -120.20, -122.34, -122.37.

EXAMPLE 45A, 45B

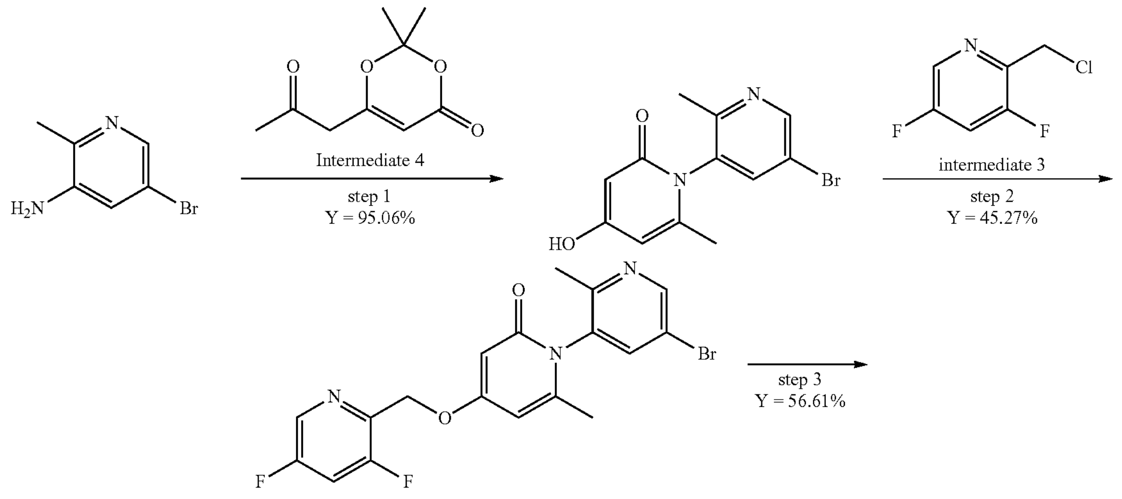

-continued
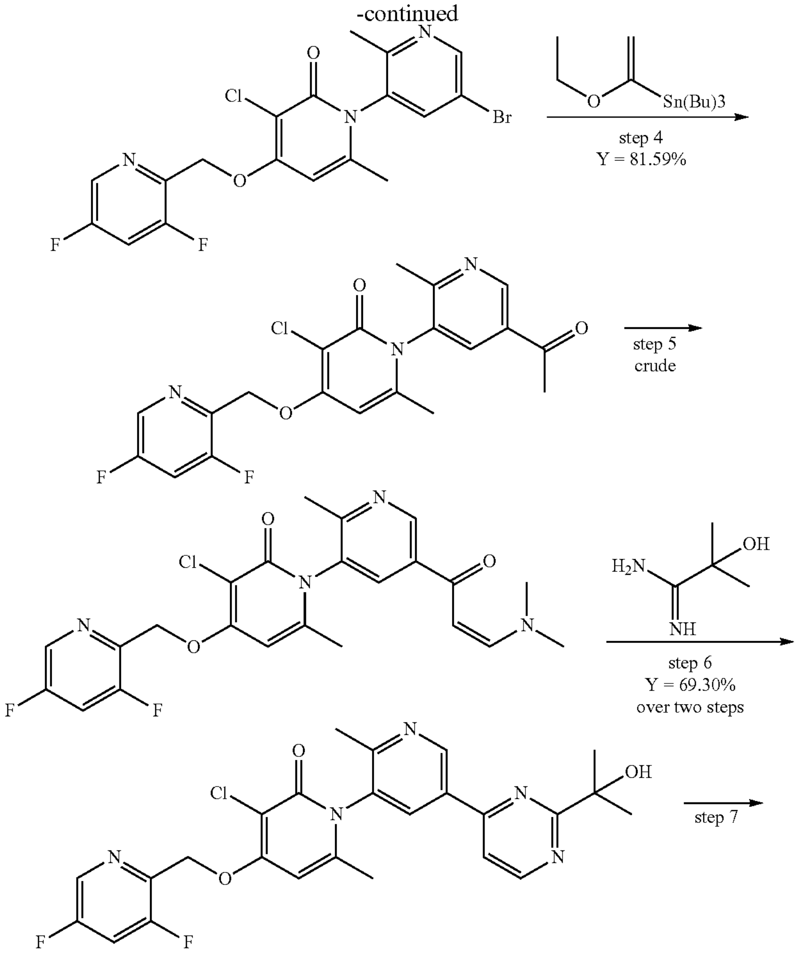
Example 45
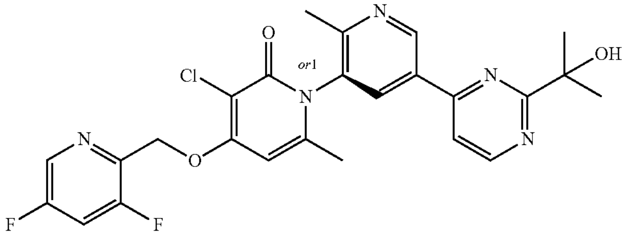
isomer 1
Example 45A
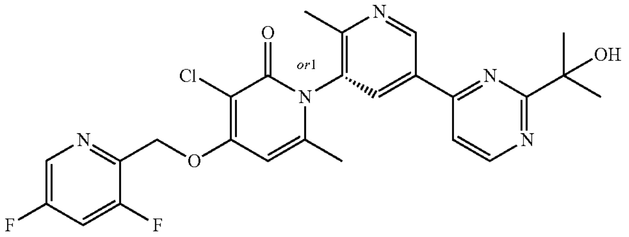
isomer 2
Example 45B Step 1: Preparation of 5'-bromo-4-hydroxy-2',6-dimethyl-[1,3'-bipyridin]-2-one A solution of 5-bromo-2-methylpyridin-3-amine (10.00 g, 53.46 mmol, 1.00 equiv) and 2,2-dimethyl-6-(2-oxopropyl)-1,3-dioxin-4-one (19.70 g, 106.92 mmol, 2.00 equiv) in 1,4-dioxane (100 mL) was stirred for 2 h at 80° C., under nitrogen atmosphere. To the above mixture was added $H_2SO_4$ (3.99 mL, 74.85 mmol, 1,40 equiv) dropwise at 0° C. The resulting mixture was stirred for another 2 h at 80° C., under nitrogen atmosphere. The reaction was monitored by LCMS. The mixture was allowed to r.t. The resulting mixture was concentrated under reduced pressure. The residue was dissolved in water (50 mL) and Et.O (100 mL). The precipitated solids were collected by filtration and washed with Et.O (3×10 mL), to afford 5'-bromo-4-hydroxy-2',6-dimethyl-[1,3'-bipyridin]-2-one (15.00 g, 95.06%) as a white solid. LC-MS: (ES+H, m/z): $[M+H]^+$=294.9.

Step 2: Preparation of 5'-bromo-4-[(3,5-difluoropyridin-2-yl)methoxy]-2',6-dimethyl-[1,3'-bipyridin]-2-one To a stirred solution of 5'-bromo-4-hydroxy-2',6-dimethyl-[1,3'-bipyridin]-2-one (5.40 g, 18.29 mmol, 1.00 equiv) and 2-(chloromethyl)-3,5-difluoropyridine (5.98 g, 36.59 mmol, 2.00 equiv) in DMF (100 mL) was added $K_2CO_3$ (10.00 g, 73.18 mmol, 4.00 equiv) and 18-Crown-6 (1,45 g, 5.48 mmol, 0.30 equiv) at room temperature under nitrogen atmosphere. The resulting mixture was stirred for 6 h at 60° C., under nitrogen atmosphere. The reaction was monitored by LCMS. The mixture was allowed to r.t. The reaction was quenched with sat. $NH_4Cl$ (aq.) at room temperature. The aqueous layer was extracted with EtOAc (3×300 mL). The residue was purified by silica gel column chromatography to afford 5'-bromo-4-[(3,5-difluoropyridin-2-yl)methoxy]-2',6-dimethyl-[1,3'-bipyridin]-2-one (4.30 g, 55.66%) as a light yellow solid. LC-MS: (ES+H, m/z): $[M+H]^+$=422.0.

Step 3: Preparation of 2-propanol (3×3 mL) to afford 5'-bromo-3-chloro-4-[(3,5-difluoropyridin-2-yl)methoxy]-2',6-dimethyl-[1,3'-bipyridin]-2-one To a stirred solution of 5'-bromo-4-[(3.5-difluoropyridin-2-yl)methoxy]-2'0.6-dimethyl-[1,3'-bipyridin]-2-one (4.90 g. 11.60 mmol. 1.00 equiv) and NCS (1.55 g. 11.60 mmol. 1.00 equiv) in IPA (25 mL) was added 2.2-dichloroacetic acid (0.45 g. 3.48 mmol. 0.30 equiv) at room temperature under nitrogen atmosphere. The resulting mixture was stirred for 2 h at 60° C., under nitrogen atmosphere. The precipitated solids were collected by filtration and washed with 2-propanol (3×3 mL) to afford 5'-bromo-3-chloro-4-[(3.5-difluoropyridin-2-yl)methoxy]-2'0.6-dimethyl-[1,3'-bipyridin]-2-one (3.00 g. 56.61%) as a white solid. LC-MS: (ES+H, m/z): $[M+H]^+$=457.9. $^1$H NMR (300 MHz. DMSO-$d_6$) δ 8.73 (d, 1H), 8.60 (d, 1H), 8.19 (d. J=2.2 Hz, 1H), 8.15-8.02 (m, 1H), 6.80 (d, 1H), 5.48 (d, 2H), 2.15 (s, 3H), 1.96 (s, 3H).

Step 4: Preparation of 5'-acetyl-3-chloro-4-[(3,5-difluoropyridin-2-yl)methoxy]-2',6-dimethyl-[1,3'-bipyridin]-2-one To a stirred mixture of 5'-bromo-3-chloro-4-[(3.5-difluoropyridin-2-yl)methoxy]-2'0.6-dimethyl-[1,3'-bipyridin]-2-one (2.40 g. 5.25 mmol. 1.00 equiv) and tributyl (1-ethoxyethenyl) stannane (3.80 g. 10.51 mmol. 2.00 equiv) in 1,4-dioxane (10 ml) was added Pd(PPh;): $C_1$:(0.74 g. 1.05 mmol. 0.20 equiv) at room temperature. The resulting mixture was stirred overnight at 120° C., under nitrogen atmosphere. The mixture was allowed to cool down to r.t . . . . The resulting mixture was filtered, the filter cake was washed with EA (3×30 mL). The filtrate was concentrated under reduced pressure. The resulting mixture was dissolved in THF (20 mL). To the above mixture was added HCl (2 mL) dropwise at 0° C. The resulting mixture was stirred for additional 1 h at room temperature. The residue was basified to pH 9 with saturated $NaHCO_3$(aq.). The resulting mixture was extracted with EtOAc (3×200 mL). The combined organic layers were washed with brine (1×100 mL), dried over anhydrous $Na_2SO_4$. After filtration, the filtrate was concentrated under reduced pressure. The residue was purified by silica gel column chromatography to afford 5'-acetyl-3-chloro-4-[(3.5-difluoropyridin-2-yl)methoxy]-2'0.6-dimethyl-[1,3'-bipyridin]-2-one (1.80 g. 81.59%) as a yellow oil. LC-MS: (ES+H, m/z): $[M+H]^+$=420.1. $^1$H NMR (300 MHz. DMSO-$d_6$) δ 9.09 (d, 1H), 8.61 (d. 1H), 8.27 (d, 1H), 8.15-7.95 (m, 1H), 6.82 (s, 1H), 5.49 (d, 2H), 2.64 (s, 3H), 2.27 (s, 3H), 1.95 (s, 3H). Step 5: Preparation of 3-chloro-4-[(3,5-difluoropyridin-2-yl)methoxy]-5'-[(2Z)-3-(dimethylamino) prop-2-enoyl]-2',6-dimethyl-[1,3'-bipyridin]-2-one Into a 250 mL round-bottom flask were added 5'-acetyl-3-chloro-4-[(3.5-difluoropyridin-2-yl) methoxy]-2'0.6-dimethyl-[1,3'-bipyridin]-2-one (1.80 g. 4.28 mmol. 1.00 equiv) and DMF-DMA (30 mL) at room temperature. The resulting mixture was stirred overnight at 80° C. The mixture was allowed to cool down to r.t . . . . The resulting mixture was concentrated under vacuum to afford 3-chloro-4-[(3.5-difluoropyridin-2-yl)methoxy]-5'-[(2Z)-3-(dimethylamino) prop-2-enoyl]-2'0.6-dimethyl-[1,3'-bipyridin]-2-one (crude) as a yellow solid. The crude product was used in the next step directly without further purification. LC-MS: (ES+H, m/z): $[M+H]^+$=475.0.

Step 6: Preparation of 3-chloro-4-[(3,5-difluoropyridin-2-yl)methoxy]-5'-[2-(2-hydroxypropan-2-yl) pyrimidin-4-yl]-2',6-dimethyl-[1,3'-bipyridin]-2-one To a stirred mixture of 3-chloro-4-[(3.5-difluoropyridin-2-yl)methoxy]-5'-[(2Z)-3-(dimethylamino) prop-2-enoyl]-2'0.6-dimethyl-[1,3'-bipyridin]-2-one (1.00 g. 2.10 mmol. 1.00 equiv) and $K_2CO_3$ (1.74 g, 12.63 mmol, 6.00 equiv) in 2-propanol (20 ml) were added 2-hydroxy-2-methylpropanimidamide (1.08 g, 10.53 mmol, 5.00 equiv) at room temperature under air atmosphere. The resulting mixture was stirred for 12 h at 80° C. The mixture was allowed to cool down to r.t, and then poured into water (200 mL). The resulting mixture was extracted with EtOAc (3×300 mL). The combined organic layers were washed with brine (300 mL), dried over anhydrous $Na_2SO_4$. After filtration, the filtrate was concentrated under reduced pressure. The residue was purified by silica gel column chromatography to afford 3-chloro-4-[(3,5-difluoropyridin-2-yl)methoxy]-5'-[2-(2-hydroxypropan-2-yl)pyrimidin-4-yl]-2',6-dimethyl-[1,3'-bipyridin]-2-one (750 mg, 69.30%) as a yellow solid. LC-MS: (ES+H, m/z): $[M+H]^+$=514.4. Step 7: Preparation of rel-3-chloro-4-[(3,5-difluoropyridin-2-yl)methoxy]-5'-[2-(2-hydroxypropan-2-yl)pyrimidin-4-yl]-2',6-dimethyl-[1,3'-bipyridin]-2-one and rel-3-chloro-4-[(3,5-difluoropyridin-2-yl)methoxy]-5'-[2-(2-hydroxypropan-2-yl)pyrimidin-4-yl]-2',6-dimethyl-[1,3'-bipyridin]-2-one The race-mixture (750 mg) was isolated by PREP-CHIRAL-HPLC to afford rel-3-chloro-4-[(3,5-difluoropyridin-2-yl)methoxy]-5'-[2-(2-hydroxypropan-2-yl)pyrimidin-4-yl]-2',6-dimethyl-[1,3'-bipyridin]-2-one (Example 45A: 260.7 mg, ee=100%) as a yellow solid, and rel-3-chloro-4-[(3,5-difluoropyridin-2-yl)methoxy]-5'-[2-(2-hydroxypropan-2-yl)pyrimidin-4-yl]-2', 6-dimethyl-[1,3'-bipyridin]-2-one (Example 45B: 286.4 mg, ee=100%) as a yellow solid.

EXAMPLE 45A

LC-MS: (ES+H, m/z): $[M+H]^+$=514.00. $^1$H NMR (300 MHz, DMSO-$d_6$) δ 9.48 (d, 1H), 8.93 (d, 1H), 8.73 (d, 1H), 8.62 (d, 1H), 8.16-8.11 (m, 1H), 8.09 (s, 1H), 6.85 (d, 1H), 5.51 (d, 2H), 5.23 (s, 1H), 2.29 (s, 3H), 1.99 (s, 3H), 1.55 (s, 3H), 1.54 (s, 3H). $^{19}$F NMR (282 MHz, DMSO) δ-120.14,-120.16,-122.34,-122.36.

EXAMPLE 45B

LC-MS: (ES+H, m/z): $[M+H]^+$=514.20. $^1$H NMR (300 MHz, DMSO-$d_6$) δ 9.48 (d, 1H), 8.93 (d, 1H), 8.73 (d, 1H), 8.62 (d, 1H), 8.15-8.10 (m, 1H), 8.09 (d, 1H), 6.85 (d, 1H), 5.51 (d, 2H), 5.23 (s, 1H), 2.29 (s, 3H), 1.99 (s, 3H), 1.55 (s, 3H), 1.54 (s, 3H). $^{19}$F NMR (282 MHz, DMSO) δ-120.14,-120.16,-122.34,-122.36.

EXAMPLE 46A, 46B

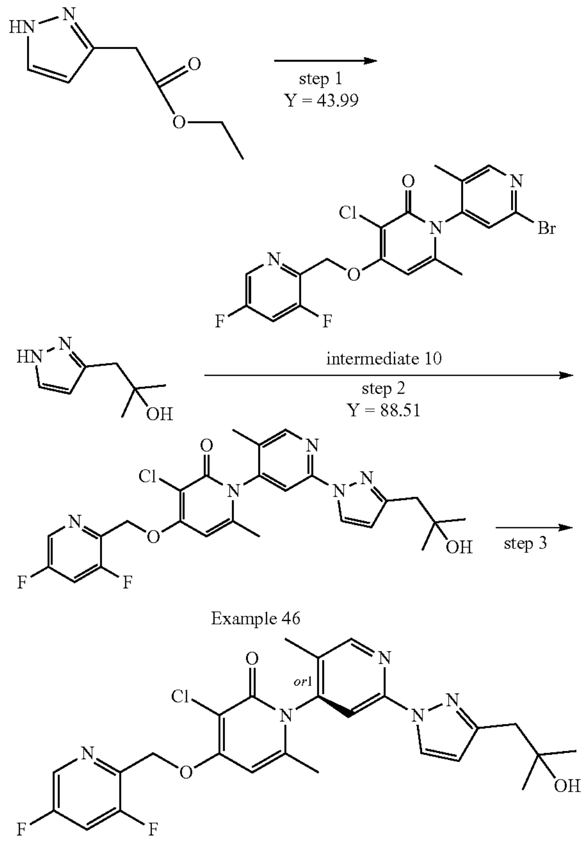

Example 46 isomer 1
Example 46A

-continued

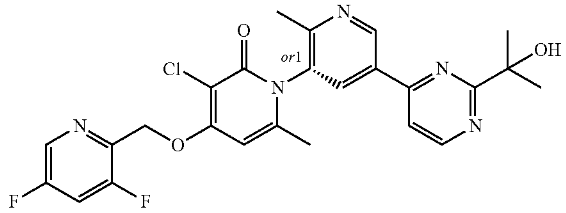

isomer 2
Example 46B

Step 1: Preparation of 2-methyl-1-(1H-pyrazol-3-yl) propan-2-ol

To a stirred solution of ethyl 2-(1H-pyrazol-3-yl)acetate (1.50 g. 9.73 mmol. 1.00 equiv) in THF (15 mL) was added MeMgBr in THF (22.70 mL. 68.11 mmol. 7.00 equiv) dropwise at −5° C., under nitrogen atmosphere. The resulting mixture was stirred for 2 h at 0° C., under nitrogen atmosphere. The reaction was monitored by LCMS. The reaction was quenched with sat. $NH_4Cl$ (aq.) at room temperature. The resulting mixture was extracted with EtOAc (7×10 mL). The combined organic layers were dried over anhydrous $Na_2SO_4$. After filtration, the filtrate was concentrated under reduced pressure. The residue was purified by silica gel column chromatography to afford 2-methyl-1-(1H-pyrazol-3-yl) propan-2-ol (600 mg. 43.99%) as a yellow oil. LC-MS: (ES+H, m/z): $[M+H]^+$=141.3.

Step 2: Preparation of 3-chloro-4-[(3,5-difluoropyridin-2-yl)methoxy]-2'-[3-(2-hydroxy-2-methylpropyl) pyrazol-1-yl]-5',6-dimethyl-[1,4'-bipyridin]-2-one To a stirred solution of 2'-bromo-3-chloro-4-[(3.5-difluoropyridin-2-yl)methoxy]-5'0.6-dimethyl-[1,4'-bipyridin]-2-one (500 mg, 1.09 mmol. 1.00 equiv), 2-methyl-1-(1H-pyrazol-3-yl) propan-2-ol (230 mg. 1.64 mmol. 1.50 equiv) and (IR.2R)-N1.N2-dimethylcyclohexane-1.2-diamine (311 mg. 2.19 mmol. 2.00 equiv) in dioxane (7 mL) were added CuI (417 mg. 2.19 mmol. 2.00 equiv) and $K_2CO_3$ (302 mg. 2.19 mmol. 2.00 equiv) at room temperature under nitrogen atmosphere. The resulting mixture was stirred overnight at 80° C., under nitrogen atmosphere. The mixture was allowed to cool down to room temperature. The reaction was monitored by LCMS. The reaction was quenched with sat. $NH_4Cl$ (aq.) at room temperature. The resulting mixture was extracted with EtOAc (3×30 mL). The combined organic layers were washed with brine (1×30 mL), dried over anhydrous $Na_2SO_4$. After filtration, the filtrate was concentrated under reduced pressure. The residue was purified by silica gel column chromatography to afford 3-chloro-4-[(3.5-difluoropyridin-2-yl)methoxy]-2'-[3-(2-hydroxy-2-methylpropyl)pyrazol-1-yl]-5'0.6-dimethyl-[1,4'-bipyridin]-2-one (500 mg. 88.51%) as a white solid. LC-MS: (ES+H, m/z): $[M+H]^+$=516.2. $^1$H NMR (400 MHz. DMSO-$d_6$) δ 8.60 (d, 1H), 8.54 (t. 1H), 8.51 (d, 1H), 8.10 (m. 1H), 7.77 (s.1H), 6.80 (d. 1H), 6.45 (d. 1H), 5.48 (d, 2H), 4.43 (s, 1H), 2.72 (s, 2H), 2.01 (s, 3H), 2.00 (s, 3H), 1.14 (s, 3H), 1.12 (s, 3H).

Step 3: Preparation of rel-3-chloro-4-[(3,5-difluoropyridin-2-yl)methoxy]-2'-[3-(2-hydroxy-2-methylpropyl)pyrazol-1-yl]-5',6-dimethyl-[1,4'-bipyridin]-2-one and rel-3-chloro-4-[(3,5-difluoropyridin-2-yl)methoxy]-2'-[3-(2-hydroxy-2-methylpropyl)pyrazol-1-yl]-5',6-dimethyl-[1,4'-bipyridin]-2-one The 3-chloro-4-[(3.5-difluoropyridin-2-yl)methoxy]-2'-[3-(2-hydroxy-2-methylpropyl)pyrazol-1-yl]-5'0.6-dimethyl-[1,4'-bipyridin]-2-one (500 mg, 0.996 mmol. I equiv) was isolated by PREP-HPLC to afford rel-3-chloro-4-[(3.5-difluoropyridin-2-yl)methoxy]-2'-[3-(2-hydroxy-2-methylpropyl)pyrazol-1-yl]-5'0.6-dimethyl-] 1,4'-bipyridin]-2-one (Example 46A) (208.1 mg. 97.7% purity, ce=100%) and rel-3-chloro-4-[(3.5-difluoropyridin-2-yl)methoxy]-2'-[3-(2-hydroxy-2-methylpropyl)pyrazol-1-yl]-5'0.6-dimethyl-] 1,4'-bipyridin]-2-one (Example 46B) (243.4 mg. 96.9% purity, ce=100%) as a white solid.

EXAMPLE 46A

LC-MS: (ES+H, m/z): $[M+H]^+$=516.05. $^1H$ NMR (400 MHZ. DMSO-$d_6$) δ 8.60 (d, 1H), 8.54 (t. 1H), 8.51 (d, 1H), 8.10 (m. 1H), 7.77 (s, 1H), 6.80 (d, 1H), 6.45 (d, 1H), 5.48 (d, 2H), 4.43 (s, 1H), 2.72 (s, 2H), 2.01 (s, 3H), 2.00 (s, 3H), 1.14 (s, 3H), 1.12 (s, 3H). $^{19}F$ NMR (377 MHz, DMSO) δ-120.15,-120.17,-122.35,-122.37.

EXAMPLE 46B

LC-MS: (ES+H, m/z): $[M+H]^+$=516.00. $^1H$ NMR (400 MHZ, DMSO-$d_6$) δ 8.60 (d, 1H), 8.54 (t, 1H), 8.51 (d, 1H), 8.10 (m, 1H), 7.77 (s, 1H), 6.80 (d, 1H), 6.45 (d, 1H), 5.48 (d, 2H), 4.43 (s, 1H), 2.72 (s, 2H), 2.01 (s, 3H), 2.00 (s, 3H), 1.14 (s, 3H), 1.12 (s, 3H). $^{19}F$ NMR (377 MHz, DMSO) δ-120.15,-120.16,-122.35,-122.37.

EXAMPLE 47A, 47B

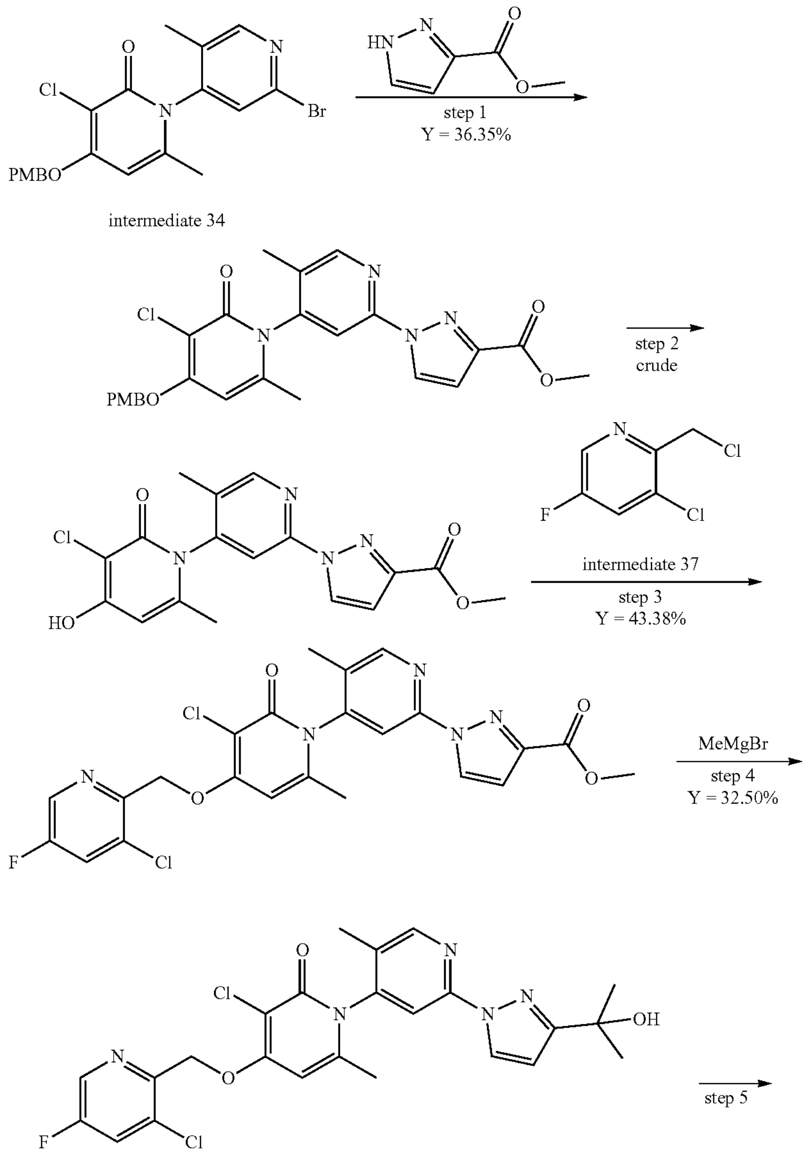

Example 47

-continued

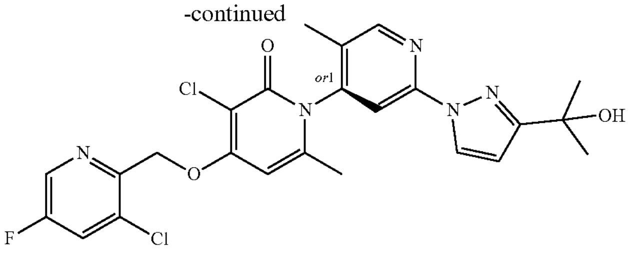

isomer 1
Example 47A

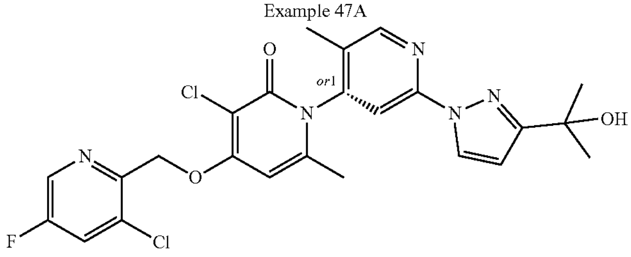

isomer 2
Example 47B

Step 1: Preparation of methyl 1-{3-chloro-4-[(4-methoxyphenyl)methoxy]-5',6-dimethyl-2-oxo-[1,4'-bipyridin]-2'-yl}pyrazole-3-carboxylate To a mixture of 2'-bromo-3-chloro-4-[(4-methoxyphenyl) methoxy]-5',6-dimethyl-[1,4'-bipyridin]-2-one (2.00 g, 4.44 mmol, 1.00 equiv), methyl 1H-pyrazole-3-carboxylate (673 mg, 5.33 mmol, 1.20 equiv), $K_2CO_3$ (1229 mg, 8.89 mmol, 2.00 equiv) and (1S,2S)-N1,$N_2$-dimethylcyclohexane-1,2-diamine (253 mg, 1.77 mmol, 0.40 equiv) in 1,4-dioxane (20 mL) was added CuI (169 mg, 0.88 mmol, 0.20 equiv) at room temperature. The resulting mixture was stirred for 2 h at 80° C., under nitrogen atmosphere. The reaction was monitored by LCMS. The mixture was allowed to cool down to room temperature. The reaction was poured into water (100 ml), then extracted with EtOAc (3×100 mL). The combined organic layers were dried over anhydrous $Na_2SO_4$. After filtration, the filtrate was concentrated under reduced pressure. The residue was purified by silica gel column chromatography to afford methyl 1-{3-chloro-4-[(4-methoxyphenyl)methoxy]-5',6-dimethyl-2-oxo-[1,4'-bipyridin]-2'-yl}pyrazole-3-carboxylate (800 mg, 36.35%) as a white solid. LC-MS: (ES+H, m/z): $[M+H]^+$=495.0. $^1$H NMR (400 MHZ, Chloroform-d) 8 8.59 (d, 1H), 8.45 (s, 1H), 7.92 (s, 1H), 7.42-7.37 (m, 2H), 6.99-6.96 (m, 2H), 6.96-6.94 (m, 1H), 6.15 (s, 1H), 5.23 (s, 2H), 3.95 (s, 3H), 3.85 (s, 3H), 2.14 (s, 3H), 1.98 (s, 3H).

Step 2: Preparation of methyl 1-{3-chloro-4-hydroxy-5',6-dimethyl-2-oxo-[1,4'-bipyridin]-2'-yl}pyrazole-3-carboxylate To a mixture of methyl 1-{3-chloro-4-[(4-methoxyphenyl)methoxy]-5',6-dimethyl-2-oxo-[1,4'-bipyridin]-2'-yl}pyrazole-3-carboxylate (700 mg, 1,41 mmol, 1.00 equiv) in DCM (6.00 mL) was added TFA (2.00 mL) at room temperature. The resulting mixture was stirred for 1 h at room temperature under nitrogen atmosphere. The reaction was monitored by LCMS. The resulting mixture was concentrated under reduced pressure, to afford crude product methyl 1-{3-chloro-4-hydroxy-5',6-dimethyl-2-oxo-[1,4'-bipyridin]-2'-yl}pyrazole-3-carboxylate (1 g, crude) as a yellow oil, which was used in the next step directly without further purification. LC-MS: (ES+H, m/z): $[M+H]^+$=375.2.

Step 3: Preparation of methyl 1-{3-chloro-4-[(3-chloro-5-fluoropyridin-2-yl)methoxy]-5',6-dimethyl-2-oxo-[1,4'-bipyridin]-2'-yl}pyrazole-3-carboxylate To a mixture of methyl 1-{3-chloro-4-hydroxy-5'0.6-dimethyl-2-oxo-[1,4'-bipyridin]-2'-yl}pyrazole-3-carboxylate (1.00 g. 2.66 mmol. 1.00 equiv). K_$CO_3$ (1.11 g. 8.00 mmol. 3.00 equiv) and 3-chloro-2-(chloromethyl)-5-fluoropyridine (0.96 g. 5.32 mmol. 2.00 equiv) in DMF (15.00 mL) was added 18-Crown-6 (0.35 g. 1.33 mmol. 0.50 equiv) at room temperature. The resulting mixture was stirred for 3 h at 60° C., under nitrogen atmosphere. The reaction was monitored by LCMS. Desired product could be detected by LCMS. The reaction was poured into water (200 ml), extracted with EtOAc (3×200 mL). The combined organic layers were dried over anhydrous $Na_2SO_4$. After filtration, the filtrate was concentrated under reduced pressure. The residue was purified by silica gel column chromatography to afford methyl 1-{3-chloro-4-[(3-chloro-5-fluoropyridin-2-yl) methoxy]-5'0.6-dimethyl-2-oxo-[1,4'-bipyridin]-2'-yl}pyrazole-3-carboxylate (600 mg. 43.38%) as a white solid. LC-MS: (ES+H, m/z): $[M+H]^+$=518.1. $^1$H NMR (400 MHz. Chloroform-d) δ 8.59 (d, 1H), 8.46 (s.1H), 8.45 (s.1H), 7.92 (s, 1H), 7.62-7.57 (m. 1H), 6.98 (d. 1H), 6.31 (s, 1H), 5.47 (s, 2H), 3.95 (s, 3H), 2.15 (s, 3H), 2.00 (s, 3H).

Step 4: Preparation of 3-chloro-4-[(3-chloro-5-fluoropyridin-2-yl)methoxy]-2'-[3-(2-hydroxypropan-2-yl)pyrazol-1-yl]-5',6-dimethyl-[1,4'-bipyridin]-2-one To a stirred solution of methyl 1-{3-chloro-4-[(3-chloro-5-fluoropyridin-2-yl)methoxy]-5'0.6-dimethyl-2-oxo-[1,4'-bipyridin]-2'-yl}pyrazole-3-carboxylate (400 mg, 0.77 mmol. 1.00 equiv) in THF (10 mL) was added MeMgBr (2.57 mL. 7.72 mmol. 10.00 equiv) dropwise at 0° C., under nitrogen atmosphere. The resulting mixture was stirred for 1 h at 0° C., under nitrogen atmosphere. The reaction was monitored by LCMS. Desired product could be detected by LCMS. The reaction was quenched with sat. $NH_4Cl$ (aq.) (150 ml) at 0° C. The resulting mixture was extracted with EtOAc (3×150 mL). The combined organic layers were dried over anhydrous $Na_2SO_4$. After filtration, the filtrate was concentrated under reduced pressure. The residue was purified by reverse flash chromatography. The resulting mixture was concentrated under reduced pressure to afford 3-chloro-4-[(3-chloro-5-fluoropyridin-2-yl)methoxy]-2'-[3-(2-hydroxypropan-2-yl)pyrazol-1-yl]-5'0.6-dimethyl-] 1,4'-bipyridin]-2-one (130 mg. 32.50%) as a white solid. LC-MS: (ES+H, m/z): $[M+H]^+$=518.2.

Step 5: Preparation of rel-3-chloro-4-[(3-chloro-5-fluoropyridin-2-yl)methoxy]-2'-[3-(2-hydroxypropan-2-yl)pyrazol-1-yl]-5',6-dimethyl-[1,4'-bipyridin]-2-one and rel-3-chloro-4-[(3-chloro-5-fluoropyridin-2-yl)methoxy]-2'-[3-(2-hydroxypropan-2-yl)pyrazol-1-yl]-5',6-dimethyl-[1,4'-bipyridin]-2-one The racemate 3-chloro-4-[(3-chloro-5-fluoropyridin-2-yl)methoxy]-2'-]3-(2-hydroxypropan-2-yl)pyrazol-1-yl]-5'0.6-dimethyl-[1,4'-bipyridin]-2-one (130 mg) was separated by Prep-Chiral-HPLC to afford rel-3-chloro-4-[(3-chloro-5-fluoropyridin-2-yl)methoxy]-2'-[3-(2-hydroxypropan-2-yl)pyrazol-1-yl]-5'0.6-dimethyl-[1,4'-bipyridin]-2-one (Example 47A, 38.2 mg, ce=100.00%) as a white solid and rel-3-chloro-4-[(3-chloro-5-fluoropyridin-2-yl)methoxy]-2'-[3-(2-hydroxypropan-2-yl)pyrazol-1-yl]-5',6-dimethyl-[1, 4'-bipyridin]-2-one (Example 47B, 36.4 mg, ee=100.00%) as a white solid.

EXAMPLE 47A

LC-MS: (ES+H, m/z): $[M+H]^+$=518.2. $^1H$ NMR (400 MHZ, DMSO-$d_6$) δ 8.68 (d, 1H), 8.54 (s, 1H), 8.51 (d, 1H), 8.29-8.22 (m, 1H), 7.78 (s, 1H), 6.77 (s, 1H), 6.56 (d, 1H), 5.50 (s, 2H), 5.09 (s, 1H), 2.01 (s, 3H), 1.99 (s, 3H), 1,48 (s, 6H). $^{19}F$ NMR (377 MHz, DMSO) δ-124.16,-124.20.

EXAMPLE 47B

LC-MS: (ES+H, m/z): $[M+H]^+$=518.20. $^1H$ NMR (400 MHZ, DMSO-$d_6$) δ 8.68 (d, 1H), 8.54 (s, 1H), 8.51 (d, 1H), 8.30-8.21 (m, 1H), 7.78 (s, 1H), 6.77 (s, 1H), 6.56 (d, 1H), 5.50 (s, 2H), 5.09 (s, 1H), 2.01 (s, 3H), 1.99 (s, 3H), 1,48 (s, 6H). $^{19}F$ NMR (377 MHz, DMSO) δ-124.21.

EXAMPLE 48A, 48B

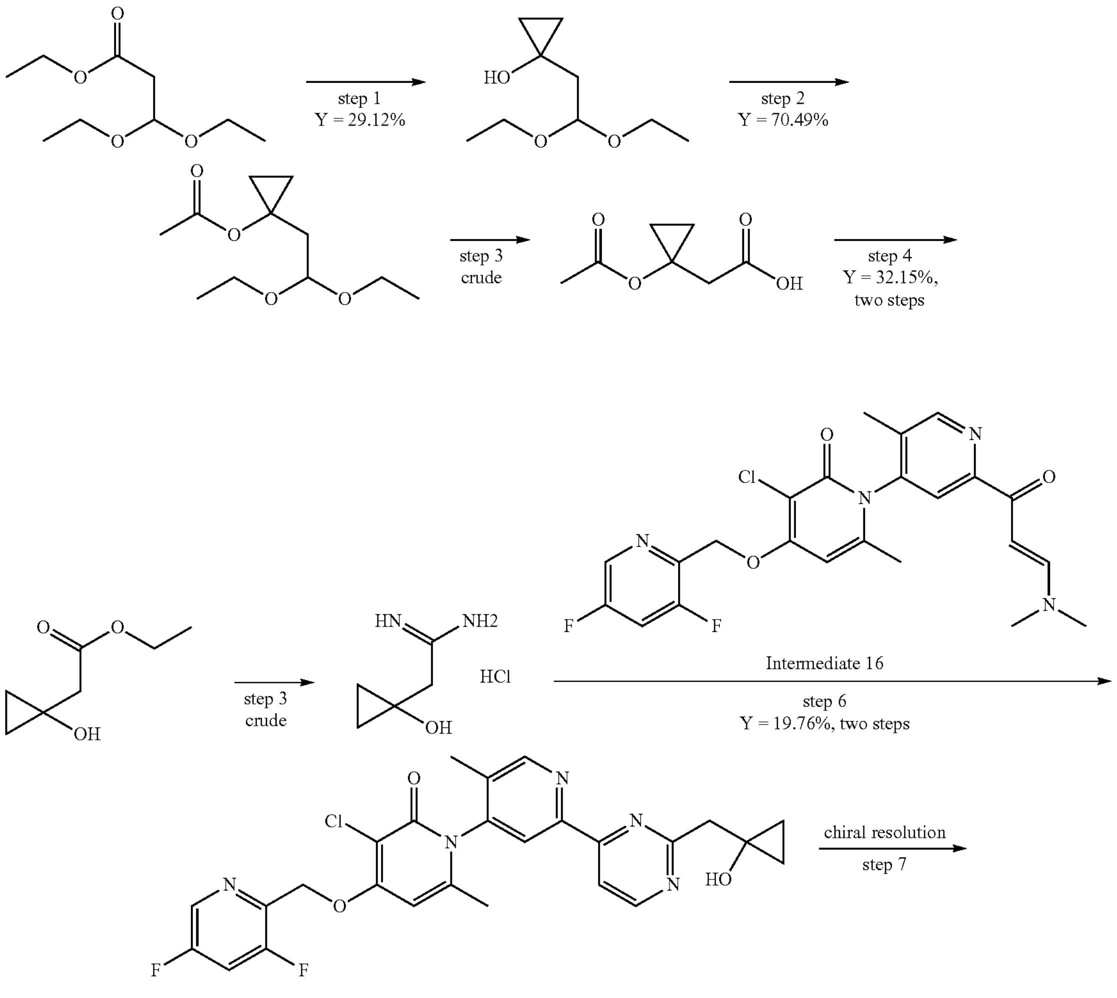

Example 48

-continued

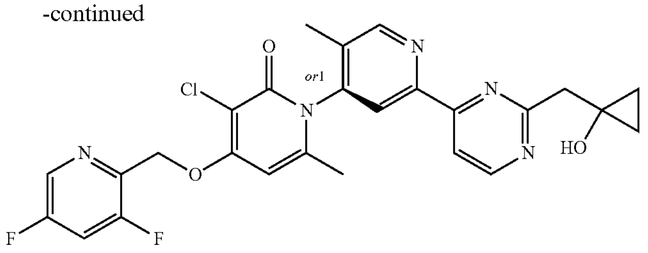

isomer 1
Example 48A

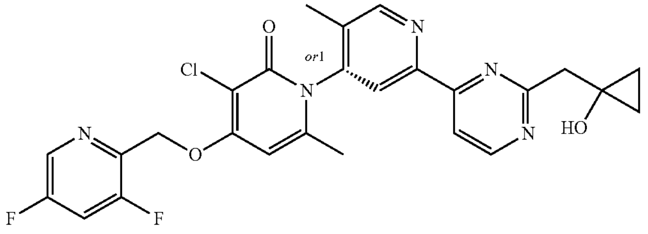

isomer 2
Example 48B

Step 1: Preparation of 1-(2,2-diethoxyethyl)cyclopropan-1-ol

To a stirred mixture of ethyl 3,3-diethoxypropanoate (30.00 g, 157.69 mmol, 1.00 equiv) and Ti (Oi-Pr)+ (67.20 g, 236.54 mmol, 1.50 equiv) in $Et_2O$ (200 mL) and THF (50 mL) was added EtMgBr in 2-methyl-THF (2M, 233.6 mL, 630.784 mmol, 4.00 equiv) dropwise at 0° C., under nitrogen atmosphere. The resulting mixture was stirred overnight at room temperature under nitrogen atmosphere. The reaction was monitored by TLC (PE/EA=7:1, Rf-0.4). The reaction was quenched by the addition of water (400 mL) at 0° C. The resulting mixture was extracted with Et.O (2×500 mL), the organic phase was combined and dried over anhydrous $Na_2SO_4$. After filtration, the filtrate was concentrated under reduced pressure. The residue was purified by silica gel column chromatography, the pure fraction was concentrated under reduced pressure to afford 1-(2,2-diethoxyethyl)cyclopropan-1-ol (8.00 g, 29.12%) as a yellow liquid. $^1H$ NMR (300 MHz, Chloroform-d) δ 4.81 (t, 1H), 3.70-3.76 (m, 3H), 3.62-3.55 (m, 2H), 1.91 (d, 2H), 1.25 (t, 6H), 0.78 (d, 2H), 0.47-0.44 (m, 2H).

Step 2: Preparation of 1-(2,2-diethoxyethyl)cyclopropyl acetate

To a stirred solution of 1-(2.2-diethoxyethyl)cyclopropan-1-ol (8.00 g. 45.91 mmol. 1.00 equiv) and DMAP (6.17 g. 50.50 mmol. 1.10 equiv) in Et-O (100 mL) was added acetic anhydride (7.03 g. 68.87 mmol. 1.50 equiv) dropwise at 0° C., under nitrogen atmosphere. The resulting mixture was stirred for 1 h at 0° C., under nitrogen atmosphere. The reaction was monitored by TLC (PE/EA=10:1. Rf-0.5). The reaction was quenched with sat. NaHCO; (aq.) at 0° C. The aqueous layer was extracted with Et.O (3×100 mL). The resulting mixture was concentrated under vacuum. The residue was purified by silica gel column chromatography, the pure fraction was concentrated under reduced pressure to afford 1-(2.2-diethoxyethyl)cyclopropyl acetate (7.00 g. 70.49%) as a yellow liquid. $^1H$ NMR (400 MHZ. Chloroform-d) & 4.71 (t. 1H), 3.63 (q. 2H), 3.52 (q. 2H), 2.08 (d, 2H), 1.98 (s, 3H), 1.20 (t. 6H), 0.89-0.83 (m, 2H), 0.77-0.74 (m, 2H).

Step 3: Preparation of [1—(acetyloxy)cyclopropyl] acetic acid

To a stirred solution of 1-(2.2-diethoxyethyl)cyclopropyl acetate (7.00 g. 32.36 mmol. 1.00 equiv) in THF (40 mL) and $H_2O$ (80 mL) was added oxone (8.16 g. 48.54 mmol. 1.50 equiv) in portions at room temperature. The resulting mixture was stirred overnight at room temperature. The reaction was monitored by TLC (100% EA. Rf=0.1). The resulting mixture was diluted with water (200 mL). The resulting mixture was extracted with EtOAc (5×200 mL). The combined organic layers were dried over anhydrous $Na_2SO_4$. After filtration, the filtrate was concentrated under reduced pressure to afford [1-(acctyloxy)cyclopropyl]acetic acid (6 g, crude) as a yellow oil. $^1H$ NMR (400 MHZ. Chloroform-d) δ 2.82 (s. 2H), 2.02 (s, 3H), 1.03-0.97 (m, 2H), 0.90-0.86 (m, 2H).

Step 4: Preparation of ethyl 2-(1-hydroxycyclopropyl)acetate

To a stirred solution of] 1—(acetyloxy)cyclopropyl]acetic acid (6.00 g. 37.93 mmol. 1.00 equiv) in EtOH (200 mL) was added $H_2SO_4$ (60 drops) dropwise at room temperature. The resulting mixture was stirred overnight at room temperature. The reaction was monitored by TLC (PE/EA=10:1. Rf=0.5). The reaction was quenched with sat. NaHCO; (aq.) at room temperature. The aqueous layer was extracted with EtOAc (3×200 mL). The resulting mixture was concentrated under vacuum. The residue was purified by silica gel column chromatography, the pure fraction was concentrated under reduced pressure to afford ethyl 2-(1-hydroxycyclopropyl) acetate (1.50 g. 32.15%) as a yellow liquid. $^1H$ NMR (300 MHz. Chloroform-d) & 4.22 (q. 2H), 2.60 (s, 2H), 1.32 (t. 3H), 0.88 (d, 2H), 0.55-0.48 (m, 2H).

Step 5: Preparation of 2-(1-hydroxycyclopropyl)ethanimidamide hydrochloride

To a stirred mixture of $NH_4Cl$ (927 mg, 17.34 mmol. 5.00 equiv) in Toluene (20 mL) was added AlMc; (8 mL. 2 M in Toluene. 17.34 mmol. 5.00 equiv) dropwise at 0° C., under nitrogen atmosphere. The resulting mixture was stirred for 10 min at 0° C., under nitrogen atmosphere, and then was stirred at room temperature until no generation of gas. To the above mixture was added a solution of ethyl 2-(1-hydroxy-cyclopropyl)acetate (500 mg. 3.46 mmol. 1.00 equiv) in toluene dropwise at r.t. The resulting mixture was stirred overnight at 80° C. The reaction was monitored by LCMS. The mixture was allowed to cool down to room temperature. The reaction was quenched by the addition of MeOH (10 mL) at 0° C. The resulting mixture was filtered, the filter cake was washed with MeOH (6×30 mL). The filtrate was concentrated under reduced pressure. The residue was dissolved in EtOH (8 mL). The resulting mixture was filtered, the filter cake was washed with EtOH (5 mL). The filtrate was concentrated under reduced pressure. This resulted in 2-(1-hydroxycyclopropyl)ethanimidamide hydrochloride (450 mg, crude) as an orange oil. $^1$H NMR (300 MHz. DMSO-$d_6$) δ 9.01-8.72 (m, 4H), 5.76 (s, 1H), 2.60 (s, 2H), 0.65 (s. 4H).

Step 6: Preparation of 3-chloro-4-[(3,5-difluoropyridin-2-yl)methoxy]-2'-{2-[(1-hydroxycyclopropyl) methyl] pyrimidin-4-yl}-5',6-dimethyl-[1,4'-bipyridin]-2-one To a stirred solution of 3-chloro-4-[(3.5-difluoropyridin-2-yl)methoxy]-2'-[(2E)-3-(dimethylamino) prop-2-cnoyl]-5'0.6-dimethyl-]1,4'-bipyridin]-2-one (315 mg, 0.66 mmol. 1.00 equiv) and 2-(1-hydroxycyclopropyl)ethanimidamide hydrochloride (300 mg, 1.99 mmol. 3.00 equiv) in DMF (10 mL) was added $K_2CO_3$ (1.84 g. 13.28 mmol. 20.00 equiv) at room temperature. The resulting mixture was stirred overnight at 60° C. The reaction was monitored by LCMS. The mixture was allowed to cool down to room temperature. The resulting mixture was diluted with water (20 mL). The aqueous layer was extracted with EtOAc (3×20 mL). The resulting mixture was concentrated under vacuum. The crude product was purified by Prep-HPLC to afford 3-chloro-4-[(3.5-difluoropyridin-2-yl)methoxy]-2'-{2-[(1-hydroxycyclopropyl)methyl]pyrimidin-4-yl}-5',6-dimethyl-] 1,4'-bipyridin]-2-one (69.0 mg, 19.76%) as a white solid. LC-MS: (ES+H, m/z): $[M+H]^+$=526.1. $^1$H NMR (400 MHz. DMSO-$d_6$) δ 8.92 (d, 1H), 8.87 (s. 1H), 8.61 (d, 1H), 8.31 (s, 1H), 8.22 (d, 1H), 8.11-8.08 (m, 1H), 6.83 (s.1H), 5.50 (d, 2H), 5.27 (s, 1H). 3.23-3.10 (m, 2H), 2.09 (s, 3H), 1.97 (s, 3H), 0.66-0.59 (m, 4H).

Step7: Preparation of rel-3-chloro-4-[(3,5-difluoropyridin-2-yl)methoxy]-2'-{2-[(1-hydroxycyclopropyl)methyl]pyrimidin-4-yl}-5',6-dimethyl-[1,4'-bipyridin]-2-one and rel-3-chloro-4-[(3,5-difluoropyridin-2-yl)methoxy]-2'-{2-[(1-hydroxycyclopropyl)methyl]pyrimidin-4-yl}-5',6-dimethyl-[1,4'-bipyridin]-2-one The racemate (69 mg) was separated by Prep-Chiral-HPLC to afford Example 48A (26.0 mg. 98.7% purity, ee=100%) as a white solid and Example 48B (27.3 mg. 99.2% purity, ee=100%) as a white solid.

EXAMPLE 48A

LC-MS: (ES+H, m/z): $[M+H]^+$=526.20. $^1$H NMR (400 MHZ, DMSO-$d_6$) δ 8.92 (d, 1H), 8.87 (s. 1H), 8.61 (d, 1H), 8.31 (s, 1H), 8.22 (d, 1H), 8.11-8.08 (m, 1H), 6.83 (s, 1H), 5.50 (d, 2H), 5.27 (s, 1H). 3.23-3.10 (m, 2H), 2.09 (s, 3H), 1.97 (s, 3H), 0.66-0.59 (m, 4H), $^{19}$F NMR (282 MHz. DMSO) δ-120.13. -120.15, -122.32, -122.35.

EXAMPLE 48B

LC-MS: (ES+H, m/z): $[M+H]^+$=526.20. $^1$H NMR (400 MHZ. DMSO-$d_6$) δ 8.92 (d, 1H), 8.87 (s. 1H), 8.61 (d, 1H), 8.31 (s, 1H), 8.22 (d, 1H), 8.11-8.08 (m, 1H), 6.83 (s, 1H), 5.50 (d, 2H), 5.27 (s, 1H). 3.23-3.10 (m, 2H), 2.09 (s, 3H), 1.97 (s, 3H), 0.66-0.59 (m, 4H). $^{19}$F NMR (282 MHZ, DMSO) δ-120.13. -120.15, -122.32, -122.35.

EXAMPLE 49A, 49B

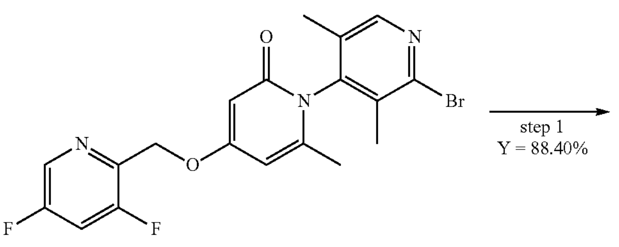

intermediate 41

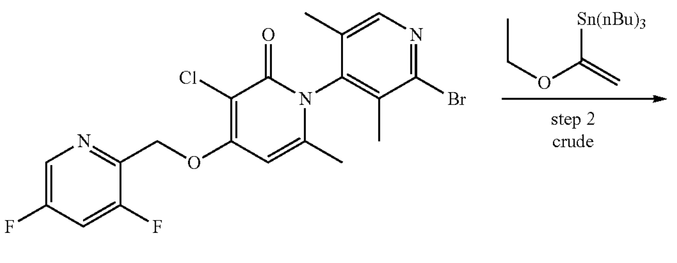

-continued
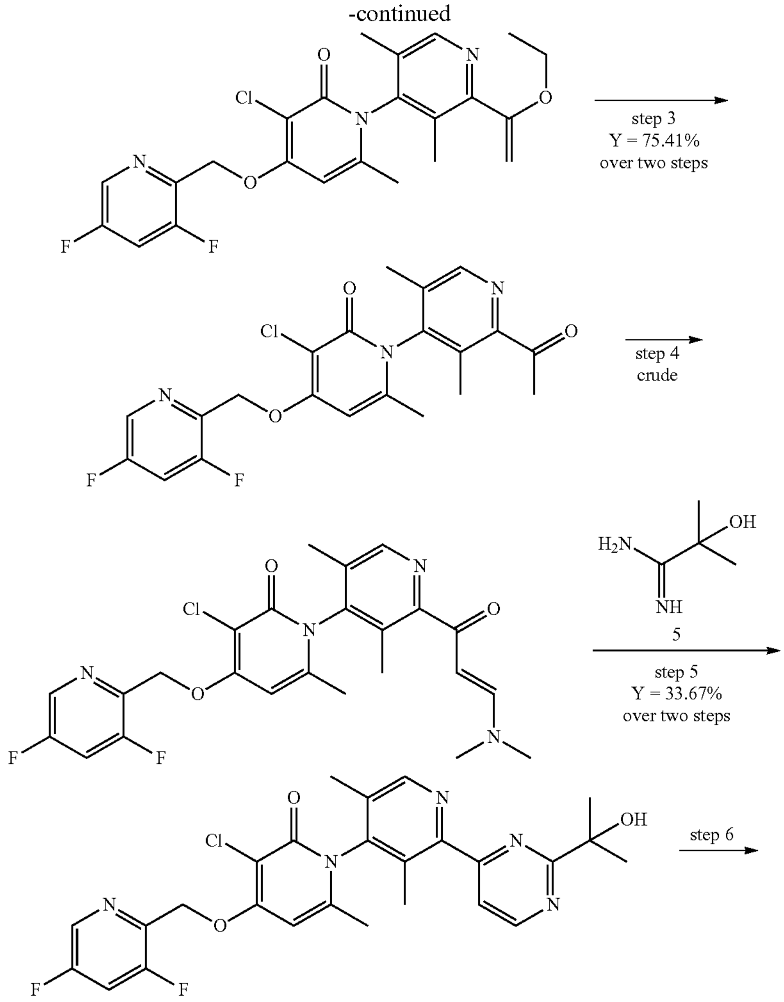
Example 49
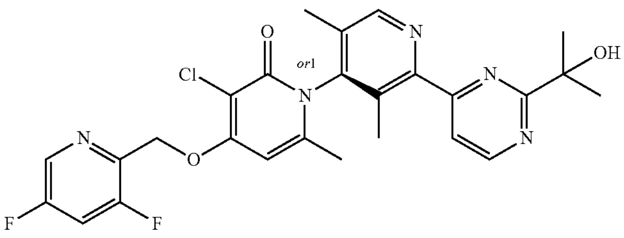
isomer 1
Example 49A
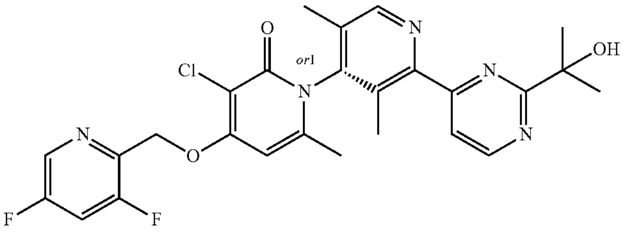
isomer 2
Example 49B Step 1: Preparation of 2'-bromo-3-chloro-4-[(3,5-difluoropyridin-2-yl)methoxy]-3',5',6-trimethyl-[1,4'-bipyridin]-2-one To a stirred solution of 2'-bromo-4-[(3,5-difluoropyridin-2-yl)methoxy]-3',5',6-trimethyl-[1,4'-bipyridin]-2-one (2.60 g, 5.96 mmol, 1.00 equiv) and NCS (954 mg, 7.15 mmol, 1.20 equiv) in IPA (10 mL) was added 2,2-dichloroacetic acid (76 mg, 0.59 mmol, 0.10 equiv) dropwise at room temperature under air atmosphere. The resulting mixture was stirred for 1 h at 60° C., under nitrogen atmosphere. The reaction was monitored by LCMS. The precipitated solids were collected by filtration and washed with IPA (5 mL), to afford 2'-bromo-3-chloro-4-[(3,5-difluoropyridin-2-yl)methoxy]-3',5',6-trimethyl-[1,4'-bipyridin]-2-one (2.48 g, 88.40%) as a white solid. LC-MS: (ES+H, m/z): $[M+H]^+$=470.1/472.1. $^1H$ NMR (400 MHZ, DMSO-$d_6$) δ 8.60 (d, 1H), 8.38 (s, 1H), 8.13-8.04 (m, 1H), 6.87 (d, 1H), 5.49 (d, 2H), 2.02 (s, 3H), 1.94 (s, 3H), 1.92 (s, 3H).

Step 2: Preparation of 2'-bromo-4-[(3,5-difluoropyridin-2-yl)methoxy]-3',5',6-trimethyl-[1,4'-bipyridin]-2-one To a stirred mixture of 2'-bromo-3-chloro-4-[(3,5-difluoropyridin-2-yl)methoxy]-3',5',6-trimethyl-[1,4'-bipyridin]-2-one (1.50 g. 3.18 mmol, 1.00 equiv) and tributyl (1-ethoxyethenyl) stannane (3.45 g, 9.56 mmol, 3.00 equiv) in 1,4-dioxane (5 mL) was added dichloropalladium: bis (triphenylphosphane) (223 mg, 0.31 mmol, 0.10 equiv) at room temperature under air atmosphere. The resulting mixture was stirred for 12 h at 100° C., under nitrogen atmosphere. The reaction was monitored by LCMS. The mixture was allowed to cool down to r.t . . . . The resulting mixture was filtered, the filter cake was washed with ethyl EA (3 ×50 mL). The filtrate was concentrated under reduced pressure. The crude product was used in the next step directly without further purification. LC-MS: (ES+H, m/z): $[M+H]^+$=462.2.

Step 3: Preparation of 2'-acetyl-3-chloro-4-[(3,5-difluoropyridin-2-yl)methoxy]-3',5',6-trimethyl-[1,4'-bipyridin]-2-one To a stirred solution of the above residue in THF (20 mL) were added HCl (2 mL) dropwise at 0° C., under nitrogen atmosphere. The resulting mixture was stirred for 2 h at room temperature under nitrogen atmosphere. The reaction was monitored by LCMS. The residue was basified to pH 10 with saturated $Na_2CO_3$ (aq.) at 0° C. The resulting mixture was extracted with EtOAc (3×100 mL). The combined organic layers were concentrated under reduced pressure. The residue was purified by silica gel column chromatography to afford 2'-acetyl-3-chloro-4-[(3.5-difluoropyridin-2-yl)methoxy]-3'0.5'0.6-trimethyl-[1,4'-bipyridin]-2-one (980 mg. 75.61%, over two steps) as a white solid. LC-MS: (ES+H, m/z): $[M+H]^+$=434.2. $^1H$ NMR (400 MHZ. DMSO-$d_6$) § 8.66 (s, 1H), 8.61 (d, 1H), 8.13-8.04 (m. 1H), 6.88 (d, 1H), 5.49 (d, 2H). 2.66 (s, 3H), 2.11 (s, 3H).2.04 (s, 3H), 1.88 (s, 3H).

Step 4: Preparation of 3-chloro-4-[(3,5-difluoropyridin-2-yl)methoxy]-2'-[(2E)-3-(dimethylamino) prop-2-enoyl]-3',5',6-trimethyl-[1,4'-bipyridin]-2-one A solution of 2'-acetyl-3-chloro-4-[(3.5-difluoropyridin-2-yl)methoxy]-3'0.5'0.6-trimethyl-[1,4'-bipyridin]-2-one (980 mg) in DMF-DMA (5 mL) was stirred for 3 h at 100° C., under nitrogen atmosphere. The reaction was monitored by LCMS. The mixture was allowed to cool down to r.t. The resulting mixture was concentrated under vacuum. The crude product was used in the next step directly without further purification. LC-MS: (ES+H, m/z): $[M+H]^+$=489.2.

Step 5: Preparation of 3-chloro-4-[(3,5-difluoropyridin-2-yl)methoxy]-2'-[2-(2-hydroxypropan-2-yl) pyrimidin-4-yl]-3',5',6-trimethyl-[1,4'-bipyridin]-2-one A mixture of 3-chloro-4-[(3.5-difluoropyridin-2-yl) methoxy]-2'-[(2E)-3-(dimethylamino) prop-2-cnoyl]-3', 5'0.6-trimethyl-[1,4'-bipyridin]-2-one (1100 mg, assumed 100% yield. 2.25 mmol. 1.00 equiv) 2-hydroxy-2-methyl-propanimidamide (689 mg. 6.75 mmol. 3.00 equiv) $K_2CO_3$ (1500 mg, 11.25 mmol. 5.00 equiv) in propan-2-ol (10 mL) was stirred for 12 h at 80° C., under nitrogen atmosphere. The reaction was monitored by LCMS. The mixture was allowed to cool down to r.t . . . . The resulting mixture was diluted with EA (300 mL) and washed with water (1×100 mL). The organic layer was concentrated under reduced pressure. The residue was purified by silica gel column chromatography to afford crude product. The crude product was isolated by PREP-HPLC to afford3-chloro-4-[(3.5-difluoropyridin-2-yl)methoxy]-2'-]2-(2-hydroxypropan-2-yl) pyrimidin-4-yl]-3'0.5'0.6-trimethyl-] 1,4'-bipyridin]-2-one (400 mg. 33.67%, over two steps) as a white solid. LC-MS: (ES+H, m/z): $[M+H]^+$=528.0.

Step 6: Preparation of rel-3-chloro-4-((3,5-difluoropyridin-2-yl)methoxy)-2'-(2-(2-hydroxypropan-2-yl) pyrimidin-4-yl)-3',5',6-trimethyl-2H-[1,4'-bipyridin]-2-one and rel-3-chloro-4-((3,5-difluoropyridin-2-yl) methoxy)-2'-(2-(2-hydroxypropan-2-yl)pyrimidin-4-yl)-3',5',6-trimethyl-2H-[1,4'-bipyridin]-2-one The racemate (190 mg) was separated by Prep-Chiral-HPLC to afford rel-3-chloro-4-((3.5-difluoropyridin-2-yl) methoxy)-2'-(2-(2-hydroxypropan-2-yl)pyrimidin-4-yl)-3'0.5'0.6-trimethyl-2H-[1,4'-bipyridin]-2-one (Example 49A: 66.6 mg. 96.8% purity, ce=100%) as a white solid and rel-3-chloro-4-((3.5-difluoropyridin-2-yl)methoxy)-2'-(2-(2-hydroxypropan-2-yl)pyrimidin-4-yl)-3'0.5'0.6-trimethyl-2H-[1,4'-bipyridin]-2-one (Example 49B: 73.0 mg. 97.9% purity, ce=99.34%) as a white solid.

EXAMPLE 49A

LC-MS: (ES+H, m/z): $[M+H]^+$=528.00. $^1H$ NMR (400 MHZ. DMSO-$d_6$) δ 8.97 (d, 1H), 8.70 (s. 1H), 8.61 (d, 1H), 8.16-8.05 (m, 1H), 7.90 (d, 1H), 6.89 (s, 1H), 5.50 (d, 2H), 5.22-5.00 (m, 1H), 2.21 (s. 3H), 2.06 (s, 3H), 1.95 (s, 3H), 1.53 (s, 6H). $^{19}F$ NMR (377 MHz, DMSO) δ-120.13,-120.15,-122.31,-122.32.

EXAMPLE 49B

LC-MS: (ES+H, m/z): $[M+H]^+$=528.00. $^1H$ NMR (400 MHZ, DMSO-$d_6$) δ 8.97 (d, 1H), 8.70 (s, 1H), 8.61 (d, 1H), 8.17-8.06 (m, 1H), 7.90 (d, 1H), 6.89 (d, 1H), 5.50 (d, 2H), 5.12 (s, 1H), 2.21 (s, 3H), 2.06 (s, 3H), 1.95 (s, 3H), 1.54 (s, 6H). $^{19}F$ NMR (377 MHz, DMSO) δ-120.13,-120.15,-122.30,-122.32.

EXAMPLE 50A, 50B

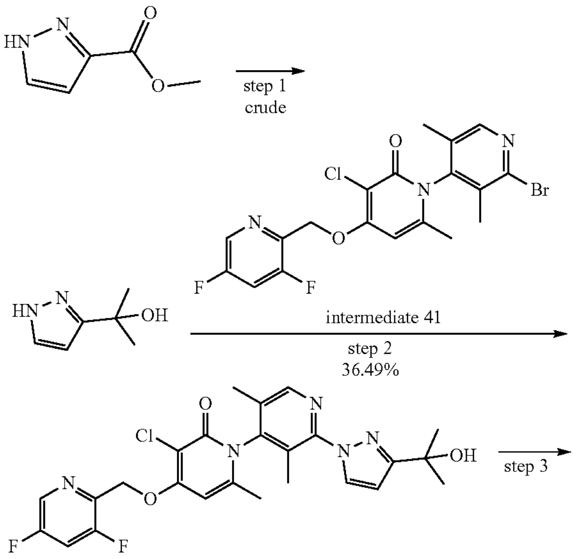

Example 50

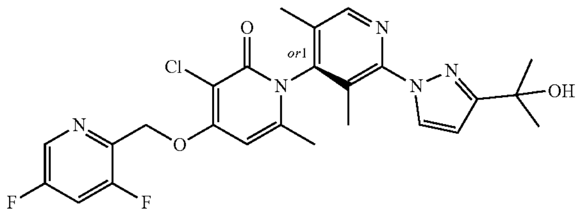

isomer 1
Example 50A

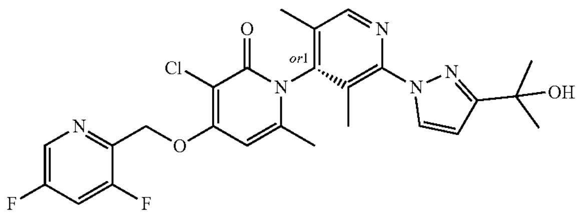

isomer 2
Example 50B

Step 1: Preparation of 2-(1H-pyrazol-3-yl) propan-2-ol

To a stirred solution of methyl 1H-pyrazole-3-carboxylate (5.00 g, 39.64 mmol, 1.00 equiv) in THF was added bromo (methyl) magnesium (132 mL, 3 M in 2-MeTHF, 396.46 mmol, 10.00 equiv) dropwise at 0° C., under nitrogen atmosphere. The resulting mixture was stirred for 1 h at 0° C., under nitrogen atmosphere. The reaction was monitored by LCMS. The reaction was quenched with sat. $NH_4Cl$ (aq.) at 0° C. The resulting mixture was extracted with EtOAc (3×100 mL). The combined organic layers were washed with brine (200 mL), dried over anhydrous $Na_2SO_4$. After filtration, the filtrate was concentrated under reduced pressure. This resulted in 2-(1H-pyrazol-3-yl) propan-2-ol (3.00 g, crude) as a yellow oil. The crude product was used in the next step directly without further purification. LC-MS: (ES+H, m/z): $[M+H]^+$ =127.08.

Step 2: Preparation of 3-chloro-4-[(3,5-difluoropyridin-2-yl)methoxy]-2'-[3-(2-hydroxypropan-2-yl) pyrazol-1-yl]-3',5',6-trimethyl-[1,4'-bipyridin]-2-one To a stirred mixture of 2'-bromo-3-chloro-4-[(3,5-difluoropyridin-2-yl)methoxy]-3',5',6-trimethyl-[1,4'-bipyridin]-2-one (300 mg, 0.63 mmol, 1.00 equiv) and 2-(1H-pyrazol-3-yl) propan-2-ol (160 mg, 1.27 mmol, 2.00 equiv) in dioxane (15 mL) were added $K_2CO_3$ (176 mg, 1.27 mmol, 2.00 equiv), CuI (242 mg, 1.27 mmol, 2.00 equiv) and (1R,2R)-1-N,2-N-dimethylcyclohexane-1,2-diamine (181 mg, 1.27 mmol, 2.00 equiv) at room temperature under nitrogen atmosphere. The resulting mixture was stirred overnight at 80° C. under nitrogen atmosphere. The reaction was monitored by LCMS. The mixture was allowed to cool down to room temperature. The resulting mixture was filtered, the filter cake was washed with EtOAc (3 ×50 mL).

The filtrate was concentrated under reduced pressure. The residue was purified by PREP-HPLC to afford 3-chloro-4-[(3,5-difluoropyridin-2-yl)methoxy]-2'-[3-(2-hydroxypropan-2-yl)pyrazol-1-yl]-3',5',6-trimethyl-[1,4'-bipyridin]-2-one (120 mg, 36.49%) as a white solid. LC-MS: (ES+H, m/z): $[M+H]^+$=516.3.

Step 3: Preparation of rel-3-chloro-4-[(3,5-difluoropyridin-2-yl)methoxy]-2'-[3-(2-hydroxypropan-2-yl) pyrazol-1-yl]-3',5',6-trimethyl-[1,4'-bipyridin]-2-one & rel-3-chloro-4-[(3,5-difluoropyridin-2-yl) methoxy]-2'-[3-(2-hydroxypropan-2-yl)pyrazol-1-yl]-3',5',6-trimethyl-[1,4'-bipyridin]-2-one The 3-chloro-4-[(3,5-difluoropyridin-2-yl)methoxy]-2'-[3-(2-hydroxypropan-2-yl)pyrazol-1-yl]-3',5',6-trimethyl-[1,4'-bipyridin]-2-one (120 mg) was separated by Prep-Chiral-HPLC to afford Example 50A (31.7 mg, 99.7% purity, ee=100%) and Example 50B (66.5 mg, 99.8% purity, ee=100%) as a white solid.

EXAMPLE 50A

LC-MS: (ES+H, m/z): $[M+H]^+$=516.2. $^1H$ NMR (300 MHz, DMSO-$d_6$) δ 8.61 (d, 1H), 8.47 (s, 1H), 8.23 (d, 1H), 8.11 (ddd, 1H), 6.88 (d, 1H), 6.51 (d, 1H), 5.50 (d, 2H), 5.05 (s, 1H), 2.08 (s, 3H), 2.01 (s, 3H), 1.87 (s, 3H), 1,48 (s, 3H), 1,47 (s, 3H). $^{19}F$ NMR (282 MHz, DMSO) δ-120.12,-120.14,-122.29,-122.32.

EXAMPLE 50B

LC-MS: (ES+H, m/z): $[M+H]^+$=516.2. $^1H$ NMR (300 MHz, DMSO-$d_6$) δ 8.61 (d, 1H), 8.47 (s, 1H), 8.23 (d, 1H), 8.10 (ddd, 1H), 6.88 (d, 1H), 6.51 (d, 1H), 5.50 (d, 2H), 5.05 (s, 1H), 2.08 (s, 3H), 2.01 (s, 3H), 1.87 (s, 3H), 1,48 (s, 3H), 1,43 (s, 3H). $^{19}F$ NMR (282 MHz, DMSO) δ-120.12,-120.14,-122.29,-122.31.

EXAMPLE 51A, 51B
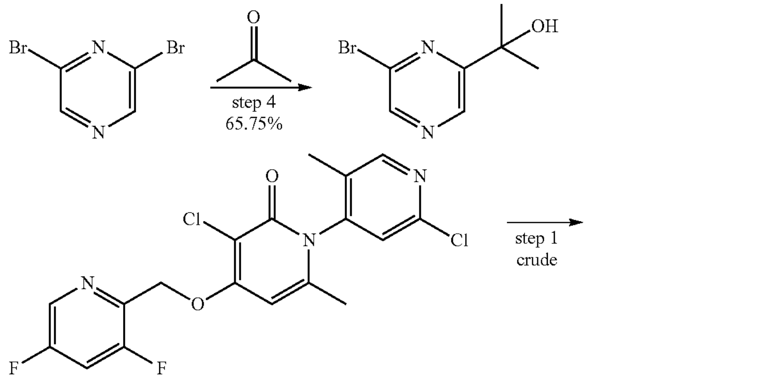
intermediate 7
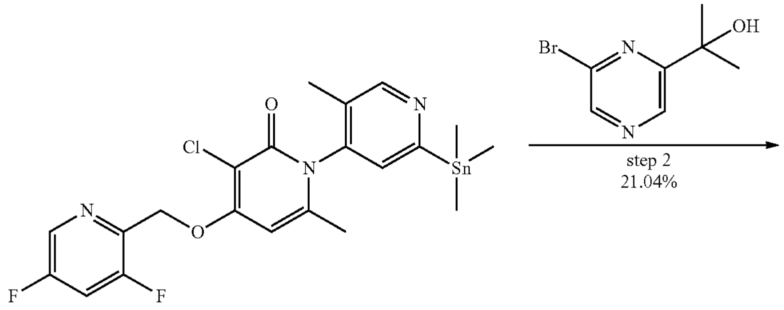
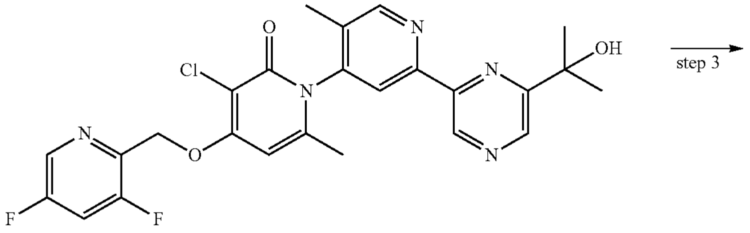
Example 51
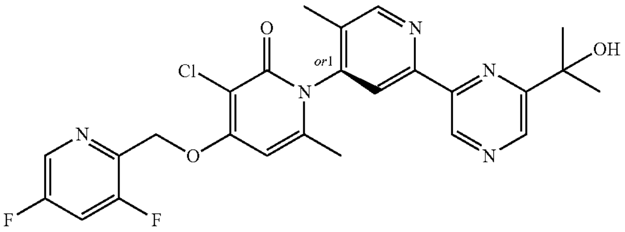
isomer 1
Example 51A
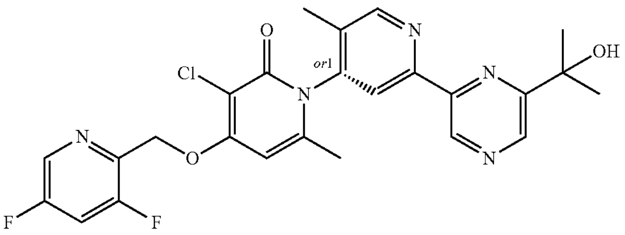
isomer 2
Example 51B Step 1: Preparation of 3-chloro-4-[(3,5-difluoropyridin-2-yl)methoxy]-5',6-dimethyl-2'-(trimethylstannyl)-[1,4'-bipyridin]-2-one To a stirred solution of 2'0.3-dichloro-4-[(3.5-difluoropyridin-2-yl)methoxy]-5'0.6-dimethyl-[1,4'-bipyridin]-2-one (1.00 g. 2.4 mmol. 1.00 equiv) and $Sn_2Me_6$ (3.18 g. 9.70 mmol. 4.00 equiv) in dioxane (20 mL) was added AsPh; (222 mg, 0.72 mmol. 0.3 equiv) and Pd(PPh;): $Cl_2$ (510 mg, 0.72 mmol. 0.30equiv) at room temperature under nitrogen atmosphere. The resulting mixture was stirred overnight at 80° C., under nitrogen atmosphere. The reaction was monitored by LCMS. The mixture was allowed to cool down to room temperature. The resulting mixture was diluted with EtOAc (100 mL). The resulting mixture was washed with 4×300 mL of KF (aq). The combined organic layers were washed with brine (100 mL), dried over anhydrous $Na_2SO_4$. After filtration, the filtrate was concentrated under reduced pressure. This resulted in 3-chloro-4-[(3.5-difluoropyridin-2-yl)methoxy]-5'0.6-dimethyl-2'-(trimethylstannyl)-[1,4'-bipyridin]-2-one (1.30 g crude) as a brown solid. The crude product was used in the next step directly without further purification. LC-MS: (ES+H, m/z): $[M+H]^+$=542.0.

Step 2: Preparation of 3-chloro-4-[(3,5-difluoropyridin-2-yl)methoxy]-2'-[6-(2-hydroxypropan-2-yl)pyrazin-2-yl]-5',6-dimethyl-[1,4'-bipyridin]-2-one To a stirred mixture of 3-chloro-4-[(3.5-difluoropyridin-2-yl)methoxy]-5'0.6-dimethyl-2'-(trimethylstannyl)-[1,4'-bipyridin]-2-one (500 mg, 0.92 mmol. 1.00 equiv) and 2-(6-bromopyrazin-2-yl) propan-2-ol (200 mg, 0.92 mmol. 1.00 equiv) in dioxane (15 mL) were added CuI (176 mg, 0.925 mmol. 1.00 equiv) and Pd(PPh;): $Cl_2$ (129 mg, 0.18 mmol. 0.20 equiv) at room temperature under nitrogen atmosphere. The resulting mixture was stirred for 3 h at 80° C., under nitrogen atmosphere. The reaction was monitored by LCMS. The mixture was allowed to cool down to room temperature. The resulting mixture was concentrated under reduced pressure. The residue was purified by silica gel column chromatography to afford 3-chloro-4-[(3.5-difluoropyridin-2-yl)methoxy]-2'-[6-(2-hydroxypropan-2-yl) pyrazin-2-yl]-5'0.6-dimethyl-[1,4'-bipyridin]-2-one (130 mg crude) as a yellow solid. The crude was purified by reverse flash chromatography. The pure fractions were concentrated under reduced pressure, to afford 3-chloro-4-[(3.5-difluoropyridin-2-yl)methoxy]-2'-[6-(2-hydroxypropan-2-yl) pyrazin-2-yl]-5'0.6-dimethyl-[1,4'-bipyridin]-2-one (100 mg. 21.04%) as a white solid. LC-MS: (ES+H, m/z): $[M+H]^+$=514.2.

Step 3: Preparation of rel-3-chloro-4-[(3,5-difluoropyridin-2-yl)methoxy]-2'-[6-(2-hydroxypropan-2-yl)pyrazin-2-yl]-5',6-dimethyl-[1,4'-bipyridin]-2-one & rel-3-chloro-4-[(3,5-difluoropyridin-2-yl)methoxy]-2'-[6-(2-hydroxypropan-2-yl)pyrazin-2-yl]-5',6-dimethyl-[1,4'-bipyridin]-2-one The 3-chloro-4-[(3.5-difluoropyridin-2-yl)methoxy]-2'-[6-(2-hydroxypropan-2-yl)pyrazin-2-yl]-5'0.6-dimethyl-[1,4'-bipyridin]-2-one (250 mg) was separated by prep-chiral-HPLC to afford Example 51A (37.0 mg. 99.6% purity, ee=100%) and Example 51B (60.4 mg. =98.0% purity, ce=100%) as a white solid.

EXAMPLE 51A

LC-MS: (ES+H, m/z): $[M+H]^+$=514.2. $^1H$ NMR (300 MHz. DMSO-$d_6$) δ 9.49 (s, 1H), 9.03 (s. 1H), 8.91 (s, 1H), 8.68 (d, 1H), 8.40 (s, 1H), 8.18 (ddd. 1H), 6.90 (s, 1H), 5.60 (s, 1H), 5.53 (d, 2H), 2.16 (s. 3H), 2.05 (s, 3H), 1.61 (s, 3H), 1.60 (s, 3H). $^{19}F$ NMR (282 MHz. DMSO) δ-120.12, -120.15, -122.30,-122.32.

EXAMPLE 51B

LC-MS: (ES+H, m/z): $[M+H]^+$=514.1. $^1H$ NMR (400 MHZ, DMSO-$d_6$) δ 9.42 (s, 1H), 8.97 (s, 1H), 8.84 (s, 1H), 8.62 (d, 1H), 8.35 (s, 1H), 8.15 (ddd, 1H), 6.84 (s, 1H), 5.53 (s, 1H), 5.49 (d, 2H), 2.10 (s, 3H), 1.99 (s, 3H), 1.54 (s, 3H), 1.53 (s, 3H). $^{19}F$ NMR (377 MHz, DMSO) δ-120.11,-120.13,-122.29,-122.31.

Step 4: Preparation of 2-(6-bromopyrazin-2-yl) propan-2-ol

To a stirred solution of 2,6-dibromopyrazine (5.00 g, 21.01 mmol, 1.00 equiv) in Toluene (125 mL) was added n-BuLi (8.4 mL, 2.5 M in hexane, 21.01 mmol, 1.00 equiv) dropwise over 15 min at −78° C. under nitrogen atmosphere. The resulting mixture was stirred for 30 min at −78° C., under nitrogen atmosphere. To the above mixture was added acetone (1.83 g, 31.52 mmol, 1.50 equiv) dropwise over 30 min at −78° C. The resulting mixture was stirred for additional Ih at −78° C. The reaction was monitored by LCMS. The reaction was quenched by the addition of sat. $NH_4Cl$ (aq.) (20 mL) at 0° C. The resulting mixture was extracted with EtOAc (3×100 mL). The combined organic layers were washed with brine (1×200 mL), dried over anhydrous $Na_2SO_4$. After filtration, the filtrate was concentrated under reduced pressure. The residue was purified by silica gel column chromatography to afford 2-(6-bromopyrazin-2-yl) propan-2-ol (3.00 g, 65.75%) as a yellow oil. LC-MS: (ES+H, m/z): $[M+H]^+$=217.2.

EXAMPLE 52A, 52B

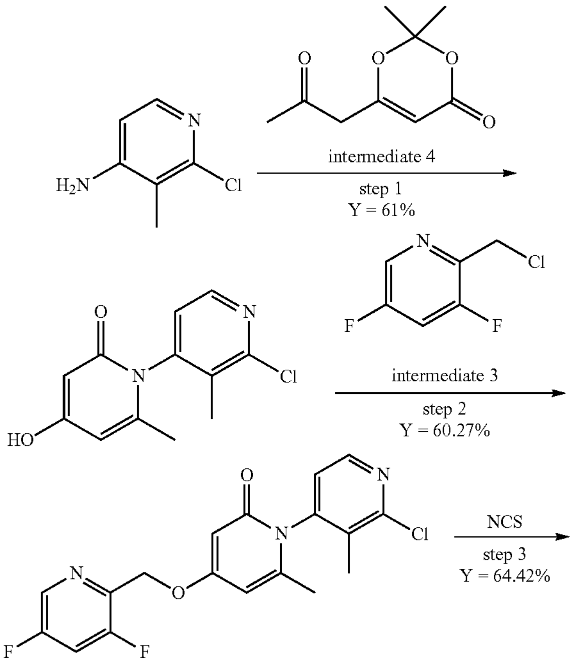

-continued

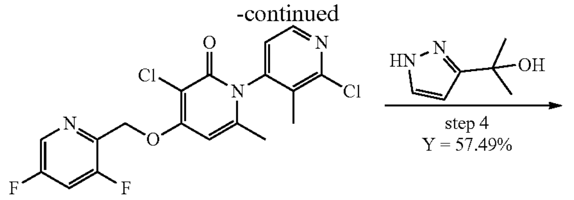

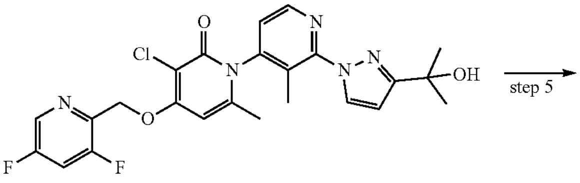

Example 52

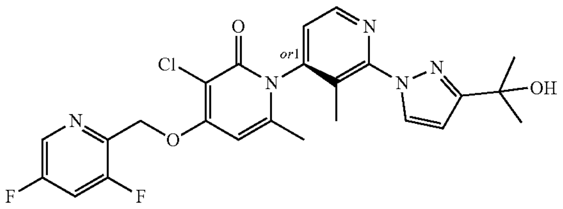

isomer 1
Example 52A

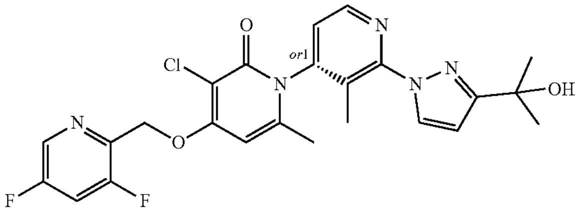

isomer 2
Example 52B

Step 1: Preparation of 2'-chloro-4-hydroxy-3',6-dimethyl-2H-[1,4'-bipyridin]-2-one A solution of 2-chloro-3-methylpyridin-4-amine (5.00 g, 35.06 mmol, 1.00 equiv) and 2,2-dimethyl-6-(2-oxopropyl)-1,3-dioxin-4-one (9.69 g, 52.60 mmol, 1.50 equiv) in 1,4-dioxane was stirred for 3 h at 90° C., under nitrogen atmosphere. The reaction was allowed to r.t, and monitored by LCMS. To the above mixture was added $H_2SO_4$ (3.44 g, 35.06 mmol, 1.00 equiv) dropwise at room temperature under nitrogen atmosphere. The resulting mixture was stirred for additional 1 h at 90° C., under nitrogen atmosphere. The mixture was allowed to cool down to room temperature. The reaction was monitored by LCMS. The resulting mixture was concentrated then water (10 mL) was added and the slurry stirred for additional 10 minutes at room temperature. Then ether (10 mL) was added and the mixture stirred for additional 10 minutes at room temperature. The solid was collected by filtration to afford 2'-chloro-4-hydroxy-3',6-dimethyl-[1,4'-bipyridin]-2-one (5.40 g, 61.0%) as a white solid. LC-MS: (ES+H, m/z): $[M+H]^+$=251.0.

Step 2: Preparation of 2'-chloro-4-((3,5-difluoro-pyridin-2-yl)methoxy)-3',6-dimethyl-2H-[1,4'-bipyridin]-2-one To a stirred mixture of 2'-chloro-4-hydroxy-3'0.6-dimethyl-[1,4'-bipyridin]-2-one (5.00 g. 19.94 mmol. 1.00 equiv) and 2-(chloromethyl)-3.5-difluoropyridine (13.05 g. 79.78 mmol. 4.00 equiv) in DMF (50 mL) were added $K_2CO_3$ (27.57 g. 199.46 mmol. 10.00 equiv) and 18-Crown-6 (2.64 g. 9.97 mmol. 0.5 equiv) at room temperature under nitrogen atmosphere. The resulting mixture was stirred for additional 6 h at 60° C., under nitrogen atmosphere. The mixture was allowed to cool down to room temperature. The reaction was monitored by LCMS. The resulting mixture was diluted with ethyl acetate (400 mL). The organic layer was washed with water (100 mL) and brine (100 mL), and then dried over $Na_2SO_4$. The solution was concentrated under reduced pressure. The residue was purified by silica gel column chromatography to afford 2'-chloro-4-[(3.5-difluoropyridin-2-yl)methoxy]-3'0.6-dimethyl-[1,4'-bipyridin]-2-one (5.22 g. 60.3%) as a white solid. LC-MS: (ES+H, m/z): $[M+H]^+$=378.0.

Step 3: Preparation of 2',3-dichloro-4-((3,5-difluoropyridin-2-yl)methoxy)-3',6-dimethyl-2H-[1,4'-bipyridin]-2-one To a stirred mixture of 2'-chloro-4-[(3.5-difluoropyridin-2-yl)methoxy]-3'0.6-dimethyl-] 1,4'-bipyridin]-2-one (5.00 g. 13.23 mmol. 1.00 equiv) and 2.2-dichloroacetic acid (0.34 g. 2.64 mmol. 0.2 equiv) in i-PrOH (15 mL) were added NCS (1.77 g. 13.23 mmol. 1.00 equiv) at room temperature under nitrogen atmosphere. The resulting mixture was stirred for 2 h at 60° C., under nitrogen atmosphere. The mixture was allowed to cool down to room temperature. The reaction was monitored by LCMS. The precipitated solids were collected by filtration and washed with IPA (2×10 mL), to afford 2'0.3-dichloro-4-[(3.5-difluoropyridin-2-yl) methoxy]-3'0.6-dimethyl-[1,4'-bipyridin]-2-one (3.82 g. 64.4%) as a white solid. LC-MS: (ES+H, m/z): $[M+H]^+$=411.9. $^1$H NMR (400 MHz. DMSO-$d_6$) δ 8.60 (d, 1H), 8.46 (d, 1H), 8.15-8.03 (m. 1H), 7.49 (d. 1H), 6.82 (s.1H), 5.49 (d, 2H), 2.03 (s, 3H), 1.96 (s, 3H).

Step 4: Preparation of 3-chloro-4-((3,5-difluoropyridin-2-yl)methoxy)-2'-(3-(2-hydroxypropan-2-yl)-1H-pyrazol-1-yl)-3',6-dimethyl-2H-[1,4'-bipyridin]-2-one To a stirred mixture of 2'0.3-dichloro-4-[(3.5-difluoro-pyridin-2-yl)methoxy]-3'0.6-dimethyl-[1,4'-bipyridin]-2-one (500 mg, 1.21 mmol. 1.00 equiv), 2-(1H-pyrazol-3-yl) propan-2-ol (459 mg. 3.64 mmol. 3.00 equiv) in 1,4-dioxane were added (IR.2R)-N1.$N_2$-dimethylcyclohexane-1.2-diamine (345 mg, 0.48 mmol. 2.00 equiv). CuI (230 mg, 0.24 mmol. 1.00 equiv). $K_2CO_3$ (335 mg. 2.42 mmol. 2.00 equiv) and NaI (363 mg. 2.42 mmol. 2.00 equiv) at room temperature under nitrogen atmosphere. The resulting mixture was stirred overnight at 100° C., under nitrogen atmosphere. The mixture was allowed to cool down to room temperature. Desired product could be detected by LCMS. The resulting mixture was diluted with EA (100 mL), then washed with water (2×50 mL) and brine (50 mL), dried over anhydrous $Na_2SO_4$. After filtration, the resulting mixture was concentrated under reduced pressure. The residue was purified by silica gel column chromatography to afford 3-chloro-4-((3.5-difluoropyridin-2-yl)methoxy)-2'-(3-(2-hydroxypropan-2-yl)-1H-pyrazol-1-yl)-3'0.6-dimethyl-2H-[1,4'-bipyridin]-2-one (350 mg. 57.5%, crude), which was further purified by PREP-HPLC. This resulted in 3-chloro-4-[(3.5-difluoropyridin-2-yl)methoxy]-2'-[3-(2-hydroxypropan-2-yl)pyrazol-1-yl]-3',6-dimethyl-[1,4'-bipyridin]-2-one (90 mg, 14.8%) as a white solid. LC-MS: (ES+H, m/z): $[M+H]^+$=502.1.

Step 5: Preparation of rel-3-chloro-4-((3,5-difluoropyridin-2-yl)methoxy)-2'-(3-(2-hydroxypropan-2-yl)-1H-pyrazol-1-yl)-3',6-dimethyl-2H-[1,4'-bipyridin]-2-one and rel-3-chloro-4-((3,5-difluoropyridin-2-yl)methoxy)-2'-(3-(2-hydroxypropan-2-yl)-1H-pyrazol-1-yl)-3',6-dimethyl-2H-[1,4'-bipyridin]-2-one The racemate (350 mg) was separated by prep-chiral-HPLC, the pure fraction was concentrated under vacuum and was lyophilized to afford Example 52A (32.4 mg, 99.4% purity, ee=100%) as a white solid and Example 52B (32.2 mg, 99.0% purity, ee=99.6%) as a white solid.

EXAMPLE 52A

LC-MS: (ES+H, m z): $[M+H]^+$=502.1. $^1$H NMR (400 MHZ, DMSO-$d_6$) δ 8.60 (d, 1H), 8.53 (d, 1H), 8.28 (d, 1H), 8.12-8.06 (m, 1H), 7.45 (d, 1H), 6.82 (s, 1H), 6.52 (d, 1H), 5.49 (d, 2H), 5.08 (s, 1H), 2.12 (s, 3H), 1.99 (s, 3H), 1,48 (s, 3H), 1,47 (s, 3H). $^{19}$F NMR (377 MHz, DMSO) δ-120.13,-120.15.,-122.31,-122.33.

EXAMPLE 52B

LC-MS: (ES+H, m z): $[M+H]^+$=502.1. $^1$H NMR (400 MHZ, DMSO-$d_6$) δ 8.61 (s, 1H), 8.54 (d, 1H), 8.29 (s, 1H), 8.14-8.05 (m, 1H), 7.48-7.42 (m, 1H), 6.83 (s, 1H), 6.53 (s, 1H), 5.49 (s, 2H), 5.08 (s, 1H), 2.13 (s, 3H), 2.00 (s, 3H), 1,48 (s, 3H), 1,47 (s, 3H). $^{19}$F NMR (377 MHz, DMSO) δ-120.13,-120.15.,-122.31,-122.33.

EXAMPLE 53A, 53B

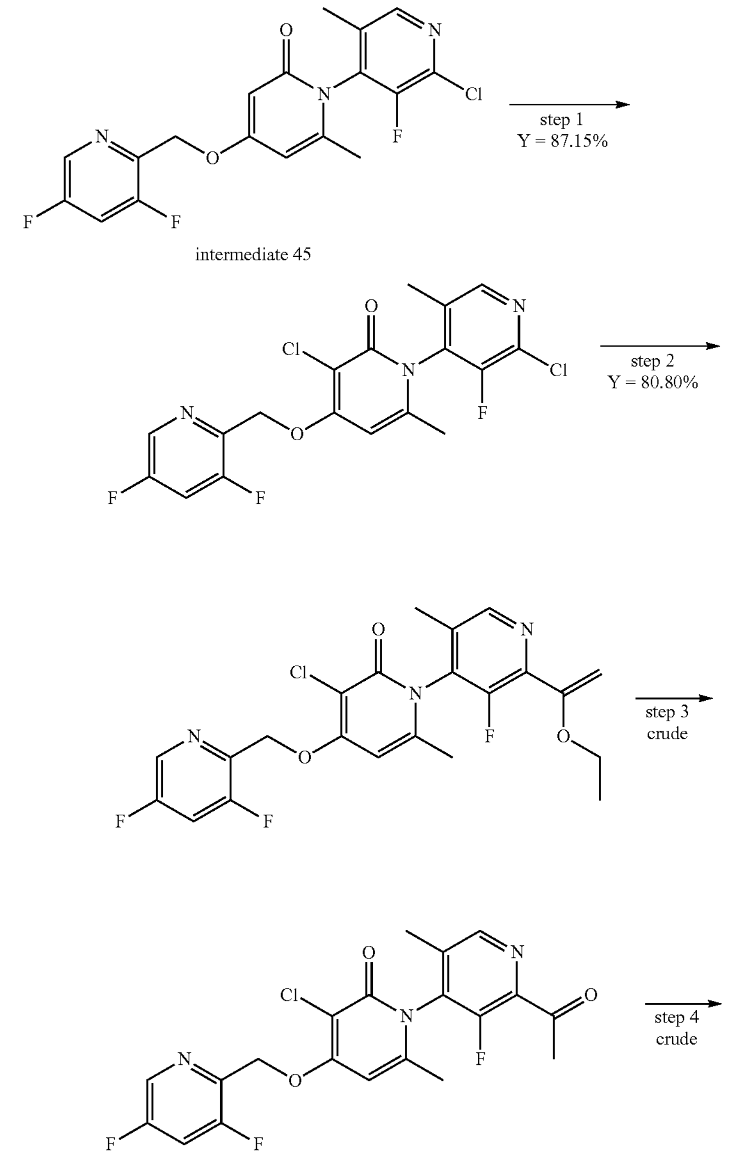

-continued

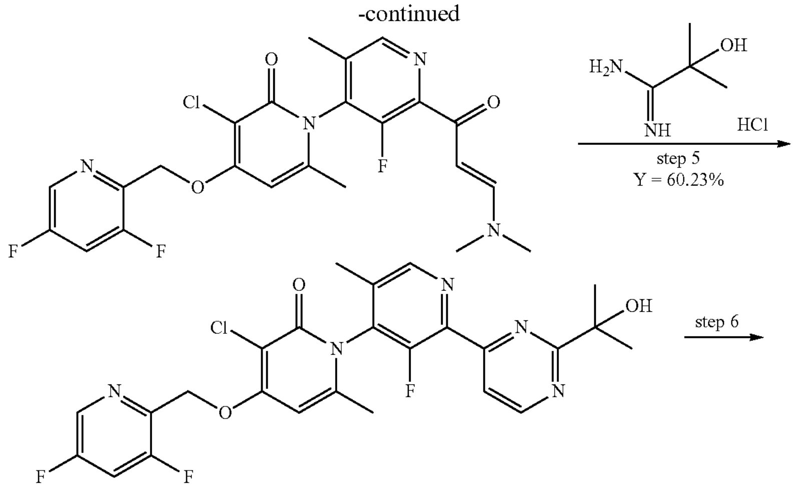

Example 53

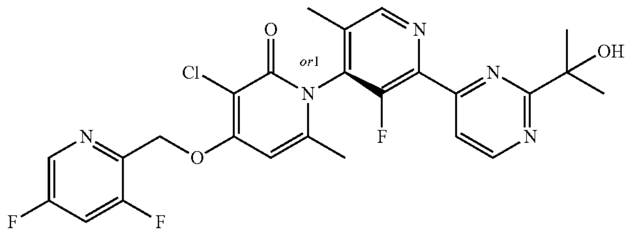

isomer 1
Example 53A

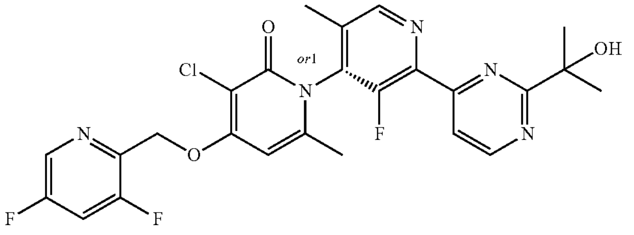

isomer 2
Example 53B

Step 1: Preparation of 2',3-dichloro-4-[(3,5-difluoropyridin-2-yl)methoxy]-3'-fluoro-5',6-dimethyl-[1,4'-bipyridin]-2-one To a stirred solution of 2'-chloro-4-[(3,5-difluoropyridin-2-yl)methoxy]-3'-fluoro-5',6-dimethyl-[1,4'-bipyridin]-2-one (1.90 g, 4.80 mmol, 1.00 equiv) and NCS (0.83 g, 6.21 mmol, 1.30 equiv) in DCM (40 mL) were added 2,2-dichloroacetic acid (61 mg, 0.48 mmol, 0.1 equiv) dropwise at room temperature under nitrogen atmosphere. The resulting mixture was stirred overnight at room temperature under nitrogen atmosphere. The reaction was monitored by LCMS. The resulting mixture was poured into water (100 mL). The resulting mixture was extracted with EtOAc (3 ×50 mL). The combined organic layers were washed with brine (3 ×50 mL), dried over anhydrous $Na_2SO_4$. After filtration, the filtrate was concentrated under reduced pressure. The residue was purified by silica gel column chromatography, the filtrate was concentrated under reduced pressure to afford 2'0.3-dichloro-4-[(3.5-difluoropyridin-2-yl)methoxy]-3'-fluoro-5'0.6-dimethyl-[1,4'-bipyridin]-2-one (1.80 g. 87.15%) as a yellow solid. LC-MS: (ES+H, m/z): $[M+H]^+$=429.8. $^1H$ NMR (300 MHz. DMSO-$d_6$) δ 8.61 (d, 1H), 8.49 (s, 1H), 8.15-8.03 (m, 1H), 6.90 (s, 1H), 5.52 (d, 2H), 2.08 (s, 3H), 2.03 (s, 3H).

Step 2: Preparation of 3-chloro-4-[(3,5-difluoropyridin-2-yl)methoxy]-2'-(1-ethoxyethenyl)-3'-fluoro-5',6-dimethyl-[1,4'-bipyridin]-2-one To a stirred solution of 2'0.3-dichloro-4-[(3.5-difluoropyridin-2-yl)methoxy]-3'-fluoro-5'0.6-dimethyl-[1,4'-bipyridin]-2-one (800 mg, 1.86 mmol. 1.00 equiv) and $Pd(PPh_3)$: $C_1$, (65 mg, 0.09 mmol. 0.05 equiv) in 1,4-dioxane (10 ml) was added tributyl (1-ethoxyethenyl) stannane (1.34 g. 3.72 mmol. 2.00 equiv) at room temperature under nitrogen atmosphere. The resulting mixture was stirred for 2 h at 100° C., under nitrogen atmosphere. The reaction was monitored by LCMS. The mixture was allowed to cool down to room temperature. The resulting mixture was poured into water (80 mL). The resulting mixture was extracted with EtOAc (3×100 mL). The combined organic layers were washed with brine (3×10 mL), dried over anhydrous $Na_2SO_4$. After filtration, the filtrate was concentrated under reduced pressure. The residue was purified by silica gel column chromatography, the filtrate was concentrated under reduced pressure to afford 3-chloro-4-[(3.5-difluoropyridin-2-yl)methoxy]-2'-(1-ethoxyethenyl)-3'-fluoro-5'0.6-dimethyl-[1,4'-bipyridin]-2-one (700 mg. 80.80%) as a white solid. LC-MS: (ES+H, m/z): $[M+H]^+$=466.0.

Step 3: Preparation of 2'-acetyl-3-chloro-4-[(3,5-difluoropyridin-2-yl)methoxy]-3'-fluoro-5',6-dimethyl-[1,4'-bipyridin]-2-one To a stirred solution of 3-chloro-4-[(3.5-difluoropyridin-2-yl)methoxy]-2'-(1-ethoxyethenyl)-3'-fluoro-5'0.6-dimethyl-[1,4'-bipyridin]-2-one (700 mg, 1.50 mmol. 1.00 equiv) in THF (30 ml) was added conc.HCl (3 mL) at 0° C., under nitrogen atmosphere. The resulting mixture was stirred for 1 h at room temperature under nitrogen atmosphere. The reaction was monitored by LCMS. The resulting mixture was poured into water (100 mL) at 0° C. The resulting mixture was extracted with EtOAc (3×100 mL). The combined organic layers were washed with brine (3×10 mL), dried over anhydrous $Na_2SO_4$. After filtration, the filtrate was concentrated under reduced pressure to afford 2'-acetyl-3-chloro-4-[(3.5-difluoropyridin-2-yl)methoxy]-3'-fluoro-5'0.6-dimethyl-[1,4'-bipyridin]-2-one (680 mg, crude) as a white solid. LC-MS: (ES+H, m/z): $[M+H]^+$=438.0.

Step 4: Preparation of 3-chloro-4-[(3,5-difluoropyridin-2-yl)methoxy]-2'-[(2E)-3-(dimethylamino) prop-2-enoyl]-3'-fluoro-5',6-dimethyl-[1,4'-bipyridin]-2-one Into a 40 mL sealed tube were added 2'-acetyl-3-chloro-4-[(3.5-difluoropyridin-2-yl)methoxy]-3'-fluoro-5'0.6-dimethyl-[1,4'-bipyridin]-2-one (680 mg, 1.55 mmol. 1.00 equiv) and DMF-DMA (6 mL) at room temperature. The resulting mixture was stirred for 2 h at 100° C., under nitrogen atmosphere. The reaction was monitored by LCMS. The mixture was allowed to cool down to room temperature. The resulting mixture was concentrated under reduced pressure to afford 3-chloro-4-[(3.5-difluoropyridin-2-yl) methoxy]-2'-[(2E)-3-(dimethylamino) prop-2-enoyl]-3'-fluoro-5'0.6-dimethyl-]1,4'-bipyridin]-2-one (820 mg, crude) as a brown solid. LC-MS: (ES+H, m/z): $[M+H]^+$=493.0.

Step 5: Preparation of 3-chloro-4-[(3,5-difluoropyridin-2-yl)methoxy]-3'-fluoro-2'-[2-(2-hydroxypropan-2-yl)pyrimidin-4-yl]-5',6-dimethyl-[1,4'-bipyridin]-2-one (TFA salt)

To a stirred solution of 3-chloro-4-[(3.5-difluoropyridin-2-yl)methoxy]-2'-[(2E)-3-(dimethylamino) prop-2-cnoyl]-3'-fluoro-5'0.6-dimethyl-[1,4'-bipyridin]-2-one (200 mg, 0.41 mmol. 1.00 equiv) and 2-hydroxy-2-methyl-propionamidine hydrochloride (282 mg. 2.03 mmol. 5.00 equiv) in DMF (4 ml) was added $K_2CO_3$ (168 mg, 1.22 mmol. 3.00 equiv) at room temperature under nitrogen atmosphere. The resulting mixture was stirred for 3 h at 80° C., under nitrogen atmosphere. The reaction was monitored by LCMS. The resulting mixture was poured into water (80 mL). The resulting mixture was extracted with EtOAc (3×100 mL). The combined organic layers were washed with brine (3×10 mL), dried over anhydrous $Na_2SO_4$. After filtration, the filtrate was concentrated under reduced pressure. The crude product was purified by Prep-HPLC to afford 3-chloro-4-[(3.5-difluoropyridin-2-yl)methoxy]-3'-fluoro-2'-[2-(2-hydroxypropan-2-yl)pyrimidin-4-yl]-5'0.6-dimethyl-[1,4'-bipyridin]-2-one (TFA salt) (130 mg. 60.23%) as a brown solid. LC-MS: (ES+H, m/z): $[M+H]^+$=532.1.

Step 6: Preparation of rel-3-chloro-4-[(3,5-difluoropyridin-2-yl)methoxy]-3'-fluoro-2'-[2-(2-hydroxypropan-2-yl)pyrimidin-4-yl]-5',6-dimethyl-[1,4'-bipyridin]-2-one & rel-3-chloro-4-[(3,5-difluoropyridin-2-yl)methoxy]-3'-fluoro-2'-[2-(2-hydroxypropan-2-yl)pyrimidin-4-yl]-5',6-dimethyl-[1,4'-bipyridin]-2-one The 3-chloro-4-[(3.5-difluoropyridin-2-yl)methoxy]-3'-fluoro-2'-]2-(2-hydroxypropan-2-yl)pyrimidin-4-yl]-5'0.6-dimethyl-[1,4'-bipyridin]-2-one (TFA salt) (130 mg) was basified to pH=9 with $NH_3$ $H_2O$ then purified by Prep-Chiral-HPLC, the pure fraction was concentrated under pressure then lyophilized to afford (Example 53A) (32.7 mg. 98.0% purity, ee=100%) as a white solid and (Example 53B) (32.4 mg. 98.0% purity, ee=100%) as a white solid.

EXAMPLE 53A

LC-MS: (ES+H, m/z): $[M+H]^+$=532.0. 1HNMR (300 MHz. DMSO-$d_6$) δ 9.03 (d, 1H), 8.78 (s, 1H), 8.61 (d. 1H), 8.15-8.07 (m, 1H), 8.04 (d, 1H), 6.91 (s.1H), 5.53 (d, 2H), 5.08 (s, 1H), 2.18 (s, 3H), 2.06 (s, 3H), 1.53 (s. 3H), 1.50 (s, 3H), $^{19}F$ NMR (282 MHz. DMSO) δ-120.17, -120.19, -122.35, -122.38, -132.08.

EXAMPLE 53B

LC-MS: (ES+H, m/z): $[M+H]^+$=532.0. 1HNMR (300 MHz. DMSO-$d_6$) δ 9.03 (d, 1H), 8.78 (s, 1H), 8.61 (d. 1H), 8.15-8.07 (m, 1H), 8.04 (d, 1H), 6.91 (s, 1H), 5.53 (d, 2H), 5.08 (s, 1H), 2.18 (s, 3H), 2.06 (s, 3H), 1.53 (s. 3H), 1.50 (s, 3H), $^{19}F$ NMR (282 MHz. DMSO) δ-120.17, -120.19, -122.35, -122.37.-132.08.

EXAMPLE 54A, 54B

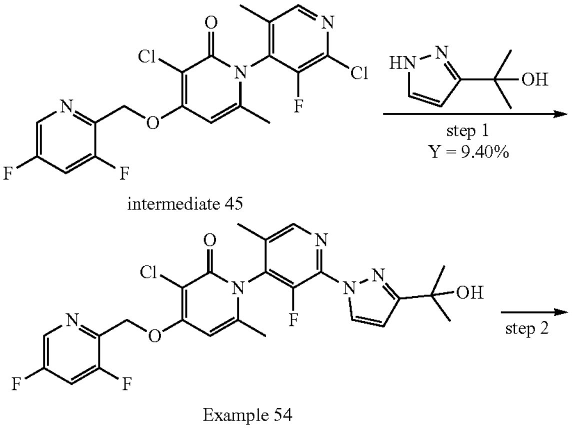

intermediate 45

Example 54

-continued

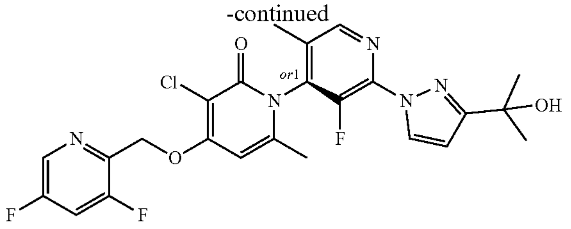

isomer 1
Example 54A

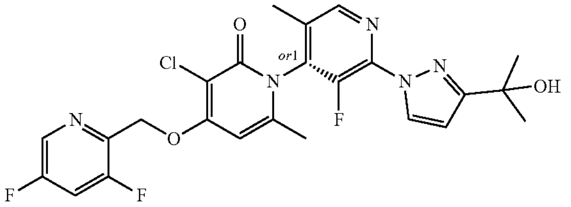

isomer 2
Example 54B

Step 1: Preparation of 3-chloro-4-[(3,5-difluoropyridin-2-yl)methoxy]-3'-fluoro-2'-[3-(2-hydroxypropan-2-yl)pyrazol-1-yl]-5',6-dimethyl-[1,4'-bipyridin]-2-one To a stirred mixture of 2',3-dichloro-4-[(3,5-difluoropyridin-2-yl)methoxy]-3'-fluoro-5',6-dimethyl-[1,4'-bipyridin]-2-one (880 mg. 2.04 mmol, 1.00 equiv) and 2-(1H-pyrazol-3-yl) propan-2-ol (516 mg. 4.09 mmol. 2.00 equiv) in 1,4-dioxane (10 mL) were added (1S,2S)-$N_1$,$N_2$-dimethylcyclohexane-1,2-diamine (290 mg. 2.04 mmol. 1.00 equiv) .CuI (38 mg, 0.20 mmol, 0.10 equiv) and $K_2CO_3$ (565 mg, 4.09 mmol, 2.00 equiv) at room temperature under nitrogen atmosphere. The resulting mixture was stirred overnight at 80° C., under nitrogen atmosphere. The reaction was monitored by LCMS. The mixture was allowed to cool down to room temperature. The resulting mixture was diluted with water (20 mL). The resulting mixture was extracted with EtOAc (3 ×50 mL). The combined organic layers were washed with brine (2×50 mL), dried over anhydrous $Na_2SO_4$. After filtration, the filtrate was concentrated under reduced pressure. The residue was purified by silica gel column chromatography, the pure fraction was concentrated under vacuum to afford the crude product. The crude product was purified by Prep-HPLC to afford 3-chloro-4-[(3,5-difluoropyridin-2-yl)methoxy]-3'-fluoro-2'-[3-(2-hydroxypropan-2-yl)pyrazol-1-yl]-5',6-dimethyl-[1,4'-bipyridin]-2-one (100 mg. 9.40%) as a white solid. LC-MS: (ES+H, m/z): $[M+H]^+$=520.0.

Step 2: Preparation of rel-3-chloro-4-((3,5-difluoropyridin-2-yl)methoxy)-3'-fluoro-2'-(3-(2-hydroxypropan-2-yl)-1H-pyrazol-1-yl)-5',6-dimethyl-2H-[1,4'-bipyridin]-2-one9 (Example 54A) & rel-3-chloro-4-((3,5-difluoropyridin-2-yl)methoxy)-3'-fluoro-2'-(3-(2-hydroxypropan-2-yl)-1H-pyrazol-1-yl)-5',6-dimethyl-2H-[1,4'-bipyridin]-2-one (Example 54B)

The 3-chloro-4-[(3,5-difluoropyridin-2-yl)methoxy]-3'-fluoro-2'-[3-(2-hydroxypropan-2-yl)pyrazol-1-yl]-5',6-dimethyl-[1,4'-bipyridin]-2-one (100 mg) was separated by Prep-CHIRAL to afford Example 54A (25.4 mg. 99.6% purity, ee=100%) and Example 54B (27.6 mg. 99.7% purity, ee=98.8%) as a white solid.

EXAMPLE 54A

LC-MS: (ES+H, m/z): $[M+H]^+$=520.1. $^1$H NMR (300 MHz, DMSO-$d_6$) δ 8.61 (d, 1H), 8.50 (s. 1H), 8.36 (d, 1H), 8.30-8.11 (m, 1H), 6.90 (s, 1H), 6.59 (d, 1H), 5.53 (s, 2H), 5.11 (s, 1H), 2.11 (s, 3H), 2.07 (s. 3 H), 1,47 (s, 3H), 1,43 (s, 3H). $^{19}$F NMR (282 MHz, DMSO) δ-120.18,-120.21,-122.35,-122.38,-138.00.

EXAMPLE 54B

LC-MS: (ES+H, m/z): $[M+H]^+$=520.1. $^1$H NMR (300 MHz, DMSO-$d_6$) δ 8.61 (d, 1H), 8.49 (s, 1H), 8.35 (d, 1H), 8.15-8.04 (m, 1H), 6.90 (s, 1H), 6.59 (d, 1H), 5.53 (s, 2H), 5.11 (s, 1H), 2.11 (s, 3H), 2.07 (s, 3H), 1,47 (s, 3H), 1,43 (s, 3H). $^{19}$F NMR (282 MHz, DMSO) δ-120.18,-120.21,-122.35,-122.38-137.99.

EXAMPLE 55

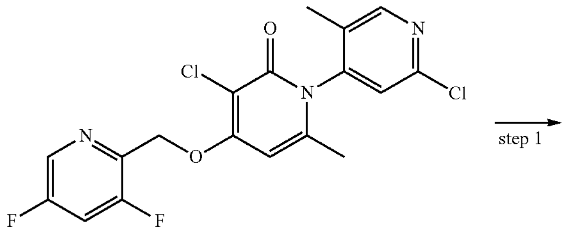

intermeidate 7

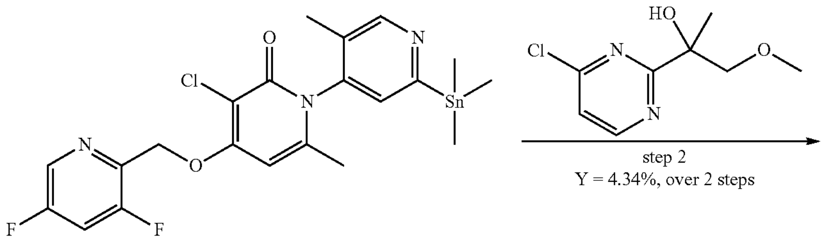

-continued

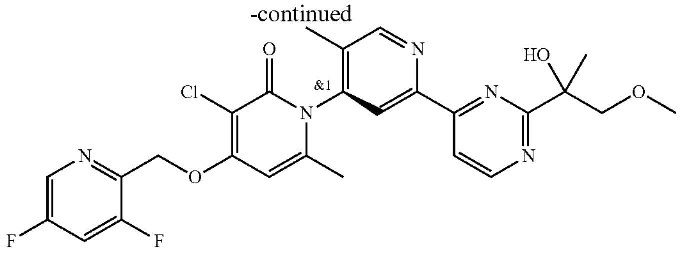

Example 55

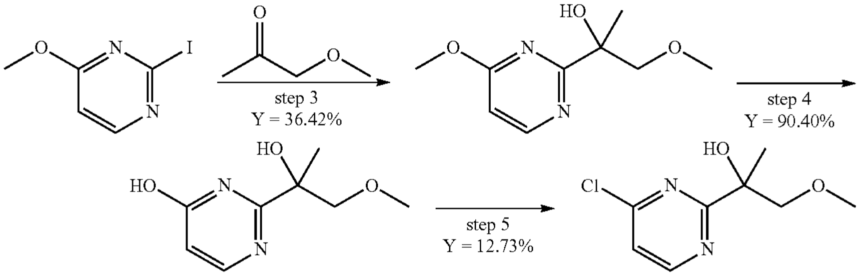

Step 1: Preparation of 3-chloro-4-[(3,5-difluoropyridin-2-yl)methoxy]-5',6-dimethyl-2'-(trimethylstannyl)-[1,4'-bipyridin]-2-one A solution of 2',3-dichloro-4-[(3,5-difluoropyridin-2-yl) methoxy]-5',6-dimethyl-[1,4'-bipyridin]-2-one (2.00 g, 4.85 mmol, 1.00 equiv) and $Sn_2Me_6$ (6.36 g, 19.41 mmol, 4.00 equiv) in dioxane (20 mL) was added $AsPh_3$ (0.74 g, 2.43 mmol, 0.50 equiv), $Pd(PPh_3)$: $Cl_2$ (0.68 g, 0.97 mmol, 0.20 equiv) at room temperature under nitrogen atmosphere. The resulting mixture was stirred for 2 h at 80° C., under nitrogen atmosphere. Desired product was detected by LCMS, the mixture was allowed to cool down to room temperature. The resulting mixture was diluted with ethyl acetate (50 mL). The resulting mixture was washed with 5×20 mL of sat. KF aq. The combined organic layers were washed with brine (50 mL), dried over anhydrous $Na_2SO_4$. After filtration, the filtrate was concentrated under reduced pressure to afford 3-chloro-4-[(3,5-difluoropyridin-2-yl)methoxy]-5',6-dimethyl-2'-(trimethylstannyl)-[1,4'-bipyridin]-2-one (3.00 g, crude) as a brown semi-solid. LC-MS: (ES+H, m/z): $[M+H]^+$=541.9.

Step 2: Preparation of 3-chloro-4-[(3,5-difluoropyridin-2-yl)methoxy]-2'-[2-(2-hydroxy-1-methoxypropan-2-yl)pyrimidin-4-yl]-5',6-dimethyl-[1,4'-bipyridin]-2-one To a stirred mixture of 3-chloro-4-[(3,5-difluoropyridin-2-yl)methoxy]-5',6-dimethyl-2'-(trimethylstannyl)-[1,4'-bipyridin]-2-one (1.60 g. 2.96 mmol, 1.00 equiv) and 2-(4-chloropyrimidin-2-yl)-1-methoxypropan-2-ol (299.89 mg, 1,48 mmol, 0.50 equiv) in dioxane (10 mL) were added $Pd(PPh_3)$: $Cl_2$ (623.24 mg, 0.89 mmol, 0.30 equiv) and CuI (563.69 mg, 2.96 mmol, 1.00 equiv) at room temperature under nitrogen atmosphere. The resulting mixture was stirred for 2 h at 100° C., under nitrogen atmosphere. Desired product was detected by LCMS. The mixture was allowed to cool down to room temperature. The resulting mixture was diluted with water (50 mL). The resulting mixture was extracted with EtOAc (3 ×50 mL). The combined organic layers were washed with brine (2×50 mL), dried over anhydrous $Na_2SO_4$. After filtration, the filtrate was concentrated under reduced pressure. The residue was purified by silica gel column chromatography to afford the crude product (200 mg) as a yellow oil, which was further purified by HP-Flash to afford 3-chloro-4-[(3.5-difluoropyridin-2-yl)methoxy]-2'-]2-(2-hydroxy-1-methoxypropan-2-yl)pyrimidin-4-yl]-5'0.6-dimethyl-[1,4'-bipyridin]-2-one (60.8 mg. 4.34%, racemate) as a white solid. LC-MS: (ES+H, m/z): $[M+H]^+$=544.15. $^1$H NMR (400 MHZ. DMSO-$d_6$) δ 8.98 (d, 1H), 8.86 (s.1H), 8.75 (s. 0.5H), 8.70 (s. 0.5H), 8.61 (d, 1H), 8.26 (d, 1H), 8.15-8.05 (m, 1H), 6.85 (s, 1H), 5.50 (s, 2H), 5.35 (s. 0.5H), 5.31 (s. 0.5H), 3.78-3.55 (m, 2H), 3.18 (s. 1.5H), 3.16 (s. 1.5H), 2.11 (s, 3H), 1.99 (d, 3H), 1,48 (s. 1.5H), 1,47 (s. 1.5H). $^{19}$F NMR (377 MHz. DMSO) δ-120.13, -120.15, -122.31, -122.33.

Step 3: Preparation of 2-methoxy-1-(4-methl-methoxy-2-(4-methoxypyrimidin-2-yl) propan-2-ol A solution of 2-iodo-4-methoxypyrimidine (17.00 g. 72.03 mmol. 1.00 equiv) in toluene (400 mL) was treated with i-PrMgCl (1.3 mol/L in THF. 46.82 mL. 93.64 mmol. 1.30 equiv) for 0.5 h at 0° C., under nitrogen atmosphere. LCMS showed the reactant was consumed completely and a new peak was detected. Then 1-methoxypropan-2-one (9.52 g. 108.05 mmol. 1.50 equiv) was added to the above solution and the mixture reaction was stirred at 0° C. for 2 h. LCMS showed the desired MS was found. The reaction was quenched by the addition of sat. $NH_4Cl$ (aq.) (200 mL) at room temperature. The resulting mixture was extracted with EtOAc (2×200 mL). The combined organic layers were washed with brine (100 mL), dried over anhydrous $Na_2SO_4$. After filtration, the filtrate was concentrated under reduced pressure. The residue was purified by reverse flash chromatography. This resulted in 2-methoxy-1-(4-meth 1-methoxy-2-(4-methoxypyrimidin-2-yl) propan-2-ol (5.20 g. 36.42%) as a yellow oil. LC-MS: (ES+H, m/z): $[M+H]^+$=199.2. $^1$H NMR (400 MHz. DMSO-$d_6$) δ 8.51 (d, 1H), 6.82 (d, 1H), 4.99 (s.1H), 3.95 (s, 3H), 3.66-3.55 (m. 2H), 3.19 (s, 3H), 1,42 (s, 3H).

Step 4: Preparation of 2-methoxy-1-(4-methl-methoxy-2-(4-methoxypyrimidin-2-yl) propan-2-ol Into a 500 mL round-bottom flask were added 1-methoxy-2-(4-methoxypyrimidin-2-yl) propan-2-ol (5.00 g. 25.22 mmol. 1.00 equiv) and (cthylsulfanyl) sodium (25.46 g. 302.69 mmol. 12.00 equiv) in DMF (300 mL) at room temperature. The resulting mixture was stirred overnight at 100° C., under nitrogen atmosphere. LCMS showed the reactant was consumed completely desired MS was found. The mixture was allowed to cool down to r.t, and the reaction was acidified to pH 6 with HCl (4M in dioxane), the resulting mixture was concentrated under reduced pressure. Then the residue was dissolved in ACN(100 mL) and filtrated, the filtrate was concentrated under reduced pressure. The residue was purified by silica gel column chromatography to afford 2-(2-hydroxy-1-methoxypropan-2-yl) pyrimidin-4-ol (4.20 g. 90.40%) as a yellow solid. LC-MS: (ES+H, m/z): $[M+H]^+$=185.2.

Step 5: Preparation of 2-(4-chloropyrimidin-2-yl)-1-methoxypropan-2-ol

To a solution of 2-(2-hydroxy-1-methoxypropan-2-yl)pyrimidin-4-ol (2.50 g. 13.57 mmol. 1.00 equiv) in DCE (20 mL) was added $POCl_3$ (3.80 mL. 40.72 mmol. 3.00 equiv) dropwise at 0° C. The resulting mixture was stirred for 2 h at 50° C., under nitrogen atmosphere. Desired product was detected by LCMS. The mixture was allowed to cool down to r.t, and concentrated under reduced pressure. The residue was purified by silica gel column chromatography to afford 2-(4-chloropyrimidin-2-yl)-1-methoxypropan-2-ol (350 mg. 12.73%) as a yellow oil. LC-MS: (ES+H, m/z): $[M+H]^+$=203.2. $^1H$ NMR (300 MHz. DMSO-$d_6$) δ 8.86 (d. 1H), 7.68 (d, 1H), 5.32 (s.1H), 3.69 (s, 2H), 3.26 (s, 3H), 1.52 (s, 3H).

EXAMPLE 56A, 56B

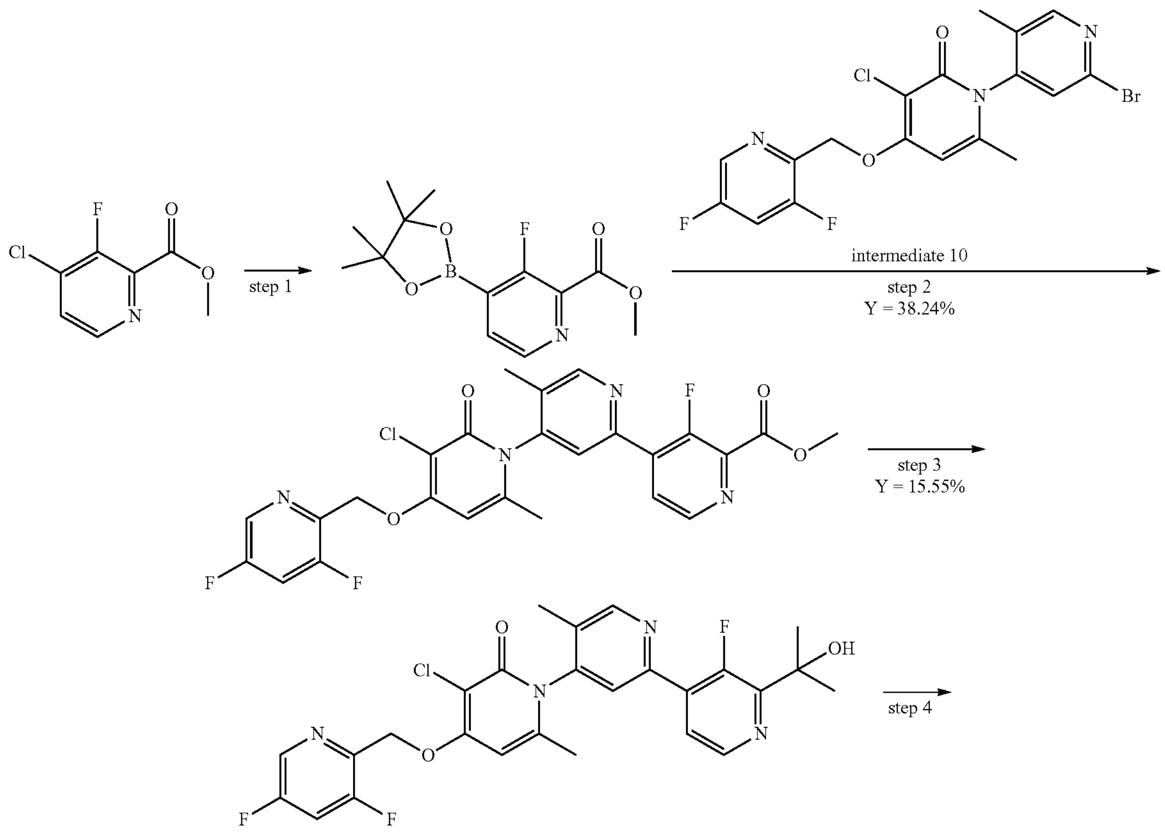

Example 56

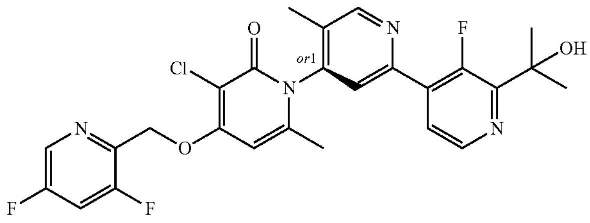

isomer 1
Example 56A

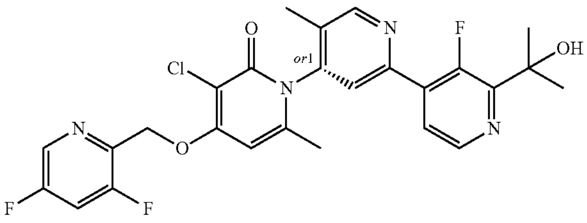

isomer 2
Example 56B

Step 1&2: Preparation of methyl 4-{3-chloro-4-[(3,5-difluoropyridin-2-yl)methoxy]-6-methyl-2-oxopyridin-1-yl}-3'-fluoro-5-methyl-[2,4'-bipyridine]-2'-carboxylate To a stirred solution of methyl 4-chloro-3-fluoropyridine-2-carboxylate (3 g. 15.825 mmol, 1 equiv) and 4,4,5,5-tetramethyl-2-(tetramethyl-1,3,2-dioxaborolan-2-yl)-1,3,2-dioxaborolane (16.07 g, 63.300 mmol, 4 equiv) in 1,4-dioxane (200 mL) were added AcOK (4.66 g. 47.475 mmol, 3 equiv) and XPhos Palladacycl Gen.4 (113.48 mg, 0.132 mmol. 0.05 equiv) at room temperature under nitrogen atmosphere. The resulting mixture was stirred for 1 h at 80° C., under nitrogen atmosphere. The reaction was monitored by LCMS. The mixture was allowed to cool down to room temperature. The resulting mixture was used in the next step directly without further purification. LC-MS: (ES+H, m/z): $[M+H]^+$=200.0.

To the above mixture were added 2'-bromo-3-chloro-4-[(3,5-difluoropyridin-2-yl)methoxy]-5',6-dimethyl-[1,4'-bipyridin]-2-one (1.8 g. 3.942 mmol, 1 equiv), $K_2CO_3$ (1.63 g. 11.826 mmol, 3 equiv). $Pd(PPh_3)$ 4 (455.07 mg, 0.394 mmol, 0.1 equiv) and $H_2O$ (50 mL) at room temperature under nitrogen atmosphere. The resulting mixture was stirred for 1.5 h at 80° C., under nitrogen atmosphere. The reaction was monitored by LCMS. The mixture was allowed to cool down to room temperature. The resulting mixture was poured into water (500 mL). The resulting mixture was extracted with EtOAc (3 ×500 mL). The combined organic layers were washed with brine (3 ×500 mL), dried over anhydrous $Na_2SO_4$. After filtration, the filtrate was concentrated under reduced pressure. The residue was purified by silica gel column chromatography, the pure fraction was concentrated under pressure to afford methyl 4-{3-chloro-4-[(3,5-difluoropyridin-2-yl)methoxy]-6-methyl-2-oxopyridin-1-yl}-3'-fluoro-5-methyl-[2.4'-bipyridine]-2'-carboxylate (800 mg, 38.23%) as a brown solid.LC-MS: (ES+H, m/z): $[M+H]^+$=531.2. $^1$H NMR (400 MHZ. DMSO-$d_6$) δ 8.90 (s, 1H), 8.65 (d, 1H), 8.60 (d, 1H), 8.21 (t, 1H), 8.11-8.07 (m, 1H), 7.95 (s, 1H), 6.81 (s, 1H), 5.49 (d, 2H), 3.93 (s, 3H), 2.10 (s, 3H), 1.98 (s, 3H).

Step 3: Preparation of 3-chloro-4-[(3,5-difluoropyridin-2-yl)methoxy]-1-[3'-fluoro-2'-(2-hydroxypropan-2-yl)-5-methyl-[2,4'-bipyridin]-4-yl]-6-methylpyridin-2-one To a stirred solution of methyl 4-{3-chloro-4-[(3,5-difluoropyridin-2-yl)methoxy]-6-methyl-2-oxopyridin-1-yl}-3'-fluoro-5-methyl-[2.4'-bipyridine]-2'-carboxylate (450 mg, 0.84 mmol, 1.00 equiv) in THF (20 mL) was added $CH_3MgBr$ (1.70 mL, 5.08 mmol, 6.00 equiv, 3.4 M in 2-MeTHF) dropwise at 0° C. under nitrogen atmosphere. The resulting mixture was stirred for 1 h at 0° C., under nitrogen atmosphere. The reaction was monitored by LCMS. The reaction was quenched with sat. $NH_4Cl$ (aq.) (50 mL) at 0° C. The resulting mixture was extracted with EtOAc (3×30 mL). The combined organic layers were washed with brine (3×20 mL), dried over anhydrous $Na_2SO_4$. After filtration, the filtrate was concentrated under reduced pressure. The residue was purified by Prep-TLC (EA) to afford crude product, which was further purified by Prep-HPLC, the pure fraction was concentrated under pressure to afford 3-chloro-4-[(3,5-difluoropyridin-2-yl)methoxy]-1-[3'-fluoro-2'-(2-hydroxypropan-2-yl)-5-methyl-[2,4'-bipyridin]-4-yl]-6-methylpyridin-2-one (70 mg, 15.55%) as a white solid. LC-MS: (ES+H, m/z): $[M+H]^+$=531.1.

Step 4: Preparation of rel-3-chloro-4-[(3,5-difluoropyridin-2-yl)methoxy]-1-[3'-fluoro-2'-(2-hydroxypropan-2-yl)-5-methyl-[2,4'-bipyridin]-4-yl]-6-methylpyridin-2-one & rel-3-chloro-4-[(3,5-difluoropyridin-2-yl)methoxy]-1-[3'-fluoro-2'-(2-hydroxypropan-2-yl)-5-methyl-[2,4'-bipyridin]-4-yl]-6-methylpyridin-2-one The crude product (70 mg) was separated by Prep-Chiral-HPLC, the pure fraction was concentrated under reduced pressure and lyophilized to afford 3-chloro-4-[(3,5-difluoropyridin-2-yl)methoxy]-1-[3'-fluoro-2'-(2-hydroxypropan-2-yl)-5-methyl-[2,4'-bipyridin]-4-yl]-6-methylpyridin-2-one (Example 56A, 21.8 mg, 36.33%, ee=100%) as a white solid and 3-chloro-4-[(3,5-difluoropyridin-2-yl)methoxy]-1-[3'-fluoro-2'-(2-hydroxypropan-2-yl)-5-methyl-[2,4'-bipyridin]-4-yl]-6-methylpyridin-2-one (Example 56B, 18.6 mg, 31.00%, ee=100%) as a white solid.

EXAMPLE 56A

LC-MS: (ES+H, m/z): $[M+H]^+$=531.25. 1HNMR (300 MHz, DMSO-$d_6$) δ 8.88 (s, 1H), 8.61 (d, 1H), 8.48 (d, 1H), 8.19-8.05 (m, 1H), 7.96-7.81 (m, 2H), 6.82 (s, 1H), 5.55-5.45 (m, 2H), 5.37 (s, 1H), 2.10 (s, 3H), 1.99 (s, 3H), 1.56 (s, 6H). $^{19}$F NMR (282 MHz, DMSO) δ-120.158,-120.177,-122.350,-122.368,-125.910.

EXAMPLE 56B

LC-MS: (ES+H, m/z): $[M+H]^+$=531.25. 1HNMR (300 MHz, DMSO-$d_6$) δ 8.88 (s, 1H), 8.61 (d, 1H), 8.48 (d, 1H), 8.19-8.05 (m, 1H), 7.96-7.81 (m, 2H), 6.82 (s, 1H), 5.55-5.45 (m, 2H), 5.37 (s, 1H), 2.10 (s, 3H), 1.99 (s, 3H), 1.56 (s, 6H). $^{19}$F NMR (282 MHz, DMSO) δ-120.140,-120.159,-122.310,-122.330,-125.923.

EXAMPLE 57A, 57B

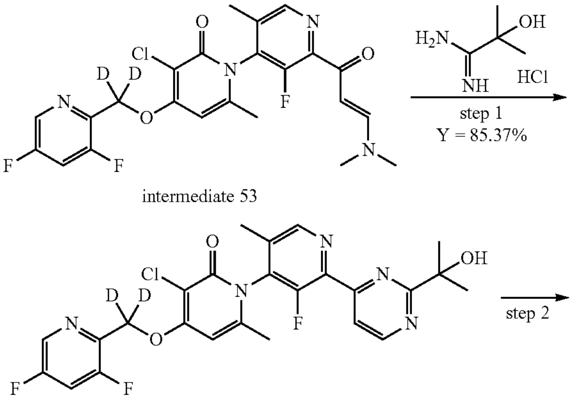

intermediate 53

Example 57

-continued

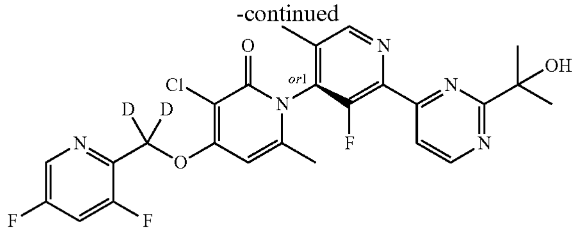

isomer 1
Example 57A

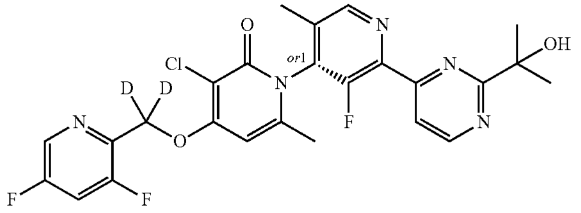

isomer 2
Example 57B

Step 1: Preparation of 3-chloro-4-[(3,5-difluoropyridin-2-yl) ($^2H_2$)methoxy]-3'-fluoro-2'-[2-(2-hydroxypropan-2-yl)pyrimidin-4-yl]-5',6-dimethyl-[1,4'-bipyridin]-2-one To a stirred solution of 3-chloro-4-[(3,5-difluoropyridin-2-yl) ($^2H_2$)methoxy]-2'-] (2E)-3-(dimethylamino) prop-2-enoyl]-3'-fluoro-5',6-dimethyl-[1,4'-bipyridin]-2-one (0.76 g, 1.53 mmol, 1.00 equiv) and 2-hydroxy-2-methylpropanimidamide hydrochloride (1.06 g. 7.68 mmol, 5.00 equiv) in i-PrOH (10 mL) were added $K_2CO_3$ (1.06 g. 7.68 mmol, 5.00 equiv) at room temperature under nitrogen atmosphere. The resulting mixture was stirred for 2 h at 80° C., under nitrogen atmosphere. Desired product could be detected by LCMS. The resulting mixture was filtered, the filter cake was washed with i-PrOH (3x3 mL). The filtrate was concentrated under reduced pressure. The residue was purified by silica gel column chromatography. This resulted in 3-chloro-4-[(3,5-difluoropyridin-2-yl) ($^2H_2$)methoxy]-3'-fluoro-2'-[2-(2-hydroxypropan-2-yl)pyrimidin-4-yl]-5',6-dimethyl-[1,4'-bipyridin]-2-one (700 mg, 85.37%) as a yellow solid. LC-MS: (ES+H, m/z): $[M+H]^+$=534.1.

Step 2: Preparation of rel-3-chloro-4-[(3,5-difluoropyridin-2-yl) ($^2H_2$)methoxy]-3'-fluoro-2'-[2-(2-hydroxypropan-2-yl)pyrimidin-4-yl]-5',6-dimethyl-[1,4'-bipyridin]-2-one & rel-3-chloro-4-[(3,5-difluoropyridin-2-yl) ($^2H_2$)methoxy]-3'-fluoro-2'-[2-(2-hydroxypropan-2-yl)pyrimidin-4-yl]-5',6-dimethyl-[1,4'-bipyridin]-2-one The rac-mixture (550 mg) was separated by Prep-Chiral HPLC to afford rel-3-chloro-4-[(3,5-difluoropyridin-2-yl) ($^2H_2$)methoxy]-3'-fluoro-2'-[2-(2-hydroxypropan-2-yl)pyrimidin-4-yl]-5',6-dimethyl-[1,4'-bipyridin]-2-one (Example 57A, 170.1 mg, 98.7% purity, 96.4% deuterium purity, ee=100%) & rel-3-chloro-4-[(3,5-difluoropyridin-2-yl) ($^2H_2$)methoxy]-3'-fluoro-2'-[2-(2-hydroxypropan-2-yl)pyrimidin-4-yl]-5',6-dimethyl-[1,4'-bipyridin]-2-one (Example 57B 194.9 mg. 98.8% purity, 96.5% deuterium purity, ee=98.6%)

EXAMPLE 57A

LC-MS: (ES+H, m/z): $[M+H]^+$=534.00. $^1H$ NMR (300 MHz, DMSO-$d_6$) δ 9.03 (d, 1H), 8.78 (d. 1H), 8.61 (d, 1H), 8.15-8.07 (m, 1H), 8.04 (d, 1H), 6.91 (d, 1H), 5.09 (s, 1H), 2.18 (s, 3H), 2.06 (s, 3H), 1.53 (s, 6H). $^{19}F$ NMR (282 MHz, DMSO) δ-120.25,-120.28,-122.32,-122.34,-132.08.

EXAMPLE 57B

LC-MS: (ES+H, m/z): $[M+H]^+$=534.1. $^1H$ NMR (300 MHz, DMSO-$d_6$) δ 9.03 (d, 1H), 8.78 (d. 1H), 8.61 (d, 1H), 8.15-8.06 (m, 1H), 8.04 (d1H), 6.91 (d, 1H), 5.09 (s, 1H), 2.18 (s, 3H), 2.06 (s, 3H), 1.53 (s, 6H). $^{19}F$ NMR (282 MHZ, DMSO) δ-120.25,-120.27,-122.31,-122.34,-132.07.

EXAMPLE 58A

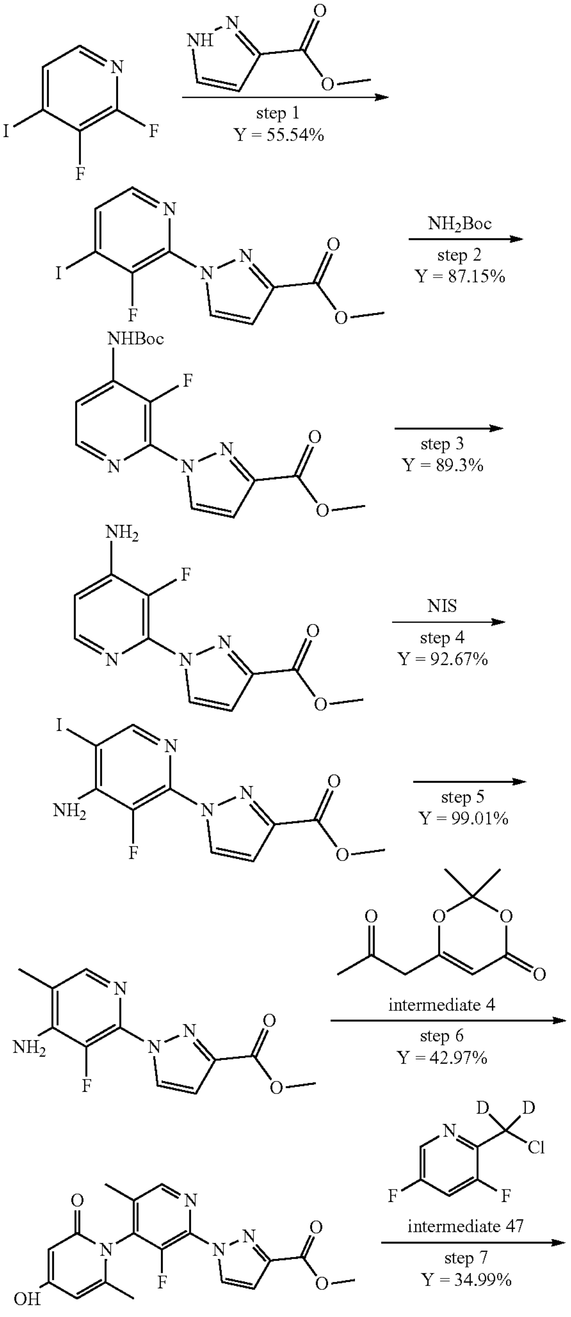

-continued

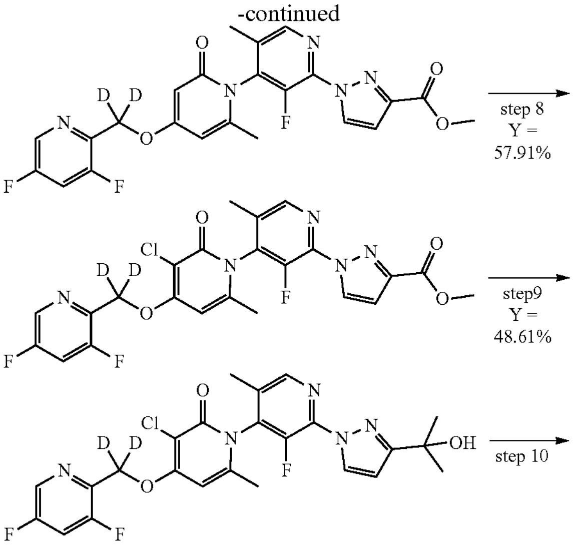

Example 58

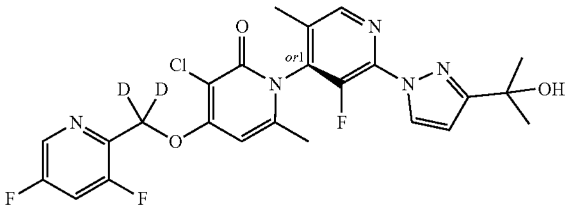

Isomer 1
Example 58A

Step 1: Preparation of methyl 1-(3-fluoro-4-iodopyridin-2-yl)pyrazole-3-carboxylate A mixture of 2,3-difluoro-4-iodopyridine (50.00 g, 207.49 mmol, 1.00 equiv), methyl 1H-pyrazole-3-carboxylate (23.53 g, 186.74 mmol, 0.90 equiv) and $Cs_2CO_3$ (67.60 g, 207.49 mmol, 1.00 equiv) in DMF (500 mL) was stirred for 2 h at 100° C., under nitrogen atmosphere. The reaction was monitored by LCMS. The mixture was allowed to cool down to room temperature. The resulting mixture was filtered, the filter cake was washed with EtOAc (3×300 mL). The filtrate was concentrated under reduced pressure. The residue was purified by trituration with water (1000 mL). The precipitated solids were collected by filtration and washed with $Et_2O$ (3×100 mL). This resulted in methyl 1-(3-fluoro-4-iodopyridin-2-yl)pyrazole-3-carboxylate (40.00 g, 55.54%) as a white solid. LC-MS: (ES+H, m/z): $[M+H]^+$=348.0. $^1H$ NMR (300 MHz. DMSO-$d_6$) δ 8.51 (d, J=2.7, 1H), 8.13-8.00 (m, 2H), 7.03 (d, J=2.7 Hz, 1H), 3.87 (s, 3H). Step 2: Preparation of methyl 1-{4-[(tert-butoxycarbonyl)amino]-3-fluoropyridin-2-yl}pyrazole-3-carboxylate To a stirred mixture of methyl 1-(3-fluoro-4-iodopyridin-2-yl)pyrazole-3-carboxylate (50.00 g, 144.06 mmol, 1.00 equiv) and tert-butyl carbamate (33.75 g, 288.12 mmol, 2.00 equiv) in dioxane (200 mL) were added CsF (65.65 g, 432.18 mmol, 3.00 equiv), XantPhos (8.33 g, 14.41 mmol, 0.10 equiv) and Pd: (dba) 3 (6.59 g. 7.20 mmol, 0.05 equiv) at room temperature under nitrogen atmosphere. The resulting mixture was stirred for 2 h at 100° C., under nitrogen atmosphere. The reaction was monitored by LCMS. The mixture was allowed to cool down to room temperature. The resulting mixture was filtered, the filter cake was washed with EtOAc (3 ×400 mL). The filtrate was concentrated under reduced pressure. The residue was purified by silica gel column chromatography to afford methyl 1-{4-[(tert-butoxycarbonyl)amino]-3-fluoropyridin-2-yl}pyrazole-3-carboxylate (42.2 g, 87.15%) as a yellow solid. LC-MS: (ES+H, m/z): $[M+H]^+$=337.15.

Step 3: Preparation of methyl 1-(4-amino-3-fluoropyridin-2-yl)pyrazole-3-carboxylate A solution of methyl 1-{4-[(tert-butoxycarbonyl)amino]-3-fluoropyridin-2-yl}pyrazole-3-carboxylate (50 g. 148.67 mmol, 1.00 equiv) in DCM (500 mL) was treated with TFA (250 mL) for 1 h at room temperature under nitrogen atmosphere. The reaction was monitored by LCMS. The resulting mixture was concentrated under reduced pressure. The resulting mixture was diluted with DCM (250 mL). The mixture was basified to pH 9 with saturated $NaHCO_3$(aq.). The resulting mixture was extracted with $CH_2Cl_2$ (3×250 mL). The combined organic layers were washed with brine (1×1000 mL), dried over anhydrous $Na_2SO_4$. After filtration, the filtrate was concentrated under reduced pressure, to afford methyl 1-(4-amino-3-fluoropyridin-2-yl)pyrazole-3-carboxylate (31.36 g. 89.30%) as a white solid. LC-MS: (ES+H, m/z): $[M+H]^+$=237.1

Step 4: Preparation of methyl 1-(4-amino-3-fluoro-5-iodopyridin-2-yl)pyrazole-3-carboxylate A solution of methyl 1-(4-amino-3-fluoropyridin-2-yl) pyrazole-3-carboxylate (40.00g. 169.34 mmol. 1.00 equiv). NIS (45.70 g. 203.21 mmol. 1.20 equiv) and TsOH.$H_2O$ (1.61 g. 8.47 mmol. 0.05 equiv) in MeCN(250 mL) was stirred for 2 h at 60° C., under nitrogen atmosphere. The reaction was monitored by LCMS. The mixture was allowed to cool down to room temperature. The resulting mixture was diluted with ethyl acetate (500 mL). The combined organic layers were washed with brine (3 ×500 mL), dried over anhydrous $Na_2SO_4$ to afford methyl 1-(4-amino-3-fluoro-5-iodopyridin-2-yl)pyrazole-3-carboxylate (58.7 g. 92.67%) as a yellow solid. LC-MS: (ES+H, m/z): $[M+H]^+$=362.90. $^1H$ NMR (300 MHz. DMSO-$d_6$) δ 8.40 (d. J=2.6 Hz, 1H), 8.24 (s, 1H), 6.99 (d. J=2.6 Hz, 1H), 6.78 (s, 2H), 3.86 (s, 3H).

Step 5: Preparation of methyl 1-(4-amino-3-fluoro-5-methylpyridin-2-yl)pyrazole-3-carboxylate A mixture of methyl 1-(4-amino-3-fluoro-5-iodopyridin-2-yl)pyrazole-3-carboxylate (25.00 g. 69.04 mmol. 1.00 equiv). Pd(dppf) $Cl_2$ (5.01 g. 6.90 mmol. 0.10 equiv). $Cs_2CO_3$ (67.49 g. 207.12 mmol. 3.00 equiv) and trimethyl-1.3.5.2.4.6-trioxatriborinanc (87.05 g. 345.20 mmol. 5.00 equiv. 50 wt %) in dioxane (400 mL) was stirred for 2 h at 100° C., under nitrogen atmosphere. The reaction was monitored by LCMS. The mixture was allowed to cool down to room temperature. The resulting mixture was filtered, the filter cake was washed with ethyl acetate (3×1000 mL). The filtrate was concentrated under reduced pressure. The residue was purified by silica gel column chromatography to afford methyl 1-(4-amino-3-fluoro-5-methylpyridin-2-yl) pyrazole-3-carboxylate (17.10 g. 99.01%) as a light-yellow solid. LC-MS: (ES+H, m/z): $[M+H]^+$=251.2.

Step 6: Preparation of methyl 1-{3'-fluoro-4-hydroxy-2,5'-dimethyl-6-oxo-[1,4'-bipyridin]-2'-yl} pyrazole-3-carboxylate To a solution of methyl 1-(4-amino-3-fluoro-5-methylpyridin-2-yl)pyrazole-3-carboxylate (25.00g. 99.91 mmol.

1.00 equiv) and 2.2-dimethyl-6-(2-oxopropyl)-1,3-dioxin-4-one (36.78 g. 199.82 mmol. 2.00 equiv) in dioxane (260 mL) was added Ti (Oi-Pr)+ (2.84 g. 9.99 mmol. 0.10 equiv), the resulting mixture was stirred for 1 h at 90° C., under nitrogen atmosphere. The reaction was monitored by LCMS. The mixture was allowed to cool down to room temperature. The mixture was followed by the addition of $H_2SO_4$ (9.79 g. 99.91 mmol. 1.00 equiv) dropwise at room temperature. The resulting mixture was stirred for Ih at 90° C., under nitrogen atmosphere. The reaction was monitored by LCMS. The mixture was allowed to cool down to room temperature. The resulting mixture was concentrated under reduced pressure. The residue was purified by trituration with water (200 mL) and Et.O (100 mL). The precipitated solids were collected by filtration and washed with Et,O (3×100 mL), to afford methyl 1-{3'-fluoro-4-hydroxy-2.5'-dimethyl-6-oxo-[1,4'-bipyridin]-2'-x1} pyrazole-3-carboxylate (15.38 g. 42.97%) as a brown solid. LC-MS: (ES+H, m/z): $[M+H]^+$=359.0.

Step 7: Preparation of methyl 1-{4-[(3,5-difluoro-pyridin-2-yl) ($^2H_2$)methoxy]-3'-fluoro-2,5'-dimethyl-6-oxo-[1,4'-bipyridin]-2'-yl}pyrazole-3-carboxylate To a stirred mixture of methyl 1-{3'-fluoro-4-hydroxy-2.5'-dimethyl-6-oxo-[1,4'-bipyridin]-2'-yl}pyrazole-3-carboxylate (10.00 g. 42.51 mmol. 1.00 equiv) and 2-[chloro ($H_2$) methyl]-3,5-difluoropyridine (10.52 g. 63.77 mmol. 1.50 equiv) in DMF (100 mL) were added $Cs_2CO_3$ (41.56 g. 127.53 mmol. 3.00 equiv) and 18-Crown-6 (1.12 g. 4.25 mmol, 0.10 equiv) at room temperature under nitrogen atmosphere. The resulting mixture was stirred for 2 h at 70° C., under nitrogen atmosphere. The reaction was monitored by LCMS. The mixture was allowed to cool down to room temperature. The resulting mixture was diluted with EtOAc (500 mL). The organic layers were washed with water (5×500 mL), dried over anhydrous $Na_2SO_4$. After filtration, the filtrate was concentrated under reduced pressure. The residue was purified by silica gel column chromatography to afford methyl 1-{4-[(3.5-difluoropyridin-2-yl) ($^2H_2$) methoxy]-3'-fluoro-2.5'-dimethyl-6-oxo-[1,4'-bipyridin]-2'-yl}pyrazole-3-carboxylate (7.25 g. 34.99%) as a white solid. LC-MS: (ES+H, m/z): $[M+H]^+$=488.15.

Step 8: Preparation of methyl 1-{3-chloro-4-[(3,5-difluoropyridin-2-yl) ($^2H_2$)methoxy]-3'-fluoro-5',6-dimethyl-2-oxo-[1,4'-bipyridin]-2'-yl}pyrazole-3-carboxylate A mixture of methyl 1-{4-[(3.5-difluoropyridin-2-yl) ($^2H_2$)methoxy]-3'-fluoro-2.5'-dimethyl-6-oxo-[1,4'-bipyridin]-2'-x1} pyrazole-3-carboxylate (10.00 g. 20.52 mmol. 1.00 equiv). NCS (3.56 g. 26.68 mmol. 1.30 equiv) and 2.2-dichloroacetic acid (0.26 g. 2.05 mmol. 0.10 equiv) in i-PrOH (100 mL) was stirred for Ih at 60° C., under nitrogen atmosphere. The reaction was monitored by LCMS. The mixture was allowed to cool down to room temperature. The resulting mixture was diluted with EtOAc (200 mL). The resulting mixture was washed with 3×200 ml of water. The resulting mixture was concentrated under reduced pressure. The residue was purified by silica gel column chromatography to afford methyl 1-{3-chloro-4-[(3.5-difluoropyridin-2-yl) ($^2H_2$)methoxy]-3'-fluoro-5'.6-dimethyl-2-oxo-[1,4'-bipyridin]-2'-yl}pyrazole-3-carboxylate (6.20g. 57.91%) as a white solid. LC-MS: (ES+H, m/z): $[M+H]^+$=522.2.

Step 9: Preparation of 3-chloro-4-[(3,5-difluoropyridin-2-yl) ($^2H_2$)methoxy]-3'-fluoro-2'-[3-(2-hydroxypropan-2-yl)pyrazol-1-yl]-5',6-dimethyl-[1,4'-bipyridin]-2-one To a stirred solution of methyl 1-{3-chloro-4-[(3.5-difluoropyridin-2-yl) ($^2H_2$)methoxy]-3'-fluoro-5'0.6-dimethyl-2-oxo-[1,4'-bipyridin]-2'-yl}pyrazole-3-carboxylate (5.00g. 9.58 mmol. 1.00 equiv) in THF (50 mL) was added $CH_3MgBr$ (31.93 mL. 95.80 mmol. 10.00 equiv (3M in THF)) dropwise at 0° C., under nitrogen atmosphere. The resulting mixture was stirred for 2 h at 0° C., under nitrogen atmosphere. Desired product could be detected by LCMS. The mixture was allowed to cool down to 0° C. The reaction was quenched by the addition of sat. $NH_4Cl$ (aq.) (150 mL) at 0° C. The resulting mixture was extracted with EtOAc (4×300 mL). The combined organic layers were washed with brine (300 mL), dried over anhydrous $Na_2SO_4$. After filtration, the filtrate was concentrated under reduced pressure. The residue was purified by silica gel column chromatography the filtrate was concentrated under reduced pressure to afford 3-chloro-4-[(3.5-difluoropyridin-2-yl) ($^2H_2$)methoxy]-3'-fluoro-2'-[3-(2-hydroxypropan-2-yl)pyrazol-1-yl]-5'0.6-dimethyl-[1,4'-bipyridin]-2-one (2.43 g. 48.61%) as a white solid. LC-MS: (ES+H, m/z): $[M+H]^+$=522.1.

Step 10: Preparation of (Example 58A) rel-3-chloro-4-[(3,5-difluoropyridin-2-yl) ($^2H_2$)methoxy]-3'-fluoro-2'-[3-(2-hydroxypropan-2-yl)pyrazol-1-yl]-5',6-dimethyl-[1,4'-bipyridin]-2-one The rac-mixture (17.50 g) was separated by Prep-Chiral SFC to afford rel-3-chloro-4-[(3,5-difluoropyridin-2-yl) ($^2H_2$)methoxy]-3'-fluoro-2'-[3-(2-hydroxypropan-2-yl)pyrazol-1-yl]-5',6-dimethyl-[1,4'-bipyridin]-2-one (Example 58A, 6.49 g, ee=100%).

EXAMPLE 58A

LC-MS: (ES+H, m/z): $[M+H]^+$=522.15. $^1H$ NMR (400 MHZ, DMSO-$d_6$) δ 8.61 (d, J=2.3 Hz, 1H), 8.50 (s, 1H), 8.37 (d, J=2.6 Hz, 1H), 8.15-8.06 (m, 1H), 6.91 (s, 1H), 6.60 (d, J=2.6 Hz, 1H), 5.13 (s, 1H), 2.09 (d, J=16.1 Hz, 6H), 1,48 (s, 6H). $^{19}F$ NMR (377 MHz, DMSO) δ-120.25,-120.27,-122.29,-122.31,-137.97.

EXAMPLE 59A, 59B

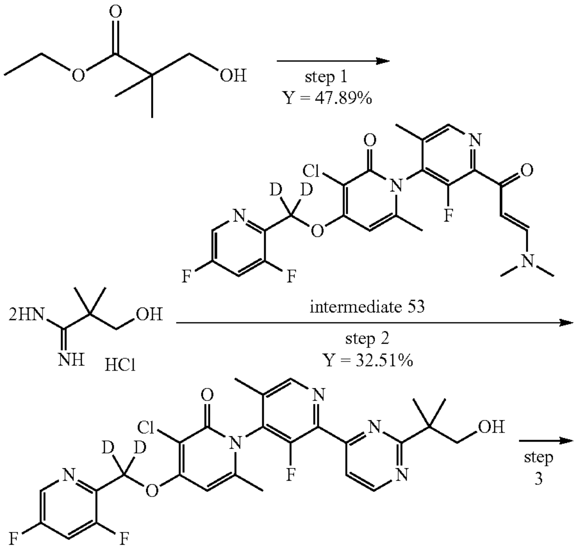

Example 59

-continued

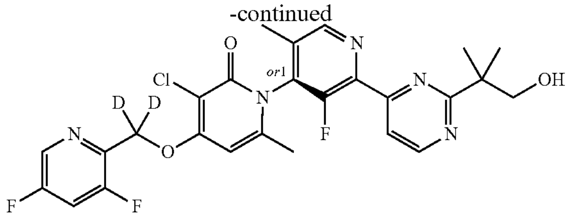

isomer 1
Example 59A

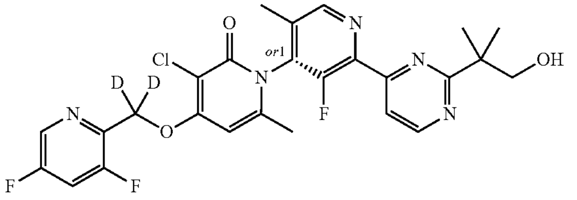

isomer 2
Example 59B

Step 1: Preparation of 3-hydroxy-2,2-dimethylpropanimidamide hydrochloride

To a stirred mixture of $NH_4Cl$ (7.32 g, 136.81 mmol, 5.00 equiv) in Toluene (20 mL) was added $AlMe_3$ (9.86 g, 136.81 mmol, 5.00 equiv) dropwise at 0° C., under nitrogen atmosphere. The resulting mixture was stirred for 10 min at 0° C., under nitrogen atmosphere, then the mixture was warmed to r.t, until no generation of gas. To the above mixture was added a solution of ethyl 3-hydroxy-2,2-dimethylpropanoate (4.00 g, 27.36 mmol, 1.00 equiv) in Tol dropwise at r.t. The resulting mixture was stirred overnight at 80° C. The reaction was monitored by LCMS. The reaction was quenched by the addition of MeOH (50 mL) at 0° C. The resulting mixture was filtered, the filter cake was washed with MeOH (300 mL). The filtrate was concentrated under reduced pressure. The residue was dissolved in EtOH (20 mL). The resulting mixture was filtered, the filter cake was washed with EtOH (5 mL). The filtrate was concentrated under reduced pressure. This resulted in 3-hydroxy-2,2-dimethylpropanimidamide hydrochloride (2 g, 47.89%) as a white solid. $^1$H NMR (300 MHz, DMSO-$d_6$) δ 9.01 (s, 2H), 8.61 (s, 2H), 5.41 (t, 1H), 3.46 (d, 2H), 1.15 (s, 6H). Step 2: Preparation of 3-chloro-4-((3,5-difluoropyridin-2-yl)methoxy-d2)-3'-fluoro-2'-(2-(1-hydroxy-2-methylpropan-2-yl)pyrimidin-4-yl)-5',6-dimethyl-2H-[1,4'-bipyridin]-2-one A solution of (E)-3-chloro-4-((3,5-difluoropyridin-2-yl)methoxy-d2)-2'-(3-(dimethy lamino) acryloyl)-3'-fluoro-5',6-dimethyl-2H- [1,4'-bipyridin]-2-one (500 mg, 1.01 mmol, 1.00 equiv) in DMF (20 mL) was added 3-hydroxy-2,2-dimethylpropanimidamide hydrochloride (1.17 g, 10.10 mmol, 10.00 equiv) and $K_2CO_3$ (1,40 g, 10.10 mmol, 10.00 equiv). The resulting mixture was stirred for 2 h at 80° C., under nitrogen atmosphere. The reaction was monitored by LCMS. Desired product could be detected by LCMS. The mixture was allowed to cool down to room temperature. The resulting mixture was poured into water (20 mL) and extracted with EtOAc (3×20 mL). The combined organic layers were washed with brine (2×10 mL), dried over anhydrous $Na_2SO_4$. After filtration, the filtrate was concentrated under reduced pressure. The crude residue (500 mg) was purified by HP-Flash to afford the crude product (280 mg) which was further purified by PREP-HPLC to afford 3-chloro-4-((3,5-difluoropyridin-2-yl)methoxy-d2)-3'-fluoro-2'-(2-(1-hydroxy-2-methylpropan-2-yl)pyrimidin-4-yl)-5',6-dimethyl-2H-[1,4'-bipyridin]-2-one (180 mg, 32.51%) as a yellow solid. LC-MS: (ES+H, m/z): $[M+H]^+$=548.2.

Step 3: Preparation of rel-3-chloro-4-((3,5-difluoropyridin-2-yl)methoxy-d2)-3'-fluoro-2'-(2-(1-hydroxy-2-methylpropan-2-yl)pyrimidin-4-yl)-5',6-dimethyl-2H-[1,4'-bipyridin]-2-one & rel-3-chloro-4-((3,5-difluoropyridin-2-yl)methoxy-d2)-3'-fluoro-2'-(2-(1-hydroxy-2-methylpropan-2-yl)pyrimidin-4-yl)-5',6-dimethyl-2H-[1,4'-bipyridin]-2-one- The racemate (180 mg) was separated by Prep-CHIRAL-HPLC to afford Example 59A (66.6 mg, 99.1% purity, 95.1% deuterium purity, ee=97.7%) as a white solid and Example 59B (62.0 mg, 99.3% purity, 95.5% deuterium purity, ee=98.3%).

EXAMPLE 59A

LC-MS: (ES+H, m/z): $[M+H]^+$=548.1. $^1$H NMR (300 MHz, DMSO-$d_6$) δ 8.97 (d, 1H), 8.77 (s, 1H), 8.62 (d, 1H), 8.17-8.06 (m, 1H), 7.97 (d, 1H), 6.91 (s, 1H), 4.58 (t, 1H), 3.69 (d, 2H), 2.17 (s, 3H), 2.05 (s, 3H), 1.32 (s, 6H). $^{19}$F NMR (282 MHz, DMSO) δ-120.25,-120.27,-122.33,-122.35,-132.33.

EXAMPLE 59B

LC-MS: (ES+H, m/z): $[M+H]^+$=548.1. $^1$H NMR (300 MHz, DMSO-$d_6$) δ 8.97 (d, 1H), 8.77 (d, 1H), 8.62 (d, 1H), 8.17-8.04 (m, 1H), 7.97 (d, 1H), 6.91 (d, 1H), 4.58 (t, 1H), 3.69 (d, 2H), 2.17 (s, 3H), 2.05 (s, 3H), 1.32 (s, 6H). $^{19}$F NMR (282 MHz, DMSO) δ-120.25,-120.28,-122.33,-122.35,-132.33.

EXAMPLE 60A, 60B

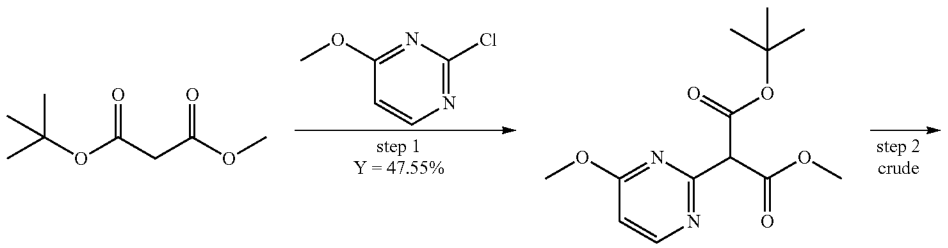

-continued
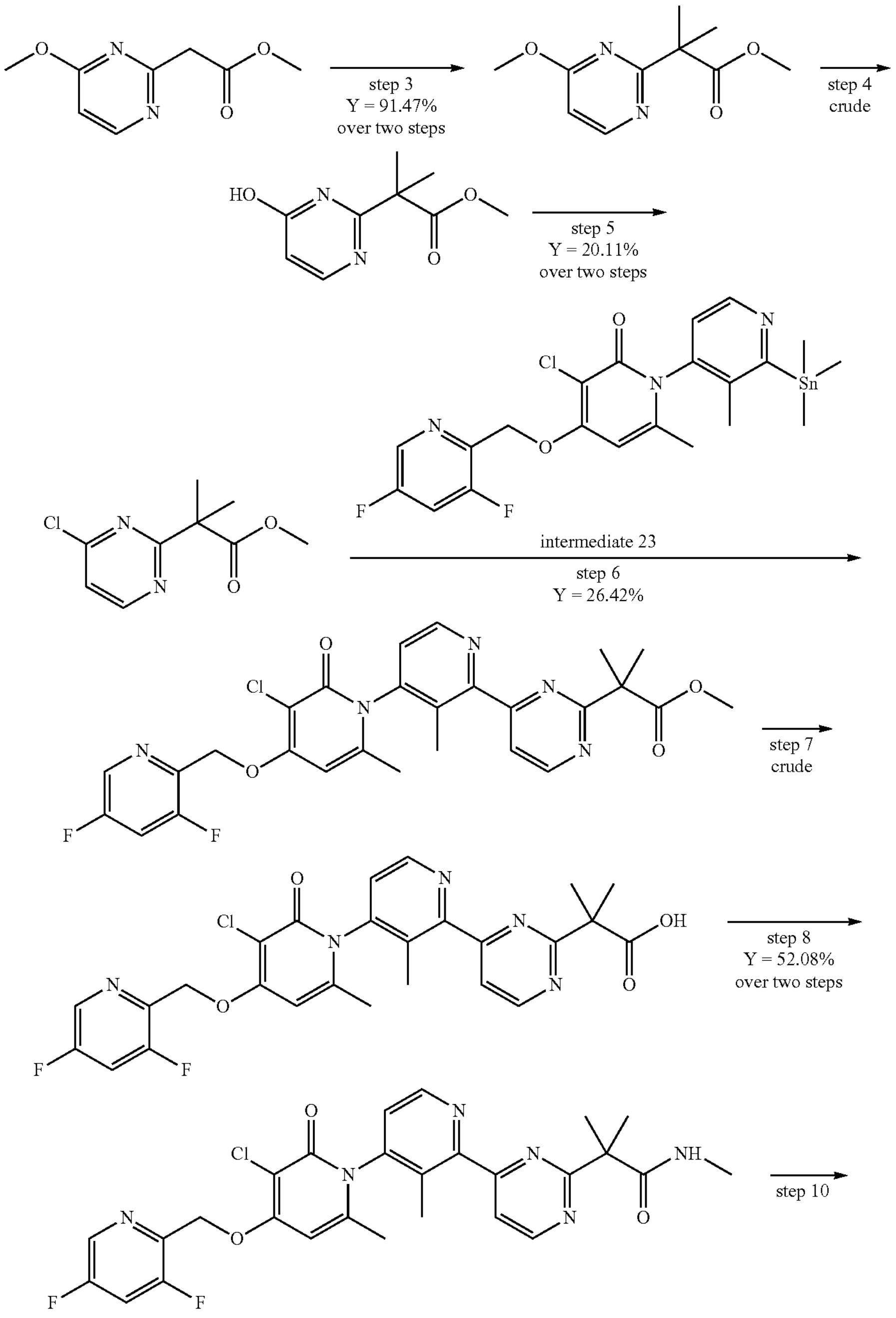
Example 60
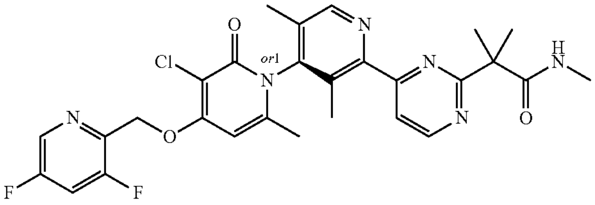
isomer 1
Example 60A
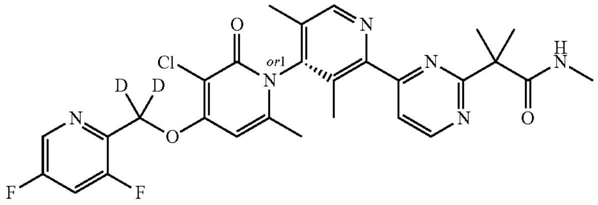
isomer 2
Example 60B Step 1: Preparation of 1-tert-butyl 3-methyl 2-(4-methoxypyrimidin-2-yl) propanedioate To a stirred solution of 1-tert-butyl 3-methyl propanedioate (33.74 g, 193.69 mmol, 4.00 equiv) in DMF (70 mL) was added NaH (6.97 g, 290.53 mmol, 6.00 equiv) in portions at 0° C. The resulting mixture was stirred for 30 min at room temperature under nitrogen atmosphere. To the above mixture was added 2-chloro-4-methoxypyrimidine (7.00 g, 48.42 mmol, 1.00 equiv). The resulting mixture was stirred overnight at 80° C., under nitrogen atmosphere. The reaction was monitored by LCMS. The reaction was quenched by the addition of sat. $NH_4Cl$ (aq.) (100 mL) at 0° C. The resulting mixture was extracted with EtOAc (3 ×100 mL). The combined organic layers were washed with brine (200 ml), dried over anhydrous $Na_2SO_4$. After filtration, the filtrate was concentrated under reduced pressure. The residue was purified by silica gel column chromatography to afford 1-tert-butyl 3-methyl 2-(4-methoxypyrimidin-2-yl) propanedioate (6.50 g, 47.55%) as a yellow liquid. LC-MS: (ES+H, m/z): $[M+H]^+$=283.1. $^1$H NMR (400 MHZ, DMSO-$d_6$) δ 8.51 (d, 1H), 6.91 (d, 1H), 4.96 (s, 1H), 3.89 (s, 3H), 3.70 (s, 3H), 1,42 (s, 9H).

Step 2: Preparation of methyl 2-(4-methoxypyrimidin-2-yl)acetate

To a stirred mixture of 1-tert-butyl 3-methyl 2-(4-methoxypyrimidin-2-yl) propanedioate (6.5 g, 23.02 mmol, 1 equiv) in DCM (60 mL) was added TFA (30 mL) dropwise at room temperature. The resulting mixture was stirred for 1 h at room temperature. The reaction was monitored by LCMS. The resulting mixture was concentrated under reduced pressure to afford methyl 2-(4-methoxypyrimidin-2-yl) acetate (4.5 g, crude) as a yellow liquid. LC-MS: (ES+H, m/z): $[M+H]^+$=183.1. $^1$H NMR (300 MHZ, DMSO-$d_6$) δ 8.47 (d, 1H), 6.85 (d, 1H), 3.90 (s, 3H), 3.89 (s, 2H), 3.65 (s, 3H).

Step 3: Preparation of methyl 2-(4-methoxypyrimidin-2-yl)-2-methylpropanoate

To a stirred mixture of methyl 2-(4-methoxypyrimidin-2-yl)acetate (4.41 g, assumed 100% yield, 24.20 mmol, 1.00 equiv) in THF (50 mL) was added LiHMDS (26.62 mL, 26.62 mmol, 1.10 equiv) dropwise at −78° C., under nitrogen atmosphere. The resulting mixture was stirred for 30 min at −78° C., under nitrogen atmosphere. To the above mixture was added $CH_3I$ (3.78 g, 26.62 mmol, 1.10 equiv) dropwise at −78° C., under nitrogen atmosphere. The resulting mixture was stirred for additional 1h at room temperature. Then to the above mixture was added LiHMDS (26.62 mL, 26.62 mmol, 1.10 equiv) dropwise at −78° C. The resulting mixture was stirred for 30 min at −78° C., under nitrogen atmosphere. To the above mixture was added $CH_3I$ (3.78 g. 26.62 mmol. 1.10 equiv) dropwise at −78° C., under nitrogen atmosphere. The resulting mixture was stirred for additional Ih at room temperature. The reaction was monitored by LCMS. The reaction was quenched with sat. $NH_4Cl$ (aq.) at 0° C. The resulting mixture was extracted with EtOAc (3 ×200 mL). The combined organic layers were washed with brine, dried over anhydrous $Na_2SO_4$. After filtration, the filtrate was concentrated under reduced pressure to afford methyl 2-(4-methoxypyrimidin-2-yl)-2-methylpropanoate (4.75 g. 91.47%) as a yellow liquid. LC-MS: (ES+H, m/z): $[M+H]^+$=211.05. 1H NMR (300 MHz. DMSO-$d_6$) δ 8.47 (d, 1H), 6.86 (d, 1H), 3.89 (s, 3H), 3.61 (s, 3H), 1.52 (s. 6H).

Step 4: Preparation of methyl 2-(4-hydroxypyrimidin-2-yl)-2-methylpropanoate

A mixture of methyl 2-(4-methoxypyrimidin-2-yl)-2-methylpropanoate (4.75 g. 22.59 mmol. 1.00 equiv) and TMSI (18.08 g. 90.37 mmol. 4.00 equiv) in ACN (50 mL) was stirred overnight at 80° C. The reaction was monitored by LCMS. The resulting mixture was concentrated under reduced pressure to afford methyl 2-(4-hydroxypyrimidin-2-yl)-2-methylpropanoate (8.24 g, crude) as a brown solid. LC-MS: (ES+H, m/z): $[M+H]^+$=197.1.

Step 6: Preparation of methyl 2-(4-{3-chloro-4-[(3,5-difluoropyridin-2-yl)methoxy]-3',6-dimethyl-2-oxo-[1,4'-bipyridin]-2'-yl}pyrimidin-2-yl)-2-methylpropanoate To a stirred solution of 3-chloro-4-[(3.5-difluoropyridin-2-yl)methoxy]-3'0.6-dimethyl-2'-(trimethylstannyl)-[1,4'-bipyridin]-2-one (920 mg, assumed 100% yield. 1.70 mmol. 1.00 equiv), methyl 2-(4-chloropyrimidin-2-yl)-2-methylpropanoate (365 mg, 1.70 mmol. 1.00 equiv) in 1,4-dioxane (15 ml) were added $Pd(PPh_3)$: $Cl_2$ (238 mg, 0.34 mmol. 0.20 equiv) and CuI (324 mg, 1.70 mmol. 1.00 equiv). The resulting mixture was stirred for 2 h at 120° C., under nitrogen atmosphere. The reaction was monitored by LCMS. Desired product could be detected by LCMS. The mixture was allowed to cool down to room temperature. The resulting mixture was concentrated under reduced pressure. The residue was purified by silica gel column chromatography to afford crude product. The crude product was purified by reverse phase flash to afford methyl 2-(4-{3-chloro-4-[(3.5-difluoropyridin-2-yl)methoxy]-3'0.6-dimethyl-2-oxo-[1,4'-bipyridin]-2'-yl}pyrimidin-2-yl)-2-methylpropanoate (250 mg. 26.42%, over two steps) as a yellow oil. LC-MS: (ES+H, m/z): $[M+H]^+$=556.1. $^1$H NMR (400 MHz. DMSO-$d_6$) δ 8.98 (d, 1H), 8.77 (d, 1H), 8.60 (d. 1H), 8.14-8.04 (m, 1H), 7.94 (d, 1H), 7.58 (d, 1H), 6.83 (s, 1H), 5.49 (d, 2H), 3.59 (s, 3H), 2.16 (s, 3H), 1.96 (s. 3H), 1.59 (s. 6H).

Step 8: Preparation of 2-(4-{3-chloro-4-[(3,5-difluoropyridin-2-yl)methoxy]-3',6-dimethyl-2-oxo-[1,4'-bipyridin]-2'-yl}pyrimidin-2-yl)-2-methylpropanoic acid To a stirred solution methyl 2-(4-{3-chloro-4-[(3.5-difluoropyridin-2-yl)methoxy]-3'0.6-dimethyl-2-oxo-[1,4'-bipyridin]-2'-yl}pyrimidin-2-yl)-2-methylpropanoate (300 mg, 0.54 mmol. 1.00 equiv) in THF (6 mL) was added a solution of LiOH (26 mg, 1.08 mmol. 2.00 equiv) in $H_2O$ (3 mL) dropwise at room temperature under nitrogen atmosphere. The resulting mixture was stirred for 2 h at 80° C., under nitrogen atmosphere. The reaction was monitored by LCMS. Desired product could be detected by LCMS. The mixture was allowed to cool down to room temperature. The resulting mixture was concentrated under reduced pressure. The resulting mixture (300 mg) was used in the next step directly without further purification. LC-MS: (ES+H, m/z): $[M+H]^+$=542.3.

Step 9: Preparation of 2-(4-{3-chloro-4-[(3,5-difluoropyridin-2-yl)methoxy]-3',6-dimethyl-2-oxo-[1,4'-bipyridin]-2'-yl}pyrimidin-2-yl)-N,2-dimethylpropanamide To a stirred solution of 2-(4-{3-chloro-4-[(3.5-difluoropyridin-2-yl)methoxy]-3'0.6-dimethyl-2-oxo-[1,4'-bipyridin]-2'-yl}pyrimidin-2-yl)-2-methylpropanoic acid (292 mg, assumed 100% yield. 0.55 mmol. 1.00 equiv) in ACN(3 mL) were added Methylamine (0.8 mL. 2M in THF) and NMI (454 mg. 5.540 mmol. 10.00 equiv) and TCFH (776 mg. 2.77 mmol. 5.00 equiv) at room temperature under nitrogen atmosphere. The resulting mixture was stirred for 1 h at room temperature under nitrogen atmosphere. The reaction was monitored by LCMS. The resulting mixture was diluted with EA (50 mL), then washed with water (2×50 mL) and brine (50 mL), the organic layer was concentrated to afford crude product (300 mg), which was further purified by Prep-HPLC to afford 2-(4-{3-chloro-4-[(3.5-difluoropyridin-2-yl)methoxy]-3'0.6-dimethyl-2-oxo-[1,4'-bipyridin]-2'-yl}pyrimidin-2-yl)-N.2-dimethylpropanamide (160 mg. 52.08%, over two steps) as a white solid. LC-MS: (ES+H, m/z): [M+H]$^+$=555.3.

Step 10: Preparation of rel-2-(4-(3-chloro-4-((3,5-difluoropyridin-2-yl)methoxy)-3',6-dimethyl-2-oxo-2H-[1,4'-bipyridin]-2'-yl)pyrimidin-2-yl)-N,2-dimethylpropanamide and rel-2-(4-(3-chloro-4-((3,5-difluoropyridin-2-yl)methoxy)-3',6-dimethyl-2-oxo-2H-[1,4'-bipyridin]-2'-yl)pyrimidin-2-yl)-N,2-dimethylpropanamide The racemate (160 mg) was separated by PREP-CHIRAL-HPLC to afford rel-2-(4-(3-chloro-4-((3.5-difluoropyridin-2-yl)methoxy)-3'0.6-dimethyl-2-oxo-2H-[1,4'-bipyridin]-2'-yl)pyrimidin-2-yl)-N.2-dimethylpropanamide (Example 60A: 44.2 mg. 99.6% purity, ee=100%) as a white solid and rel-2-(4-(3-chloro-4-((3.5-difluoropyridin-2-yl) methoxy)-3'0.6-dimethyl-2-oxo-2H-[1,4'-bipyridin]-2'-yl) pyrimidin-2-yl)-N.2-dimethylpropanamide (Example 60B: 42.6 mg. 99.2% purity, ee=100%) as a white solid.

EXAMPLES 60A

LC-MS: (ES+H, m/z): [M+H]$^+$=555.1. $^{1}$H NMR (400 MHZ. DMSO-$d_6$) δ 8.95 (d, 1H), 8.77 (d. 1H), 8.61 (d, 1H), 8.15-8.05 (m, 1H), 7.91 (d, 1H), 7.57 (d, 1H), 7.41 (q. 1H), 6.83 (s, 1H), 5.49 (d, 2H). 2.54 (d, 3H), 2.19 (s, 3H), 1.96 (s, 3H), 1.54 (s, 3H), 1.54 (s, 3H). $^{19}$F NMR (377 MHz. DMSO) δ-120.14, —120.16, -122.34, -122.36.

EXAMPLE 60B

LC-MS: (ES+H, m/z): [M+H]$^+$=555.1. $^{1}$H NMR (400 MHZ. DMSO-$d_6$) δ 8.95 (d, 1H), 8.77 (d. 1H), 8.61 (d, 1H), 8.14-8.05 (m. 1H), 7.91 (d, 1H), 7.57 (d, 1H), 7.41 (q. 1H), 6.83 (s, 1H), 5.49 (d, 2H). 2.55 (d, 3H), 2.19 (s, 3H), 1.96 (s, 3H), 1.54 (s, 3H), 1.54 (s, 3H). $^{19}$F NMR (377 MHz. DMSO) δ-120.14, —120.16, -122.34, -122.36.

EXAMPLE 61A, 61B

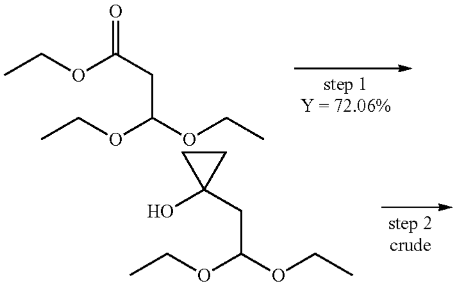

-continued

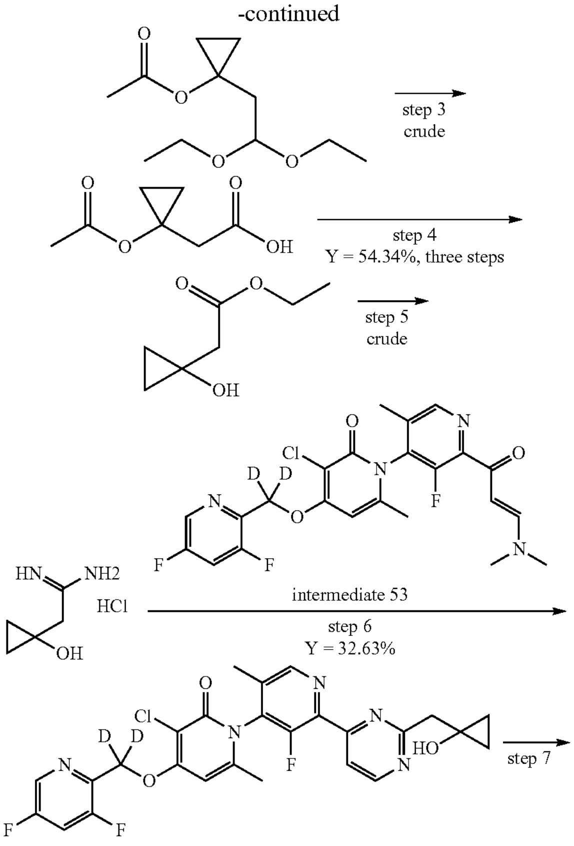

Example 61

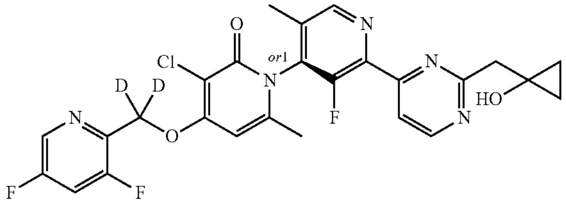

isomer 1
Example 61A

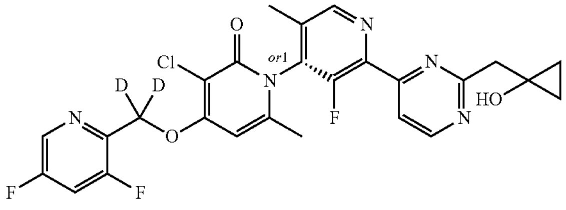

isomer 2
Example 61B

Step 1: Preparation of 1-(2,2-diethoxyethyl)cyclopropan-1-ol

To a stirred mixture of ethyl 3,3-diethoxypropanoate (10.00 g, 52.56 mmol, 1.00 equiv) and Ti (Oi-Pr)+ (22.41 g, 78.84 mmol, 1.50 equiv) in Et,O (80 mL) and THF (20 mL) was added EtMgBr in 2-methyl-THF (3.4 M, 61 mL, 210.26 mmol, 4.00 equiv) dropwise at 0° C., under nitrogen atmosphere. The resulting mixture was stirred overnight at room temperature under nitrogen atmosphere. The reaction was monitored by TLC (PE/EA=5:1, Rf=0.3). The reaction was quenched by the addition of water (100 mL) at 0° C. The resulting mixture was extracted with Et.O (3×100 mL), the organic phase was combined and dried over anhydrous $Na_2SO_4$. After filtration, the filtrate was concentrated under reduced pressure. The residue was purified by silica gel column chromatography, the pure fraction was concentrated under reduced pressure to afford 1-(2,2-diethoxyethyl)cyclopropan-1-ol (6.60 g. 72.06%) as a yellow liquid. $^1$H NMR (300 MHZ, Chloroform-d) § 4.82 (t, 1H), 3.79-3.70 (m, 3H), 3.59-3.55 (m, 2H), 1.91 (d, 2H), 1.28-1.23 (m, 6H), 0.81-0.76 (m, 2H), 0.49-0.44 (m, 2H).

Step 2: Preparation of 1-(2,2-diethoxyethyl)cyclopropyl acetate

To a stirred solution of 1-(2,2-diethoxyethyl)cyclopropan-1-ol (6.60 g, 37.87 mmol, 1.00 equiv) and DMAP (5.09 g, 41.66 mmol, 1.10 equiv) in $Et_2O$ (60 mL) was added acetic anhydride (5.80 g, 56.81 mmol, 1.50 equiv) dropwise at 0° C., under nitrogen atmosphere. The resulting mixture was stirred for 1 h at 0° C., under nitrogen atmosphere. The reaction was monitored by TLC (PE/EA=5:1,Rf=0.4). The reaction was quenched with sat. $NaHCO_3$(aq.) at 0° C. The aqueous layer was extracted with Et-O (3×100 mL). The resulting mixture was concentrated under vacuum. The residue was purified by silica gel column chromatography, the pure fraction was concentrated under reduced pressure to afford 1-(2,2-diethoxyethyl)cyclopropyl acetate (7.00 g, crude) as a yellow liquid. $^1$H NMR (400 MHZ, Chloroform-d) 8 4.71 (t, 1H), 3.63-3.59 (m, 2H), 3.51-3.47 (m, 2H), 2.08 (d, 2H), 1.98 (s, 3H), 1.20 (t, 6H), 0.85-0.81 (m, 2H), 0.78-0.73 (m, 2H).

Step 3: Preparation of [1—(acetyloxy)cyclopropyl]acetic acid

To a stirred solution of 1-(2,2-diethoxyethyl)cyclopropyl acetate (7.00 g, 32.36 mmol, 1.00 equiv) in THF (25 mL) and $H_2O$ (50 mL) was added oxone (12.23 g. 72.75 mmol, 1.50 equiv) in portions at room temperature. The resulting mixture was stirred overnight at room temperature. The reaction was monitored by TLC (100% EA, Rf=0.1). The resulting mixture was diluted with water (100 mL). The resulting mixture was extracted with EtOAc (5×100 mL). The combined organic layers were dried over anhydrous $Na_2SO_4$. After filtration, the filtrate was concentrated under reduced pressure to afford [1-(acctyloxy)cyclopropyl]acetic acid (5.00 g, crude) as a yellow oil. $^1$H NMR (300 MHz. Chloroform-d) δ 2.85 (s, 2H), 2.04 (s, 3H), 1.06-0.99 (m, 2H), 0.93-0.90 (m, 2H).

Step 4: Preparation of ethyl 2-(1-hydroxycyclopropyl)acetate

To a stirred solution of [1—(acetyloxy)cyclopropyl]acetic acid (4.00 g. 25.29 mmol. 1.00 equiv) in EtOH (50 mL) was added $H_2SO_4$ (40 drops) dropwise at room temperature. The resulting mixture was stirred overnight at room temperature. The reaction was monitored by TLC (PE/EA=10:1. Rf=0.5). The reaction was quenched with sat. $NaHCO_3$(aq.) at room temperature. The aqueous layer was extracted with EtOAc (3×100 mL). The resulting mixture was concentrated under vacuum. The residue was purified by silica gel column chromatography, the pure fraction was concentrated under reduced pressure to afford ethyl 2-(1-hydroxycyclopropyl) acetate (2.50 g. 53.43%) as a yellow liquid. $^1$H NMR (400 MHZ. Chloroform-d) & 4.21 (q. 2H), 2.58 (s, 2H), 1.29 (t. 3H), 0.89-0.85 (m, 2H), 0.53-0.47 (m, 2H).

Step 5: Preparation of 2-(1-hydroxycyclopropyl)ethanimidamide hydrochloride

To a stirred mixture of NHCl (4.64 g. 86.70 mmol. 5.00 equiv) in Toluene (50 mL) was added AlMc3 (43 mL. 2 M in Toluene. 86.70 mmol. 5.00 equiv) dropwise at 0° C., under nitrogen atmosphere. The resulting mixture was stirred for 10 min at 0° C., under nitrogen atmosphere, and then was stirred at room temperature until no generation of gas. To the above mixture was added a solution of ethyl 2-(1-hydroxycyclopropyl)acetate (2.50 g. 17.34 mmol. 1.00 equiv) in toluene dropwise at r.t. The resulting mixture was stirred overnight at 80° C. The reaction was monitored by LCMS. The mixture was allowed to cool down to room temperature. The reaction was quenched by the addition of MeOH (30 mL) at 0° C. The resulting mixture was filtered, the filter cake was washed with MeOH (6×50 mL). The filtrate was concentrated under reduced pressure. The residue was dissolved in EtOH (50 mL). The resulting mixture was filtered, the filter cake was washed with EtOH (20 mL). The filtrate was concentrated under reduced pressure. This resulted in 2-(1-hydroxycyclopropyl)ethanimidamide hydrochloride (2.4 g, crude) as an orange oil. $^1$H NMR (300 MHz. DMSO-$d_6$) δ 8.98-8.72 (m, 4H), 5.80 (s, 1H), 2.62 (s, 2H), 0.67 (s. 4H). Step 6: Preparation of 3-chloro-4-((3,5-difluoropyridin-2-yl)methoxy-d2)-3'-fluoro-2'-(2-((1-hydroxycyclopropyl)methyl)pyrimidin-4-yl)-5',6-dimethyl-2H-[1,4'-bipyridin]-2-one To a stirred solution of 3-chloro-4-[(3.5-difluoropyridin-2-yl) ($^2H_2$)methoxy]-2'-[(2E)-3-(dimethylamino) prop-2-cnoyl]-3'-fluoro-5'0.6-dimethyl-[1,4'-bipyridin]-2-one (500 mg, 1.01 mmol. 1.00 equiv) and 2-(1-hydroxycyclopropyl) ethanimidamide hydrochloride (1.52 g. 10.10 mmol. 10.00 equiv) in DMF (5 mL) was added $K_2CO_3$ (2.79 g. 20.20 mmol. 20.00 equiv) at room temperature. The resulting mixture was stirred overnight at 60° C. The reaction was monitored by LCMS. The mixture was allowed to cool down to room temperature. The resulting mixture was diluted with water (20 mL). The aqueous layer was extracted with EtOAc (3×20 mL). The resulting mixture was concentrated under vacuum. The crude product was purified twice by Prep-HPLC to afford 3-chloro-4-((3.5-difluoropyridin-2-yl) methoxy-d2)-3'-fluoro-2'-(2-((1-hydroxycyclopropyl) methyl)pyrimidin-4-yl )-5'0.6-dimethyl-2H-[1,4'-bipyridin]-2-one (180 mg. 32.63%) as a yellow solid. LC-MS: (ES+H, m/z): $[M+H]^+$=546.3.

Step7: Preparation of rel-3-chloro-4-((3,5-difluoropyridin-2-yl)methoxy-d2)-3'-fluoro-2'-(2-((1-hydroxycyclopropyl)methyl)pyrimidin-4-yl)-5',6-dimethyl-2H-[1,4'-bipyridin]-2-one and rel-3-chloro-4-((3,5-difluoropyridin-2-yl)methoxy-d2)-3'-fluoro-2'-(2-((1-hydroxycyclopropyl)methyl)pyrimidin-4-yl)-5',6-dimethyl-2H-[1,4'-bipyridin]-2-one The racemate (180 mg) was separated by Prep-Chiral-HPLC, the pure fraction was concentrated under reduced pressure and lyophilized to afford Example 61A (62.1 mg, 98.9% purity, 95.3% deuterium purity, ee=100%) as a yellow solid and Example 61B (65.6 mg, 99.3% purity, 95.3% deuterium purity, ee=100%) as a white solid.

EXAMPLE 61A

LC-MS: (ES+H, m/z): $[M+H]^+$=546.3. $^1$H NMR (400 MHZ, DMSO-$d_6$) δ 8.95 (d, 1H), 8.77 (s, 1H), 8.61 (d, 1H), 8.16-8.05 (m, 1H), 8.00 (d, 1H), 6.90 (s, 1H), 5.33 (s, 1H), 3.26-3.07 (m, 2H), 2.17 (s, 3H), 2.05 (s, 3H), 0.59 (s, 4H). $^{19}$F NMR (377 MHz, DMSO) δ-120.25,-120.27,-122.33,-122.34,-132.52.

EXAMPLE 61B

LC-MS: (ES+H, m/z): $[M+H]^+$=546.3. $^1$H NMR (400 MHZ, DMSO-$d_6$) δ 8.95 (d, 1H), 8.77 (s, 1H), 8.61 (d, 1H), 8.14-8.07 (m, 1H), 8.00 (d, 1H), 6.90 (d, 1H), 5.33 (s, 1H), 3.23-3.08 (m, 2H), 2.17 (s, 3H), 2.05 (s, 3H), 0.59 (s, 4H). $^{19}$F NMR (377 MHz, DMSO) δ-120.24,-120.26,-122.32,-122.34,-132.51.

EXAMPLE 62A, 62B

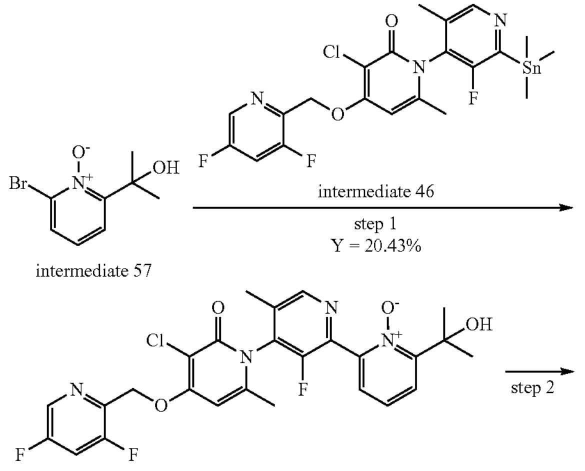

Example 62

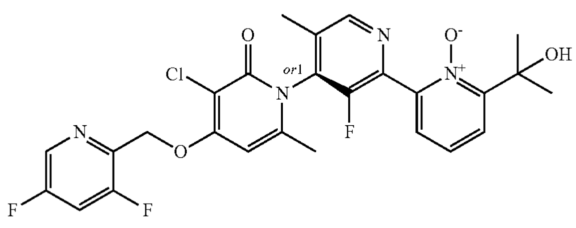
isomer 1
Example 62A

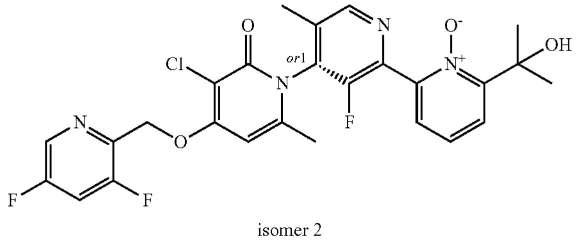
isomer 2
Example 62B

Step 1: Preparation of 4'-{3-chloro-4-[(3,5-difluoro-pyridin-2-yl)methoxy]-6-methyl-2-oxopyridin-1-yl}-3'-fluoro-6-(2-hydroxypropan-2-yl)-5'-methyl-[2,2'-bipyridin]-1-ium-1-olate To the reaction solution of 3-chloro-4-[(3,5-difluoropyridin-2-yl)methoxy]-3'-fluoro-5',6-dimethyl-2'-(trimethylstannyl)-[1,4'-bipyridin]-2-one (assumed 100% yield, 1.00 g, 1.79 mmol, 1.00 equiv) was added 2-bromo-6-(2-hydroxypropan-2-yl)pyridin-1-ium-1-olate (0.83 g, 3.58 mmol, 2.00 equiv), CuI (0.34 g, 1.79 mmol, 1.00 equiv) and $Pd(PPh_3)$: $Cl_2$ (0.25 g, 0.35 mmol, 0.20 equiv), the mixture was stirred for 2 h at 80° C., under nitrogen atmosphere. The reaction was monitored by LCMS. The reaction was monitored by LCMS. The mixture was allowed to r.t . . . . The residue was dissolved in EtOAc (200 mL). The resulting mixture was washed with sat. $NaHCO_3$(aq.) (2×100 mL). The combined organic layers were concentrated under reduced pressure. The residue was purified by silica gel column chromatography to afford crude product (400 mg). The crude product was isolated by PREP-HPLC to afford 4'-{3-chloro-4-[(3,5-difluoropyridin-2-yl)methoxy]-6-methyl-2-oxopyridin-1-yl}-3'-fluoro-6-(2-hydroxypropan-2-yl)-5'-methyl-[2,2'-bipyridin]-1-ium-1-olate (200 mg, 20.43%) as a white solid. LC-MS: (ES+H, m/z): $[M+H]^+$ =547.2. $^1$H NMR (400 MHz, DMSO-$d_6$) δ 8.70 (d, 1H), 8.60 (d, 1H), 8.14-8.04 (m, 1H), 7.82 (dd, 1H), 7.75 (dd, 1H), 7.60 (t, 1H), 6.89 (d, 1H), 6.62 (s, 1H), 5.52 (d, 2H), 2.17 (s, 3H), 2.06 (s, 3H), 1.60 (s, 6H).

Step 2: Preparation of rel-3-chloro-4-((3,5-difluoro-pyridin-2-yl)methoxy)-3'-fluoro-6-(2-hydroxypropan-2-yl)-5',6-dimethyl-2-oxo-2H-[1,4': 2',2"-ter-pyridine] 1"-oxide and rel-3-chloro-4-((3,5-difluoropyridin-2-yl)methoxy)-3'-fluoro-6"-(2-hydroxypropan-2-yl)-5',6-dimethyl-2-oxo-2H-[1,4': 2',2"-terpyridine] 1"-oxide The racemate (250 mg) was separated by Prep-HPLC to afford rel-3-chloro-4-((3,5-difluoropyridin-2-yl)methoxy)-3'-fluoro-6"-(2-hydroxypropan-2-yl)-5', 6-dimethyl-2-oxo-2H-[1,4': 2',2"-terpyridine] 1"-oxide (Example 62A: 78.2 mg, 98.1% purity, ee=100%) as a white solid and rel-3-chloro-4-((3,5-difluoropyridin-2-yl)methoxy)-3'-fluoro-6"-(2-hydroxypropan-2-yl)-5',6-dimethyl-2-oxo-2H-[1,4': 2',2"-terpyridine] 1"-oxide (Example 62B: 78.6 mg, 98.7% purity, ee=98.7%) as a white solid.

EXAMPLE 62A

LC-MS: (ES+H, m/z): $[M+H]^+$=547.1. $^1$H NMR (400 MHZ, DMSO-$d_6$) δ 8.69 (d, 1H), 8.60 (d, 1H), 8.18-8.01 (m, 1H), 7.82 (dd, 1H), 7.75 (dd, 1H), 7.60 (t, 1H), 6.88 (d, 1H), 6.61 (s, 1H), 5.51 (d, 2H), 2.17 (s, 3H), 2.05 (s, 3H), 1.60 (s, 6H). $^{19}$F NMR (377 MHz, DMSO) δ-120.19,-120.21,-122.37,-122.39,-128.08.

EXAMPLE 62B

LC-MS: (ES+H, m/z): $[M+H]^+$=547.1. $^1$H NMR (400 MHZ, DMSO-$d_6$) δ 8.69 (d, 1H), 8.60 (d, 1H), 8.13-8.05 (m, 1H), 7.82 (dd, 1H), 7.75 (dd, 1H), 7.60 (t, 1H), 6.88 (d, 1H), 6.61 (s, 1H), 5.51 (d, 2H), 2.17 (s, 3H), 2.05 (s, 3H), 1.60 (s, 6H). $^{19}$F NMR (377 MHz, DMSO) δ-120.19,-120.21,-122.37,-122.39,-128.08.

EXAMPLE 63A, 63B

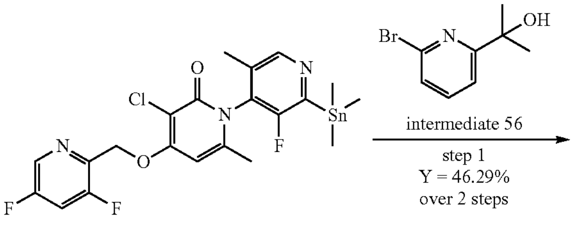

intermediate 46

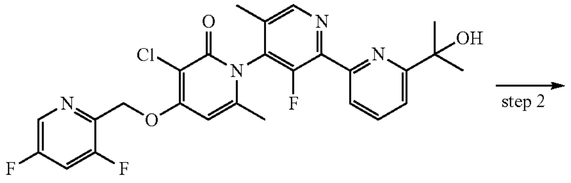

Example 63

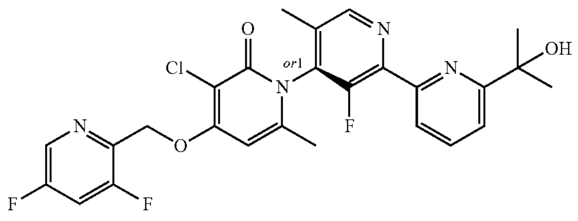

isomer 1
Example 63A

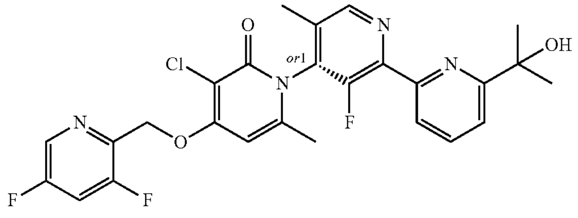

isomer 2
Example 63B

Step 1: Preparation of 3-chloro-4-[(3,5-difluoropyridin-2-yl)methoxy]-1-[3-fluoro-6'-(2-hydroxypropan-2-yl)-5-methyl-[2,2'-bipyridin]-4-yl]-6-methylpyridin-2-one To the above mixture of step 3 was added 2-(6-bromopyridin-2-yl) propan-2-ol (754.34 mg. 3.49 mmol. 3.00 equiv). Pd(PPh;): $Cl_2$ (163.36 mg, 0.23 mmol. 0.20 equiv) and CuI (221.62 mg, 1.16 mmol. 1.00 equiv) at room temperature under nitrogen atmosphere. The resulting mixture was stirred for 1 h at 80° C. under nitrogen atmosphere. The reaction was monitored by LCMS. The mixture was allowed to cool down to room temperature. The resulting mixture was diluted with water (50 mL). The resulting mixture was extracted with EtOAc (3×100 mL). The combined organic layers were washed with brine (3×100 mL), dried over anhydrous $Na_2SO_4$. After filtration, the filtrate was concentrated under reduced pressure. The crude product was purified by Prep-HPLC to afford 3-chloro-4-[(3.5-difluoropyridin-2-yl)methoxy]-1-[3-fluoro-6'-(2-hydroxypropan-2-yl)-5-methyl-[2.2'-bipyridin]-4-yl]-6-methylpyridin-2-one (286.00 mg. 46.29%) as a white solid. LC-MS: (ES+H, m/z): $[M+H]^+$=531.00. $^1$H NMR (300 MHz. DMSO-$d_6$) δ 8.69 (d, 1H), 8.61 (d, 1H), 8.15-8.05 (m, 1H), 8.01-7.90 (m, 2H), 7.75 (d, 1H), 6.89 (s, 1H), 5.52 (d, 2H), 5.31 (s, 1H).

2.14 (s, 3H), 2.05 (s, 3H), 1,46 (s. 6H).

Step 2: Preparation of rel-3-chloro-4-[(3,5-difluoropyridin-2-yl)methoxy]-1-[3-fluoro-6'-(2-hydroxypropan-2-yl)-5-methyl-[2,2'-bipyridin]-4-yl]-6-methylpyridin-2-one & rel-3-chloro-4-[(3,5-difluoropyridin-2-yl)methoxy]-1-[3-fluoro-6'-(2-hydroxypropan-2-yl)-5-methyl-[2,2'-bipyridin]-4-yl]-6-methylpyridin-2-one The rac-mixture (286.00 mg) was separated by Prep-Chiral HPLC to afford rel-3-chloro-4-1 (3.5-difluoropyridin-2-yl)methoxy]-1—]3-fluoro-6'-(2-hydroxypropan-2-yl )-5-methyl-]2.2'-bipyridin]-4-yl]-6-methylpyridin-2-one (Example 63A. 65.1 mg. 99.2% purity, ee=99.9%) & rel-3-chloro-4-[(3.5-difluoropyridin-2-yl)methoxy]-1-[3-fluoro-6'-(2-hydroxypropan-2-yl)-5-methyl-]2.2'-bipyridin]-4-yl]-6-methylpyridin-2-one (Example 63B. 59.0 mg. 99.6% purity, cc-99.9%) Example 63A;

LC-MS: (ES+H, m/z): $[M+H]^+$=531.1. $^1$H NMR (300 MHz. DMSO-$d_6$) δ 8.69 (d, 1H), 8.61 (d. 1H), 8.18-8.04 (m, 1H), 8.02-7.88 (m, 2H), 7.75 (d, 1H), 6.89 (s, 1H), 5.52 (d, 2H), 5.30 (s, 1H), 2.13 (s. 3H), 2.04 (s, 3H), 1,46 (s. 6H). $^{19}$F NMR (282 MHz. DMSO) δ-120.17, -120.20, -122.36, -122.39, —134.43.

EXAMPLE 63B

LC-MS: (ES+H, m/z): $[M+H]^+$=531.05. $^1$H NMR (300 MHz. DMSO-$d_6$) δ 8.69 (d, 1H), 8.61 (d. 1H), 8.18-8.04 (m, 1H), 8.01-7.87 (m, 2H), 7.75 (d, 1H), 6.89 (d, 1H), 5.52 (d, 2H), 5.30 (s, 1H), 2.13 (s. 3H), 2.04 (s, 3H), 1,46 (s. 6H). $^{19}$F NMR (282 MHz. DMSO) δ-120.17,-120.19,-122.36,-122.39,-134.42.

EXAMPLE 64A, 64B

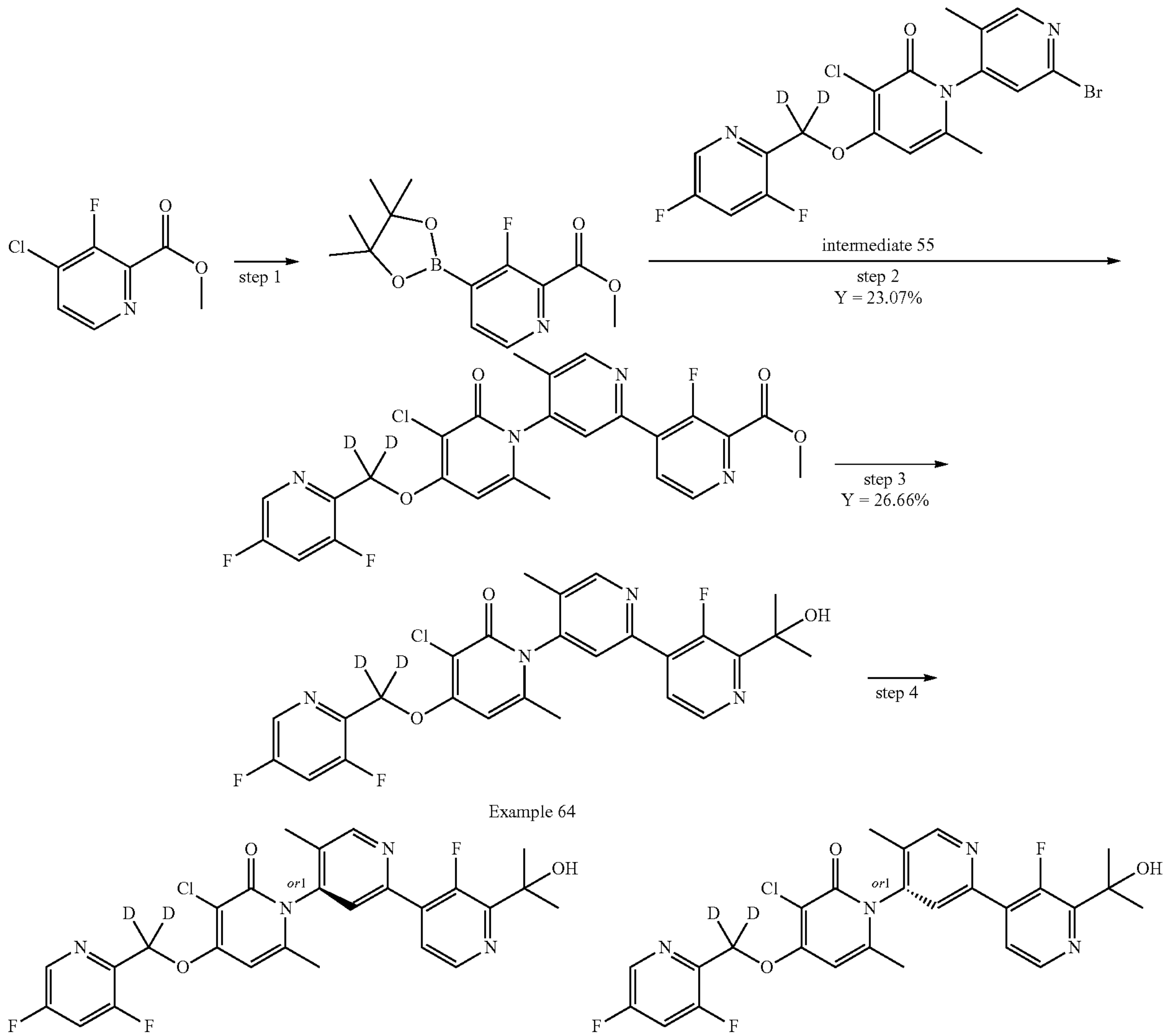

isomer 1
Example 64A isomer 2
Example 64B

Step 1: Preparation of methyl 3-fluoro-4-(4,4,5,5-tetramethyl-1,3,2-dioxaborolan-2-yl)pyridine-2-carboxylate To a stirred mixture of methyl 4-chloro-3-fluoropyridine-2-carboxylate (2.00 g, 10.55 mmol, 1.00 equiv), bis (pinacolato)diboron (13.40 g, 52.75 mmol, 5.00 equiv) in dioxane (10 mL) were added AcOK (3.11 g, 31.65 mmol, 3.00 equiv) and XPhos Pd G3 (446 mg, 0.52 mmol, 0.05 equiv) at room temperature under nitrogen atmosphere. The resulting mixture was stirred for additional 1.5 h at 80° C. The mixture was allowed to cool down to room temperature. Desired product could be detected by LCMS. The resulting mixture was used in the next step directly without further purification. LC-MS: (ES+H, m/z): $[M+H]^+$ =200.1 (boronic acid).

Step 2: Preparation of methyl 4-{3-chloro-4-[(3-chloro-5-fluoropyridin-2-yl) ($^2H_2$)methoxy]-5',6-dimethyl-2-oxo-[1,4'-bipyridin]-2'-yl}-3-oxopyrazine-2-carboxylate To the above mixture were added bis(2'-bromo-3-chloro-4-[(3,5-difluoropyridin-2-yl) ($^2H_2$)methoxy]-5',6-dimethyl-[1,4'-bipyridin]-2-one) (1.96 g. 2.13 mmol, 0.60 equiv), $K_2CO_3$ (1,48 g, 10.67 mmol, 3.00 equiv), Pd(dppf) $Cl_2$ (520 mg, 0.71 mmol, 0.20 equiv) and $H_2O$ (2.5 mL) at room temperature under nitrogen atmosphere. The resulting mixture was stirred for 1.5 h at 80° C., under nitrogen atmosphere. The reaction was monitored by LCMS. The mixture was allowed to cool down to room temperature. The resulting mixture was poured into water (50 mL). The resulting mixture was extracted with EtOAc (3 ×50 mL). The combined organic layers were dried over anhydrous $Na_2SO_4$. After filtration, the filtrate was concentrated under reduced pressure. The residue was purified by silica gel column chromatography, the pure fraction was concentrated under pressure to afford methyl 4-{3-chloro-4-[(3-chloro-5-fluoropyridin-2-yl) ($^2H_2$)methoxy]-5',6-dimethyl-2-oxo-[1,4'-bipyridin]-2'-yl}-3-oxopyrazine-2-carboxylate (450 mg, 23.07%) as a white solid. LC-MS: (ES+H, m/z): $[M+H]^+$=533.0. $^1H$ NMR (300 MHZ, DMSO-$d_6$) δ 8.91 (s, 1H), 8.66 (d, 1H), 8.61 (d, 1H), 8.22 (t, 1H), 8.10-8.07 (m, 1H), 7.97 (s, 1H), 6.82 (s, 1H), 3.93 (s, 3H), 2.11 (s, 3H), 1.99 (s, 3H).

Step 3: Preparation of 3-chloro-4-[(3,5-difluoropyridin-2-yl) ($^2H_2$)methoxy]-1-[3'-fluoro-2'-(2-hydroxypropan-2-yl)-5-methyl-[2,4'-bipyridin]-4-yl]-6-methylpyridin-2-one To a stirred mixture of methyl 4-{3-chloro-4-[(3,5-difluoropyridin-2-yl) ($^2H_2$)methoxy]-6-methyl-2-oxopyridin-1-yl}-3'-fluoro-5-methyl-[2.4'-bipyridine]-2'-carboxylate (450 mg, 0.84 mmol, 1.00 equiv) and LiCl (35 mg, 0.844 mmol, 1 equiv) in THF (40 mL) was added $CH_3Mgl$ (4 mL, 8.00 mmol, 21.32 equiv, 2.0 M in ethyl ether) dropwise at 0° C., under nitrogen atmosphere. The resulting mixture was stirred for 1 h at 0° C., under nitrogen atmosphere. The reaction was monitored by LCMS. The reaction was quenched with saturated $NH_4Cl$ (aq., 50 mL) at 0° C. The resulting mixture was extracted with EtOAc (3×30 mL). The combined organic layers were dried over anhydrous $Na_2SO_4$. After filtration, the filtrate was concentrated under reduced pressure. The residue was purified by silica gel column chromatography, the pure fraction was concentrated under pressure to afford crude product, which was further purified by Prep-HPLC, the pure fraction was concentrated under pressure to afford 3-chloro-4-[(3,5-difluoropyridin-2-yl) ($^2H_2$)methoxy]-1-[3'-fluoro-2'-(2-hydroxypropan-2-yl)-5-methyl-[2.4'-bipyridin]-4-yl]-6-methylpyridin-2-one (120 mg. 26.66%) as a white solid. LC-MS: (ES+H, m/z): $[M+H]^+$=533.1. $^1H$ NMR (300 MHz, DMSO-$d_6$) δ 8.88 (s, 1H), 8.61 (d, 1H), 8.48 (d, 1H), 8.14-8.07 (m, 1H), 7.91-7.88 (m, 2H), 6.82 (s, 1H), 5.37 (s, 1H), 2.10 (s, 3H), 2.00 (s, 3H), 1.56 (s, 6H).

Step 4: Preparation of rel-3-chloro-4-[(3,5-difluoropyridin-2-yl) ($^2H_2$)methoxy]-1-[3'-fluoro-2'-(2-hydroxypropan-2-yl)-5-methyl-[2,4'-bipyridin]-4-yl]-6-methylpyridin-2-one & rel-3-chloro-4-[(3,5-difluoropyridin-2-yl) ($^2H_2$)methoxy]-1-[3'-fluoro-2'-(2-hydroxypropan-2-yl)-5-methyl-[2,4'-bipyridin]-4-yl]-6-methylpyridin-2-one The racemate (120 mg) was separated by Prep-Chiral-HPLC, the pure fraction was concentrated under reduced pressure and lyophilized to afford Example 64A (39.3 mg. 97.6% purity, 97.3% deuterium purity, ee=100%) and Example 64B (39.5 mg. 98.4% purity, 97.9% deuterium purity, ee=100%) as a white solid.

EXAMPLE 64A

LC-MS: (ES+H, m/z): $[M+H]^+$=533.20. $^1H$ NMR (400 MHZ, DMSO-$d_6$) δ 8.88 (s, 1H), 8.60 (d. 1H), 8.47 (d, 1H), 8.12-8.07 (m, 1H), 7.90-7.88 (m, 2H), 6.81 (s, 1H), 5.37 (s, 1H), 2.09 (s, 3H), 1.98 (s. 3H), 1.56 (s, 6H). $^{19}F$ NMR (377 MHz, DMSO) δ-120.25,-120.27,-122.33,-122.35,-125.91.

EXAMPLE 64B

LC-MS: (ES+H, m/z): $[M+H]^+$=533.25. $^1H$ NMR (400 MHZ, DMSO-$d_6$) δ 8.88 (s, 1H), 8.60 (d. 1H), 8.47 (d, 1H), 8.12-8.07 (m, 1H), 7.90-7.88 (m, 2H), 6.81 (s, 1H), 5.37 (s, 1H), 2.09 (s, 3H), 1.98 (s, 3H), 1.56 (s, 6H), $^{19}F$ NMR (377 MHz, DMSO) δ-120.25,-120.27,-122.33,-122.35,-125.91.

EXAMPLE 65A, 65B

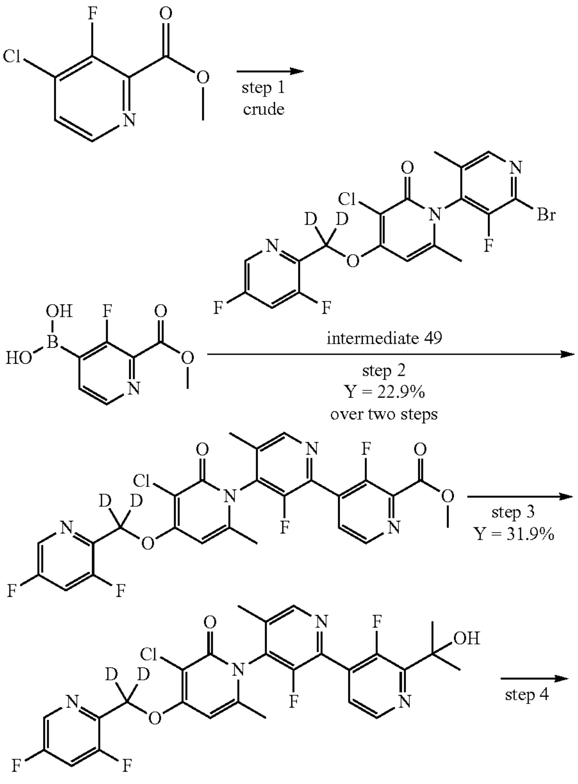

Example 65

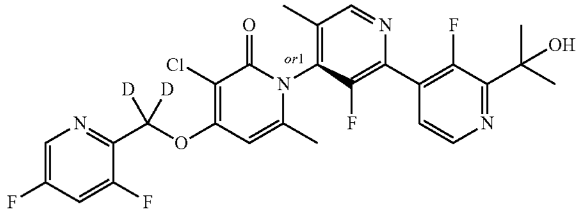

isomer 1
Example 65A

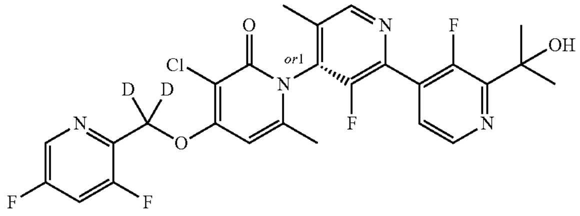

isomer 2
Example 65B

Step 1: Preparation of 3-fluoro-2-(methoxycarbonyl)pyridin-4-ylboronic acid

To a stirred mixture of methyl 4-chloro-3-fluoropyridine-2-carboxylate (1.50 g. 7.91 mmol, 1.00 equiv) and bis (pinacolato)diboron (10.05 g, 39.56 mmol, 5.00 equiv) in dioxane (30 mL) were added potassium acetate (2.33 g, 23.73 mmol, 3.00 equiv) and XPhos Pd G3 (0.33 g, 0.39 mmol, 0.05 equiv) at room temperature under nitrogen atmosphere. The resulting mixture was stirred for 1.5 h at 80° C., under nitrogen atmosphere. The mixture was allowed to cool down to room temperature. The reaction was monitored by LCMS. The crude product mixture was used in the next step directly without further purification. LC-MS: (ES+H, m/z): $[M+H]^+$=200.0.

Step 2: Preparation of methyl 4-{3-chloro-4-[(3,5-difluoropyridin-2-yl) ($^2H_2$)methoxy]-6-methyl-2-oxopyridin-1-yl}-3,3'-difluoro-5-methyl-[2,4'-bipyridine]-2'-carboxylate To the above mixture were added bis(2'-bromo-3-chloro-4-[(3,5-difluoropyridin-2-yl) ($^2H_2$)methoxy]-5',6-dimethyl-[1,4'-bipyridin]-2-one) (1.71 g, 1.87 mmol, 0.70 equiv), $K_2CO_3$ (1.11 g, 8.01 mmol, 3.00 equiv), Pd(dppf) $C_1$:(0.39 g. 0.53 mmol, 0.20 equiv), dioxane (30 mL) and $H_2O$ (3 mL) at room temperature under nitrogen atmosphere. The resulting mixture was stirred for additional 1.5 h at 80° C. The mixture was allowed to cool down to room temperature. The reaction was monitored by LCMS. The resulting mixture was poured into water (200 mL). The resulting mixture was filtered, the filter cake was washed with EtOAc (3×200 mL). The combined organic layers were washed with brine (200 mL). The filtrate was concentrated under reduced pressure. The residue was purified by silica gel column chromatography to afford methyl 4-{3-chloro-4-[(3,5-difluoropyridin-2-yl) ($^2H_2$)methoxy]-6-methyl-2-oxopyridin-1-yl}-3,3'-difluoro-5-methyl-[2,4'-bipyridine]-2'-carboxylate (1.00 g, 22.9%) as a yellow solid. LC-MS: (ES+H, m/z): $[M+H]^+$=551.1.

Step 3: Preparation of 3-chloro-1-[3,3'-difluoro-2'-(2-hydroxypropan-2-yl)-5-methyl-[2,4'-bipyridin]-4-yl]-4-[(3,5-difluoropyridin-2-yl) ($^2H_2$)methoxy]-6-methylpyridin-2-one To a stirred solution of methyl 4-{3-chloro-4-[(3-fluoropyridin-2-yl) ($^2H_2$)methoxy]-6-methyl-2-oxopyridin-1-yl}-3,3'-difluoro-5-methyl-[2,4'-bipyridine]-2'-carboxylate (850 mg, 1.59 mmol, 1.00 equiv) in THF (80 mL) was added $CH_3MgBr$ (5.32 mL, 15.95 mmol, 10.00 equiv, 3 M in 2-MeTHF) dropwise at 0° C., under nitrogen atmosphere. The resulting mixture was stirred for 1.5 h at 0° C. under nitrogen atmosphere. The reaction was monitored by LCMS. The reaction was quenched with sat. $NH_4Cl$ (aq., 20 ml) at 0° C. The resulting mixture was extracted with EtOAc (3 ×80 ml). The combined organic layers were washed with brine (3 ×80 mL), dried over anhydrous $Na_2SO_4$. After filtration, the filtrate was concentrated under reduced pressure. The residue was purified by silica gel column chromatography to afford crude product, which was further purified by Prep-HPLC, the pure fraction was concentrated under pressure to afford 3-chloro-1-[3,3'-difluoro-2'-(2-hydroxypropan-2-yl)-5-methyl-[2,4'-bipyridin]-4-yl]-4-[(3,5-difluoropyridin-2-yl) ($^2H_2$)methoxy]-6-methylpyridin-2-one (280 mg, 85% purity, 31.9% yield) as a white solid. LC-MS: (ES+H, m/z): $[M+H]^+$=551.1. $^1H$ NMR (400 MHZ, DMSO-$d_6$) 8.79 (s, 1H), 8.61 (d, 1H), 8.53 (d, 1H), 8.12-8.10 (m, 1H), 7.68 (t, 1H), 6.92 (s, 1H), 5.39 (s, 1H), 2.19 (s, 3H), 2.07 (s, 3H), 1.56 (s, 6H).

Step 4: Preparation of rel-3-chloro-1-[3,3'-difluoro-2'-(2-hydroxypropan-2-yl)-5-methyl-[2,4'-bipyridin]-4-yl]-4-[(3,5-difluoropyridin-2-yl) ($^2H_2$)methoxy]-6-methylpyridin-2-one & rel-3-chloro-1-[3,3'-difluoro-2'-(2-hydroxypropan-2-yl)-5-methyl-[2,4'-bipyridin]-4-yl]-4-[(3,5-difluoropyridin-2-yl) ($^2H_2$)methoxy]-6-methylpyridin-2-one The racemate (270 mg) was separated by Prep-Chiral-HPLC, the pure fraction was concentrated under reduced pressure and lyophilized to afford Example 65A 61.8 mg. 99.9% purity, ee=100%, 96.4% deuterium purity) as a white solid and Example 65B (53.1 mg, 99.8% purity, ee-99.3%, 96.6% deuterium purity) as a white solid.

EXAMPLE 65A

LC-MS: (ES+H, m/z): $[M+H]^+$=551.3. $^1H$ NMR (300 MHz, DMSO-$d_6$) δ 8.79 (s, 1H), 8.61 (d, 1H), 8.53 (d, 1H), 8.13-8.06 (m, 1H), 7.68 (t, 1H), 6.94 (s, 1H), 5.38 (s, 1H), 2.18 (s, 3H), 2.06 (s, 3H), 1.55 (s, 6H). $^{19}F$ NMR (282 MHz, DMSO) δ-120.216,-120.284,-122.313,-122.350,-123.233,-123.343,-132.080,-132.190.

EXAMPLE 65B

LC-MS: (ES+H, m/z): $[M+H]^+$=551.3. $^1H$ NMR (300 MHz, DMSO-$d_6$) δ 8.79 (s, 1H), 8.60 (d, 1H), 8.53 (d, 1H), 8.12-8.06 (m, 1H), 7.68 (t, 1H), 6.91 (s, 1H), 5.38 (s, 1H), 2.18 (s, 3H), 2.06 (s, 3H), 1.55 (s, 6H). $^{19}F$ NMR (282 MHz, DMSO) δ-120.211,-120.279,-122.305,-122.343,-123.230,-123.340,-132.074,-132.185

EXAMPLE 66A, 66B

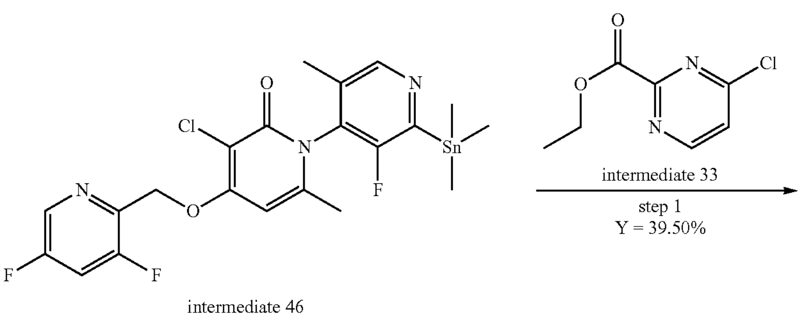

intermediate 46

-continued

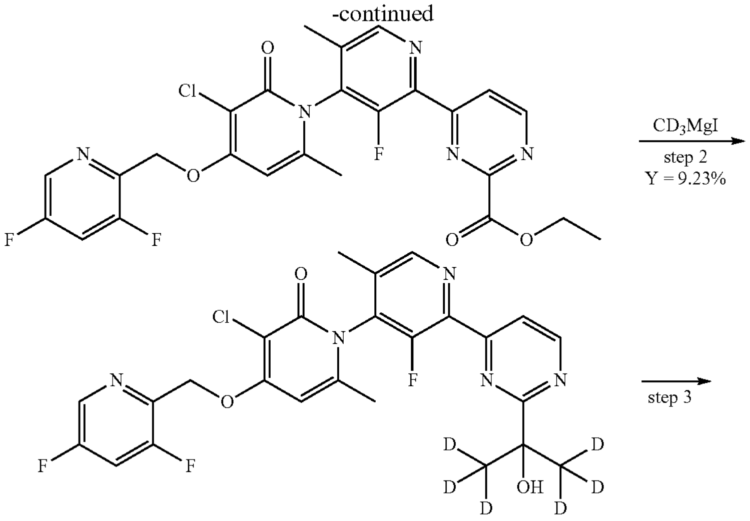

Example 66

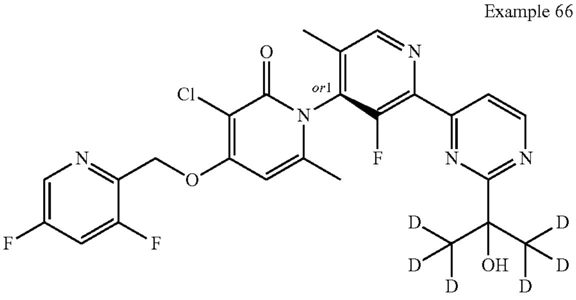

isomer 1
Example 66A

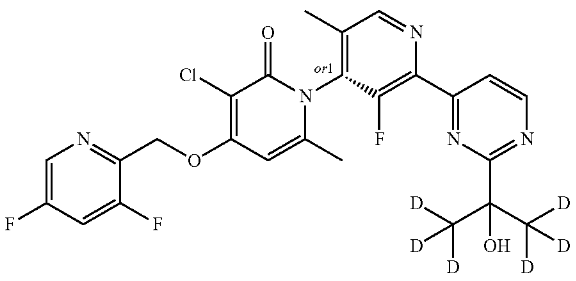

isomer 2
Example 66B

Step 1: Preparation of ethyl 4-(3-chloro-4-(2-(3,5-difluoropyridin-2-yl)ethyl)-3'-fluoro-5',6-dimethyl-2-oxo-2H-[1,4'-bipyridin]-2'-yl)pyrimidine-2-carboxylate To 3-chloro-4-[(3,5-difluoropyridin-2-yl)methoxy]-3'-fluoro-5',6-dimethyl-2'-(trimethylstannyl)-[1,4'-bipyridin]-2-one (1 g crude) was added ethyl 4-chloropyrimidine-2-carboxylate (1302 mg. 6.98 mmol, 3.00 equiv), $Pd(PPh_3)$: $Cl_2$ (326 mg, 0.46 mmol. 0.20 equiv) and CuI (443 mg. 2.32 mmol. 1.00 equiv) at room temperature. The resulting mixture was stirred for 2 h at 80° C., under nitrogen atmosphere. The reaction was monitored by LCMS. The mixture was allowed to cool down to room temperature. The resulting mixture was diluted with water (50 mL). The resulting mixture was extracted with EtOAc (3×100 mL). The resulting mixture was concentrated under reduced pressure. The residue was purified by silica gel column chromatography to afford ethyl 4-(3-chloro-4-(2-(3,5-difluoropyridin-2-yl)ethyl)-3'-fluoro-5',6-dimethyl-2-oxo-2H-[1,4'-bipyridin]-2'-yl)pyrimidine-2-carboxylate (500 mg, 39.50%, over two steps) as a yellow solid. LC-MS: (ES+H, m/z): $[M+H]^+$=546.1.

Step 2: Preparation of 3-chloro-4-[(3,5-difluoropyridin-2-yl)methoxy]-3'-fluoro-2'-{2-[2-hydroxy (1,1,1,3,3 ,3-$2H_6$) propan-2-yl]pyrimidin-4-yl}-5',6-dimethyl-[1,4'-bipyridin]-2-one To a stirred solution of ethyl 4-{3-chloro-4-[(3,5-difluoropyridin-2-yl)methoxy]-3'-fluoro-5',6-dimethyl-2-oxo-[1,4'-bipyridin]-2'-yl}pyrimidine-2-carboxylate (550 mg, 1.00 mmol, 1.00 equiv) and LiCl (85 mg. 2.01 mmol. 2.00 equiv) in THF (8 mL) was added iodo (($2H_3$) methyl) magnesium (3.02 mL. 3.00 mmol, 3 equiv. 1 M) dropwise at −10° C., under nitrogen atmosphere. The resulting mixture was stirred for 30 min at −10° C., under nitrogen atmosphere. The reaction was monitored by LCMS. The reaction was quenched with sat. $NH_4Cl$ (aq.) at −10° C. The resulting mixture was extracted with EtOAc (3 ×50 mL). The combined organic layers were dried over anhydrous $Na_2SO_4$. After filtration, the filtrate was concentrated under reduced pressure. The crude product was isolated by PREP-HPLC to afford 3-chloro-4-[(3,5-difluoropyridin-2-yl)methoxy]-3'-fluoro-2'-{2-[2-hydroxy (l. 1. 1.3.3 .3-$2H_6$) propan-2-yl] pyrimidin-4-yl}-5',6-dimethyl-[1,4'-bipyridin]-2-one (50 mg. 9.23%). LC-MS: (ES+H, m/z): $[M+H]^+$=538.2. Step 3: Preparation of rel-3-chloro-4-((3,5-difluoropyridin-2-yl) methoxy)-3'-fluoro-2'-(2-(2-hydroxypropan-2-yl-1,1,1,3,3 ,3-d6) pyrimidin-4-yl)-5',6-dimethyl-2H-[1,4'-bipyridin]-2-one & rel-3-chloro-4-((3,5-difluoropyridin-2-yl) methoxy)-3'-fluoro-2'-(2-(2-hydroxypropan-2-yl-1,1,1,3,3 ,3-d6) pyrimidin-4-yl)-5',6-dimethyl-2H-[1,4'-bipyridin]-2-one The rac-mixture (50 mg) was separated by Prep-Chiral HPLC to afford rel-3-chloro-4-((3,5-difluoropyridin-2-yl) methoxy)-3'-fluoro-2'-(2-(2-hydroxypropan-2-yl-1,1,1,3,3 ,3-d6) pyrimidin-4-yl)-5',6-dimethyl-2H-[1,4'-bipyridin]-2-one (Example 66A: 22.6 mg, 99.7% purity, ee=100%) as a white solid and rel-3-chloro-4-((3,5-difluoropyridin-2-yl) methoxy)-3'-fluoro-2'-(2-(2-hydroxypropan-2-yl-1,1,1,3, 3 ,3-d6) pyrimidin-4-yl)-5',6-dimethyl-2H-[1,4'-bipyridin]-2-one (Example 66B: 21.2 mg, 99.6% purity, ee=100%) as a white solid.
EXAMPLE 66A
LC-MS: (ES+H, m/z): $[M+H]^+$=538.2. $^1H$ NMR (400 MHZ, DMSO-$d_6$) δ 9.02 (d, 1H), 8.78 (s, 1H), 8.61 (d, 1H), 8.15-8.06 (m, 1H), 8.04 (d, 1H), 6.90 (s, 1H), 5.53 (d, 2H), 5.06 (d, 1H), 2.18 (s, 3H), 2.05 (s, 3H). $^{19}F$ NMR (377 MHz, DMSO) δ-120.17,-120.19,-122.35,-122.36,-132.09.
EXAMPLE 66B
LC-MS: (ES+H, m/z): $[M+H]^+$=538.2. $^1H$ NMR (400 MHZ, DMSO-$d_6$) δ 9.02 (d, 1H), 8.78 (s, 1H), 8.61 (d, 1H), 8.15-8.06 (m, 1H), 8.04 (d, 1H), 6.90 (s, 1H), 5.52 (d, 2H), 5.05 (d, 1H), 2.18 (s, 3H), 2.05 (s, 3H). $^{19}F$ NMR (377 MHz, DMSO) δ-120.17,-120.19,-122.36,-122.38,-132.09.
EXAMPLE 67A, 67B
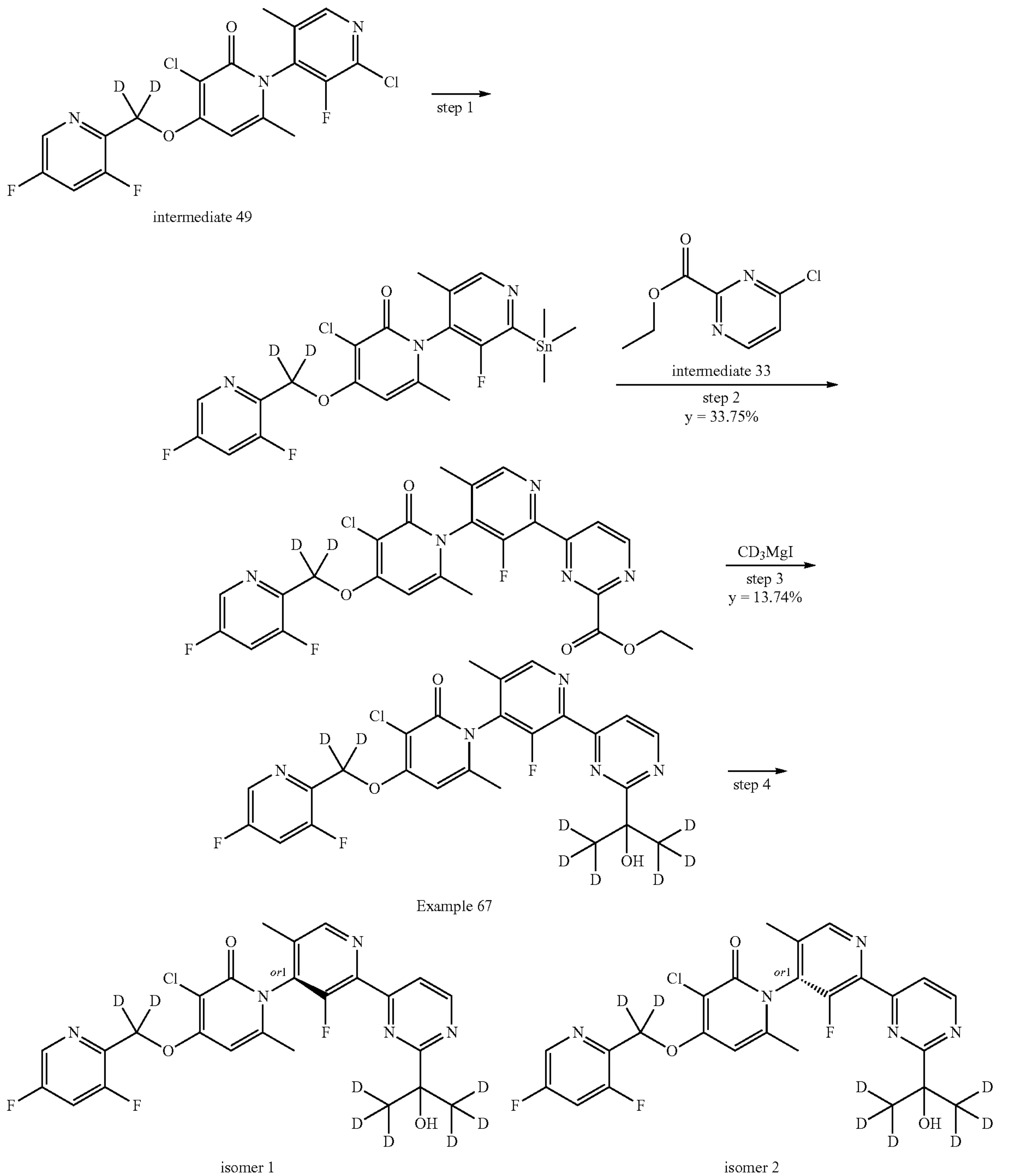
intermediate 49
Example 67
isomer 1
Example 67A
isomer 2
Example 67B Step 1: Preparation of 3-chloro-4-((3,5-difluoropyridin-2-yl)methoxy-d2)-3'-fluoro-5',6-dimethyl-2'-(trimethylstannyl)-2H-[1,4'-bipyridin]-2-one To a stirred mixture of 2',3-dichloro-4-[(3,5-difluoropyridin-2-yl) ($^2H_2$)methoxy]-3'-fluoro-5',6-dimethyl-[1,4'-bipyridin]-2-one (2.00 g, 4.62 mmol, 1.00 equiv) and $Pd(PPh_3)_2Cl_2$ (649 mg, 0.92 mmol, 0.20 equiv) in THF (20 mL) were added $AsPh_3$ (283 mg, 0.92 mmol, 0.20 equiv) and $Sn_2Me_6$ (3.02 g, 9.25 mmol, 2.00 equiv) at room temperature under nitrogen atmosphere. The resulting mixture was stirred for 2 h at 80° C., under nitrogen atmosphere. The reaction was monitored by LCMS. Desired product could be detected by LCMS. The resulting mixture was used in the next step directly without further purification. LC-MS: (ES+H, m/z): $[M+H]^+$=562.1.

Step 2: Preparation of ethyl 4-(3-chloro-4-((3,5-difluoropyridin-2-yl)methoxy-d2)-3'-fluoro-5',6-dimethyl-2-oxo-2H-[1,4'-bipyridin]-2'-yl)pyrimidine-2-carboxylate To a stirred mixture of 3-chloro-4-[(3.5-difluoropyridin-2-yl) ($^2H_2$)methoxy]-3'-fluoro-5'0.6-dimethyl-2'-(trimethylstannyl)-] 1,4'-bipyridin]-2-one hydrofluoride (2.70 g. 4.65 mmol. 1.00 equiv) and ethyl 4-chloropyrimidine-2-carboxylate (1.73 g. 9.30 mmol. 2.00 equiv) in THF (20 ml) were added $Pd(PPh_3)$: $Cl_2$ (652 mg, 0.93 mmol. 0.20 equiv) and CuI (885 mg. 4.65 mmol. 1.00 equiv) at room temperature under nitrogen atmosphere. The resulting mixture was stirred for 2 h at 80° C., under nitrogen atmosphere. The reaction was monitored by LCMS. The resulting mixture was cooled down to r.t, and poured into 20 ml of water. The resulting mixture was extracted with EtOAc (3×20 mL). The combined organic layers were washed with brine (50 mL), dried over anhydrous $Na_2SO_4$. After filtration, the filtrate was concentrated under reduced pressure. The residue was purified by silica gel column chromatography to afford ethyl 4-(3-chloro-4-((3.5-difluoropyridin-2-yl)methoxy-d2)-3'-fluoro-5'0.6-dimethyl-2-oxo-2H-[1,4'-bipyridin]-2'-yl)pyrimidine-2-carboxylate (860 mg. 33.75%) as a white solid. LC-MS: (ES+H, m/z): $[M+H]^+$=548.1. $^1H$ NMR (300 MHz. Chloroform-d) δ 9.08 (d, 1H), 8.70-8.63 (m, 1H), 8.42 (d, 1H), 8.20 (d, 1H), 7.35-7.33 (m, 1H), 6.47 (d, 1H).4.56 (q. 2H), 2.26 (s, 3H), 2.07 (s, 3H), 1,49 (t. 3H). Step 3: Preparation of 3-chloro-4-((3,5-difluoropyridin-2-yl) methoxy-d2)-3'-fluoro-2'-(2-(2-hydroxypropan-2-yl-1,1,1, 3,3 ,3-d6) pyrimidin-4-yl)-5',6-dimethyl-2H-[1,4'-bipyridin]-2-one To a stirred mixture of ethyl 4-{3-chloro-4-[(3.5-difluoropyridin-2-yl) ($^2H_2$)methoxy]-3'-fluoro-5'0.6-dimethyl-2-oxo-[1,4'-bipyridin]-2'-yl}pyrimidine-2-carboxylate (480 mg, 0.87 mmol. 1.00 equiv) in THF was added iodo (('$H_3$) methyl) magnesium (9 mL. 8.76 mmol. 10.00 equiv) dropwise at 0° C., under nitrogen atmosphere. The resulting mixture was stirred for 1 h at 0° C., under nitrogen atmosphere. The reaction was monitored by LCMS. Desired product could be detected by LCMS. The reaction was quenched with sat. $NH_4Cl$ (aq.) at 0° C. The resulting mixture was extracted with EtOAc (3×20 mL). The combined organic layers were washed with brine (50 mL), dried over anhydrous $Na_2SO_4$. After filtration, the filtrate was concentrated under reduced pressure. The residue was purified by silica gel column chromatography to afford the crude product. The crude product was purified by Prep-HPLC to afford 3-chloro-4-((3.5-difluoropyridin-2-yl)methoxy-d2)-3'-fluoro-2'-(2-(2-hydroxypropan-2-yl-1.1.1.3.3 .3-d6)

pyrimidin-4-yl)-5'0.6-dimethyl-2H-[1,4'-bipyridin]-2-one (65 mg, 13.74%) as a white solid. LC-MS: (ES+H, m/z): $[M+H]^+$=540.2.

Step 4: Preparation of rel-3-chloro-4-((3,5-difluoropyridin-2-yl)methoxy-d2)-3'-fluoro-2'-(2-(2-hydroxypropan-2-yl-1,1,1,3,3 ,3-d6) pyrimidin-4-yl)-5',6-dimethyl-2H-[1,4'-bipyridin]-2-one & rel-3-chloro-4-((3,5-difluoropyridin-2-yl)methoxy-d2)-3'-fluoro-2'-(2-(2-hydroxypropan-2-yl-1,1,1,3,3 ,3-d6) pyrimidin-4-yl)-5',6-dimethyl-2H-[1,4'-bipyridin]-2-one The racemate (65 mg) was separated by prep-chiral-HPLC to afford Example 67A (9.7 mg. 97.4% purity, 98.9% deuterium purity, ee=97.44%) and Example 67B (8.8 mg. 98.4% purity, 98.6% deuterium purity, ee=97.02%) as a white solid.

EXAMPLE 67A

LC-MS: (ES+H, m/z): $[M+H]^+$=540.10. $^1H$ NMR (300 MHz, DMSO-$d_6$) δ9.03 (d, 1H), 8.77 (s, 1H), 8.61 (d, 1H), 8.13-8.02 (m, 2H), 6.90 (s, 1H), 5.04 (s, 1H), 2.17 (s, 3H), 2.05 (s, 3H). $^{19}F$ NMR (282 MHz, DMSO) δ-119.61,-119.66,-120.85,-120.87,-132.49.

EXAMPLE 67B

LC-MS: (ES+H, m/z): $[M+H]^+$=540.2. $^1H$ NMR (300 MHz, DMSO-$d_6$) δ9.03 (d, 1H), 8.77 (s, 1H), 8.61 (d, 1H), 8.13-8.03 (m, 2H), 6.90 (s, 1H), 5.05 (s, 1H), 2.17 (s, 3H), 2.05 (s, 3H). $^{19}F$ NMR (282 MHz, DMSO) δ-120.23,-120.25,-122.32,-122.34,-132.06.

EXAMPLE 68A, 68B

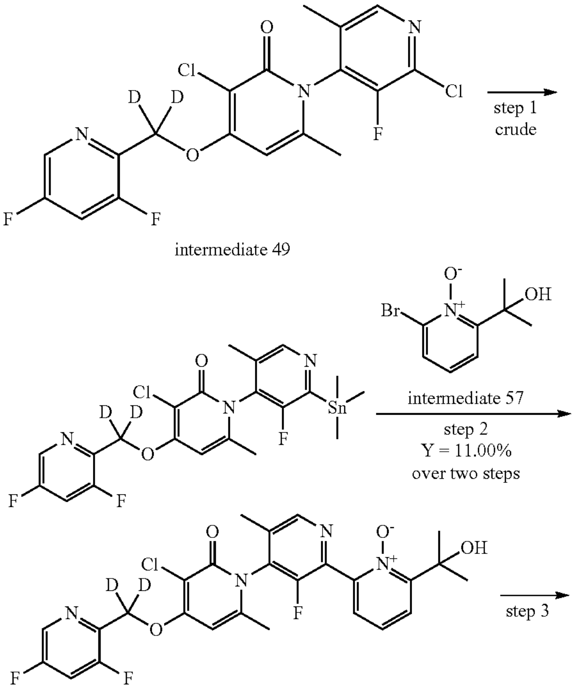

Exapmle 68

-continued

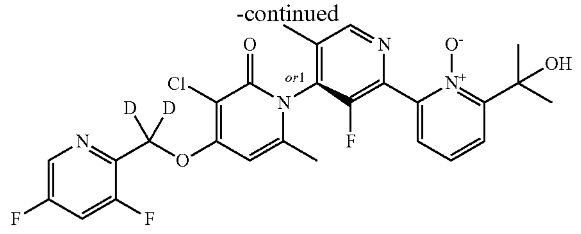

isomer 1
Example 68A

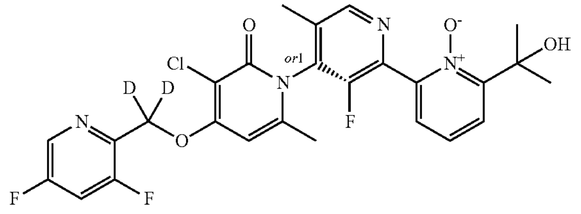

isomer 2
Example 68B

Step 1: Preparation of 3-chloro-4-[(3,5-difluoropyridin-2-yl) ($^2H_2$)methoxy]-3'-fluoro-5',6-dimethyl-2'-(trimethylstannyl)-[1,4'-bipyridin]-2-one A mixture of 2',3-dichloro-4-[(3,5-difluoropyridin-2-yl) ($^2H_2$)methoxy]-3'-fluoro-5',6-dimethyl-[1,4'-bipyridin]-2-one (1.00 g, 2.31 mmol, 1.00 equiv), $Sn_2Me_6$ (1.51 g, 4.62 mmol, 2.00 equiv), $Pd(PPh_3)$: $Cl_2$ (0.32 g, 0.46 mmol, 0.20 equiv), $AsPh_3$ (0.14 g, 0.46 mmol, 0.20 equiv) in dioxane (10 mL) was stirred for 2 h at 80° C., under nitrogen atmosphere. The reaction was monitored by LCMS. The resulting mixture was used in the next step directly without further purification. LC-MS: (ES+H, m/z): $[M+H]^+$ =562.1.

Step 2: Preparation of 4'-{3-chloro-4-[(3,5-difluoropyridin-2-yl) ($^2H_2$)methoxy]-6-methyl-2-oxopyridin-1-yl}-3'-fluoro-6-(2-hydroxypropan-2-yl)-5'-methyl-[2,2'-bipyridin]-1-ium-1-olate To the above mixture of step 1 was added 2-bromo-6-(2-hydroxypropan-2-yl)pyridin-1-ium-1-olate (0.83 g, 3.58 mmol, 2.00 equiv), CuI (0.34 g, 1.79 mmol, 1.00 equiv) and $Pd(PPh_3)_2Cl_2$ (0.25 g, 0.35 mmol, 0.20 equiv), the mixture was stirred for 2 h at 80° C., under nitrogen atmosphere. The reaction was monitored by LCMS. The mixture was allowed to r.t, and then diluted with EtOAc (200 mL). The resulting mixture was washed with sat. $NaHCO_3$(aq.) (2×100 mL). The organic layer was concentrated under reduced pressure. The residue was purified by silica gel column chromatography to afford crude product. The crude product was isolated by PREP-HPLC to afford 4'-{3-chloro-4-[(3,5-difluoropyridin-2-yl) ($^2H_2$) methoxy]-6-methyl-2-oxopyridin-1-yl}-3'-fluoro-6-(2-hydroxypropan-2-yl)-5'-methyl-[2.2'-bipyridin]-1-ium-1-olate (140 mg, 11.00%). LC-MS: (ES+H, m/z): $[M+H]^+$=549.2. $^1H$ NMR (300 MHz, Chloroform-d) δ 8.53 (s, 1H), 8.36 (d, 1H), 7.56 (d, 1H), 7.49-7.39 (m, 2H), 7.34-7.26 (m, 1H), 6.46 (d, 1H), 2.20 (s. 3H), 2.10 (s, 3H), 1.67 (s, 3H), 1.63 (s, 3H).

Step 3: Preparation of rel-4'-{3-chloro-4-[(3,5-difluoropyridin-2-yl) ($^2H_2$)methoxy]-6-methyl-2-oxopyridin-1-yl}-3'-fluoro-6-(2-hydroxypropan-2-yl)-5'-methyl-[2,2'-bipyridin]-1-ium-1-olate & rel-4'-{3-chloro-4-[(3,5-difluoropyridin-2-yl) ($^2H_2$) methoxy]-6-methyl-2-oxopyridin-1-yl}-3'-fluoro-6-(2-hydroxypropan-2-yl)-5'-methyl-[2,2'-bipyridin]-1-ium-1-olate The rac-mixture (140 mg) was separated by Prep-Chiral HPLC to afford rel-4'-{3-chloro-4-1 (3.5-difluoropyridin-2-yl) ($^2H_2$)methoxy]-6-methyl-2-oxopyridin-1-yl}-3'-fluoro-6-(2-hydroxypropan-2-yl)-5'-methyl-[2.2'-bipyridin]-1-ium-1-olatc (Example 68A: 40.8 mg. 99.0% purity, ee=100.0%) as a white solid and rel-4'-{3-chloro-4-[(3.5-difluoropyridin-2-yl) ($^2H_2$)methoxy]-6-methyl-2-oxopyridin-1-yl}-3'-fluoro-6-(2-hydroxypropan-2-yl )-5'-methyl-[2.2'-bipyridin]-1-ium-1-olate (Example 68B: 40.3 mg. 98.2% purity, ee=100.0%) as a white solid.

EXAMPLE 68A

LC-MS: (ES+H, m/z): $[M+H]^+$=549.25. $^1H$ NMR (300 MHz. DMSO-$d_6$) δ 8.70 (s, 1H), 8.61 (d. 1H), 8.14-8.04 (m, 1H), 7.83 (d, 1H), 7.75 (d, 1H), 7.60 (t. 1H), 6.89 (d, 1H), 6.62 (s, 1H), 2.17 (s, 3H). 2.06 (s, 3H), 1.61 (s, 3H), 1.59 (s, 3H). $^{19}F$ NMR (282 MHz. DMSO) δ-120.27, -120.29, -122.33, -122.36, —128.07.

EXAMPLE 68B

LC-MS: (ES+H, m/z): $[M+H]^+$=549.20. $^1H$ NMR (300 MHz. DMSO-$d_6$) δ 8.70 (s, 1H), 8.61 (d. 1H), 8.17-8.01 (m, 1H), 7.83 (d, 1H), 7.75 (d, 1H), 7.60 (t. 1H), 6.89 (d, 1H), 6.62 (s, 1H), 2.17 (s, 3H). 2.06 (s, 3H), 1.61 (s, 3H), 1.59 (s, 3H), $^{19}F$ NMR (282 MHz. DMSO) δ-120.27, -120.29, -122.33, -122.36, —128.07.

BIOLOGICAL EXAMPLES

Protein Expression and Purification

Expression vectors of the recombinant MK2 and PRAK kinases were constructed by cloning of the codon optimized gene sequences of MK2 (Uniprot ID P49137, amino acid fragment F46-$H_{400}$), or PRAK (Uniprot ID Q8IW41, amino acid fragment MI-Q471) into pGEX-4TI (GE) for over expression of these kinases with N-terminal GST-tag. Protein expression was carried out in *E, coli* BL21 by growing the hosts in TB medium, induction of protein expression with 0.5 mM IPTG at approximate 0.8 OD600, and incubation of the cultures at 18° C. for 14-20 hours afterwards. The harvested cells were resuspended in 100 ml of Lysis buffer (50 mM Tris —HCl, pH 8.0. 500 mM NaCl. I mM DTT. 5% glycerol, and 1 mM PMSF) per gram of wet cell mass and homogenized at 4° C., in a microfluidizer (ATS. Suzhou. China) at 14.000 psi pressure. 3 passes. The cell lysates were clarified by centrifugation and the supernatants containing the GST-fusion proteins were purified by affinity chromatography using GSH-Sepharose (GE) gravity flow columns pre-equilibrated in Buffer A (50 mM Tris —HCl, pH 8.0, 500 mM NaCl. 1 mM DTT, and 5% glycerol). After thorough washing of the columns with Buffer A, the bound GST-proteins were eluted by Buffer B (50 mM Tris, pH 8.0, 500 mM NaCl, 1 mM DTT, 5% glycerol, 10 mM glutathione), followed by size-exclusion purification on Superdex 200 column equilibrated in Buffer A. The purified proteins were concentrated to approximately 1 mg/ml and stored at −80° C.

Biochemical Assay

This study evaluates the inhibitory potency of invention compound on p38/MK2 pathway vs p38/PRAK pathway. More specially the compound concentration (${}_{I}$C50) was determined that inhibited half of the maximal activation of MK2 or PRAK by p38. MK2 activation study was set up without or with a serial of 10-point 1:3 dilution of invention compound at top dose of 1 or 10 μM, and PRAK activation study was set up without or with a serial of 10-point 1:3 dilution of invention compound at top dose of 300 μM. The MK2 and PRAK activity were determined by the phosphorylation level of HSP27 peptide conjugated with FITC.

A typical assay was conducted in 20 μL volume including 60 pM active p38a (Carna, cat #04-152), 10 μM ATP, luM FITC-HSP27 peptide (Sangon, Cat #P22354), and 1 nM inactive MK2, or PRAK in 1× reaction buffer (20 mM HEPES, pH7.5, 10 mM MgCl2, 1 mM DTT, 0.01% Triton X-100, 0.01% BSA). After 2h incubation of the reaction mixture with various concentration of invention compound (200 nL), 60 μL 1× IMAP solution Mixture (Molecular Devices, Cat #R8127) was added to the reaction mixture and incubated for another half hour. The signal was then read by Synergy™ Neo2 Multi-Mode Microplate Reader with filter setting (Ex/Em=485 nm/FITC FP-P pol 528 nm & FITC FP-S pol 528 nm)

The signal was then normalized to vehicle control and fitted in Xfit to generate $IC_{50}$. The selectivity of MK2 over PRAK was calculated by the formular Selectivity=$IC_{50}$ of PRAK/$IC_{50}$ of MK2.

The data from the above assays is found in table 2.

TABLE 2

| Ex. number | p38a/MK2 (10 μM) Enzyme $pIC_{50}$ | p38a/MK2 (1 μM) Enzyme $pIC_{50}$ | p38a/PRAK Enzyme $pIC_{50}$ |
|---|---|---|---|
| 1 | 5.2 | | <3.5 |
| 2 | 7.5 | | 5.4 |
| 3 | 7.7 | | 5.3 |
| 3A | | 8 | 5.4 |
| 3B | <5.0 | | <3.5 |
| 4 | 7.8 | | 5.1 |
| 4A | | 8.8 | 5.4 |
| 4B | 6.1 | | <3.5 |
| 5 | 7.8 | | 5.5 |
| 5A | 8.2 | | 5.6 |
| 5B | 5.7 | | <3.5 |
| 6 | 7.5 | | 4.9 |
| 6A | 7.6 | | 5 |
| 6B | | 8.3 | 5 |
| 6C | 5.5 | | <3.5 |
| 6D | 5.6 | | <3.5 |
| 7 | 6.3 | | 4.2 |
| 8 | <5.0 | | <3.5 |
| 9A | | 8.4 | 5.5 |
| 10 | 5.8 | | 5.3 |
| 14 | 7.7 | | 4.7 |
| 15 | 5.4 | | 3.8 |
| 16 | 7.4 | | 4.8 |
| 17 | 5.6 | | 4.4 |
| 18A | 6.8 | | 4.6 |
| 18B | <5.0 | | <3.5 |
| 18C | <5.0 | | <3.5 |
| 18D | 7.1 | | 5.5 |
| 19A | 6.6 | | 5.3 |
| 19B | <5.0 | | <3.5 |
| 20A | 5.7 | | 5.3 |
| 20B | <5.0 | | <3.5 |
| 21A | <5.0 | | <3.5 |
| 21B | | 8.5 | 5.7 |

TABLE 2-continued

| Ex. number | p38a/MK2 (10 μM) Enzyme $pIC_{50}$ | p38a/MK2 (1 μM) Enzyme $pIC_{50}$ | p38a/PRAK Enzyme $pIC_{50}$ |
|---|---|---|---|
| 22A | 7.5 | | 4.8 |
| 22B | <5.0 | | <3.5 |
| 23A | | 8.5 | 4.9 |
| 23B | <5.0 | | <3.5 |
| 24A | | 8.8 | 5.2 |
| 24B | 5.8 | | <3.5 |
| 25A | 7.5 | | 5.5 |
| 25B | 5.5 | | <3.5 |
| 26A | | 7.9 | 5.7 |
| 26B | 5.8 | | <3.5 |
| 27A | 7.2 | | 3.9 |
| 27B | 5.3 | | <3.5 |
| 28A | 5.4 | | <3.5 |
| 28B | <5.0 | | <3.5 |
| 29A | | 8.1 | 4.9 |
| 29B | <5.0 | | <3.5 |
| 30 | 6.2 | | 4.6 |
| 31A | 5.7 | | 5.5 |
| 31B | <5.0 | | <3.5 |
| 32A | | 7.7 | 5.2 |
| 32B | 6 | | <3.5 |
| 32C | 7.2 | | 5.2 |
| 32D | 5.9 | | <3.5 |
| 33A | | 7.6 | 5.3 |
| 33B | 6.5 | | 4.3 |
| 34A | | 7.7 | 5 |
| 34B | 7.9 | | 5.2 |
| 34C | 5.7 | | <3.5 |
| 34D | 5.5 | | <3.5 |
| 35A | | 7.3 | 5 |
| 35B | | 7.8 | 5.3 |
| 35C | | <6.0 | <3.5 |
| 35D | | <6.0 | <3.5 |
| 36A | | 8.3 | 5.3 |
| 36B | | 8.2 | 4.8 |
| 36C | | <6.0 | <3.5 |
| 36D | | <6.0 | <3.5 |
| 37A | | 8.3 | 5.6 |
| 37B | | <6.0 | <3.5 |
| 38A | | 7 | 4.5 |
| 38B | | <6.0 | <3.5 |
| 39A | | 8 | 4.9 |
| 39B | | <6.0 | <3.5 |
| 40A | | 6.9 | 4.8 |
| 40B | | <6.0 | <3.5 |
| 41A | | 8.3 | 5.5 |
| 41B | | <6.0 | <3.5 |
| 42A | | 6.3 | 5.2 |
| 42B | | <6.0 | <3.5 |
| 43A | | 7.9 | 5.6 |
| 43B | | <6.0 | <3.5 |
| 44A | | 7.6 | 5.2 |
| 44B | | <6.0 | <3.5 |
| 45A | | <6.0 | <3.5 |
| 45B | | 6.3 | 4.4 |
| 46A | | 7.8 | 5.6 |
| 46B | | <6.0 | <3.5 |
| 47A | | 8.7 | 5.3 |
| 47B | | <6.0 | <3.5 |
| 48A | | 8.3 | 5.7 |
| 48B | | <6.0 | <3.5 |
| 49A | | 8.2 | 5.5 |
| 49B | | <6.0 | <3.5 |
| 50A | | 7.9 | 5 |
| 50B | | <6.0 | <3.5 |
| 51A | | 7.1 | 5.3 |
| 51B | | <6.0 | <3.5 |
| 52A | | <6.0 | <3.5 |
| 52B | | 7.8 | 4.6 |
| 53A | | <6.0 | <3.5 |
| 53B | | 9.9 | 6.1 |
| 54A | | <6.0 | <3.5 |
| 54B | | 9.2 | 5.8 |
| 55 | | 7.2 | 5 |
| 56A | | 8.7 | 5.8 |
| 56B | | <6.0 | <3.5 |
| 57A | | 8.9 | 6.1 |

TABLE 2-continued

| Ex. number | p38a/MK2 (10 μM) Enzyme $pIC_{50}$ | p38a/MK2 (1 μM) Enzyme $pIC_{50}$ | p38a/PRAK Enzyme $pIC_{50}$ |
|---|---|---|---|
| 57B | | <8.0 | 3.9 |
| 58A | | 8.9 | 6 |
| 58B | | <6.0 | <3.5 |
| 59A | | <6.0 | <3.5 |
| 59B | | 9 | 6.5 |
| 60A | | <7.0 | <3.5 |
| 60B | | 7.6 | 4.7 |
| 61A | | <7.0 | 3.8 |
| 61B | | 8.5 | 6.2 |
| 62A | | 8.8 | 6.1 |
| 62B | | <7.0 | <3.5 |
| 63A | | <7.0 | <3.5 |
| 63B | | 9.5 | 6.5 |
| 64A | | 8.7 | 5.7 |
| 64B | | <7.0 | <3.5 |
| 65A | | 8.4 | 6.7 |
| 65B | | <7.0 | 4.1 |
| 66A | | <7.0 | <3.5 |
| 66B | | 8.2 | 6 |
| 67A | | 8.8 | 6.5 |
| 67B | | 7.1 | 4.5 |
| 68A | | <7.0 | <3.5 |
| 68B | | 9.7 | 6.4 |

The invention claimed is:

1. A method of treating atopic dermatitis in a subject in need thereof comprising administering to the subject a therapeutically effective amount of a compound of Formula (II), or a pharmaceutically acceptable salt or stereoisomer thereof:

Formula (II)

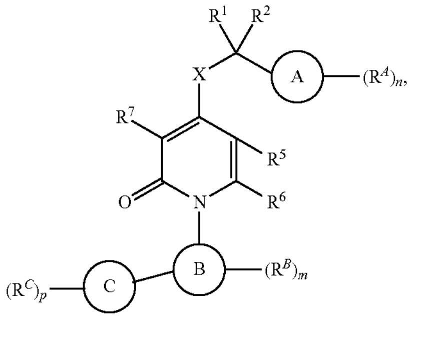

wherein:

Ring A is phenyl or heteroaryl;

each $R^A$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O)$_2NR^cR^d$, —$NR^cR^d$, —$NR^b$C(═O)$NR^cR^d$, —$NR^b$C(═O)$R^a$, —$NR^b$C(═O)$OR^b$, —$NR^b$S(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, or heteroaryl is optionally and independently substituted with one or more $R^{Aa}$;

or two $R^A$ on the same atom are taken together to form an oxo;

each $R^{Aa}$ is independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O) 2$NR^cR^d$, —$NR^cR^d$, —$NR^b$C(═O)$NR^cR^d$, —$NR^b$C(═O)$R^a$, —$NR^b$C(═O)$OR^b$, —$NR^b$S(═O)$_2R^a$, —C(═O)$R^a$, —C(═O)C(═O)$R^a$, —C(═O)$OR^b$, —C(═O)$NR^cR^d$, —C(═O)C(═O)$NR^cR^d$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Aa}$ on the same atom are taken together to form an oxo;

n is 0-4;

$R^1$ and $R^2$ are independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or $R^1$ and $R^2$ are taken together to form an oxo;

or $R^1$ and $R^2$ are taken together to form a cycloalkyl or heterocycloalkyl; wherein the cycloalkyl or heterocycloalkyl is optionally substituted with deuterium, halogen, —CN, —OH, —$OCH_3$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

X is —C$(R^3)_2$—, —$NR^4$—, —O—, or —S—;

each $R^3$ is independently hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

or two $R^3$ are taken together to form an oxo;

$R^4$ is hydrogen, —C(═O)$R^a$, —C(═O)$OR^b$, —C(═O)$NR^cR^d$, $C_1$-$C_6$alkyl, $C_1$-$C_6$haloalkyl, $C_1$-Codeuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^5$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^7$ is hydrogen, deuterium, halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

Ring B is pyridyl;

each $R^B$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O) 2$NR^cR^d$, —$NR^cR^d$, —$NR^b$C(═O)$NR^cR^d$, —$NR^b$C(═O)$R^a$, —NR$^b$C(═O)OR$^b$, —NR$^b$S(═O)$_2$R$^a$, —C(═O)R$^a$, —C(═O)OR$^b$, —C(═O)NR$^c$R$^d$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, or heteroaryl is optionally or independently substituted with one or more R$^{Ba}$;

each R$^{Ba}$ is independently deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O) 2NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)C(═O)R$^a$, —C(═O)OR$^b$, —C(═O)NR$^c$R$^d$, —C(═O)C(═O)NR$^c$R$^d$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two R$^{Ba}$ on the same atom are taken together to form an oxo;

m is 0-3;

Ring C is 5-membered heteroaryl;

each R$^C$ is independently hydrogen, deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O) 2NR$^c$R$^d$, —S(═O) (═NR$^b$)R$^a$, —SiRCRdORD, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl) aryl, or ($C_1$-$C_6$alkyl)heteroaryl; wherein each alkyl, alkenyl, alkynyl, cycloalkyl, heterocycloalkyl, aryl, or heteroaryl is optionally or independently substituted with one or more R$^{Ca}$;

each R$^{Ca}$ is independently deuterium, halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O) 2NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)C(═O)R$^a$, —C(═O)OR$^b$, —C(═O)NR$^c$R$^d$, —C(═O)C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-Calkenyl, $C_2$-$C_6$alkynyl, cycloalkyl, heterocycloalkyl, aryl, or heteroaryl;

or two R$^{Ca}$ on the same atom are taken together to form an oxo;

p is 0-4;

each R$^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, or heteroaryl is independently optionally substituted with one or more oxo, deuterium, halogen, —CN, —OH, —$OCH_3$, —S(═O)$CH_3$, —S(═O) 2$CH_3$, —S(═O) 2$NH_2$, —S(═O) 2$NHCH_3$, —S(═O) 2N$(CH_3)_2$, —$NH_2$, —$NHCH_3$, —N$(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each R$^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$ heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, or heteroaryl is independently optionally substituted with one or more oxo, deuterium, halogen, —CN, —OH, —$OCH_3$, —S(═O)$CH_3$, —S(═O) 2$CH_3$, —S(═O) 2$NH_2$, —S(═O) 2$NHCH_3$, —S(═O) 2N$(CH_3)_2$, —$NH_2$, —$NHCH_3$, —N$(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each R$^c$ and R$^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl (cycloalkyl), $C_1$-$C_6$alkyl (heterocycloalkyl), $C_1$-$C_6$alkyl (aryl), or $C_1$-$C_6$alkyl (heteroaryl); wherein each alkyl, alkenyl, alkynyl, cycloalkyl, heterocycloalkyl, aryl, or heteroaryl is independently optionally substituted with one or more oxo, deuterium, halogen, —CN, —OH, —$OCH_3$, —S(═O)$CH_3$, —S(═O) 2$CH_3$, —S(═O) 2$NH_2$, —S(═O) 2$NHCH_3$, —S(═O) 2N$(CH_3)_2$, —$NH_2$, —$NHCH_3$, —N$(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or R$^c$ and R$^d$ are taken together with the atom to which they are attached to form a heterocycloalkyl optionally substituted with one or more oxo, deuterium, halogen, —CN, —OH, —$OCH_3$, —S(═O)$CH_3$, —S(═O) 2$CH_3$, —S(═O) 2$NH_2$, —S(═O) 2$NHCH_3$, —S(═O) 2N$(CH_3)_2$, —$NH_2$, —$NHCH_3$, —N$(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

provided that the compound is not

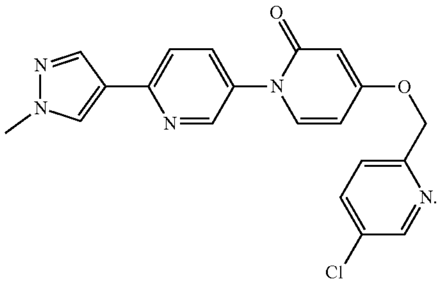 [SMILES: Cn1cc(-c2ccc(-n3ccc(OCc4ccc(Cl)cn4)cc3=O)cn2)cn1]

2. The method of claim 1, wherein Ring A is pyridyl.

3. The method of claim 1, wherein each R$^A$ is independently halogen.

4. The method of claim 1, wherein n is 1 or 2.

5. The method of claim 1, wherein $R^1$ and $R^2$ are hydrogen or deuterium.

6. The method of claim 1, wherein X is —O—.

7. The method of claim 1, wherein $R^5$ is hydrogen, deuterium, halogen, —CN, or $C_1$-$C_6$alkyl.

8. The method of claim 1, wherein $R^6$ is hydrogen, deuterium, halogen, —CN, or $C_1$-$C_6$alkyl.

9. The method of claim 1, wherein $R_7$ is hydrogen, deuterium, halogen, —CN, or $C_1$-$C_6$alkyl.

10. The method of claim 1, wherein each $R^B$ is independently halogen or $C_1$-$C_6$alkyl.

11. The method of claim 1, wherein m is 1 or 2.

12. The method of claim 1, wherein Ring C is thiazolyl, pyrazolyl, imidazolyl, oxazolyl, thiadiazole, or triazolyl.

13. The method of claim 1, wherein Ring C is pyrazolyl.

14. The method of claim 1, wherein each $R^C$ is independently $C_1$-$C_6$hydroxyalkyl.

15. The method of claim 1, wherein p is 1 or 2.

16. The method of claim 1, wherein the compound is selected from the group consisting of:

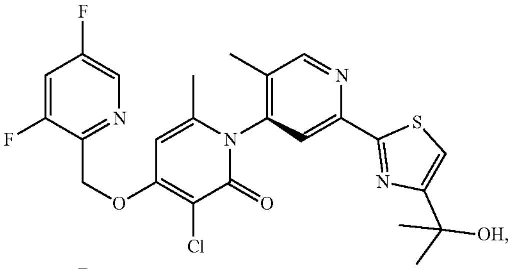

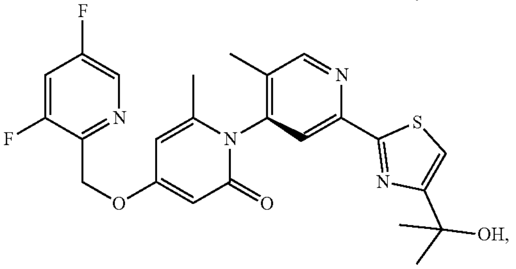

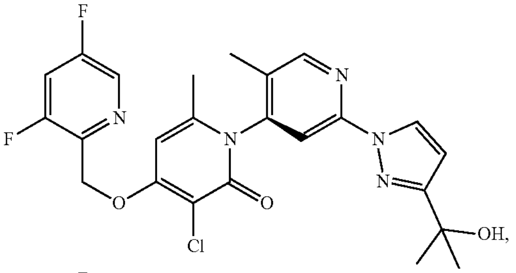

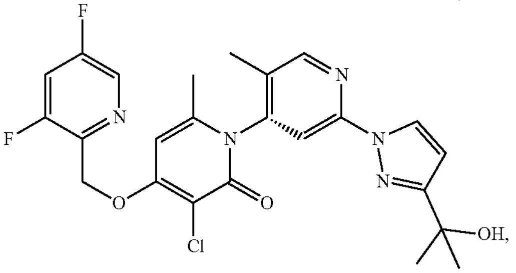

-continued

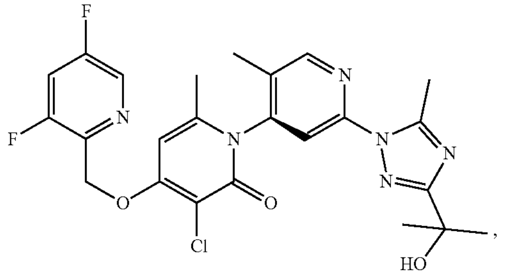

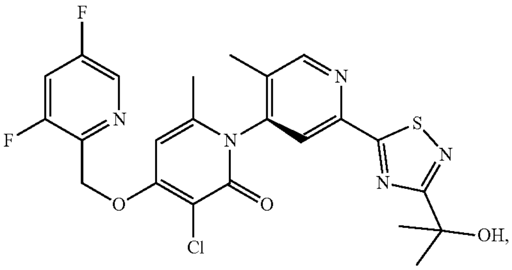

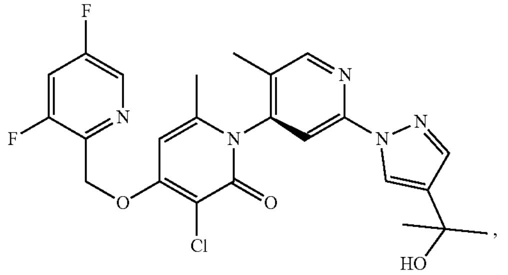

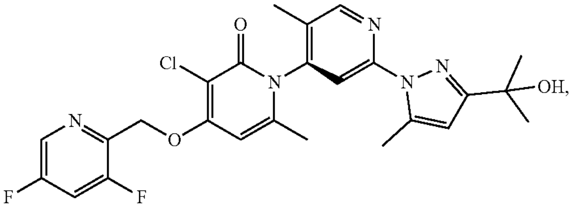

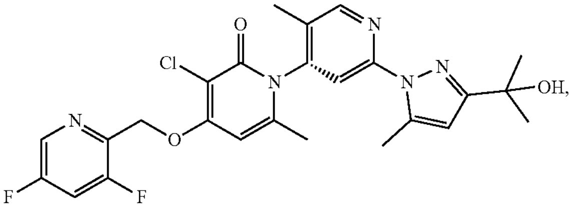

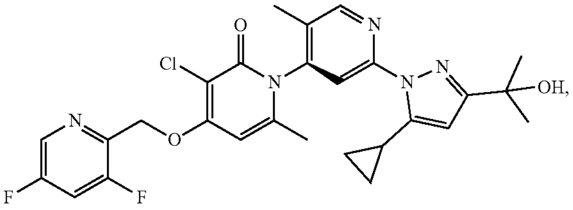

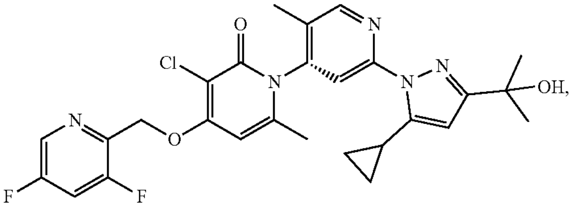

-continued
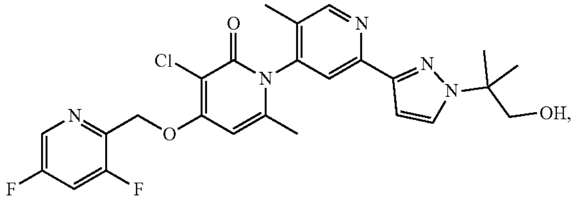
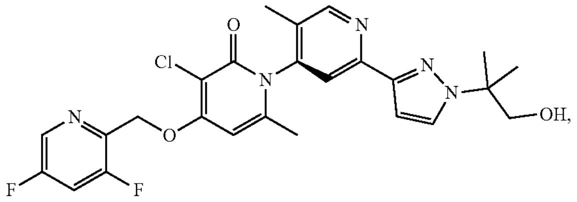
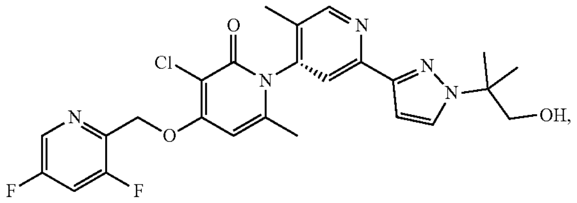
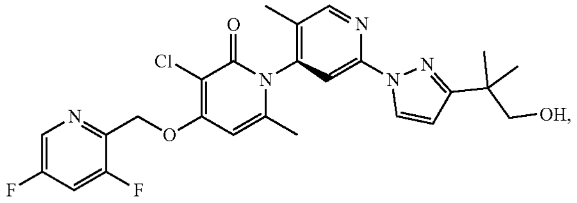
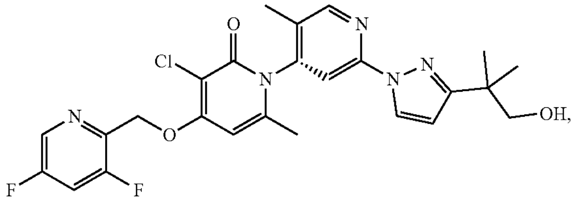
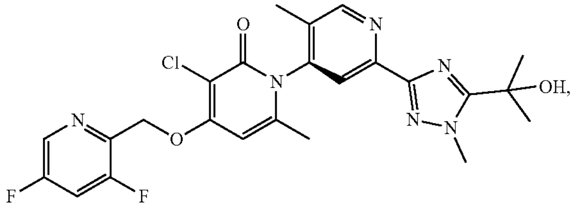
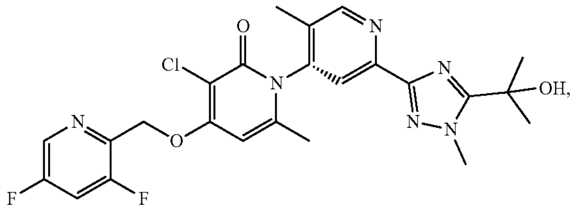
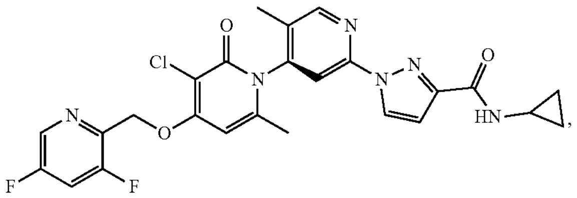
-continued
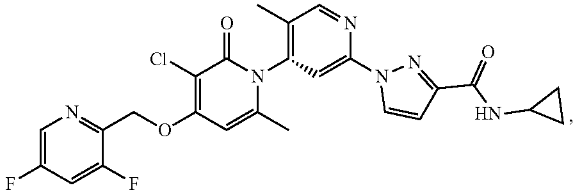
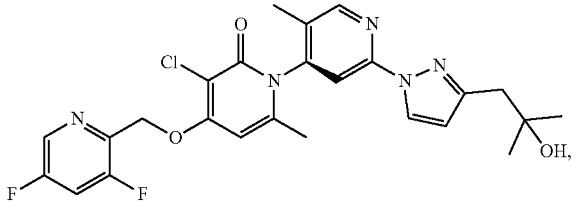
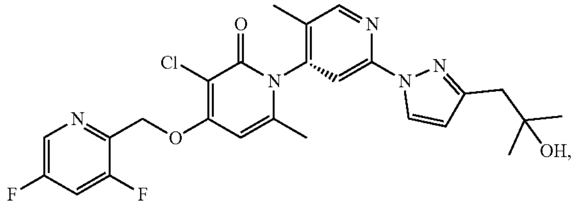
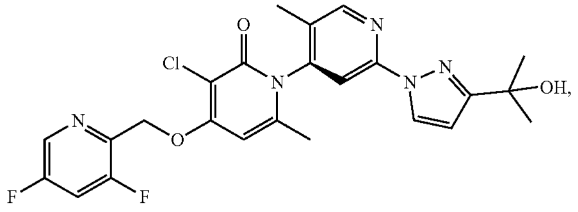
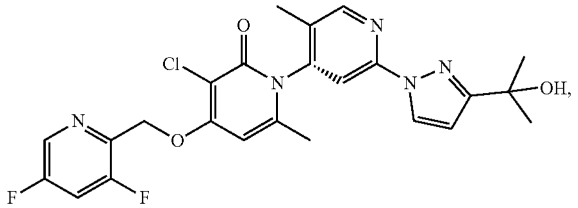
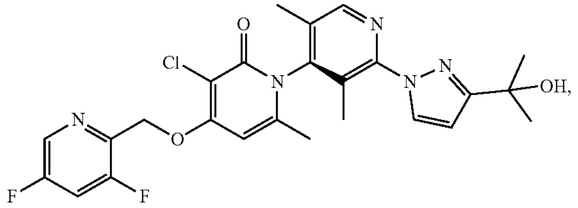
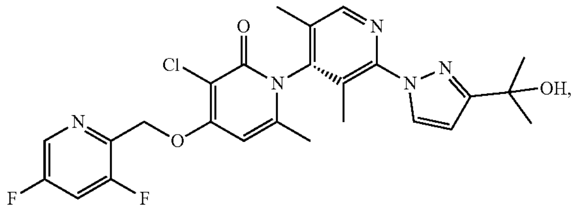
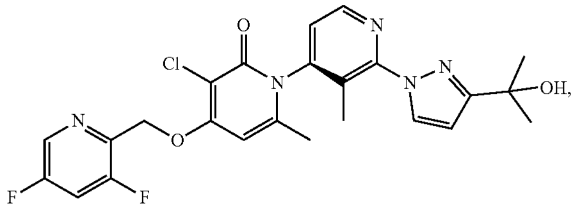

-continued
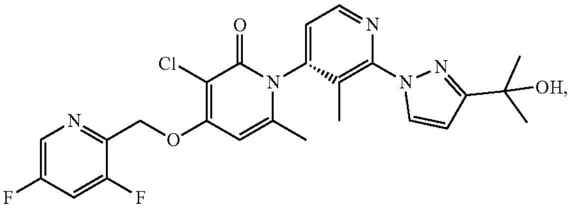
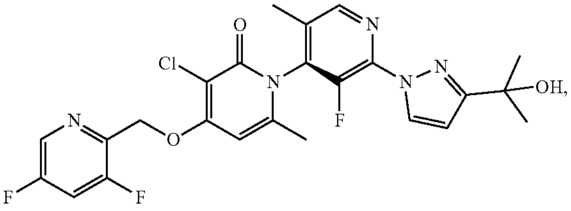
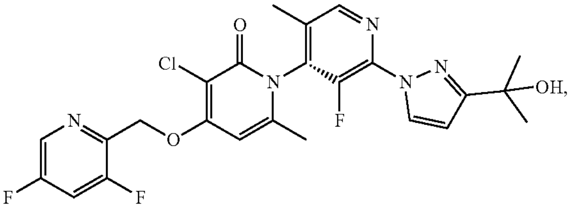
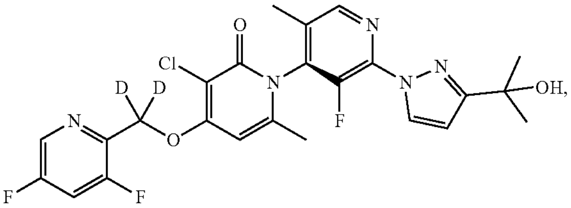
and
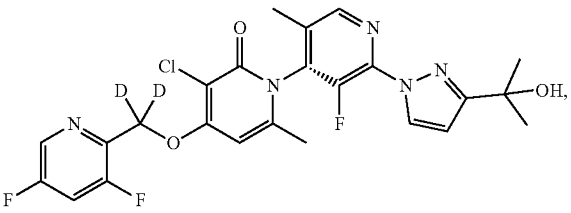
or a pharmaceutically acceptable salt thereof.
17. The method of claim 1, wherein the compound is selected from the group consisting of:
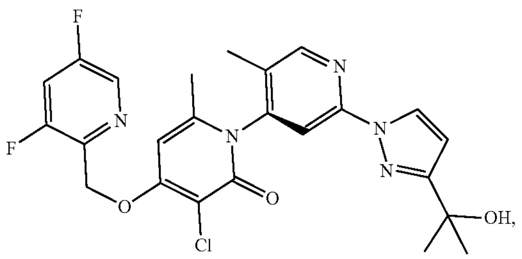
-continued
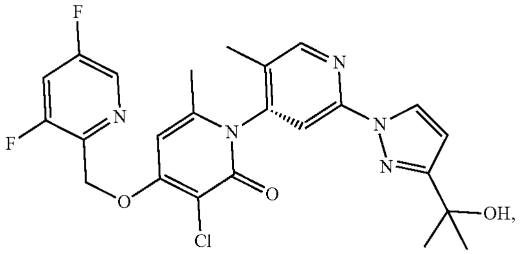
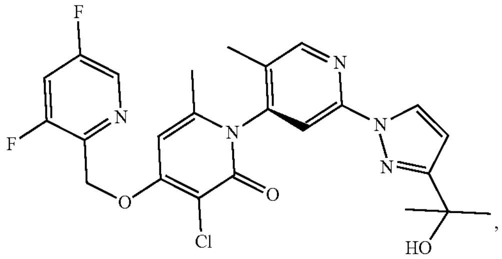
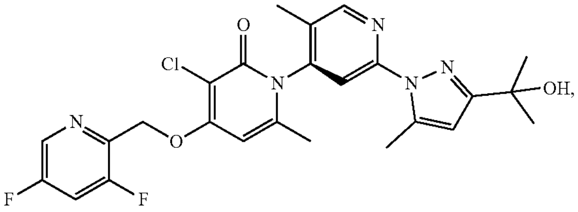
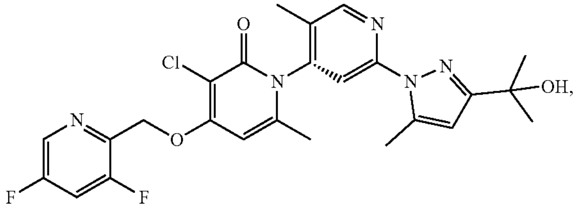
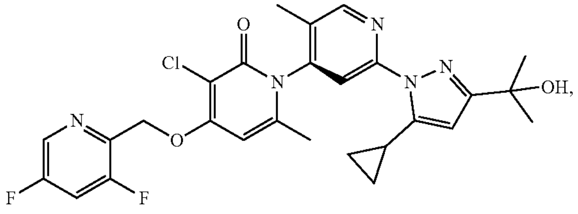
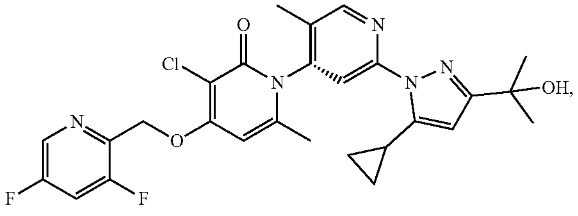
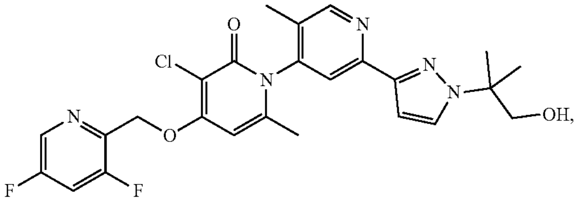

-continued
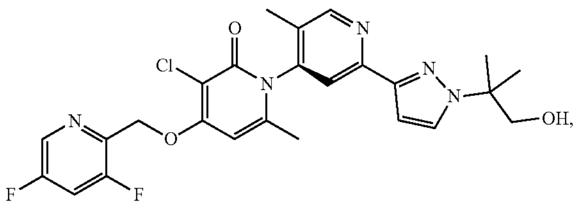
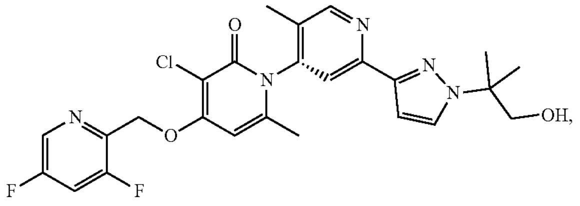
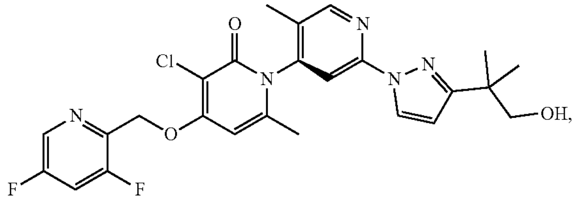
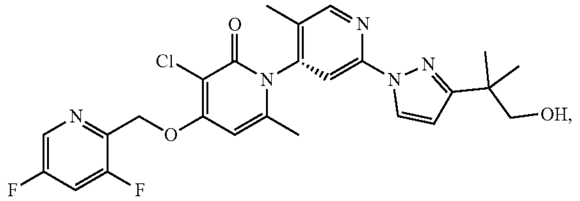
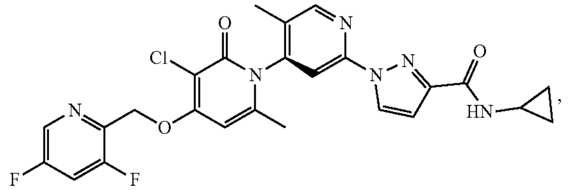
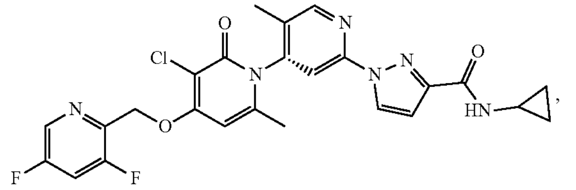
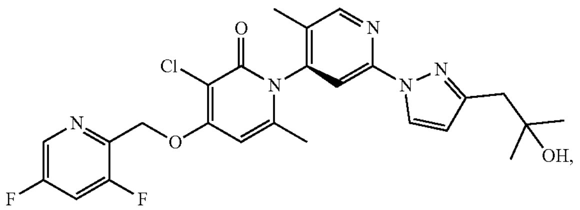
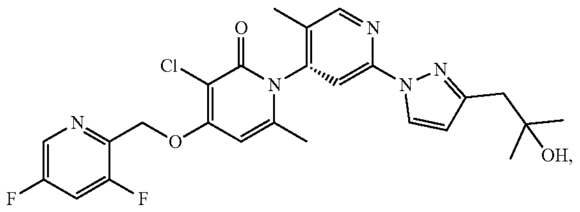
-continued
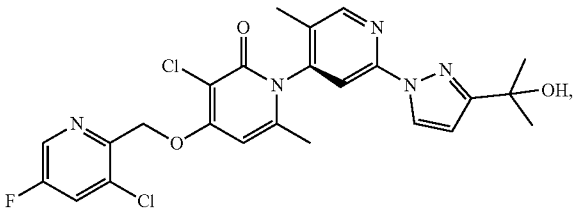
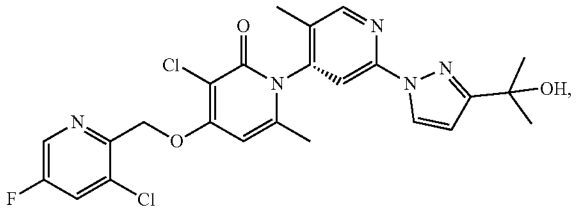
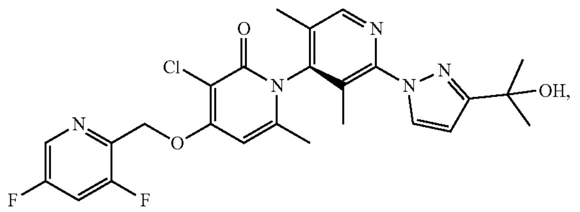
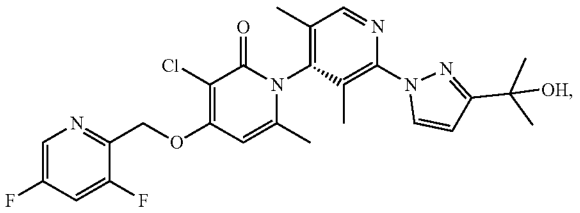
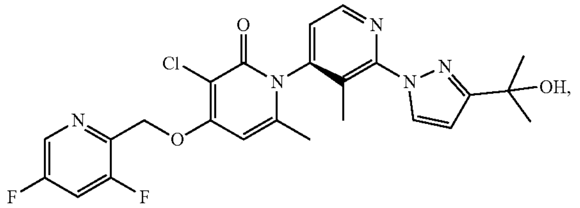
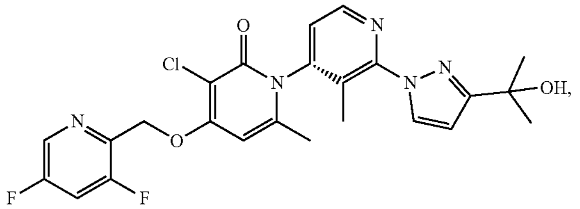
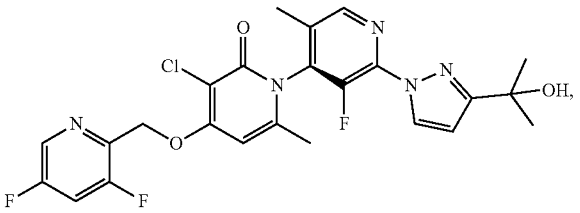
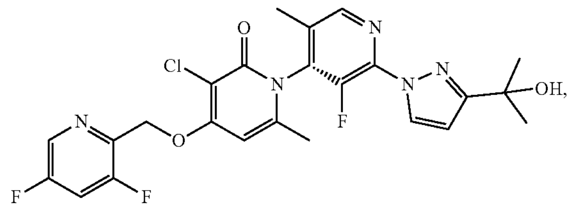

-continued

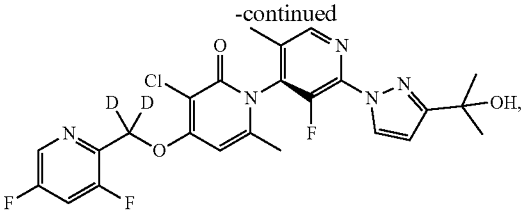

and

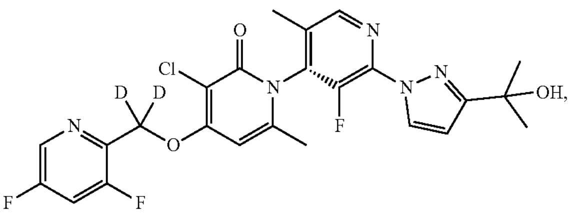

or a pharmaceutically acceptable salt thereof.

18. The method of claim 1, wherein the compound is

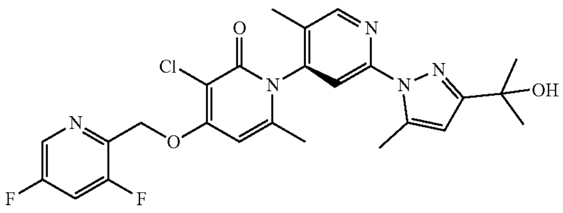

or a pharmaceutically acceptable salt thereof.

19. The method of claim 1, wherein the compound is

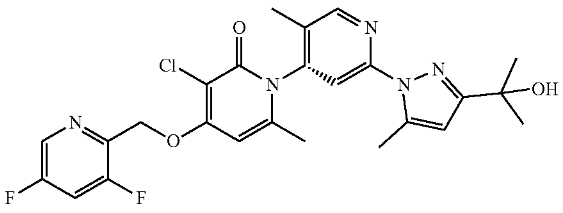

or a pharmaceutically acceptable salt thereof.

20. The method of claim 1, wherein the compound is

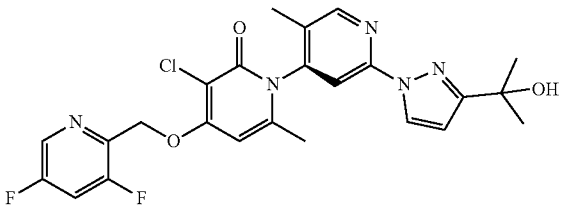

or a pharmaceutically acceptable salt thereof.

21. The method of claim 1, wherein the compound is

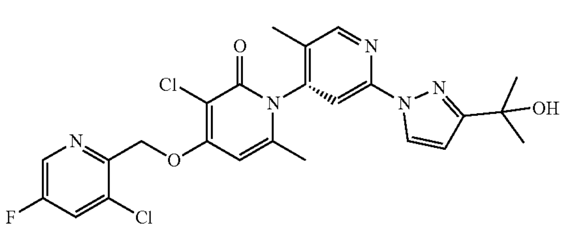

or a pharmaceutically acceptable salt thereof.

22. The method of claim 1, wherein the compound is:

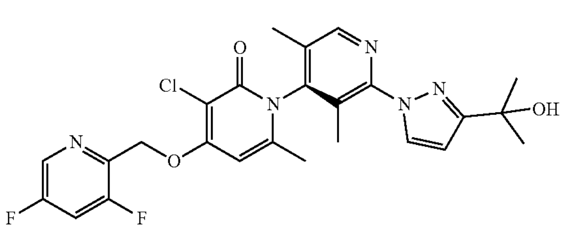

or a pharmaceutically acceptable salt thereof.

23. The method of claim 1, wherein the compound is

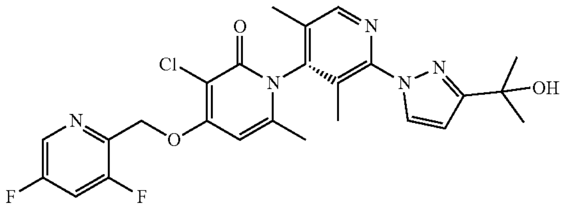

or a pharmaceutically acceptable salt thereof.

24. The method of claim 1, wherein the compound is

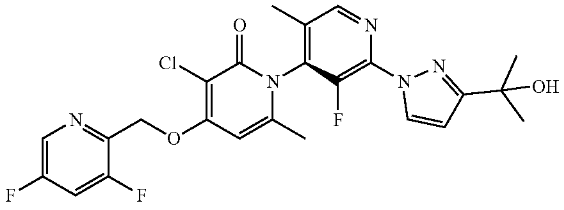

or a pharmaceutically acceptable salt thereof.

25. The method of claim 1, wherein the compound is

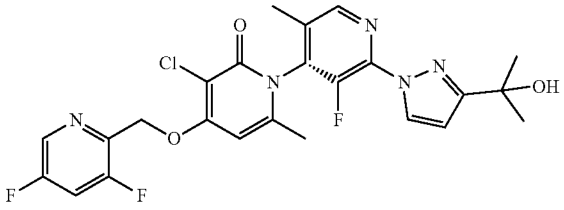

or a pharmaceutically acceptable salt thereof.

26. The method of claim 1, wherein the compound is
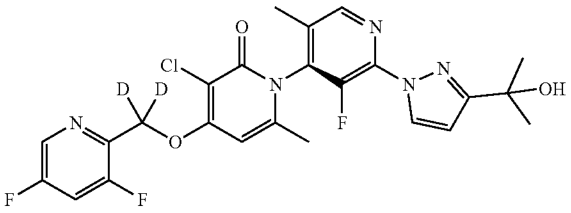
or a pharmaceutically acceptable salt thereof.
27. The method of claim 1, wherein the compound is
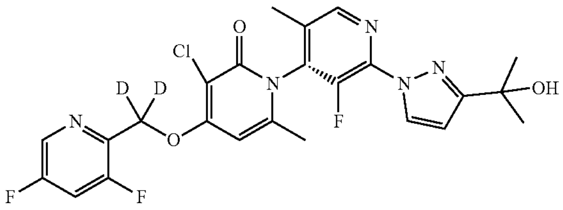
or a pharmaceutically acceptable salt thereof.
* * * * *